(12) United States Patent
Karve et al.

(10) Patent No.: US 12,195,505 B2
(45) Date of Patent: Jan. 14, 2025

(54) TREATMENT OF CYSTIC FIBROSIS BY DELIVERY OF NEBULIZED mRNA ENCODING CFTR

(71) Applicant: Translate Bio, Inc., Lexington, MA (US)

(72) Inventors: Shrirang Karve, Lexington, MA (US); Frank DeRosa, Lexington, MA (US); Michael Heartlein, Lexington, MA (US); Zarna Patel, Lexington, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 181 days.

(21) Appl. No.: 17/693,120

(22) Filed: Mar. 11, 2022

(65) Prior Publication Data
US 2022/0324926 A1    Oct. 13, 2022

Related U.S. Application Data

(63) Continuation of application No. 16/691,268, filed on Nov. 21, 2019, now abandoned.

(60) Provisional application No. 62/848,401, filed on May 15, 2019, provisional application No. 62/846,458, filed on May 10, 2019, provisional application No. 62/829,461, filed on Apr. 4, 2019, provisional application No. 62/770,596, filed on Nov. 21, 2018.

(51) Int. Cl.
| | |
|---|---|
| *C07H 21/04* | (2006.01) |
| *A61K 9/00* | (2006.01) |
| *A61K 9/127* | (2006.01) |
| *A61K 9/19* | (2006.01) |
| *A61K 9/51* | (2006.01) |
| *A61K 45/06* | (2006.01) |
| *A61K 47/26* | (2006.01) |
| *A61P 11/00* | (2006.01) |
| *B82Y 5/00* | (2011.01) |
| *C07K 14/47* | (2006.01) |
| *A61K 38/00* | (2006.01) |

(52) U.S. Cl.
CPC ........ *C07K 14/4702* (2013.01); *A61K 9/0078* (2013.01); *A61K 9/1272* (2013.01); *A61K 9/19* (2013.01); *A61K 9/51* (2013.01); *A61K 45/06* (2013.01); *A61K 47/26* (2013.01); *A61P 11/00* (2018.01); *B82Y 5/00* (2013.01); *C07K 14/4712* (2013.01); *A61K 38/00* (2013.01); *Y10S 977/80* (2013.01)

(58) Field of Classification Search
None
See application file for complete search history.

(56) References Cited

U.S. PATENT DOCUMENTS

| | | | |
|---|---|---|---|
| 2,647,121 | A | 7/1953 | Jacoby |
| 2,717,909 | A | 9/1955 | Kosmin |
| 2,819,718 | A | 1/1958 | Goldman |
| 2,844,629 | A | 7/1958 | William et al. |
| 3,096,560 | A | 7/1963 | Liebig |
| 3,535,289 | A | 10/1970 | Yoshihara et al. |
| 3,614,954 | A | 10/1971 | Mirowski et al. |
| 3,614,955 | A | 10/1971 | Mirowski |
| 3,656,185 | A | 4/1972 | Carpentier |
| 3,805,301 | A | 4/1974 | Liebig |
| 3,945,052 | A | 3/1976 | Liebig |
| 3,995,623 | A | 12/1976 | Blake et al. |
| 4,013,507 | A | 3/1977 | Rembaum |
| 4,072,146 | A | 2/1978 | Howes |
| 4,096,860 | A | 6/1978 | McLaughlin |
| 4,099,528 | A | 7/1978 | Sorenson et al. |
| 4,106,129 | A | 8/1978 | Carpentier et al. |
| 4,134,402 | A | 1/1979 | Mahurkar |
| 4,140,126 | A | 2/1979 | Choudhury |
| 4,180,068 | A | 12/1979 | Jacobsen et al. |
| 4,182,833 | A | 1/1980 | Hicks |
| 4,227,533 | A | 10/1980 | Godfrey |
| 4,284,459 | A | 8/1981 | Patel et al. |
| 4,308,085 | A | 12/1981 | Horhold et al. |
| 4,323,525 | A | 4/1982 | Bornat |
| 4,335,723 | A | 6/1982 | Patel |
| 4,339,369 | A | 7/1982 | Hicks et al. |
| 4,355,426 | A | 10/1982 | MacGregor |
| 4,375,817 | A | 3/1983 | Engle et al. |
| 4,385,631 | A | 5/1983 | Uthmann |

(Continued)

FOREIGN PATENT DOCUMENTS

| | | |
|---|---|---|
| CA | 2518132 A1 | 3/2006 |
| CA | 2807552 A1 | 2/2012 |

(Continued)

OTHER PUBLICATIONS

U.S. Appl. No. 60/083,294, filed Apr. 28, 1998, Chen et al.

(Continued)

*Primary Examiner* — Kimberly Chong
(74) *Attorney, Agent, or Firm* — LATHROP GPM LLP; James H. Velema, Esq.

(57) ABSTRACT

The present invention provides, among other things, an improved method of treating cystic fibrosis (CF) in a human subject. The method comprises administering a composition comprising an mRNA encoding a Cystic Fibrosis Transmembrane Conductance Regulator (CFTR) protein at a concentration of 0.5 mg/mL or greater to a human subject via nebulization. The composition is aerosolized using a nebulizer and a nominal dose of the mRNA is administered to the human subject via the nebulizer over a period of time, typically at least 30 minutes, at a suitable nebulization rate, e.g., at least 0.2 mL/minute.

16 Claims, 22 Drawing Sheets

Specification includes a Sequence Listing.

(56) References Cited

U.S. PATENT DOCUMENTS

| | | |
|---|---|---|
| 4,401,472 A | 8/1983 | Gerber |
| 4,406,656 A | 9/1983 | Hattler et al. |
| 4,475,972 A | 10/1984 | Wong |
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,737,323 A | 4/1988 | Martin et al. |
| 4,762,915 A | 8/1988 | Kung et al. |
| 4,782,836 A | 11/1988 | Alt |
| 4,856,521 A | 8/1989 | Irnich |
| 4,860,751 A | 8/1989 | Callaghan |
| 4,878,908 A | 11/1989 | Martin et al. |
| 4,892,540 A | 1/1990 | Vallana |
| 4,897,355 A | 1/1990 | Eppstein et al. |
| 4,920,016 A | 4/1990 | Allen et al. |
| 4,946,683 A | 8/1990 | Forssen |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,171,678 A | 12/1992 | Behr et al. |
| 5,176,661 A | 1/1993 | Evard et al. |
| 5,194,654 A | 3/1993 | Hostetler et al. |
| 5,200,395 A | 4/1993 | Eto et al. |
| 5,223,263 A | 6/1993 | Hostetler et al. |
| 5,261,419 A | 11/1993 | Osypka |
| 5,264,618 A | 11/1993 | Felgner et al. |
| 5,279,833 A | 1/1994 | Rose |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,334,761 A | 8/1994 | Gebeyehu et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,464,924 A | 11/1995 | Silvis et al. |
| 5,503,852 A | 4/1996 | Steiner et al. |
| 5,528,023 A | 6/1996 | Butturini et al. |
| 5,552,155 A | 9/1996 | Bailey et al. |
| 5,595,756 A | 1/1997 | Bally et al. |
| 5,607,385 A | 3/1997 | Francischelli et al. |
| 5,609,624 A | 3/1997 | Kalis |
| 5,610,283 A | 3/1997 | Buechler |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,677,124 A | 10/1997 | DuBois et al. |
| 5,693,088 A | 12/1997 | Lazarus |
| 5,697,953 A | 12/1997 | Kroll et al. |
| 5,700,437 A | 12/1997 | Fujii et al. |
| 5,705,188 A | 1/1998 | Junichi et al. |
| 5,705,385 A | 1/1998 | Bally et al. |
| 5,736,573 A | 4/1998 | Galat |
| 5,744,335 A | 4/1998 | Wolff et al. |
| 5,772,694 A | 6/1998 | Bokros et al. |
| 5,776,165 A | 7/1998 | Ripart |
| 5,776,747 A | 7/1998 | Schinstine et al. |
| 5,783,383 A | 7/1998 | Kondo et al. |
| 5,844,107 A | 12/1998 | Hanson et al. |
| 5,874,105 A | 2/1999 | Watkins et al. |
| 5,885,613 A | 3/1999 | Holland et al. |
| 5,910,168 A | 6/1999 | Myers et al. |
| 5,916,208 A | 6/1999 | Luther et al. |
| 5,965,434 A | 10/1999 | Wolff et al. |
| 5,976,567 A | 11/1999 | Wheeler et al. |
| 5,976,569 A | 11/1999 | Milstein |
| 5,981,501 A | 11/1999 | Wheeler et al. |
| 6,055,454 A | 4/2000 | Heemels |
| 6,067,471 A | 5/2000 | Warren |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,147,055 A | 11/2000 | Hobart et al. |
| 6,152,955 A | 11/2000 | KenKnight et al. |
| 6,165,763 A | 12/2000 | Brown et al. |
| 6,169,923 B1 | 1/2001 | Kroll |
| 6,176,877 B1 | 1/2001 | Buchanan et al. |
| 6,204,297 B1 | 3/2001 | Tracy et al. |
| 6,210,892 B1 | 4/2001 | Bennett et al. |
| 6,214,804 B1 | 4/2001 | Felgner et al. |
| 6,271,208 B1 | 8/2001 | Bischoff |
| 6,271,209 B1 | 8/2001 | Smith et al. |
| 6,287,591 B1 | 9/2001 | Semple et al. |
| 6,299,604 B1 | 10/2001 | Ragheb et al. |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,417,326 B1 | 7/2002 | Cullis et al. |
| 6,485,726 B1 | 11/2002 | Blumberg et al. |
| 6,534,484 B1 | 3/2003 | Wheeler et al. |
| 6,585,410 B1 | 7/2003 | Ryan |
| 6,586,410 B1 | 7/2003 | Wheeler et al. |
| 6,670,178 B1 | 12/2003 | Selden et al. |
| 6,696,424 B1 | 2/2004 | Wheeler |
| 6,733,777 B2 | 5/2004 | Erbacher et al. |
| 6,743,823 B1 | 6/2004 | Summar et al. |
| 6,756,055 B2 | 6/2004 | McDonald et al. |
| 6,790,838 B2 | 9/2004 | Alison et al. |
| 6,815,432 B2 | 11/2004 | Wheeler et al. |
| 6,821,530 B2 | 11/2004 | Koob et al. |
| 6,835,395 B1 | 12/2004 | Semple et al. |
| 6,858,224 B2 | 2/2005 | Wheeler et al. |
| 6,858,225 B2 | 2/2005 | Semple et al. |
| 6,887,665 B2 | 5/2005 | Trulson et al. |
| 6,998,115 B2 | 2/2006 | Langer et al. |
| 7,022,214 B2 | 4/2006 | Olech |
| 7,067,697 B2 | 6/2006 | Gao |
| 7,084,303 B2 | 8/2006 | Watanabe et al. |
| 7,341,738 B2 | 3/2008 | Semple et al. |
| 7,422,902 B1 | 9/2008 | Wheeler et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,901,708 B2 | 3/2011 | MacLachlan et al. |
| 7,972,435 B2 | 7/2011 | Bury et al. |
| 8,021,686 B2 | 9/2011 | Semple et al. |
| 8,071,082 B2 | 12/2011 | Zugates et al. |
| 8,101,741 B2 | 1/2012 | MacLachlan et al. |
| 8,106,022 B2 | 1/2012 | Manoharan et al. |
| 8,158,601 B2 | 4/2012 | Chen et al. |
| 8,188,263 B2 | 5/2012 | MacLachlan et al. |
| RE43,612 E | 8/2012 | Anderson et al. |
| 8,236,943 B2 | 8/2012 | Lee et al. |
| 8,278,036 B2 | 10/2012 | Kariko et al. |
| 8,287,849 B2 | 10/2012 | Langer et al. |
| 8,329,070 B2 | 12/2012 | MacLachlan et al. |
| 8,389,238 B2 | 3/2013 | Cooper et al. |
| 8,450,298 B2 | 5/2013 | Mahon et al. |
| 8,450,467 B2 | 5/2013 | Manoharan et al. |
| 8,513,403 B2 | 8/2013 | MacLachlan et al. |
| 8,557,231 B2 | 10/2013 | Langer et al. |

(56) References Cited

U.S. PATENT DOCUMENTS

| | | |
|---|---|---|
| 8,562,966 B2 | 10/2013 | Zugates et al. |
| 8,569,256 B2 | 10/2013 | Heyes et al. |
| 8,652,512 B2 | 2/2014 | Schmehl et al. |
| 8,691,966 B2 | 4/2014 | Kariko et al. |
| 8,710,200 B2 | 4/2014 | Schrum et al. |
| 8,748,089 B2 | 6/2014 | Kariko et al. |
| 8,802,644 B2 | 8/2014 | Chen et al. |
| 8,808,681 B2 | 8/2014 | Anderson et al. |
| 8,808,982 B2 | 8/2014 | Dahl et al. |
| 8,822,663 B2 | 9/2014 | Schrum et al. |
| 8,828,956 B2 | 9/2014 | Manoharan et al. |
| 8,835,108 B2 | 9/2014 | Kariko et al. |
| 8,846,348 B2 | 9/2014 | Jendrisak et al. |
| 8,853,377 B2 | 10/2014 | Guild et al. |
| 8,859,229 B2 | 10/2014 | Rabinovich et al. |
| 8,883,202 B2 | 11/2014 | Manoharan et al. |
| 8,936,942 B2 | 1/2015 | Heyes et al. |
| 8,969,353 B2 | 3/2015 | Mahon et al. |
| 8,980,864 B2 | 3/2015 | Hoge et al. |
| 8,999,351 B2 | 4/2015 | Manoharan et al. |
| 8,999,950 B2 | 4/2015 | MacLachlan et al. |
| 9,005,930 B2 | 4/2015 | Jendrisak et al. |
| 9,012,219 B2 | 4/2015 | Kariko et al. |
| 9,012,498 B2 | 4/2015 | Manoharan et al. |
| 9,018,187 B2 | 4/2015 | Heyes et al. |
| 9,040,256 B2 | 5/2015 | Grunenwald et al. |
| 9,051,567 B2 | 6/2015 | Fitzgerald et al. |
| 9,061,021 B2 | 6/2015 | Guild et al. |
| 9,061,059 B2 | 6/2015 | Chakraborty et al. |
| 9,074,208 B2 | 7/2015 | MacLachlan et al. |
| 9,080,211 B2 | 7/2015 | Grunenwald et al. |
| 9,085,801 B2 | 7/2015 | Grunenwald et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,181,319 B2 | 11/2015 | Schrum et al. |
| 9,181,321 B2 | 11/2015 | Heartlein et al. |
| 9,186,325 B2 | 11/2015 | Manoharan et al. |
| 9,186,372 B2 | 11/2015 | de Fougerolles et al. |
| 9,187,748 B2 | 11/2015 | Geisbert et al. |
| 9,192,651 B2 | 11/2015 | Chakraborty et al. |
| 9,220,682 B2 | 12/2015 | Manoharan et al. |
| 9,220,683 B2 | 12/2015 | Manoharan et al. |
| 9,220,755 B2 | 12/2015 | Chakraborty et al. |
| 9,220,792 B2 | 12/2015 | Chakraborty et al. |
| 9,233,141 B2 | 1/2016 | Chakraborty et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,394,234 B2 | 7/2016 | Chen et al. |
| 9,404,127 B2 | 8/2016 | Yaworski et al. |
| 9,428,751 B2 | 8/2016 | MacDonald et al. |
| 9,464,124 B2 | 10/2016 | Bancel et al. |
| 9,492,386 B2 | 11/2016 | MacLachlan et al. |
| 9,504,651 B2 | 11/2016 | MacLachlan et al. |
| 9,504,734 B2 | 11/2016 | Bancel et al. |
| 9,518,272 B2 | 12/2016 | Yaworksi et al. |
| 9,572,874 B2 | 2/2017 | Fotin-Mleczek et al. |
| 9,587,003 B2 | 3/2017 | Bancel et al. |
| 9,616,084 B2 | 4/2017 | Mutzke |
| 10,471,153 B2 | 11/2019 | DeRosa et al. |
| 2002/0022721 A1 | 2/2002 | Trulson et al. |
| 2002/0094528 A1 | 7/2002 | Salafsky |
| 2002/0192651 A1 | 12/2002 | Wheeler et al. |
| 2002/0192721 A1 | 12/2002 | Rizzuto et al. |
| 2002/0193622 A1 | 12/2002 | Watanabe et al. |
| 2003/0082154 A1 | 5/2003 | Leamon |
| 2003/0083272 A1 | 5/2003 | Wiederholt et al. |
| 2003/0104044 A1 | 6/2003 | Semple et al. |
| 2003/0181410 A1 | 9/2003 | Wheeler et al. |
| 2003/0215395 A1 | 11/2003 | Yu et al. |
| 2004/0110709 A1 | 6/2004 | Li et al. |
| 2004/0132683 A1 | 7/2004 | Felgner et al. |
| 2004/0142025 A1 | 7/2004 | MacLachlan et al. |
| 2004/0224912 A1 | 11/2004 | Dobie et al. |
| 2004/0235982 A1 | 11/2004 | Rabasco et al. |
| 2005/0004058 A1 | 1/2005 | Benoit et al. |
| 2005/0008689 A1 | 1/2005 | Semple et al. |
| 2005/0032730 A1 | 2/2005 | Von Der Mulbe et al. |
| 2005/0054026 A1 | 3/2005 | Atsushi et al. |
| 2005/0059005 A1 | 3/2005 | Tuschl et al. |
| 2005/0059624 A1 | 3/2005 | Hoerr et al. |
| 2005/0065107 A1 | 3/2005 | Hobart et al. |
| 2005/0069590 A1 | 3/2005 | Buehler et al. |
| 2005/0079212 A1 | 4/2005 | Wheeler et al. |
| 2005/0143332 A1 | 6/2005 | Monahan et al. |
| 2005/0148786 A1 | 7/2005 | Ikeda et al. |
| 2005/0158302 A1 | 7/2005 | Faustman et al. |
| 2005/0244961 A1 | 11/2005 | Short et al. |
| 2005/0250723 A1 | 11/2005 | Hoerr et al. |
| 2006/0008910 A1 | 1/2006 | MacLachlan et al. |
| 2006/0059576 A1 | 3/2006 | Pasinetti et al. |
| 2006/0069225 A1 | 3/2006 | Wintermantel et al. |
| 2006/0083780 A1 | 4/2006 | Heyes et al. |
| 2006/0172003 A1 | 8/2006 | Meers et al. |
| 2006/0204566 A1 | 9/2006 | Smyth-Templeton et al. |
| 2006/0216343 A1 | 9/2006 | Panzner et al. |
| 2006/0223939 A1 | 10/2006 | Lange et al. |
| 2006/0228404 A1 | 10/2006 | Anderson et al. |
| 2006/0241071 A1 | 10/2006 | Grinstaff et al. |
| 2007/0135372 A1 | 6/2007 | MacLachlan et al. |
| 2007/0142628 A1 | 6/2007 | Ghoshal et al. |
| 2007/0172950 A1 | 7/2007 | Wheeler et al. |
| 2007/0252295 A1 | 11/2007 | Panzner et al. |
| 2007/0275923 A1 | 11/2007 | Chen et al. |
| 2007/0281336 A1 | 12/2007 | Jendrisak et al. |
| 2008/0145338 A1 | 6/2008 | Anderson et al. |
| 2008/0160048 A1 | 7/2008 | Fuller |
| 2008/0242626 A1 | 10/2008 | Zugates et al. |
| 2008/0260706 A1 | 10/2008 | Rabinovich et al. |
| 2009/0023673 A1 | 1/2009 | Manoharan et al. |
| 2009/0093433 A1 | 4/2009 | Woolf et al. |
| 2009/0163705 A1 | 6/2009 | Manoharan et al. |
| 2009/0186805 A1 | 7/2009 | Tabor et al. |
| 2009/0221684 A1 | 9/2009 | Grinstaff et al. |
| 2009/0263407 A1 | 10/2009 | Dande et al. |
| 2009/0270481 A1 | 10/2009 | MacLachlan et al. |
| 2009/0286852 A1 | 11/2009 | Kariko et al. |
| 2009/0326051 A1 | 12/2009 | Corey et al. |
| 2010/0028943 A1 | 2/2010 | Thomas et al. |
| 2010/0035249 A1 | 2/2010 | Hayashizaki et al. |
| 2010/0036084 A1 | 2/2010 | Langer et al. |
| 2010/0041152 A1 | 2/2010 | Wheeler et al. |
| 2010/0047261 A1 | 2/2010 | Hoerr et al. |
| 2010/0120129 A1 | 5/2010 | Amshey et al. |
| 2010/0178699 A1 | 7/2010 | Gao et al. |
| 2010/0189729 A1 | 7/2010 | Hoerr et al. |
| 2010/0267806 A1 | 10/2010 | Bumcrot et al. |
| 2010/0323356 A1 | 12/2010 | Inoue et al. |
| 2010/0331234 A1 | 12/2010 | Mahon et al. |
| 2011/0009641 A1 | 1/2011 | Anderson et al. |
| 2011/0035819 A1 | 2/2011 | Cooper et al. |
| 2011/0038941 A1 | 2/2011 | Lee et al. |
| 2011/0092739 A1 | 4/2011 | Chen et al. |
| 2011/0143397 A1 | 6/2011 | Kariko et al. |
| 2011/0200582 A1 | 8/2011 | Baryza et al. |
| 2011/0244026 A1 | 10/2011 | Guild et al. |
| 2011/0256175 A1 | 10/2011 | Hope et al. |
| 2011/0287435 A1 | 11/2011 | Grunenwald et al. |
| 2011/0293703 A1 | 12/2011 | Mahon et al. |
| 2011/0311583 A1 | 12/2011 | Manoharan et al. |
| 2012/0007803 A1 | 1/2012 | Takatsuka |
| 2012/0009222 A1 | 1/2012 | Nguyen et al. |
| 2012/0065252 A1 | 3/2012 | Schrum et al. |
| 2012/0065358 A1 | 3/2012 | Langer et al. |
| 2012/0114831 A1 | 5/2012 | Semple et al. |
| 2012/0128760 A1 | 5/2012 | Manoharan et al. |

(56) References Cited

U.S. PATENT DOCUMENTS

| | | |
|---|---|---|
| 2012/0129910 A1 | 5/2012 | Thompson et al. |
| 2012/0142756 A1 | 6/2012 | Guild et al. |
| 2012/0195936 A1 | 8/2012 | Rudolph et al. |
| 2012/0202871 A1 | 8/2012 | Heyes et al. |
| 2012/0237975 A1 | 9/2012 | Schrum et al. |
| 2012/0251560 A1 | 10/2012 | Dahlman et al. |
| 2012/0251618 A1 | 10/2012 | Schrum et al. |
| 2012/0328668 A1 | 12/2012 | MacLachlan et al. |
| 2013/0017223 A1 | 1/2013 | Hope et al. |
| 2013/0158021 A1 | 6/2013 | Dong et al. |
| 2013/0195967 A1 | 8/2013 | Guild et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2013/0302401 A1 | 11/2013 | Ma et al. |
| 2014/0010861 A1 | 1/2014 | Bancel et al. |
| 2014/0044772 A1 | 2/2014 | MacLachlan et al. |
| 2014/0094399 A1 | 4/2014 | Langer et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0161830 A1 | 6/2014 | Anderson et al. |
| 2014/0162897 A1 | 6/2014 | Grunenwald et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200163 A1 | 7/2014 | Mikkelsen et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221248 A1 | 8/2014 | Jendrisak et al. |
| 2014/0221465 A1 | 8/2014 | Bancel et al. |
| 2014/0227300 A1 | 8/2014 | Chin et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0288160 A1 | 9/2014 | Guild et al. |
| 2014/0294937 A1 | 10/2014 | MacLachlan et al. |
| 2014/0294938 A1 | 10/2014 | Guild et al. |
| 2014/0294939 A1 | 10/2014 | Guild et al. |
| 2014/0294940 A1 | 10/2014 | Guild et al. |
| 2014/0329884 A1 | 11/2014 | Dong et al. |
| 2014/0343129 A1 | 11/2014 | de Fougerolles et al. |
| 2014/0363876 A1 | 12/2014 | Jendrisak et al. |
| 2015/0004217 A1 | 1/2015 | Guild et al. |
| 2015/0005372 A1 | 1/2015 | Hoge et al. |
| 2015/0011615 A1 | 1/2015 | Manoharan et al. |
| 2015/0011633 A1 | 1/2015 | Shorr et al. |
| 2015/0017211 A1 | 1/2015 | de Fougerolles et al. |
| 2015/0038556 A1 | 2/2015 | Heartlein et al. |
| 2015/0038558 A1 | 2/2015 | Kariko et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0110857 A1 | 4/2015 | DeRosa et al. |
| 2015/0110858 A1 | 4/2015 | DeRosa et al. |
| 2015/0110859 A1 | 4/2015 | Heartlein et al. |
| 2015/0111248 A1 | 4/2015 | Bancel et al. |
| 2015/0111945 A1 | 4/2015 | Geisbert et al. |
| 2015/0119444 A1 | 4/2015 | Manoharan et al. |
| 2015/0119445 A1 | 4/2015 | Manoharan et al. |
| 2015/0157565 A1 | 6/2015 | Heartlein et al. |
| 2015/0166465 A1 | 6/2015 | Chen et al. |
| 2015/0190515 A1 | 7/2015 | Manoharan et al. |
| 2015/0191760 A1 | 7/2015 | Jendrisak et al. |
| 2015/0265708 A1 | 9/2015 | Manoharan et al. |
| 2015/0267192 A1 | 9/2015 | Heartlein et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0199485 A1 | 7/2016 | Manoharan et al. |
| 2016/0213785 A1 | 7/2016 | Manoharan et al. |
| 2016/0237108 A1 | 8/2016 | Fraley et al. |
| 2016/0237134 A1 | 8/2016 | Hoge et al. |
| 2016/0250354 A1 | 9/2016 | Manoharan et al. |
| 2016/0251681 A1 | 9/2016 | Yaworski et al. |
| 2016/0256567 A1 | 9/2016 | Heyes et al. |
| 2016/0256568 A1 | 9/2016 | Heyes et al. |
| 2016/0256573 A1 | 9/2016 | de Fougerolles et al. |
| 2016/0264971 A1 | 9/2016 | Geisbert et al. |
| 2016/0264975 A1 | 9/2016 | Schrum et al. |
| 2016/0274089 A1 | 9/2016 | Ciufolini et al. |
| 2016/0304552 A1 | 10/2016 | Roy et al. |
| 2016/0317647 A1 | 11/2016 | Ciaramella et al. |
| 2016/0317676 A1 | 11/2016 | Hope et al. |
| 2016/0331828 A1 | 11/2016 | Ciaramella et al. |
| 2016/0348099 A1 | 12/2016 | Roy et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2016/0367687 A1 | 12/2016 | Manoharan et al. |
| 2016/0367702 A1 | 12/2016 | Hoge et al. |
| 2016/0375134 A1 | 12/2016 | Bancel et al. |
| 2016/0375137 A9 | 12/2016 | Manoharan et al. |
| 2017/0000858 A1 | 1/2017 | Fotin-Mleczek et al. |
| 2017/0000870 A1 | 1/2017 | Hoerr et al. |
| 2017/0000871 A1 | 1/2017 | Probst et al. |
| 2017/0002060 A1 | 1/2017 | Bolen et al. |
| 2017/0007702 A1 | 1/2017 | Heyes et al. |
| 2017/0014496 A1 | 1/2017 | Fotin-Mleczek et al. |
| 2017/0028059 A1 | 2/2017 | Baumhof et al. |
| 2017/0029847 A1 | 2/2017 | Thess |
| 2017/0056528 A1 | 3/2017 | De Fougerolles et al. |
| 2017/0056529 A1 | 3/2017 | Thess et al. |
| 2017/0065727 A1 | 3/2017 | Fotin-Mleczek et al. |
| 2018/0161451 A1 | 1/2018 | Fotin-Mleczek et al. |
| 2020/0157157 A1 | 5/2020 | Karve |

FOREIGN PATENT DOCUMENTS

| | | |
|---|---|---|
| CN | 100569877 C | 12/2009 |
| CN | 101863544 A | 10/2010 |
| DE | 24 30 998 A1 | 1/1975 |
| DE | 2520814 A1 | 11/1976 |
| DE | 3728917 A1 | 3/1989 |
| EP | 6 73 637 A1 | 9/1995 |
| EP | 0783297 A1 | 7/1997 |
| EP | 0853123 A1 | 7/1998 |

(56) References Cited

FOREIGN PATENT DOCUMENTS

| | | |
|---|---|---|
| EP | 0959092 A1 | 11/1999 |
| EP | 1519714 B1 | 4/2005 |
| EP | 1979364 A2 | 10/2008 |
| EP | 2045251 A1 | 4/2009 |
| EP | 2338478 B1 | 6/2011 |
| EP | 2338520 A1 | 6/2011 |
| EP | 2449106 A1 | 5/2012 |
| EP | 2532649 A1 | 12/2012 |
| EP | 2578685 A2 | 4/2013 |
| EP | 2823809 A1 | 1/2015 |
| FR | 1 378 382 A | 11/1964 |
| FR | 2 235 112 A1 | 1/1975 |
| GB | 1072118 A | 6/1967 |
| GB | 1602085 A | 11/1981 |
| JP | H07-053535 | 2/1955 |
| JP | S48-022365 | 3/1973 |
| JP | S49-127908 A | 12/1974 |
| JP | S51-023537 | 2/1976 |
| JP | 51-125144 | 11/1976 |
| JP | S52-010847 | 1/1977 |
| JP | S63125144 A | 5/1988 |
| JP | 63-154788 | 6/1988 |
| JP | H09-505593 A | 6/1997 |
| JP | H10-197978 A | 7/1998 |
| JP | 11-005786 A | 1/1999 |
| JP | 11-080142 | 3/1999 |
| JP | 2001-523215 A | 11/2001 |
| JP | 2002-167368 A | 6/2002 |
| JP | 2003-519199 A | 6/2003 |
| JP | 4-108173 B2 | 6/2008 |
| JP | 2008-247749 A | 10/2008 |
| JP | 50-24216 B2 | 9/2012 |
| WO | WO-90/11092 A1 | 10/1990 |
| WO | WO-93/18229 A1 | 9/1993 |
| WO | WO-93/18754 A1 | 9/1993 |
| WO | WO-95/11004 A1 | 4/1995 |
| WO | WO-95/14651 A1 | 6/1995 |
| WO | WO-95/27478 A1 | 10/1995 |
| WO | WO-96/18372 A2 | 6/1996 |
| WO | WO-96/26179 A1 | 8/1996 |
| WO | WO-96/37211 A1 | 11/1996 |
| WO | WO-96/40964 A2 | 12/1996 |
| WO | WO-97/46223 A1 | 12/1997 |
| WO | WO-98/10748 A1 | 3/1998 |
| WO | WO-98/16202 A2 | 4/1998 |
| WO | WO-98/51278 A2 | 11/1998 |
| WO | WO-99/14346 A2 | 3/1999 |
| WO | WO-00/03044 A1 | 1/2000 |
| WO | WO-00/62813 A2 | 10/2000 |
| WO | WO-00/64484 A2 | 11/2000 |
| WO | WO-00/69913 A1 | 11/2000 |
| WO | WO-01/05375 A1 | 1/2001 |
| WO | WO-01/07599 A1 | 2/2001 |
| WO | WO-02/00870 A2 | 1/2002 |
| WO | WO-02/22709 A1 | 3/2002 |
| WO | WO-02/31025 A2 | 4/2002 |
| WO | WO-02/34236 A2 | 5/2002 |
| WO | WO-02/42317 A2 | 5/2002 |
| WO | WO-03/040288 A2 | 5/2003 |
| WO | WO-03/070735 A2 | 8/2003 |
| WO | WO-2004/043588 A2 | 5/2004 |
| WO | WO-2004/048345 A2 | 6/2004 |
| WO | WO-2004/106411 A2 | 12/2004 |
| WO | WO-2005/026372 A1 | 3/2005 |
| WO | WO-2005/028619 A2 | 3/2005 |
| WO | WO-2005/037226 A2 | 4/2005 |
| WO | WO-2005/121348 A1 | 12/2005 |
| WO | WO-2006/000448 A2 | 1/2006 |
| WO | WO-2006/016097 A2 | 2/2006 |
| WO | WO-2006/082088 A1 | 8/2006 |
| WO | WO-2006/105043 A2 | 10/2006 |
| WO | WO-2006/138380 A2 | 12/2006 |
| WO | WO-2007/024708 A2 | 3/2007 |
| WO | WO-2007/031091 A2 | 3/2007 |
| WO | WO-2007/120863 A2 | 10/2007 |
| WO | WO-2007/126386 A1 | 11/2007 |
| WO | WO-2007/143659 A2 | 12/2007 |
| WO | WO-2008/011561 A2 | 1/2008 |
| WO | WO-2008/042973 A2 | 4/2008 |
| WO | WO-2008/045548 A2 | 4/2008 |
| WO | WO-2008/083949 A2 | 7/2008 |
| WO | WO-2008/113364 A2 | 9/2008 |
| WO | WO-2009/046220 A2 | 4/2009 |
| WO | WO-2009/127060 A1 | 10/2009 |
| WO | WO-2009/127230 A1 | 10/2009 |
| WO | WO-2010/037408 A1 | 4/2010 |
| WO | WO-2010/042877 A1 | 4/2010 |
| WO | WO-2010/045512 A2 | 4/2010 |
| WO | WO-2010/053572 A2 | 5/2010 |
| WO | WO-2010/054401 A1 | 5/2010 |
| WO | WO-2010/054405 A1 | 5/2010 |
| WO | WO-2010/056403 A1 | 5/2010 |
| WO | WO-2010/099387 A1 | 9/2010 |
| WO | WO-2010/114789 A1 | 10/2010 |
| WO | WO-2010/119256 A1 | 10/2010 |
| WO | WO-2010/129709 A1 | 11/2010 |
| WO | WO-2010/144740 A1 | 12/2010 |
| WO | WO-2010/147992 A1 | 12/2010 |
| WO | WO-2010/148013 A2 | 12/2010 |
| WO | WO-2011/012316 A2 | 2/2011 |
| WO | WO-2011/012746 A2 | 2/2011 |
| WO | WO-2011/039144 A1 | 4/2011 |
| WO | WO-2011/068810 A1 | 6/2011 |
| WO | WO-2011/075656 A1 | 6/2011 |
| WO | WO-2011/141705 A1 | 11/2011 |
| WO | WO-2012/019168 A2 | 2/2012 |
| WO | WO-2012/019630 A1 | 2/2012 |
| WO | WO-2012/019780 A1 | 2/2012 |
| WO | WO-2012/027675 A2 | 3/2012 |
| WO | WO-2012/045075 A1 | 4/2012 |
| WO | WO-2012/045082 A2 | 4/2012 |
| WO | WO-2012/075040 A2 | 6/2012 |
| WO | WO-2012/133737 A1 | 10/2012 |
| WO | WO-2012/135025 A2 | 10/2012 |
| WO | WO-2012/135805 A2 | 10/2012 |
| WO | WO-2012/170889 A1 | 12/2012 |
| WO | WO-2012/170930 A1 | 12/2012 |
| WO | WO-2013/039857 A1 | 3/2013 |
| WO | WO-2013/039861 A2 | 3/2013 |
| WO | WO-2013/063468 A1 | 5/2013 |
| WO | WO2013/090186 | 6/2013 |
| WO | WO-2013/101690 A1 | 7/2013 |
| WO | WO-2013/102203 A1 | 7/2013 |
| WO | WO-2013/126803 A1 | 8/2013 |
| WO | WO-2013/130161 A1 | 9/2013 |
| WO | WO-2013/149140 A1 | 10/2013 |
| WO | WO-2013/149141 A1 | 10/2013 |
| WO | WO-2013/151663 A1 | 10/2013 |
| WO | WO-2013/151664 A1 | 10/2013 |
| WO | WO-2013/151666 A2 | 10/2013 |
| WO | WO-2013/151667 A1 | 10/2013 |
| WO | WO-2013/151668 A2 | 10/2013 |
| WO | WO-2013/151670 A2 | 10/2013 |
| WO | WO-2013/151671 A1 | 10/2013 |
| WO | WO-2013/151672 A2 | 10/2013 |
| WO | WO-2013/151736 A2 | 10/2013 |
| WO | WO-2013/182683 A1 | 12/2013 |
| WO | WO-2013/185067 A1 | 12/2013 |
| WO | WO-2013/185069 A1 | 12/2013 |
| WO | WO-2014/028487 A1 | 2/2014 |
| WO | WO-2014/089486 A1 | 6/2014 |
| WO | WO-2014/113089 A2 | 7/2014 |
| WO | WO-2014/143884 A2 | 9/2014 |
| WO | WO-2014/144039 A1 | 9/2014 |
| WO | WO-2014/144196 A1 | 9/2014 |
| WO | WO-2014/144711 A1 | 9/2014 |
| WO | WO-2014/144767 A1 | 9/2014 |
| WO | WO-2014/152027 A1 | 9/2014 |
| WO | WO-2014/152030 A1 | 9/2014 |
| WO | WO-2014/152031 A1 | 9/2014 |
| WO | WO-2014/152211 A1 | 9/2014 |
| WO | WO-2014/152513 A1 | 9/2014 |
| WO | WO-2014/152540 A1 | 9/2014 |
| WO | WO-2014/152659 A1 | 9/2014 |

(56) References Cited

FOREIGN PATENT DOCUMENTS

| | | |
|---|---|---|
| WO | WO-2014/152673 A1 | 9/2014 |
| WO | WO-2014/152774 A1 | 9/2014 |
| WO | WO-2014/152940 A1 | 9/2014 |
| WO | WO-2014/152966 A1 | 9/2014 |
| WO | WO-2014/153052 A2 | 9/2014 |
| WO | WO-2014/158795 A1 | 10/2014 |
| WO | WO-2014/159813 A1 | 10/2014 |
| WO | WO-2014/179562 A1 | 11/2014 |
| WO | WO-2014/210356 A1 | 12/2014 |
| WO | WO-2015/006747 A2 | 1/2015 |
| WO | WO-2015/011633 A1 | 1/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/058069 A1 | 4/2015 |
| WO | WO-2015/085318 | 6/2015 |
| WO | WO-2015/089511 | 6/2015 |
| WO | WO-2016/054421 | 4/2016 |
| WO | WO-2016/071857 | 5/2016 |
| WO | WO-2016/077123 | 5/2016 |
| WO | WO-2016/077125 | 5/2016 |
| WO | WO-2016/118724 | 7/2016 |
| WO | WO-2016/118725 | 7/2016 |
| WO | WO-2016/154127 | 9/2016 |
| WO | WO-2016/164762 | 10/2016 |
| WO | WO-2016/183366 A2 | 11/2016 |
| WO | WO-2016/197132 A1 | 12/2016 |
| WO | WO-2016/197133 A1 | 12/2016 |
| WO | WO-2016/201377 A1 | 12/2016 |
| WO | WO-2017/019891 A2 | 2/2017 |
| WO | WO-2017/049074 A1 | 3/2017 |
| WO | WO-2017/049275 A2 | 3/2017 |
| WO | WO-2017/049286 A1 | 3/2017 |
| WO | WO-2017/106799 A1 | 6/2017 |
| WO | WO-2018/089790 | 5/2018 |
| WO | WO-2019/207060 | 10/2019 |

OTHER PUBLICATIONS

U.S. Appl. No. 61/494,714, filed Jun. 8, 2011, Guild.
Adami, R.C. et al., An amino acid-based amphoteric liposomal delivery system for systemic administration of siRNA. Molecular Therapy 19(6):1141-1151 (2011).
Akinc, A. et al., A combinatorial library of lipid-like materials for delivery of RNAi therapeutics. Nature Biotechnology 26(5):561-569 (2008).
Akinc, A. et al., Development of lipidoid-siRNA formulations for systemic delivery to the liver. Molecular Therapy 17(5):872-879 (2009).
Alton, E.W.F.W. et al., Cationic Lipid-Mediated CFTR Gene Transfer to the Lungs and Nose of Patients with Cystic Fibrosis: a Double-Blind Placebo-Controlled Trial, Lancet, 353:947-954 (1999).
Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, vol. 3, Issue 5, (2016).
Anderson, D.G. et al., Structure/property studies of polymeric gene delivery using a library of poly(beta-amino esters). Molecular Therapy 11(3):426-434 (2005).
Anderson, D.M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-202 (2003).
Anderson, J. Biological Responses to Materials. Annual Review of Materials Research 31:81-110 (2001).
Anderson, W. French, Human gene therapy, Nature, 392, 25-30 (1998).
Andries, O. et al., Comparison of the Gene Transfer Efficiency of mRNA/GL67 and pDNA/GL67 Complexes in Respiratory Cells, Mol. Pharmaceut., 9: 2136-2145 (2012).
Auffray, C. et al., Purification of Mouse Immunoglubulin Heavy-Chain Messenger RNAs from Total Myeloma Tumor RNA, European Journal of Biochemistry, 107(2):303-314 (1980).
Bajaj, A. et al., Synthesis and gene transfection efficacies of PEI-cholesterol-based lipopolymers. Bioconjugate Chemistry 19(8):1640-516511 (2008).
Barreau, C. et al., Liposome-mediated RNA transfection should be used with caution, RNA, 12:1790-1793 (2006).
Behlke, M. A. et al., Progress towards in vivo use of siRNAs, Molecular Therapy, 13:644-670 (2006).
Behr, J. et al., Efficient Gene Transfer into Mammalian Primary Endocrine Cells with Lipo Polyamine-Coated DNA, Proc. Nat.'l Acad. Sci., 86: 6982-6986 (1989).
Bennett, J. Immune response following intraocular delivery of recombinant viral vectors, Gene Therapy, 10: 977-982 (2003).
Bhaduri, S. et al., Procedure for the preparation of milligram quantities of adenovirus messenger ribonucleic acid, J. Virol., 10(6): 1126-1129 (1972).
Bloomfield, V.A., Quasi-Elastic Light Scattering Applications in Biochemistry and Biology, Ann. Rev. Biophys. Bioeng. 10:421-450 (1981).
Boussif, O. et al., A versatile vector for gene and oligonucleotide transfer into cells in culture and in vivo: polyethylenimine. Proceedings of the National Academy of Sciences of the USA. 92(16):7297-7301 (1995).
Braun, C.S. et al., ucture/function relationships of polyamidoamine/ DNA dendrimers as gene delivery vehicles. Journal of Pharmaceutical Sciences 94(2):423-436 (2005).
Breunig, M. et al., Breaking up the correlation between efficacy and toxicity for nonviral gene delivery. Proceedings of the National Academy of Sciences of the U S A. 104(36):14454-14459 (2007).
Breunig, M. et al., Mechanistic investigation of poly(ethylene imine)-based siRNA delivery: disulfide bonds boost intracellular release of the cargo. Journal of Controlled Release 130(1):57-63 (2008).
Brey, D.M. et al., Controlling poly(beta-amino ester) network properties through macromer branching. Acta Biomaterialia 4(2):207-217 (2008).
Brey, D.M. et al., Influence of macromer molecular weight and chemistry on poly(beta-amino ester) network properties and initial cell interactions. Journal of Biomedical Materials Research Part A 85(3):731-741 (2007).
Brown, M.D. et al., Gene Delivery with synthetic (non viral) carriers, Int. J. Pharm., 1-21 (2001).
Budker, V. et al., Protein/Amphipathic Polyamine Complexes Enable Highly Efficient Transfection with Minimal Toxicity, BioTechniques, 23: 139-147 (1997).
Burger, G. et al., Sequencing complete mitochondrial and plastid genomes, Nature Protocols, 2: 603-614 (2007).
Burnett, J.C. et al., Current progress of siRNA/shRNA therapeutics in clinical trials. Biotechnology Journal 6(9):1130-1146 (2011).
Byk, G. et al., Synthesis, activity, and structure—activity relationship studies of novel cationic lipids for DNA transfer. Journal of Medical Chemistry 41(2):224-235 (1998).
Caplen, N.J. et al., In vitro liposome-mediated DNA transfection of epithelial cell lines using the cationic liposome DC-Chol/DOPE, Gene Therapy, 2:603-613 (1995).
Cassiman, D. Gene transfer for inborn errors of metabolism of the liver: the clinical perspective, Current Pharmaceutical Design, 17(24):2550-2557 (2011).
Castanotto, D. et al., The promises and pitfalls of RNA-interference-based therapeutics. Nature 457(7228):426-433 (2009).
Chakraborty, C. Potentiality of Small Interfering RNAs (siRNA) as Recent Therapeutic Targets for Gene-Silencing. Current Drug Targets 8(3):469-82 (2007).
Chandler, R. et al., Liver-directed adeno-associated virus serotype 8 gene transfer rescues a lethal murine model of citrullinemmia type 1, Gene Therapy, 20:1188-1191 (2013).
Chau, Y. et al., Investigation of targeting mechanism of new dextran-peptide-methotrexate conjugates using biodistribution study in matrix-metalloproteinase-overexpressing tumor Xenograft model, J. Pharm. Sci., 95(3): 542-551 (2006).

(56) References Cited

OTHER PUBLICATIONS

Chen, D. et al., Rapid discovery of potent siRNA-containing lipid nanoparticles enabled by controlled microfluidic formulation. Journal of the American Chemical Society 134(16):6948-6951 (2012).
Chen, Y. and Huang, L., Tumor-targeted delivery of siRNA by non-viral vector: safe and effective cancer therapy. Expert Opinion on Drug Delivery 5(12):1301-1311 (2008).
Chiou, H.C. et al., Enhanced resistance to nuclease degradation of nucleic acids complexed to; asialoglycoprotein-polylysine carriers, Nucleic Acids Research, 22(24):5439-5446 (1994).
Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).
Conese, M. et al., Gene and Cell Therapy for Cystic Fibrosis: From Bench to Bedside, J. Cyst. Fibros., 10 Suppl 2:S114-s128 (2011).
Cotten, M. et al., Receptor-mediated transport of DNA into eukaryotic cells. Methods in Enzymology 217 (H):618-644 (1993).
Cowling, V.H., Regulation of mRNA cap methylation, Biochemical Journal, 425:295-302 (2010).
Creusat, G. et al., Proton sponge trick for pH-sensitive disassembly of polyethylenimine-based siRNA delivery systems. Bioconjugate Chemistry 21(5):994-1002 (2010).
Crooke, S.T. Molecular mechanisms of action of antisense drugs. Biochimica et Biophysica Acta 1489(1):31-44. Review (1999).
Crystal, R.G. Transfer of genes to humans: early lessons and obstacles to success. Science 270(5235):404-410. Review (1995).
Damen, M. et al., Delivery of DNA and siRNA by novel gemini-like amphiphilic peptides. Journal of Controlled Release 145(1):33-39 (2010).
Dande, P. et al., Improving RNA interference in mammalian cells by 4'-thio-modified small interfering Rna (SiRNA): effect on siRNA activity and nuclease stability when used in combination with 2'-0-alkyl modifications, Journal of Medicinal Chemistry, 49(5):1624-1634 (2006).
Davis, M. E., The first targeted delivery of siRNA in humans via a self-assembling, cyclodextrin polymer-based nanoparticle: from concept to clinic. Molecular Pharmacuetics 6(3):659-668 (2009).
Davis, M.E. et al., Evidence of RNAi in humans from systemically administered siRNA via targeted nanoparticles. Nature 464(7291):1067-1070 (2010).
Debus, H. et al., Delivery of Messenger RNA Using Poly(ethylene imine)-poly(ethylene glycol)-Copolymer Blends for Polyplex Formation: Biophysical Characterization and In Vitro Transfection Properties, J. Control. Rel., 148:334-343 (2010).
Decher, G. Fuzzy Nanoassemblies: Toward Layered Polymeric Multicomposites. Science 277: 1232-1237 (1997).
Demeshkina, N. et al., Interactions of the ribosome with mRNA and tRNA, Current Opinion in Structural Biology, 20(3):325-332 (2010).
Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N, N', N", N'"-Tetraacetic Acid (DOTA)-Peptide versus 2IT-DOTA Monoclonal Antibody Linkage for RIT1, Clin. Cancer Res., 9: 3665s (2003).
Dern, R.J. et al., Toxicity studies of pyrimethamine (daraprim). The American Journal of Tropical Medicine and Hygiene 4(2):217-220 (1955).
Deshmukh, H. M and Huang, L., Liposome and polylysine mediated gene therapy. New Journal of Chemistry 21:113-124 (1997).
Ding et al., "Systemic Messenger RNA Therapy as a Treatment for Methylmalonic Acidemia", vol. 1, No. 12, pp. 3548-3558, (2017).
Discher, B.M. et al., Polymersomes: tough vesicles made from diblock copolymers. Science 284(5417):1143-1146 (1999).
Discher, D.E. and Eisenberg, A., Polymer vesicles. Science 297(5583):967-973. Review (2002).
Dong, Y. et al., Lipopeptide nanoparticles for potent and selective siRNA delivery in rodents and nonhuman primates, Proceedings of the National Academy of Sciences, 111(11): 3955-3960 (2014).

Driscoll, K.E. et al., Intratracheal instillation as an exposure technique for the evaluation of respiratory tract toxicity: uses and limitations, Toxicol. Sci., 55(1): 24-35 (2000).
Drummond, D.C. et al., Optimizing Liposomes for Delivery of Chemotherapeutic Agents to Solid Tumors, Pharmacological Reviews, 51(4): 691-743 (1999).
Dwarki, V. et al., Cationic liposome-mediated RNA transfection, Methods in Enzymology, 217:644-654 (1993).
Eck, et al., Goodman & Gilman's The Pharmacological Basis of Therapeutics, McGraw-Hill, New York, 77-101 (1996).
Elbashir, S.M. et al., RNA interference is mediated by 21- and 22-nucleotide RNAs. Genes & Development 15: 188-200 (2001).
Elton, C., The Next Next Big Thing, Boston Magazine, 106-118 (Mar. 2013).
Emlen, W. et al., Effect of DNA size and strandedness on the in vivo clearance and organ localization of DNA, Clinical & Experimental Immunology, 56:185-192 (1984).
Eon-Duval, A. et al., Removal of RNA impurities by tangential flow filtration in an RNase-free plasmid DNA purification process, Analytical Biochemistry, 316(1):66-73 (2003).
Ernst, N. et al., Interaction of Liposomal and Polycationic Transfection Complexes with Pulmonary Surfactant, J. Gene. Med., 1:331-340 (1999).
Estimated Number of Animal and Plant Species on Earth, http://www.factmonster.com/ipka/A0934288.html, 2000-2014, 3 pages, (Retrieved Aug. 2, 2014).
Ewert, K. et al., Cationic lipid-DNA complexes for gene therapy: understanding the relationship between complex structure and gene delivery pathways at the molecular level. Current Medicinal Chemistry 11(2): 133-149 (2004).
Fath, S. et al., Multiparameter RNA and Codon Optimization: A Standardized Tool to Assess and Enhance Autologous Mammalian Gene Expression, PLoS One, 6(3):e17596 (14 pages) 2011.
Fechter, P. and Brownlee, G. G., Recognition of mRNA cap structures by viral and cellular proteins, Journal of General Virology, 86:1239-1249 (2005).
Felgner, P.L. and Ringold, G.M., Cationic liposome-mediated transfection, Nature, 337(6205):387-388 (1989).
Felgner, P.L. et al., Lipofection: A Highly Efficient, Lipid-Mediated DNA-Transfection Procedure, Proc. Natl. Acad., 84:7413-7417 (1987).
Fenske, D.B. and Cullis, P., Liposomal nanomedicines. Expert Opinion on Drug Delivery 5(1):25-44 (2008).
Fernandez, V. et al., Cross Flow Filtration of RNA Extracts by Hollow Fiber Membrane, Acta Biotechnologica, 12(1):49-56 (1992).
Ferruti, P.F. and Barbucci, R. , Linear amino polymers: Synthesis, protonation and complex formation. Advances in Polymer Science 58:55-92 (1984).
Ferruti, P.F. et al., A novel modification of poly(l-lysine) leading to a soluble cationic polymer with reduced toxicity and with potential as a transfection agent. Macromolecular Chemistry and Physics 199:2565-2575 (1998).
Fire, A. et al., Potent and specific genetic interference by double-stranded RNA in Caenorhabditis elegans. Nature 391(6669):806-811 (1998).
Fischer, D. et al., Effect of poly(ethylene imine) molecular weight and pegylation on organ distribution and pharmacokinetics; of polyplexes with oligodeoxynucleotides in mice, Drug Metabolism and Disposition, 32(9):983-992 (2004).
Fumoto, S. et al., Targeted Gene Delivery: Importance of Administration Routes, Novel Gene Therapy Approaches, 3-31 (2013).
Furgeson, D.Y. et al., Modified linear polyethylenimine-cholesterol conjugates for DNA complexation. Bioconjugate Chemistry 14(4):840-847 (2003).
Furgeson, D.Y. et al., Novel water insoluble lipoparticulates for gene delivery. Pharmaceutical Research 19(4): 382-390 (2002).
Galipon, J. et al., Stress-induced lncRNAs evade nuclear degradation and enter the translational machinery, Genes to Cells, 18(5):353-368 (2013).
Gao, X. and Huang, L., A novel cationic liposome reagent for efficient transfection of mammalian cells, Biochem. Biophys. Res. Comm., 179(1): 280-285 (1991).

(56) References Cited

OTHER PUBLICATIONS

Garbuzenko, O.B. et al., Intratracheal Versus Intravenous Liposomal Delivery of siRNA, Antisense Oligonucleotides and Anticancer Drug, Pharmaceutical Research, 26(2):382-394 (2009).
Geraerts, M. et al., Upscaling of lentiviral vector production by tangential flow filtration, Journal of Gene Medicine, 7(10):1299-1310 (2005).
Godbey, W.T. et al., Size matters: molecular weight affects the efficiency of poly(ethylenimine) as a gene delivery vehicle. Journal of Biomedical Materials Research 45(3):268-275 (1998).
Gonzalez, H. et al., New class of polymers for the delivery of macromolecular therapeutics. Bioconjugate Chemistry 10(6):1068-1074 (1999).
Gonzalez-Aseguinolaza, G. et al., Gene therapy of liver diseases: A 2011 perspective, Clinics and Research in Hepatology and Gastroenterology, 35(11):699-708 (2011).
Gordon, N. Ornithine transcarbamylase deficiency: a urea cycle defect, European Journal of Paediatric Neurology, 7:115-121 (2003).
Gorecki, et al., Prospects and problems of gene therapy: an update, Expert Opin. Emerging Drugs, 6(2): 187-198 (2001).
Grayson, A.C.R. et al., Biophysical and structural characterization of polyethylenimine-mediated siRNA delivery in vitro. Pharmaceutical Research 23(8): 1868-1876 (2006).
Grudzien, E. et al., Novel cap analogs for in vitro synthesis of mRNAs with high translational efficiency, RNA Biology, 10(9):1479-1487 (2004).
Grunlan, M.A. et al., Synthesis of 1,9-bis[glycidyloxypropyl]penta(1'H,1'H, 2'H, 2'H-perfluoroalkylmethylsiloxane)s and copolymerization with piperazine. Polymer 45:2517-2523 (2004).
Gupta, U. et al., A review of in vitro-in vivo investigations on dendrimers: the novel nanoscopic drug carriers. Nanomedicine: Nanotechnology, Biology, and Medicine 2(2):66-73 (2006).
Gust, T.C. et al., RNA-containing adenovirus/polyethylenimine transfer complexes effectively transduce dendritic cells and induce antigen-specific T cell responses, The Journal of Gene Medicine, 6(4): 464-470 (2004).
Guttman, M. et al., Chromatin signature reveals over a thousand highly conserved large non-coding RNAs in mammals, Nature, 458:223-227 (2009).
Haensler, J. and Szoka, F., Polyamidoamine cascade polymers mediate efficient transfection of cells in culture. Bioconjugate Chemistry 4(5):372-379 (1993).
Harada-Shiba, M. et al., Polyion complex micelles as vectors in gene therapy—pharmacokinetics and in vivo; gene transfer, Gene Therapy, 9(6):407-414 (2002).
Haskins M., Gene Therapy for Lysosomal Storage Disorders (LDSs) in Large Animal Models, Ilar J., 50(2):112-121 (2009).
Hata, A. et al., Isolation and Characterization of the Human Ornithine Transcarbamylase Gene: Structure of the 5'-End Region, Journal of Biochemistry, 100:717-725 (1986).
Hecker, J. et al., Advances in Self-Limited Gene Expression of Protective Intracellular Proteins In-Vivo in Rat Brain Using mRNA / Cationic Lipid Complexes, Anesthesia and Analgesia, 86(2S):346S (1994).
Heidenreich, O. et al., High Activity and Stability of Hammerhead Ribozymes Containing 2'-Modified Pyrimidine Nucleosides and Phosphorothioates, The Journal of Biological Chemistry, 269(3):2131-2138 (1994).
Henkin, R. I. et al., Inhaled Insulin-Intrapulmonary, intranasal, and other routes of administration: Mechanisms of action, Nutrition, 26: 33-39 (2010).
Hess, P. R. et al., Vaccination with mRNAs Encoding Tumor-Associated Antigens and Granulocyte-Macrophage Colony-Stimulating Factor Efficiently Primes CTL Responses, but is Insufficient to Overcome Tolerance to a Model Tumor/Self Antigen, Cancer Immunology, Immunotherapy:CII, 55(6): 672-683 (2006).
Heyes, J. et al., Cationic Lipid Saturation Influences Intracellular Delivery of Encapsulated Nucleic Acids, J. Controlled Release, 107:276-287 (2005).
Higman, M.A. et al., The mRNA (Guanine-7-)methyltransferase Domain of the Vaccinia Virus mRNA Capping Enzyme, The Journal of Biological Chemistry, 269(21):14974-14981 (1994).
Hill, I.R.C. et al., In vitro cytotoxicity of poly(amidoamine)s: relevance to DNA delivery. Biochimica et Biophysica Acta 1427: 161-174 (1999).
Hill, J.G. et al., Enantioselective Epoxidation of Allylic Alcohols: (2S,3S)-3-Propyloxiranemethanol. Organic Syntheses Collection 7: 461 (1990) and 63: 66 (1985) (8 pages).
Hillery, A.M. et al., Drug Delivery and Targeting for Pharmacists and Pharmaceutical Scientists, Taylor and Francis (2005).
Hoerr, I. et al., In Vivo Application of RNA Leads to Induction of Specific Cytotoxic T Lymphocytes and Antibodies, European Journal of Immunology, 30(1):1-7 (2000).
Hofland, H.E.J et al., Formation of stable cationic lipid/DNA complexes for gene transfer. Proceedings of the National Academy of Sciences of the USA 93 (14): 7305-7309 (1996).
*Homo sapiens* galactosidase, alpha (GLA) mRNA, NCBI Reference Sequence NM_000169.1, Modification Date: Nov. 17, 2006.
Hope, M.J. et al., Cationic Lipids, Phosphatidylethanolamine and the Intracellular Delivery of Polymeric, Nucleic Acid-Based Drugs. Molecular Membrane Technology 15:1-14 (1998).
Hope, M.J. et al., Reduction of Liposome Size and Preparation of Unilamellar Vesicles by Extrusion Techniques, In: Liposome Technology, 1:123-139 (1993).
Hornung, V. et al., Quantitative expression of toll-like receptor 1-10 mRNA in cellular subsets of human peripheral blood mononuclear cells and sensitivity to CpG oligodeoxynucleotides. The Journal of Immunology 168: 4531-4537 (2002).
Horwich, A.L. et al., Structure and Expression of a Complementary DNA for the Nuclear Coded Precursor of Human Mitochondrial Ornithine Transcarbamylase, Science, 224(4653):1068-1074 (1984).
Horwich, A.L. et al., Targeting of Pre-Ornithine Transcarbamylase to Mitochondria: Definition of Critical Regions and Residues in the Leader Peptide, Cell, 44:451-459 (1986).
Howard, K.A. Delivery of RNA interference therapeutics using polycation-based nanoparticles. Advanced Drug Delivery Reviews 61: 710-720 (2009).
Huang, Z. et al., Thiocholesterol-based lipids for ordered assembly of bioresponsive gene carriers, Molecular Therapy, 11(3):409-417 (2005).
Huttenhofer, A. and Noller, H., Footprinting mRNA-ribosome complexes with chemical probes, The EMBO Journal, 13(16):3892-3901 (1994).
Incani, V. et al., Lipid and hydrophobic modification of cationic carriers on route to superior gene vectors. Soft Matter 6: 2124-2138 (2010).
International Preliminary Report on Patentability for PCT/US2010/058457, 12 pages (Jun. 14, 2012).
International Search Report for PCT/US15/27563, 5 pages (Sep. 18, 2015).
International Search Report for PCT/US2010/058457, 4 pages (May 6, 2011).
International Search Report for PCT/US2011/062459, 3 pages (Apr. 11, 2012).
International Search Report for PCT/US2012/041663, 4 pages (Oct. 8, 2012).
International Search Report for PCT/US2012/041724, 5 pages (Oct. 25, 2012).
International Search Report for PCT/US2013/034602, 2 pages (Jun. 17, 2013).
International Search Report for PCT/US2013/034604, 4 pages (Jun. 17, 2013).
International Search Report for PCT/US2013/044769, 4 pages (Nov. 12, 2013).
International Search Report for PCT/US2013/044771, 6 pages (Nov. 1, 2013).
International Search Report for PCT/US2013/073672, 6 pages (Mar. 3, 2014).
International Search Report for PCT/US2014/027422, 5 pages (Jul. 31, 2014).
International Search Report for PCT/US2014/027585, 3 pages (Jul. 14, 2014).

(56) References Cited

OTHER PUBLICATIONS

International Search Report for PCT/US2014/027587, 6 pages (Jul. 24, 2014).
International Search Report for PCT/US2014/027602, 6 pages (Jul. 28, 2014).
International Search Report for PCT/US2014/027717, 5 pages (Jul. 16, 2014).
International Search Report for PCT/US2014/028330, 5 pages (Jul. 22, 2014).
International Search Report for PCT/US2014/028441, 6 pages (Jul. 22, 2014).
International Search Report for PCT/US2014/028498, 5 pages (Jul. 28, 2014).
International Search Report for PCT/US2014/028849, 6 pages (Jul. 17, 2015).
International Search Report for PCT/US2014/061786, 6 pages (Feb. 6, 2015).
International Search Report for PCT/US2014/061793, 4 pages (Feb. 6, 2015).
International Search Report for PCT/US2014/061830, 5 pages (Feb. 4, 2015).
International Search Report for PCT/US2014/061841, 6 pages (Feb. 24, 2015).
International Search Report for PCT/US2015/039004, 4 pages (Oct. 6, 2015).
International Search Report for PCT/US2015/21403 (4 pages) mailed Jun. 15, 2015.
Jakobsen, K. et al., Purification of MRNA Directly From Crude Plant Tissues in 15 Minutes Using Magnetic Oligo DT Microsheres, Nucleic Acids Research, 18(12):3669 (1990).
Jeffs, L.B. et al., A scalable, extrusion-free method for efficient liposomal encapsulation of plasmid DNA, Pharmacol. Res., 22(3): 362-372 (2005).
Jemielity, J. et al., Novel "anti-reverse" cap analogs with superior translational properties, Cold Spring Harbor Laboratory Press, 9(9):1108-1122 (2003).
Jiang, G. et al., Hyaluronic acid-polyethyleneimine conjugate for target specific intracellular delivery of siRNA. Biopolymers 89 (7): 635-642 (2008).
Jiang, M. et al., Electrochemically controlled release of lipid/DNA complexes: a new tool for synthetic gene delivery system. Electrochemistry Communications (6): 576-582 (2004).
Jiang, S. and Cao, Z., Ultralow-fouling, functionalizable, and hydrolyzable zwitterionic materials and their derivatives for biological applications. Advanced Materials 22(9):920-932 (2010).
Jolck, R.I. et al., Solid-phase synthesis of PEGylated lipopeptides using click chemistry. Bioconjugate Chemistry 21(5):807-810 (2010).
Jon, S. et al., Degradable poly(amino alcohol esters) as potential DNA vectors with low cytotoxicity. Biomacromolecules 4(6):1759-1762 (2003).
Jones, G. et al., Duplex- and Triplex-Forming Properties of 4'-Thio-Modified Oligodeoxynucleotides, Bioorganic & Medicinal Chemistry Letters, 7(10):1275-1278 (1997).
Kabanov, A.V. and Kabanov, V.A., DNA complexes with polycations for the delivery of genetic material into cells. Bioconjugate Chemistry 6(1): 7-20 (1995).
Kamath, S. et al., Surface chemistry influences implant-mediated host tissue responses. Journal of Biomedical Materials Research A 86(3):617-626 (2007).
Kariko, K. et al., In vivo protein expression from mRNA delivered into adult rat brain, Journal of Neuroscience Methods, 105:77-86 (2001).
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).
Kasuya, T. et al., In Vivo Delivery of Bionanocapsules Displaying *Phaseolus vulgaris* Agglutinin-L₄ Isolectin to Malignant Tumors Overexpressing *N*-Acetylglucosaminyltransferase V, Human Gene Therapy, 19:887-895 (2008).

Kaur, N. et al., A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).
Kaur, T. et al., Addressing the Challenge: Current and Future Directions in Ovarian Cancer THerapy, Current Gene Therapy, 9: 434-458 (2009).
Kiew, L.V. et al., Effect of antisense oligodeoxynucleotides for ICAM-1 on renal ischaemia-reperfusion injury in the anaesthetised rat, The Journal of Physiology, 557(3):981-989 (2004).
Kim, S.H. et al., Comparative evaluation of target-specific GFP gene silencing efficiencies for antisense ODN, synthetic siRNA, and siRNA plasmid complexed with PEI-PEG-FOL conjugate. Bioconjugate Chemistry 17(1): 241-244 (2006).
Kim, T. et al., Synthesis of biodegradable cross-linked poly(beta-amino ester) for gene delivery and its modification, inducing enhanced transfection efficiency and stepwise degradation. Bioconjugate Chemistry 16(5):1140-1148 (2005).
Klibanov, A.L. et al., Amphipathic polyethyleneglycols effectively prolong the circulation time of liposomes, FEBS, 268(1): 235-237 (1990).
Kober, L. et al., Optimized Signal Peptides for the Development of High Expressing CHO Cell Lines, Biotechnol. Bioeng., 110:1164-1173 (2012).
Kodama, K. et al., The Features and Shortcomings for Gene Delivery of Current Non-Viral Carriers, Current Medicinal Chemistry, 13: 2155-2161 (2006).
Kore, A. and Charles, I., Synthesis and evaluation of 2'-O-allyl substituted dinucleotide cap analog for mRNA translation, Bioorganics & Medicinal Chemistry, 18:8061-8065 (2010).
Kore, A. and Shanmugasundaram, M., Synthesis and biological evaluation of trimethyl-substituted cap analogs, Bioorganic & Medicinal Chemistry, 18:880-884 (2008).
Kormann, M.S.D. et al., Expression of therapeutic proteins after delivery of chemically modified mRNA in mice, Nature Biotechnology, 29(2):154-157 (2011).
Kozak, M. An analysis of 5'-noncoding sequences from 699 vertebrate messenger RNAs, Nucleic Acid Research, 15(20):8125-8148 (1987).
Krieg, P.A. et al., In vitro RNA synthesis with SP6 RNA polymerase, Methods in Enzymology, 155:397-415 (1987).
Kvasnica, M. et al., Platinum(II) complexes with steroidal esters of L-methionine and L-histidine: Synthesis, characterization and cytotoxic activity, Bioorganic & Medicinal Chemistry, 16:3704-3713 (2008).
Lam, J.K.W et al., Pulmonary delivery of therapeutic siRNA, Advanced Drug Delivery Reviews (2011).
Lasic, D.D. et al., Gelation of liposome interior: A novel method for drug encapsulation, FEBS, 312(2,3):255-258 (1992).
Lasic, D.D. Novel applications of liposomes, Trends in Biotechnology, 16:307-321 (1998).
Lechardeur, et al., Metabolic instability of plasmid DNA in the cytosol: a potential barrier to gene transfer, Gene Therapy, 6: 482-497 (1999).
Lee, S. et al., Stability and cellular uptake of polymerized siRNA (poly-siRNA)/polyethylenimine (PEI) complexes for efficient gene silencing. Journal of Controlled Release 141: 339-346 (2010).
Li, L. et al., Preparation and Gene Delivery of Alkaline Amino Acids-Based Cationic Liposomes, Archives of Pharmaceutical Research, 31(7):924-931 (2008).
Li, S. et al., In vivo gene transfer via intravenous administration of cationic lipid-protamine-DNA (LPD) complexes, Gene Therapy, 4:891-900 (1997).
Li, W. et al., Lipid-based Nanoparticles for Nucleic Acid Delivery, Pharmaceutical Research, 24(3):438-449 (2007).
Liebhaber, S.A. et al., Translation inhibition by an mRNA coding region secondary structure is determined by its proximity to the AUG initiation codon, Journal of Molecular Biology, 226(3):609-621 (1992).
Lim, Y. et al., A self-destroying polycationic polymer: biodegradable poly(4-hydroxy-l-proline ester). Journal of American Chemical Society 121: 5633-5639 (1999).

(56) References Cited

OTHER PUBLICATIONS

Lindgren, V. et al., Human Ornithine Transcarbamylase Locus Mapped to Band Xp21.1 Near the Duchenne Muscular Dystrophy Locus, Science, 226(2675):698-700 (1984).
Liu, X. et al., COStar: a D-star Lite-based Dynamic Search Algorithm for Codon Optimization, Journal of Theoretical Biology, 344:19-30 (2014).
Liu, Y. and Huang, L., Designer Lipids Advance Systematic siRNA Delivery, Molecular Therapy, 18(4):669-670 (2010).
Liu, Y. et al., Factors influencing the efficiency of cationic liposome-mediated intravenous gene delivery, Nature Biotechnology, 15:167-173 (1997).
Lo, K-M et al., High level expression and secretion of Fc-X fusion proteins in mammalian cells, Protein Engineering, 11(6):495-500 (1998).
Lorenzi, J. C. C. et al., Intranasal Vaccination with Messenger RNA as a New Approach in Gene Therapy: Use Against Tuberculosis, BMC Biotechnology, 10(77):1-11 (2010).
Love, K.T. et al., Lipid-like materials for low-dose, in vivo gene silencing, PNAS, 107(5):1864-1869 (2010).
Lu, D. et al., Optimization of methods to achieve mRNA-mediated transfection of tumor cells in vitro and in vivo employing cationic liposome vectors, Cancer Gene Therapy, 1(4):245-252 (1994).
Lukyanov, A.N. and Torchilin, V.P., Micelles from lipid derivatives of water-soluble polymers as delivery systems for poorly soluble drugs. Advanced Drug Delivery Reviews 56: 1273-1289 (2004).
Luo, D. and Saltzman, M., Synthetic DNA delivery systems. Nature Biotechnology 18: 33-37. Review (2000).
Lynn, D.M. and Langer, R., Degradable Poly(ß-amino esters): Synthesis, Characterization, and Self-Assembly with Plasmid DNA. Journal of American Chemical Society 122(44): 10761-10768 (2000).
Lynn, D.M. et al., Accelerated discovery of synthetic transfection vectors: parallel synthesis and screening of a degradable polymer library. Journal of American Chemical Society 123 (33): 8155-8156 (2001).
Lynn, D.M. et al., pH-Responsive Polymer Microspheres: Rapid Release of Encapsulated Material within the Range of Intracellular pH. Angewandte Chemie International Edition 40(9): 1707-1710 (2001).
Ma, M. et al., Development of Cationic Polymer Coatings to Regulate Foreign Body Responses. Advanced Healthcare Materials 23: H189-H194. Reviews (2011).
MacLachlan, I., Lipid nanoparticle-mediated delivery of messenger RNA, 1st International mRNA Health Conference; Tubingen Germany, (Oct. 24, 2013) Retrieved from the Internet: URL: <http://files.shareholder.com/downloads/ABEA-50QJTB/2628241206x0x699789/47543d12-db34-4e6e-88a9-f3ae5d97b1d2/MacLachlan_mRNA_Conf_2013>.
Maeda-Mamiya, R. et al., In vivo gene delivery by cationic tetraamino; fullerene. Proceedings of National Academy of Sciences U S A, 107(12):5339-5344 (2010).
Malone, R.W., et al., Cationic liposome-mediated RNA transfection, PNAS, 86:6077-6081 (1989).
Mammal, http://en.wikipedia.org/wiki/Mammal, 2007, Pearson Education, NY, NY, Author unkown (Source: The international union for conservation of nature and natural resources), 2 pages, (Retrieved Aug. 2, 2014).
Mansour, H.M. et al., Nanomedicine in pulmonary delivery, International Journal of Nanomedicine, 4:299-319 (2009).
Margus, H. et al., Cell-penetrating peptides as versatile vehicles for oligonucleotide delivery. Molecular Therapy 20 (3): 525-533 (2012).
Martell, A.E. and Chaberek, S., The Preparation and the Properties of Some N, N'- Disubstituted-ethylenediaminedipropionic Acids. Journal of the American Chemical Society 72: 5357-5361 (1950).
Martinon, F. et al., Induction of Virus-Specific Cytotoxic T Lymphocytes in Vivo by Liposome-Entrapped mRNA, European Journal of Immunology, 23(7):1719-1722 (1993).
Mathiowitz, E. and Langer, R., Polyanhydride microspheres as drug carriers I. Hot-melt microencapsulation. Journal of Controlled Release 5: 13-22 (1987).

Mathiowitz, E. et al., Novel microcapsules for delivery systems. Reactive Polymers 6: 275-283 (1987).
Mathiowitz, E. et al., Polyanhydride microspheres as drug carriers II. Microencapsulation by solvent removal. Journal of Applied Polymer Sciences 35: 755-774 (1988).
McCracken, S. et al., 5'-Capping Enzymes are Targeted to Pre-MRNA by Binding to the Phosphorylated Carboxy-Terminal Domain of RNA Polymerase II, Genes and Development, 22(24):3306-3318 (1997).
McIvor, R. S., Therapeutic Delivery of mRNA: The Medium is the Message, Molecular Therapy, 19(5):822-823 (2011).
Mclachlan, et al., "Pre-clinical evaluation of three non-viral gene transfer agents for cystic fibrosis after aerosol the bovine lung", Gene Ther., 18(10): 996-1005 (2011).
Melton, D.A. et al., Efficient in vitro synthesis of biologically active RNA and RNA hybridization probes from; plasmids containing a bacteriophage SP6 promoter, Nucleic Acids Research, 12(18):7035-7056 (1984).
Mendelsohn, J.D. et al., Rational design of cytophilic and cytophobic polyelectrolyte multilayer thin films. Biomacromolecules 4(1): 96-106 (2003).
Merkel, O.M. and Kissel, T., Nonviral Pulmonary Delivery of siRNA, Accounts of Chemical Research, 45(7):961-970 (2012).
Merten, O. et al., Large-Scale Manufacture and Characterization of a Lentiviral Vector Produced for Clinical Ex Vivo Gene Therapy Application, Human Gene Therapy, 22(3):343-356 (2011).
Miller, A. Cationic Liposomes for Gene Therapy. Angewandte Chemie International Edition 37: 1768-1785 (1998).
Monia, B.P. et al., Evaluation of 2'-Modified Oligonucleotides Containing 2'-Deoxy Gaps as Antisense Inhibitors of Gene Epression, The Journal of Biological Chemistry, 268(19):14514-14522 (1993).
Morrissey, D.V. et al., Potent and Persistent in vivo Anti-HBV Activity of Chemically Modified siRNAs, Nat. Biotechnol., 23(8): 1003-1007 (2005).
Narang, A.S. et al., Cationic lipids with increased DNA binding affinity for nonviral gene transfer in dividing and nondividing cells. Bioconjugate Chemistry 16(1): 156-168 (2005).
Navarro, G. et al., Phospholipid-polyethylenimine conjugate-based micelle-like nanoparticles for siRNA delivery. Drug Delivery and Translational Research 1: 25-33 (2011).
Neamnark, A. et al., Aliphatic lipid substitution on 2 kDa polyethylenimine improves plasmid delivery and transgene expression. Molecular Pharmaceutics 6(6): 1798-1815 (2009).
Ng, J. et al., LincRNAs join the pluripotency alliance, Nature Genetics, 42:1035-1036 (2010).
Nguyen, D.N. et al., A novel high-throughput cell-based method for integrated quantification of type I interferons and in vitro screening of immunostimulatory RNA drug delivery. Biotechnology and Bioengineering 103(4): 664-675 (2009).
Nguyen, D.N. et al., Drug delivery-mediated control of RNA immunostimulation. Molecular Therapy 17(9): 1555-1562 (2009).
Nojima, T. et al., The Interaction between Cap-binding Complex and RNA Export Factor is Required for Intronless mRNA Export, Journal of Biological Chemistry, 282(21):15645-15651 (2007).
Nori, A. et al., Tat-conjugated synthetic macromolecules facilitate cytoplasmic drug delivery to human ovarian carcinoma cells, Bioconj. Chem., 14(1): 44-50 (2003).
Okumura, K. et al., Bax mRNA therapy using cationic liposomes for human malignant melanoma, The Journal of Gene Medicine, 10:910-917 (2008).
Otsuka, Y. et al., Identification of a Cytoplasmic Complex That Adds a Cap onto 5'-Monophosphate RNA, Molecular and Cellular Biology, 29(8):2155-2167 (2009).
Ozer, A., Alternative applications for drug delivery: nasal and pulmonary routes, Nanomaterials and Nanosystems for Biomedical Applications, M.R. Mozafari (ed.): 99-112 (2007).
Painter, H. et al., Topical Delivery of mRNA to the Murine Lung and Nasal Epithelium, Molecular Therapy, 9:S187 (2004).
Painter, H., An Investigation of mRNA as a Gene Transfer Agent, Gene Medicine Research Group Nuffield Department of Clinical Laboratory Sciences and Merton College, University of Oxford, 1-282 (2007).

(56) References Cited

OTHER PUBLICATIONS

Painter, H., An Investigation of mRNA as a Gene Transfer Agent, Oxford University GeneMedicine, Abstract Only, 1 page (2007).
Parrish, D.A. and Mathias, L.J., Five- and six-membered ring opening of pyroglutamic diketopiperazine. Journal of Organic Chemistry 67(6): 1820-1826 (2002).
Paulus, C. and Nevels, M., The Human Cytomegalovirus Major Immediate-Early Proteins as Antagonists of Intrinsic and Innate Antiviral Host Responses, Viruses, 1:760-779 (2009).
Pearson, H., One Gene, Twenty Years, Nature 460:165-169 (2009).
Peppas, N.A. et al., Hydrogels in Biology and Medicine: From Molecular Principles to Bionanotechnology. Advanced Materials 18: 1345-1360 (2006).
Philipp, A. et al., Hydrophobically modified oligoethylenimines as highly efficient transfection agents for siRNA delivery. Bioconjugate Chemistry 20(11): 2055-2061 (2009).
Pons, M. et al., Liposomes obtained by the ethanol injection method, Int. J. Pharm., 95: 51-56. (1993).
Prata, C.A. et al., Lipophilic peptides for gene delivery. Bioconjugate Chemistry 19(2): 418-420 (2008).
Probst, J. et al., Spontaneous cellular uptake of exogenous messenger RNA in vivo is nucleic acid-specific, saturable and ion dependent, Gene Therapy, 14:1175-1180 (2007).
Promega, PolyATract mRNA Isolation Systems, Instructions for Use of Products Z5200, Z5210, Z2300 and Z5310, Technical Manual (2012).
Putnam, D. Polymers for gene delivery across length scales. Nature Materials 5: 439-451 (2006).
Putnam, D. and Langer, R., Poly(4-hydroxy-I-proline ester): Low-Temperature Polycondensation and Plasmid DNA Complexation. Macromolecules 32(11): 3658-3662 (1999).
Qiagen, Oligotex Handbook, Second Edition (2002).
Rabinovich, P.M. et al., Synthetic Messenger RNA as a Tool for Gene Therapy, Human Gene Therapy, 17:1027-1035 (2006).
Raper, S.E. et al., Developing adenoviral-mediated in vivo gene therapy for ornithine transcarbamylase deficiency, Journal of Inherited Metabolic Disease, 21:119-137 (1998).
Ratajczak, J. et al., Membrane-derived microvesicles: important and underappreciated mediators of cell-to-cell communication, Leukemia, 20:1487-1495 (2006).
Ratner, B.D. and Bryant, S., Biomaterials: where we have been and where we are going. Annual Review of Biomedical Engineering 6: 41-75 (2004).
Reddy, A. et al., The Effect of Labour and Placental Separation on the Shedding of Syncytiotrophoblast Microparticles, Cell-free DNA and mRNA in Normal Pregnancy and Pre- eclampsia, Placenta, 29: 942-949 (2008).
Rejman, J. et al., Characterization and transfection properties of lipoplexes stabilized with novel exchangeable polyethylene glycol-lipid conjugates, Biochimica et Biophysica Acta, 1660:41-52 (2004).
Remington: The Science and Practice of Pharmacy, 21st Edition, Philadelphia, PA. Lippincott Williams & Wilkins (2005).
Robinson, et al. "Lipid Nanoparticle-Delivered Chemically Modified mRNA Restores Chloride Secrection in Cystic Fibrosis", Molecular Therapy, 26(8): 1-13 (2018).
Rosenecker, J. et al., Gene Therapy for Cystic Fibrosis Lung Disease: Current Status and Future Perspectives, Curr. Opin. Mol. Ther., 8:439-445 (2006).
Rosenecker, J. et al., Interaction of Bronchoalveolar Lavage Fluid with Polyplexes and Lipoplexes: Analysing the Role of Proteins and Glycoproteins, J. Gene. Med., 5:49-60 (2003).
Rowe, S.M. et al., Cystic Fibrosis, New Engl. J. Med. 352:1992-2001 (2005).
Rudolph, C. et al., Aerosolized Nanogram Quantities of Plasmid DNA Mediate Highly Efficient Gene Delivery to Mouse Airway Epithelium, Molecular Therapy, 12(3): 493-501 (2005).
Rudolph, C. et al., Methodological optimization of polyethylenimine (PEI)-based gene delivery to the lungs of mice via aerosol application, Journal of Gene Medicine, 7(1): 59-66 (2005).
Ruiz et al., "A clinical inflammatory syndrome attributable to aerosolized lipid-DNA administration in cystic fibrosis", Hum Gene Ther., 12(7): 751-61 (2001).
Ryng, S. et al., Synthesis and structure elucidation of 5-aminomethinimino-3-methyl-4-isoxazolecarboxylic acid phenylamides and their immunological activity. Arch. Pharm. Pharm. Med. Chem 330(11):319-26 (1997).
Sahay, G. et al., Endocytosis of nanomedicines. Journal of Controlled Release 145: 182-195 (2010).
Sakiyama-Elbert, S.E. and Hubbell, J.A., Functional Biomaterials: Design of Novel Biomaterials. Annual Review of Materials Research 31: 183-201 (2001).
Schnierle, B.S. et al., Cap-specific mRNA (nucleoside-O2'-)-methyltransferase and poly(A) polymerase stimulatory activities of vaccinia virus are mediated by a single protein, Proceedings of the National Academy of Sciences, 89:2897-2901 (1992).
Schreier, H., The new frontier: gene and oligonucleotide therapy, Pharmaceutica Acta Helvetiae, 68(3):145-159 (1994).
Semple, S.C. et al., Rational design of cationic lipids for siRNA delivery, Nature Biotechnology, 28(2): 172-176 (2010).
Shchori E., Poly(secondary Amine)s from Diacrylates and Diamines. Journal of Polymer Science 21(6):413-15 (1983).
Sherwood, R.F. Advanced drug delivery reviews: enzyme prodrug therapy, Adv. Drug Del. Rev., 22: 269-288 (1996).
Shimada, A. et al., Translocation Pathway of the Intratracheally Instilled Ultrafine Particles from the Lung into the Blood Circulation in the Mouse, Toxicologic Pathology, 34:949-957 (2006).
Siegwart, D.J. et al., Combinatorial synthesis of chemically diverse core-shell nanoparticles for intracellular delivery. Proceedings of the National Academy of the Sciences of the USA 108(32):12996-123001 (2011).
Smisterova, J. et al., Molecular Shape of the Cationic Lipid Controls the Structure of Cationic Lipid/Dioleylphosphatidylethanolamine-DNA Complexes and the Efficiency of Gene Delivery, The Journal of Biological Chemistry, 276(50):47615-47622 (2001).
Stern, L. et al., A novel antitumor prodrug platform designed to be cleaved by the endoprotease legumain, Bioconj. Chem., 20: 500-510 (2009).
Su, X. et al., Cytosolic Delivery Mediated via Electrostatic Surface Binding of mRNA to Degradable Lipid-Coated Polymeric Nanoparticles, Polymer Preprints, 51(2):668-669 (2010).
Su, X. et al., In Vitro and in Vivo mRNA Delivery Using Lipid-Enveloped pH-Responsive Polymer Nanoparticles, Molecular Pharmaceutics, 8(3):774-787 (2011).
Suri, M. et al., Genetics for Pediatricians, Remedica Publishing, (2005).
Szoka, F. and Papahadjopoulos, D., Comparative properties and methods of preparation of lipid vesicles (liposomes). Annual Review of Biophysics Bioengineering 9: 467-508 (1980).
Tagawa, M. et al., Gene expression and active virus replication in the liver after injection of duck hepatitis B virus DNA into the peripheral vein of ducklings, Journal of Hepatology, 24:328-334 (1996).
Takahashi, Y. et al., Development of safe and effective nonviral gene therapy by eliminating CpG motifs from plasmid DNA vector, Frontiers in Bioscience, S4: 133-141 (2012).
Tan, S. et al., Engineering Nanocarriers for siRNA Delivery. Small 7(7): 841-856 (2011).
Tang, F. and Hughes, J. et al., Introduction of a Disulfide Bond into a Cationic Lipid Enhances Transgene Expression of Plasmid DNA, Biochemical and Biophysical Research Communications, 242(1):141-145 (1998).
Tang, M.X. et al., In vitro gene delivery by degraded polyamidoamine dendrimers. Bioconjugate Chemistry 7(6): 703-714 (1996).
Tarcha, P.J. et al., Synthesis and characterization of chemically condensed oligoethylenimine containing beta-aminopropionamide linkages for siRNA delivery. Biomaterials 28: 3731-3740 (2007).
Tavernier, G. et al., mRNA as gene therapeutic: How to control protein expression, Journal of Controlled Release, 150:238-247 (2011).

(56) References Cited

OTHER PUBLICATIONS

Tcherepanova, I. et al., Ectopic expression of a truncated CD40L protein from synthetic post-transcriptionally capped RNA in dendritic cells induces high levels of IL-12 secretion, BMC Molecular Biology, 9(1):pp. 1-13 (2008).
Theus, S. and Liarakos, C., A Simple Assay for Determining the Capping Efficiencies of RNA Polymerases Used for In Vitro Transcription, BioChromatography, 9(5):610-614 (1990).
Third Party Preissuance Submission Under 37 CFR § 1.290 (Oct. 25, 2013).
Thomas, C. E. et al., Progress and problems with the use of viral vectors for gene therapy, Nature Reviews/Genetics, 4: 346-358 (2003).
Thompson, P.E. et al., Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki, B.E. et al., Protease-mediated fragmentation of p-amidobenzyl ethers: a new strategy for the activation of anticancer prodrugs, J. Org. Chem., 67(6): 1866-1872 (2002).
Tranchant, I. et al., Physicochemical optimisation of plasmid delivery by cationic lipids. Journal of Gene Medicine 6: S24-S35 (2004).
Tsui, N.B. et al., Stability of endogenous and added RNA in blood specimens, serum, and plasma, Clinical Chemistry, 48(10):1647-1653 (2002).
Tsvetkov, D.E. et al., Neoglycoconjugates based on dendrimeric poly(aminoamides). Russian Journal of Bioorganic Chemistry 28(6): 470-486 (2002).
Tuschl, T. et al., Targeted mRNA degradation by double-stranded RNA in vitro, Genes and Development, 13(24):3191-3197 (1999).
Urban-Klein, B. et al., RNAi-mediated gene-targeting through systemic application of polyethylenimine (PEI)-complexed siRNA in vivo. Gene Therapy 12(5): 461-466 (2005).
Van Balen, G.P. et al., Liposome/water lipophilicity: methods, information content, and pharmaceutical applications. Medicinal Research Reviews 24(3): 299-324 (2004).
Van De Wetering, P. et al., Structure-activity relationships of water-soluble cationic methacrylate/methacrylamide polymers for nonviral gene delivery. Bioconjugate Chemistry 10(4): 589-597 (1999).
Van Der Gun, B.T.F et al., Serum insensitive, intranuclear protein delivery by the multipurpose cationic lipid Saint-2, Journal of Controlled Release, 123:228-238 (2007).
Van Tendeloo, V.F.I et al., mRNA-based gene transfer as a tool for gene and cell therapy, Current Opinion in Molecular Therapeutics, 9(5):423-431 (2007).
Vandenbroucke, R.E. et al., Prolonged gene silencing in hepatoma cells and primary hepatocytes after small interfering RNA delivery with biodegradable poly(beta-amino esters). Journal of Gene Medicine 10: 783-794 (2008).
Varambally, S. et al., Genomic Loss of microRNA-101 Leads to Overexpression of Histone Methyltransferase EZH2 in Cancer, Science, 322:1695-1699 (2008).
Veronese, F.M. et al., PEG-doxorubicin conjugates: influence of polymer structure on drug release, in vitro cytotoxicity, biodistribution, and antitumor activity, Bioconj. Chem., 16(4):775-784 (2005).
Viecelli, H. et al., Gene Therapy for Hepatic Diseases Using Non-Viral Minicircle-DNA Vector, Journal of Inherited Metabolic Disease, 35(1):S144 (2012).
Viecelli, H. et al., Gene therapy for liver diseases using non-viral minicircle-DNA vector, Human Gene Therapy, 23(10):A145 (2012).
Viecelli, H. et al., Gene therapy for liver diseases using non-viral minicircle-DNA vector, Molecular Therapy, 21(1):S136 (2013).
Vomelova, I. et al., Methods of RNA Purification. All Ways (Should) Lead to Rome, Folia Biologica, 55(6):242-251 (2009).
Von Harpe et al., Characterization of commercially available and synthesized polyethylenimines for gene delivery. Journal of Controlled Release 69(2):309-322 (2000).
Walde, P. et al., Preparation of Vesicles (Liposomes). Encyclopedia of Nanoscience and Nanotechnology. Nalwa, ed. American Scientific Publishers, Los Angeles 9:43-79 (2004).
Wang, H. et al., N-acetylgalactosamine functionalized mixed micellar nanoparticles for targeted delivery of siRNA to liver, Journal of Controlled Release, 166(2):106-114 (2013).
Wang, Y. et al., Systemic delivery of modified mRNA encoding herpes simplex virus 1 thymidine kinase for targeted cancer gene therapy, Molecular Therapy, 21(2):358-367 (2013).
Webb, M. et al., Sphinogomyeline-cholesterol liposomes significantly enhance the pharmacokinetic and therapeutic properties of vincristine in murine and human tumour models, British Journal of Cancer, 72(4):896-904 (1995).
Werth, S. et al., A low molecular weight fraction of polyethylenimine (PEI) displays increased transfection efficiency of DNA and siRNA in fresh or lyophilized complexes. Journal of Controlled Release 112: 257-270 (2006).
Wetzer, B. et al., Reducible cationic lipids for gene transfer, Biochem. J., 356:747-756 (2001).
White, J.E. et al., Poly(hydroxyaminoethers): A New Family of Epoxy-Based Thermoplastics. Advanced Materials 12(23): 1791-1800 (2000).
White, J.E. et al., Step-growth polymerization of 10, 11-epoxyundecanoic acid. Synthesis and properties of a new hydroxy-functionalized thermopastic polyester. Advanced Materials 48: 3990-3998 (2007).
Whitehead, K.A. et al., Knocking down barriers: advances in siRNA delivery. Nature Reviews Drug Discovery 8(2): 129-139 (2009).
Wiehe, J.M. et al., mRNA-mediated gene delivery into human progenitor cells promotes highly efficient protein expression, Journal of Cellular and Molecular Medicine, 11(3):521-530 (2007).
Williams, D. et al., A simple, highly efficient method for heterologous expression in mammalian primary neurons using cationic lipid-mediated mRNA transfection, Frontiers in Neuroscience, 4(181):1-20 (2010).
Written Opinion for PCT/US15/27563, 12 pages (Sep. 18, 2015).
Written Opinion for PCT/US2010/058457, 14 pages (May 6, 2011).
Written Opinion for PCT/US2011/062459, 9 pages (Apr. 11, 2012).
Written Opinion for PCT/US2012/041663, 7 pages (Oct. 8, 2012).
Written Opinion for PCT/US2012/041724, 11 pages (Oct. 25, 2012).
Written Opinion for PCT/US2013/034602, 4 pages (Jun. 17, 2013).
Written Opinion for PCT/US2013/034604, 9 pages (Jun. 17, 2013).
Written Opinion for PCT/US2013/044769, 8 pages (Nov. 12, 2013).
Written Opinion for PCT/US2013/044771, 7 pages (Nov. 1, 2013).
Written Opinion for PCT/US2013/073672, 7 pages (Mar. 3, 2014).
Written Opinion for PCT/US2014/027422, 6 pages (Jul. 31, 2014).
Written Opinion for PCT/US2014/027587, 5 pages (Jul. 24, 2014).
Written Opinion for PCT/US2014/027602, 7 pages (Jul. 28, 2014).
Written Opinion for PCT/US2014/027717, 5 pages (Jul. 16, 2014).
Written Opinion for PCT/US2014/028330, 7 pages (Jul. 22, 2014).
Written Opinion for PCT/US2014/028441, 6 pages (Jul. 22, 2014).
Written Opinion for PCT/US2014/028498, 6 pages (Jul. 28, 2014).
Written Opinion for PCT/US2014/028849, 7 pages (Jul. 17, 2015).
Written Opinion for PCT/US2014/061786, 5 pages (Feb. 6, 2015).
Written Opinion for PCT/US2014/061793, 4 pages (Feb. 6, 2015).
Written Opinion for PCT/US2014/061830, 7 pages (Feb. 4, 2015).
Written Opinion for PCT/US2014/061841, 8 pages (Feb. 24, 2015).
Written Opinion for PCT/US2015/039004, 8 pages (Oct. 6, 2015).
Written Opinion for PCT/US2015/21403 (7 pages) mailed Jun. 15, 2015.
Wu, J. and Zern, M., Modification of liposomes for liver targeting, Journal of Hepatology, 24(6):757-763 (1996).
Wu, J. et al., Cationic lipid polymerization as a novel approach for constructing new DNA delivery agents. Bioconjugate Chemistry 12(2): 251-257 (2001).
Wurdinger, T. et al., A secreted luciferase for ex-vivo monitoring of in vivo processes, Nat. Methods, 5(2):171-173 (2008).
Xiong, et al., "Biomedical applications of mRNA nanomedicine", Nano Research, vol. 11, No. 10, pp. 5283-5287, (2018).
Yamamoto, A. et al., Current prospects for mRNA gene delivery, European Journal of Pharmaceutics and Biopharmaceutics, 71(3): 484-489 (2009).
Yamamoto, Y. et al., Important Role of the Proline Residue in the Signal Sequence that Directs the Secretion of Human Lysozyme in *Saccharomyces cerevisiae*, Biochemistry, 28:2728-2732 (1989).

(56) References Cited

OTHER PUBLICATIONS

Yasuda, M. et al., Fabry Disease: Novel [alpha]-Galactosidase A 3-terminal Mutations Result in Multiple Transcripts Due to Aberrant 3-End Formation, American Journal of Human Genetics, 73:162-173 (2003).

Ye, X. et al., Nucleic Acids, Protein Synthesis, and Molecular Genetics: Prolonged Metabolic Correction in Adult Ornithine Transcarbamylase-deficient Mice with Adenoviral Vectors, The Journal of Biological Chemistry, 271:3639-3646 (1996).

Yokoe, H. et al., Spatial dynamics of GFP-tagged proteins investigated by local fluorescence enhancement, Nature Biotechnology, 14(10):1252-1256 (1996).

Yoneda et al., A cell-penetrating peptidic GRP78 ligand for tumor cell-specific prodrug therapy, Bioorg. Med. Chern. Lett., 18(5): 1632-1636 (2008).

Yoshioka, Y. and Calvert, P., Epoxy-based Electroactive Polymer Gels. Experimental Mechanics 42(4): 404-408 (2002).

Zagridullin, P.H. et al., Monobasic amines. II. Cycloalkylation and hydroxyalkylation of cyclic and acyclic di- and polyamines. Journal of Organic Chemistry, 26(1):184-88. Russian (1990).

Zaugg, H.E. et al., 3-Carboxy-2,5-piperazinedione and Derivatives. Journal of American Chemical Society 78(11):2626-2631 (1956).

Zauner, W. et al., Polylysine-based transfection systems utilizing receptor-mediated delivery. Advanced Drug Delivery Reviews 30(1-3):97-113(1998).

Zintchenko, A. et al., Simple modifications of branched PEI lead to highly efficient siRNA carriers with low toxicity. Bioconjugate Chemistry 19(7):1448-1455 (2008).

Zou, S. et al., Lipid-mediated delivery of RNA is more efficient than delivery of DNA in non-dividing cells, International Journal of Pharmaceutics, 389(1-2):232-243 (2010).

U.S. Appl. No. 16/691,268 2020/0157157, filed Nov. 21, 2019 May 21, 2020, Sjrorang Karve, Treatment of Cystic Fibrosis by Delivery of Nebulized mRNA Encoding CFTR.

Painter et al., "494. Topical Delivery of mRNA to the Murine Lung and Nasal Epithelium", Pulmonary Disease, May 2004, 9(Suppl 1): S187.

Patton, "Market Trends in Pulmonary Therapies", Trends and Opportunities, 2007, VI: 372-377.

Wikipedia, Blood Protein, Apr. 15, 2004, obtained from url: <https://en.wikipedia.org/wiki/Blood_protein>.

Alveolar region
Group 1, 10% Trehalose

CFTR

ZO1

MERGED

TREATMENT OF CYSTIC FIBROSIS BY DELIVERY OF NEBULIZED mRNA ENCODING CFTR

CROSS-REFERENCE TO RELATED APPLICATIONS

This application is a Continuation to U.S. patent application Ser. No. 16/691,268, filed on Nov. 21, 2019, which claims benefit of, and priority to U.S. Provisional Patent Application Ser. No. 62/848,401, filed on May 15, 2019, which claims benefit of, and priority to U.S. Provisional Patent Application Ser. No. 62/846,458, filed on May 10, 2019, which claims benefit of, and priority to U.S. Provisional Patent Application Ser. No. 62/829,461, filed on Apr. 4, 2019, and claims benefit of, and priority to U.S. Provisional Patent Application Ser. No. 62/770,596, filed on Nov. 21, 2018, the contents of each of which are incorporated herein in its entirety.

INCORPORATION-BY-REFERENCE OF SEQUENCE LISTING

The contents of the text file named "MRT-2050US2 ST25.txt", which was created on Mar. 11, 2022 and is 167 KB in size, are hereby incorporated by reference in its entirety.

BACKGROUND

Cystic fibrosis is an autosomal inherited disorder resulting from mutation of the Cystic Fibrosis Transmembrane Conductance Regulator (CFTR gene), which encodes a chloride ion channel believed to be involved in regulation of multiple other ion channels and transport systems in epithelial cells. Loss of function of CFTR results in chronic lung disease, aberrant mucus production, and dramatically reduced life expectancy. See generally Rowe et al., New Engl. J. Med. 352, 1992-2001 (2005).

Currently there is no cure for cystic fibrosis. The literature has documented numerous difficulties encountered in attempting to induce expression of CFTR in the lung. For example, viral vectors comprising CFTR DNA triggered immune responses and CF symptoms persisted after administration. Conese et al., J. Cyst. Fibros. 10 Suppl 2, S114-28 (2011); Rosenecker et al., Curr. Opin. Mol. Ther. 8, 439-45 (2006). Non-viral delivery of DNA, including CFTR DNA, has also been reported to trigger immune responses. Alton et al., Lancet 353, 947-54 (1999); Rosenecker et al., J Gene Med. 5, 49-60 (2003). Furthermore, non-viral DNA vectors encounter the additional problem that the machinery of the nuclear pore complex does not ordinarily import DNA into the nucleus, where transcription would occur. Pearson, Nature 460, 164-69 (2009).

Experiments performed in rodents in which liposome-encapsulated CFTR mRNA was delivered to the lungs of the test animals have yielded promising results (see, e.g., WO2018/089790). The inventors have combined data from rodent and non-human primate experiments with in vitro data obtained with commercially available nebulizers to optimize pulmonary delivery of liposome-encapsulated CFTR mRNA to human adult and pediatric subjects.

SUMMARY OF THE INVENTION

The present invention provides a particularly effective method of administering liposome-encapsulated CFTR mRNA by nebulization to the lungs of a human subject for the treatment of Cystic Fibrosis. Accordingly, the invention relates to an improved method of treating cystic fibrosis (CF) in a human subject. In particular, the method comprises administering a composition comprising an mRNA encoding a Cystic Fibrosis Transmembrane Conductance Regulator (CFTR) protein at a concentration of 0.5 mg/mL or greater to a human subject via nebulization. The composition is aerosolized using a nebulizer and a nominal dose of the mRNA is administered to the human subject via the nebulizer over a period of time, typically at least 30 minutes, at a suitable nebulization rate, e.g., at least 0.2 mL/minute.

In some embodiments, the concentration of the mRNA encoding the CFTR protein ranges from 0.5 mg/mL to 0.8 mg/mL. In a specific embodiment, the concentration is 0.6 mg/mL.

During the treatment at least 25% of the nominal dose of the mRNA encoding the CFTR protein is delivered to the lungs of the human subject. More typically at least 35% or at least 40% of the mRNA encoding the CFTR protein is delivered to the lungs of the human subject The period over which the aerosolized composition is administered to the human subject may exceed 35 min. In some embodiments, the treatment time is 45 min, 1 hour, 2 hours or 3 hours. A typical treatment time may be 35 min to 4.5 hours, e.g., 1.5 hours to 2 hours or 2.5 hours to 4 hours.

Generally, the nominal dose administered to the human subject during a single treatment exceeds 5 mg. In some embodiments, the nominal dose is between 4 mg and 40 mg, e.g., between 6 mg and 30 mg. In specific embodiments, the nominal dose administered to the human subject is 8 mg, 16 mg or 24 mg.

The nebulization rate may range from 0.2 mL/minute to 0.5 mL/minute. In some embodiments, the volume of the composition that is aerosolized in a single treatment session ranges from 13.0 mL to 42.0 mL. In certain embodiments, the volume of the composition that is aerosolized does not exceed 20 mL in a single treatment.

A suitable nebulizer for use with the method of the invention produces droplets with an average size between 4 μm and 6 μm.

At least some portion of the mRNA encoding the CFTR protein may be complexed to or encapsulated within nanoparticles. Suitable nanoparticles include liposomes. Typically, the mRNA encoding the CFTR protein is encapsulated within the liposome. In certain embodiments, at least 75% of the mRNA encoding the CFTR protein is encapsulated within a nanoparticle. In certain embodiments, at least 80% of the mRNA encoding the CFTR protein is encapsulated within a nanoparticle. In certain embodiments, at least 85% of the mRNA encoding the CFTR protein is encapsulated within a nanoparticle. In a specific embodiment, at least 90% of the mRNA encoding the CFTR protein is encapsulated within a nanoparticle. In any of the above embodiments, the nanoparticle may be a liposome.

A liposome suitable for use with the present invention may have a size less than about 100 nm. For example, the liposome may have a size ranging from 40 nm to 60 nm.

In some embodiments, a liposome in accordance with the invention comprises one or more cationic lipids, one or more non-cationic lipids, and one or more PEG-modified lipids. In some embodiments, the liposome comprises no more than three distinct lipid components. In certain embodiments, one distinct lipid component is a sterol-based cationic lipid. In other embodiments, the no more than three distinct lipid components are a cationic lipid, a non-cationic lipid and a PEG-modified lipid. In a specific embodiment, the cationic lipid is imidazole cholesterol ester (ICE), the non-cationic lipid is 1,2-dioleoyl-sn-glycero-3-phosphoethanolamine (DOPE), and the PEG-modified lipid is 1,2-dimyristoyl-sn-glycerol, methoxypolyethylene glycol (DMG-PEG-2K). In some embodiments, ICE and DOPE are present at a molar ratio of >1:1. In some embodiments, ICE and DMG-PEG-2K are present at a molar ratio of >10:1. In some embodiments, DOPE and DMG-PEG-2K are present at a molar ratio of >5:1.

In certain embodiments, the mRNA has poly-A tail with an average length of at least 100 bases. In certain embodiments, the mRNA has poly-A tail with an average length of at least 200 bases. In certain embodiments, the mRNA has poly-A tail with an average length of at least 500 bases. For example, a suitable length of the poly-A tail is between 400 and 700 bases. In some embodiments, the mRNA encoding the CFTR protein comprises a polynucleotide sequence at least 85%, at least 90%, at least 95%, or at least 99% identical to SEQ ID NO: 1. In a specific embodiment, the mRNA encoding the CFTR protein comprises a polynucleotide sequence identical to SEQ ID NO: 1. The mRNA encoding the CFTR protein may further comprise a 5' untranslated region (UTR) sequence of SEQ ID NO: 3 and/or a 3' untranslated region (UTR) sequence of SEQ ID NO: 4 or SEQ ID NO: 5. In some embodiments, the mRNA encoding the CFTR protein comprises a polynucleotide sequence at least 85%, at least 90% or at least 91% or at least 92% or at least 93% or at least 94% or at least 95% or at least 96% or at least 97% or at least 98% or at least 99% or 100% identical to any one of SEQ ID NO: 6 to SEQ ID NO: 27. In a specific embodiment, the mRNA encoding the CFTR protein comprises a polynucleotide sequence identical to SEQ ID NO: 6.

In some embodiments, a composition for use with the invention is provided in lyophilized form and reconstituted in an aqueous solution prior to nebulization.

In certain embodiments, the composition comprising the mRNA encoding the CFTR protein comprises trehalose. A suitable trehalose concentration is 10% (w/v).

In some embodiments, the human subject is administered the composition at least once per week for a period of at least six months.

In some embodiments, the human subject receives concomitant CFTR modulator therapy.

In some embodiments, the concomitant CFTR modulator therapy is selected from ivacaftor, ivacaftor/lumacaftor, or tezacaftor/lumacaftor. Accordingly, in some embodiments, the concomitant CFTR modulator therapy comprises ivacaftor. In some embodiments, the CFTR modulator therapy comprises ivacaftor/lumacaftor. In some embodiments, the CFTR modulator therapy comprises tezacaftor/lumacaftor.

In some embodiments, the human subject has an F508del mutation.

In some embodiments, the human subject is selected for treatment based on the presence of an F508del mutation.

In some embodiments, the human subject has a heterozygous or homozygous F508del mutation. Accordingly, in some embodiments, the human subject has a heterozygous F508del mutation. In some embodiments, the human subject has a homozygous F508del mutation.

In some embodiments, the subject does not have an F508del mutation.

In some embodiments, the subject is selected for treatment based on the absence of an F508del mutation.

In some embodiments, the human subject has a forced expiratory volume in one second (FEV1) of between about 50% and 90% of predicted normal. For example, the human subject has an FEV1 of about 50%, about 55%, about 60%, about 65%, about 70%, about 80%, about 85%, or about 90% of predicted normal.

In some embodiments, the human subject has an FEV1 of between about 60% and 70% predicted of predicted normal. For example, the human subject has an FEV1 of about 60%, about 61%, about 62%, about 63%, about 64%, about 65%, about 66%, about 67%, about 68%, about 69%, or about 70% of predicted normal.

It is to be understood that all embodiments as described above are applicable to all aspects of the present invention. Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWINGS

The drawings are for illustration purposes only not for limitation.

FIG. 10A depicts microscopic immunostaining images of upper bronchial epithelial cells from control animal treated with 10% trehalose; CFTR staining (left), ZO1 staining (middle) and optical merge of CFTR and ZO1 staining (right). FIG.

10B depicts microscopic immunostaining images of upper bronchial epithelial cells from an animal treated with low dose CFTR mRNA (500 µg/kg); CFTR staining (left), ZO1staining (middle) and optical merge of CFTR and ZO1 staining (right). FIG. 10C shows representative microscopic immunostaining images of upper bronchial epithelial cells from an animal treated with high dose CFTR mRNA (1000 µg/kg); CFTR staining (left), ZO1staining (middle) and optical merge of CFTR and ZO1 staining (right). Arrows indicate positive staining for both CFTR and ZO1.

FIG. 11A depicts microscopic immunostaining images of lower airway epithelial cells from control animal treated with 10% trehalose; CFTR staining (left), ZO1 staining (middle) and optical merge of CFTR and ZO1 staining (right). FIG. 11B depicts microscopic immunostaining images of lower airway epithelial cells from an animal treated with low dose CFTR mRNA (500 µg/kg); CFTR staining (left), ZO1staining (middle) and optical merge of CFTR and ZO1 staining (right). FIG. 11C shows representative microscopic immunostaining images of lower airway epithelial cells from an animal treated with high dose CFTR mRNA (1000 µg/kg); CFTR staining (left), ZO1staining (middle) and optical merge of CFTR and ZO1 staining (right). Arrows indicate positive staining for both CFTR and ZO1.

FIG. 12A depicts microscopic immunostaining images from control animal treated with 10% trehalose; CFTR staining (left), ZO1 staining (middle) and optical merge of CFTR and ZO1 staining (right).

FIG. 12B depicts microscopic immunostaining images from an animal treated with low dose CFTR mRNA (500 µg/kg); CFTR staining (left), ZO1staining (middle) and optical merge of CFTR and ZO1 staining (right). FIG. 12C shows representative microscopic immunostaining images from an animal treated with high dose CFTR mRNA (1000 µg/kg); CFTR staining (left), ZO1 staining (middle) and optical merge of CFTR and ZO1 staining (right). Arrows indicate positive staining for both CFTR and ZO1.

DEFINITIONS

Figure 1:
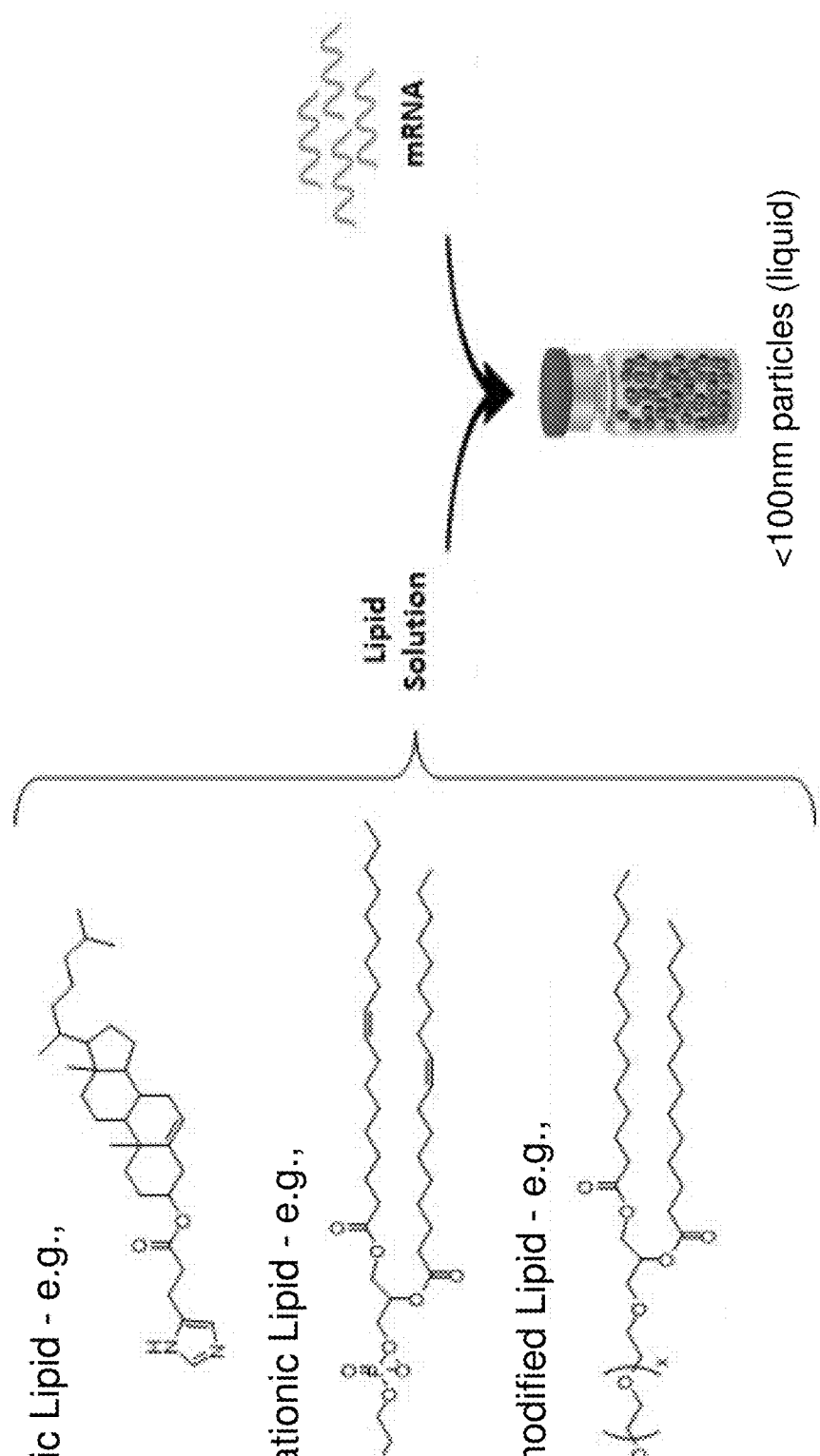
FIG. 1 depicts the general structure of the composition comprising an mRNA encoding a CFTR protein and a simplified formulation process.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery). In some embodiments, delivery is pulmonary delivery, e.g., comprising nebulization.

Encapsulation: As used herein, the term "encapsulation," or its grammatical equivalent, refers to the process of confining an mRNA molecule within a nanoparticle.

Expression: As used herein, "expression" of a nucleic acid sequence refers to translation of an mRNA into a polypeptide, assemble multiple polypeptides (e.g., heavy chain or light chain of antibody) into an intact protein (e.g., antibody) and/or post-translational modification of a polypeptide or fully assembled protein (e.g., antibody). In this application, the terms "expression" and "production," and their grammatical equivalents, are used interchangeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated.

Nominal dose: As used herein, the term "nominal dose" refers to a dose of a mRNA administered to a subject by nebulization. The nominal dose may not be identical to the dose actually delivered to the subject. For example, if a human subject is given a nominal dose of 8 µg of a CFTR mRNA composition disclosed herein, the actual dose that is delivered to the lungs of the subject may vary, e.g., depending on the nebulization parameters used to administer the composition. The actual dose cannot exceed the nominal dose, but typically the actual dose of mRNA delivered by nebulization to the lungs of the human subject is lower than the nominal dose that is administered via the nebulizer.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery. In some embodiments, the nucleotides T and U are used interchangeably in sequence descriptions.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In specific embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, an improved method of treating cystic fibrosis (CF) in a human subject. In some embodiments, the method comprises administering a composition comprising an mRNA encoding a Cystic Fibrosis Transmembrane Conductance Regulator (CFTR) protein at a concentration of 0.5 mg/mL or greater to a human subject via nebulization. The composition is aerosolized using a nebulizer and a nominal dose of the mRNA is administered to the human subject via the nebulizer over a period of time, typically at least 30 minutes, at a suitable nebulization rate, e.g., at least 0.2 mL/minute.

Various aspects of the invention are described in detail in the following sections. The use of sections is not meant to limit the invention. Each section can apply to any aspect of the invention. In this application, the use of "or" means "and/or" unless stated otherwise.

Cystic Fibrosis

Cystic fibrosis, also known as mucoviscidosis, is an autosomal recessive genetic disorder that affects most critically the lungs, and also the pancreas, liver, and intestine (Gibson et al., *Am J Respir Crit Care Med.* (2003) 168(8): 918-951; Ratjen et al., *Lancet Lond Engl.* (2003) 361(9358): 681-689; O'Sullivan et al., *Lancet Lond Engl.* (2009) 373 (9678):1891-1904). Cystic fibrosis is caused by mutations in the gene encoding for the cystic fibrosis transmembrane conductance regulator (CFTR) protein. This protein functions as a channel that transports chloride ions across the membrane of cells and is required to regulate the components of mucus, sweat, saliva, tears, and digestive enzymes. Disease-causing mutations in the CFTR protein cause dysfunction of its channel activity resulting in abnormal transport of chloride and sodium ions across the epithelium, leading to the thick, viscous secretions in the lung, pancreas and other organs characteristic of CF disease (O'Sulliven et al., *Lancet Lond Engl.* (2009) 373(9678):1891-1904; Rowe et al., *N Engl J Med.* (2005) 352(19):1992-2001). Most CF patients develop severe, chronic lung disease related to airway obstruction partly due to increased levels of sulfated mucins, inflammation, and recurrent infections that are eventually lethal; the median predicted survival age in the US is 40.7 years. Cystic fibrosis is the most frequent lethal genetic disease in the white population.

Symptoms often appear in infancy and childhood, with respiratory symptoms the most frequent followed by failure to thrive, steatorrhea, and meconium ileus (Gibson et al., *Am J Respir Crit Care Med.* (2003) 168(8):918-951). The most common complications of CF are pulmonary related and include blockages of the narrow passages of affected organs with thickened secretions. These blockages lead to remodeling and infection in the lung, cause damage in the pancreas due to accumulated digestive enzymes, and blockages of the intestines. Diabetes is the most common non-pulmonary complication and is a distinct entity known as CF-related diabetes.

The lungs of individuals with CF are colonized and infected by bacteria from an early age. This leads to chronic airway infection and inflammation, progressing to bronchiectasis, gas trapping, hypoxemia, and hypercarbia. Pulmonary insufficiency is responsible for 68.1% of CF-related deaths in the US. In the initial stage, common bacteria such as *Staphylococcus aureus* and *Hemophilus influenzae* colonize and infect the lungs. Eventually, *Pseudomonas aeruginosa* (and sometimes *Burkholderia cepacia*) dominates. By 18 years of age, 80% of patients with classic CF harbor *P. aeruginosa*, and 3.5% harbor *B. cepacia*. Once within the lungs, these bacteria adapt to the environment and develop resistance to commonly used antibiotics.

The underlying defect causing CF is abnormal epithelial anion transport due to the lack of expression or dysfunction of the CFTR protein. The CFTR protein primarily functions as a chloride channel in epithelial cell membranes; however, it also involved in a number of other cellular membrane functions such as inhibition of sodium transport through the epithelial sodium channel, regulation of the outwardly rectifying chloride channel, and regulation of adenosine triphosphate (ATP) channels (O'Sullivan et al., *Lancet Lond Engl.* (2009) 373(9678):1891-1904). CF is caused by mutations in the gene encoding for the CFTR protein, of which more than 1,500 disease-causing mutations have been identified (O'Sullivan et al., *Lancet Lond Engl.* (2009) 373 (9678):1891-1904). The more common gene mutations result in the lack of synthesis of the CFTR protein (class I), defective processing and maturation of the CFTR protein (class II), or the expression of a CFTR protein defective in regulation, e.g., diminished ATP binding and hydrolysis (class III) (Rowe et al., *N Engl J Med.* (2005) 352(19):1992-2001). A deletion of phenylalanine at position 508 (F508del) is the most common CFTR mutation worldwide and is a class II defect in which the misfolded protein is rapidly degraded by the cell soon after synthesis (Rowe et al., *N Engl J Med.* (2005) 352(19):1992-2001). The lack of a functional CFTR protein causes mucosal obstruction of exocrine glands in CF patients secondary to abnormal transport of chloride and sodium across the epithelium. In the lung, this leads to the development of thick, tenacious secretions that obstruct the airways and submucosal glands, which in turn leads to chronic bacterial infection and inflammation, as described above.

Respiratory symptoms of cystic fibrosis include: a persistent cough that produces thick mucus (sputum), wheezing, breathlessness, exercise intolerance, repeated lung infections and inflamed nasal passages or a stuffy nose. Digestive symptoms of cystic fibrosis include: foul-smelling, greasy stools, poor weight gain and growth, intestinal blockage, particularly in newborns (meconium ileus), and severe constipation.

There are several different methods for assessing symptoms of cystic fibrosis. In one embodiment, one or more symptoms of cystic fibrosis are assessed by forced expiratory volume (FEV), which measures how much air a person can exhale during a forced breath. In one embodiment, the amount of air exhaled in the first second of the forced breath is measured ($FEV_1$). In one embodiment, the amount of air exhaled in the second of the forced breath is measured ($FEV_2$). In one embodiment, the amount of air exhaled in the third second of the forced breath is measured ($FEV_3$). In one embodiment, the forced vital capacity (FVC), which is the total amount of air exhaled during a FEV test, is measured. In one embodiment, one or more symptoms of cystic fibrosis are assessed by Cystic Fibrosis Questionnaire Revise (CFQ-R) respiratory domain score. CFQ-R respiratory domain score is a measure of respiratory symptoms relevant to patients with CF such as cough, sputum production, and difficulty breathing. In one embodiment, one or more symptoms of cystic fibrosis are assessed by relative risk of pulmonary exacerbation. In one embodiment, one or more symptoms of cystic fibrosis are assessed by change in body weight. In one embodiment, one or more symptoms of cystic fibrosis are assessed by change in sweat chloride (mmol/L).

Patient Selection

The present invention is suitable for treatment of patients with various CFTR defects including, but not limited to, patients with different CFTR symptoms, mutations or classes described herein.

In some embodiments, the present invention may be used to treat patients carrying one or more, two or more, three or more, four or more, or five or more mutations from Class I (Defective Protein Synthesis) shown in Table 1. In some embodiments, the present invention may be used to treat patients carrying one or more, two or more, three or more, four or more, or five or more mutations from Class II (Abnormal Processing and Trafficking) shown in Table 1. In some embodiments, the present invention may be used to treat patients carrying one or more, two or more, three or more, four or more, or five or more mutations from Class III (Defective Chanel Regulation/Gating) shown in Table 1. In some embodiments, the present invention may be used to treat patients carrying one or more, two or more, three or more, four or more, or five or more mutations from Class IV (Decreased Channel Conductance) shown in Table 1. In some embodiments, the present invention may be used to treat patients carrying one or more, two or more, three or more, four or more, or five or more mutations from Class V (Reduced Synthesis and/or Trafficking) shown in Table 1. In some embodiments, the present invention may be used to treat patients carrying any combination of specific mutations selected from Table 1 (e.g., one or more, two or more, three or more, four or more, five or more, six or more, seven or more, eight or more, nine or more, or ten or more mutations from different classes shown in Table 1).

19 years or older, or of 25 years or older, or of 25 years or older, or of 30 years or older, or of 35 years or older, or of 40 years or older, or of 45 years or older, or of 50 years or older. In some embodiments, a patient in need of treatment is less than 50 years old, or less than 45 years old, or less than 40 years old, or less than 35 years old, or less than 30 years old, or less than 25 years old, or less than 20 years old, or less than 19 years old, or less than 18 years old, or less than 13 years old, or less than 12 years old, or less than 7 years old, or less than 6 years old, or less than 3 years old, or less than 2 years old. In some embodiments, a patient in need of treatment is a male or female from 2 to 18 years old, or from 2 to 12 years old, or from 2 to 6 years old, or from 6 to 12 years old, or from 6 to 18 years old, or from 12 to 16 years old, or from 2 to 50 years old, or from 6 to 50 years old, or from 12 to 50 years old, or from 18 to 50 years old. In some embodiments, a patient in need of treatment is a female who is pregnant or who may become pregnant.

In some embodiments, a patient is selected for treatment who has an F508del mutation. In some embodiments, the patient who is selected for treatment has a homozygous F508del mutation. In some embodiments, the patient who is selected for treatment has a heterozygous F508del mutation. In some embodiments, the patient who is selected for treatment does not have an F508del mutation.

In some embodiments, a patient in need of treatment has a sweat chloride value of ≥60 mmol/L, ≥65 mmol/L, ≥70 mmol/L, ≥75 mmol/L, ≥80 mmol/L, ≥85 mmol/L, ≥90 mmol/L, ≥95 mmol/L, ≥100 mmol/L, ≥110 mmol/L, ≥120 mmol/L, ≥130 mmol/L, ≥140 mmol/L or ≥150 mmol/L by quantitative pilocarpine iontophoresis (documented in the subject's medical record). In some embodiments, a patient in need of treatment has chronic sinopulmonary disease and/or

TABLE 1

Classification of CFTR Gene Mutations

| Category | Mutation | Specific mutations |
|---|---|---|
| Class I | Defective Protein Synthesis (nonsense, frameshift, aberrant splicng) | 1078delT, 1154 insTC, 1525-2A > G, 1717-1G > A, 1898 + 1G > A, 2184delA, 2184 ins A, 3007delG, 3120 + 1G > A, 3659delC, 3876delA, 3905insT, 394delTT, 4010del4, 4016insT, 4326delTC, 4374 + 1G > T, 441delA, 556delA, 621 + 1G > T, 621 − 1G > T, 711 + 1G > T, 875 + 1G > C, El 104X, E585X, E60X, E822X, G542X, G551D/R553X, Q493X, Q552X, Q814X, R1066C, R1162X, R553X, V520F, W1282X, Y1092X |
| Class II | Abnormal Processing and Trafficking | A559T, D979A, AF508, AI507, G480C, G85E, N1303K, S549I, S549N, S549R |
| Class III | Defective Chanel Regulation/Gating | G1244E, G1349D, G551D, G551S, G85E, H199R, I1072T, I48T, L1077P, R560T, S1255P, S549N (R75Q) |
| Class IV | Decreased Channel Conductance | A800G, D1152H, D1154G, D614G, delM1140, E822K, G314E, G576A, G622D, G85E, H620Q, I1139V, I1234V, L1335P, Ml 137V, P67L, RI 17C, R117P, RI 17H, R334W, R347H, R347P, R347P/R347H, R792G, S125 IN, V232D |
| Class V | Reduced Synthesis and/or Trafficking | 2789 + 5G > A, 3120G > A, 3272-26A > G, 3849 + 10kbC > T, 5T variant, 621 + 3A > G, 711 + 3A > G, A445E, A455E, IVS8 poly T, P574H, 875 + 1G > C |

In some embodiments, a patient in need of treatment is a male or female of 2 years or older, or of 3 years or older, or of 6 years or older, or of 7 years or older, or of 12 years or older, or of 13 years or older, or of 18 years or older, or of gastrointestinal/nutritional abnormalities consistent with CF disease. In some embodiments, a patient in need of treatment has chronic sinopulmonary disease and/or gastrointestinal/nutritional abnormalities consistent with CF disease.

In some embodiments, a patient in need of treatment has FEV$_1 \geq$50% and $\leq$90% (e.g., $\leq$85%, $\leq$80%, $\leq$75%, $\leq$70%, $\leq$65%, $\leq$60%, or $\leq$55%) of the predicted normal (i.e., the average FEV of non-CF patients) based on the patient's age, gender, and height. In some embodiments, a patient in need of treatment has resting oxygen saturation $\geq$92% on room air (pulse oximetry). In some embodiments, a patient in need of treatment has a body mass index>17.5 kg/m' and weight $\geq$40 kg.

In some embodiments, a patient in need of treatment has received or is concurrently receiving other CF medications. For example, a patient in need of treatment may be receiving lumacaftor/ivacaftor combination drug (ORKAMBI®) or may have been on this treatment for at least 28 days prior to commencement of the treatment according to the present invention. Other CF medications may include, but are not limited to, routine inhaled therapies directed at airway clearance and management of respiratory infections, such as bronchodilators, rhDNase (PULMOZYME®), hypertonic saline, antibiotics, and steroids; and other routine CF-related therapies such as systemic antibiotics, pancreatic enzymes, multivitamins, and diabetes and liver medications.

In some embodiments, a patient in need of treatment has been a non-smoker for a minimum of 2 years. In some embodiments, a patient in need of treatment does not receive inhaled rhDNase (PULMOZYME®) treatment for 24 hours before and/or after administration of a composition comprising an mRNA encoding a CFTR protein according to the present invention.

In some embodiments, a patient in need of treatment has been treated or is currently being treated with hormone replacement therapies, thyroid hormone replacement therapy, non-steroidal inflammatory drugs, and prescription dronabinol (MARINOL®) during treatment.

In some embodiments, a patient in need of treatment has discontinued use of one or more other cystic fibrosis treatments described herein. In some embodiments, the patient has discontinued use of one or more other cystic fibrosis treatments for at least 12 hours, at least 24 hours, at least 36 hours, at least 48 hours, at least 72 hours, at least 1 week, at least 2 weeks, at least 3 weeks, at least 4 weeks, at least 5 weeks, at least 6 weeks, at least 7 weeks, or at least 8 weeks prior to administration of a CFTR mRNA according to the present invention. In some embodiments, the patient has discontinued use of one or more other cystic fibrosis treatments for less than 12 hours, less than 24 hours, less than 36 hours, less than 48 hours, less than 72 hours, less than 1 week, less than 2 weeks, less than 3 weeks, less than 4 weeks, less than 5 weeks, less than 6 weeks, less than 7 weeks, less than 8 weeks, less than 9 weeks, or less than 10 weeks prior to administration of a CFTR mRNA according to the present invention.

Formulation and Administration

According to the present invention, a suitable formulation for the treatment contains an mRNA encoding any full length, fragment or portion of a CFTR protein which can be substituted for naturally-occurring CFTR protein activity and/or reduce the intensity, severity, and/or frequency of one or more symptoms associated with cystic fibrosis.

In some embodiments, a suitable mRNA sequence is an mRNA sequence encoding a human CFTR (hCFTR) protein. In some embodiments, a suitable mRNA sequence is codon optimized for efficient expression human cells. An exemplary codon-optimized CFTR mRNA coding sequence and the corresponding amino acid sequence are shown in Table 2:

TABLE 2

Exemplary CFTR mRNA and Protein Sequences

| | |
|---|---|
| Codon-Optimized Human CFTR mRNA coding sequence | AUGCAACGCUCUCCUCUUGAAAAGGCCUCGGUGGUGUCCAAGCUCUU<br>CUUCUCGUGGACUAGACCCAUCCUGAGAAAGGGGUACAGACAGCGCU<br>UGGAGCUGUCCGAUAUCUAUCAAAUCCCUUCCGUGGACUCCGCGGAC<br>AACCUGUCCGAGAAGCUCGAGAGAGAAUGGGACAGAGAACUCGCCUC<br>AAAGAAGAACCCGAAGCUGAUUAAUGCGCUUAGGCGGUGCUUUUUC<br>UGGCGGUUCAUGUUCUACGGCAUCUUCCUCUACCUGGGAGAGGUCAC<br>CAAGGCCGUGCAGCCCCUGUUGCUGGGACGGAUUAUUGCCUCCUACG<br>ACCCCGACAACAAGGAAGAAAGAAGCAUCGCUAUCUACUUGGGCAUC<br>GGUCUGUGCCUGCUUUUCAUCGUCCGGACCCUCUUGUUGCAUCCUGC<br>UAUUUUCGGCCUGCAUCACAUUGGCAUGCAGAUGAGAAUUGCCAUG<br>UUUUCCUGAUCUACAAGAAAACUCUGAAGCUCUCGAGCCGCGUGCU<br>UGACAAGAUUUCCAUCGGCCAGCUCGUGUCCCUGCUCUCCAACAAUC<br>UGAACAAGUUCGACGAGGGCCUCGCCCUGGCCCACUUCGUGUGGAUC<br>GCCCCUCUGCAAGUGGCGCUUCUGAUGGGCCUGAUCUGGGAGCUGCU<br>GCAAGCCUCGGCAUUCUGUGGGCUUGGAUUCCUGAUCGUGCUGGCAC<br>UGUUCCAGGCCGGACUGGGGCGGAUGAUGAUGAAGUACAGGGACCA<br>GAGAGCCGGAAAGAUUUCCGAACGGCUGGUGAUCACUUCGGAAAUG<br>AUCGAAAACAUCCAGUCAGUGAAGGCCUACUGCUGGGAAGAGGCCAU<br>GGAAAAGAUGAUUGAAAACCUCCGGCAAACCGAGCUGAAGCUGACCC<br>GCAAGGCCGCUUACGUGCGCUAUUUCAACUCGUCCGCUUUCUUCUUC<br>UCCGGGUUCUUCGUGGUGUUUCUCUCCGUGCUCCCCUACGCCCUGAU<br>UAAGGGAAUCAUCCUCAGGAAGAUCUUCACCACCAUUUCCUUCUGUA<br>UCGUGCUCCGCAUGGCCGUGACCCGGCAGUUCCCAUGGGCCGUGCAG<br>ACUUGGUACGACUCCCUGGGGAGCCAUUAACAAGAUCCAGGACUUCCU<br>UCAAAAGCAGGAGUACAAGACCCUCGAGUACAACCUGACUACUACCG<br>AGGUCGUGAUGGAAAACGUCACCGCCUUUUGGGAGGAGGGAUUUGG<br>CGAACUGUUCGAGAAGGCCAAGCAGAACAACAACAACCGCAAGACCU<br>CGAACGUGACGACUCCCUCUUCUUUUCAAACUUCAGCCUGCUCGGG<br>ACGCCCGUGCUGAAGGACAUUAACUUCAAGAUCGAAAGAGGACAGCU<br>CCUGGCCGGUGGCCGGAUCGACCGGAGCCGGAAAGACUUCCCUGCUGA<br>UGGUGAUCAUGGGAGAGCUUGAACCUAGCGAGGGAAAGAUCAAGCA<br>CUCCGGCCGCAUCAGCUUCUGUAGCCAGUUUUCCUGGAUCAUGCCCG<br>GAACCAUUAAGGAAAACAUCAUCUUCGGCGUGUCCUACGAUGAAUAC<br>CGCUACCGGUCCGUGAUCAAAGCCUGCCAGCUGGAAGAGGAUAUUUC<br>AAAGUUCGCGGAGAAAGAUAACAUCGUGCUGGGCGAAGGGGGUAUU<br>ACCUUGUCGGGGGGCCAGCGGGCUAGAAUCUCGCUGGCCAGAGCCGU |

TABLE 2-continued

Exemplary CFTR mRNA and Protein Sequences

```
GUAUAAGGACGCCGACCUGUAUCUCCUGGACUCCCCCUUCGGAUACC
UGGACGUCCUGACCGAAAAGGAGAUCUUCGAAUCGUGCGUGUGCAA
GCUGAUGGCUAACAAGACUCGCAUCCUCGUGACCUCCAAAAUGGAGC
ACCUGAAGAAGGCAGACAAGAUUCUGAUUCUGCAUGAGGGGUCCUCC
UACUUUUACGGCACCUUCUCGGAGUUGCAGAACUUGCAGCCCGACUU
CUCCAUCGAAGCUGAUGGGUUGCGACAGCUUCGACCAGUUCUCCGCCG
AAAGAAGGAACUCGAUCCUGACGGAAACCUUGCACCGCUUCUCUUUG
GAAGGCGACGCCCCUGUGUCAUGGACCGAGACUAAGAAGCAGAGCUU
CAAGCAGACCGGGGAAUUCGGCGAAAAGAGGAAGAACAGCAUCUUG
AACCCCAUUAACUCCAUCCGCAAGUUCUCAAUCGUGCAAAAGACGCC
ACUGCAGAUGAACGGCAUUGAGGAGGACUCCGACGAACCCCUUGAGA
GGCGCCUGUCCCUGGUGCCGGACAGCGAGCAGGGAGAAGCCAUCCUG
CCUCGGAUUUCGUGAUCUCCACUGGUCCGACGCUCCAAGCCCGGCG
GCGGCAGUCCGUGCUGAACCUGAUGACCCACAGCGUGAACCAGGGCC
AAAACAUUCACCGCAAGACUACCGCAUCCACCCGGAAAGUGUCCCUG
GCACCUCAAGCGAAUCUUACCGAGCUCGACAUCUACUCCCGGAGACU
GUCGCAGGAAACCGGGCUCGAAAUUUCCGAAGAAAUCAACGAGGAG
GAUCUGAAAGAGUGCUUCUUCGACGAUAUGGAGUCGAUACCCGCCGU
GACGACUUGGAACACUUAUCUGCGGUACAUCACUGUGCACAAGUCAU
UGAUCUUCGUGCUGAUUUGGUGCCUGGUGAUUUUCCUGGCCGAGGU
CGCGGCCUCACUGGUGGUGCUCUGGCUGUUGGGAAACACGCCUCUGC
AAGACAAGGGAAACUCCACGCACUCGAGAAACAACAGCUAUGCCGUG
AUUAUCACUUCCACCUCCUCUUAUUACGUGUUCUACAUCUACGUCGG
AGUGGCGGAUACCCUGCUCGCGAUGGGUUUCUUCAGAGGACUGCCGC
UGGUCCACACCUUGAUCACCGUCAGCAAGAUUCUUCACCACAAGAUG
UUGCAUAGCGUGCUGCAGGCCCCAUGUCCACCCUCAACACUCUGAA
GGCCGGAGGCAUUCUGAACAGAUUCUCCAAGGACAUCGCUAUCCUGG
ACGAUCUCCUGCCGCUUACCAUCUUUGACUUCAUCCAGCUGCUGCUG
AUCGUGAUUGGAGCAAUCGCAGUGGUGGCGGUGCUGCAGCCUUACA
UUUUCGUGGCCACUGUGCCGGUCAUUGUGGCGUUCAUCAUGCUGCGG
GCCUACUUCCUCCAAACCAGCCAGCAGCUGAAGCAACUGGAAUCCGA
GGGACGAUCCCCCAUCUUCACUCACCUUGUGACGUCGUUGAAGGGAC
UGUGGACCCCUCGGGCUUUCGGACGGCAGCCCACUUCGAAACCCUC
UUCCACAAGGCCCUGAACCUCCACACCGCCAAUUGGUUCCUGUACCU
GUCCACCCUGCGGUGGUUCCAGAUGCGCAUCGAGAUGAUUUUCGUCA
UCUUCUUCAUCGCGGUCACAUUCAUCAGCAUCCUGACUACCGGAGAG
GGAGAGGGACGGGUCGAAUAAUCCUGACCCUCGCCAUGAACAUUAU
GAGCACCCUGCAGUGGGCAGUGAACAGCUCGAUCGACGUGGACAGCC
UGAUGCGAAGCGUCAGCCGCGUGUUCAAGUUCAUCGACAUGCCUACU
GAGGGAAAACCCACUAAGUCCACUAAGCCCUACAAAAAAUGGCCAGCU
GAGCAAGGUCAUGAUCAUCGAAAACUCCCACGUGAAGAAGGACGAU
AUUUGGCCCUCCGGAGGUCAAAUGACCGUGAAGGACCUGACCGCAAA
GUACACCGAGGGAGGAAACGCCAUUCUCGAAAACAUCAGCUUCUCCA
UUUCGCGGGACAGCGGGUCGGCCUUCUCGGGCGGACCGGUUCCGGG
AAGUCAACUCUGCUGCGGCUUUCCUCCGGCUGCUGAAUACCGAGGG
GGAAAUCCAAAUUGACGGCGUGUCUUGGGAUUCCAUUACUCUGCAGC
AGUGGCGGAAGGCCUUCGGCGUGAUCCCCAGAAGGUGUUCAUCUUC
UCGGGUACCUUCCGGAAGAACCUGGAUCCUUACGAGCAGUGGAGCGA
CCAAGAAAUCUGGAAGGUCGCCGACGAGGUCGGCCUGCGCUCCGUGA
UUGAACAAUUUCCUGGAAAGCUGGACUUCGUGCUCGUCGACGGGGG
AUGUGUCCUGUCGCACGGACAUAAGCAGCUCAUGUGCCUCGCACGGU
CCGUGCUCUCCAAGGCCAAGAUUCUGCUGCUGGACGAACCUUCGCC
CACCUGGAUCCGGUCACCUACCAGAUCAUCAGGAGGACCCUGAAGCA
GGCCUUUGCCGAUUGCACCGUGAUUCUCUGCGAGCACCGCAUCGAGG
CCAUGCUGGAGUGCCAGCAGUUCCUGGUCAUCGAGGAGAACAAGGUC
CGCCAAUACGACUCCAUUCAAAAGCUCCUCAACGAGCGGUCGCUGUU
CAGACAAGCUAUUUCACCGUCCGAUAGAGUGAAGCUCUUCCCGCAUC
GGAACAGCUCAAAGUGCAAAUCGAAGCCGCAGAUCGCAGCCUUGAAG
GAAGAGACUGAGGAAGAGGUGCAGGACACCCCGGCUUUAA (SEQ ID
NO: 1)
```

Human MQRSPLEKASVVSKLFFSWTRPILRKGYRQRLELSDIYQIPSVDSADNLSEK
CFTR LEREWDRELASKKNPKLINALRRCFFWRFMFYGIFLYLGEVTKAVQPLLL
Protein GRIIASYDPDNKEERSIAIYLGIGLCLLFIVRTLLLHPAIFGLHHIGMQMRIA
Sequence MFSLIYKKTLKLSSRVLDKISIGQLVSLLSNNLNKFDEGLALAHFVWIAPLQ
VALLMGLIWELLQASAFCGLGFLIVLALFQAGLGRMMMKYRDQRAGKIS
ERLVITSEMIENIQSVKAYCWEEAMEKMIENLRQTELKLTRKAAYVRYFN
SSAFFFSGFFVVFLSVLPYALIKGIILRKIFTTISFCIVLRMAVTRQFPWAVQT
WYDSLGAINKIQDFLQKQEYKTLEYNLTTTEVVMENVTAFWEEGFGELFE
KAKQNNNNRKTSNGDDSLFFSNFSLLGTPVLKDINFKIERGQLLAVAGSTG
AGKTSLLMVIMGELEPSEGKIKHSGRISFCSQFSWIMPGTIKENIIFGVSYDE
YRYRSVIKACQLEEDISKFAEKDNIVLGEGGITLSGGQRARISLARAVYKD
ADLYLLDSPFGYLDVLTEKEIFESCVCKLMANKTRILVTSKMEHLKKADKI
LILHEGSSYFYGTFSELQNLQPDFSSKLMGCDSFDQFSAERRNSILTETLHR
FSLEGDAPVSWTETKKQSFKQTGEFGEKRKNSILNPINSIRKFSIVQKTPLQ
MNGIEEDSDEPLERRLSLVPDSEQGEAILPRISVISTGPTLQARRRQSVLNL
MTHSVNQGQNIHRKTTASTRKVSLAPQANLTELDIYSRRLSQETGLEISEEI
NEEDLKECFFDDMESIPAVTTWNTYLRYITVHKSLIFVLIWCLVIFLAEVAA TABLE 2-continued Exemplary CFTR mRNA and Protein Sequences

```
SLVVLWLLGNTPLQDKGNSTHSRNNSYAVIITSTSSYYVFYIYVGVADTLL
AMGFFRGLPLVHTLITVSKILHHKMLHSVLQAPMSTLNTLKAGGILNRFSK
DIAILDDLLPLTIFDFIQLLLIVIGAIAVVAVLQPYIFVATVPVIVAFIMLRAY
FLQTSQQLKQLESEGRSPIFTHLVTSLKGLWTLRAFGRQPYFETLFHKALN
LHTANWFLYLSTLRWFQMRIEMIFVIFFIAVTFISILTTGEGEGRVGIILTLA
MNIMSTLQWAVNSSIDVDSLMRSVSRVFKFIDMPTEGKPTKSTKPYKNGQ
LSKVMIIENSHVKKDDIWPSGGQMTVKDLTAKYTEGGNAILENISFSISPGQ
RVGLLGRTGSGKSTLLSAFLRLLNTEGEIQIDGVSWDSITLQQWRKAFGVIP
QKVFIFSGTFRKNLDPYEQWSDQEIWKVADEVGLRSVIEQFPGKLDFVLVD
GGCVLSHGHKQLMCLARSVLSKAKILLLDEPSAHLDPVTYQIIRRTLKQAF
ADCTVILCEHRIEAMLECQQFLVIEENKVRQYDSIQKLLNERSLFRQAISPS
DRVKLFPHRNSSKCKSKPQIAALKEETEEEVQDTRL (SEQ ID NO: 2)
```

In one embodiment, a codon-optimized CFTR mRNA sequence includes SEQ ID NO: 1. In some embodiments, a codon-optimized CFTR mRNA sequence suitable for the present invention shares at least 60%, 65%, 70%, 75%, 80%, 85%, 90%, 95%, 96%, 97%, 98%, or 99% identity to SEQ ID NO:1 and encodes a CFTR protein having an amino acid sequence of SEQ ID NO:2.

In some embodiments, a CFTR mRNA suitable for the invention also contains 5' and 3' UTR sequences. Exemplary 5' and 3' UTR sequences are shown below:

```
Exemplary 5' UTR Sequence
                                         (SEQ ID NO: 3)
GGACAGAUCGCCUGGAGACGCCAUCCACGCUGUUUUGACCUCCAUAGAAGA

CACCGGGACCGAUCCAGCCUCCGCGGCCGGGAACGGUGCAUUGGAACGCGG

AUUCCCCGUGCCAAGAGUGACUCACCGUCCUUGACACG
```

```
Exemplary 3' UTR Sequence
                                         (SEQ ID NO: 4)
CGGGUGGCAUCCCUGUGACCCCUCCCCAGUGCCUCUCCUGGCCCUGGAAGU

UGCCACUCCAGUGCCCACCAGCCUUGUCCUAAUAAAAUUAAGUUGCAUCAA

GCU
or
                                         (SEQ ID NO: 5)
GGGUGGCAUCCCUGUGACCCCUCCCCAGUGCCUCUCCUGGCCCUGGAAGUU

GCCACUCCAGUGCCCACCAGCCUUGUCCUAAUAAAAUUAAGUUGCAUCAAA

GCU
```

Thus, in one embodiment, an exemplary full-length codon-optimized CFTR mRNA sequence suitable for the invention is:

```
                                         (SEQ ID NO: 6)
GGACAGAUCGCCUGGAGACGCCAUCCACGCUGUUUUGACCUCCAUAGAAGACACCGG

GACCGAUCCAGCCUCCGCGGCCGGGAACGGUGCAUUGGAACGCGGAUUCCCCGUGCC

AAGAGUGACUCACCGUCCUUGACACGAUGCAACGCUCUCCUCUUGAAAAGGCCUCGG

UGGUGUCCAAGCUCUUCUUCUCGUGGACUAGACCCAUCCUGAGAAAGGGGUACAGAC

AGCGCUUGGAGCUGUCCGAUAUCUAUCAAAUCCCUUCCGUGGACUCCGCGGACAACC

UGUCCGAGAAGCUCGAGAGAGAAUGGGACAGAGAACUCGCCUCAAAGAAGAACCCGA

AGCUGAUUAAUGCGCUUAGGCGGUGCUUUUUCUGGCGGUUCAUGUUCUACGGCAUC

UUCCUCUACCUGGGAGAGGUCACCAAGGCCGUGCAGCCCCUGUUGCUGGGACGGAUU

AUUGCCUCCUACGACCCCGACAACAAGGAAGAAAGAAGCAUCGCUAUCUACUUGGGC

AUCGGUCUGUGCCUGCUUUUCAUCGUCCGGACCCUCUUGUUGCAUCCUGCUAUUUUC

GGCCUGCAUCACAUUGGCAUGCAGAUGAGAAUUGCCAUGUUUUCCCUGAUCUACAAG

AAAACUCUGAAGCUCUCGAGCCGCGUGCUUGACAAGAUUUCCAUCGGCCAGCUCGUG

UCCCUGCUCUCCAACAAUCUGAACAAGUUCGACGAGGGCCUCGCCCUGGCCCACUUC

GUGUGGAUCGCCCCUCUGCAAGUGGCGCUUCUGAUGGGCUGAUCUGGGGAGCUGCUG

CAAGCCUCGGCAUUCUGUGGGCUUGGAUUCCUGAUCGUGCUGGCACUGUUCCAGGCC

GGACUGGGGCGAUGAUGAUGAAGUACAGGGACCAGAGAGCCGGAAAGAUUUCCGA

ACGGCUGGUGAUCACUUCGGAAAUGAUCGAAAACAUCCAGUCAGUGAAGGCCUACUG

CUGGGAAGAGGCCAUGGAAAAGAUGAUUGAAAACCUCCGGCAAACCGAGCUGAAGC

UGACCCGCAAGGCCGCUUACGUGCGCUAUUUCAACUCGUCCGCUUUCUUCUUCUCCG
```

-continued

```
GGUUCUUCGUGGUGUUUCUCUCCGUGCUCCCCUACGCCCUGAUUAAGGGAAUCAUCC
UCAGGAAGAUCUUCACCACCAUUUCCUUCUGUAUCGUGCUCCGCAUGGCCGUGACCC
GGCAGUUCCCAUGGGCCGUGCAGACUUGGUACGACUCCCUGGGAGCCAUUAACAAGA
UCCAGGACUUCCUUCAAAAGCAGGAGUACAAGACCCUCGAGUACAACCUGACUACUA
CCGAGGUCGUGAUGGAAAACGUCACCGCCUUUUGGGAGGAGGGAUUUGGCGAACUG
UUCGAGAAGGCCAAGCAGAACAACAACAACCGCAAGACCUCGAACGGUGACGACUCC
CUCUUCUUUUCAAACUUCAGCCUGCUCGGGACGCCCGUGCUGAAGGACAUUAACUUC
AAGAUCGAAAGAGGACAGCUCCUGGCGGUGGCCGGAUCGACCGGAGCCGGAAAGACU
UCCCUGCUGAUGGUGAUCAUGGGAGAGCUUGAACCUAGCGAGGGAAAGAUCAAGCA
CUCCGGCCGCAUCAGCUUCUGUAGCCAGUUUCCUGGAUCAUGCCCGGAACCAUUAA
GGAAAACAUCAUCUUCGGCGUGUCCUACGAUGAAUACCGCUACCGGUCCGUGAUCAA
AGCCUGCCAGCUGGAAGAGGAUAUUUCAAAGUUCGCGGAGAAAGAUAACAUCGUGC
UGGGCGAAGGGGUAUUACCUUGUCGGGGGCCAGCGGGCUAGAAUCUCGCUGGCCA
GAGCCGUGUAUAAGGACGCCGACCUGUAUCUCCUGGACUCCCCCUUCGGAUACCUGG
ACGUCCUGACCGAAAAGGAGAUCUUCGAAUCGUGCGUGUGCAAGCUGAUGGCUAACA
AGACUCGCAUCCUCGUGACCUCCAAAAUGGAGCACCUGAAGAAGGCAGACAAGAUUC
UGAUUCUGCAUGAGGGGUCCUCCUACUUUUACGGCACCUUCUCGGAGUUGCAGAACU
UGCAGCCCGACUUCUCAUCGAAGCUGAUGGGUUGCGACAGCUUCGACCAGUUCUCCG
CCGAAAGAAGGAACUCGAUCCUGACGGAAACCUUGCACCGCUUCUCUUUGGAAGGCG
ACGCCCCUGUGUCAUGGACCGAGACUAAGAAGCAGAGCUUCAAGCAGACCGGGGAAU
UCGGCGAAAAGAGGAAGAACAGCAUCUUGAACCCCAUUAACUCCAUCCGCAAGUUCU
CAAUCGUGCAAAAGACGCCACUGCAGAUGAACGGCAUUGAGGAGGACUCCGACGAAC
CCCUUGAGAGGCGCCUGUCCCUGGUGCCGGACAGCGAGCAGGGAGAAGCCAUCCUGC
CUCGGAUUUCCGUGAUCUCCACUGGUCCGACGCUCCAAGCCCGGCGGCGGCAGUCCG
UGCUGAACCUGAUGACCCACAGCGUGAACCAGGGCCAAAACAUUCACCGCAAGACUA
CCGCAUCCACCCGGAAAGUGUCCCUGGCACCUCAAGCGAAUCUUACCGAGCUCGACA
UCUACUCCCGGAGACUGUCGCAGGAAACCGGGCUCGAAAUUUCCGAAGAAAUCAACG
AGGAGGAUCUGAAAGAGUGCUUCUUCGACGAUAUGGAGUCGAUACCCGCCGUGACG
ACUUGGAACACUUAUCUGCGGUACAUCACUGUGCACAAGUCAUUGAUCUUCGUGCUG
AUUUGGUGCCUGGUGAUUUUCCUGGCCGAGGUCGCGGCCUCACUGGUGGUGCUCUGG
CUGUUGGGAAACACGCCUCUGCAAGACAAGGGAAACUCCACGCACUCGAGAAACAAC
AGCUAUGCCGUGAUUAUCACUUCCACCUCCUCUUAUUACGUGUUCUACAUCUACGUC
GGAGUGGCGGAUACCCUGCUCGCGAUGGGUUUCUUCAGAGGACUGCCGCUGGUCCAC
ACCUUGAUCACCGUCAGCAAGAUUCUUCACCACAAGAUGUUGCAUAGCGUGCUGCAG
GCCCCCAUGUCCACCCUCAACACUCUGAAGGCCGGAGGCAUUCUGAACAGAUUCUCC
AAGGACAUCGCUAUCCUGGACGAUCUCCUGCCGCUUACCAUCUUUGACUUCAUCCAG
CUGCUGCUGAUCGUGAUUGGAGCAAUCGCAGUGGUGGCGGUGCUGCAGCCUUACAUU
UUCGUGGCCACUGUGCCGGUCAUUGUGGCGUUCAUCAUGCUGCGGGCCUACUUCCUC
CAAACCAGCCAGCAGCUGAAGCAACUGGAAUCCGAGGGACGAUCCCCAUCUUCACU
CACCUUGUGACGUCGUUGAAGGGACUGUGGACCCUCCGGGCUUUCGGACGGCAGCCC
```

-continued

```
UACUUCGAAACCCUCUUCCACAAGGCCCUGAACCUCCACACCGCCAAUUGGUUCCUG
UACCUGUCCACCCUGCGGUGGUUCCAGAUGCGCAUCGAGAUGAUUUUCGUCAUCUUC
UUCAUCGCGGUCACAUUCAUCAGCAUCCUGACUACCGGAGAGGGAGAGGGACGGGUC
GGAAUAAUCCUGACCCUCGCCAUGAACAUUAUGAGCACCCUGCAGUGGGCAGUGAAC
AGCUCGAUCGACGUGGACAGCCUGAUGCGAAGCGUCAGCCGCGUGUUCAAGUUCAUC
GACAUGCCUACUGAGGGAAAACCCACUAAGUCCACUAAGCCCUACAAAAAUGGCCAG
CUGAGCAAGGUCAUGAUCAUCGAAAACUCCCACGUGAAGAAGGACGAUAUUUGGCCC
UCCGGAGGUCAAAUGACCGUGAAGGACCUGACCGCAAAGUACACCGAGGGAGGAAAC
GCCAUUCUCGAAAACAUCAGCUUCUCCAUUUCGCCGGGACAGCGGGUCGGCCUUCUC
GGGCGGACCGGUUCCGGGAAGUCAACUCUGCUGUCGGCUUUCCUCCGGCUGCUGAAU
ACCGAGGGGAAAUCCAAAUUGACGGCGUGUCUUGGGAUUCCAUUACUCUGCAGCAG
UGGCGGAAGGCCUUCGGCGUGAUCCCCCAGAAGGUGUUCAUCUUCUCGGGUACCUUC
CGGAAGAACCUGGAUCCUUACGAGCAGUGGAGCGACCAAGAAAUCUGGAAGGUCGCC
GACGAGGUCGGCCUGCGCUCCGUGAUUGAACAAUUUCCUGGAAAGCUGGACUUCGUG
CUCGUCGACGGGGAUGUGUCCUGUCGCACGGACAUAAGCAGCUCAUGUGCCUCGCA
CGGUCCGUGCUCUCCAAGGCCAAGAUUCUGCUGCUGGACGAACCUUCGGCCCACCUG
GAUCCGGUCACCUACCAGAUCAUCAGGAGGACCCUGAAGCAGGCCUUUGCCGAUUGC
ACCGUGAUUCUCUGCGAGCACCGCAUCGAGGCCAUGCUGGAGUGCCAGCAGUUCCUG
GUCAUCGAGGAGAACAAGGUCCGCCAAUACGACUCCAUUCAAAAGCUCCUCAACGAG
CGGUCGCUGUUCAGACAAGCUAUUUCACCGUCCGAUAGAGUGAAGCUCUUCCCGCAU
CGGAACAGCUCAAAGUGCAAAUCGAAGCCGCAGAUCGCAGCCUUGAAGGAAGAGACU
GAGGAAGAGGUGCAGGACACCCGGCUUUAACGGGUGGCAUCCCUGUGACCCCUCCCC
AGUGCCUCUCCUGGCCCUGGAAGUUGCCACUCCAGUGCCCACCAGCCUUGUCCUAAU
AAAAUUAAGUUGCAUCAAGCU
                                                          40
```

In another embodiment, an exemplary full-length codon-optimized CFTR mRNA sequence is:

(SEQ ID NO: 7)
```
GGACAGAUCGCCUGGAGACGCCAUCCACGCUGUUUUGACCUCCAUAGAAGACACCGG
GACCGAUCCAGCCUCCGCGGCCGGGAACGGUGCAUUGGAACGCGGAUUCCCCGUGCC
AAGAGUGACUCACCGUCCUUGACACGAUGCAACGCUCUCCUCUUGAAAAGGCCUCGG
UGGUGUCCAAGCUCUUCUUCUCGUGGACUAGACCCAUCCUGAGAAAGGGGUACAGAC
AGCGCUUGGAGCUGUCCGAUAUCUAUCAAAUCCCUUCCGUGGACUCCGCGGACAACC
UGUCCGAGAAGCUCGAGAGAGAAUGGGACAGAGAACUCGCCUCAAAGAAGAACCCGA
AGCUGAUUAAUGCGCUUAGGCGGUGCUUUUUCUGGCGGUUCAUGUUCUACGGCAUC
UUCCUCUACCUGGGAGAGGUCACCAAGGCCGUGCAGCCCCUGUUGCUGGGACGGAUU
AUUGCCUCCUACGACCCCGACAACAAGGAAGAAAGAAGCAUCGCUAUCUACUUGGGC
AUCGGUCUGUGCCUGCUUUUCAUCGUCCGGACCCUCUUGUUGCAUCCUGCUAUUUUC
GGCCUGCAUCACAUUGGCAUGCAGAUGAGAAUUGCCAUGUUUUCCCUGAUCUACAAG
AAAACUCUGAAGCUCUCGAGCCGCUGUCUUGACAAGAUUCCAUCGGCCAGCUCGUG
UCCCUGCUCUCCAACAAUCUGAACAAGUUCGACGAGGGCCUCGCCCUGGCCCACUUC
```

-continued

```
GUGUGGAUCGCCCCUCUGCAAGUGGCGCUUCUGAUGGGCCUGAUCUGGGAGCUGCUG
CAAGCCUCGGCAUUCUGUGGGCUUGGAUUCCUGAUCGUGCUGGCACUGUUCCAGGCC
GGACUGGGGCGGAUGAUGAUGAAGUACAGGGACCAGAGAGCCGGAAAGAUUUCCGA
ACGGCUGGUGAUCACUUCGGAAAUGAUCGAAAACAUCCAGUCAGUGAAGGCCUACUG
CUGGGAAGAGGCCAUGGAAAAGAUGAUUGAAAACCUCCGGCAAACCGAGCUGAAGC
UGACCCGCAAGGCCGCUUACGUGCGCUAUUUCAACUCGUCCGCUUUCUUCUUCUCCG
GGUUCUUCGUGGUGUUUCUCUCCGUGCUCCCCUACGCCCUGAUUAAGGGAAUCAUCC
UCAGGAAGAUCUUCACCACCAUUUCCUUCUGUAUCGUGCUCCGCAUGGCCGUGACCC
GGCAGUUCCCAUGGGCCGUGCAGACUUGGUACGACUCCCUGGGAGCCAUUAACAAGA
UCCAGGACUUCCUUCAAAAGCAGGAGUACAAGACCCUCGAGUACAACCUGACUACUA
CCGAGGUCGUGAUGGAAAACGUCACCGCCUUUUGGGAGGAGGGAUUUGGCGAACUG
UUCGAGAAGGCCAAGCAGAACAACAACAACCGCAAGACCUCGAACGGUGACGACUCC
CUCUUCUUUUCAAACUUCAGCCUGCUCGGGACGCCCGUGCUGAAGGACAUUAACUUC
AAGAUCGAAAGAGGACAGCUCCUGGCGGUGGCCGGAUCGACCGGAGCCGGAAAGACU
UCCCUGCUGAUGGUGAUCAUGGGAGAGCUUGAACCUAGCGAGGGAAAGAUCAAGCA
CUCCGGCCGCAUCAGCUUCUGUAGCCAGUUUUCCUGGAUCAUGCCCGGAACCAUUAA
GGAAAACAUCAUCUUCGGCGUGUCCUACGAUGAAUACCGCUACCGGUCCGUGAUCAA
AGCCUGCCAGCUGGAAGAGGAUAUUUCAAAGUUCGCGGAGAAAGAUAACAUCGUGC
UGGGCGAAGGGGUAUUACCUUGUCGGGGGGCCAGCGGGCUAGAAUCUCGCUGGCCA
GAGCCGUGUAUAAGGACGCCGACCUGUAUCUCCUGGACUCCCCCUUCGGAUACCUGG
ACGUCCUGACCGAAAAGGAGAUCUUCGAAUCGUGCGUGUGCAAGCUGAUGGCUAACA
AGACUCGCAUCCUCGUGACCUCCAAAAUGGAGCACCUGAAGAAGGCAGACAAGAUUC
UGAUUCUGCAUGAGGGGUCCUCCUACUUUUACGGCACCUUCUCGGAGUUGCAGAACU
UGCAGCCCGACUUCUCAUCGAAGCUGAUGGGUUGCGACAGCUUCGACCAGUUCUCCG
CCGAAAGAAGGAACUCGAUCCUGACGGAAACCUUGCACCGCUUCUCUUUGGAAGGCG
ACGCCCCUGUGUCAUGGACCGAGACUAAGAAGCAGAGCUUCAAGCAGACCGGGGAAU
UCGGCGAAAAGAGGAAGAACAGCAUCUUGAACCCCAUUAACUCCAUCCGCAAGUUCU
CAAUCGUGCAAAAGACGCCACUGCAGAUGAACGGCAUUGAGGAGGACUCCGACGAAC
CCCUUGAGAGGCGCCUGUCCCUGGUGCCGGACAGCGAGCAGGGAGAAGCCAUCCUGC
CUCGGAUUUCCGUGAUCUCCACUGGUCCGACGCUCCAAGCCCGGCGGCGGCAGUCCG
UGCUGAACCUGAUGACCCACAGCGUGAACCAGGGCCAAAACAUUCACCGCAAGACUA
CCGCAUCCACCCGGAAAGUGUCCCUGGCACCUCAAGCGAAUCUUACCGAGCUCGACA
UCUACUCCCGGAGACUGUCGCAGGAAACCGGGCUCGAAAUUUCCGAAGAAAUCAACG
AGGAGGAUCUGAAAGAGUGCUUCUUCGACGAUAUGGAGUCGAUACCCGCCGUGACG
ACUUGGAACACUUAUCUGCGGUACAUCACUGUGCACAAGUCAUUGAUCUUCGUGCUG
AUUUGGUGCCUGGUGAUUUUCCUGGCCGAGGUCGCGGCCUCACUGGUGGUGCUCUGG
CUGUUGGGAAACACGCCUCUGCAAGCAAGGGAAACUCCACGCACUCGAGAAACAAC
AGCUAUGCCGUGAUUAUCACUUCCACCUCCUCUUAUUACGUGUUCUACAUCUACGUC
GGAGUGGCGGAUACCCUGCUCGCGAUGGGUUUCUUCAGAGGACUGCCGCUGGUCCAC
ACCUUGAUCACCGUCAGCAAGAUUCUUCACCACAAGAUGUUGCAUAGCGUGCUGCAG
GCCCCCAUGUCCACCCUCAACACUCUGAAGGCCGGAGGCAUUCUGAACAGAUUCUCC
```

```
AAGGACAUCGCUAUCCUGGACGAUCUCCUGCCGCUUACCAUCUUUGACUUCAUCCAG

CUGCUGCUGAUCGUGAUUGGAGCAAUCGCAGUGGUGGCGGUGCUGCAGCCUUACAUU

UUCGUGGCCACUGUGCCGGUCAUUGUGGCGUUCAUCAUGCUGCGGGCCUACUUCCUC

CAAACCAGCCAGCAGCUGAAGCAACUGGAAUCCGAGGGACGAUCCCCCAUCUUCACU

CACCUUGUGACGUCGUUGAAGGGACUGUGGACCCUCCGGGCUUUCGGACGGCAGCCC

UACUUCGAAACCCUCUUCCACAAGGCCCUGAACCUCCACACCGCCAAUUGGUUCCUG

UACCUGUCCACCCUGCGGUGGUUCCAGAUGCGCAUCGAGAUGAUUUUCGUCAUCUUC

UUCAUCGCGGUCACAUUCAUCAGCAUCCUGACUACCGGAGAGGGAGAGGGACGGGUC

GGAAUAAUCCUGACCCUCGCCAUGAACAUUAUGAGCACCCUGCAGUGGGCAGUGAAC

AGCUCGAUCGACGUGGACAGCCUGAUGCGAAGCGUCAGCCGCGUGUUCAAGUUCAUC

GACAUGCCUACUGAGGGAAAACCCACUAAGUCCACUAAGCCCUACAAAAAUGGCCAG

CUGAGCAAGGUCAUGAUCAUCGAAAACUCCCACGUGAAGAAGGACGAUAUUUGGCCC

UCCGGAGGUCAAAUGACCGUGAAGGACCUGACCGCAAAGUACACCGAGGGAGGAAAC

GCCAUUCUCGAAAACAUCAGCUUCUCCAUUUCGCCGGGACAGCGGGUCGGCCUUCUC

GGGCGGACCGGUUCCGGGAAGUCAACUCUGCUGUCGGCUUUCCUCCGGCUGCUGAAU

ACCGAGGGGAAAUCCAAAUUGACGGCGUGUCUUGGGAUUCCAUUACUCUGCAGCAG

UGGCGGAAGGCCUUCGGCGUGAUCCCCAGAAGGUGUUCAUCUUCUCGGGUACCUUC

CGGAAGAACCUGGAUCCUUACGAGCAGUGGAGCGACCAAGAAAUCUGGAAGGUCGCC

GACGAGGUCGGCCUGCGCUCCGUGAUUGAACAAUUUCCUGGAAAGCUGGACUUCGUG

CUCGUCGACGGGGAUGUGUCCUGUCGCACGGACAUAAGCAGCUCAUGUGCCUCGCA

CGGUCCGUGCUCUCCAAGGCCAAGAUUCUGCUGCUGGACGAACCUUCGGCCCACCUG

GAUCCGGUCACCUACCAGAUCAUCAGGAGGACCCUGAAGCAGGCCUUUGCCGAUUGC

ACCGUGAUUCUCUGCGAGCACCGCAUCGAGGCCAUGCUGGAGUGCCAGCAGUUCCUG

GUCAUCGAGGAGAACAAGGUCCGCCAAUACGACUCCAUUCAAAAGCUCCUCAACGAG

CGGUCGCUGUUCAGACAAGCUAUUUCACCGUCCGAUAGAGUGAAGCUCUUCCCGCAU

CGGAACAGCUCAAAGUGCAAAUCGAAGCCGCAGAUCGCAGCCUUGAAGGAAGAGACU

GAGGAAGAGGUGCAGGACACCCGGCUUUAAGGGUGGCAUCCCUGUGACCCCUCCCCA

GUGCCUCUCCUGGCCCUGGAAGUUGCCACUCCAGUGCCCACCAGCCUUGUCCUAAUA

AAAUUAAGUUGCAUCAAAGCU
```

In another embodiment, an exemplary codon-optimized CFTR mRNA sequence is:

(SEQ ID NO: 8)
```
ATGCAGAGGAGCCCACTGGAGAAAGCCTCCGTGGTGAGTAAACTCTTTTTTAGTTGGAC

CAGACCCATCCTGCGAAAAGGATACAGGCAGCGCCTCGAGTTGTCAGATATCTACCAG

ATTCCTTCTGTGGACTCAGCTGACAATTTGAGTGAGAAGCTGGAGCGGGAGTGGGATAG

AGAGCTGGCGAGCAAAAAAAACCCCAAGCTTATCAATGCTCTGCGCCGCTGCTTTTTCT

GGAGGTTCATGTTTTATGGGATCTTCCTGTACCTGGGGGAGGTCACCAAAGCTGTTCAG

CCGCTCCTTCTTGGCCGCATCATCGCCAGCTATGACCCTGATAATAAAGAAGAAAGGTC

TATTGCTATTTATCTGGGAATTGGCCTCTGCTTGCTCTTCATCGTCCGCACCCTTCTGCTG

CACCCTGCCATTTTTGGCCTTCACCACATCGGCATGCAAATGAGAATTGCCATGTTCTCC
```

-continued

```
CTCATTTACAAAAAGACCCTGAAACTTTCCTCAAGAGTGTTAGATAAAATATCCATTGG

TCAGCTGGTCAGCCTGCTGTCCAACAATCTTAACAAATTTGATGAAGGCTTGGCGCTGG

CCCACTTCGTGTGGATTGCACCTCTGCAGGTGGCCCTGTTGATGGGACTTATATGGGAG

CTGCTTCAAGCCTCTGCTTTCTGTGGGCTGGCTTTTTGATTGTACTGGCACTTTTTCAGG

CTGGGCTCGGAAGAATGATGATGAAATACAGAGATCAGCGGGCCGGGAAGATATCAGA

GCGACTTGTGATCACCAGTGAAATGATTGAAAATATTCAGAGCGTGAAAGCCTACTGCT

GGGAAGAAGCCATGGAGAAGATGATTGAGAACCTGAGGCAGACAGAGCTCAAGCTCAC

TCGGAAGGCTGCTTATGTTCGCTATTTCAACAGCAGCGCCTTCTTCTTCAGTGGCTTCTT

TGTTGTCTTCCTGTCTGTTCTGCCATATGCACTGATAAAAGGCATTATTTTACGAAAGAT

CTTCACCACCATCAGTTTTTGCATCGTTCTCAGGATGGCCGTCACAAGACAGTTCCCCTG

GGCTGTGCAGACCTGGTACGATTCCTTGGGGGCCATCAACAAGATTCAAGATTTCTTGC

AAAAACAAGAATATAAAACTTTAGAATACAACCTCACCACCACTGAAGTGGTCATGGA

AAATGTGACAGCCTTTTGGGAGGAGGGTTTTGGAGAATTGTTCGAGAAGGCAAAGCAG

AATAACAACAACAGGAAGACGAGCAATGGGGACGACTCTCTCTTCTTCAGCAACTTTTC

ACTGCTCGGGACCCCTGTGTTGAAAGATATAAACTTCAAGATCGAGAGGGGCCAGCTCT

TGGCTGTGGCAGGCTCCACTGGAGCTGGTAAAACATCTCTTCTCATGGTGATCATGGGG

GAACTGGAGCCTTCCGAAGGAAAAATCAAGCACAGTGGGAGAATCTCATTCTGCAGCC

AGTTTTCCTGGATCATGCCCGGCACCATTAAGGAAAACATCATATTTGGAGTGTCCTAT

GATGAGTACCGCTACCGGTCAGTCATCAAAGCCTGTCAGTTGGAGGAGGACATCTCCAA

GTTTGCAGAGAAAGACAACATTGTGCTTGGAGAGGGGGGTATCACTCTTTCTGGAGGAC

AAAGAGCCAGGATCTCTTTGGCCCGGGCAGTCTACAAGGATGCAGACCTCTACTTGTTG

GACAGTCCCTTCGGCTACCTCGACGTGCTGACTGAAAAAGAAATTTTTGAAAGCTGTGT

GTGCAAACTGATGGCAAACAAGACCAGGATTCTTGTCACCAGCAAGATGGAACATCTG

AAGAAAGCGGACAAAATTCTGATTCTGCATGAAGGGAGCTCCTACTTCTATGGAACATT

TAGCGAGCTTCAGAACCTACAGCCAGACTTCTCCTCCAAATTAATGGGCTGTGACTCCT

TCGACCAGTTCTCTGCAGAAAGAAGAAACTCTATACTCACAGAGACCCTCCACCGCTTC

TCCCTTGAGGGAGATGCCCCAGTTTCTTGGACAGAAACCAAGAAGCAGTCCTTTAAGCA

GACTGGCGAGTTTGGTGAAAAGAGGAAAAATTCAATTCTCAATCCAATTAACAGTATTC

GCAAGTTCAGCATTGTCCAGAAGACACCCCTCCAGATGAATGGCATCGAAGAAGATAG

TGACGAGCCGCTGGAGAGACGGCTGAGTCTGGTGCCAGATTCAGAACAGGGGGAGGCC

ATCCTGCCCCGGATCAGCGTCATTTCCACAGGCCCCACATTACAAGCACGGCGCCGGCA

GAGTGTTTTAAATCTCATGACCCATTCAGTGAACCAGGGCCAAAATATCCACAGGAAGA

CTACAGCTTCTACCCGGAAAGTGTCTCTGGCCCCTCAGGCCAATCTGACCGAGCTGGAC

ATCTACAGCAGGAGGCTCTCCCAGGAAACAGGGCTGGAAATATCTGAAGAGATTAATG

AAGAGGATCTTAAAGAGTGCTTCTTTGATGACATGGAGAGCATCCCCGCGGTGACCACA

TGGAACACCTACCTTAGATATATTACTGTCCACAAGAGCCTCATATTTGTCCTCATCTGG

TGCCTGGTTATTTTCCTCGCTGAGGTGGCGGCCAGTCTTGTTGTGCTCTGGCTGCTGGGC

AACACTCCTCTCCAGGACAAGGGCAATAGTACTCACAGCAGAAATAATTCTTATGCCGT

CATCATTACAAGCACCTCCAGCTACTACGTGTTCTACATCTATGTGGGCGTGGCTGACA

CCCTCCTGGCCATGGGTTTCTTCCGGGGCCTGCCTTTGGTGCACACCCTCATCACAGTGT
```

```
-continued
CAAAAATTCTGCACCATAAAATGCTTCATTCTGTCCTGCAGGCACCCATGAGCACTTTG

AACACATTGAAGGCTGGCGGCATCCTCAACAGATTTTCTAAAGATATTGCTATCCTGGA

TGATCTCCTCCCCCTGACAATCTTTGACTTTATCCAGCTTCTGCTGATCGTGATTGGAGC

CATAGCAGTGGTTGCTGTCCTGCAGCCCTACATTTTTGTGGCCACCGTGCCCGTGATTGT

TGCCTTTATTATGCTCAGAGCTTACTTCCTGCAAACTTCTCAACAGCTCAAACAGCTAGA

ATCTGAGGGCCGGAGCCCCATTTTTACCCACCTGGTGACTTCCCTGAAGGGACTGTGGA

CTCTGAGAGCATTCGGGCGACAGCCTTACTTTGAGACACTGTTCCACAAGGCCCTGAAC

TTGCACACTGCCAACTGGTTTCTTTACCTGAGCACACTCCGCTGGTTCCAGATGCGGATA

GAGATGATCTTCGTCATCTTTTTTATAGCTGTAACCTTCATTTCTATCCTTACAACAGGA

GAAGGAGAGGGCAGGGTGGGAATCATCCTCACGCTGGCTATGAACATAATGTCCACCT

TGCAGTGGGCCGTGAATTCCAGTATAGATGTGGATTCTCTAATGAGGAGTGTCTCCCGG

GTGTTTAAATTCATTGATATGCCTACTGAGGGGAAACCCACCAAGTCAACAAAACCTTA

TAAGAATGGACAGCTGAGCAAGGTGATGATAATTGAGAACAGCCACGTGAAGAAGGAT

GACATTTGGCCCAGCGGGGGCCAGATGACTGTGAAGGACCTGACGGCCAAGTACACCG

AAGGTGGAAATGCCATTTTGGAAAACATCAGCTTCTCAATCTCTCCTGGGCAGAGAGTT

GGATTGCTGGGTCGCACGGGCAGCGGCAAATCAACCCTGCTCAGTGCCTTCCTTCGGCT

CCTGAATACAGAAGGCGAAATCCAAATTGACGGGGTGAGCTGGGACAGCATCACCCTG

CAGCAGTGGAGAAAAGCATTTGGGGTCATTCCACAGAAAGTTTTCATCTTCTCTGGCAC

TTTCAGAAAGAACCTGGACCCCTATGAGCAGTGGAGCGACCAGGAGATCTGGAAGGTT

GCAGATGAAGTTGGCCTGCGGAGTGTGATAGAACAATTTCCTGGCAAGCTGGATTTTGT

GCTGGTAGATGGAGGCTGCGTGCTGTCCCACGGCCACAAACAGCTGATGTGCCTCGCCC

GCTCCGTTCTTTCAAAGGCCAAAATCTTGCTTTTGGATGAGCCCAGTGCTCACCTCGACC

CAGTGACCTATCAGATAATCCGCAGGACCTTAAAGCAAGCTTTTGCCGACTGCACCGTC

ATACTGTGTGAGCACCGGATTGAAGCAATGCTGGAATGCCAGCAGTTTCTGGTGATCGA

GGAGAATAAGGTCCGGCAGTACGACAGCATCCAGAAGTTGTTGAATGAGCGCAGCCTT

TTCCGCCAGGCCATCTCCCCATCTGACAGAGTCAAGCTGTTTCCACATAGGAACTCCTCT

AAGTGCAAGTCCAAGCCCCAGATCGCTGCCCTCAAGGAGGAAACTGAGGAAGAGGTGC

AGGATACCCGCCTGTGA
```

In another embodiment, an exemplary codon-optimized CFTR mRNA sequence is:

```
                                                        (SEQ ID NO: 9)
ATGCAGAGGAGCCCACTGGAGAAAGCCTCCGTGGTGAGTAAACTCTTTTTTAGTTGGAC

CAGACCCATCCTGCGAAAAGGATACAGGCAGCGCCTCGAGTTGTCTGATATCTACCAGA

TTCCTTCTGTGGACTCAGCTGACAATTTGAGTGAGAAGCTGGAGCGGGAGTGGGATAGA

GAGCTGGCGAGCAAAAAAAACCCCAAGCTTATCAATGCTCTGCGCCGCTGCTTTTTCTG

GAGGTTCATGTTTTATGGGATCTTCCTGTACCTGGGGGAGGTCACCAAAGCTGTTCAGC

CGCTCCTTCTTGGCCGCATCATCGCCAGCTATGACCCTGATAATAAAGAAGAAAGGTCT

ATTGCTATTTATCTGGGAATTGGCCTCTGCTTGCTCTTCATCGTCCGCACCCTTCTGCTGC

ACCCTGCCATTTTTGGCCTTCACCACATCGGCATGCAAATGAGAATTGCCATGTTCTCCC

TCATTTACAAAAAGACCCTGAAACTTTCCTCAAGAGTGTTAGATAAAATATCCATTGGT
```

-continued
```
CAGCTGGTCAGCCTGCTGTCCAACAATCTTAACAAATTTGATGAAGGCTTGGCGCTGGC

CCACTTCGTGTGGATTGCACCTCTGCAGGTGGCCCTGTTGATGGGACTTATATGGGAGC

TGCTTCAAGCCTCTGCTTTCTGTGGGCTGGGCTTTTTGATTGTACTGGCACTTTTTCAGGC

TGGGCTCGGAAGAATGATGATGAAATACAGAGATCAGCGGGCCGGGAAGATTTCAGAG

CGACTTGTGATCACCAGTGAAATGATTGAAAATATTCAGAGCGTGAAAGCCTACTGCTG

GGAAGAAGCCATGGAGAAGATGATTGAGAACCTGAGGCAGACAGAGCTCAAGCTCACT

CGGAAGGCTGCTTATGTTCGCTATTTCAACAGCAGCGCCTTCTTCTTCAGTGGCTTCTTT

GTTGTCTTCCTGTCTGTTCTGCCATATGCACTGATAAAAGGCATTATTTTACGAAAGATC

TTCACCACCATCAGTTTTTGCATCGTTCTCAGGATGGCCGTCACAAGACAGTTCCCCTGG

GCTGTGCAGACCTGGTACGATTCCTTGGGGGCCATCAACAAGATTCAAGATTTCTTGCA

AAAACAAGAATATAAAACTTTAGAATACAACCTCACCACCACTGAAGTGGTCATGGAA

AATGTGACAGCCTTTTGGGAGGAGGGTTTTGGAGAATTGTTCGAGAAGGCAAAGCAGA

ATAACAACAACAGGAAGACGAGCAATGGGACGACTCTCTCTTCTTCAGCAACTTTTCA

CTGCTCGGGACCCCTGTGTTGAAAGATATAAACTTCAAGATCGAGAGGGGCCAGCTCTT

GGCTGTGGCAGGCTCCACTGGAGCTGGTAAAACATCTCTTCTCATGGTGATCATGGGGG

AACTGGAGCCTTCCGAAGGAAAAATCAAGCACAGTGGGAGAATCTCATTCTGCAGCCA

GTTTTCCTGGATCATGCCCGGCACCATTAAGGAAAACATCATATTTGGAGTGTCCTATG

ATGAGTACCGCTACCGGTCAGTCATCAAAGCCTGTCAGTTGGAGGAGGACATCTCCAAG

TTTGCAGAGAAAGACAACATTGTGCTTGGAGAGGGGGGTATCACTCTTTCTGGAGGACA

AAGAGCCAGGATCTCTTTGGCCCGGGCAGTCTACAAGGATGCAGACCTCTACTTGTTGG

ACAGTCCCTTCGGCTACCTCGACGTGCTGACTGAAAAAGAAATTTTTGAAAGCTGTGTG

TGCAAACTGATGGCAAACAAGACCAGGATTCTTGTCACCAGCAAGATGGAACATCTGA

AGAAAGCGGACAAAATTCTGATTCTGCATGAAGGGAGCTCCTACTTCTATGGAACATTT

AGCGAGCTTCAGAACCTACAGCCAGACTTCTCCTCCAAATTAATGGGCTGTGACTCCTT

CGACCAGTTCTCTGCAGAAAGAAGAAACTCTATACTCACAGAGACCCTCCACCGCTTCT

CCCTTGAGGGAGATGCCCCAGTTTCTTGGACAGAAACCAAGAAGCAGTCCTTTAAGCAG

ACTGGCGAGTTTGGTGAAAAGAGGAAAAATTCAATTCTCAATCCAATTAACAGTATTCG

CAAGTTCAGCATTGTCCAGAAGACACCCCTCCAGATGAATGGCATCGAAGAAGATAGT

GACGAGCCGCTGGAGAGACGGCTGAGTCTGGTGCCAGATTCAGAACAGGGGGAGGCCA

TCCTGCCCCGGATCAGCGTCATTTCCACAGGCCCCACATTACAAGCACGGCGCCGGCAG

AGTGTTTTAAATCTCATGACCCATTCAGTGAACCAGGGCCAAAATATCCACAGGAAGAC

TACAGCTTCTACCCGGAAAGTGTCTCTGGCCCCTCAGGCCAATCTGACCGAGCTGGACA

TCTACAGCAGGAGGCTCTCCCAGGAAACAGGGCTGGAAATATCTGAAGAGATTAATGA

AGAGGATCTTAAAGAGTGCTTCTTTGATGACATGGAGAGCATCCCCGCGGTGACCACAT

GGAACACCTACCTTAGATATATTACTGTCCACAAGAGCCTCATATTTGTCCTCATCTGGT

GCCTGGTTATTTTCCTCGCTGAGGTGGCGGCCAGTCTTGTTGTGCTCTGGCTGCTGGGCA

ACACTCCTCTCCAGGACAAGGGCAATAGTACTCACAGCAGAAATAATTCTTATGCCGTC

ATCATTACAAGCACCTCCAGCTACTACGTGTTCTACATCTATGTGGGCGTGGCTGACAC

CCTCCTGGCCATGGGTTTCTTCCGGGGCCTGCCTTTGGTGCACACCCTCATCACAGTGTC

AAAAATTCTGCACCATAAAATGCTTCATTCTGTCCTGCAGGCACCCATGAGCACTTTGA

ACACATTGAAGGCTGGCGGCATCCTCAACAGATTTTCTAAAGATATTGCTATCCTGGAT
```

-continued

```
GATCTCCTCCCCCTGACAATCTTTGACTTTATCCAGCTTCTGCTGATCGTGATTGGAGCC

ATAGCAGTGGTTGCTGTCCTGCAGCCCTACATTTTTGTGGCCACCGTGCCCGTGATTGTT

GCCTTTATTATGCTCAGAGCTTACTTCCTGCAAACTTCTCAACAGCTCAAACAGCTAGAA

TCTGAGGGCCGGAGCCCCATTTTTACCCACCTGGTGACTTCCCTGAAGGGACTGTGGAC

TCTGAGAGCATTCGGGCGACAGCCTTACTTTGAGACACTGTTCCACAAGGCCCTGAACT

TGCACACTGCCAACTGGTTTCTTTACCTGAGCACACTCCGCTGGTTCCAGATGCGGATA

GAGATGATCTTCGTCATCTTTTTTATAGCTGTAACCTTCATTTCTATCCTTACAACAGGA

GAAGGAGAGGGCAGGGTGGGAATCATCCTCACGCTGGCTATGAACATAATGTCCACCT

TGCAGTGGGCCGTGAATTCCAGTATAGATGTGGATTCTCTAATGAGGAGTGTCTCCCGG

GTGTTTAAATTCATTGATATGCCTACTGAGGGGAAACCCACCAAGTCAACAAAACCTTA

TAAGAATGGACAGCTGAGCAAGGTGATGATAATTGAGAACAGCCACGTGAAGAAGGAT

GACATTTGGCCCAGCGGGGGCCAGATGACTGTGAAGGACCTGACGGCCAAGTACACCG

AAGGTGGAAATGCCATTTTGGAAAACATCAGCTTCTCAATCTCTCCTGGGCAGAGAGTT

GGATTGCTGGGTCGCACGGGCAGCGGCAAATCAACCCTGCTCAGTGCCTTCCTTCGGCT

CCTGAATACAGAAGGCGAAATCCAAATTGACGGGGTGAGCTGGGACAGCATCACCCTG

CAGCAGTGGAGAAAAGCATTTGGGGTCATTCCACAGAAAGTTTTCATCTTCTCTGGCAC

TTTCAGAAAGAACCTGGACCCCTATGAGCAGTGGAGCGACCAGGAGATCTGGAAGGTT

GCAGATGAAGTTGGCCTGCGGAGTGTGATAGAACAATTTCCTGGCAAGCTGGATTTTGT

GCTGGTAGATGGAGGCTGCGTGCTGTCCCACGGCCACAAACAGCTGATGTGCCTCGCCC

GCTCCGTTCTTTCAAAGGCCAAAATCTTGCTTTTGGATGAGCCCAGTGCTCACCTTGACC

CAGTGACCTATCAGATAATCCGCAGGACCTTAAAGCAAGCTTTTGCCGACTGCACCGTC

ATACTGTGTGAGCACCGGATTGAAGCAATGCTGGAATGCCAGCAGTTTCTGGTGATCGA

GGAGAATAAGGTCCGGCAGTACGACAGCATCCAGAAGTTGTTGAATGAGCGCAGCCTT

TTCCGCCAGGCCATCTCCCCATCTGACAGAGTCAAGCTGTTTCCACATAGGAACTCCTCT

AAGTGCAAGTCCAAGCCCCAGATCGCTGCCCTCAAGGAGGAAACTGAGGAAGAGGTGC

AGGATACCCGCCTGTGA
```

In yet another embodiment, an exemplary codon-optimized CFTR mRNA sequence is:

(SEQ ID NO: 10)
```
ATGCAGAGGAGCCCACTGGAGAAAGCCTCCGTGGTGAGTAAACTCTTTTTTAGTTGGAC

CAGACCCATCCTGCGAAAAGGATACAGGCAGCGCCTCGAGTTGTCAGATATCTACCAG

ATTCCTTCTGTGGACTCAGCTGACAATTTGAGTGAGAAGCTGGAGCGGGAGTGGGATAG

AGAGCTGGCGAGCAAAAAAAACCCCAAGCTTATCAATGCTCTGCGCCGCTGCTTTTTCT

GGAGGTTCATGTTTTATGGGATCTTCCTGTACCTGGGGGAGGTCACCAAAGCTGTTCAG

CCGCTCCTTCTTGGCCGCATCATCGCCAGCTATGACCCTGATAATAAAGAAGAAAGGTC

TATTGCTATTTATCTGGGAATTGGCCTCTGCTTGCTCTTCATCGTCCGCACCCTTCTGCTG

CACCCTGCCATTTTTGGCCTTCACCACATCGGCATGCAAATGAGAATTGCCATGTTCTCC

CTCATTTACAAAAAGACCCTGAAACTTTCCTCAAGAGTGTTAGATAAAATATCCATTGG

TCAGCTGGTCAGCCTGCTGTCCAACAATCTTAACAAATTTGATGAAGGCTTGGCGCTGG

CCCACTTCGTGTGGATTGCACCTCTGCAGGTGGCCCTGTTGATGGGACTTATATGGGAG
```

-continued

```
CTGCTTCAAGCCTCTGCTTTCTGTGGGCTGGGCTTTTTGATTGTACTGGCACTTTTTCAGG

CTGGGCTCGGAAGAATGATGATGAAATACAGAGATCAGCGGGCCGGGAAGATATCAGA

GCGACTTGTGATCACCAGTGAAATGATTGAAAATATTCAGAGCGTGAAAGCCTACTGCT

GGGAAGAAGCCATGGAGAAGATGATTGAGAACCTGAGGCAGACAGAGCTCAAGCTCAC

TCGGAAGGCTGCTTATGTTCGCTATTTCAACAGCAGCGCCTTCTTCTTCAGTGGCTTCTT

TGTTGTCTTCCTGTCTGTTCTGCCATATGCACTGATAAAAGGCATTATTTTACGAAAGAT

CTTCACCACCATCAGTTTTTGCATCGTTCTCAGGATGGCCGTCACAAGACAGTTCCCCTG

GGCTGTGCAGACCTGGTACGATTCCTTGGGGGCCATCAACAAGATTCAAGATTTCTTGC

AAAAACAAGAATATAAAACTTTAGAATACAACCTCACCACCACTGAAGTGGTCATGGA

AAATGTGACAGCCTTTTGGGAGGAGGGTTTTGGAGAATTGTTCGAGAAGGCAAAGCAG

AATAACAACAACAGGAAGACGAGCAATGGGACGACTCTCTCTTCTTCAGCAACTTTTC

ACTGCTCGGGACCCCTGTGTTGAAAGATATAAACTTCAAGATCGAGAGGGGCCAGCTCT

TGGCTGTGGCAGGCTCCACTGGAGCTGGTAAAACATCTCTTCTCATGGTGATCATGGGG

GAACTGGAGCCTTCCGAAGGAAAAATCAAGCACAGTGGGAGAATCTCATTCTGCAGCC

AGTTTTCCTGGATCATGCCCGGCACCATTAAGGAAAACATCATATTTGGAGTGTCCTAT

GATGAGTACCGCTACCGGTCAGTCATCAAAGCCTGTCAGTTGGAGGAGGACATCTCCAA

GTTTGCAGAGAAAGACAACATTGTGCTTGGAGAGGGGGGTATCACTCTTTCTGGAGGAC

AAAGAGCCAGGATCTCTTTGGCCCGGGCAGTCTACAAGGATGCAGACCTCTACTTGTTG

GACAGTCCCTTCGGCTACCTCGACGTGCTGACTGAAAAAGAAATTTTTGAAAGCTGTGT

GTGCAAACTGATGGCAAACAAGACCAGGATTCTTGTCACCAGCAAGATGGAACATCTG

AAGAAAGCGGACAAAATTCTGATTCTGCATGAAGGGAGCTCCTACTTCTATGGAACATT

TAGCGAGCTTCAGAACCTACAGCCAGACTTCTCCTCCAAATTAATGGGCTGTGACTCCT

TCGACCAGTTCTCTGCAGAAAGAAGAAACTCTATACTCACAGAGACCCTCCACCGCTTC

TCCCTTGAGGGAGATGCCCCAGTTTCTTGGACAGAAACCAAGAAGCAGTCCTTTAAGCA

GACTGGCGAGTTTGGTGAAAAGAGGAAAAATTCAATTCTCAATCCAATTAACAGTATTC

GCAAGTTCAGCATTGTCCAGAAGACACCCCTCCAGATGAATGGCATCGAAGAAGATAG

TGACGAGCCGCTGGAGAGACGGCTGAGTCTGGTGCCAGATTCAGAACAGGGGGAGGCC

ATCCTGCCCCGGATCAGCGTCATTTCCACAGGCCCCACATTACAAGCACGGCGCCGGCA

GAGTGTTTAAATCTCATGACCCATTCAGTGAACCAGGGCCAAAATATCCACAGGAAGA

CTACAGCTTCTACCCGGAAAGTGTCTCTGGCCCCTCAGGCCAATCTGACCGAGCTGGAC

ATCTACAGCAGGAGGCTCTCCCAGGAAACAGGGCTTGAAATATCTGAAGAGATTAATG

AAGAGGATCTTAAAGAGTGCTTCTTTGATGACATGGAGAGCATCCCCGCGGTGACCACA

TGGAACACCTACCTTAGATATATTACTGTCCACAAGAGCCTCATATTTGTCCTCATCTGG

TGCCTGGTTATTTTCCTCGCTGAGGTGGCGGCCAGTCTTGTTGTGCTCTGGCTGCTGGGC

AACACTCCTCTCCAGGACAAGGGCAATAGTACACACAGCAGAAATAATTCTTATGCCGT

CATCATTACAAGCACCTCCAGCTACTACGTGTTCTACATCTATGTGGGCGTGGCTGACA

CCCTCCTGGCCATGGGTTTCTTCCGGGGCCTGCCTTTGGTGCACACCCTCATCACAGTGT

CAAAAATTCTGCACCATAAAATGCTTCATTCTGTCCTGCAGGCACCCATGAGCACTTTG

AACACATTGAAGGCTGGCGGCATCCTCAACAGATTTTCTAAAGATATTGCTATCCTGGA

TGATCTCCTCCCCCTGACAATCTTTGACTTTATCCAGCTTCTGCTGATCGTGATTGGAGC
```

-continued

```
CATAGCAGTGGTTGCTGTCCTGCAGCCCTACATTTTTGTGGCCACCGTGCCCGTGATTGT

TGCCTTTATTATGCTCAGAGCTTACTTCCTGCAAACTTCTCAACAGCTCAAACAGCTAGA

ATCTGAGGGCCGGAGCCCCATTTTTACCCACCTGGTGACTTCCCTGAAGGGACTGTGGA

CTCTGAGAGCATTCGGGCGACAGCCTTACTTTGAGACACTGTTCCACAAGGCCCTGAAC

TTGCACACTGCCAACTGGTTTCTTTACCTGAGCACACTCCGCTGGTTCCAGATGCGGATA

GAGATGATCTTCGTCATCTTTTTTATAGCTGTAACCTTCATTTCTATCCTTACAACAGGA

GAAGGAGAGGGCAGGGTGGGAATCATCCTCACGCTGGCTATGAACATAATGTCCACCT

TGCAGTGGGCCGTGAATTCCAGTATAGATGTGGATTCTCTAATGAGGAGTGTCTCCCGG

GTGTTTAAATTCATTGATATGCCTACTGAGGGGAAACCCACCAAGTCAACAAAACCTTA

TAAGAATGGACAGCTGAGCAAGGTGATGATAATTGAGAACAGCCACGTGAAGAAGGAT

GACATTTGGCCCAGCGGGGGCCAGATGACTGTGAAGGACCTGACGGCCAAGTACACCG

AAGGTGGAAATGCCATTTTGGAAAACATCAGCTTCTCAATCTCTCCTGGGCAGAGAGTT

GGATTGCTGGGTCGCACGGGCAGCGGCAAATCAACCCTGCTCAGTGCCTTCCTTCGGCT

CCTGAATACAGAAGGCGAAATCCAAATTGACGGGGTGAGCTGGGACAGCATCACCCTG

CAGCAGTGGAGAAAAGCATTTGGGGTCATTCCACAGAAAGTTTTCATCTTCTCTGGCAC

TTTCAGAAAGAACCTGGACCCCTATGAGCAGTGGAGCGACCAGGAGATCTGGAAGGTT

GCAGATGAAGTTGGCCTGCGGAGTGTGATAGAACAATTTCCTGGCAAGCTGGATTTTGT

GCTGGTAGATGGAGGCTGCGTGCTGTCCCACGGCCACAAACAGCTGATGTGCCTCGCCC

GCTCCGTTCTTTCAAAGGCCAAAATCTTGCTTTTGGATGAGCCCAGTGCTCACCTTGACC

CAGTGACCTATCAGATAATCCGCAGGACCTTAAAGCAAGCTTTTGCCGACTGCACCGTC

ATACTGTGTGAGCACCGGATTGAAGCAATGCTGGAATGCCAGCAGTTTCTGGTGATCGA

GGAGAATAAGGTCCGGCAGTACGACAGCATCCAGAAGTTGTTGAATGAGCGCAGCCTT

TTCCGCCAGGCCATCTCCCCATCTGACAGAGTCAAGCTGTTTCCACATAGGAACTCCTCT

AAGTGCAAGTCCAAGCCCCAGATCGCTGCCCTCAAGGAGGAAACTGAGGAAGAGGTGC

AGGATACCCGCCTGTGA.
```

In yet another embodiment, an exemplary codon-optimized CFTR mRNA sequence is:

```
                                              (SEQ ID NO: 11)
ATGCAGAGGAGCCCACTGGAGAAAGCCTCCGTGGTGAGTAAACTCTTTTTTAGTTGGAC

CAGACCCATCCTGCGAAAAGGATACAGGCAGCGCCTCGAGTTGTCAGATATCTACCAG

ATTCCTTCTGTGGACTCAGCTGACAATTTGAGTGAGAAGCTGGAGCGGGAGTGGGATAG

AGAGCTGGCGAGCAAAAAAAACCCCAAGCTTATCAATGCTCTGCGCCGCTGCTTTTTCT

GGAGGTTCATGTTTTATGGGATCTTCCTGTACCTGGGGGAGGTCACCAAAGCTGTTCAG

CCGCTCCTTCTTGGCCGCATCATCGCCAGCTATGACCCTGATAATAAAGAAGAAAGGTC

TATTGCTATTTATCTGGGAATTGGCCTCTGCTTGCTCTTCATCGTCCGCACCCTTCTGCTG

CACCCTGCCATTTTTGGCCTTCACCACATCGGCATGCAAATGAGAATTGCCATGTTCTCC

CTCATTTACAAAAGACCCTGAAACTTTCCTCAAGAGTGTTAGATAAAATATCCATTGG

TCAGCTGGTCAGCCTGCTGTCCAACAATCTTAACAAATTTGATGAAGGCTTGGCGCTGG

CCCACTTCGTGTGGATTGCACCTCTGCAGGTGGCCCTGTTGATGGGACTTATATGGGAG

CTGCTTCAAGCCTCTGCTTTCTGTGGGCTGGGCTTTTTGATTGTACTGGCACTTTTTCAGG
```

-continued

```
CTGGGCTCGGAAGAATGATGATGAAATACAGAGATCAGCGGGCCGGGAAGATATCAGA
GCGACTTGTGATCACCAGTGAAATGATTGAAAATATTCAGAGCGTGAAAGCCTACTGCT
GGGAAGAAGCCATGGAGAAGATGATTGAGAACCTGAGGCAGACAGAGCTCAAGCTCAC
TCGGAAGGCTGCTTATGTTCGCTATTTCAACAGCAGCGCCTTCTTCTTCAGTGGCTTCTT
TGTTGTCTTCCTGTCTGTTCTGCCATATGCACTGATAAAAGGCATTATTTTACGAAAGAT
CTTCACCACCATCAGTTTTTGCATCGTTCTCAGGATGGCCGTCACAAGACAGTTCCCCTG
GGCTGTGCAGACCTGGTACGATTCCTTGGGGGCCATCAACAAGATTCAAGATTTCTTGC
AAAAACAAGAATATAAAACTTTAGAATACAACCTCACCACCACTGAAGTGGTCATGGA
AAATGTGACAGCCTTTTGGGAGGAGGGTTTTGGAGAATTGTTCGAGAAGGCAAAGCAG
AATAACAACAACAGGAAGACGAGCAATGGGGACGACTCTCTCTTCTTCAGCAACTTTTC
ACTGCTCGGGACCCCTGTGTTGAAAGATATAAACTTCAAGATCGAGAGGGGCCAGCTCT
TGGCTGTGGCAGGCTCCACTGGAGCTGGTAAAACATCTCTTCTCATGGTGATCATGGGG
GAACTGGAGCCTTCCGAAGGAAAAATCAAGCACAGTGGGAGAATCTCATTCTGCAGCC
AGTTTTCCTGGATCATGCCCGGCACCATTAAGGAAAACATCATATTTGGAGTGTCCTAT
GATGAGTACCGCTACCGGTCAGTCATCAAAGCCTGTCAGTTGGAGGAGGACATCTCCAA
GTTTGCAGAGAAAGACAACATTGTGCTTGGAGAGGGGGGTATCACTCTTTCTGGAGGAC
AAAGAGCCAGGATCTCTTTGGCCCGGGCAGTCTACAAGGATGCAGACCTCTACTTGTTG
GACAGTCCCTTCGGCTACCTCGACGTGCTGACTGAAAAAGAAATTTTTGAAAGCTGTGT
GTGCAAACTGATGGCAAACAAGACCAGGATTCTTGTCACCAGCAAGATGGAACATCTG
AAGAAAGCGGACAAAATTCTGATTCTGCATGAAGGGAGCTCCTACTTCTATGGAACATT
TAGCGAGCTTCAGAACCTACAGCCAGACTTCTCCTCCAAATTAATGGGCTGTGACTCCT
TCGACCAGTTCTCTGCAGAAAGAAGAAACTCTATACTCACAGAGACCCTCCACCGCTTC
TCCCTTGAGGGAGATGCCCCAGTTTCTTGGACAGAAACCAAGAAGCAGTCCTTTAAGCA
GACTGGCGAGTTTGGTGAAAAGAGGAAAAATTCAATTCTCAATCCAATTAACAGTATTC
GCAAGTTCAGCATTGTCCAGAAGACACCCCTCCAGATGAATGGCATCGAAGAAGATAG
TGACGAGCCGCTGGAGAGACGGCTGAGTCTGGTGCCAGATTCAGAACAGGGGGAGGCC
ATCCTGCCCCGGATCAGCGTCATTTCCACAGGCCCCACATTACAAGCACGGCGCCGGCA
GAGTGTTTTAAATCTCATGACCCATTCAGTGAACCAGGGCCAAAATATCCACAGGAAGA
CTACAGCTTCTACCCGGAAAGTGTCTCTGGCCCCTCAGGCCAATCTGACCGAGCTGGAC
ATCTACAGCAGGAGGCTCTCCCAGGAAACAGGGCTGGAAATATCTGAAGAGATTAATG
AAGAGGATCTTAAAGAGTGCTTCTTTGATGACATGGAGAGCATCCCCGCGGTGACCACA
TGGAACACCTACCTTAGATATATTACTGTCCACAAGAGCCTCATATTTGTCCTCATCTGG
TGCCTGGTTATTTTCCTCGCTGAGGTGGCGGCCAGTCTTGTTGTGCTCTGGCTGCTGGGC
AACACTCCTCTCCAGGACAAGGGCAATAGTACTCACAGCAGAAATAATTCTTATGCCGT
CATCATTACAAGCACCTCCAGCTACTACGTGTTCTACATCTATGTGGGCGTGGCTGACA
CCCTCCTGGCCATGGGTTTCTTCCGGGGCCTGCCTTTGGTGCACACCCTCATCACAGTGT
CAAAAATTCTGCACCATAAAAATGCTTCATTCTGTCCTGCAGGCACCCATGAGCACTTTG
AACACATTGAAGGCTGGCGGCATCCTCAACAGATTTTCTAAAGATATTGCTATCCTGGA
TGATCTCCTCCCCCTGACAATCTTTGACTTTATCCAGCTTCTGCTGATCGTGATTGGAGC
CATAGCAGTGGTTGCTGTCCTGCAGCCCTACATTTTTGTGGCCACCGTGCCCGTGATTGT
TGCCTTTATTATGCTCAGAGCTTACTTCCTGCAAACTTCTCAACAGCTCAAACAGCTAGA
```

```
ATCTGAGGGCCGGAGCCCCATTTTTACCCACCTGGTGACTTCCCTGAAGGGACTGTGGA

CTCTGAGAGCATTCGGGCGACAGCCTTACTTTGAGACACTGTTCCACAAGGCCCTGAAC

TTGCACACTGCCAACTGGTTTCTTTACCTGAGCACACTCCGCTGGTTCCAGATGCGGATA

GAGATGATCTTCGTCATCTTTTTTATAGCTGTAACCTTCATTTCTATCCTTACAACAGGA

GAAGGAGAGGGCAGGGTGGGAATCATCCTCACGCTGGCTATGAACATAATGTCCACCT

TGCAGTGGGCCGTGAATTCCAGTATAGATGTGGATTCTCTAATGAGGAGTGTCTCCCGG

GTGTTTAAATTCATTGATATGCCAACTGAGGGGAAACCCACCAAGTCAACAAAACCTTA

TAAGAATGGACAGCTGAGCAAGGTGATGATAATTGAGAACAGCCACGTGAAGAAGGAT

GACATTTGGCCCAGCGGGGCCAGATGACTGTGAAGGACCTGACGGCCAAGTACACCG

AAGGTGGAAATGCCATTTTGGAAAACATCAGCTTCTCAATCTCTCCTGGGCAGAGAGTT

GGATTGCTGGGTCGCACGGGCAGCGGCAAATCAACCCTGCTCAGTGCCTTCCTTCGGCT

CCTGAATACAGAAGGCGAAATCCAAATTGACGGGGTGAGCTGGGACAGCATCACCCTG

CAGCAGTGGAGAAAAGCATTTGGGGTCATTCCACAGAAAGTTTTCATCTTCTCTGGCAC

TTTCAGAAAGAACCTGGACCCCTATGAGCAGTGGAGCGACCAGGAGATCTGGAAGGTT

GCAGATGAAGTTGGCCTGCGGAGTGTGATAGAACAATTTCCTGGCAAGCTGGATTTTGT

GCTGGTAGATGGAGGCTGCGTGCTGTCCCACGGCCACAAACAGCTGATGTGCCTCGCCC

GCTCCGTTCTTTCAAAGGCCAAAATCTTGCTTTTGGATGAGCCCAGTGCTCACCTCGACC

CAGTGACCTATCAGATAATCCGCAGGACCTTAAAGCAAGCTTTTGCCGACTGCACCGTC

ATACTGTGTGAGCACCGGATTGAAGCAATGCTGGAATGCCAGCAGTTTCTGGTGATCGA

GGAGAATAAGGTCCGGCAGTACGACAGCATCCAGAAGTTGTTGAATGAGCGCAGCCTT

TTCCGCCAGGCCATCTCCCCATCTGACAGAGTCAAGCTGTTTCCACATAGGAACTCCTCT

AAGTGCAAGTCCAAGCCCCAGATCGCTGCCCTCAAGGAGGAAACTGAGGAAGAGGTGC

AGGATACCCGCCTGTGA.
```

In yet another embodiment, an exemplary codon-optimized CFTR mRNA sequence is:

```
                                                   (SEQ ID NO: 12)
ATGCAGAGGAGCCCACTGGAGAAAGCCTCCGTGGTGAGTAAACTCTTTTTTAGTTGGAC

CAGACCCATCCTGCGAAAAGGATACAGGCAGCGCCTCGAGTTGTCAGATATCTACCAG

ATTCCTTCTGTGGACTCAGCTGACAATTTGAGTGAGAAGCTGGAGCGGGAGTGGGATAG

AGAGCTGGCGAGCAAAAAAAACCCCAAGCTTATCAATGCTCTGCGCCGCTGCTTTTTCT

GGAGGTTCATGTTTTATGGGATCTTCCTGTACCTGGGGGAGGTCACCAAAGCTGTTCAG

CCGCTCCTTCTTGGCCGCATCATCGCCAGCTATGACCCTGATAATAAAGAAGAAGGTC

TATTGCTATTTATCTGGGAATTGGCCTCTGCTTGCTCTTCATCGTCCGCACCCTTCTGCTG

CACCCTGCCATTTTTGGCCTTCACCACATCGGCATGCAAATGAGAATTGCCATGTTCTCC

CTCATTTACAAAAAGACCCTGAAACTTTCCTCAAGAGTGTTAGATAAAATATCCATTGG

TCAGCTGGTCAGCCTGCTGTCCAACAATCTTAACAAATTTGATGAAGGCTTGGCGCTGG

CCCACTTCGTGTGGATTGCACCTCTGCAGGTGGCCCTGTTGATGGGACTTATATGGGAG

CTGCTTCAAGCCTCTGCTTTCTGTGGGCTGGCTTTTTGATTGTACTGGCACTTTTTCAGG

CTGGGCTCGGAAGAATGATGATGAAATACAGAGATCAGCGGGCCGGGAAGATATCAGA

GCGACTTGTGATCACCAGTGAAATGATTGAAAATATTCAGAGCGTGAAAGCCTACTGCT
```

-continued

GGGAAGAAGCCATGGAGAAGATGATTGAGAACCTGAGGCAGACAGAGCTCAAGCTCAC

TCGGAAGGCTGCTTATGTTCGCTATTTCAACAGCAGCGCCTTCTTCTTCAGTGGCTTCTT

TGTTGTCTTCCTGTCTGTTCTGCCATATGCACTGATAAAAGGCATTATTTTACGAAAGAT

CTTCACCACCATCAGTTTTTGCATCGTTCTCAGGATGGCCGTCACAAGACAGTTCCCCTG

GGCTGTGCAGACCTGGTACGATTCCTTGGGGGCCATCAACAAGATTCAAGATTTCTTGC

AAAAACAAGAATATAAAACTTTAGAATACAACCTCACCACCACTGAAGTGGTCATGGA

AAATGTGACAGCCTTTTGGGAGGAGGGTTTTGGAGAATTGTTCGAGAAGGCAAAGCAG

AATAACAACAACAGGAAGACGAGCAATGGGGACGACTCTCTCTTCTTCAGCAACTTTTC

ACTGCTCGGGACCCCTGTGTTGAAAGATATAAACTTCAAGATCGAGAGGGGCCAGCTCT

TGGCTGTGGCAGGCTCCACTGGAGCTGGTAAAACATCTCTTCTCATGGTGATCATGGGG

GAACTGGAGCCTTCCGAAGGAAAAATCAAGCACAGTGGGAGAATCTCATTCTGCAGCC

AGTTTTCCTGGATCATGCCCGGCACCATTAAGGAAAACATCATATTTGGAGTGTCCTAT

GATGAGTACCGCTACCGGTCAGTCATCAAAGCCTGTCAGTTGGAGGAGGACATCTCCAA

GTTTGCAGAGAAAGACAACATTGTGCTTGGAGAGGGGGGTATCACTCTTTCTGGAGGAC

AAAGAGCCAGGATCTCTTTGGCCCGGGCAGTCTACAAGGATGCAGACCTCTACTTGTTG

GACAGTCCCTTCGGCTACCTCGACGTGCTGACTGAAAAAGAAATTTTTGAAAGCTGTGT

GTGCAAACTGATGGCAAACAAGACCAGGATTCTTGTCACCAGCAAGATGGAACATCTG

AAGAAAGCGGACAAAATTCTGATTCTGCATGAAGGGAGCTCCTACTTCTATGGAACATT

TAGCGAGCTTCAGAACCTACAGCCAGACTTCTCCTCCAAATTAATGGGCTGTGACTCCT

TCGACCAGTTCTCTGCAGAAAGAAGAAACTCTATACTCACAGAGACCCTCCACCGCTTC

TCCCTTGAGGGAGATGCCCCAGTTTCTTGGACAGAAACCAAGAAGCAGTCCTTTAAGCA

GACTGGCGAGTTTGGTGAAAAGAGGAAAAATTCAATTCTCAATCCTATTAACAGTATTC

GCAAGTTCAGCATTGTCCAGAAGACACCCCTCCAGATGAATGGCATCGAAGAAGATAG

TGACGAGCCGCTGGAGAGACGGCTGAGTCTGGTGCCAGATTCAGAACAGGGGGAGGCC

ATCCTGCCCCGGATCAGCGTCATTTCCACAGGCCCCACATTACAAGCACGGCGCCGGCA

GAGTGTTTTAAATCTCATGACCCATTCAGTGAACCAGGGCCAAAATATCCACAGGAAGA

CTACAGCTTCTACCCGGAAAGTGTCTCTGGCCCCTCAGGCCAATCTGACCGAGCTGGAC

ATCTACAGCAGGAGGCTCTCCCAGGAAACAGGGCTTGAAATATCTGAAGAGATTAATG

AAGAGGATCTTAAAGAGTGCTTCTTTGATGACATGGAGAGCATCCCCGCGGTGACCACA

TGGAACACCTACCTTAGATATATTACTGTCCACAAGAGCCTCATATTTGTCCTCATCTGG

TGCCTGGTTATTTTCCTCGCTGAGGTGGCGGCCAGTCTTGTTGTGCTCTGGCTGCTGGGC

AACACTCCTCTCCAGGACAAGGGCAATAGTACTCACAGCAGAAATAATTCTTATGCCGT

CATCATTACAAGCACCTCCAGCTACTACGTGTTCTACATCTATGTGGGCGTGGCTGACA

CCCTCCTGGCCATGGGTTTCTTCCGGGGCCTGCCTTTGGTGCACACCCTCATCACAGTGT

CAAAAATTCTGCACCATAAAATGCTTCATTCTGTCCTGCAGGCACCCATGAGCACTTTG

AACACATTGAAGGCTGGCGGCATCCTCAACAGATTTTCTAAAGATATTGCTATCCTGGA

TGATCTCCTCCCCCTGACAATCTTTGACTTTATCCAGCTTCTGCTGATCGTGATTGGAGC

CATAGCAGTGGTTGCTGTCCTGCAGCCCTACATTTTTGTGGCCACCGTGCCCGTGATTGT

TGCCTTTATTATGCTCAGAGCTTACTTCCTGCAAACTTCTCAACAGCTCAAACAGCTAGA

ATCTGAGGGCCGGAGCCCCATTTTTACCCACCTGGTGACTTCCCTGAAGGGACTGTGGA

-continued

```
CTCTGAGAGCATTCGGGCGACAGCCTTACTTTGAGACACTGTTCCACAAGGCCCTGAAC

TTGCACACTGCCAACTGGTTTCTTTACCTGAGCACACTCCGCTGGTTCCAGATGCGGATA

GAGATGATCTTCGTCATCTTTTTTATAGCTGTAACCTTCATTTCTATCCTTACAACAGGA

GAAGGAGAGGGCAGGGTGGGAATCATCCTCACGCTGGCTATGAACATAATGTCCACCT

TGCAGTGGGCCGTGAATTCCAGTATAGATGTGGATTCTCTAATGAGGAGTGTCTCCCGG

GTGTTTAAATTCATTGATATGCCTACTGAGGGGAAACCCACCAAGTCAACAAAACCTTA

TAAGAATGGACAGCTGAGCAAGGTGATGATAATTGAGAACAGCCACGTGAAGAAGGAT

GACATTTGGCCCAGCGGGGGCCAGATGACTGTGAAGGACCTGACGGCCAAGTACACCG

AAGGTGGAAATGCCATTTTGGAAAACATCAGCTTCTCAATCTCTCCTGGGCAGAGAGTT

GGATTGCTGGGTCGCACGGGCAGCGGCAAATCAACCCTGCTCAGTGCCTTCCTTCGGCT

CCTGAATACAGAAGGCGAAATCCAAATTGACGGGGTGAGCTGGGACAGCATCACCCTG

CAGCAGTGGAGAAAAGCATTTGGGGTCATTCCACAGAAAGTTTTCATCTTCTCTGGCAC

TTTCAGAAAGAACCTGGACCCCTATGAGCAGTGGAGCGACCAGGAGATCTGGAAGGTT

GCAGATGAAGTTGGCCTGCGGAGTGTGATAGAACAATTTCCTGGCAAGCTGGATTTTGT

GCTGGTAGATGGAGGCTGCGTGCTGTCCCACGGCCACAAACAGCTGATGTGCCTCGCCC

GCTCCGTTCTTTCAAAGGCCAAAATCTTGCTTTTGGATGAGCCCAGTGCTCACCTCGACC

CAGTGACCTATCAGATAATCCGCAGGACCTTAAAGCAAGCTTTTGCCGACTGCACCGTC

ATACTGTGTGAGCACCGGATTGAAGCAATGCTGGAATGCCAGCAGTTTCTGGTGATCGA

GGAGAATAAGGTCCGGCAGTACGACAGCATCCAGAAGTTGTTGAATGAGCGCAGCCTT

TTCCGCCAGGCCATCTCCCCATCTGACAGAGTCAAGCTGTTTCCACATAGGAACTCCTCT

AAGTGCAAGTCCAAGCCCCAGATCGCTGCCCTCAAGGAGGAAACTGAGGAAGAGGTGC

AGGATACCCGCCTGTGA.
```

In another embodiment, an exemplary codon-optimized CFTR mRNA sequence is:

(SEQ ID NO: 13)
```
ATGCAGAGGAGCCCACTGGAGAAAGCCTCCGTGGTGAGTAAACTCTTTTTTAGTTGGAC

CAGACCCATCCTGCGAAAAGGATACAGGCAGCGCCTCGAGTTGTCAGATATCTACCAG

ATTCCTTCTGTGGACTCAGCTGACAATTTGAGTGAGAAGCTGGAGCGGGAGTGGGATAG

AGAGCTGGCGAGCAAAAAAACCCCAAGCTTATCAATGCTCTGCGCCGCTGCTTTTTCT

GGAGGTTCATGTTTTATGGGATCTTCCTGTACCTGGGGGAGGTCACCAAAGCTGTTCAG

CCGCTCCTTCTTGGCCGCATCATCGCCAGCTATGACCCTGATAATAAAGAAGAAAGGTC

TATTGCTATTTATCTGGGAATTGGCCTCTGCTTGCTCTTCATCGTCCGCACCCTTCTGCTG

CACCCTGCCATTTTTGGCCTTCACCACATCGGCATGCAAATGAGAATTGCCATGTTCTCC

CTCATTTACAAAAGACCCTGAAACTTTCCTCAAGAGTGTTAGATAAAATATCCATTGG

TCAGCTGGTCAGCCTGCTGTCCAACAATCTTAACAAATTTGATGAAGGCTTGGCGCTGG

CCCACTTCGTGTGGATTGCACCTCTGCAGGTGGCCCTGTTGATGGGACTTATATGGGAG

CTGCTTCAAGCCTCTGCTTTCTGTGGGCTGGCTTTTTGATTGTACTGGCACTTTTTCAGG

CTGGGCTCGGAAGAATGATGATGAAATACAGAGATCAGCGGGCCGGGAAGATTTCAGA

GCGACTTGTGATCACCAGTGAAATGATTGAAAATATTCAGAGCGTGAAAGCCTACTGCT

GGGAAGAAGCCATGGAGAAGATGATTGAGAACCTGAGGCAGACAGAGCTCAAGCTCAC
```

-continued

```
TCGGAAGGCTGCTTATGTTCGCTATTTCAACAGCAGCGCCTTCTTCTTCAGTGGCTTCTT
TGTTGTCTTCCTGTCTGTTCTGCCATATGCACTGATAAAAGGCATTATTTTACGAAAGAT
CTTCACCACCATCAGTTTTTGCATCGTTCTCAGGATGGCCGTCACAAGACAGTTCCCCTG
GGCTGTGCAGACCTGGTACGATTCCTTGGGGGCCATCAACAAGATTCAAGATTTCTTGC
AAAAACAAGAATATAAAACTTTAGAATACAACCTCACCACCACTGAAGTGGTCATGGA
AAATGTGACAGCCTTTTGGGAGGAGGGTTTTGGAGAATTGTTCGAGAAGGCAAAGCAG
AATAACAACAACAGGAAGACGAGCAATGGGACGACTCTCTCTTCTTCAGCAACTTTTC
ACTGCTCGGACCCCTGTGTTGAAAGATATAAACTTCAAGATCGAGAGGGGCCAGCTCT
TGGCTGTGGCAGGCTCCACTGGAGCTGGTAAAACATCTCTTCTCATGGTGATCATGGGG
GAACTGGAGCCTTCCGAAGGAAAAATCAAGCACAGTGGGAGAATCTCATTCTGCAGCC
AGTTTTCCTGGATCATGCCCGGCACCATTAAGGAAAACATCATATTTGGAGTGTCCTAT
GATGAGTACCGCTACCGGTCAGTCATCAAAGCCTGTCAGTTGGAGGAGGACATCTCCAA
GTTTGCAGAGAAAGACAACATTGTGCTTGGAGAGGGGGGTATCACTCTTTCTGGAGGAC
AAAGAGCCAGGATCTCTTTGGCCCGGGCAGTCTACAAGGATGCAGACCTCTACTTGTTG
GACAGTCCCTTCGGCTACCTCGACGTGCTGACTGAAAAAGAAATTTTTGAAAGCTGTGT
GTGCAAACTGATGGCAAACAAGACCAGGATTCTTGTCACCAGCAAGATGGAACATCTG
AAGAAAGCGGACAAAATTCTGATTCTGCATGAAGGGAGCTCCTACTTCTATGGAACATT
TAGCGAGCTTCAGAACCTACAGCCAGACTTCTCCTCCAAATTAATGGGCTGTGACTCCT
TCGACCAGTTCTCTGCAGAAAGAAGAAACTCTATACTCACAGAGACCCTCCACCGCTTC
TCCCTTGAGGGAGATGCCCCAGTTTCTTGGACAGAAACCAAGAAGCAGTCCTTTAAGCA
GACTGGCGAGTTTGGTGAAAAGAGGAAAAATTCAATTCTCAATCCAATTAACAGTATTC
GCAAGTTCAGCATTGTCCAGAAGACACCCCTCCAGATGAATGGCATCGAAGAAGATAG
TGACGAGCCGCTGGAGAGACGGCTGAGTCTGGTGCCAGATTCAGAACAGGGGGAGGCC
ATCCTGCCCCGGATCAGCGTCATTTCCACAGGCCCCACATTACAAGCACGGCGCCGGCA
GAGTGTTTTAAATCTCATGACCCATTCAGTGAACCAGGGCCAAAATATCCACAGGAAGA
CTACAGCTTCTACCCGGAAAGTGTCTCTGGCCCCTCAGGCCAATCTGACCGAGCTGGAC
ATCTACAGCAGGAGGCTCTCCCAGGAAACAGGGCTGGAAATATCTGAAGAGATTAATG
AAGAGGATCTTAAAGAGTGCTTCTTTGATGACATGGAGAGCATCCCCGCGGTGACCACA
TGGAACACCTACCTTAGATATATTACTGTCCACAAGAGCCTCATATTTGTCCTCATCTGG
TGCCTGGTTATTTTCCTCGCTGAGGTGGCGGCCAGTCTTGTTGTGCTCTGGCTGCTGGGC
AACACTCCTCTCCAGGACAAGGGCAATAGTACTCACAGCAGAAATAATTCTTATGCCGT
CATCATTACAAGCACCTCCAGCTACTACGTGTTCTACATCTATGTGGGCGTGGCTGACA
CCCTCCTGGCCATGGGTTTCTTCCGGGGCCTGCCTTTGGTGCACACCCTCATCACAGTGT
CAAAAATTCTGCACCATAAAATGCTTCATTCTGTCCTGCAGGCACCCATGAGCACTTTG
AACACATTGAAGGCTGGCGGCATCCTCAACAGATTTTCTAAAGATATTGCTATCCTGGA
TGATCTCCTCCCCCTGACAATCTTTGACTTTATCCAGCTTCTGCTGATCGTGATTGGAGC
CATAGCAGTGGTTGCTGTCCTGCAGCCCTACATTTTTGTGGCCACCGTGCCCGTGATTGT
TGCCTTTATTATGCTCAGAGCTTACTTCCTGCAAACTTCTCAACAGCTCAAACAGCTAGA
ATCTGAGGGCCGGAGCCCCATTTTTACCCACCTGGTGACTTCCTGAAGGGACTGTGGA
CTCTGAGAGCATTCGGGCGACAGCCTTACTTTGAGACACTGTTCCACAAGGCCCTGAAC
TTGCACACTGCCAACTGGTTTCTTTACCTGAGCACACTCCGCTGGTTCCAGATGCGGATA
```

-continued

```
GAGATGATCTTCGTCATCTTTTTTATAGCTGTAACCTTCATTTCTATCCTTACAACAGGA

GAAGGAGAGGGCAGGGTGGGAATCATCCTCACGCTGGCTATGAACATAATGTCCACCT

TGCAGTGGGCCGTGAATTCCAGTATAGATGTGGATTCTCTAATGAGGAGTGTCTCCCGG

GTGTTTAAATTCATTGATATGCCAACTGAGGGGAAACCCACCAAGTCAACAAAACCTTA

TAAGAATGGACAGCTGAGCAAGGTGATGATAATTGAGAACAGCCACGTGAAGAAGGAT

GACATTTGGCCCAGCGGGGGCCAGATGACTGTGAAGGACCTGACGGCCAAGTACACCG

AAGGTGGAAATGCCATTTTGGAAAACATCAGCTTCTCAATCTCTCCTGGGCAGAGAGTT

GGATTGCTGGGTCGCACGGGCAGCGGCAAATCAACCCTGCTCAGTGCCTTCCTTCGGCT

CCTGAATACAGAAGGCGAAATCCAAATTGACGGGGTGAGCTGGGACAGCATCACCCTG

CAGCAGTGGAGAAAAGCATTTGGGGTCATTCCACAGAAAGTTTTCATCTTCTCTGGCAC

TTTCAGAAAGAACCTGGACCCCTATGAGCAGTGGAGCGACCAGGAGATCTGGAAGGTT

GCAGATGAAGTTGGCCTGCGGAGTGTGATAGAACAATTTCCTGGCAAGCTGGATTTTGT

GCTGGTAGATGGAGGCTGCGTGCTGTCCCACGGCCACAAACAGCTGATGTGCCTCGCCC

GCTCCGTTCTTTCAAAGGCCAAAATCTTGCTTTTGGATGAGCCCAGTGCTCACCTCGACC

CAGTGACCTATCAGATAATCCGCAGGACCTTAAAGCAAGCTTTTGCCGACTGCACCGTC

ATACTGTGTGAGCACCGGATTGAAGCAATGCTGGAATGCCAGCAGTTTCTGGTGATCGA

GGAGAATAAGGTCCGGCAGTACGACAGCATCCAGAAGTTGTTGAATGAGCGCAGCCTT

TTCCGCCAGGCCATCTCCCCATCTGACAGAGTCAAGCTGTTTCCACATAGGAACTCCTCT

AAGTGCAAGTCCAAGCCCCAGATCGCTGCCCTCAAGGAGGAAACTGAGGAAGAGGTGC

AGGATACCCGCCTGTGA.
```

In another embodiment, an exemplary codon-optimized CFTR mRNA sequence is:

```
                                        (SEQ ID NO: 14)
ATGCAGAGGAGCCCACTGGAGAAAGCCTCCGTGGTGAGTAAACTCTTTTTTAGTTGGAC

CAGACCCATCCTGCGAAAAGGATACAGGCAGCGCCTCGAGTTGTCTGATATCTACCAGA

TTCCTTCTGTGGACTCAGCTGACAATTTGAGTGAGAAGCTGGAGCGGGAGTGGGATAGA

GAGCTGGCGAGCAAAAAAAACCCCAAGCTTATCAATGCTCTGCGCCGCTGCTTTTTCTG

GAGGTTCATGTTTTATGGGATCTTCCTGTACCTGGGGGAGGTCACCAAAGCTGTTCAGC

CGCTCCTTCTTGGCCGCATCATCGCCAGCTATGACCCTGATAATAAAGAAGAAAGGTCT

ATTGCTATTTATCTGGGAATTGGCCTCTGCTTGCTCTTCATCGTCCGCACCCTTCTGCTGC

ACCCTGCCATTTTTGGCCTTCACCACATCGGCATGCAAATGAGAATTGCCATGTTCTCCC

TCATTTACAAAAAGACCCTGAAACTTTCCTCAAGAGTGTTAGATAAAATATCCATTGGT

CAGCTGGTCAGCCTGCTGTCCAACAATCTTAACAAATTTGATGAAGGCTTGGCGCTGGC

CCACTTCGTGTGGATTGCACCTCTGCAGGTGGCCCTGTTGATGGGACTTATATGGGAGC

TGCTTCAAGCCTCTGCTTTCTGTGGGCTGGGCTTTTTGATTGTACTGGCACTTTTTCAGGC

TGGGCTCGGAAGAATGATGATGAAATACAGAGATCAGCGGGCCGGGAAGATATCAGAG

CGACTTGTGATCACCAGTGAAATGATTGAAAATATTCAGAGCGTGAAAGCCTACTGCTG

GGAAGAAGCCATGGAGAAGATGATTGAGAACCTGAGGCAGACAGAGCTCAAGCTCACT

CGGAAGGCTGCTTATGTTCGCTATTTCAACAGCAGCGCCTTCTTCTTCAGTGGCTTCTTT

GTTGTCTTCCTGTCTGTTCTGCCATATGCACTGATAAAAGGCATTATTTTACGAAAGATC
```

-continued

```
TTCACCACCATCAGTTTTTGCATCGTTCTCAGGATGGCCGTCACAAGACAGTTCCCCTGG

GCTGTGCAGACCTGGTACGATTCCTTGGGGGCCATCAACAAGATTCAAGATTTCTTGCA

AAAACAAGAATATAAAACTTTAGAATACAACCTCACCACCACTGAAGTGGTCATGGAA

AATGTGACAGCCTTTTGGGAGGAGGGTTTTGGAGAATTGTTCGAGAAGGCAAAGCAGA

ATAACAACAACAGGAAGACGAGCAATGGGGACGACTCTCTCTTCTTCAGCAACTTTTCA

CTGCTCGGGACCCCTGTGTTGAAAGATATAAACTTCAAGATCGAGAGGGGCCAGCTCTT

GGCTGTGGCAGGCTCCACTGGAGCTGGTAAAACATCTCTTCTCATGGTGATCATGGGGG

AACTGGAGCCTTCCGAAGGAAAAATCAAGCACAGTGGGAGAATCTCATTCTGCAGCCA

GTTTTCCTGGATCATGCCCGGCACCATTAAGGAAAACATCATATTTGGAGTGTCCTATG

ATGAGTACCGCTACCGGTCCGTCATCAAAGCCTGTCAGTTGGAGGAGGACATCTCCAAG

TTTGCAGAGAAAGACAACATTGTGCTTGGAGAGGGGGGTATCACTCTTTCTGGAGGACA

AAGAGCCAGGATCTCTTTGGCCCGGGCAGTCTACAAGGATGCAGACCTCTACTTGTTGG

ACAGTCCCTTCGGCTACCTCGACGTGCTGACTGAAAAAGAAATTTTTGAAAGCTGTGTG

TGCAAACTGATGGCAAACAAGACCAGGATTCTTGTCACCAGCAAGATGGAACATCTGA

AGAAAGCGGACAAAATTCTGATTCTGCATGAAGGGAGCTCCTACTTCTATGGAACATTT

AGCGAGCTTCAGAACCTACAGCCAGACTTCTCCTCCAAATTAATGGGCTGTGACTCCTT

CGACCAGTTCTCTGCAGAAAGAAGAAACTCTATACTCACAGAGACCCTCCACCGCTTCT

CCCTTGAGGGAGATGCCCCAGTTTCTTGGACAGAAACCAAGAAGCAGTCCTTTAAGCAG

ACTGGCGAGTTTGGTGAAAAGAGGAAAAATTCAATTCTCAATCCAATTAACAGTATTCG

CAAGTTCAGCATTGTCCAGAAGACACCCCTCCAGATGAATGGCATCGAAGAAGATAGT

GACGAGCCGCTGGAGAGACGGCTGAGTCTGGTGCCAGATTCAGAACAGGGGGAGGCCA

TCCTGCCCCGGATCAGCGTCATTTCCACAGGCCCCACATTACAAGCACGGCGCCGGCAG

AGTGTTTTAAATCTCATGACCCATTCAGTGAACCAGGGCCAAAATATCCACAGGAAGAC

TACAGCTTCTACCCGGAAAGTGTCTCTGGCCCCTCAGGCCAATCTGACCGAGCTGGACA

TCTACAGCAGGAGGCTCTCCCAGGAAACAGGGCTTGAAATATCTGAAGAGATTAATGA

AGAGGATCTTAAAGAGTGCTTCTTTGATGACATGGAGAGCATCCCCGCGGTGACCACAT

GGAACACCTACCTTAGATATATTACTGTCCACAAGAGCCTCATATTTGTCCTCATCTGGT

GCCTGGTTATTTTCCTCGCTGAGGTGGCGGCCAGTCTTGTTGTGCTCTGGCTGCTGGGCA

ACACTCCTCTCCAGGACAAGGGCAATAGTACTCACAGCAGAAATAATTCTTATGCCGTC

ATCATTACAAGCACCTCCAGCTACTACGTGTTCTACATCTATGTGGGCGTGGCTGACAC

CCTCCTGGCCATGGGTTTCTTCCGGGGCCTGCCTTTGGTGCACACCCTCATCACAGTGTC

AAAAATTCTGCACCATAAAATGCTTCATTCTGTCCTGCAGGCACCCATGAGCACTTTGA

ACACATTGAAGGCTGGCGGCATCCTCAACAGATTTTCTAAAGATATTGCTATCCTGGAT

GATCTCCTCCCCCTGACAATCTTTGACTTTATCCAGCTTCTGCTGATCGTGATTGGAGCC

ATAGCAGTGGTTGCTGTCCTGCAGCCCTACATTTTTGTGGCCACCGTGCCCGTGATTGTT

GCCTTTATTATGCTCAGAGCTTACTTCCTGCAAACTTCTCAACAGCTCAAACAGCTAGAA

TCTGAGGGCCGGAGCCCCATTTTTACCCACCTGGTGACTTCCCTGAAGGGACTGTGGAC

TCTGAGAGCATTCGGGCGACAGCCTTACTTTGAGACACTGTTCCACAAGGCCCTGAACT

TGCACACTGCCAACTGGTTTCTTTACCTGAGCACACTCCGCTGGTTCCAGATGCGGATA

GAGATGATCTTCGTCATCTTTTTTATAGCTGTAACCTTCATTTCTATCCTTACAACAGGA
```

-continued
```
GAAGGAGAGGGCAGGGTGGGAATCATCCTCACGCTGGCTATGAACATAATGTCCACCT

TGCAGTGGGCCGTGAATTCCAGTATAGATGTGGATTCTCTAATGAGGAGTGTCTCCCGG

GTGTTTAAATTCATTGATATGCCTACTGAGGGGAAACCCACCAAGTCAACAAAGCCTTA

TAAGAATGGACAGCTGAGCAAGGTGATGATAATTGAGAACAGCCACGTGAAGAAGGAT

GACATTTGGCCCAGCGGGGCCAGATGACTGTGAAGGACCTGACGGCCAAGTACACCG

AAGGTGGAAATGCCATTTTGGAAAACATCAGCTTCTCAATCTCTCCTGGGCAGAGAGTT

GGATTGCTGGGTCGCACGGGCAGCGGCAAATCAACCCTGCTCAGTGCCTTCCTTCGGCT

CCTGAATACAGAAGGCGAAATCCAAATTGACGGGGTGAGCTGGGACAGCATCACCCTG

CAGCAGTGGAGAAAAGCATTTGGGGTCATTCCACAGAAAGTTTTCATCTTCTCTGGCAC

TTTCAGAAAGAACCTGGACCCCTATGAGCAGTGGAGCGACCAGGAGATCTGGAAGGTT

GCAGATGAAGTTGGCCTGCGGAGTGTGATAGAACAATTTCCTGGCAAGCTGGATTTTGT

GCTGGTAGATGGAGGCTGCGTGCTGTCCCACGGCCACAAACAGCTGATGTGCCTCGCCC

GCTCCGTTCTTTCAAAGGCCAAAATCTTGCTTTTGGATGAGCCCAGTGCTCACCTCGACC

CAGTGACCTATCAGATAATCCGCAGGACCTTAAAGCAAGCTTTTGCCGACTGCACCGTC

ATACTGTGTGAGCACCGGATTGAAGCAATGCTGGAATGCCAGCAGTTTCTGGTGATCGA

GGAGAATAAGGTCCGGCAGTACGACAGCATCCAGAAGTTGTTGAATGAGCGCAGCCTT

TTCCGCCAGGCCATCTCCCCATCTGACAGAGTCAAGCTGTTTCCACATAGGAACTCCTCT

AAGTGCAAGTCCAAGCCCCAGATCGCTGCCCTCAAGGAGGAAACTGAGGAAGAGGTGC

AGGATACCCGCCTGTGA.
```

In another embodiment, an exemplary codon-optimized CFTR mRNA sequence is:

```
                                          (SEQ ID NO: 15)
ATGCAGAGGAGCCCACTGGAGAAAGCCTCCGTGGTGAGTAAACTCTTTTTTAGTTGGAC

CAGACCCATCCTGCGAAAAGGATACAGGCAGCGCCTCGAGTTGTCAGATATCTACCAG

ATTCCTTCTGTGGACTCAGCTGACAATTTGAGTGAGAAGCTGGAGCGGGAGTGGGATAG

AGAGCTGGCGAGCAAAAAAAACCCCAAGCTTATCAATGCTCTGCGCCGCTGCTTTTTCT

GGAGGTTCATGTTTTATGGGATCTTCCTGTACCTGGGGGAGGTCACCAAAGCTGTTCAG

CCGCTCCTTCTTGGCCGCATCATCGCCAGCTATGACCCTGATAATAAAGAAGAAAGGTC

TATTGCTATTTATCTGGGAATTGGCCTCTGCTTGCTCTTCATCGTCCGCACCCTTCTGCTG

CACCCTGCCATTTTTGGCCTTCACCACATCGGCATGCAAATGAGAATTGCCATGTTCTCC

CTCATTTACAAAAAGACCCTGAAACTTTCCTCAAGAGTGTTAGATAAAATATCCATTGG

TCAGCTGGTCAGCCTGCTGTCCAACAATCTTAACAAATTTGATGAAGGCTTGGCGCTGG

CCCACTTCGTGTGGATTGCACCTCTGCAGGTGGCCCTGTTGATGGGACTTATATGGGAG

CTGCTTCAAGCCTCTGCTTTCTGTGGGCTGGCTTTTTGATTGTACTGGCACTTTTTCAGG

CTGGGCTCGGAAGAATGATGATGAAATACAGAGATCAGCGGGCCGGGAAGATATCAGA

GCGACTTGTGATCACCAGTGAAATGATTGAAAATATTCAGAGCGTGAAAGCCTACTGCT

GGGAAGAAGCCATGGAGAAGATGATTGAGAACCTGAGGCAGACAGAGCTCAAGCTCAC

TCGGAAGGCTGCTTATGTTCGCTATTTCAACAGCAGCGCCTTCTTCTTCAGTGGCTTCTT

TGTTGTCTTCCTGTCTGTTCTGCCATATGCACTGATAAAAGGCATTATTTTACGAAAGAT

CTTCACCACCATCAGTTTTTGCATCGTTCTCAGGATGGCCGTCACAAGACAGTTCCCCTG
```

-continued

```
GGCTGTGCAGACCTGGTACGATTCCTTGGGGGCCATCAACAAGATTCAAGATTTCTTGC

AAAAACAAGAATATAAAACTTTAGAATACAACCTCACCACCACTGAAGTGGTCATGGA

AAATGTGACAGCCTTTTGGGAGGAGGGTTTTGGAGAATTGTTCGAGAAGGCAAAGCAG

AATAACAACAACAGGAAGACGAGCAATGGGGACGACTCTCTCTTCTTCAGCAACTTTTC

ACTGCTCGGGACCCCTGTGTTGAAAGATATAAACTTCAAGATCGAGAGGGGCCAGCTCT

TGGCTGTGGCAGGCTCCACTGGAGCTGGTAAAACATCTCTTCTCATGGTGATCATGGGG

GAACTGGAGCCTTCCGAAGGAAAAATCAAGCACAGTGGGAGAATCTCATTCTGCAGCC

AGTTTTCCTGGATCATGCCCGGCACCATTAAGGAAAACATCATATTTGGAGTGTCCTAT

GATGAGTACCGCTACCGGTCAGTCATCAAAGCCTGTCAGTTGGAGGAGGACATCTCCAA

GTTTGCAGAGAAAGACAACATTGTGCTTGGAGAGGGGGGTATCACTCTTTCTGGAGGAC

AAAGAGCCAGGATCTCTTTGGCCCGGGCAGTCTACAAGGATGCAGACCTCTACTTGTTG

GACAGTCCCTTCGGCTACCTCGACGTGCTGACTGAAAAAGAAATTTTTGAAAGCTGTGT

GTGCAAACTGATGGCAAACAAGACCAGGATTCTTGTCACCAGCAAGATGAACATCTG

AAGAAAGCGGACAAAATTCTGATTCTGCATGAAGGGAGCTCCTACTTCTATGGAACATT

TAGCGAGCTTCAGAACCTACAGCCAGACTTCTCCTCCAAATTAATGGGCTGTGACTCCT

TCGACCAGTTCTCTGCAGAAAGAAGAAACTCTATACTCACAGAGACCCTCCACCGCTTC

TCCCTTGAGGGAGATGCCCCAGTTTCTTGGACAGAAACCAAGAAGCAGTCCTTTAAGCA

GACTGGCGAGTTTGGTGAAAAGAGGAAAAATTCAATTCTCAATCCTATTAACAGTATTC

GCAAGTTCAGCATTGTCCAGAAGACACCCCTCCAGATGAATGGCATCGAAGAAGATAG

TGACGAGCCGCTGGAGAGACGGCTGAGTCTGGTGCCAGATTCAGAACAGGGGGAGGCC

ATCCTGCCCCGGATCAGCGTCATTTCCACAGGCCCCACATTACAAGCACGGCGCCGGCA

GAGTGTTTTAAATCTCATGACCCATTCAGTGAACCAGGGCCAAAATATCCACAGGAAGA

CTACAGCTTCTACCCGGAAAGTGTCTCTGGCCCCTCAGGCCAATCTGACCGAGCTGGAC

ATCTACAGCAGGAGGCTCTCCCAGGAAACAGGGCTTGAAATATCTGAAGAGATTAATG

AAGAGGATCTTAAAGAGTGCTTCTTTGATGACATGGAGAGCATCCCCGCGGTGACCACA

TGGAACACCTACCTTAGATATATTACTGTCCACAAGAGCCTCATATTTGTCCTCATCTGG

TGCCTGGTTATTTTCCTCGCTGAGGTGGCGGCCAGTCTTGTTGTGCTCTGGCTGCTGGGC

AACACTCCTCTCCAGGACAAGGGCAATAGTACACACAGCAGAAATAATTCTTATGCCGT

CATCATTACAAGCACCTCCAGCTACTACGTGTTCTACATCTATGTGGGCGTGGCTGACA

CCCTCCTGGCCATGGGTTTCTTCCGGGGCCTGCCTTTGGTGCACACCCTCATCACAGTGT

CAAAAATTCTGCACCATAAAAATGCTTCATTCTGTCCTGCAGGCACCCATGAGCACTTTG

AACACATTGAAGGCTGGCGGCATCCTCAACAGATTTTCTAAAGATATTGCTATCCTGGA

TGATCTCCTCCCCCTGACAATCTTTGACTTTATCCAGCTTCTGCTGATCGTGATTGGAGC

CATAGCAGTGGTTGCTGTCCTGCAGCCCTACATTTTTGTGGCCACCGTGCCCGTGATTGT

TGCCTTTATTATGCTCAGAGCTTACTTCCTGCAAACTTCTCAACAGCTCAAACAGCTAGA

ATCTGAGGGCCGGAGCCCCATTTTTACCCACCTGGTGACTTCCCTGAAGGGACTGTGGA

CTCTGAGAGCATTCGGGCGACAGCCTTACTTTGAGACACTGTTCCACAAGGCCCTGAAC

TTGCACACTGCCAACTGGTTTCTTTACCTGAGCACACTCCGCTGGTTCCAGATGCGGATA

GAGATGATCTTCGTCATCTTTTTTATAGCTGTAACCTTCATTTCTATCCTTACAACAGGA

GAAGGAGAGGGCAGGGTGGGAATCATCCTCACGCTGGCTATGAACATAATGTCCACCT

TGCAGTGGGCCGTGAATTCCAGTATAGATGTGGATTCTCTAATGAGGAGTGTCTCCCGG
```

```
GTGTTTAAATTCATTGATATGCCTACTGAGGGGAAACCCACCAAGTCAACAAAACCTTA

TAAGAATGGACAGCTGAGCAAGGTGATGATAATTGAGAACAGCCACGTGAAGAAGGAT

GACATTTGGCCCAGCGGGGGCCAGATGACTGTGAAGGACCTGACGGCCAAGTACACCG

AAGGTGGAAATGCCATTTTGGAAAACATCAGCTTCTCAATCTCTCCTGGGCAGAGAGTT

GGATTGCTGGGTCGCACGGGCAGCGGCAAATCAACCCTGCTCAGTGCCTTCCTTCGGCT

CCTGAATACAGAAGGCGAAATCCAAATTGACGGGGTGAGCTGGGACAGCATCACCCTG

CAGCAGTGGAGAAAAGCATTTGGGGTCATTCCACAGAAAGTTTTCATCTTCTCTGGCAC

TTTCAGAAAGAACCTGGACCCCTATGAGCAGTGGAGCGACCAGGAGATCTGGAAGGTT

GCAGATGAAGTTGGCCTGCGGAGTGTGATAGAACAATTTCCTGGCAAGCTGGATTTTGT

GCTGGTAGATGGAGGCTGCGTGCTGTCCCACGGCCACAAACAGCTGATGTGCCTCGCCC

GCTCCGTTCTTTCAAAGGCCAAAATCTTGCTTTTGGATGAGCCCAGTGCTCACCTCGACC

CAGTGACCTATCAGATAATCCGCAGGACCTTAAAGCAAGCTTTTGCCGACTGCACCGTC

ATACTGTGTGAGCACCGGATTGAAGCAATGCTGGAATGCCAGCAGTTTCTGGTGATCGA

GGAGAATAAGGTCCGGCAGTACGACAGCATCCAGAAGTTGTTGAATGAGCGCAGCCTT

TTCCGCCAGGCCATCTCCCCATCTGACAGAGTCAAGCTGTTTCCACATAGGAACTCCTCT

AAGTGCAAGTCCAAGCCCCAGATCGCTGCCCTCAAGGAGGAAACTGAGGAAGAGGTGC

AGGATACCCGCCTGTGA.
```

In yet another embodiment, an exemplary codon-optimized CFTR mRNA sequence is:

```
                                                  (SEQ ID NO: 16)
ATGCAGAGGAGCCCACTGGAGAAAGCCTCCGTGGTGAGTAAACTCTTTTTTAGTTGGAC

CAGACCCATCCTGCGAAAAGGATACAGGCAGCGCCTCGAGTTGTCAGATATCTACCAG

ATTCCTTCTGTGGACTCAGCTGACAATTTGAGTGAGAAGCTGGAGCGGGAGTGGGATAG

AGAGCTGGCGAGCAAAAAAAACCCCAAGCTTATCAATGCTCTGCGCCGCTGCTTTTTCT

GGAGGTTCATGTTTTATGGGATCTTCCTGTACCTGGGGGAGGTCACCAAAGCTGTTCAG

CCGCTCCTTCTTGGCCGCATCATCGCCAGCTATGACCCTGATAATAAAGAAGAAAGGTC

TATTGCTATTTATCTGGGAATTGGCCTCTGCTTGCTCTTCATCGTCCGCACCCTTCTGCTG

CACCCTGCCATTTTTGGCCTTCACCACATCGGCATGCAAATGAGAATTGCCATGTTCTCC

CTCATTTACAAAAAGACCCTGAAACTTTCCTCAAGAGTGTTAGATAAAATATCCATTGG

TCAGCTGGTCAGCCTGCTGTCCAACAATCTTAACAAATTTGATGAAGGCTTGGCGCTGG

CCCACTTCGTGTGGATTGCACCTCTGCAGGTGGCCCTGTTGATGGGACTTATATGGGAG

CTGCTTCAAGCCTCTGCTTTCTGTGGGCTGGGCTTTTTGATTGTACTGGCACTTTTTCAGG

CTGGGCTCGGAAGAATGATGATGAAATACAGAGATCAGCGGGCCGGGAAGATATCAGA

GCGACTTGTGATCACCAGTGAAATGATTGAAAATATTCAGAGCGTGAAAGCCTACTGCT

GGGAAGAAGCCATGGAGAAGATGATTGAGAACCTGAGGCAGACAGAGCTCAAGCTCAC

TCGGAAGGCTGCTTATGTTCGCTATTTCAACAGCAGCGCCTTCTTCTTCAGTGGCTTCTT

TGTTGTCTTCCTGTCTGTTCTGCCATATGCACTGATAAAAGGCATTATTTTACGAAAGAT

CTTCACCACCATCAGTTTTTGCATCGTTCTCAGGATGGCCGTCACAAGACAGTTCCCCTG

GGCTGTGCAGACCTGGTACGATTCCTTGGGGGCCATCAACAAGATTCAAGATTTCTTGC

AAAAACAAGAATATAAAACTTTAGAATACAACCTCACCACCACTGAAGTGGTCATGGA
```

```
AAATGTGACAGCCTTTTGGGAGGAGGGTTTTGGAGAATTGTTCGAGAAGGCAAAGCAG

AATAACAACAACAGGAAGACGAGCAATGGGGACGACTCTCTCTTCTTCAGCAACTTTTC

ACTGCTCGGGACCCCTGTGTTGAAAGATATAAACTTCAAGATCGAGAGGGGCCAGCTCT

TGGCTGTGGCAGGCTCCACTGGAGCTGGTAAAACATCTCTTCTCATGGTGATCATGGGG

GAACTGGAGCCTTCCGAAGGAAAAATCAAGCACAGTGGGAGAATCTCATTCTGCAGCC

AGTTTTCCTGGATCATGCCCGGCACCATTAAGGAAAACATCATATTTGGAGTGTCCTAT

GATGAGTACCGCTACCGGTCCGTCATCAAAGCCTGTCAGTTGGAGGAGGACATCTCCAA

GTTTGCAGAGAAAGACAACATTGTGCTTGGAGAGGGGGGTATCACTCTTTCTGGAGGAC

AAAGAGCCAGGATCTCTTTGGCCCGGGCAGTCTACAAGGATGCAGACCTCTACTTGTTG

GACAGTCCCTTCGGCTACCTCGACGTGCTGACTGAAAAAGAAATTTTTGAAAGCTGTGT

GTGCAAACTGATGGCAAACAAGACCAGGATTCTTGTCACCAGCAAGATGGAACATCTG

AAGAAAGCGGACAAAATTCTGATTCTGCATGAAGGGAGCTCCTACTTCTATGGAACATT

TAGCGAGCTTCAGAACCTACAGCCAGACTTCTCCTCCAAATTAATGGGCTGTGACTCCT

TCGACCAGTTCTCTGCAGAAAGAAGAAACTCTATACTCACAGAGACCCTCCACCGCTTC

TCCCTTGAGGGAGATGCCCCAGTTTCTTGGACAGAAACCAAGAAGCAGTCCTTTAAGCA

GAC TGGCGAGTTTGGTGAAAAGAGGAAAAATTCAATTCTCAATCCAATTAACAGTATTC

GCAAGTTCAGCATTGTCCAGAAGACACCCCTCCAGATGAATGGCATCGAAGAAGATAG

TGACGAGCCGCTGGAGAGACGGCTGAGTCTGGTGCCAGATTCAGAACAGGGGGAGGCC

ATCCTGCCCCGGATCAGCGTCATTTCCACAGGCCCCACATTACAAGCACGGCGCCGGCA

GAGTGTTTTAAATCTCATGACCCATTCAGTGAACCAGGGCCAAAATATCCACAGGAAGA

CTACAGCTTCTACCCGGAAAGTGTCTCTGGCCCCTCAGGCCAATCTGACCGAGCTGGAC

ATCTACAGCAGGAGGCTCTCCCAGGAAACAGGGCTGGAAATATCTGAAGAGATTAATG

AAGAGGATCTTAAAGAGTGCTTCTTTGATGACATGGAGAGCATCCCCGCGGTGACCACA

TGGAACACCTACCTTAGATATATTACTGTCCACAAGAGCCTCATATTTGTCCTCATCTGG

TGCCTGGTTATTTTCCTCGCTGAGGTGGCGGCCAGTCTTGTTGTGCTCTGGCTGCTGGGC

AACACTCCTCTCCAGGACAAGGGCAATAGTACTCACAGCAGAAATAATTCTTATGCCGT

CATCATTACAAGCACCTCCAGCTACTACGTGTTCTACATCTATGTGGGCGTGGCTGACA

CCCTCCTGGCCATGGGTTTCTTCCGGGGCCTGCCTTTGGTGCACACCCTCATCACAGTGT

CAAAAATTCTGCACCATAAAATGCTTCATTCTGTCCTGCAGGCACCCATGAGCACTTTG

AACACATTGAAGGCTGGCGGCATCCTCAACAGATTTTCTAAAGATATTGCTATCCTGGA

TGATCTCCTCCCCCTGACAATCTTTGACTTTATCCAGCTTCTGCTGATCGTGATTGGAGC

CATAGCAGTGGTTGCTGTCCTGCAGCCCTACATTTTTGTGGCCACCGTGCCCGTGATTGT

TGCCTTTATTATGCTCAGAGCTTACTTCCTGCAAACTTCTCAACAGCTCAAACAGCTAGA

GTCTGAGGGCCGGAGCCCCATTTTTACCCACCTGGTGACTTCCCTGAAGGGACTGTGGA

CTCTGAGAGCATTCGGGCGACAGCCTTACTTTGAGACACTGTTCCACAAGGCCCTGAAC

TTGCACACTGCCAACTGGTTTCTTTACCTGAGCACACTCCGCTGGTTCCAGATGCGGATA

GAGATGATCTTCGTCATCTTTTTTATAGCTGTAACCTTCATTTCTATCCTTACAACAGGA

GAAGGAGAGGGCAGGGTGGGAATCATCCTCACGCTGGCTATGAACATAATGTCCACCT

TGCAGTGGGCCGTGAATTCCAGTATAGATGTGGATTCTCTAATGAGGAGTGTCTCCCGG

GTGTTTAAATTCATTGATATGCCTACTGAGGGGAAACCCACCAAGTCAACAAAACCTTA
```

```
TAAGAATGGACAGCTGAGCAAGGTGATGATAATTGAGAACAGCCACGTGAAGAAGGAT

GACATTTGGCCCAGCGGGGCCAGATGACTGTGAAGGACCTGACGGCCAAGTACACCG

AAGGTGGAAATGCCATTTTGGAAAACATCAGCTTCTCAATCTCTCCTGGGCAGAGAGTT

GGATTGCTGGGTCGCACGGGCAGCGGCAAATCAACCCTGCTCAGTGCCTTCCTTCGGCT

CCTGAATACAGAAGGCGAAATCCAAATTGACGGGGTGAGCTGGGACAGCATCACCCTG

CAGCAGTGGAGAAAAGCATTTGGGGTCATTCCACAGAAAGTTTTCATCTTCTCTGGCAC

TTTCAGAAAGAACCTGGACCCCTATGAGCAGTGGAGCGACCAGGAGATCTGGAAGGTT

GCAGATGAAGTTGGCCTGCGGAGTGTGATAGAACAATTTCCTGGCAAGCTGGATTTTGT

GCTGGTAGATGGAGGCTGCGTGCTGTCCCACGGCCACAAACAGCTGATGTGCCTCGCCC

GCTCCGTTCTTTCAAAGGCCAAAATCTTGCTTTTGGATGAGCCCAGTGCTCACCTCGACC

CAGTGACCTATCAGATAATCCGCAGGACCTTAAAGCAAGCTTTTGCCGACTGCACCGTC

ATACTGTGTGAGCACCGGATTGAAGCAATGCTGGAATGCCAGCAGTTTCTGGTGATCGA

GGAGAATAAGGTCCGGCAGTACGACAGCATCCAGAAGTTGTTGAATGAGCGCAGCCTT

TTCCGCCAGGCCATCTCCCCATCTGACAGAGTCAAGCTGTTTCCACATAGGAACTCCTCT

AAGTGCAAGTCCAAGCCCCAGATCGCTGCCCTCAAGGAGGAAACTGAGGAAGAGGTGC

AGGATACCCGCCTGTGA.
```

In another embodiment, an exemplary codon-optimized CFTR mRNA sequence is:

```
                                                   (SEQ ID NO: 17)
ATGCAGAGGAGCCCACTGGAGAAAGCCTCCGTGGTGAGTAAACTCTTTTTTAGTTGGAC

CAGACCCATCCTGCGAAAAGGATACAGGCAGCGCCTCGAGTTGTCTGATATCTACCAGA

TTCCTTCTGTGGACTCAGCTGACAATTTGAGTGAGAAGCTGGAGCGGGAGTGGGATAGA

GAGCTGGCGAGCAAAAAAAACCCCAAGCTTATCAATGCTCTGCGCCGCTGCTTTTTCTG

GAGGTTCATGTTTTATGGGATCTTCCTGTACCTGGGGGAGGTCACCAAAGCTGTTCAGC

CGCTCCTTCTTGGCCGCATCATCGCCAGCTATGACCCTGATAATAAAGAAGAAAGGTCT

ATTGCTATTTATCTGGGAATTGGCCTCTGCTTGCTCTTCATCGTCCGCACCCTTCTGCTGC

ACCCTGCCATTTTTGGCCTTCACCACATCGGCATGCAAATGAGAATTGCCATGTTCTCCC

TCATTTACAAAAAGACCCTGAAACTTTCCTCAAGAGTGTTAGATAAAATATCCATTGGT

CAGCTGGTCAGCCTGCTGTCCAACAATCTTAACAAATTTGATGAAGGCTTGGCGCTGGC

CCACTTCGTGTGGATTGCACCTCTGCAGGTGGCCCTGTTGATGGGACTTATATGGGAGC

TGCTTCAAGCCTCTGCTTTCTGTGGGCTGGGCTTTTTGATTGTACTGGCACTTTTTCAGGC

TGGGCTCGGAAGAATGATGATGAAATACAGAGATCAGCGGGCCGGGAAGATTTCAGAG

CGACTTGTGATCACCAGTGAAATGATTGAAAATATTCAGAGCGTGAAAGCCTACTGCTG

GGAAGAAGCCATGGAGAAGATGATTGAGAACCTGAGGCAGACAGAGCTCAAGCTCACT

CGGAAGGCTGCTTATGTTCGCTATTTCAACAGCAGCGCCTTCTTCTTCAGTGGCTTCTTT

GTTGTCTTCCTGTCTGTTCTGCCATATGCACTGATAAAAGGCATTATTTTACGAAAGATC

TTCACCACCATCAGTTTTTGCATCGTTCTCAGGATGGCCGTCACAAGACAGTTCCCCTGG

GCTGTGCAGACCTGGTACGATTCCTTGGGGGCCATCAACAAGATTCAAGATTTCTTGCA

AAAACAAGAATATAAAACTTTAGAATACAACCTCACCACCACTGAAGTGGTCATGGAA

AATGTGACAGCCTTTTGGGAGGAGGGTTTTGGAGAATTGTTCGAGAAGGCAAAGCAGA
```

-continued
```
ATAACAACAACAGGAAGACGAGCAATGGGACGACTCTCTCTTCTTCAGCAACTTTTCA
CTGCTCGGGACCCCTGTGTTGAAAGATATAAACTTCAAGATCGAGAGGGGCCAGCTCTT
GGCTGTGGCAGGCTCCACTGGAGCTGGTAAAACATCTCTTCTCATGGTGATCATGGGGG
AACTGGAGCCTTCCGAAGGAAAAATCAAGCACAGTGGGAGAATCTCATTCTGCAGCCA
GTTTTCCTGGATCATGCCCGGCACCATTAAGGAAAACATCATATTTGGAGTGTCCTATG
ATGAGTACCGCTACCGGTCAGTCATCAAAGCCTGTCAGTTGGAGGAGGACATCTCCAAG
TTTGCAGAGAAAGACAACATTGTGCTTGGAGAGGGGGGTATCACTCTTTCTGGAGGACA
AAGAGCCAGGATCTCTTTGGCCCGGGCAGTCTACAAGGATGCAGACCTCTACTTGTTGG
ACAGTCCCTTCGGCTACCTCGACGTGCTGACTGAAAAAGAAATTTTTGAAAGCTGTGTG
TGCAAACTGATGGCAAACAAGACCAGGATTCTTGTCACCAGCAAGATGGAACATCTGA
AGAAAGCGGACAAAATTCTGATTCTGCATGAAGGGAGCTCCTACTTCTATGGAACATTT
AGCGAGCTTCAGAACCTACAGCCAGACTTCTCCTCCAAATTAATGGGCTGTGACTCCTT
CGACCAGTTCTCTGCAGAAAGAAGAAACTCTATACTCACAGAGACCCTCCACCGCTTCT
CCCTTGAGGGAGATGCCCCAGTTTCTTGGACAGAAACCAAGAAGCAGTCCTTTAAGCAG
ACTGGCGAGTTTGGTGAAAAGAGGAAAAATTCAATTCTCAATCCTATTAACAGTATTCG
CAAGTTCAGCATTGTCCAGAAGACACCCCTCCAGATGAATGGCATCGAAGAAGATAGT
GACGAGCCGCTGGAGAGACGGCTGAGTCTGGTGCCAGATTCAGAACAGGGGGAGGCCA
TCCTGCCCCGGATCAGCGTCATTTCCACAGGCCCCACATTACAAGCACGGCGCCGGCAG
AGTGTTTTAAATCTCATGACCCATTCAGTGAACCAGGGCCAAAATATCCACAGGAAGAC
TACAGCTTCTACCCGGAAAGTGTCTCTGGCCCCTCAGGCCAATCTGACCGAGCTGGACA
TCTACAGCAGGAGGCTCTCCCAGGAAACAGGGCTGGAAATATCTGAAGAGATTAATGA
AGAGGATCTTAAAGAGTGCTTCTTTGATGACATGGAGAGCATCCCCGCGGTGACCACAT
GGAACACCTACCTTAGATATATTACTGTCCACAAGAGCCTCATATTTGTCCTCATCTGGT
GCCTGGTTATTTTCCTCGCTGAGGTGGCGGCCAGTCTTGTTGTGCTCTGGCTGCTGGGCA
ACACTCCTCTCCAGGACAAGGGCAATAGTACACACAGCAGAAATAATTCTTATGCCGTC
ATCATTACAAGCACCTCCAGCTACTACGTGTTCTACATCTATGTGGGCGTGGCTGACAC
CCTCCTGGCCATGGGTTTCTTCCGGGGCCTGCCTTTGGTGCACACCCTCATCACAGTGTC
AAAAATTCTGCACCATAAAATGCTTCATTCTGTCCTGCAGGCACCCATGAGCACTTTGA
ACACATTGAAGGCTGGCGGCATCCTCAACAGATTTTCTAAAGATATTGCTATCCTGGAT
GATCTCCTCCCCCTGACAATCTTTGACTTTATCCAGCTTCTGCTGATCGTGATTGGAGCC
ATAGCAGTGGTTGCTGTCCTGCAGCCCTACATTTTTGTGGCCACCGTGCCCGTGATTGTT
GCCTTTATTATGCTCAGAGCTTACTTCCTGCAAACTTCTCAACAGCTCAAACAGCTAGAA
TCTGAGGGCCGGAGCCCCATTTTTACCCACCTGGTGACTTCCCTGAAGGGACTGTGGAC
TCTGAGAGCATTCGGGCGACAGCCTTACTTTGAGACACTGTTCCACAAGGCCCTGAACT
TGCACACTGCCAACTGGTTTCTTTACCTGAGCACACTCCGCTGGTTCCAGATGCGGATA
GAGATGATCTTCGTCATCTTTTTTATAGCTGTAACCTTCATTTCTATCCTTACAACAGGA
GAAGGAGAGGGCAGGGTGGGAATCATCCTCACGCTGGCTATGAACATAATGTCCACCT
TGCAGTGGGCCGTGAATTCCAGTATAGATGTGGATTCTCTAATGAGGAGTGTCTCCCGG
GTGTTTAAATTCATTGATATGCCTACTGAGGGGAAACCCACCAAGTCAACAAAACCTTA
TAAGAATGGACAGCTGAGCAAGGTGATGATAATTGAGAACAGCCACGTGAAGAAGGAT
GACATTTGGCCCAGCGGGGGCCAGATGACTGTGAAGGACCTGACGGCCAAGTACACCG
```

-continued

```
AAGGTGGAAATGCCATTTTGGAAAACATCAGCTTCTCAATCTCTCCTGGGCAGAGAGTT

GGATTGCTGGGTCGCACGGGCAGCGGCAAATCAACCCTGCTCAGTGCCTTCCTTCGGCT

CCTGAATACAGAAGGCGAAATCCAAATTGACGGGGTGAGCTGGGACAGCATCACCCTG

CAGCAGTGGAGAAAAGCATTTGGGGTCATTCCACAGAAAGTTTTCATCTTCTCTGGCAC

TTTCAGAAAGAACCTGGACCCCTATGAGCAGTGGAGCGACCAGGAGATCTGGAAGGTT

GCAGATGAAGTTGGCCTGCGGAGTGTGATAGAACAATTTCCTGGCAAGCTGGATTTTGT

GCTGGTAGATGGAGGCTGCGTGCTGTCCCACGGCCACAAACAGCTGATGTGCCTCGCCC

GCTCCGTTCTTTCAAAGGCCAAAATCTTGCTTTTGGATGAGCCCAGTGCTCACCTCGACC

CAGTGACCTATCAGATAATCCGCAGGACCTTAAAGCAAGCTTTTGCCGACTGCACCGTC

ATACTGTGTGAGCACCGGATTGAAGCAATGCTGGAATGCCAGCAGTTTCTGGTGATCGA

GGAGAATAAGGTCCGGCAGTACGACAGCATCCAGAAGTTGTTGAATGAGCGCAGCCTT

TTCCGCCAGGCCATCTCCCCATCTGACAGAGTCAAGCTGTTTCCACATAGGAACTCCTCT

AAGTGCAAGTCCAAGCCCCAGATCGCTGCCCTCAAGGAGGAAACTGAGGAAGAGGTGC

AGGATACCCGCCTGTGA.
```

In another embodiment, an exemplary codon-optimized CFTR mRNA sequence is:

(SEQ ID NO: 18)
```
ATGCAGAGAAGCCCCCTGGAGAAGGCCTCTGTGGTGAGCAAGCTGTTCTTCAGCTGGAC

CAGACCCATCCTGAGAAAGGGCTACAGACAGAGACTGGAGCTGTCTGACATCTACCAG

ATCCCCTCTGTGGACTCTGCCGACAACCTGTCTGAGAAGCTGGAGAGAGAGTGGGACA

GAGAGCTGGCCAGCAAGAAGAACCCCAAGCTGATCAATGCCCTGAGAAGATGCTTCTT

CTGGAGATTCATGTTCTATGGCATCTTCCTGTACCTGGGAGAGGTGACCAAGGCCGTGC

AGCCCCTGCTGCTGGGCAGGATCATTGCCAGCTATGACCCTGACAACAAGGAGGAGAG

AAGCATTGCCATCTACCTGGGCATTGGCCTGTGCCTGCTGTTCATTGTGAGAACCCTGCT

GCTGCACCCTGCCATCTTTGGCCTGCACCACATTGGCATGCAGATGAGAATTGCCATGT

TCAGCCTGATCTACAAGAAGACCCTGAAGCTGAGCAGCAGAGTGCTGGACAAGATCAG

CATTGGCCAGCTGGTGAGCCTGCTGAGCAACAACCTGAACAAGTTTGATGAGGGCCTGG

CCCTGGCCCACTTTGTGTGGATTGCCCCCCTGCAGGTGGCCCTGCTGATGGGCCTGATCT

GGGAGCTGCTGCAGGCCTCTGCCTTCTGTGGCCTGGGCTTCCTGATTGTGCTGGCCCTGT

TCCAGGCCGGCCTGGGCAGAATGATGATGAAGTACAGAGACCAGAGAGCCGGCAAGAT

CTCTGAGAGACTGGTGATCACCTCTGAGATGATTGAGAACATCCAGTCTGTGAAGGCCT

ACTGCTGGGAGGAGGCCATGGAGAAGATGATTGAGAACCTGAGACAGACAGAGCTGAA

GCTGACCAGGAAGGCCGCCTATGTGAGATACTTCAACAGCTCTGCCTTCTTCTTCTCTGG

CTTCTTTGTGGTGTTCCTGTCTGTGCTGCCCTATGCCCTGATCAAGGGCATCATCCTGAG

GAAGATCTTCACCACCATCAGCTTCTGCATTGTGCTGAGGATGGCCGTGACCAGGCAGT

TCCCCTGGGCCGTGCAGACCTGGTATGACAGCCTGGGGGCCATCAACAAGATCCAGGA

CTTCCTGCAGAAGCAGGAGTACAAGACCCTGGAGTACAACCTGACCACCACAGAGGTG

GTGATGGAGAATGTGACAGCCTTCTGGGAGGAGGGCTTTGGAGAGCTGTTTGAGAAGG

CCAAGCAGAACAACAACAACAGAAAGACCAGCAATGGAGATGACAGCCTGTTCTTCAG

CAACTTCAGCCTGCTGGGCACCCCTGTGCTGAAGGACATCAACTTCAAGATTGAGAGGG
```

-continued

```
GCCAGCTGCTGGCCGTGGCCGGCAGCACAGGAGCCGGCAAGACCAGCCTGCTGATGGT

GATCATGGGAGAGCTGGAGCCCTCTGAGGGCAAGATCAAGCACTCTGGCAGAATCAGC

TTCTGCAGCCAGTTCAGCTGGATCATGCCTGGCACCATCAAGGAGAACATCATCTTTGG

GGTGAGCTATGATGAGTACAGGTACAGATCTGTGATCAAGGCCTGCCAGCTGGAGGAG

GACATCTCCAAGTTTGCCGAGAAGGACAACATTGTGCTGGGGGAGGGAGGCATCACCC

TGTCTGGGGGCCAGAGAGCCAGAATCAGCCTGGCCAGAGCCGTGTACAAGGATGCCGA

CCTGTACCTGCTGGACAGCCCCTTTGGCTACCTGGATGTGCTGACAGAGAAGGAGATCT

TTGAGAGCTGTGTGTGCAAGCTGATGGCCAACAAGACCAGGATCCTGGTGACCAGCAA

GATGGAGCACCTGAAGAAGGCCGACAAGATCCTGATCCTGCATGAGGGCAGCAGCTAC

TTCTATGGCACCTTCTCTGAGCTGCAGAACCTGCAGCCTGACTTCAGCAGCAAGCTGAT

GGGCTGTGACAGCTTTGACCAGTTCTCTGCTGAGAGAAGAAACAGCATCCTGACAGAG

ACCCTGCACAGGTTCAGCCTGGAGGGGGATGCCCCTGTGAGCTGGACAGAGACCAAGA

AGCAGAGCTTCAAGCAGACAGGAGAGTTTGGGGAGAAGAGGAAGAACAGCATCCTGA

ACCCCATCAACAGCATCAGGAAGTTCAGCATTGTGCAGAAGACCCCCCTGCAGATGAA

TGGCATTGAGGAGGACTCTGATGAGCCCCTGGAGAGAAGACTGAGCCTGGTGCCAGAC

TCTGAGCAGGGAGAGGCCATCCTGCCCAGGATCTCTGTGATCAGCACAGGCCCCACCCT

GCAGGCCAGAAGAAGACAGTCTGTGCTGAACCTGATGACCCACTCTGTGAACCAGGGC

CAGAATATCCACAGAAAGACCACAGCCAGCACCAGAAAGGTGAGCCTGGCCCCCCAGG

CCAACCTGACAGAGCTGGACATCTACAGCAGAAGGCTGAGCCAGGAGACAGGCCTGGA

GATCTCTGAGGAGATCAATGAGGAGGACCTGAAGGAGTGCTTCTTTGATGACATGGAG

AGCATCCCTGCCGTGACCACCTGGAACACCTACCTGAGATACATCACAGTGCACAAGA

GCCTGATCTTTGTGCTGATCTGGTGCCTGGTGATCTTCCTGGCCGAGGTGGCCGCCAGCC

TGGTGGTGCTGTGGCTGCTGGGCAACACCCCCTGCAGGACAAGGGCAACAGCACCCA

CAGCAGAAACAACAGCTATGCTGTGATCATCACCAGCACCAGCAGCTACTATGTGTTCT

ACATCTATGTGGGAGTGGCTGACACCCTGCTGGCCATGGGCTTCTTCAGAGGCCTGCCC

CTGGTGCACACCCTGATCACAGTGAGCAAGATCCTGCACCACAAGATGCTGCACTCTGT

GCTGCAGGCCCCCATGAGCACCCTGAACACCCTGAAGGCTGGAGGCATCCTGAACAGA

TTCAGCAAGGACATTGCCATCCTGGATGACCTGCTGCCCCTGACCATCTTTGACTTCATC

CAGCTGCTGCTGATTGTGATTGGAGCCATTGCCGTGGTGGCCGTGCTGCAGCCCTACAT

CTTTGTGGCCACAGTGCCTGTGATTGTGGCCTTCATCATGCTGAGGGCCTACTTCCTGCA

GACCAGCCAGCAGCTGAAGCAGCTGGAGTCTGAGGGCAGAAGCCCCATCTTCACCCAC

CTGGTGACCAGCCTGAAGGGCCTGTGGACCCTGAGGGCCTTTGGCAGACAGCCCTACTT

TGAGACCCTGTTCCACAAGGCCCTGAACCTGCACACAGCCAACTGGTTCCTGTACCTGA

GCACCCTGAGATGGTTCCAGATGAGGATTGAGATGATCTTTGTGATCTTCTTCATTGCCG

TGACCTTCATCAGCATCCTGACCACAGGGGAGGGCGAGGGCAGAGTGGGCATCATCCT

GACCCTGGCCATGAACATCATGAGCACCCTGCAGTGGGCCGTGAACAGCAGCATTGAT

GTGGACAGCCTGATGAGATCTGTGAGCAGAGTGTTCAAGTTCATTGACATGCCCACAGA

GGGCAAGCCCACCAAGAGCACCAAGCCCTACAAGAATGGCCAGCTGAGCAAGGTGATG

ATCATTGAGAACAGCCATGTGAAGAAGGATGACATCTGGCCCTCTGGAGGCCAGATGA

CAGTGAAGGACCTGACAGCCAAGTACACAGAGGGGGGCAATGCCATCCTGGAGAACAT
```

```
CAGCTTCAGCATCAGCCCTGGCCAGAGGGTGGGCCTGCTGGGCAGAACAGGCTCTGGC

AAGAGCACCCTGCTGTCTGCCTTCCTGAGGCTGCTGAACACAGAGGGAGAGATCCAGA

TTGATGGGGTGAGCTGGGACAGCATCACCCTGCAGCAGTGGAGGAAGGCCTTTGGGGT

GATCCCCCAGAAGGTGTTCATCTTCTCTGGCACCTTCAGGAAGAACCTGGACCCCTATG

AGCAGTGGTCTGACCAGGAGATCTGGAAGGTGGCCGATGAGGTGGGCCTGAGATCTGT

GATTGAGCAGTTCCCTGGCAAGCTGGACTTTGTGCTGGTGGATGGAGGCTGTGTGCTGA

GCCATGGCCACAAGCAGCTGATGTGCCTGGCCAGATCTGTGCTGAGCAAGGCCAAGAT

CCTGCTGCTGGATGAGCCCTCTGCCCACCTGGACCCTGTGACCTACCAGATCATCAGAA

GAACCCTGAAGCAGGCCTTTGCCGACTGCACAGTGATCCTGTGTGAGCACAGAATTGAG

GCCATGCTGGAGTGCCAGCAGTTCCTGGTGATTGAGGAGAACAAGGTGAGGCAGTATG

ACAGCATCCAGAAGCTGCTGAATGAGAGAAGCCTGTTCAGACAGGCCATCAGCCCCTC

TGACAGAGTGAAGCTGTTCCCCCACAGGAACAGCAGCAAGTGCAAGAGCAAGCCCCAG

ATTGCCGCCCTGAAGGAGGAGACAGAGGAGGAGGTGCAGGACACCAGACTGTGA.
```

In yet another embodiment, an exemplary codon-optimized CFTR mRNA sequence is:

```
                                                  (SEQ ID NO: 19)
ATGCAGAGGAGCCCCCTGGAGAAGGCCAGCGTGGTGAGCAAGCTGTTCTTCAGCTGGA

CCAGGCCCATCCTGAGGAAGGGCTACAGGCAGAGGCTGGAGCTGAGCGACATCTACCA

GATCCCCAGCGTGGACAGCGCCGACAACCTGAGCGAGAAGCTGGAGAGGGAGTGGGA

CAGGGAGCTGGCCAGCAAGAAGAACCCCAAGCTGATCAACGCCCTGAGGAGGTGCTTC

TTCTGGAGGTTCATGTTCTACGGCATCTTCCTGTACCTGGGCGAGGTGACCAAGGCCGT

GCAGCCCCTGCTGCTGGGCAGGATCATCGCCAGCTACGACCCCGACAACAAGGAGGAG

AGGAGCATCGCCATCTACCTGGGCATCGGCCTGTGCCTGCTGTTCATCGTGAGGACCCT

GCTGCTGCACCCCGCCATCTTCGGCCTGCACCACATCGGCATGCAGATGAGGATCGCCA

TGTTCAGCCTGATCTACAAGAAGACCCTGAAGCTGAGCAGCAGGGTGCTGGACAAGAT

CAGCATCGGCCAGCTGGTGAGCCTGCTGAGCAACAACCTGAACAAGTTCGACGAGGGC

CTGGCCCTGGCCCACTTCGTGTGGATCGCCCCCCTGCAGGTGGCCCTGCTGATGGGCCT

GATCTGGGAGCTGCTGCAGGCCAGCGCCTTCTGCGGCCTGGGCTTCCTGATCGTGCTGG

CCCTGTTCCAGGCCGGCCTGGGCAGGATGATGATGAAGTACAGGGACCAGAGGGCCGG

CAAGATCAGCGAGAGGCTGGTGATCACCAGCGAGATGATCGAGAACATCCAGAGCGTG

AAGGCCTACTGCTGGGAGGAGGCCATGGAGAAGATGATCGAGAACCTGAGGCAGACCG

AGCTGAAGCTGACCAGGAAGGCCGCCTACGTGAGGTACTTCAACAGCAGCGCCTTCTTC

TTCAGCGGCTTCTTCGTGGTGTTCCTGAGCGTGCTGCCCTACGCCCTGATCAAGGGCATC

ATCCTGAGGAAGATCTTCACCACCATCAGCTTCTGCATCGTGCTGAGGATGGCCGTGAC

CAGGCAGTTCCCCTGGGCCGTGCAGACCTGGTACGACAGCCTGGGCGCCATCAACAAG

ATCCAGGACTTCCTGCAGAAGCAGGAGTACAAGACCCTGGAGTACAACCTGACCACCA

CCGAGGTGGTGATGGAGAACGTGACCGCCTTCTGGGAGGAGGGCTTCGGCGAGCTGTT

CGAGAAGGCCAAGCAGAACAACAACAACAGGAAGACCAGCAACGGCGACGACAGCCT

GTTCTTCAGCAACTTCAGCCTGCTGGGCACCCCCGTGCTGAAGGACATCAACTTCAAGA

TCGAGAGGGGCCAGCTGCTGGCCGTGGCCGGCAGCACCGGCGCCGGCAAGACCAGCCT
```

-continued

```
GCTGATGGTGATCATGGGCGAGCTGGAGCCCAGCGAGGGCAAGATCAAGCACAGCGGC
AGGATCAGCTTCTGCAGCCAGTTCAGCTGGATCATGCCCGGCACCATCAAGGAGAACAT
CATCTTCGGCGTGAGCTACGACGAGTACAGGTACAGGAGCGTGATCAAGGCCTGCCAG
CTGGAGGAGGACATCAGCAAGTTCGCCGAGAAGGACAACATCGTGCTGGGCGAGGGCG
GCATCACCCTGAGCGGCGGCCAGAGGGCCAGGATCAGCCTGGCCAGGGCCGTGTACAA
GGACGCCGACCTGTACCTGCTGGACAGCCCCTTCGGCTACCTGGACGTGCTGACCGAGA
AGGAGATCTTCGAGAGCTGCGTGTGCAAGCTGATGGCCAACAAGACCAGGATCCTGGT
GACCAGCAAGATGGAGCACCTGAAGAAGGCCGACAAGATCCTGATCCTGCACGAGGGC
AGCAGCTACTTCTACGGCACCTTCAGCGAGCTGCAGAACCTGCAGCCCGACTTCAGCAG
CAAGCTGATGGGCTGCGACAGCTTCGACCAGTTCAGCGCCGAGAGGAGGAACAGCATC
CTGACCGAGACCCTGCACAGGTTCAGCCTGGAGGGCGACGCCCCCGTGAGCTGGACCG
AGACCAAGAAGCAGAGCTTCAAGCAGACCGGCGAGTTCGGCGAGAAGAGGAAGAACA
GCATCCTGAACCCCATCAACAGCATCAGGAAGTTCAGCATCGTGCAGAAGACCCCCCTG
CAGATGAACGGCATCGAGGAGGACAGCGACGAGCCCCTGGAGAGGAGGCTGAGCCTG
GTGCCCGACAGCGAGCAGGGCGAGGCCATCCTGCCCAGGATCAGCGTGATCAGCACCG
GCCCCACCCTGCAGGCCAGGAGGAGGCAGAGCGTGCTGAACCTGATGACCCACAGCGT
GAACCAGGGCCAGAACATCCACAGGAAGACCACCGCCAGCACCAGGAAGGTGAGCCT
GGCCCCCCAGGCCAACCTGACCGAGCTGGACATCTACAGCAGGAGGCTGAGCCAGGAG
ACCGGCCTGGAGATCAGCGAGGAGATCAACGAGGAGGACCTGAAGGAGTGCTTCTTCG
ACGACATGGAGAGCATCCCCGCCGTGACCACCTGGAACACCTACCTGAGGTACATCAC
CGTGCACAAGAGCCTGATCTTCGTGCTGATCTGGTGCCTGGTGATCTTCCTGGCCGAGG
TGGCCGCCAGCCTGGTGGTGCTGTGGCTGCTGGGCAACACCCCCCTGCAGGACAAGGG
CAACAGCACCCACAGCAGGAACAACAGCTACGCCGTGATCATCACCAGCACCAGCAGC
TACTACGTGTTCTACATCTACGTGGGCGTGGCCGACACCCTGCTGGCCATGGGCTTCTTC
AGGGGCCTGCCCCTGGTGCACACCCTGATCACCGTGAGCAAGATCCTGCACCACAAGAT
GCTGCACAGCGTGCTGCAGGCCCCCATGAGCACCCTGAACACCCTGAAGGCCGGCGGC
ATCCTGAACAGGTTCAGCAAGGACATCGCCATCCTGGACGACCTGCTGCCCCTGACCAT
CTTCGACTTCATCCAGCTGCTGCTGATCGTGATCGGCGCCATCGCCGTGGTGGCCGTGCT
GCAGCCCTACATCTTCGTGGCCACCGTGCCCGTGATCGTGGCCTTCATCATGCTGAGGG
CCTACTTCCTGCAGACCAGCCAGCAGCTGAAGCAGCTGGAGAGCGAGGGCAGGAGCCC
CATCTTCACCCACCTGGTGACCAGCCTGAAGGGCCTGTGGACCCTGAGGGCCTTCGGCA
GGCAGCCCTACTTCGAGACCCTGTTCCACAAGGCCCTGAACCTGCACACCGCCAACTGG
TTCCTGTACCTGAGCACCCTGAGGTGGTTCCAGATGAGGATCGAGATGATCTTCGTGAT
CTTCTTCATCGCCGTGACCTTCATCAGCATCCTGACCACCGGCGAGGGCGAGGGCAGGG
TGGGCATCATCCTGACCCTGGCCATGAACATCATGAGCACCCTGCAGTGGGCCGTGAAC
AGCAGCATCGACGTGGACAGCCTGATGAGGAGCGTGAGCAGGGTGTTCAAGTTCATCG
ACATGCCCACCGAGGGCAAGCCCACCAAGAGCACCAAGCCCTACAAGAACGGCCAGCT
GAGCAAGGTGATGATCATCGAGAACAGCCACGTGAAGAAGGACGACATCTGGCCCAGC
GGCGGCCAGATGACCGTGAAGGACCTGACCGCCAAGTACACCGAGGGCGGCAACGCCA
TCCTGGAGAACATCAGCTTCAGCATCAGCCCCGGCCAGAGGGTGGGCCTGCTGGGCAG
GACCGGCAGCGGCAAGAGCACCCTGCTGAGCGCCTTCCTGAGGCTGCTGAACACCGAG
```

-continued

```
GGCGAGATCCAGATCGACGGCGTGAGCTGGGACAGCATCACCCTGCAGCAGTGGAGGA

AGGCCTTCGGCGTGATCCCCCAGAAGGTGTTCATCTTCAGCGGCACCTTCAGGAAGAAC

CTGGACCCCTACGAGCAGTGGAGCGACCAGGAGATCTGGAAGGTGGCCGACGAGGTGG

GCCTGAGGAGCGTGATCGAGCAGTTCCCCGGCAAGCTGGACTTCGTGCTGGTGGACGG

CGGCTGCGTGCTGAGCCACGGCCACAAGCAGCTGATGTGCCTGGCCAGGAGCGTGCTG

AGCAAGGCCAAGATCCTGCTGCTGGACGAGCCCAGCGCCCACCTGGACCCCGTGACCT

ACCAGATCATCAGGAGGACCCTGAAGCAGGCCTTCGCCGACTGCACCGTGATCCTGTGC

GAGCACAGGATCGAGGCCATGCTGGAGTGCCAGCAGTTCCTGGTGATCGAGGAGAACA

AGGTGAGGCAGTACGACAGCATCCAGAAGCTGCTGAACGAGAGGAGCCTGTTCAGGCA

GGCCATCAGCCCCAGCGACAGGGTGAAGCTGTTCCCCCACAGGAACAGCAGCAAGTGC

AAGAGCAAGCCCCAGATCGCCGCCCTGAAGGAGGAGACCGAGGAGGAGGTGCAGGAC

ACCAGGCTGTGA.
```

In another embodiment, an exemplary codon-optimized CFTR mRNA sequence is:

```
                                              (SEQ ID NO: 20)
ATGCAGAGATCCCCTCTGGAGAAGGCCTCAGTGGTGTCCAAGCTTTTCTTCTCCTGGAC

CAGGCCCATTTTAAGAAAGGGCTACAGGCAGAGACTTGAGCTGTCTGACATCTATCAGA

TCCCTTCTGTGGATTCTGCTGACAATCTTAGTGAAAAATTGGAAGGGAGTGGGACAGA

GAGCTGGCAAGTAAAAAGAACCCCAAGCTGATTAATGCCCTGAGGCGCTGCTTTTTTG

GAGATTCATGTTCTATGGCATATTCCTCTACCTTGGAGAAGTAACCAAAGCTGTACAGC

CTCTCCTCCTTGGCAGAATCATTGCCTCCTATGATCCTGATAACAAGGAGGAGAGAAGC

ATAGCCATCTACCTGGGCATTGGGCTGTGCCTCTTGTTTATTGTGAGGACCCTTCTCTTG

CACCCTGCCATCTTTGGCCTTCATCACATTGGCATGCAAATGAGAATAGCAATGTTTAGT

CTTATTTACAAAAAAACATTAAAACTCTCTTCCAGGGTGTTGGACAAGATCAGTATTGG

ACAACTGGTCAGCCTGCTGAGCAACAACCTGAACAAGTTTGATGAAGGACTGGCCCTG

GCCCACTTTGTCTGGATTGCCCCCCTTCAGGTGGCTCTTTTGATGGGCCTGATCTGGGAA

CTCCTGCAGGCCTCTGCCTTCTGTGGGTTAGGCTTCCTGATAGTGCTAGCTCTCTTTCAG

GCAGGGTTGGGTAGAATGATGATGAAGTACAGAGACCAGAGGGCTGGGAAGATATCTG

AGAGGCTGGTCATTACTTCTGAAATGATAGAAAACATCCAGTCTGTTAAAGCTTACTGC

TGGGAGGAGGCTATGGAAAAGATGATTGAGAACTTGAGGCAAACAGAGCTCAAGCTGA

CTAGGAAGGCAGCCTATGTCAGGTATTTCAACAGCAGTGCTTTCTTCTTCTCAGGCTTTT

TCGTGGTCTTCTTGAGTGTTCTGCCCTATGCCCTCATCAAGGGGATAATTTTGAGAAAGA

TTTTCACCACTATTTCCTTTTGCATTGTCCTGAGGATGGCTGTCACCAGGCAATTCCCCT

GGGCTGTGCAGACATGGTATGACTCTCTGGGGGCCATCAACAAAATCCAAGATTTCCTG

CAGAAGCAGGAGTACAAGACCCTGGAATACAACCTCACCACCACAGAAGTTGTGATGG

AGAATGTGACTGCATTCTGGGAGGAAGGATTTGGGGAGCTGTTTGAGAAAGCAAAACA

AAACAATAATAACAGGAAAACCAGCAATGGAGATGACTCCCTGTTCTTTTCCAACTTCT

CTTTGTTGGGCACCCCTGTCCTGAAAGATATAAACTTTAAAATTGAAAGAGGGCAGCTG

TTGGCAGTTGCTGGCTCCACAGGAGCTGGAAAAACTTCACTACTGATGGTGATCATGGG

GGAGTTAGAACCCTCTGAAGGGAAAATAAAACATTCTGGGAGGATTAGTTTCTGCAGCC
```

-continued

```
AGTTCAGCTGGATCATGCCTGGGACCATTAAAGAAAATATTATATTTGGAGTGAGCTAT
GATGAATATAGATATAGGAGTGTCATCAAAGCCTGTCAGTTGGAGGAAGACATCAGCA
AATTTGCAGAGAAAGACAACATTGTTCTGGGTGAAGGTGGCATCACCCTGTCAGGAGG
GCAAAGGGCCAGGATCAGCTTGGCCAGAGCAGTCTATAAAGATGCTGATCTGTACCTCC
TGGATAGCCCTTTTGGCTATCTGGATGTTTTGACAGAGAAGGAAATTTTTGAGTCCTGTG
TCTGCAAGTTAATGGCAAATAAAACAAGGATACTTGTGACCTCAAAAATGGAACACCT
GAAGAAGGCTGACAAAATTCTGATCCTGCATGAGGGCAGCAGCTACTTTTATGGAACAT
TTTCTGAACTGCAGAATTTGCAACCAGACTTTTCATCAAAGCTCATGGGATGTGACAGT
TTTGATCAGTTTTCTGCAGAAAGGAGAAACTCCATTTTGACTGAGACCCTGCACAGGTT
CAGTCTGGAGGGGATGCCCCAGTGAGTTGGACTGAGACAAAGAAACAGAGCTTCAAG
CAGACTGGAGAGTTTGGAGAAAAGAGGAAAAACTCAATTCTCAATCCCATCAATAGCA
TCAGGAAGTTCAGCATAGTTCAGAAGACTCCTTTGCAGATGAATGGGATTGAAGAGGA
CTCAGATGAGCCCCTGGAAAGGAGACTCTCCTTGGTGCCAGATTCAGAGCAGGGGGAA
GCCATACTGCCAAGGATCTCTGTGATTTCTACAGGGCCCACCCTCCAAGCAAGAAGGAG
ACAGTCAGTTTTAAACCTGATGACCCACTCTGTCAACCAGGGACAGAACATTCATAGAA
AGACAACAGCATCTACAAGAAAAGTTTCACTGGCCCCTCAAGCCAATTTAACTGAACTA
GATATCTACAGCAGGAGGCTCAGCCAAGAAACAGGCCTGGAGATCTCAGAAGAAATAA
ATGAGGAGGATTTGAAGGAATGCTTCTTTGATGATATGGAGAGCATCCCAGCTGTCACA
ACCTGGAACACCTACCTGAGATACATCACAGTGCACAAATCCCTCATCTTTGTACTTAT
ATGGTGCCTTGTCATCTTCTTAGCTGAGGTGGCTGCTTCCCTGGTGGTGCTGTGGCTGCT
GGGAAACACACCCCTCCAGGATAAAGGGAACTCTACTCACAGCAGGAACAACAGTTAT
GCTGTGATCATCACCAGTACCTCCTCCTACTATGTGTTCTACATTTATGTTGGAGTTGCA
GACACATTGCTTGCCATGGGTTTTTTTAGAGGACTCCCCCTGGTGCATACTCTCATCACT
GTTTCCAAAATCCTTCACCACAAGATGCTGCACAGTGTACTACAGGCTCCCATGAGCAC
CCTCAACACTCTTAAAGCAGGAGGAATCTTGAACAGATTTAGCAAGGACATTGCAATTC
TTGATGACCTGCTTCCACTGACCATCTTTGACTTCATCCAGCTTCTGCTCATTGTAATTG
GTGCCATTGCTGTGGTAGCAGTGCTCCAGCCATATATTTTTGTGGCCACTGTGCCTGTTA
TTGTGGCCTTCATTATGTTGAGAGCCTACTTCCTGCAGACCTCTCAGCAGCTCAAGCAAC
TTGAAAGTGAGGGCAGGAGCCCCATATTTACACACTTGGTCACTTCCCTCAAAGGCCTC
TGGACACTCAGAGCTTTTGGAAGACAACCTTATTTTGAAACTCTCTTCCACAAGGCTCTG
AATCTCCACACAGCCAACTGGTTTCTGTATCTTTCAACACTGCGCTGGTTCCAGATGAGG
ATTGAGATGATCTTTGTTATCTTCTTCATAGCTGTTACCTTCATCTCTATTCTGACAACTG
GTGAGGGGAAGGGAGAGTAGGCATCATCCTCACACTAGCCATGAACATAATGTCTAC
CTTACAATGGGCCGTGAACAGCTCCATAGATGTGGACAGCCTCATGAGAAGTGTGTCAA
GAGTTTTCAAATTCATTGACATGCCCACAGAAGGCAAACCAACCAAGAGCACAAAACC
CTACAAGAATGGCCAGCTGAGTAAGGTCATGATCATTGAAAATTCTCATGTGAAGAAG
GATGATATTTGGCCCAGTGGGGCCAGATGACAGTCAAGGACCTCACTGCCAAATACA
CAGAGGGTGGAAATGCTATCCTAGAGAACATCTCCTTCTCCATCTCCCCAGGCCAAAGA
GTTGGCTTGCTGGGCAGGACTGGCAGTGGCAAGTCCACCTTGCTCTCAGCATTTCTCAG
GCTTTTAAATACAGAGGGAGAGATTCAAATTGATGGGGTGTCTTGGGATAGTATAACAC
```

-continued

```
TTCAACAGTGGAGGAAAGCCTTTGGTGTGATTCCTCAGAAAGTGTTTATCTTCTCTGGCA

CTTTCAGAAAAAATCTGGACCCCTATGAACAGTGGAGTGACCAGGAAATCTGGAAGGT

GGCAGATGAAGTGGGCCTAAGATCAGTCATAGAGCAGTTTCCTGGAAAGTTGGATTTTG

TGCTTGTAGATGGAGGCTGTGTGCTGTCCCATGGCCATAAACAGCTAATGTGCCTGGCT

AGGTCAGTGCTGAGCAAGGCCAAGATCCTGCTGTTAGATGAGCCTTCAGCCCATCTGGA

CCCTGTGACATACCAGATTATCAGAAGAACTCTGAAGCAGGCCTTTGCTGACTGCACTG

TCATCCTGTGTGAGCACAGAATTGAGGCCATGCTGGAGTGCCAGCAGTTCCTTGTTATA

GAAGAGAATAAGGTTAGGCAGTATGACAGCATTCAGAAACTGCTAAATGAAAGATCTC

TCTTCAGGCAAGCTATTTCACCATCTGATAGAGTGAAACTTTTTCCCCACAGAAATTCCT

CTAAATGTAAATCTAAGCCCCAGATAGCTGCCTTGAAAGAGGAGACTGAAGAAGAAGT

CCAGGACACCAGACTGTGA.
```

In another embodiment, an exemplary codon-optimized CFTR mRNA sequence is:

```
                                                   (SEQ ID NO: 21)
ATGCAGAGATCCCCGCTGGAGAAGGCATCTGTGGTGTCAAAACTGTTCTTTAGCTGGAC

AAGGCCCATCCTTAGGAAAGGGTACAGACAGAGGTTGGAGCTGTCAGACATATATCAG

ATCCCTTCAGTGGACTCTGCAGACAACCTCTCTGAAAAGCTGGAGAGGGAATGGGACA

GGGAACTGGCCAGCAAAAAAAACCCTAAACTGATTAATGCCCTGAGGAGGTGCTTCTTT

TGGAGATTCATGTTCTATGGGATCTTCCTTTACCTGGGGGAGGTGACTAAAGCTGTTCA

GCCTCTTCTTCTGGGGAGGATTATTGCCTCCTATGACCCAGACAACAAAGAAGAAAGAA

GCATAGCCATTTACTTAGGCATAGGCCTCTGCTTGCTCTTCATAGTTAGAACCCTCCTAC

TCCACCCAGCCATCTTTGGTCTCCACCACATAGGTATGCAGATGAGAATAGCAATGTTC

TCCTTGATCTACAAGAAGACCCTCAAGCTGTCCAGCAGGGTGCTGGACAAGATCTCCAT

AGGCCAGTTAGTCAGTCTACTGTCCAATAACTTAAATAAGTTTGATGAGGGACTGGCAC

TGGCACATTTTGTGTGGATTGCCCCCCTCCAAGTGGCCCTTCTTATGGGCCTTATCTGGG

AGCTGTTGCAGGCCTCTGCTTTCTGTGGCCTGGGTTTCCTCATAGTCCTAGCCTTATTCC

AGGCTGGACTGGGCAGAATGATGATGAAGTATAGGGACCAAAGAGCAGGGAAGATTTC

TGAAAGGCTGGTTATAACTTCTGAGATGATTGAGAACATTCAGTCAGTGAAAGCTTACT

GCTGGGAAGAAGCTATGGAAAAAATGATTGAAAATCTCAGACAGACTGAATTAAAGTT

GACCAGGAAAGCTGCTTATGTCAGATACTTCAACTCCTCAGCCTTCTTTTTTCTGGCTT

CTTTGTTGTATTCCTTTCAGTCCTCCCCTATGCCCTGATTAAGGGCATTATCTTGAGGAA

AATTTTCACAACCATCTCCTTTTGTATTGTCCTCAGGATGGCTGTTACAAGGCAATTTCC

TTGGGCTGTGCAAACTTGGTATGATAGCCTTGGAGCAATCAACAAGATCCAGGATTTCC

TGCAAAAGCAGGAGTACAAGACATTGGAATACAACCTTACCACCACTGAGGTGGTGAT

GGAAAATGTGACTGCCTTCTGGGAGGAGGGGTTTGGAGAGCTGTTTGAGAAAGCCAAA

CAGAACAACAACAATAGAAAGACCTCTAATGGTGATGATTCCCTGTTCTTTTCTAACTTT

AGTCTTCTGGGGACCCCAGTTCTGAAAGATATTAACTTTAAAATTGAAAGGGGACAGTT

GCTGGCTGTGGCTGGGTCCACTGGGGCTGGGAAGACAAGCCTGCTCATGGTGATCATGG

GAGAGCTGGAACCCAGTGAAGGAAAGATCAAACACTCAGGCAGGATCTCCTTCTGCAG

CCAGTTCTCATGGATTATGCCAGGCACTATTAAAGAAAATATCATCTTTGGTGTAAGCT
```

-continued
```
ATGATGAGTACAGGTATAGATCTGTAATTAAAGCCTGCCAGCTGGAGGAAGACATCTCT
AAGTTTGCTGAGAAGGATAACATTGTGTTGGGGGAAGGGGGCATCACCCTTTCTGGTGG
GCAGAGGGCTAGGATCTCCCTTGCTAGGGCAGTATACAAGGATGCTGACTTGTACCTCT
TGGATAGTCCTTTTGGCTACCTAGATGTGCTGACAGAGAAAGAAATATTTGAAAGCTGT
GTGTGTAAGCTCATGGCTAACAAGACCAGGATCCTGGTCACCAGTAAAATGGAACACCT
CAAAAAAGCAGACAAGATCCTTATTCTCCATGAGGGCTCCTCCTACTTCTATGGGACCT
TCAGTGAGCTGCAGAATCTGCAGCCAGACTTCTCCTCAAAACTTATGGGCTGTGACTCC
TTTGACCAATTCTCTGCAGAAAGAAGGAATAGCATACTGACAGAAACACTGCATAGATT
CTCCCTGGAAGGAGATGCCCCAGTGAGTTGGACAGAAACCAAAAAGCAGAGCTTCAAG
CAGACTGGTGAGTTTGGTGAAAAGAGGAAGAATTCTATCCTGAACCCCATCAATAGCAT
CAGGAAATTTAGCATAGTCCAAAAGACCCCCCTCCAGATGAATGGAATAGAGGAGGAT
AGTGATGAGCCTCTTGAGAGAAGGCTGTCCCTGGTTCCAGACAGTGAACAGGGTGAAG
CCATTCTTCCGAGGATCAGTGTCATCTCCACTGGGCCCACATTGCAGGCCAGAAGAAGA
CAGTCTGTTCTGAATTTGATGACACATTCTGTGAATCAAGGCCAGAATATCCATAGAAA
AACCACTGCCAGCACCAGAAAAGTTTCTCTAGCCCCCCAGGCTAACCTGACTGAGTTAG
ACATCTACAGCAGAAGGCTGAGCCAAGAGACTGGCTTGGAAATATCTGAGGAGATCAA
TGAGGAGGACCTCAAGGAGTGCTTCTTTGATGACATGGAGTCAATCCCTGCAGTCACTA
CATGGAACACTTACCTAAGGTACATCACAGTTCATAAGAGCCTCATCTTTGTCCTCATAT
GGTGTCTGGTCATCTTTTTAGCAGAAGTGGCTGCCAGCCAGTTGTGCTGTGGTTACTGG
GCAATACACCTCTTCAGGACAAAGGCAATAGCACACACAGCAGAAACAACTCCTATGC
AGTGATCATCACCTCTACAAGCTCTTACTATGTATTCTATATATATGTGGGAGTGGCAGA
TACTCTCCTGGCCATGGGATTCTTCAGGGGATTACCTCTAGTTCACACATTGATCACAGT
GTCAAAAATTCTCCACCACAAGATGTTACACAGTGTCCTGCAAGCCCCAATGTCTACTC
TGAACACACTTAAGGCAGGTGGAATTTTGAATAGGTTTAGCAAGGACATAGCTATCCTG
GATGATCTCCTCCCTCTGACCATCTTTGACTTCATCCAGTTACTGCTCATTGTAATTGGA
GCCATTGCAGTGGTAGCAGTCCTACAGCCTTACATTTTTGTGGCTACTGTTCCTGTTATT
GTGGCCTTCATTATGCTAAGAGCTTACTTCCTGCAAACAAGCCAACAGTTGAAACAGCT
AGAAAGTGAGGGAAGGTCCCCCATCTTCACCCACCTGGTGACATCACTCAAGGGGCTAT
GGACTCTTAGGGCTTTTGGGAGACAGCCGTACTTTGAGACCTTATTCCATAAGGCCCTT
AACCTCCATACAGCAAACTGGTTCTTATACCTGAGTACTCTGAGGTGGTTTCAAATGAG
GATTGAAATGATTTTTGTGATCTTCTTCATTGCTGTGACCTTCATCTCAATCTTGACCAC
AGGAGAGGGGAGGGCAGGGTGGGCATCATACTGACCTTGGCCATGAACATTATGTCA
ACCCTGCAGTGGGCTGTCAATAGCTCCATTGATGTGGACAGTCTGATGAGGAGTGTCTC
CAGGGTCTTCAAGTTTATTGACATGCCAACTGAGGGCAAACCCACCAAAAGCACTAAG
CCATATAAAAATGGCCAACTGTCCAAAGTGATGATCATTGAAAATTCACATGTAAAGAA
GGATGATATCTGGCCCTCTGGAGGACAGATGACAGTGAAAGACCTGACTGCCAAGTAC
ACAGAGGGTGGTAATGCCATTCTTGAGAACATTAGTTTCAGTATTTCCCCGGGGCAAAG
GGTGGGCCTCCTTGGCAGAACAGGCTCTGGCAAGAGTACCCTGCTGTCAGCCTTTTTAA
GACTGTTGAACACTGAGGGAGAAATTCAGATTGATGGTGTCTCCTGGGATAGCATCACC
CTCCAGCAGTGGAGAAAAGCTTTTGGAGTGATCCCGCAAAAGGTTTTCATCTTTTCAGG
CACCTTCCGGAAGAACCTGGACCCCTATGAGCAGTGGTCTGACCAGGAAATATGGAAG
```

```
GTAGCTGATGAAGTTGGGCTTAGGTCAGTCATAGAGCAGTTCCCAGGCAAACTGGACTT

TGTCCTGGTGGATGGTGGATGTGTACTGAGTCATGGGCACAAACAGCTGATGTGCCTAG

CCAGGTCTGTGCTCAGCAAGGCAAAGATATTGCTGCTTGATGAACCCAGTGCCCATCTG

GACCCAGTCACATATCAGATCATCAGAAGAACATTGAAGCAGGCCTTTGCTGATTGCAC

AGTTATCCTCTGTGAGCACAGGATTGAGGCCATGCTGGAGTGCCAGCAGTTTCTGGTGA

TTGAGGAGAATAAAGTAAGGCAGTATGACTCCATCCAGAAGCTGCTCAATGAAAGAAG

CCTCTTTAGACAAGCTATCTCCCCCTCAGACAGGGTCAAATTGTTCCCTCACAGAAACA

GCAGCAAGTGCAAGAGCAAGCCCCAAATTGCAGCCTTGAAAGAGGAGACAGAGGAAG

AGGTGCAGGACACCAGACTCTGA.
```

In another embodiment, an exemplary codon-optimized CFTR mRNA sequence is:

(SEQ ID NO: 22)
```
ATGCAGAGAAGCCCCCTGGAGAAGGCCAGCGTGGTGAGCAAGCTGTTCTTCAGCTGGA

CCAGACCCATCCTGAGAAAGGGCTACAGACAGAGACTGGAGCTGAGCGACATCTACCA

GATCCCCAGCGTGGACAGCGCCGACAACCTGAGCGAGAAGCTGGAGAGAGAGTGGGA

CAGAGAGCTGGCCAGCAAGAAGAACCCCAAGCTGATCAACGCCCTGAGAAGATGCTTC

TTCTGGAGATTCATGTTCTACGGCATCTTCCTGTACCTGGGCGAGGTGACCAAGGCCGT

GCAGCCCCTGCTGCTGGGCAGAATCATCGCCAGCTACGACCCCGACAACAAGGAGGAG

AGAAGCATCGCCATCTACCTGGGCATCGGCCTGTGCCTGCTGTTCATCGTGAGAACCCT

GCTGCTGCACCCCGCCATCTTCGGCCTGCACCACATCGGCATGCAGATGAGAATCGCCA

TGTTCAGCCTGATCTACAAGAAGACCCTGAAGCTGAGCAGCAGAGTGCTGGACAAGAT

CAGCATCGGCCAGCTGGTGAGCCTGCTGAGCAACAACCTGAACAAGTTCGACGAGGGC

CTGGCCCTGGCCCACTTCGTGTGGATCGCCCCCCTGCAGGTGGCCCTGCTGATGGGCCT

GATCTGGGAGCTGCTGCAGGCCAGCGCCTTCTGCGGCCTGGGCTTCCTGATCGTGCTGG

CCCTGTTCCAGGCCGGCCTGGGCAGAATGATGATGAAGTACAGAGACCAGAGAGCCGG

CAAGATCAGCGAGAGACTGGTGATCACCAGCGAGATGATCGAGAACATCCAGAGCGTG

AAGGCCTACTGCTGGGAGGAGGCCATGGAGAAGATGATCGAGAACCTGAGACAGACCG

AGCTGAAGCTGACCAGAAAGGCCGCCTACGTGAGATACTTCAACAGCAGCGCCTTCTTC

TTCAGCGGCTTCTTCGTGGTGTTCCTGAGCGTGCTGCCCTACGCCCTGATCAAGGGCATC

ATCCTGAGAAAGATCTTCACCACCATCAGCTTCTGCATCGTGCTGAGAATGGCCGTGAC

CAGACAGTTCCCCTGGGCCGTGCAGACCTGGTACGACAGCCTGGGCGCCATCAACAAG

ATCCAGGACTTCCTGCAGAAGCAGGAGTACAAGACCCTGGAGTACAACCTGACCACCA

CCGAGGTGGTGATGGAGAACGTGACCGCCTTCTGGGAGGAGGGCTTCGGCGAGCTGTT

CGAGAAGGCCAAGCAGAACAACAACAACAGAAAGACCAGCAACGGCGACGACAGCCT

GTTCTTCAGCAACTTCAGCCTGCTGGGCACCCCCGTGCTGAAGGACATCAACTTCAAGA

TCGAGAGAGGCCAGCTGCTGGCCGTGGCCGGCAGCACCGGCGCCGGCAAGACCAGCCT

GCTGATGGTGATCATGGGCGAGCTGGAGCCCAGCGAGGGCAAGATCAAGCACAGCGGC

AGAATCAGCTTCTGCAGCCAGTTCAGCTGGATCATGCCCGGCACCATCAAGGAGAACAT

CATCTTCGGCGTGAGCTACGACGAGTACAGATACAGAAGCGTGATCAAGGCCTGCCAG

CTGGAGGAGGACATCAGCAAGTTCGCCGAGAAGGACAACATCGTGCTGGGCGAGGGCG
```

```
GCATCACCCTGAGCGGCGGCCAGAGAGCCAGAATCAGCCTGGCCAGAGCCGTGTACAA

GGACGCCGACCTGTACCTGCTGGACAGCCCCTTCGGCTACCTGGACGTGCTGACCGAGA

AGGAGATCTTCGAGAGCTGCGTGTGCAAGCTGATGGCCAACAAGACCAGAATCCTGGT

GACCAGCAAGATGGAGCACCTGAAGAAGGCCGACAAGATCCTGATCCTGCACGAGGGC

AGCAGCTACTTCTACGGCACCTTCAGCGAGCTGCAGAACCTGCAGCCCGACTTCAGCAG

CAAGCTGATGGGCTGCGACAGCTTCGACCAGTTCAGCGCCGAGAAGAAACAGCATC

CTGACCGAGACCCTGCACAGATTCAGCCTGGAGGGCGACGCCCCCGTGAGCTGGACCG

AGACCAAGAAGCAGAGCTTCAAGCAGACCGGCGAGTTCGGCGAGAAGAGAAAGAACA

GCATCCTGAACCCCATCAACAGCATCAGAAAGTTCAGCATCGTGCAGAAGACCCCCCTG

CAGATGAACGGCATCGAGGAGGACAGCGACGAGCCCCTGGAGAGAAGACTGAGCCTG

GTGCCCGACAGCGAGCAGGGCGAGGCCATCCTGCCCAGAATCAGCGTGATCAGCACCG

GCCCCACCCTGCAGGCCAGAAGAAGACAGAGCGTGCTGAACCTGATGACCCACAGCGT

GAACCAGGGCCAGAACATCCACAGAAAGACCACCGCCAGCACCAGAAAGGTGAGCCT

GGCCCCCCAGGCCAACCTGACCGAGCTGGACATCTACAGCAGAAGACTGAGCCAGGAG

ACCGGCCTGGAGATCAGCGAGGAGATCAACGAGGAGGACCTGAAGGAGTGCTTCTTCG

ACGACATGGAGAGCATCCCCGCCGTGACCACCTGGAACACCTACCTGAGATACATCAC

CGTGCACAAGAGCCTGATCTTCGTGCTGATCTGGTGCCTGGTGATCTTCCTGGCCGAGG

TGGCCGCCAGCCTGGTGGTGCTGTGGCTGCTGGGCAACACCCCCCTGCAGGACAAGGG

CAACAGCACCCACAGCAGAAACAACAGCTACGCCGTGATCATCACCAGCACCAGCAGC

TACTACGTGTTCTACATCTACGTGGGCGTGGCCGACACCCTGCTGGCCATGGGCTTCTTC

AGAGGCCTGCCCCTGGTGCACACCCTGATCACCGTGAGCAAGATCCTGCACCACAAGAT

GCTGCACAGCGTGCTGCAGGCCCCCATGAGCACCCTGAACACCCTGAAGGCCGGCGGC

ATCCTGAACAGATTCAGCAAGGACATCGCCATCCTGGACGACCTGCTGCCCCTGACCAT

CTTCGACTTCATCCAGCTGCTGCTGATCGTGATCGGCGCCATCGCCGTGGTGGCCGTGCT

GCAGCCCTACATCTTCGTGGCCACCGTGCCCGTGATCGTGGCCTTCATCATGCTGAGAG

CCTACTTCCTGCAGACCAGCCAGCAGCTGAAGCAGCTGGAGAGCGAGGGCAGAAGCCC

CATCTTCACCCACCTGGTGACCAGCCTGAAGGGCCTGTGGACCCTGAGAGCCTTCGGCA

GACAGCCCTACTTCGAGACCCTGTTCCACAAGGCCCTGAACCTGCACACCGCCAACTGG

TTCCTGTACCTGAGCACCCTGAGATGGTTCCAGATGAGAATCGAGATGATCTTCGTGAT

CTTCTTCATCGCCGTGACCTTCATCAGCATCCTGACCACCGGCGAGGGCGAGGGCAGAG

TGGGCATCATCCTGACCCTGGCCATGAACATCATGAGCACCCTGCAGTGGGCCGTGAAC

AGCAGCATCGACGTGGACAGCCTGATGAGAAGCGTGAGCAGAGTGTTCAAGTTCATCG

ACATGCCCACCGAGGGCAAGCCCACCAAGAGCACCAAGCCCTACAAGAACGGCCAGCT

GAGCAAGGTGATGATCATCGAGAACAGCCACGTGAAGAAGGACGACATCTGGCCCAGC

GGCGGCCAGATGACCGTGAAGGACCTGACCGCCAAGTACACCGAGGGCGGCAACGCCA

TCCTGGAGAACATCAGCTTCAGCATCAGCCCCGGCCAGAGAGTGGGCCTGCTGGGCAG

AACCGGCAGCGGCAAGAGCACCCTGCTGAGCGCCTTCCTGAGACTGCTGAACACCGAG

GGCGAGATCCAGATCGACGGCGTGAGCTGGGACAGCATCACCCTGCAGCAGTGGAGAA

AGGCCTTCGGCGTGATCCCCCAGAAGGTGTTCATCTTCAGCGGCACCTTCAGAAAGAAC

CTGGACCCCTACGAGCAGTGGAGCGACCAGGAGATCTGGAAGGTGGCCGACGAGGTGG
```

```
GCCTGAGAAGCGTGATCGAGCAGTTCCCCGGCAAGCTGGACTTCGTGCTGGTGGACGG

CGGCTGCGTGCTGAGCCACGGCCACAAGCAGCTGATGTGCCTGGCCAGAAGCGTGCTG

AGCAAGGCCAAGATCCTGCTGCTGGACGAGCCCAGCGCCCACCTGGACCCCGTGACCT

ACCAGATCATCAGAAGAACCCTGAAGCAGGCCTTCGCCGACTGCACCGTGATCCTGTGC

GAGCACAGAATCGAGGCCATGCTGGAGTGCCAGCAGTTCCTGGTGATCGAGGAGAACA

AGGTGAGACAGTACGACAGCATCCAGAAGCTGCTGAACGAGAGAAGCCTGTTCAGACA

GGCCATCAGCCCCAGCGACAGAGTGAAGCTGTTCCCCCACAGAAACAGCAGCAAGTGC

AAGAGCAAGCCCCAGATCGCCGCCCTGAAGGAGGAGACCGAGGAGGAGGTGCAGGAC

ACCAGACTGTGA.
```

In another embodiment, an exemplary codon-optimized CFTR mRNA sequence is:

```
                                               (SEQ ID NO: 23)
ATGCAGCGCAGCCCCCTGGAGAAGGCCAGCGTGGTGAGCAAGCTGTTCTTCAGCTGGA

CCCGCCCCATCCTGCGCAAGGGCTACCGCCAGCGCCTGGAGCTGAGCGACATCTACCAG

ATCCCCAGCGTGGACAGCGCCGACAACCTGAGCGAGAAGCTGGAGCGCGAGTGGGACC

GCGAGCTGGCCAGCAAGAAGAACCCCAAGCTGATCAACGCCCTGCGCCGCTGCTTCTTC

TGGCGCTTCATGTTCTACGGCATCTTCCTGTACCTGGGCGAGGTGACCAAGGCCGTGCA

GCCCCTGCTGCTGGGCCGCATCATCGCCAGCTACGACCCCGACAACAAGGAGGAGCGC

AGCATCGCCATCTACCTGGGCATCGGCCTGTGCCTGCTGTTCATCGTGCGCACCCTGCTG

CTGCACCCCGCCATCTTCGGCCTGCACCACATCGGCATGCAGATGCGCATCGCCATGTT

CAGCCTGATCTACAAGAAGACCCTGAAGCTGAGCAGCCGCGTGCTGGACAAGATCAGC

ATCGGCCAGCTGGTGAGCCTGCTGAGCAACAACCTGAACAAGTTCGACGAGGGCCTGG

CCCTGGCCCACTTCGTGTGGATCGCCCCCCTGCAGGTGGCCCTGCTGATGGGCCTGATC

TGGGAGCTGCTGCAGGCCAGCGCCTTCTGCGGCCTGGGCTTCCTGATCGTGCTGGCCCT

GTTCCAGGCCGGCCTGGGCCGCATGATGATGAAGTACCGCGACCAGCGCGCCGGCAAG

ATCAGCGAGCGCCTGGTGATCACCAGCGAGATGATCGAGAACATCCAGAGCGTGAAGG

CCTACTGCTGGGAGGAGGCCATGGAGAAGATGATCGAGAACCTGCGCCAGACCGAGCT

GAAGCTGACCCGCAAGGCCGCCTACGTGCGCTACTTCAACAGCAGCGCCTTCTTCTTCA

GCGGCTTCTTCGTGGTGTTCCTGAGCGTGCTGCCCTACGCCCTGATCAAGGGCATCATCC

TGCGCAAGATCTTCACCACCATCAGCTTCTGCATCGTGCTGCGCATGGCCGTGACCCGC

CAGTTCCCCTGGGCCGTGCAGACCTGGTACGACAGCCTGGGCGCCATCAACAAGATCCA

GGACTTCCTGCAGAAGCAGGAGTACAAGACCCTGGAGTACAACCTGACCACCACCGAG

GTGGTGATGGAGAACGTGACCGCCTTCTGGGAGGAGGGCTTCGGCGAGCTGTTCGAGA

AGGCCAAGCAGAACAACAACAACCGCAAGACCAGCAACGGCGACGACAGCCTGTTCTT

CAGCAACTTCAGCCTGCTGGGCACCCCCGTGCTGAAGGACATCAACTTCAAGATCGAGC

GCGGCCAGCTGCTGGCCGTGGCCGGCAGCACCGGCGCCGGCAAGACCAGCCTGCTGAT

GGTGATCATGGGCGAGCTGGAGCCCAGCGAGGGCAAGATCAAGCACAGCGGCCGCATC

AGCTTCTGCAGCCAGTTCAGCTGGATCATGCCCGGCACCATCAAGGAGAACATCATCTT

CGGCGTGAGCTACGACGAGTACCGCTACCGCAGCGTGATCAAGGCCTGCCAGCTGGAG

GAGGACATCAGCAAGTTCGCCGAGAAGGACAACATCGTGCTGGGCGAGGGCGGCATCA
```

-continued

```
CCCTGAGCGGCGGCCAGCGCGCCCGCATCAGCCTGGCCCGCGCCGTGTACAAGGACGC

CGACCTGTACCTGCTGGACAGCCCCTTCGGCTACCTGGACGTGCTGACCGAGAAGGAGA

TCTTCGAGAGCTGCGTGTGCAAGCTGATGGCCAACAAGACCCGCATCCTGGTGACCAGC

AAGATGGAGCACCTGAAGAAGGCCGACAAGATCCTGATCCTGCACGAGGGCAGCAGCT

ACTTCTACGGCACCTTCAGCGAGCTGCAGAACCTGCAGCCCGACTTCAGCAGCAAGCTG

ATGGGCTGCGACAGCTTCGACCAGTTCAGCGCCGAGCGCCGCAACAGCATCCTGACCG

AGACCCTGCACCGCTTCAGCCTGGAGGGCGACGCCCCCGTGAGCTGGACCGAGACCAA

GAAGCAGAGCTTCAAGCAGACCGGCGAGTTCGGCGAGAAGCGCAAGAACAGCATCCTG

AACCCCATCAACAGCATCCGCAAGTTCAGCATCGTGCAGAAGACCCCCCTGCAGATGA

ACGGCATCGAGGAGGACAGCGACGAGCCCCTGGAGCGCCGCCTGAGCCTGGTGCCCGA

CAGCGAGCAGGGCGAGGCCATCCTGCCCCGCATCAGCGTGATCAGCACCGGCCCCACC

CTGCAGGCCCGCCGCCGCCAGAGCGTGCTGAACCTGATGACCCACAGCGTGAACCAGG

GCCAGAACATCCACCGCAAGACCACCGCCAGCACCCGCAAGGTGAGCCTGGCCCCCCA

GGCCAACCTGACCGAGCTGGACATCTACAGCCGCCGCCTGAGCCAGGAGACCGGCCTG

GAGATCAGCGAGGAGATCAACGAGGAGGACCTGAAGGAGTGCTTCTTCGACGACATGG

AGAGCATCCCCGCCGTGACCACCTGGAACACCTACCTGCGCTACATCACCGTGCACAAG

AGCCTGATCTTCGTGCTGATCTGGTGCCTGGTGATCTTCCTGGCCGAGGTGGCCGCCAG

CCTGGTGGTGCTGTGGCTGCTGGGCAACACCCCCCTGCAGGACAAGGGCAACAGCACC

CACAGCCGCAACAACAGCTACGCCGTGATCATCACCAGCACCAGCAGCTACTACGTGTT

CTACATCTACGTGGGCGTGGCCGACACCCTGCTGGCCATGGGCTTCTTCCGCGGCCTGC

CCCTGGTGCACACCCTGATCACCGTGAGCAAGATCCTGCACCACAAGATGCTGCACAGC

GTGCTGCAGGCCCCCATGAGCACCCTGAACACCCTGAAGGCCGGCGGCATCCTGAACC

GCTTCAGCAAGGACATCGCCATCCTGGACGACCTGCTGCCCCTGACCATCTTCGACTTC

ATCCAGCTGCTGCTGATCGTGATCGGCGCCATCGCCGTGGTGGCCGTGCTGCAGCCCTA

CATCTTCGTGGCCACCGTGCCCGTGATCGTGGCCTTCATCATGCTGCGCGCCTACTTCCT

GCAGACCAGCCAGCAGCTGAAGCAGCTGGAGAGCGAGGGCCGCAGCCCCATCTTCACC

CACCTGGTGACCAGCCTGAAGGGCCTGTGGACCCTGCGCGCCTTCGGCCGCCAGCCCTA

CTTCGAGACCCTGTTCCACAAGGCCCTGAACCTGCACACCGCCAACTGGTTCCTGTACC

TGAGCACCCTGCGCTGGTTCCAGATGCGCATCGAGATGATCTTCGTGATCTTCTTCATCG

CCGTGACCTTCATCAGCATCCTGACCACCGGCGAGGGCGAGGGCCGCGTGGGCATCATC

CTGACCCTGGCCATGAACATCATGAGCACCCTGCAGTGGGCCGTGAACAGCAGCATCG

ACGTGGACAGCCTGATGCGCAGCGTGAGCCGCGTGTTCAAGTTCATCGACATGCCCACC

GAGGGCAAGCCCACCAAGAGCACCAAGCCCTACAAGAACGGCCAGCTGAGCAAGGTG

ATGATCATCGAGAACAGCCACGTGAAGAAGGACGACATCTGGCCCAGCGGCGGCCAGA

TGACCGTGAAGGACCTGACCGCCAAGTACACCGAGGGCGGCAACGCCATCCTGGAGAA

CATCAGCTTCAGCATCAGCCCCGGCCAGCGCGTGGGCCTGCTGGGCCGCACCGGCAGC

GGCAAGAGCACCCTGCTGAGCGCCTTCCTGCGCCTGCTGAACACCGAGGGCGAGATCC

AGATCGACGGCGTGAGCTGGGACAGCATCACCCTGCAGCAGTGGCGCAAGGCCTTCGG

CGTGATCCCCCAGAAGGTGTTCATCTTCAGCGGCACCTTCCGCAAGAACCTGGACCCCT

ACGAGCAGTGGAGCGACCAGGAGATCTGGAAGGTGGCCGACGAGGTGGGCCTGCGCA

GCGTGATCGAGCAGTTCCCCGGCAAGCTGGACTTCGTGCTGGTGGACGGCGGCTGCGTG
```

```
CTGAGCCACGGCCACAAGCAGCTGATGTGCCTGGCCCGCAGCGTGCTGAGCAAGGCCA

AGATCCTGCTGCTGGACGAGCCCAGCGCCCACCTGGACCCCGTGACCTACCAGATCATC

CGCCGCACCCTGAAGCAGGCCTTCGCCGACTGCACCGTGATCCTGTGCGAGCACCGCAT

CGAGGCCATGCTGGAGTGCCAGCAGTTCCTGGTGATCGAGGAGAACAAGGTGCGCCAG

TACGACAGCATCCAGAAGCTGCTGAACGAGCGCAGCCTGTTCCGCCAGGCCATCAGCC

CCAGCGACCGCGTGAAGCTGTTCCCCCACCGCAACAGCAGCAAGTGCAAGAGCAAGCC

CCAGATCGCCGCCCTGAAGGAGGAGACCGAGGAGGAGGTGCAGGACACCCGCCTGTAA.
```

In yet another embodiment, an exemplary codon-optimized CFTR mRNA sequence is:

(SEQ ID NO: 24)
```
ATGCAGAGAAGCCCCCTGGAGAAGGCCAGCGTGGTGAGCAAGCTGTTCTTCAGCTGGA

CCAGACCCATCCTGAGAAAGGGCTACAGACAGAGACTGGAGCTGAGCGACATCTACCA

GATCCCCAGCGTGGACAGCGCCGACAACCTGAGCGAGAAGCTGGAGAGAGAGTGGGA

CAGAGAGCTGGCCAGCAAGAAGAACCCCAAGCTGATCAACGCCCTGAGAAGATGCTTC

TTCTGGAGATTCATGTTCTACGGCATCTTCCTGTACCTGGGCGAGGTGACCAAGGCCGT

GCAGCCCCTGCTGCTGGGCAGAATCATCGCCAGCTACGACCCCGACAACAAGGAGGAG

AGAAGCATCGCCATCTACCTGGGCATCGGCCTGTGCCTGCTGTTCATCGTGAGAACCCT

GCTGCTGCACCCCGCCATCTTCGGCCTGCACCACATCGGCATGCAGATGAGAATCGCCA

TGTTCAGCCTGATCTACAAGAAGACCCTGAAGCTGAGCAGCAGAGTGCTGGACAAGAT

CAGCATCGGCCAGCTGGTGAGCCTGCTGAGCAACAACCTGAACAAGTTCGACGAGGGC

CTGGCCCTGGCCCACTTCGTGTGGATCGCCCCCCTGCAGGTGGCCCTGCTGATGGGCCT

GATCTGGGAGCTGCTGCAGGCCAGCGCCTTCTGCGGCCTGGGCTTCCTGATCGTGCTGG

CCCTGTTCCAGGCCGGCCTGGGCAGAATGATGATGAAGTACAGGGACCAGAGAGCCGG

CAAGATCAGCGAGAGACTGGTGATCACCAGCGAGATGATCGAGAACATCCAGAGCGTG

AAGGCCTACTGCTGGGAGGAGGCCATGGAGAAGATGATCGAGAACCTGAGACAGACCG

AGCTGAAGCTGACCAGAAAGGCCGCCTACGTGAGATACTTCAACAGCAGCGCCTTCTTC

TTCAGCGGCTTCTTCGTGGTGTTCCTGAGCGTGCTGCCCTACGCCCTGATCAAGGGCATC

ATCCTGAGAAAGATCTTCACCACCATCAGCTTCTGCATCGTGCTGAGAATGGCCGTGAC

CAGACAGTTCCCCTGGGCCGTGCAGACCTGGTACGACAGCCTGGGCGCCATCAACAAG

ATCCAGGACTTCCTGCAGAAGCAGGAGTACAAGACCCTGGAGTACAACCTGACCACCA

CCGAGGTGGTGATGGAGAACGTGACCGCCTTCTGGGAGGAGGGCTTCGGCGAGCTGTT

CGAGAAGGCCAAGCAGAACAACAACAACAGAAAGACCAGCAACGGCGACGACAGCCT

GTTCTTCAGCAACTTCAGCCTGCTGGGCACCCCCGTGCTGAAGGACATCAACTTCAAGA

TCGAGAGAGGCCAGCTGCTGGCCGTGGCCGGCAGCACCGGCGCCGGCAAGACCAGCCT

GCTGATGGTGATCATGGGCGAGCTGGAGCCCAGCGAGGGCAAGATCAAGCACAGCGGC

AGAATCAGCTTCTGCAGCCAGTTCAGCTGGATCATGCCCGGCACCATCAAGGAGAACAT

CATCTTCGGCGTGAGCTACGACGAGTACAGATACAGAAGCGTGATCAAGGCCTGCCAG

CTGGAGGAGGACATCAGCAAGTTCGCCGAGAAGGACAACATCGTGCTGGGCGAGGGCG

GCATCACCCTGAGCGGCGGCCAGAGAGCCAGAATCAGCCTGGCCAGAGCCGTGTACAA

GGACGCCGACCTGTACCTGCTGGACAGCCCCTTCGGCTACCTGGACGTGCTGACCGAGA
```

-continued

```
AGGAGATCTTCGAGAGCTGCGTGTGCAAGCTGATGGCCAACAAGACCAGAATCCTGGT

GACCAGCAAGATGGAGCACCTGAAGAAGGCCGACAAGATCCTGATCCTGCACGAGGGC

AGCAGCTACTTCTACGGCACCTTCAGCGAGCTGCAGAACCTGCAGCCCGACTTCAGCAG

CAAGCTGATGGGCTGCGACAGCTTCGACCAGTTCAGCGCCGAGAAGAAACAGCATC

CTGACCGAGACCCTGCACAGATTCAGCCTGGAGGGCGACGCCCCCGTGAGCTGGACCG

AGACCAAGAAGCAGAGCTTCAAGCAGACCGGCGAGTTCGGCGAGAAGAGAAAGAACA

GCATCCTGAACCCCATCAACAGCATCAGAAAGTTCAGCATCGTGCAGAAGACCCCCCTG

CAGATGAACGGCATCGAGGAGGACAGCGACGAGCCCCTGGAGAGAAGACTGAGCCTG

GTGCCCGACAGCGAGCAGGGCGAGGCCATCCTGCCCAGAATCAGCGTGATCAGCACCG

GCCCCACCCTGCAGGCCAGAAGAAGACAGAGCGTGCTGAACCTGATGACCCACAGCGT

GAACCAGGGCCAGAACATCCACAGAAAGACCACCGCCAGCACCAGAAAGGTGAGCCT

GGCCCCCCAGGCCAACCTGACCGAGCTGGACATCTACAGCAGAAGACTGAGCCAGGAG

ACCGGCCTGGAGATCAGCGAGGAGATCAACGAGGAGGACCTGAAGGAGTGCTTCTTCG

ACGACATGGAGAGCATCCCCGCCGTGACCACCTGGAACACCTACCTGAGATACATCAC

CGTGCACAAGAGCCTGATCTTCGTGCTGATCTGGTGCCTGGTGATCTTCCTGGCCGAGG

TGGCCGCCAGCCTGGTGGTGCTGTGGCTGCTGGGCAACACCCCCCTGCAGGACAAGGG

CAACAGCACCCACAGCAGAAACAACAGCTACGCCGTGATCATCACCAGCACCAGCAGC

TACTACGTGTTCTACATCTACGTGGGCGTGGCCGACACCCTGCTGGCCATGGGCTTCTTC

AGAGGCCTGCCCCTGGTGCACACCCTGATCACCGTGAGCAAGATCCTGCACCACAAGAT

GCTGCACAGCGTGCTGCAGGCCCCCATGAGCACCCTGAACACCCTGAAGGCCGGCGGC

ATCCTGAACAGATTCAGCAAGGACATCGCCATCCTGGACGACCTGCTGCCCCTGACCAT

CTTCGACTTCATCCAGCTGCTGCTGATCGTGATCGGCGCCATCGCCGTGGTGGCCGTGCT

GCAGCCCTACATCTTCGTGGCCACCGTGCCCGTGATCGTGGCCTTCATCATGCTGAGAG

CCTACTTCCTGCAGACCAGCCAGCAGCTGAAGCAGCTGGAGAGCGAGGGCAGGAGCCC

CATCTTCACCCACCTGGTGACCAGCCTGAAGGGCCTGTGGACCCTGAGAGCCTTCGGCA

GACAGCCCTACTTCGAGACCCTGTTCCACAAGGCCCTGAACCTGCACACCGCCAACTGG

TTCCTGTACCTGAGCACCCTGAGATGGTTCCAGATGAGAATCGAGATGATCTTCGTGAT

CTTCTTCATCGCCGTGACCTTCATCAGCATCCTGACCACCGGCGAGGGCGAGGGCAGAG

TGGGCATCATCCTGACCCTGGCCATGAACATCATGAGCACCCTGCAGTGGGCCGTGAAC

AGCAGCATCGACGTGGACAGCCTGATGAGAAGCGTGAGCAGAGTGTTCAAGTTCATCG

ACATGCCCACCGAGGGCAAGCCCACCAAGAGCACCAAGCCCTACAAGAACGGCCAGCT

GAGCAAGGTGATGATCATCGAGAACAGCCACGTGAAGAAGGACGACATCTGGCCCAGC

GGCGGCCAGATGACCGTGAAGGACCTGACCGCCAAGTACACCGAGGGCGGCAACGCCA

TCCTGGAGAACATCAGCTTCAGCATCAGCCCCGGCCAGAGAGTGGGCCTGCTGGGCAG

AACCGGCAGCGGCAAGAGCACCCTGCTGAGCGCCTTCCTGAGACTGCTGAACACCGAG

GGCGAGATCCAGATCGACGGCGTGAGCTGGACAGCATCACCCTGCAGCAGTGGAGAA

AGGCCTTCGGCGTGATCCCCCAGAAGGTGTTCATCTTCAGCGGCACCTTCAGAAAGAAC

CTGGACCCCTACGAGCAGTGGAGCGACCAGGAGATCTGGAAGGTGGCCGACGAGGTGG

GCCTGAGAAGCGTGATCGAGCAGTTCCCCGGCAAGCTGGACTTCGTGCTGGTGGACGG

CGGCTGCGTGCTGAGCCACGGCCACAAGCAGCTGATGTGCCTGGCCAGAAGCGTGCTG
```

```
-continued
AGCAAGGCCAAGATCCTGCTGCTGGACGAGCCCAGCGCCCACCTGGACCCCGTGACCT

ACCAGATCATCAGAAGAACCCTGAAGCAGGCCTTCGCCGACTGCACCGTGATCCTGTGC

GAGCACAGAATCGAGGCCATGCTGGAGTGCCAGCAGTTCCTGGTGATCGAGGAGAACA

AGGTGAGACAGTACGACAGCATCCAGAAGCTGCTGAACGAGAGAAGCCTGTTCAGACA

GGCCATCAGCCCCAGCGACAGAGTGAAGCTGTTCCCCCACAGAAACAGCAGCAAGTGC

AAGAGCAAGCCCCAGATCGCCGCCCTGAAGGAGGAGACCGAGGAGGAGGTGCAGGAC

ACCAGACTGTGA.
```

In another embodiment, an exemplary codon-optimized CFTR mRNA sequence is:

```
                                                       (SEQ ID NO: 25)
ATGCAGAGGTCACCTCTGGAAAAGGCTAGCGTGGTCAGCAAGCTATTTTTTTCCTGGAC

CCGCCCGATACTCAGGAAGGGCTACCGACAGCGGCTGGAGCTGAGTGACATTTATCAG

ATTCCCTCCGTCGATTCCGCTGACAACCTGTCTGAGAAACTGGAGCGGGAATGGGATAG

GGAACTGGCGTCCAAAAAAAACCCCAAACTCATCAATGCACTCCGCAGATGCTTCTTCT

GGCGGTTTATGTTTTATGGCATATTCCTGTATCTGGGGGAGGTGACGAAAGCCGTGCAG

CCGCTGCTGCTTGGTCGCATTATCGCGTCATACGATCCAGATAACAAGGAGGAAAGAAG

TATCGCTATCTATCTCGGGATAGGGCTGTGCCTGCTCTTCATTGTGCGGACTCTTCTCTT

GCACCCCGCCATTTTCGGTCTGCATCATATAGGTATGCAGATGAGAATTGCGATGTTCTC

ATTGATTTACAAAAAAACGCTTAAGCTAAGTTCAAGGGTGCTAGATAAGATATCGATCG

GCCAGCTGGTGTCTCTGCTTAGCAACAACCTCAATAAATTCGACGAAGGCCTTGCACTG

GCCCACTTCGTGTGGATCGCCCCTCTGCAGGTGGCTCTGCTGATGGGGTTAATATGGGA

GCTGTTGCAGGCCTCCGCTTTTTGTGGCCTGGGGTTTCTCATCGTGTTGGCCTTGTTTCA

GGCAGGGCTGGGACGTATGATGATGAAATATAGGGATCAGAGGGCTGGCAAAATCTCT

GAGCGCCTGGTTATTACGAGTGAAATGATTGAGAACATCCAGTCAGTGAAGGCCTATTG

CTGGGAGGAGGCCATGGAAAAAATGATTGAGAACCTACGCCAGACTGAGCTGAAGTTA

ACCAGAAAAGCCGCCTATGTGCGCTACTTTAACAGTAGCGCATTTTTCTTCTCCGGTTTT

TTCGTGGTGTTTCTTAGTGTGTTGCCGTATGCCTTAATCAAGGGAATAATACTCCGGAAG

ATTTTCACTACCATCAGCTTCTGTATCGTGTTGCGGATGGCCGTCACCCGGCAGTTTCCC

TGGGCAGTACAGACTTGGTACGATTCTCTCGGAGCAATTAACAAAATCCAAGACTTTCT

ACAAAAGCAGGAGTACAAGACCCTGGAGTACAATCTGACCACCACAGAAGTCGTAATG

GAGAATGTAACTGCCTTCTGGGAAGAGGGCTTTGGCGAACTCTTTGAAAAGGCCAAGC

AGAACAATAACAACCGGAAGACCTCCAACGGGGACGACAGCTTATTTTTCAGCAATTTT

TCTTTGCTCGGGACCCCTGTACTGAAAGATATTAACTTTAAGATCGAGCGCGGACAACT

CCTGGCTGTCGCCGGCAGCACTGGAGCTGGAAAAACATCACTGCTTATGGTGATAATGG

GAGAACTCGAACCAAGCGAGGGAAAAATAAAGCACTCTGGACGGATTAGTTTTTGCTC

CCAGTTCTCGTGGATAATGCCTGGCACCATTAAGGAGAATATCATCTTTGGAGTGAGTT

ACGACGAATACCGGTACCGGTCCGTTATCAAGGCTTGTCAACTCGAGGAGGACATTTCT

AAATTCGCCGAAAAAGATAATATAGTGCTGGGCGAAGGAGGCATTACACTGAGCGGGG

GTCAGAGAGCTCGAATTAGCCTCGCCCGAGCAGTCTATAAAGACGCCGATCTTTACCTG

CTGGATTCCCCTTTTGGGTATTTGGATGTTCTGACAGAGAAGGAAATCTTTGAATCATGT
```

-continued

```
GTCTGTAAACTGATGGCCAATAAGACTAGGATTCTAGTGACTTCGAAAATGGAGCACCT
GAAAAAAGCGGACAAAATTCTGATACTCCATGAAGGGTCTTCCTACTTCTACGGCACCT
TCTCAGAGTTGCAGAACTTACAACCTGATTTTTCATCTAAGCTTATGGGGTGCGACTCGT
TTGACCAGTTCTCCGCTGAAAGACGAAACAGCATCTTAACGGAAACTCTTCACAGGTTC
TCATTAGAGGGAGATGCGCCGGTGTCCTGGACAGAGACAAAAAAACAGTCTTTCAAAC
AGACAGGAGAGTTTGGCGAGAAGAGAAAAAACTCAATCCTCAATCCCATCAATTCTATT
AGAAAGTTTAGCATCGTCCAAAAAACACCATTGCAGATGAATGGGATTGAGGAGGACA
GTGATGAGCCTTTGGAACGAAGACTGTCCCTGGTACCCGATAGCGAACAGGGTGAGGC
CATCCTTCCTAGGATCTCGGTCATAAGTACAGGGCCCACACTGCAGGCCAGGCGACGTC
AAAGTGTCCTCAATCTTATGACGCACAGTGTGAATCAGGGGCAGAACATCCATCGTAAG
ACGACAGCTTCAACTCGAAAGGTCAGTCTAGCTCCACAAGCCAATCTTACAGAGCTGGA
CATTTATTCCCGCCGCCTCAGTCAGGAGACCGGATTGGAAATATCAGAGGAAATTAATG
AAGAGGATCTGAAGGAATGCTTCTTTGATGACATGGAATCGATCCCCGCTGTTACTACC
TGGAACACATATCTGAGATATATTACCGTCCATAAGAGCTTAATCTTTGTACTGATATG
GTGCTTGGTGATTTTCCTGGCAGAGGTTGCGGCGAGTTTGGTCGTGCTATGGCTCCTTGG
AAACACTCCCCTGCAGGATAAGGGGAACTCCACTCATAGCAGGAATAACAGCTATGCC
GTGATCATCACCTCTACCTCCTCTTATTACGTGTTTTACATATACGTCGGTGTTGCGGAT
ACCCTGTTGGCAATGGGGTTCTTTAGAGGACTACCCCTAGTTCACACCCTGATCACCGTT
TCGAAGATCTTGCACCACAAGATGCTTCATAGCGTTCTCCAAGCTCCTATGAGCACCCT
TAATACACTGAAAGCAGGAGGTATCCTTAACCGCTTTTCCAAAGACATCGCTATACTCG
ACGATTTGCTCCCATTGACCATCTTCGACTTCATTCAGCTGCTCCTCATTGTGATCGGCG
CCATTGCCGTGGTCGCAGTGTTACAGCCATATATTTTCGTAGCCACCGTGCCCGTCATCG
TGGCATTTATCATGCTGCGCGCATATTTCTTACAGACATCTCAGCAACTGAAGCAGCTG
GAATCTGAGGGCAGATCTCCTATTTTTACACACCTGGTTACCAGCCTGAAGGGCCTGTG
GACCCTGCGTGCTTTCGGTCGCCAACCCTACTTTGAGACTCTCTTCCATAAGGCTCTGAA
TTTACATACTGCCAATTGGTTCCTATACCTTAGTACCCTTCGGTGGTTCCAGATGCGGAT
AGAAATGATCTTCGTGATTTTCTTCATCGCAGTCACTTTCATCTCTATTTTGACGACCGG
TGAGGGCGAGGGCAGGGTGGGCATCATTCTGACTTTGGCCATGAACATTATGTCAACAC
TCCAGTGGGCCGTTAATTCAAGCATTGATGTGGATTCCTTGATGCGTTCCGTCAGCAGG
GTATTTAAATTCATAGACATGCCCACCGAGGGCAAGCCAACAAAATCTACCAAGCCAT
ACAAAAATGGCCAACTAAGCAAGGTCATGATTATCGAGAATTCTCATGTGAAAAAGGA
CGACATTTGGCCTTCCGGGGGTCAAATGACTGTAAAGGACCTGACGGCTAAATACACTG
AGGGCGGTAATGCTATCTTGGAGAACATCTCTTTCAGCATCTCCCCTGGCCAGAGAGTG
GGACTGCTCGGGCGGACAGGCTCCGGAAAGTCTACGCTCCTTTCAGCATTCCTTAGACT
TCTGAACACCGAAGGTGAGATTCAGATTGACGGGGTCTCTTGGGACTCCATCACACTTC
AGCAATGGAGGAAGGCATTCGGTGTAATCCCCAAAAGGTTTTTATCTTCTCCGGAACA
TTTCGTAAGAATCTGGACCCGTACGAGCAGTGGTCAGATCAGGAGATCTGGAAAGTAG
CAGACGAGGTCGGGCTACGGAGCGTTATTGAACAGTTTCCTGGCAAACTGGACTTCGTT
TTGGTGGACGGAGGCTGTGTGCTGAGTCACGGCCATAAACAACTGATGTGCTTAGCTAG
GTCTGTTCTCAGCAAGGCAAAGATTTTACTGCTGGATGAACCAAGCGCCCACCTTGATC
CAGTGACATATCAAATCATCAGAAGAACTCTTAAACAGGCGTTCGCCGACTGCACAGTG
```

-continued

```
ATCCTGTGTGAGCACAGAATAGAAGCCATGCTGGAATGTCAACAGTTTCTCGTGATTGA

GGAGAACAAGGTGCGCCAGTACGATAGCATCCAGAAGTTACTCAATGAAAGGTCACTC

TTCAGGCAGGCCATCTCACCCAGCGACCGCGTTAAGCTGTTTCCACACCGAAACAGTTC

CAAGTGCAAAAGTAAGCCACAGATTGCTGCACTGAAGGAAGAGACAGAAGAAGAAGTT

CAGGACACTCGGCTCTGA.
```

In another embodiment, an exemplary codon-optimized CFTR mRNA sequence is:

(SEQ ID NO: 26)
```
ATGCAGAGGAGCCCACTGGAGAAAGCCTCCGTGGTGAGTAAACTCTTTTTTAGTTGGAC

CAGACCCATCCTGCGAAAAGGATACAGGCAGCGCCTCGAGTTGTCAGATATCTACCAG

ATTCCTTCTGTGGACTCAGCTGACAATTTGAGTGAGAAGCTGGAGCGGGAGTGGGATAG

AGAGCTGGCGAGCAAAAAAAACCCCAAGCTTATCAATGCTCTGCGCCGCTGCTTTTTCT

GGAGGTTCATGTTTTATGGGATCTTCCTGTACCTGGGGGAGGTCACCAAAGCTGTTCAG

CCGCTCCTTCTTGGCCGCATCATCGCCAGCTATGACCCTGATAATAAAGAAGAAAGGTC

TATTGCTATTTATCTGGGAATTGGCCTCTGCTTGCTCTTCATCGTCCGCACCCTTCTGCTG

CACCCTGCCATTTTTGGCCTTCACCACATCGGCATGCAAATGAGAATTGCCATGTTCTCC

CTCATTTACAAAAAGACCCTGAAACTTTCCTCAAGAGTGTTAGATAAAATATCCATTGG

TCAGCTGGTCAGCCTGCTGTCCAACAATCTTAACAAATTTGATGAAGGCTTGGCGCTGG

CCCACTTCGTGTGGATTGCACCTCTGCAGGTGGCCCTGTTGATGGGACTTATATGGGAG

CTGCTTCAAGCCTCTGCTTTCTGTGGGCTGGCTTTTTGATTGTACTGGCACTTTTTCAGG

CTGGGCTCGGAAGAATGATGATGAAATACAGAGATCAGCGGGCCGGGAAGATATCAGA

GCGACTTGTGATCACCAGTGAAATGATTGAAAATATTCAGAGCGTGAAAGCCTACTGCT

GGGAAGAAGCCATGGAGAAGATGATTGAGAACCTGAGGCAGACAGAGCTCAAGCTCAC

TCGGAAGGCTGCTTATGTTCGCTATTTCAACAGCAGCGCCTTCTTCTTCAGTGGCTTCTT

TGTTGTCTTCCTGTCTGTTCTGCCATATGCACTGATAAAAGGCATTATTTTACGAAAGAT

CTTCACCACCATCAGTTTTTGCATCGTTCTCAGGATGGCCGTCACAAGACAGTTCCCCTG

GGCTGTGCAGACCTGGTACGATTCCTTGGGGGCCATCAACAAGATTCAAGATTTCTTGC

AAAAACAAGAATATAAAACTTTAGAATACAACCTCACCACCACTGAAGTGGTCATGGA

AAATGTGACAGCCTTTTGGGAGGAGGGTTTTGGAGAATTGTTCGAGAAGGCAAAGCAG

AATAACAACAACAGGAAGACGAGCAATGGGACGACTCTCTCTTCTTCAGCAACTTTTC

ACTGCTCGGACCCCTGTGTTGAAAGATATAAACTTCAAGATCGAGAGGGGCCAGCTCT

TGGCTGTGGCAGGCTCCACTGGAGCTGGTAAAACATCTCTTCTCATGGTGATCATGGGG

GAACTGGAGCCTTCCGAAGGAAAAATCAAGCACAGTGGGAGAATCTCATTCTGCAGCC

AGTTTTCCTGGATCATGCCCGGCACCATTAAGGAAAACATCATATTTGGAGTGTCCTAT

GATGAGTACCGCTACCGGTCAGTCATCAAAGCCTGTCAGTTGGAGGAGGACATCTCCAA

GTTTGCAGAGAAAGACAACATTGTGCTTGGAGAGGGGGGTATCACTCTTTCTGGAGGAC

AAAGAGCCAGGATCTCTTTGGCCCGGGCAGTCTACAAGGATGCAGACCTCTACTTGTTG

GACAGTCCCTTCGGCTACCTCGACGTGCTGACTGAAAAAGAAATTTTTGAAAGCTGTGT

GTGCAAACTGATGGCAAACAAGACCAGGATTCTTGTCACCAGCAAGATGGAACATCTG

AAGAAAGCGGACAAAATTCTGATTCTGCATGAAGGGAGCTCCTACTTCTATGGAACATT
```

-continued

```
TAGCGAGCTTCAGAACCTACAGCCAGACTTCTCCTCCAAATTAATGGGCTGTGACTCCT
TCGACCAGTTCTCTGCAGAAAGAAGAAACTCTATACTCACAGAGACCCTCCACCGCTTC
TCCCTTGAGGGAGATGCCCCAGTTTCTTGGACAGAAACCAAGAAGCAGTCCTTTAAGCA
GACTGGCGAGTTTGGTGAAAAGAGGAAAAATTCAATTCTCAATCCAATTAACAGTATTC
GCAAGTTCAGCATTGTCCAGAAGACACCCCTCCAGATGAATGGCATCGAAGAAGATAG
TGACGAGCCGCTGGAGAGACGGCTGAGTCTGGTGCCAGATTCAGAACAGGGGGAGGCC
ATCCTGCCCCGGATCAGCGTCATTTCCACAGGCCCCACATTACAAGCACGGCGCCGGCA
GAGTGTTTTAAATCTCATGACCCATTCAGTGAACCAGGGCCAAAATATCCACAGGAAGA
CTACAGCTTCTACCCGGAAAGTGTCTCTGGCCCCTCAGGCCAATCTGACCGAGCTGGAC
ATCTACAGCAGGAGGCTCTCCCAGGAAACAGGGCTGGAAATATCTGAAGAGATTAATG
AAGAGGATCTTAAAGAGTGCTTCTTTGATGACATGGAGAGCATCCCCGCGGTGACCACA
TGGAACACCTACCTTAGATATATTACTGTCCACAAGAGCCTCATATTTGTCCTCATCTGG
TGCCTGGTTATTTTCCTCGCTGAGGTGGCGGCCAGTCTTGTTGTGCTCTGGCTGCTGGGC
AACACTCCTCTCCAGGACAAGGGCAATAGTACTCACAGCAGAAATAATTCTTATGCCGT
CATCATTACAAGCACCTCCAGCTACTACGTGTTCTACATCTATGTGGGCGTGGCTGACA
CCCTCCTGGCCATGGGTTTCTTCCGGGGCCTGCCTTTGGTGCACACCCTCATCACAGTGT
CAAAAATTCTGCACCATAAAATGCTTCATTCTGTCCTGCAGGCACCCATGAGCACTTTG
AACACATTGAAGGCTGGCGGCATCCTCAACAGATTTTCTAAAGATATTGCTATCCTGGA
TGATCTCCTCCCCCTGACAATCTTTGACTTTATCCAGCTTCTGCTGATCGTGATTGGAGC
CATAGCAGTGGTTGCTGTCCTGCAGCCCTACATTTTTGTGGCCACCGTGCCCGTGATTGT
TGCCTTTATTATGCTCAGAGCTTACTTCCTGCAAACTTCTCAACAGCTCAAACAGCTAGA
ATCTGAGGGCCGGAGCCCCATTTTTACCCACCTGGTGACTTCCCTGAAGGGACTGTGGA
CTCTGAGAGCATTCGGGCGACAGCCTTACTTTGAGACACTGTTCCACAAGGCCCTGAAC
TTGCACACTGCCAACTGGTTTCTTTACCTGAGCACACTCCGCTGGTTCCAGATGCGGATA
GAGATGATCTTCGTCATCTTTTTTATAGCTGTAACCTTCATTTCTATCCTTACAACAGGA
GAAGGAGAGGGCAGGGTGGGAATCATCCTCACGCTGGCTATGAACATAATGTCCACCT
TGCAGTGGGCCGTGAATTCCAGTATAGATGTGGATTCTCTAATGAGGAGTGTCTCCCGG
GTGTTTAAATTCATTGATATGCCTACTGAGGGGAAACCCACCAAGTCAACAAAACCTTA
TAAGAATGGACAGCTGAGCAAGGTGATGATAATTGAGAACAGCCACGTGAAGAAGGAT
GACATTTGGCCCAGCGGGGGCCAGATGACTGTGAAGGACCTGACGGCCAAGTACACCG
AAGGTGGAAATGCCATTTTGGAAAACATCAGCTTCTCAATCTCTCCTGGGCAGAGAGTT
GGATTGCTGGGTCGCACGGGCAGCGGCAAATCAACCCTGCTCAGTGCCTTCCTTCGGCT
CCTGAATACAGAAGGCGAAATCCAAATTGACGGGGTGAGCTGGGACAGCATCACCCTG
CAGCAGTGGAGAAAAGCATTTGGGGTCATTCCACAGAAAGTTTTCATCTTCTCTGGCAC
TTTCAGAAAGAACCTGGACCCCTATGAGCAGTGGAGCGACCAGGAGATCTGGAAGGTT
GCAGATGAAGTTGGCCTGCGGAGTGTGATAGAACAATTTCCTGGCAAGCTGGATTTTGT
GCTGGTAGATGGAGGCTGCGTGCTGTCCCACGGCCACAAACAGCTGATGTGCCTCGCCC
GCTCCGTTCTTTCAAAGGCCAAAATCTTGCTTTTGGATGAGCCCAGTGCTCACCTCGACC
CAGTGACCTATCAGATAATCCGCAGGACCTTAAAGCAAGCTTTTGCCGACTGCACCGTC
ATACTGTGTGAGCACCGGATTGAAGCAATGCTGGAATGCCAGCAGTTTCTGGTGATCGA
```

-continued

```
GGAGAATAAGGTCCGGCAGTACGACAGCATCCAGAAGTTGTTGAATGAGCGCAGCCTT

TTCCGCCAGGCCATCTCCCCATCTGACAGAGTCAAGCTGTTTCCACATAGGAACTCCTCT

AAGTGCAAGTCCAAGCCCCAGATCGCTGCCCTCAAGGAGGAAACTGAGGAAGAGGTGC

AGGATACCCGCCTGTGA.
```

In another embodiment, an exemplary codon-optimized CFTR mRNA sequence is:

(SEQ ID NO: 27)
```
ATGCAACGGAGTCCTCTGGAAAAAGCCTCTGTCGTATCTAAGCTTTTCTTCAGTTGGAC

ACGCCCGATTTTGAGAAAGGGTTATCGGCAACGCTTGGAACTTAGTGACATCTACCAA

TTCCAAGTGTAGACTCAGCCGATAACTTGAGCGAAAAGCTCGAACGAGAGTGGGATCG

AGAACTGGCTAGCAAAAAAAATCCCAAACTCATAAATGCCCTGCGACGCTGTTTCTTTT

GGCGATTTATGTTTTACGGTATTTTCCTTTATTTGGGTGAGGTCACGAAGGCTGTACAGC

CACTGCTGCTGGGTCGCATCATTGCCTCTTACGACCCTGACAACAAAGAGGAGCGGTCA

ATAGCTATCTACCTTGGTATAGGACTTTGCTTGCTCTTCATAGTCCGCACGTTGCTTCTC

CACCCTGCTATATTTGGTCTCCATCACATTGGGATGCAAATGCGGATCGCGATGTTCAGT

CTTATATATAAAAAGACTCTTAAACTTTCCAGCCGGGTTCTGGATAAGATCTCTATTGGT

CAACTGGTATCTCTTTTGTCTAACAACCTGAATAAGTTCGACGAGGGCCTTGCATTGGCC

CATTTTGTATGGATTGCCCCTTTGCAAGTCGCCCTCCTGATGGGATTGATCTGGGAACTC

CTGCAAGCTAGTGCTTTTTGCGGATTGGGATTCCTCATAGTCCTTGCGCTCTTTCAGGCG

GGACTTGGACGCATGATGATGAAGTATCGCGACCAACGAGCTGGCAAGATCAGTGAAC

GGCTTGTAATAACCAGTGAAATGATAGAGAACATCCAGAGCGTAAAAGCTTACTGTTG

GGAAGAAGCGATGGAAAAGATGATTGAGAACCTTCGCCAGACAGAACTTAAACTTACA

CGAAAGGCCGCTTATGTCCGGTACTTCAACTCTTCAGCATTTTTTTTAGTGGCTTCTTTG

TAGTGTTCCTGTCCGTCCTTCCGTATGCACTTATCAAGGGTATAATACTTAGGAAAATCT

TCACAACAATCAGTTTTTGCATAGTCCTTCGCATGGCAGTAACTCGCCAATTTCCCTGGG

CAGTTCAGACGTGGTACGACTCACTTGGCGCAATTAACAAAATTCAAGATTTCCTCCAA

AAGCAAGAGTATAAAACCTTGGAATACAACCTTACCACCACAGAAGTTGTAATGGAAA

ATGTCACAGCCTTCTGGGAGGAAGGTTTCGGCGAACTTTTTGAGAAGGCGAAGCAAAAT

AACAATAATCGGAAAACATCAAACGGTGACGATTCACTGTTCTTTTCTAACTTTAGCCTT

CTTGGGACGCCCGTCCTGAAGGACATAAACTTTAAGATTGAACGGGGTCAACTTCTCGC

GGTCGCAGGGAGTACTGGAGCGGGGAAAACGAGCCTGCTGATGGTGATAATGGGGGAG

TTGGAGCCCTCAGAAGGCAAGATCAAGCATAGTGGTAGAATTAGCTTCTGCAGTCAATT

TAGTTGGATTATGCCGGGCACGATCAAAGAAAATATAATCTTTGGGGTATCCTACGATG

AATACAGGTACCGATCAGTGATAAAAGCGTGCCAGCTTGAAGAAGACATTTCAAAGTTT

GCTGAGAAGGATAATATCGTACTTGGAGAAGGAGGTATCACCCTGTCTGGGGGTCAAC

GAGCGAGGATCTCCCTGGCACGCGCCGTCTACAAGGACGCGGACCTCTATCTGTTGGAT

TCACCGTTCGGATATTTGGACGTGCTTACGGAGAAAGAAATATTTGAGAGCTGTGTTTG

CAAGCTCATGGCAAATAAAACCAGAATATTGGTTACAAGCAAGATGGAGCATCTTAAG

AAAGCAGATAAAATCCTGATATTGCACGAGGGCTCTTCATACTTCTACGGGACGTTTTC

TGAGTTGCAGAACCTCCAGCCGGATTTCAGCTCTAAGCTGATGGGCTGTGATTCCTTTG
```

-continued
ATCAGTTTAGTGCGGAAAGACGAAACAGTATACTCACCGAAACACTGCACAGGTTCTCT

CTGGAGGGCGACGCCCCGGTTTCCTGGACAGAGACGAAGAAGCAGTCCTTCAAACAGA

CAGGCGAGTTTGGGGAGAAAAGGAAAAATAGCATACTCAACCCGATTAACAGCATTCG

CAAGTTCAGTATAGTACAAAAGACCCCGTTGCAGATGAACGGTATAGAGGAAGATTCT

GATGAGCCACTGGAAAGACGGCTTTCTCTCGTTCCGGACAGTGAACAGGGAGAGGCAA

TACTGCCTCGGATCAGCGTTATCTCTACAGGACCTACTTTGCAAGCTCGGCGCCGACAG

TCAGTCTTGAATCTTATGACTCATAGTGTTAATCAAGGCCAGAATATCCATCGCAAGAC

CACCGCAAGTACAAGGAAAGTGAGCTTGGCACCTCAAGCAAACCTTACTGAACTTGAT

ATCTACTCACGGCGACTTTCACAGGAGACCGGACTTGAAATTAGTGAAGAAATTAACGA

GGAGGACCTCAAGGAGTGCTTCTTCGATGACATGGAATCAATCCCCGCAGTCACAACCT

GGAACACTTATCTGAGGTATATAACAGTTCACAAGAGCCTCATTTTTGTACTTATTTGGT

GTTTGGTAATTTTCCTGGCGGAGGTTGCTGCTTCTTTGGTCGTCCTTTGGCTCCTCGGGA

ATACACCGCTCCAAGACAAAGGCAACTCTACCCATAGTAGGAACAATTCATATGCAGT

GATTATAACCAGTACATCATCTTATTACGTTTTCTATATTTATGTCGGGGTAGCTGACAC

GCTGTTGGCGATGGGCTTCTTTAGGGGCCTCCCCTTGGTACACACCCTTATCACGGTGAG

TAAAATCCTGCATCACAAAATGCTTCATTCTGTACTCCAAGCGCCGATGAGTACGCTTA

ATACGCTGAAAGCAGGAGGGATACTGAATCGGTTCAGCAAGGACATCGCCATTCTGGA

TGACCTGCTTCCATTGACAATATTTGATTTCATTCAGCTCCTTCTCATAGTTATTGGAGC

CATAGCGGTGGTGGCTGTGCTTCAGCCTTATATATTCGTTGCCACAGTTCCCGTTATAGT

GGCATTTATAATGCTCAGGGCCTACTTTCTCCAGACTTCCCAGCAGTTGAAGCAACTCG

AATCAGAAGGAAGGTCACCTATTTTCACACATCTTGTGACTTCCTTGAAGGGCTTGTGG

ACGCTGCGGGCCTTCGGAAGACAACCATATTTTGAAACTCTCTTCCACAAAGCTTTGAA

TCTTCATACTGCGAACTGGTTCCTGTATTTGAGTACTTTGCGCTGGTTCCAGATGAGGAT

AGAAATGATATTCGTTATCTTCTTTATCGCGGTTACGTTCATAAGTATCCTCACTACGGG

GGAGGGTGAGGGTAGAGTGGGCATAATACTGACCCTCGCCATGAACATTATGTCCACCC

TGCAGTGGGCGGTAAACAGCAGCATAGATGTGGATTCTTTGATGCGCAGTGTGAGCAG

GGTTTTTAAGTTTATCGATATGCCGACGGAAGGAAAGCCCACTAAAAGCACGAAACCCT

ATAAAAATGGACAGCTTAGCAAAGTAATGATAATCGAGAATAGCCATGTGAAAAAGGA

TGACATATGGCCTTCCGGAGGCCAAATGACTGTTAAAGATCTGACCGCTAAATATACCG

AGGGCGGCAACGCAATACTCGAAAACATAAGCTTTTCCATAAGCCCCGGCCAACGCGT

GGGTCTTCTGGGGAGGACTGGCTCCGGAAAATCAACGTTGCTTAGCGCGTTTTTGCGGC

TCCTTAACACTGAAGGTGAGATCCAAATAGATGGCGTTAGTTGGGACTCTATAACACTG

CAACAATGGCGGAAAGCTTTCGGCGTCATACCTCAGAAGGTGTTCATCTTTAGCGGAAC

GTTCAGGAAGAACTTGGATCCCTACGAACAATGGAGTGATCAAGAAATATGGAAAGTG

GCAGATGAGGTAGGCTTGCGCAGTGTCATTGAACAATTCCCAGGGAAACTCGACTTTGT

ACTGGTGGACGGCGGTTGCGTCTTGTCACACGGGCACAAACAGTTGATGTGTTTGGCCC

GCAGTGTTTTGTCTAAGGCGAAGATTCTGTTGCTCGACGAACCGAGTGCTCATCTTGATC

CCGTCACCTACCAAATCATCAGAAGGACGTTGAAGCAAGCTTTCGCCGACTGCACTGTA

ATCCTTTGTGAGCATAGGATCGAAGCAATGCTCGAGTGCCAACAGTTCTTGGTTATAGA

```
-continued
GGAGAATAAGGTTCGGCAATACGACTCAATACAGAAACTGCTTAATGAGCGGTCACTCT

TTCGACAAGCTATCTCTCCTAGTGACAGGGTAAAGCTTTTTCCTCATCGGAATTCCAGCA

AGTGTAAGAGTAAACCACAGATCGCCGCCCTTAAAGAGGAGACCGAAGAAGAGGTGCA

GGATACGAGACTTTAG.
```

In some embodiments, a codon-optimized CFTR mRNA sequence suitable for the present invention shares at least 60%, 65%, 70%, 75%, 80%, 85%, 90%, 95%, 96%, 97%, 98%, or 99% identity to SEQ ID NO:6 or SEQ ID NO:7 and encodes a CFTR protein having an amino acid sequence of SEQ ID NO:2. In a specific embodiment, a codon-optimized CFTR mRNA sequence suitable for the present invention has the nucleotide sequence of SEQ ID NO:6.

In some embodiments, a suitable mRNA sequence may be an mRNA sequence encoding a homolog or an analog of human CFTR (hCFTR) protein. For example, a homolog or an analog of hCFTR protein may be a modified hCFTR protein containing one or more amino acid substitutions, deletions, and/or insertions as compared to a wild-type or naturally-occurring hCFTR protein while retaining substantial hCFTR protein activity. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 2. In some embodiments, an mRNA suitable for the present invention encodes a protein substantially identical to hCFTR protein. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 2. In some embodiments, an mRNA suitable for the present invention encodes a fragment or a portion of hCFTR protein. In some embodiments, an mRNA suitable for the present invention encodes a fragment or a portion of hCFTR protein, wherein the fragment or portion of the protein still maintains CFTR activity similar to that of the wild-type protein. Thus, in some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical SEQ ID NO: 1, SEQ ID NO: 6 or SEQ ID NO: 7.

In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to any one of SEQ ID NO: 8, SEQ ID NO: 29, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 27.

In some embodiments, a suitable mRNA encodes a fusion protein comprising a full length, fragment or portion of an hCFTR protein fused to another protein (e.g., an N or C terminal fusion). In some embodiments, the protein fused to the mRNA encoding a full length, fragment or portion of an hCFTR protein encodes a signal or a cellular targeting sequence.

mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7, or SP6 RNA polymerase), DNAse I, pyrophosphatase, and/or RNAse inhibitor. The exact conditions will vary according to the specific application.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs (e.g., mRNAs encoding CFTR) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'-5' triphosphate linkage; and the 7-nitrogen of guanine is then methylated by a methyltransferase. In some embodiments, the nucleotide forming the cap is further methylated at the 3'position. In some embodiments, the nucleotide directly adjacent to the cap is further methylated at the 2' position. Examples of cap structures include, but are not limited to, m7G(5')ppp(5')(2'OMeG), m7G(5')ppp(5')(2'OMeA), m7(3'OMeG)(5')ppp(5')(2'OMeG), m7(3'OMeG)(5')ppp(5')(2'OMeA), m7G(5')ppp (5'(A,G(5')ppp(5')A and G(5')ppp(5')G. In a specific embodiment, the cap structure is m7G(5')ppp(5')(2'OMeG). Additional cap structures are described in published US Application No. US 2016/0032356 and U.S. Provisional Application 62/464,327, filed Feb. 27, 2017, which are incorporated herein by reference.

In some embodiments, mRNAs (e.g., mRNAs encoding CFTR) include a 3' tail structure. Typically, a tail structure includes a poly(A) and/or poly(C) tail. A poly-A or poly-C tail on the 3' terminus of mRNA typically includes at least 50 adenosine or cytosine nucleotides, at least 100 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, at least 950 adenosine or cytosine nucleotides, or at least 1 kb adenosine or cytosine nucleotides, respectively. In some embodiments, a poly-A or poly-C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly(A) and poly(C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

In a specific embodiment, an mRNA encoding CFTR that has a poly(A) tail of between 200 and 1000 adenosine nucleotides (e.g., as determined using agarose gel electrophoresis) is particularly suitable for practicing the invention. Typically, an mRNA encoding CFTR for use with the invention has a poly(A) tail that is between 400 and 700 adenosine nucleotides (e.g., as determined using agarose gel electrophoresis).

In a specific embodiment, the mRNA encoding CFTR has the following sequence and structural elements:

(SEQ ID NO: 28)
GGACAGAUCGCCUGGAGACGCCAUCCACGCUGUUUGACCUCCAUAGAAGACACCGG

GACCGAUCCAGCCUCCGCGGCCGGGAACGGUGCAUUGGAACGCGGAUUCCCCGUGCC

AAGAGUGACUCACCGUCCUUGACACGAUGCAACGCUCUCCUCUUGAAAAGGCCUCGG

UGGUGUCCAAGCUCUUCUUCUCGUGGACUAGACCCAUCCUGAGAAAGGGGUACAGAC

AGCGCUUGGAGCUGUCCGAUAUCUAUCAAAUCCCUUCCGUGGACUCCGCGGACAACC

UGUCCGAGAAGCUCGAGAGAGAAUGGGACAGAGAACUCGCCUCAAAGAAGAACCCGA

AGCUGAUUAAUGCGCUUAGGCGGUGCUUUUUCUGGCGGUUCAUGUUCUACGGCAUC

UUCCUCUACCUGGGAGAGGUCACCAAGGCCGUGCAGCCCCUGUUGCUGGGACGGAUU

AUUGCCUCCUACGACCCCGACAACAAGGAAGAAAGAAGCAUCGCUAUCUACUUGGGC

AUCGGUCUGUGCCUGCUUUUCAUCGUCCGGACCCUCUUGUUGCAUCCUGCUAUUUUC

GGCCUGCAUCACAUUGGCAUGCAGAUGAGAAUUGCCAUGUUUUCCCUGAUCUACAAG

AAAACUCUGAAGCUCUCGAGCCGCGUGCUUGACAAGAUUUCCAUCGGCCAGCUCGUG

UCCCUGCUCUCCAACAAUCUGAACAAGUUCGACGAGGGCCUCGCCCUGGCCCACUUC

GUGUGGAUCGCCCCUCUGCAAGUGGCGCUUCUGAUGGGCCUGAUCUGGGAGCUGCUG

CAAGCCUCGGCAUUCUGUGGGCUUGGAUUCCUGAUCGUGCUGGCACUGUUCCAGGCC

GGACUGGGGCGGAUGAUGAUGAAGUACAGGGACCAGAGAGCCGGAAAGAUUUCCGA

ACGGCUGGUGAUCACUUCGGAAAUGAUCGAAAACAUCCAGUCAGUGAAGGCCUACUG

CUGGGAAGAGGCCAUGGAAAAGAUGAUUGAAAACCUCCGGCAAACCGAGCUGAAGC

UGACCCGCAAGGCCGCUUACGUGCGCUAUUUCAACUCGUCCGCUUUCUUCUUCUCCG

GGUUCUUCGUGGUGUUUCUCUCCGUGCUCCCCUACGCCCUGAUUAAGGGAAUCAUCC

UCAGGAAGAUCUUCACCACCAUUUCCUUCUGUAUCGUGCUCCGCAUGGCCGUGACCC

GGCAGUUCCCAUGGGCCGUGCAGACUUGGUACGACUCCCUGGGAGCCAUUAACAAGA

UCCAGGACUUCCUUCAAAAGCAGGAGUACAAGACCCUCGAGUACAACCUGACUACUA

CCGAGGUCGUGAUGGAAAACGUCACCGCCUUUUGGGAGGAGGGAUUUGGCGAACUG

UUCGAGAAGGCCAAGCAGAACAACAACAACCGCAAGACCUCGAACGGUGACGACUCC

CUCUUCUUUUCAAACUUCAGCCUGCUCGGGACGCCCGUGCUGAAGGACAUUAACUUC

AAGAUCGAAAGAGGACAGCUCCUGGCGGUGGCCGGAUCGACCGGAGCCGGAAAGACU

UCCCUGCUGAUGGUGAUCAUGGGAGAGCUUGAACCUAGCGAGGGAAAGAUCAAGCA

CUCCGGCCGCAUCAGCUUCUGUAGCCAGUUUUCCUGGAUCAUGCCCGGAACCAUUAA

-continued

```
GGAAAACAUCAUCUUCGGCGUGUCCUACGAUGAAUACCGCUACCGGUCCGUGAUCAA
AGCCUGCCAGCUGGAAGAGGAUAUUUCAAAGUUCGCGGAGAAAGAUAACAUCGUGC
UGGGCGAAGGGGUAUUACCUUGUCGGGGGCCAGCGGGCUAGAAUCUCGCUGGCCA
GAGCCGUGUAUAAGGACGCCGACCUGUAUCUCCUGGACUCCCCCUUCGGAUACCUGG
ACGUCCUGACCGAAAAGGAGAUCUUCGAAUCGUGCGUGUGCAAGCUGAUGGCUAACA
AGACUCGCAUCCUCGUGACCUCCAAAAUGGAGCACCUGAAGAAGGCAGACAAGAUUC
UGAUUCUGCAUGAGGGGUCCUCCUACUUUUACGGCACCUUCUCGGAGUUGCAGAACU
UGCAGCCCGACUUCUCAUCGAAGCUGAUGGGUUGCGACAGCUUCGACCAGUUCUCCG
CCGAAAGAAGGAACUCGAUCCUGACGGAAACCUUGCACCGCUUCUCUUUGGAAGGCG
ACGCCCUGUGUCAUGGACCGAGACUAAGAAGCAGAGCUUCAAGCAGACCGGGGAAU
UCGGCGAAAAGAGGAAGAACAGCAUCUUGAACCCCAUUAACUCCAUCCGCAAGUUCU
CAAUCGUGCAAAAGACGCCACUGCAGAUGAACGGCAUUGAGGAGGACUCCGACGAAC
CCCUUGAGAGGCGCCUGUCCCUGGUGCCGGACAGCGAGCAGGGAGAAGCCAUCCUGC
CUCCGGAUUUCCGUGAUCUCCACUGGUCCGACGCUCCAAGCCCGGCGGCGGCAGUCCG
UGCUGAACCUGAUGACCCACAGCGUGAACCAGGGCCAAAACAUUCACCGCAAGACUA
CCGCAUCCACCCGGAAAGUGUCCCUGGCACCUCAAGCGAAUCUUACCGAGCUCGACA
UCUACUCCCGGAGACUGUCGCAGGAAACCGGGCUCGAAAUUUCCGAAGAAAUCAACG
AGGAGGAUCUGAAAGAGUGCUUCUUCGACGAUAUGGAGUCGAUACCCGCCGUGACG
ACUUGGAACACUUAUCUGCGGUACAUCACUGUGCACAAGUCAUUGAUCUUCGUGCUG
AUUUGGUGCCUGGUGAUUUUCCUGGCCGAGGUCGCGGCCUCACUGGUGGUGCUCUGG
CUGUUGGGAAACACGCCUCUGCAAGACAAGGGAAACUCCACGCACUCGAGAAACAAC
AGCUAUGCCGUGAUUAUCACUUCCACCUCCUCUUUAUUACGUGUUCUACAUCUACGUC
GGAGUGGCGGAUACCCUGCUCGCGAUGGGUUUCUUCAGAGGACUGCCGCUGGUCCAC
ACCUUGAUCACCGUCAGCAAGAUUCUUCACCACAAGAUGUUGCAUAGCGUGCUGCAG
GCCCCCAUGUCCACCCUCAACACUCUGAAGGCCGGAGGCAUUCUGAACAGAUUCUCC
AAGGACAUCGCUAUCCUGGACGAUCUCCUGCCGCUUACCAUCUUUGACUUCAUCCAG
CUGCUGCUGAUCGUGAUUGGAGCAAUCGCAGUGGUGGCGGUGCUGCAGCCUUACAUU
UUCGUGGCCACUGUGCCGGUCAUUGUGGCGUUCAUCAUGCUGCGGGCCUACUUCCUC
CAAACCAGCCAGCAGCUGAAGCAACUGGAAUCCGAGGGACGAUCCCCCAUCUUCACU
CACCUUGUGACGUCGUUGAAGGGACUGUGGACCCUCCGGGCUUUCGGACGGCAGCCC
UACUUCGAAACCCUCUUCCACAAGGCCCUGAACCUCCACACCGCCAAUUGGUUCCUG
UACCUGUCCACCCUGCGGUGGUUCCAGAUGCGCAUCGAGAUGAUUUUCGUCAUCUUC
UUCAUCGCGGUCACAUUCAUCAGCAUCCUGACUACCGGAGAGGGAGAGGGACGGGUC
GGAAUAAUCCUGACCCUCGCCAUGAACAUUAUGAGCACCCUGCAGUGGGCAGUGAAC
AGCUCGAUCGACGUGGACAGCCUGAUGCGAAGCGUCAGCCGCGUGUUCAAGUUCAUC
GACAUGCCUACUGAGGGAAAACCCACUAAGUCCACUAAGCCCUACAAAAAUGGCCAG
CUGAGCAAGGUCAUGAUCAUCGAAAACUCCCACGUGAAGAAGGACGAUAUUUGGCCC
UCCGGAGGUCAAAUGACCGUGAAGGACCUGACCGCAAAGUACACCGAGGGAGGAAAC
GCCAUUCUCGAAAACAUCAGCUUCUCCAUUUCGCCGGGACAGCGGGUCGGCCUUCUC
GGGCGGACCGGUUCCGGGAAGUCAACUCUGCUGUCGGCUUUCCUCCGGCUGCUGAAU
ACCGAGGGGGAAAUCCAAAUUGACGGCGUGUCUUGGGAUUCCAUUACUCUGCAGCAG
```

-continued

UGGCGGAAGGCCUUCGGCGUGAUCCCCCAGAAGGUGUUCAUCUUCUCGGGUACCUUC

CGGAAGAACCUGGAUCCUUACGAGCAGUGGAGCGACCAAGAAAUCUGGAAGGUCGCC

GACGAGGUCGGCCUGCGCUCCGUGAUUGAACAAUUUCCUGGAAAGCUGGACUUCGUG

CUCGUCGACGGGGAUGUGUCCUGUCGCACGGACAUAAGCAGCUCAUGUGCCUCGCA

CGGUCCGUGCUCUCCAAGGCCAAGAUUCUGCUGCUGGACGAACCUUCGGCCCACCUG

GAUCCGGUCACCUACCAGAUCAUCAGGAGGACCCUGAAGCAGGCCUUUGCCGAUUGC

ACCGUGAUUCUCUGCGAGCACCGCAUCGAGGCCAUGCUGGAGUGCCAGCAGUUCCUG

GUCAUCGAGGAGAACAAGGUCCGCCAAUACGACUCCAUUCAAAAGCUCCUCAACGAG

CGGUCGCUGUUCAGACAAGCUAUUUCACCGUCCGAUAGAGUGAAGCUCUUCCCGCAU

CGGAACAGCUCAAAGUGCAAAUCGAAGCCGCAGAUCGCAGCCUUGAAGGAAGAGACU

GAGGAAGAGGUGCAGGACACCCGGCUUUAACGGGUGGCAUCCCUGUGACCCCUCCCC

AGUGCCUCUCCUGGCCCUGGAAGUUGCCACUCCAGUGCCCACCAGCCUUGUCCUAAU

AAAAUUAAGUUGCAUCAAGCU

TABLE A mRNA Structural Elements

| Structural Element | Description | | Sequence Coordinates |
|---|---|---|---|
| Cap Structure | | | 7 mG is attached to the nucleotide in position 1 of the CFTR mRNA where the first nucleotide (underlined) is methylated at the 2'position |
| 5' UTR | GGAC . . . CACG | | 1-140 |
| Start Codon hCFTR | <u>A</u>UG (Bold) | | 141-143 |
| Stop Codon hCFTR | UAA (Bold) | | 4581-4583 |
| 3' UTR | CGGG . . . AGCU | | 4584-4688 |
| Poly A tail | $(A)_x$, x = 200-1000* | | 4689-ff |

In another embodiment, the mRNA encoding CFTR has the following sequence and structural elements:

(SEQ ID NO: 29)

GGACAGAUCGCCUGGAGACGCCAUCCACGCUGUUUUGACCUCCAUAGA

AGACACCGGGACCGAUCCAGCCUCCGCGGCCGGGAACGGUGCAUUGGAACGCGGAUU

CCCCGUGCCAAGAGUGACUCACCGUCCUUGACACGAUGCAGCGGUCCCCGCUCGAAA

AGGCCAGUGUCGUGUCCAAACUCUUCUUCUCAUGGACUCGGCCUAUCCUUAGAAAGG

GGUAUCGGCAGAGGCUUGAGUUGUCUGACAUCUACCAGAUCCCCUCGGUAGAUUCGG

CGGAUAACCUCUCGGAGAAGCUCGAACGGGAAUGGGACCGCGAACUCGCGUCUAAGA

AAAACCCGAAGCUCAUCAACGCACUGAGAAGGUGCUUCUUCUGGCGGUUCAUGUUCU

ACGGUAUCUUCUUGUAUCUCGGGGAGGUCACAAAAGCAGUCCAACCCCUGUUGUUGG

GUCGCAUUAUCGCCUCGUACGACCCCCGAUAACAAAGAAGAACGGAGCAUCGCGAUCU

ACCUCGGGAUCGGACUGUGUUUGCUUUUCAUCGUCAGAACACUUUUGUUGCAUCCAG

```
CAAUCUUCGGCCUCCAUCACAUCGGUAUGCAGAUGCGAAUCGCUAUGUUUAGCUUGA
UCUACAAAAGACACUGAAACUCUCGUCGCGGGUGUUGGAUAAGAUUUCCAUCGGUC
AGUUGGUGUCCCUGCUUAGUAAUAACCUCAACAAAUUCGAUGAGGGACUGGCGCUG
GCACAUUUCGUGUGGAUUGCCCCGUUGCAAGUCGCCCUUUUGAUGGGCCUUAUUUGG
GAGCUGUUGCAGGCAUCUGCCUUUUGUGGCCUGGGAUUUCUGAUUGUGUUGGCAUU
GUUUCAGGCUGGGCUUGGGCGGAUGAUGAUGAAGUAUCGCGACCAGAGAGCGGGUA
AAAUCUCGGAAAGACUCGUCAUCACUUCGGAAAUGAUCGAAAACAUCCAGUCGGUCA
AAGCCUAUUGCUGGGAAGAAGCUAUGGAGAAGAUGAUUGAAAACCUCCGCCAAACU
GAGCUGAAACUGACCCGCAAGGCGGCGUAUGUCCGGUAUUUCAAUUCGUCAGCGUUC
UUCUUUUCCGGGUUCUUCGUUGUCUUUCUCUCGGUUUUGCCUUAUGCCUUGAUUAAG
GGGAUUAUCCUCCGCAAGAUUUUCACCACGAUUUCGUUCUGCAUUGUAUUGCGCAUG
GCAGUGACACGGCAAUUUCCGUGGGCCGUGCAGACAUGGUAUGACUCGCUUGGAGCG
AUCAACAAAAUCCAAGACUUCUUGCAAAAGCAAGAGUACAAGACCCUGGAGUACAAU
CUUACUACUACGGAGGUAGUAAUGGAGAAUGUGACGGCUUUUUGGGAAGAGGGUUU
UGGAGAACUGUUUGAGAAAGCAAAGCAGAAUAACAACAACCGCAAGACCUCAAAUG
GGGACGAUUCCCUGUUUUUCUCGAACUUCUCCCUGCUCGGAACACCCGUGUUGAAGG
ACAUCAAUUUCAAGAUUGAGAGGGGACAGCUUCUCGCGGUAGCGGGAAGCACUGGU
GCGGGAAAAACUAGCCUCUUGAUGGUGAUUAUGGGGGAGCUUGAGCCCAGCGAGGG
GAAGAUUAAACACUCCGGGCGUAUCUCAUUCUGUAGCCAGUUUUCAUGGAUCAUGCC
CGGAACCAUUAAAGAGAACAUCAUUUUCGGAGUAUCCUAUGAUGAGUACCGAUACA
GAUCGGUCAUUAAGGCGUGCCAGUUGGAAGAGGACAUUUCUAAGUUCGCCGAGAAG
GAUAACAUCGUCUUGGGAGAAGGGGGUAUUACAUUGUCGGGAGGGCAGCGAGCGCG
GAUCAGCCUCGCGAGAGCGGUAUACAAAGAUGCAGAUUUGUAUCUGCUUGAUUCACC
GUUUGGAUACCUCGACGUAUUGACAGAAAAAGAAAUCUUCGAGUCGUGCGUGUGUA
AACUUAUGGCUAAUAAGACGAGAAUCCUGGUGACAUCAAAAAUGGAACACCUUAAG
AAGGCGGACAAGAUCCUGAUCCUCCACGAAGGAUCGUCCUACUUUUACGGCACUUUC
UCAGAGUUGCAAAACUUGCAGCCGGACUUCUCAAGCAAACUCAUGGGGUGUGACUCA
UUCGACCAGUUCAGCGCGGAACGGCGGAACUCGAUCUUGACGGAAACGCUGCACCGA
UUCUCGCUUGAGGGUGAUGCCCCGGUAUCGUGGACCGAGACAAAGAAGCAGUCGUUU
AAGCAGACAGGAGAAUUUGGUGAGAAAAGAAAGAACAGUAUCUUGAAUCCUAUUAA
CUCAAUUCGCAAGUUCUCAAUCGUCCAGAAAACUCCACUGCAGAUGAAUGGAAUUGA
AGAGGAUUCGGACGAACCCCUGGAGCGCAGGCUUAGCCUCGUGCCGGAUUCAGAGCA
AGGGGAGGCCAUUCUUCCCCGGAUUUCGGUGAUUUCAACCGGACCUACACUUCAGGC
GAGGCGAAGGCAAUCCGUGCUCAACCUCAUGACGCAUUCGGUAAACCAGGGGCAAAA
CAUUCACCGCAAAACGACGGCCUCAACGAGAAAAGUGUCACUUGCACCCCAGGCGAA
UUUGACUGAACUCGACAUCUACAGCCGUAGGCUUUCGCAAGAAACCGGACUUGAGAU
CAGCGAAGAAAUCAAUGAAGAAGAUUUGAAAGAGUGUUUCUUUGAUGACAUGGAAU
CAAUCCCAGCGGUGACAACGUGGAACACAUACUUGCGUUACAUCACGGUGCACAAGU
CCUUGAUUUUCGUCCUCAUCUGGUGUCUCGUGAUCUUUCUCGCUGAGGUCGCAGCGU
CACUUGUGGUCCUCUGGCUGCUUGGUAAUACGCCCUUGCAAGACAAAGGCAAUUCUA
```

-continued

```
CACACUCAAGAAACAAUUCCUAUGCCGUGAUUAUCACUUCUACAAGCUCGUAUUACG

UGUUUUACAUCUACGUAGGAGUGGCCGACACUCUGCUCGCGAUGGGUUUCUUCCGAG

GACUCCCACUCGUUCACACGCUUAUCACUGUCUCCAAGAUUCUCCACCAUAAGAUGC

UUCAUAGCGUACUGCAGGCUCCCAUGUCCACCUUGAAUACGCUCAAGGCGGGAGGUA

UUUUGAAUCGCUUCUCAAAAGAUAUUGCAAUUUGGAUGACCUUCUGCCCCUGACGA

UCUUCGACUUCAUCCAGUUGUUGCUGAUCGUGAUUGGGGCUAUUGCAGUAGUCGCU

GUCCUCCAGCCUUACAUUUUUGUCGCGACCGUUCCGGUGAUCGUGGCGUUUAUCAUG

CUGCGGGCCUAUUUCUUGCAGACGUCACAGCAGCUUAAGCAACUGGAGUCUGAAGGG

AGGUCGCCUAUCUUUACGCAUCUUGUGACCAGUUUGAAGGGAUUGUGGACGUUGCG

CGCCUUUGGCAGGCAGCCCUACUUUGAAACACUGUUCCACAAAGCGCUGAAUCUCCA

UACGGCAAAUUGGUUUUUGUAUUUGAGUACCCUCCGAUGGUUUCAGAUGCGCAUUG

AGAUGAUUUUUGUGAUCUUCUUUAUCGCGGUGACUUUUAUCUCCAUCUUGACCACG

GGAGAGGGCGAGGGACGGGUCGGUAUUAUCCUGACACUCGCCAUGAACAUUAUGAG

CACUUUGCAGUGGGCAGUGAACAGCUCGAUUGAUGUGGAUAGCCUGAUGAGGUCCG

UUUCGAGGGUCUUUAAGUUCAUCGACAUGCCGACGGAGGGAAAGCCCACAAAAAGU

ACGAAACCCUAUAAGAAUGGGCAAUUGAGUAAGGUAAUGAUCAUCGAGAACAGUCA

CGUGAAGAAGGAUGACAUCUGGCCUAGCGGGGGUCAGAUGACCGUGAAGGACCUGA

CGGCAAAAUACACCGAGGGAGGGAACGCAAUCCUUGAAAACAUCUCGUUCAGCAUUA

GCCCCGGUCAGCGUGUGGGGUUGCUCGGGAGGACCGGGUCAGGAAAAUCGACGUUGC

UGUCGGCCUUCUUGAGACUUCUGAAUACAGAGGGUGAGAUCCAGAUCGACGGCGUU

UCGUGGGAUAGCAUCACCUUGCAGCAGUGGCGGAAAGCGUUUGGAGUAAUCCCCCAA

AAGGUCUUUAUCUUUAGCGGAACCUUCCGAAAGAAUCUCGAUCCUUAUGAACAGUG

GUCAGAUCAAGAGAUUUGGAAAGUCGCGGACGAGGUUGGCCUUCGGAGUGUAAUCG

AGCAGUUUCCGGGAAAACUCGACUUUGUCCUUGUAGAUGGGGGAUGCGUCCUGUCGC

AUGGGCACAAGCAGCUCAUGUGCCUGGCGCGAUCCGUCCUCUCUAAAGCGAAAAUUC

UUCUCUUGGAUGAACCUUCGGCCCAUCUGGACCCGGUAACGUAUCAGAUCAUCAGAA

GGACACUUAAGCAGGCGUUUGCCGACUGCACGGUGAUUCUCUGUGAGCAUCGUAUCG

AGGCCAUGCUCGAAUGCCAGCAAUUUCUUGUCAUCGAAGAGAAUAAGGUCCGCCAGU

ACGACUCCAUCCAGAAGCUGCUUAAUGAGAGAUCAUUGUUCCGGCAGGCGAUUUCAC

CAUCCGAUAGGGUGAAACUUUUUCCACACAGAAAUUCGUCGAAGUGCAAGUCCAAAC

CGCAGAUCGCGGCCUUGAAAGAAGAGACUGAAGAAGAAGUUCAAGACACGCGUCUU

UAACGGGUGGCAUCCCUGUGACCCCUCCCCAGUGCCUCUCCUGGCCCUGGAAGUUGC

CACUCCAGUGCCCACCAGCCUUGUCCUAAUAAAAUUAAGUUGCAUCAAGCU
```

TABLE B mRNA Structural Elements

| Structural Element | Description | Sequence Coordinates |
|---|---|---|
| Cap Structure | | 7 mG is attached to the nucleotide in position 1 of the CFTR mRNA where the first nucleotide (underlined) is methylated at the 2' position |
| 5' UTR | GGAC...CACG | 1-140 |
| Start Codon hCFTR | AUG (Bold) | 141-143 |
| Stop Codon hCFTR | UAA (Bold) | 4581-4583 |
| 3' UTR | CGGG...AGCU | 4584-4689 |
| Poly A tail | (A)$_x$, x = 200-1000* | 4690-ff |

In another embodiment, the mRNA encoding CFTR has the following sequence and structural elements:

(SEQ ID NO: 30)

GGACAGAUCGCCUGGAGACGCCAUCCACGCUGUUUUGACCUCCAUAGA

AGACACCGGGACCGAUCCAGCCUCCGCGGCCGGGAACGGUGCAUUGGAACGCGGAUU

CCCCGUGCCAAGAGUGACUCACCGUCCUUGACACGAUGCAGAGGAGCCCACUGGAGA

AAGCCUCCGUGGUGAGUAAACUCUUUUUUAGUUGGACCAGACCCAUCCUGCGAAAAG

GAUACAGGCAGCGCCUCGAGUUGUCUGAUAUCUACCAGAUUCCUUCUGUGGACUCAG

CUGACAAUUUGAGUGAGAAGCUGGAGCGGGAGUGGGAUAGAGAGCUGGCGAGCAAA

AAAAACCCCAAGCUUAUCAAUGCUCUGCGCCGCUGCUUUUUCUGGAGGUUCAUGUUU

UAUGGGAUCUUCCUGUACCUGGGGGAGGUCACCAAAGCUGUUCAGCCGCUCCUUCUU

GGCCGCAUCAUCGCCAGCUAUGACCCUGAUAAUAAAGAAGAAAGGUCUAUUGCUAUU

UAUCUGGGAAUUGGCCUCUGCUUGCUCUUCAUCGUCCGCACCCUUCUGCUGCACCCU

GCCAUUUUUGGCCUUCACCACAUCGGCAUGCAAAUGAGAAUUGCCAUGUUCUCCCUC

AUUUACAAAAAGACCCUGAAACUUUCCUCAAGAGUGUUAGAUAAAAUAUCCAUUGG

UCAGCUGGUCAGCCUGCUGUCCAACAAUCUUAACAAAUUUGAUGAAGGCUUGGCGCU

GGCCCACUUCGUGUGGAUUGCACCUCUGCAGGUGGCCCUGUUGAUGGGACUUAUAUG

GGAGCUGCUUCAAGCCUCUGCUUUCUGUGGGCUGGGCUUUUUGAUUGUACUGGCACU

UUUUCAGGCUGGGCUCGGAAGAAUGAUGAUGAAAUACAGAGAUCAGCGGGCCGGGA

AGAUUUCAGAGCGACUUGUGAUCACCAGUGAAAUGAUUGAAAAUAUUCAGAGCGUG

AAAGCCUACUGCUGGGAAGAAGCCAUGGAGAAGAUGAUUGAGAACCUGAGGCAGAC

AGAGCUCAAGCUCACUCGGAAGGCUGCUUAUGUUCGCUAUUUCAACAGCAGCGCCUU

CUUCUUCAGUGGCUUCUUUGUUGUCUUCCUGUCUGUUCUGCCAUAUGCACUGAUAAA

AGGCAUUAUUUUACGAAAGAUCUUCACCACCAUCAGUUUUUGCAUCGUUCUCAGGAU

GGCCGUCACAAGACAGUUCCCCUGGGCUGUGCAGACCUGGUACGAUUCCUUGGGGGC

CAUCAACAAGAUUCAAGAUUUCUUGCAAAAACAAGAAUAUAAAACUUUAGAAUACA

ACCUCACCACCACUGAAGUGGUCAUGGAAAAUGUGACAGCCUUUUGGGAGGAGGGU

UUUGGAGAAUUGUUCGAGAAGGCAAAGCAGAAUAACAACAACAGGAAGACGAGCAA

-continued

```
UGGGGACGACUCUCUCUUCUUCAGCAACUUUUCACUGCUCGGGACCCCUGUGUUGAA

AGAUAUAAACUUCAAGAUCGAGAGGGGCCAGCUCUUGGCUGUGGCAGGCUCCACUGG

AGCUGGUAAACAUCUCUUCUCAUGGUGAUCAUGGGGGAACUGGAGCCUUCCGAAG

GAAAAAUCAAGCACAGUGGGAGAAUCUCAUUCUGCAGCCAGUUUUCCUGGAUCAUGC

CCGGCACCAUUAAGGAAAACAUCAUAUUUGGAGUGUCCUAUGAUGAGUACCGCUACC

GGUCAGUCAUCAAAGCCUGUCAGUUGGAGGAGGACAUCUCCAAGUUUGCAGAGAAA

GACAACAUUGUGCUUGGAGAGGGGGUAUCACUCUUUCUGGAGGACAAAGAGCCAG

GAUCUCUUUGGCCCGGGCAGUCUACAAGGAUGCAGACCUCUACUUGUUGGACAGUCC

CUUCGGCUACCUCGACGUGCUGACUGAAAAGAAAUUUUUGAAAGCUGUGUGUGCA

AACUGAUGGCAAACAAGACCAGGAUUCUUGUCACCAGCAAGAUGGAACAUCUGAAG

AAAGCGGACAAAAUUCUGAUUCUGCAUGAAGGGAGCUCCUACUUCUAUGGAACAUU

UAGCGAGCUUCAGAACCUACAGCCAGACUUCUCCUCCAAAUUAAUGGGCUGUGACUC

CUUCGACCAGUUCUCUGCAGAAAGAAGAAACUCUAUACUCACAGAGACCCUCCACCG

CUUCUCCCUUGAGGGAGAUGCCCCAGUUUCUUGGACAGAAACCAAGAAGCAGUCCUU

UAAGCAGACUGGCGAGUUUGGUGAAAAGAGGAAAAAUUCAAUUCUCAAUCCAAUUA

ACAGUAUUCGCAAGUUCAGCAUUGUCCAGAAGACACCCCUCCAGAUGAAUGGCAUCG

AAGAAGAUAGUGACGAGCCGCUGGAGAGACGGCUGAGUCUGGUGCCAGAUUCAGAA

CAGGGGGAGGCCAUCCUGCCCCGGAUCAGCGUCAUUUCCACAGGCCCCACAUUACAA

GCACGGCGCCGGCAGAGUGUUUUAAAUCUCAUGACCCAUUCAGUGAACCAGGGCCAA

AAUAUCCACAGGAAGACUACAGCUUCUACCCGGAAAGUGUCUCUGGCCCCUCAGGCC

AAUCUGACCGAGCUGGACAUCUACAGCAGGAGGCUCUCCCAGGAAACAGGGCUGGAA

AUAUCUGAAGAGAUUAAUGAAGAGGAUCUUAAAGAGUGCUUCUUUGAUGACAUGGA

GAGCAUCCCCGCGGUGACCACAUGGAACACCUACCUUAGAUAUAUUACUGUCCACAA

GAGCCUCAUAUUUGUCCUCAUCUGGUGCCUGGUUAUUUCCUCGCUGAGGUGGCGGC

CAGUCUUGUUGUGCUCUGGCUGCUGGGCAACACUCCUCUCCAGGACAAGGGCAAUAG

UACUCACAGCAGAAAUAAUUCUUAUGCCGUCAUCAUUACAAGCACCUCCAGCUACUA

CGUGUUCUACAUCUAUGUGGGCGUGGCUGACACCCUCCUGGCCAUGGGUUUCUUCCG

GGGCCUGCCUUUGGUGCACACCCUCAUCACAGUGUCAAAAAUUCUGCACCAUAAAAU

GCUUCAUUCUGUCCUGCAGGCACCCAUGAGCACUUUGAACACAUUGAAGGCUGGCGG

CAUCCUCAACAGAUUUUCUAAAGAUAUUGCUAUCCUGGAUGAUCUCCUCCCCCUGAC

AAUCUUUGACUUUAUCCAGCUUCGCUGAUCGUGAUUGGAGCCAUAGCAGUGGUUG

CUGUCCUGCAGCCCUACAUUUUUGUGGCCACCGUGCCCGUGAUUGUUGCCUUUAUUA

UGCUCAGAGCUUACUUCCUGCAAACUUCUCAACAGCUCAAACAGCUAGAAUCUGAGG

GCCGGAGCCCCAUUUUUACCCACCUGGUGACUUCCCUGAAGGGACUGUGGACUCUGA

GAGCAUUCGGGCGACAGCCUUACUUUGAGACACUGUUCCACAAGGCCCUGAACUUGC

ACACUGCCAACUGGUUUCUUUACCUGAGCACACUCCGCUGGUUCCAGAUGCGGAUAG

AGAUGAUCUUCGUCAUCUUUUUUAUAGCUGUAACCUUCAUUUCUAUCCUUACAACAG

GAGAAGGAGAGGGCAGGGUGGGAAUCAUCCUCACGCUGGCUAUGAACAUAAUGUCC

ACCUUGCAGUGGGCCGUGAAUUCCAGUAUAGAUGUGGAUUCUCUAAUGAGGAGUGU

CUCCCGGGUGUUUAAAUUCAUUGAUAUGCCUACUGAGGGGAAACCCACCAAGUCAAC

AAAACCUUAUAAGAAUGGACAGCUGAGCAAGGUGAUGAUAAUUGAGAACAGCCACG
```

-continued

```
UGAAGAAGGAUGACAUUUGGCCCAGCGGGGGCCAGAUGACUGUGAAGGACCUGACG

GCCAAGUACACCGAAGGUGGAAAUGCCAUUUUGGAAAACAUCAGCUUCUCAAUCUCU

CCUGGGCAGAGAGUUGGAUUGCUGGGUCGCACGGGCAGCGGCAAAUCAACCCUGCUC

AGUGCCUUCCUUCGGCUCCUGAAUACAGAAGGCGAAAUCCAAAUUGACGGGGUGAGC

UGGGACAGCAUCACCCUGCAGCAGUGGAGAAAAGCAUUUGGGGUCAUUCCACAGAAA

GUUUUCAUCUUCUCUGGCACUUUCAGAAAGAACCUGGACCCCUAUGAGCAGUGGAGC

GACCAGGAGAUCUGGAAGGUUGCAGAUGAAGUUGGCCUGCGGAGUGUGAUAGAACA

AUUUCCUGGCAAGCUGGAUUUUGUGCUGGUAGAUGGAGGCUGCGUGCUGUCCCACG

GCCACAAACAGCUGAUGUGCCUCGCCCGCUCCGUUCUUUCAAAGGCCAAAAUCUUGC

UUUUGGAUGAGCCCAGUGCUCACCUUGACCCAGUGACCUAUCAGAUAAUCCGCAGGA

CCUUAAAGCAAGCUUUUGCCGACUGCACCGUCAUACUGUGUGAGCACCGGAUUGAAG

CAAUGCUGGAAUGCCAGCAGUUUCUGGUGAUCGAGGAGAAUAAGGUCCGGCAGUAC

GACAGCAUCCAGAAGUUGUUGAAUGAGCGCAGCCUUUUCCGCCAGGCCAUCUCCCCA

UCUGACAGAGUCAAGCUGUUUCCACAUAGGAACUCCUCUAAGUGCAAGUCCAAGCCC

CAGAUCGCUGCCCUCAAGGAGGAAACUGAGGAAGAGGUGCAGGAUACCCGCCUGUGA

CGGGUGGCAUCCCUGUGACCCCUCCCCAGUGCCUCUCCUGGCCCUGGAAGUUGCCAC

UCCAGUGCCCACCAGCCUUGUCCUAAUAAAAUUAAGUUGCAUCAAGCU
```

TABLE C mRNA Structural Elements

| Structural Element | Description | Sequence Coordinates |
|---|---|---|
| Cap Structure | [chemical structure diagram] | 7 mG is attached to the nucleotide in position 1 of the CFTR mRNA where the first nucleotide (underlined) is methylated at the 2' position |
| 5' UTR | GGAC...CACG | 1-140 |
| Start Codon hCFTR | AUG (Bold) | 141-143 |
| Stop Codon hCFTR | UGA (Bold) | 4581-4583 |
| 3' UTR | CGGG...AGCU | 4584-4688 |
| Poly A tail | $(A)_x$, x = 200-1000* | 4689-ff |

Modified mRNA

A CFTR mRNA may contain only naturally-occurring nucleotides (or unmodified nucleotides). In some embodiments, however, a suitable CFTR mRNA may contain backbone modifications, sugar modifications and/or base modifications. For example, modified nucleotides may include, but not be limited to, modified purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g., from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs (e.g., mRNAs encoding CFTR) may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g., cytidine 5'-O-(1-thiophosphate)), boranophosphates, positively charged guanidinium groups etc., which means by replacing the phosphodiester linkage by other anionic, cationic or neutral groups.

In some embodiments, mRNAs (e.g., mRNAs encoding CFTR) may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In a specific embodiment of the invention, mRNAs encoding CFTR are unmodified.

Delivery Vehicles

According to the present invention, mRNA encoding a CFTR protein (e.g., a full length, fragment, or portion of a CFTR protein) as described herein may be delivered as naked mRNA (unpackaged) or via delivery vehicles. As used herein, the terms "delivery vehicle," "transfer vehicle," "nanoparticle" or grammatical equivalent, are used interchangeably.

Delivery vehicles can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition. A particular delivery vehicle is selected based upon its ability to facilitate the transfection of a nucleic acid to a target cell.

According to various embodiments, suitable delivery vehicles include, but are not limited to polymer based carriers, such as polyethyleneimine (PEI), lipid nanoparticles (LNPs) and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

Liposomal Delivery Vehicles

In some embodiments, a suitable delivery vehicle is a liposomal delivery vehicle, e.g., a lipid nanoparticle (LNP) or liposome. In some embodiments, liposomes may comprise one or more cationic lipids. In some embodiments, a liposome comprises one or more cationic lipids, one or more non-cationic lipids, one or more cholesterol-based lipids and one or more PEG-modified lipids. In some embodiments, a liposome comprises one or more cationic lipids, one or more non-cationic lipids, and one or more PEG-modified lipids. In some embodiments, a liposome comprises no more than four distinct lipid components. In some embodiments, a liposome comprises no more than three distinct lipid components. In some embodiments, one distinct lipid component is a sterol-based cationic lipid.

As used herein, the phrase "cationic lipid" refers to any of a number of lipid species that have a net positive charge at a selected pH, such as physiological pH. Several cationic lipids have been described in the literature, many of which are commercially available. An example of suitable cationic lipids for use in the compositions and methods of the invention include those described in international patent publications WO 2010/053572 (for example, C12-200 described at paragraph [00225]) and WO 2012/170930, both of which are incorporated herein by reference. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g., (15Z, 18Z)-N,N-dimethyl-6-(9Z, 12Z)-octadeca-9, 12-dien-1-yl)tetracosa-15,18-dien-1-amine (HGT5000), (15Z, 18Z)-N,N-dimethyl-6-((9Z, 12Z)-octadeca-9, 12-dien-1-yl)tetracosa-4,15,18-trien-1-amine (HGT5001), and (15Z,18Z)-N,N-dimethyl-6-((9Z, 12Z)-octadeca-9, 12-dien-1-yl)tetracosa-5, 15, 18-trien-1-amine (HGT5002).

In some embodiments, provided liposomes include a cationic lipid described in international patent publications WO 2013/063468 and WO 2015/061467 both of which are incorporated by reference herein.

In particular embodiments, provided liposomes include a cationic lipid cKK-E12, or (3,6-bis(4-(bis(2-hydroxydodecyl)amino)butyl)piperazine-2,5-dione, OF-00, OF-01, OF-02, or OF-03 (see, e.g., Fenton, Owen S., et al. "Bioinspired Alkenyl Amino Alcohol Ionizable Lipid Materials for Highly Potent In Vivo mRNA Delivery." Advanced materials (2016)).

In some embodiments, suitable cationic lipids may be N-[1-(2,3-dioleyloxy)propyl]-N,N,N-trimethylammonium chloride or "DOTMA" (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP".

Additional exemplary cationic lipids also include 1,2-di stearyloxy-N,N-dimethyl-3-aminopropane or "DSDMA", 1,2-dioleyloxy-N,N-dimethyl-3-aminopropane or "DODMA," 1,2-dilinoleyloxy-N,N-dimethyl-3-aminopropane or "DLinDMA," 1,2-dilinolenyloxy-N,N-dimethyl-3-aminopropane or "DLenDMA," N-dioleyl-N,N-dimethyl-ammonium chloride or "DODAC," N,N-di stearyl-N,N-dimethylarnrnonium bromide or "DDAB," N-(1,2-dimyristyloxyprop-3-yl)-N,N-dimethyl-N-hydroxyethyl ammonium bromide or "DMRIE," 3-dimethylamino-2-(cholest-5-en-3-beta-oxybutan-4-oxy)-1-(cis,cis-9,12-octadecadienoxy)propane or "CLinDMA," 2-[5'-(cholest-5-en-3-beta-oxy)-3'-oxapentoxy)-3-dimethy 1-1-(cis,cis-9', 1-2'-octadecadienoxy)propane or "CpLinDMA," N,N-dimethyl-3,4-dioleyloxybenzylamine or"DMOBA," 1,2-N,N'-dioleylcarbamyl-3-dimethylaminopropane or "DOcarbDAP," 2,3-Dilinoleoyloxy-N,N-dimethylpropylamine or "DLinDAP,"1,2-N,N'-Dilinoleylcarbamyl-3-dimethylaminopropane or "DLincarbDAP," 1,2-Dilinoleoyl-carbamyl-3-dimethylaminopropane or "DLinCDAP," 2,2-dilinoleyl-4-dimethylaminomethyl-[1,3]-dioxolane or "DLinDMA," 2,2-dilinoleyl-4-dimethylaminoethyl-[1,3]-dioxolane or "DLin-K-XTC2-DMA," and 2-(2,2-di((9Z, 12Z)-octadeca-9,1 2-dien-1-yl)-1,3-dioxolan-4-yl)-N,N-dimethylethanamine (DLin-KC2-DMA)) (See WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, the one or more cationic lipids may be chosen from XTC (2,2-Dilinoleyl-4-dimethylaminoethyl-[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6aS)-N,N-dimethyl-2,2-di((9Z, 12Z)-octadeca-9,12-dienyl)tetrahydro-3aH-cyclopenta[d] [1,3]dioxol-5-amine)), NC98-5 (4,7,13-tris(3-oxo-3-(undecylamino)propyl)-N1,N16-diundecyl-4,7,10,13-tetraazahexadecane-1,16-diamide), HGT4003 (WO 2012/170889, the teachings of which are incorporated herein by reference in their entirety), ICE (WO 2011/068810, the teachings of which are incorporated herein by reference in their entirety), and aminoalcohol lipidoids such as those disclosed in WO2010/053572.

In some embodiments, sterol-based cationic lipids may be use instead or in addition to cationic lipids described herein. Suitable sterol-based cationic lipids are dialkylamino-, imidazole-, and guanidinium-containing sterol-based cationic lipids. For example, certain embodiments are directed to a composition comprising one or more sterol-based cationic lipids comprising an imidazole, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta [a]phenanthren-3-yl 3-(1H-imidazol-4-yl)propanoate, as represented by structure (I) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta [a]phenanthren-3-yl 3-(1H-imidazol-4-yl)propanoate, as represented by structure (I).

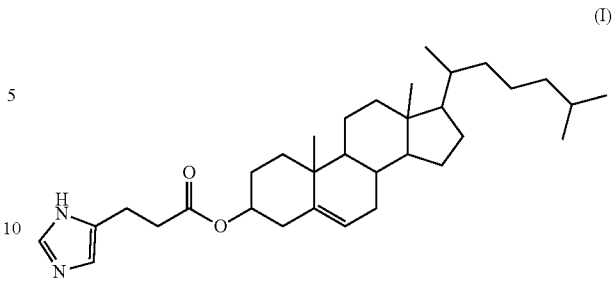

(I)

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., ICE lipid) constitutes about 30%, about 35%, about 40%, about 45%, or about 50% of the liposome by molar ratio.

As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other lipids, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Suitable cholesterol-based cationic lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744, 335), or ICE. In some embodiments, the cholesterol-based lipid may comprise a molar ration of about 2% to about 30%, or about 5% to about 20% of the total lipid present in a liposome. In some embodiments, the percentage of cholesterol-based lipid in the lipid nanoparticle may be greater than 5%, greater than 10%, greater than 20%, greater than 30%, or greater than 40%.

The use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipid formulations together which comprise the transfer vehicle (e.g., a lipid nanoparticle). Contemplated PEG-modified lipids include, but are not limited to, a polyethylene glycol chain of up to S kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in the liposomal transfer vehicle.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus, the molar ratios may be adjusted accordingly.

In some embodiments, a suitable delivery vehicle is formulated using a polymer as a carrier, alone or in combination with other carriers including various lipids described herein. Thus, in some embodiments, liposomal delivery vehicles, as used herein, also encompass nanoparticles comprising polymers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

A suitable liposome for the present invention may include one or more of any of the cationic lipids, non-cationic lipids, cholesterol lipids, PEG-modified lipids and/or polymers described herein at various ratios. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; ICE, DOPE, cholesterol and DMG-PEG2K; or ICE, DOPE, and DMG-PEG2K.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEG-modified lipid(s) may be between about 30-60:25-35:20-30:1-15, respectively. In some embodiments, the ratio of cationic lipid(s) to non-cationic lipid(s) to cholesterol-based lipid(s) to PEG-modified lipid(s) is approximately 40:30:20:10, respectively. In some embodiments, the ratio of cationic lipid(s) to non-cationic lipid(s) to cholesterol-based lipid(s) to PEG-modified lipid(s) is approximately 40:30:25:5, respectively. In some embodiments, the ratio of cationic lipid(s) to non-cationic lipid(s) to cholesterol-based lipid(s) to PEG-modified lipid(s) is approximately 40:32:25:3, respectively. In some embodiments, the ratio of cationic lipid(s) to non-cationic lipid(s) to cholesterol-based lipid(s) to PEG-modified lipid(s) is approximately 50:25:20:5. In some embodiments, the ratio of sterol lipid(s) to non-cationic lipid(s) to PEG-modified lipid(s) is 50:45:5. In some embodiments, the ratio of sterol lipid(s) to non-cationic lipid(s) to PEG-modified lipid(s) is 50:40:10. In some embodiments, the ratio of sterol lipid(s) to non-cationic lipid(s) to PEG-modified lipid(s) is 55:40:5. In some embodiments, the ratio of sterol lipid(s) to non-cationic lipid(s) to PEG-modified lipid(s) is 55:35:10. In some embodiments, the ratio of sterol lipid(s) to non-cationic lipid(s) to PEG-modified lipid(s) is 60:35:5. In some embodiments, the ratio of sterol lipid(s) to non-cationic lipid(s) to PEG-modified lipid(s) is 60:30:10.

In some embodiments, the nominal nitrogen/phosphorus (N/P) charge ratio which refers to the positively charged nitrogens in the cationic lipid and the negatively charged phosphodiester linkages within mRNA is about between 1 and 10. In some embodiments, the N/P is about 1. In some embodiments, the N/P is about 2. In some embodiments, the N/P is about 3. In some embodiments, the N/P is about 4. In some embodiments, the N/P is about 5. In some embodiments, the N/P is about 6. In some embodiments, the N/P is about 7. In some embodiments, the N/P is about 8. In some embodiments, the N/P is about 9. In some embodiments, the N/P is about 10.

A liposome comprising ICE, DOPE, and DMG-PEG2K is particularly suitable for use with the present invention. In some embodiments, a suitable liposome for the present invention comprises ICE and DOPE at an ICE:DOPE molar ratio of >1:1. In some embodiments, the ICE:DOPE molar ratio is <2.5:1. In some embodiments, the ICE:DOPE molar ratio is between 1:1 and 2.5:1. In some embodiments, the ICE:DOPE molar ratio is approximately 1.5:1. In some embodiments, the ICE:DOPE molar ratio is approximately 1.7:1. In some embodiments, the ICE:DOPE molar ratio is approximately 2:1. In some embodiments, a suitable liposome for the present invention comprises ICE and DMG-PEG-2K at an ICE:DMG-PEG-2K molar ratio of >10:1. In some embodiments, the ICE:DMG-PEG-2K molar ratio is <16:1. In some embodiments, the ICE:DMG-PEG-2K molar ratio is approximately 12:1. In some embodiments, the ICE:DMG-PEG-2K molar ratio is approximately 14:1. In some embodiments, a suitable liposome for the present invention comprises DOPE and DMG-PEG-2K at a DOPE:DMG-PEG-2K molar ratio of >5:1. In some embodiments, the DOPE: DMG-PEG-2K molar ratio is <11:1. In some embodiments, the DOPE: DMG-PEG-2K molar ratio is approximately 7:1. In some embodiments, the DOPE: DMG-PEG-2K molar ratio is approximately 10:1. In some embodiments, a suitable liposome for the present invention comprises ICE, DOPE and DMG-PEG-2K at a molar ratio of 50%-60% ICE, 30%-40% DOPE and 5%-10% DMG-PEG-2K. In some embodiments, a suitable liposome for the present invention comprises ICE, DOPE and DMG-PEG-2K at an ICE:DOPE:DMG-PEG-2K molar ratio of 50:45:5. In some embodiments, a suitable liposome for the present invention comprises ICE, DOPE and DMG-PEG-2K at an ICE:DOPE:DMG-PEG-2K molar ratio of 50:40:10. In some embodiments, a suitable liposome for the present invention comprises ICE, DOPE and DMG-PEG-2K at an ICE:DOPE:DMG-PEG-2K molar ratio of 55:40:5. In some embodiments, a suitable liposome for the present invention comprises ICE, DOPE and DMG-PEG-2K at an ICE:DOPE:DMG-PEG-2K molar ratio of 55:35:10. In some embodiments, a suitable liposome for the present invention comprises ICE, DOPE and DMG-PEG-2K at an ICE:DOPE:DMG-PEG-2K molar ratio of 60:35:5. In some embodiments, a suitable liposome for the present invention comprises ICE, DOPE and DMG-PEG-2K at an ICE:DOPE:DMG-PEG-2K molar ratio of 60:30:10.

The liposomal transfer vehicles for use in the compositions of the invention can be prepared by various techniques which are presently known in the art. Various methods are described in published U.S. Application No. US 2011/0244026, published U.S. Application No. US 2016/0038432 and provisional U.S. Application No. 62/580,155, filed Nov. 1, 2017 and can be used to practice the present invention, all of which are incorporated herein by reference.

Briefly, the process of preparing improved CFTR-mRNA lipid liposomes includes a step of heating one or more of the solutions (i.e., applying heat from a heat source to the solution) to a temperature (or to maintain at a temperature) greater than ambient temperature, the one more solutions being the solution comprising the pre-formed lipid nanoparticles, the solution comprising the mRNA and the mixed solution comprising the lipid nanoparticle encapsulated mRNA. In some embodiments, the process includes the step of heating one or both of the mRNA solution and the pre-formed lipid nanoparticle solution, prior to the mixing step. In some embodiments, the process includes heating one or more one or more of the solution comprising the pre-formed lipid nanoparticles, the solution comprising the mRNA and the solution comprising the lipid nanoparticle encapsulated mRNA, during the mixing step. In some embodiments, the process includes the step of heating the lipid nanoparticle encapsulated mRNA, after the mixing step. In some embodiments, the temperature to which one or more of the solutions is heated (or at which one or more of the solutions is maintained) is or is greater than about 30° C., 37° C., 40° C., 45° C., 50° C., 55° C., 60° C., 65° C., or 70° C. In some embodiments, the temperature to which one or more of the solutions is heated ranges from about 25-70° C., about 30-70° C., about 35-70° C., about 40-70° C., about 45-70° C., about 50-70° C., or about 60-70° C. In some embodiments, the temperature greater than ambient temperature to which one or more of the solutions is heated is about 65° C.

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating cystic fibrosis). For example, a therapeutically effective amount may be an amount sufficient to achieve a desired therapeutic and/or prophylactic effect.

In some embodiments, the composition comprising an mRNA encoding CFTR comprises mRNA at a concentration of at least 0.1 mg/mL. In some embodiments, the composition comprising an mRNA encoding CFTR comprises mRNA at a concentration of at least 0.2 mg/mL. In some embodiments, the composition comprising an mRNA encoding CFTR comprises mRNA at a concentration of at least 0.3 mg/mL. In some embodiments, the composition comprising an mRNA encoding CFTR comprises mRNA at a concentration of at least 0.4 mg/mL. In some embodiments, the mRNA encoding a CFTR protein is at a concentration of at least 0.5 mg/mL. In some embodiments, the mRNA encoding a CFTR protein is at a concentration of at least 0.6 mg/mL. In some embodiments, the mRNA encoding a CFTR protein is at a concentration of at least 0.7 mg/mL. In some embodiments, the mRNA encoding a CFTR protein is at a concentration of at least 0.8 mg/mL. In some embodiments, the mRNA encoding a CFTR protein is at a concentration of at least 0.9 mg/mL. In some embodiments, the mRNA encoding a CFTR protein is at a concentration of at least 1.0 mg/mL. In some embodiments, the mRNA encoding a CFTR protein is at a concentration of at least 2.0 mg/mL. In some embodiments, the mRNA encoding a CFTR protein is at a concentration of at least 3.0 mg/mL. In some embodiments, the mRNA encoding a CFTR protein is at a concentration of at least 4.0 mg/mL. In some embodiments, the mRNA encoding a CFTR protein is at a concentration of at least 5.0 mg/mL. In some embodiments, the mRNA encoding a CFTR protein is at a concentration of at least 6.0 mg/mL. In some embodiments, the mRNA encoding a CFTR protein is at a concentration of at least 7.0 mg/mL. In some embodiments, the mRNA encoding a CFTR protein is at a concentration of at least 8.0 mg/mL. In some embodiments, the mRNA encoding a CFTR protein is at a concentration of at least 9.0 mg/mL. In some embodiments, the mRNA encoding a CFTR protein is at a concentration of at least 10.0 mg/mL. In some embodiments, the mRNA encoding a CFTR protein is at a concentration ranging from 0.1 mg/mL to 10.0 mg/mL. Typically, the mRNA encoding a CFTR protein is at a concentration ranging from 0.5 mg/mL to 0.8 mg/mL, e.g., 0.6 mg/mL.

In some embodiments, the composition comprising an mRNA encoding CFTR is formulated with a diluent. In some embodiments, the diluent is selected from a group consisting of DMSO, ethylene glycol, glycerol, 2-Methyl-2,4-pentanediol (MPD), propylene glycol, sucrose, and trehalose. In some embodiments, the formulation comprises 1%, 2%, 3%, 4%, 5%, 6%, 7%, 8%, 9%, 10%, 11%, 12%, 13%, 14%, 15%, 16%, 17%, 18%, 19% or 20% diluent.

Trehalose as a diluent has been shown to be particularly effective in providing a stable composition comprising liposome-encapsulated mRNA encoding CFTR. A suitable trehalose concentration is between about 5% and about 15% (w/v), e.g., about 10% (w/v).

Lyophilization

The liposomal CFTR mRNA compositions of the invention may be provided in form of a dry powder. In some embodiments, CFTR mRNA dry powder is formed by lyophilization of the mRNA-lipid complex. Applicant hereby fully incorporates by reference their earlier patent application U.S. Ser. No. 14/124,615 filed on Jun. 8, 2012, which was granted a U.S. Pat. No. 9,717,690 on 8 Jan. 2017.

The lyophilized dry powder is suitable for long term storage. It can be reconstituted with purified water for administration to a subject in need thereof. In certain embodiments, upon reconstitution with an appropriate rehydration media (e.g., purified water, deionized water, 5% dextrose (w/v), 10% trehalose (w/v) and/or normal saline, the reconstituted composition demonstrates pharmacological or biological activity comparable with that observed prior to lyophilization. For example, in certain embodiments, the pharmacological and biological activity of an encapsulated polynucleotide is equivalent to that observed prior to lyophilization of the composition; or alternatively demonstrates a negligible reduction in pharmacological and biological activity (e.g., less than about a 1%, 2%, 2.5%, 3%, 4%, 5%, 6%, 7%, 8% 9% or 10% reduction in the biological or pharmacological activity of an encapsulated polynucleotide).

In certain embodiments, the pharmaceutical compositions comprising lyophilized nanoparticles or liposomal delivery vehicles are characterized as being stable (e.g., as stable as pharmaceutical compositions comprising an equivalent unlyophilized vehicles). Lyophilization of the lipid nanoparticles does not appreciably change or alter the particle size of the lipid nanoparticles following lyophilizaiton and/or reconstitution. For example, disclosed herein are pharmaceutical compositions comprising lyophilized lipid delivery vehicles, wherein upon reconstitution (e.g., with purified water) the lipid nanoparticles do not flocculate or aggregate, or alternatively demonstrated limited or negligible flocculation or aggregation (e.g., as determined by the particle size of the reconstituted lipid nanoparticles).

Accordingly, in certain embodiments, upon reconstitution of a lyophilized lipid nanoparticle the lipid nanoparticles have a $Dv_{50}$ of less than about 500 nm (e.g., less than about 300 nm, 200 nm, 150 nm, 125 nm, 120 nm, 100 nm, 75 nm, 50 nm, 25 nm, or smaller). Similarly, in certain embodiments, upon reconstitution of a lyophilized lipid nanoparticle the lipid nanoparticles have a $Dv_{90}$ of less than about 750 nm (e.g., less than about 700 nm, 500 nm, 300 nm, 200 nm, 150 nm, 125 nm, 100 nm, 75 nm, 50 nm, 25 nm, or smaller).

In other embodiments, the pharmaceutical compositions comprising lyophilized lipid delivery vehicles are characterized as having a polydispersion index of less than about 1 (e.g., less than 0.95, 0.9, 0.8, 0.75, 0.7, 0.6, 0.5, 0.4, 0.3, 0.25, 0.2, 0.1, 0.05, or less). In some embodiments, the pharmaceutical compositions comprising lyophilized lipid delivery vehicles demonstrate a reduced tendency to flocculate or otherwise aggregate (e.g., during lyophilization or upon reconstitution). For example, upon reconstitution the lipid delivery vehicles may have an average particle size (Zave) of less than 500 nm (e.g., less than about 400 nm, 300 nm, 200 nm, 175 nm, 150 nm, 125 nm, 100 nm, 75 nm, 50 nm, 25 nm, or smaller in a PBS solution). Typically, the average particle size (Iave) of lipid delivery vehicles for use with the invention is between 40 nm and 60 nm.

In some embodiments, the lyophilized lipid delivery vehicles (e.g., lyophilized lipid nanoparticles) further comprise or are alternatively prepared using one or more lyoprotectants (e.g., sugars and/or carbohydrates). In certain embodiments, the inclusion of one or more lyoprotectants in the lipid nanoparticle may improve or otherwise enhance the stability of the lyophilized lipid delivery vehicles (e.g., under normal storage conditions) and/or facilitate reconstitution of the lyophilized lipid delivery vehicles using a rehydration media, thereby preparing an aqueous formulation. For example, in certain embodiments the lipid nanoparticles are prepared and prior to lyophilization the buffer present in the liposomal formulation may be replaced (e.g., via centrifugation) with a lyoprotectant such as a sucrose solution or suspension (e.g., an aqueous solution comprising between about 1-50% (w/v) or 10-25% (w/v) sucrose). In some embodiments, the lyoprotectant in trehalose. In some embodiments, the lyoprotectant comprises 10-50% (w/v), or 10-25% (w/v) or 10-20% (w/v) or 10-15% (w/v) trehalose. Other lyoprotectants that may be used to prepare the lyophilized compositions described herein include, for example, dextran (e.g., 1.5 kDa, 5 kDa and/or 40 kDa) and inulin (e.g., 1.8 kDa and/or 4 kDa). The lyophilized lipid delivery vehicles have an encapsulation efficiency of greater than about 80%.

A pharmaceutical composition comprising a lyophilized lipid nanoparticle comprising CFTR-encoding mRNA is stable at 4° C. for at least 1 month, at least 2 months, at least 3 months, at least 4 months, at least 5 months, at least 6 months, or for at least 1 year. In some embodiments, the lyophilized lipid delivery vehicles may be stored under refrigeration and remain stable (e.g., as demonstrated by minimal or no losses in their intended pharmaceutical or biological activity) for extended periods of time (e.g., stable for at least about 1, 2, 3, 4, 5, 6, 9, 12, 18, 24, 36 months or longer upon storage at about 4° C.). In other embodiments, the lyophilized lipid delivery vehicles may be stored without refrigeration and remain stable for extended periods of time (e.g., stable for at least about 1, 2, 3, 4, 5, 6, 9, 12, 18, 24, 36 months or longer upon storage at about 25° C.).

The pharmaceutical composition in lyophilized form can be stored in frozen condition for 1, 2, 3, 4, 5 or 10 years without loss of pharmacological or biological activity.

Accordingly, also provided herein are methods for treating disease in a subject by administering an effective amount of pharmaceutical compositions comprising lyophilized CFTR mRNA-lipid delivery vehicles to a subject (e.g., upon reconstitution with a rehydrating media such as sterile water for injection).

In some embodiments, the formulation is administered by a metered-dose inhaler.

In some embodiments, the formulation is administered by a nebulizer.

Suitable CFTR mRNA formulation for nebulization may be stored as a frozen liquid, or sterile liquid, or lyophilized or dry powder and reconstituted prior to nebulization. In some embodiments, the composition is stored in a single-use vial prior to nebulization. In some embodiments, the single-use vial comprises 50 mL or less of the composition. In some embodiments, the single-use vial comprises 40 mL or less of the composition. In some embodiments, the single-use vial comprises 30 mL or less of the composition. In some embodiments, the single-use vial comprises 20 mL or less of the composition. In some embodiments, the single-use vial comprises 10 mL or less of the composition. In some embodiments, the single-use vial comprises 9.0 mL or less of the composition. In some embodiments, the single-use vial comprises 8.0 mL or less of the composition. In some embodiments, the single-use vial comprises 7.0 mL or less of the composition. In some embodiments, the single-use vial comprises 6.0 mL or less of the composition. In some embodiments, the single-use vial comprises 5.0 mL or less of the composition. In some embodiments, the single-use vial comprises between 4.0 mL and 5.0 mL of the composition. More typically, the single-use vial comprises between 3.0 and 4.0 mL of the composition. In a specific embodiment, the single-use vial comprises 3.2 mL of the composition.

Exemplary Formulations
Compositions Comprising SEQ ID NO: 28
In embodiments, a composition comprises:
a. an mRNA encoding the CFTR protein, wherein the mRNA comprises:
  i. the sequence as set out in SEQ ID NO: 28;
  ii. a 5' cap structure, wherein the 5' cap structure is

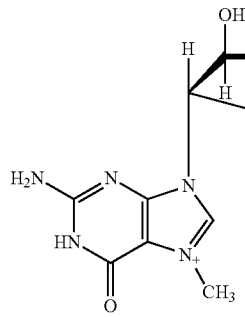
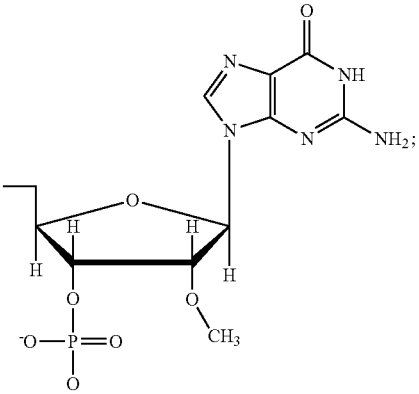

("m7G(5')ppp(5')(2'OMeG)")

and
  iii. a poly A tail of between 200 and 1000 adenosine nucleotides;
b. imidazole cholesterol ester (ICE);
c. 1,2-dioleoyl-SN-glycero-3-phosphoethanolamine (DOPE)
d. 1,2-dimyristoyl-rac-glycero-3-methylpolyoxyethylene (DMG-PEG-2K); and
e. trehalose.

In embodiments, the mRNA of SEQ ID NO: 28 has an average molecular weight of about 1.63 megadaltons. In embodiments, the 5' UTR, hCFTR start codon, hCFTR stop codon, and 3' UTR of the mRNA of SEQ ID NO: 28 are as set forth in Table A. In embodiments, the concentration of mRNA is about 0.6 mg/mL.

In embodiments, the nitrogen/phosphorus (N/P) ratio (i.e., the ratio of positively-charged nitrogens within ICE and the negatively charged phosphodiester lipids with the mRNA) is about 4. In embodiments, the average particle size range for the LNP formulation is about 40-60 nm.

Exemplary compositions comprising the mRNA of SEQ ID NO: 28 also include those described in Table D.

TABLE D

Exemplary Formulations of SEQ ID NO: 28

| CFTR mRNA | Formulation 1 SEQ ID NO: 28 | Formulation 2 SEQ ID NO: 28 | Formulation 3 SEQ ID NO: 28 | Formulation 4 SEQ ID NO: 28 |
|---|---|---|---|---|
| 5' Cap | m7G(5')ppp(5')(2'OMeG) | m7G(5')ppp(5')(2'OMeG) | m7G(5')ppp(5')(2'OMeG) | m7G(5')ppp(5')(2'OMeG) |
| 5' UTR | as described in Table A | as described in Table A | as described in Table A | as described in Table A |
| Start Codon hCFTR | AUG | AUG | AUG | AUG |
| Stop Codon hCFTR | UAA | UAA | UAA | UAA |
| 3'UTR | as described in Table A | as described in Table A | as described in Table A | as described in Table A |
| PolyA Tail | 200-1000 adenosine nucleotides | 200-1000 adenosine nucleotides | 200-1000 adenosine nucleotides | 200-1000 adenosine nucleotides |
| ICE:DOPE: DMG-PEG-2K | 60:35:5 | 60:30:10 | 60:35:5 | 60:35:5 |
| Diluent | 10% trehalose | 10% trehalose | 10% sucrose | 10% glucose |

TABLE D -continued

Exemplary Formulations of SEQ ID NO: 28

| CFTR mRNA | Formulation 1 SEQ ID NO: 28 | Formulation 2 SEQ ID NO: 28 | Formulation 3 SEQ ID NO: 28 | Formulation 4 SEQ ID NO: 28 |
|---|---|---|---|---|
| Average particle size | 40-60 nM | 40-60 nM | 40-60 nM | 40-60 nM |
| N/P charge ratio | 4 | 4 | 4 | 4 |

In embodiments, a formulation is Formulation 1. In embodiments, Formulation 1 is further characterized by a concentration of the mRNA that is about 0.6 mg/ml.

In embodiments, a formulation is Formulation 2. In embodiments, Formulation 2 is further characterized by a concentration of the mRNA that is about 0.6 mg/ml.

In embodiments, a formulation is Formulation 3. In embodiments, Formulation 3 is further characterized by a concentration of the mRNA that is about 0.6 mg/ml.

In embodiments, a formulation is Formulation 4. In embodiments, Formulation 4 is further characterized by a concentration of the mRNA that is about 0.6 mg/ml.

Compositions Comprising SEQ ID NO: 29

In embodiments, a composition comprises:
a. an mRNA encoding the CFTR protein, wherein the mRNA comprises:
  i. the sequence as set out in SEQ ID NO: 29;
  ii. a 5' cap structure, wherein the 5' cap structure is

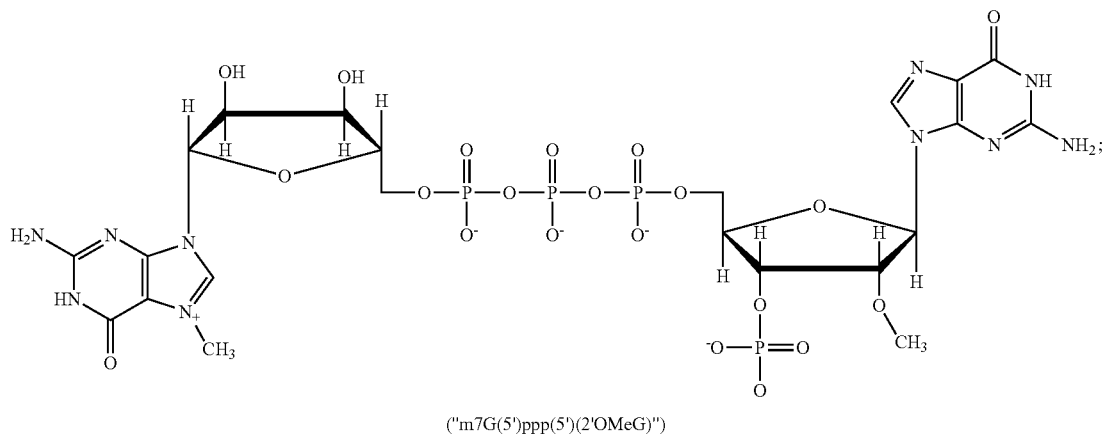

("m7G(5')ppp(5')(2'OMeG)")

and
  iii. a poly A tail of between 200 and 1000 adenosine nucleotides;
b. imidazole cholesterol ester (ICE);
c. 1,2-dioleoyl-SN-glycero-3-phosphoethanolamine (DOPE)
d. 1,2-dimyristoyl-rac-glycero-3-methylpolyoxyethylene (DMG-PEG-2K); and
e. trehalose.

In embodiments, the mRNA of SEQ ID NO: 29 has an average molecular weight of about 1.63 megadaltons. In embodiments, the 5' UTR, hCFTR start codon, hCFTR stop codon, and 3' UTR of the mRNA of SEQ ID NO: 29 are as set forth in Table B. In embodiments, the concentration of mRNA is about 0.6 mg/mL.

In embodiments, the nitrogen/phosphorus (N/P) ratio (i.e., the ratio of positively-charged nitrogens within ICE and the negatively charged phosphodiester lipids with the mRNA) is about 4. In embodiments, the average particle size range for the LNP formulation is about 40-60 nm.

Exemplary compositions comprising the mRNA of SEQ ID NO: 29 also include those described in Table E.

In embodiments, a formulation is Formulation 7. In embodiments, Formulation 7 is further characterized by a concentration of the mRNA that is about 0.6 mg/ml.

In embodiments, a formulation is Formulation 8. In embodiments, Formulation 8 is further characterized by a concentration of the mRNA that is about 0.6 mg/ml.

TABLE E

Exemplary Formulations of SEQ ID NO: 29

| CFTR mRNA | Formulation 5 SEQ ID NO: 29 | Formulation 6 SEQ ID NO: 29 | Formulation 7 SEQ ID NO: 29 | Formulation 8 SEQ ID NO: 29 |
|---|---|---|---|---|
| 5' Cap | m7G(5')ppp(5') (2'OMeG) | m7G(5')ppp(5') (2'OMeG) | m7G(5')ppp(5') (2'OMeG) | m7G(5')ppp(5') (2'OMeG) |
| 5' UTR | as described in Table B | as described in Table B | as described in Table B | as described in Table B |
| Start Codon hCFTR | AUG | AUG | AUG | AUG |
| Stop Codon hCFTR | UAA | UAA | UAA | UAA |
| 3'UTR | as described in Table B | as described in Table B | as described in Table B | as described in |
| PolyA Tail | ~200-1000 adenosine nucleotides | ~200-1000 adenosine nucleotides | ~200-1000 adenosine nucleotides | ~200-1000 adenosine nucleotides |
| ICE:DOPE: DMG-PEG-2K | 60:30:10 | 60:35:5 | 60:35:5 | 60:35:5 |
| Diluent | 10% trehalose | 10% trehalose | 10% sucrose | 10% glucose |
| Average particle size | 40-60 nM | 40-60 nM | 40-60 nM | 40-60 nM |
| N/P charge ratio | 4 | 4 | 4 | 4 |

In embodiments, a formulation is Formulation 5. In embodiments, Formulation 5 is further characterized by a concentration of the mRNA that is about 0.6 mg/ml.

In embodiments, a formulation is Formulation 6. In embodiments, Formulation 6 is further characterized by a concentration of the mRNA that is about 0.6 mg/ml.

Compositions Comprising SEQ ID NO: 30

In embodiments, a composition comprises:
a. an mRNA encoding the CFTR protein, wherein the mRNA comprises:
  i. the sequence as set out in SEQ ID NO: 30;
  ii. a 5' cap structure, wherein the 5' cap structure is

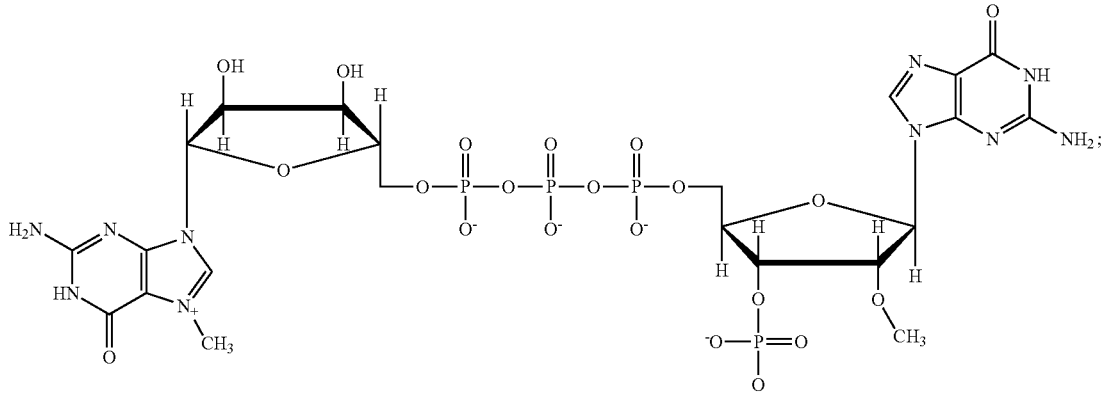

("m7G(5')ppp(5')(2'OMeG)")

and
  iii. a poly A tail of between 200 and 1000 adenosine nucleotides;
  b. imidazole cholesterol ester (ICE);
  c. 1,2-dioleoyl-SN-glycero-3-phosphoethanolamine (DOPE)
  d. 1,2-dimyristoyl-rac-glycero-3-methylpolyoxyethylene (DMG-PEG-2K); and
  e. trehalose.

In embodiments, the mRNA of SEQ ID NO: 30 has an average molecular weight of about 1.63 megadaltons. In embodiments, the 5' UTR, hCFTR start codon, hCFTR stop codon, and 3' UTR of the mRNA of SEQ ID NO: 30 are as set forth in Table C. In embodiments, the concentration of mRNA is about 0.6 mg/mL.

In embodiments, the nitrogen/phosphorus (N/P) ratio (i.e., the ratio of positively-charged nitrogens within ICE and the negatively charged phosphodiester lipids with the mRNA) is about 4. In embodiments, the average particle size range for the LNP formulation is about 40-60 nm.

Exemplary compositions comprising the mRNA of SEQ ID NO: 30 also include those described in Table F.

Assessment of Formulation Characteristics

The formulation may be assessed for one or more of the following characteristics: appearance, identity, quantity, concentration, presence of impurities, microbiological assessment, pH level and activity.

In some embodiments, acceptable appearance of the formulation includes a clear, colorless solution, essentially free of visible particulates.

In some embodiments, the identity of the CFTR mRNA is assessed by sequencing methods. The sequencing methods are performed to confirm the correct sequence of the desired CFTR mRNA.

In some embodiments, the concentration of the CFTR mRNA is assessed by a suitable method, such as UV spectrophotometry. In some embodiments, a suitable concentration is between about 90% and 110% nominal (0.9-1.1 mg/mL). Accordingly, in some embodiments, a suitable concentration is about 90% nominal (0.9 mg/mL). In some embodiments, a suitable concentration is about 91% nominal (0.91 mg/mL). In some embodiments, a suitable concentration is about 92% nominal (0.92 mg/mL). In some embodiments, a suitable concentration is about 93% nomi-

TABLE F

Exemplary Formulations of SEQ ID NO: 30

| CFTR mRNA | Formulation 9 SEQ ID NO: 30 | Formulation 10 SEQ ID NO: 30 | Formulation 11 SEQ ID NO: 30 | Formulation 12 SEQ ID NO: 30 |
|---|---|---|---|---|
| 5' Cap | m7G(5')ppp(5') (2'OMeG) | m7G(5')ppp(5') (2'OMeG) | m7G(5')ppp(5') (2'OMeG) | m7G(5')ppp(5') (2'OMeG) |
| 5' UTR | as described in Table C | as described in Table C | as described in Table C | as described in Table C |
| Start Codon hCFTR | AUG | AUG | AUG | AUG |
| Stop Codon hCFTR | UGA | UGA | UGA | UGA |
| 3'UTR | as described in Table C | as described in Table C | as described in Table C | as described in Table C |
| PolyA Tail | ~200-1000 adenosine nucleotides | ~200-1000 adenosine nucleotides | ~200-1000 adenosine nucleotides | ~200-1000 adenosine nucleotides |
| ICE:DOPE: DMG-PEG-2K | 60:35:5 | 60:30:10 | 60:35:5 | 60:35:5 |
| Diluent | 10% trehalose | 10% trehalose | 10% sucrose | 10% glucose |
| Average particle size | 40-60 nM | 40-60 nM | 40-60 nM | 40-60 nM |
| N/P charge ratio | 4 | 4 | 4 | 4 |

In embodiments, a formulation is Formulation 9. In embodiments, Formulation 9 is further characterized by a concentration of the mRNA that is about 0.6 mg/ml.

In embodiments, a formulation is Formulation 10. In embodiments, Formulation 10 is further characterized by a concentration of the mRNA that is about 0.6 mg/ml.

In embodiments, a formulation is Formulation 11. In embodiments, Formulation 11 is further characterized by a concentration of the mRNA that is about 0.6 mg/ml.

In embodiments, a formulation is Formulation 12. In embodiments, Formulation 12 is further characterized by a concentration of the mRNA that is about 0.6 mg/ml.

nal (0.93 mg/mL). In some embodiments, a suitable concentration is about 94% nominal (0.94 mg/mL). In some embodiments, a suitable concentration is about 95% nominal (0.95 mg/mL). In some embodiments, a suitable concentration is about 96% nominal (0.96 mg/mL). In some embodiments, a suitable concentration is about 97% nominal (0.97 mg/mL). In some embodiments, a suitable concentration is about 98% nominal (0.98 mg/mL). In some embodiments, a suitable concentration is about 99% nominal (0.99 mg/mL). In some embodiments, a suitable concentration is about 100% nominal (1.0 mg/mL). In some embodiments, a suitable concentration is about 101% nominal (1.01 mg/mL). In some embodiments, a suitable concentration is about 102% nominal (1.02 mg/mL). In some embodiments, a suitable concentration is about 103% nominal (1.03 mg/mL). In some embodiments, a suitable concentration is about 104% nominal (1.04 mg/mL). In some embodiments, a suitable concentration is about 105% nominal (1.05 mg/mL). In some embodiments, a suitable concentration is about 106% nominal (1.06 mg/mL). In some embodiments, a suitable concentration is about 107% nominal (1.07 mg/mL). In some embodiments, a suitable concentration is about 108% nominal (1.08 mg/mL). In some embodiments, a suitable concentration is about 109% nominal (1.09 mg/mL). In some embodiments, a suitable concentration is about 110% nominal (1.10 mg/mL).

In some embodiments, the formulation is assessed to determine CFTR mRNA integrity, to determine whether there is residual plasmid DNA, and to determine the presence of residual solvent. In some embodiments, CFTR mRNA integrity is assessed by agarose gel electrophoresis. The gels are analyzed to determine whether the banding pattern and apparent nucleotide length is consistent with an analytical reference standard. For example, gels are assessed to determine whether banding pattern and apparent nucleotide length is consistent with an analytical reference standard and is oriented between the 7,000 nt and 3,000 nt bands. Additional methods to assess CFTR mRNA integrity include, for example, assessment of the purified mRNA using capillary gel electrophoresis (CGE). In some embodiments, acceptable purity of the CFTR mRNA in the formulation as determined by CGE is that the main peak is not less than about 55%, 50%, 45%, 40%, 35%, or 30%. Accordingly, in some embodiments, acceptable purity of the CFTR mRNA in the formulation is a CGE with a main peak not less than about 55%. In some embodiments, acceptable purity of the CFTR mRNA in the formulation is a CGE with a main peak not less than about 50%. In some embodiments, acceptable purity of the CFTR mRNA in the formulation is a CGE with a main peak not less than about 45%. In some embodiments, acceptable purity of the CFTR mRNA in the formulation is a CGE with a main peak not less than about 40%. In some embodiments, acceptable purity of the CFTR mRNA in the formulation is a CGE with a main peak not less than about 35%. In some embodiments, acceptable purity of the CFTR mRNA in the formulation is a CGE with a main peak not less than about 30%.

The formulation can also be assessed for the presence of any residual plasmid DNA. Various methods can be used to assess the presence of residual plasmid DNA, for example qPCR. In some embodiments, less than 10 µg/mg (e.g., less than 10 µg/mg, less than 9 µg/mg, less than 8 µg/mg, less than 7 µg/mg, less than 6 µg/mg, less than 5 µg/mg, less than 4 µg/mg, less than 3 µg/mg, less than 2 µg/mg, or less than 1 µg/mg) is an acceptable level of residual plasmid DNA. Accordingly, in some embodiments, the formulation has less than 10 µg/mg of residual plasmid DNA. In some embodiments, the formulation has less than 9 µg/mg of residual plasmid DNA. In some embodiments, the formulation has less than 8 µg/mg of residual plasmid DNA. In some embodiments, the formulation has less than 7 µg/mg of residual plasmid DNA. In some embodiments, the formulation has less than 6 µg/mg of residual plasmid DNA. In some embodiments, the formulation has less than 5 µg/mg of residual plasmid DNA. In some embodiments, the formulation has less than 4 µg/mg of residual plasmid DNA. In some embodiments, the formulation has less than 3 µg/mg of residual plasmid DNA. In some embodiments, the formulation has less than 2 µg/mg of residual plasmid DNA. In some embodiments, the formulation has less than 1 µg/mg of residual plasmid DNA.

The formulation can also be assessed for the presence of any residual solvents. Various methods can be used to determine the presence of residual solvent. In some embodiments, acceptable residual solvent levels are not more than 10,000 ppm. In some embodiments, acceptable residual solvent levels are not more than 9,000 ppm. In some embodiments, acceptable residual solvent levels are not more than 8,000 ppm. In some embodiments, acceptable residual solvent levels are not more than 7,000 ppm. In some embodiments, acceptable residual solvent levels are not more than 6,000 ppm. In some embodiments, acceptable residual solvent levels are not more than 5,000 ppm. In some embodiments, acceptable residual solvent levels are not more than 4,000 ppm. In some embodiments, acceptable residual solvent levels are not more than 3,000 ppm. In some embodiments, acceptable residual solvent levels are not more than 2,000 ppm. In some embodiments, acceptable residual solvent levels are not more than 1,000 ppm. In some embodiments, the residual solvent is, for example, ethanol.

The formulation can also be assessed for the presence of bacterial endotoxins. In some embodiments, bacterial endotoxins are <0.5 EU/mL, <0.4 EU/mL, <0.3 EU/mL, <0.2 EU/mL or <0.1 EU/mL. Accordingly, in some embodiments, bacterial endotoxins in the purified mRNA are <0.5 EU/mL. In some embodiments, bacterial endotoxins in the purified mRNA are <0.4 EU/mL. In some embodiments, bacterial endotoxins in the purified mRNA are <0.3 EU/mL. In some embodiments, bacterial endotoxins in the purified mRNA are <0.2 EU/mL. In some embodiments, bacterial endotoxins in the purified mRNA are <0.2 EU/mL. In some embodiments, bacterial endotoxins in the purified mRNA are <0.1 EU/mL.

The formulation can also be assessed for microbial contaminants (e.g., "bioburden testing"). The tests can include for example an assessment of total aerobic microbial count ("TAMC") and/or an assessment of total yeast/mold count ("TYMC"). In some embodiments, the purified mRNA has not more than 1 CFU/10 mL, 1 CFU/25 mL, 1 CFU/50 mL, 1 CFU/75 mL, or not more than 1 CFU/100 mL. Accordingly, in some embodiments, the purified mRNA has not more than 1 CFU/10 mL. In some embodiments, the purified mRNA has not more than 1 CFU/25 mL. In some embodiments, the purified mRNA has not more than 1 CFU/50 mL. In some embodiments, the purified mRNA has not more than 1 CFR/75 mL. In some embodiments, the purified mRNA has 1 CFU/100 mL.

The pH of the formulation can also be assessed. In some embodiments, acceptable pH of the formulation is between 5 and 8. Accordingly, in some embodiments, the formulation has a pH of about 5. In some embodiments, the formulation has a pH of about 6. In some embodiments, the formulation has a pH of about 7. In some embodiments, the formulation has a pH of about 7. In some embodiments, the formulation has a pH of about 8.

The formulation can also be assessed for translational fidelity of the CFTR mRNA. The translational fidelity can be assessed by various methods such as, for example, transfection and Western blot analysis. Acceptable characteristics of the purified mRNA includes banding pattern on a Western blot that migrates at a similar molecular weight as a reference standard. For example, the sample main band migrates at a similar apparent molecular weight as the reference standard and is oriented between the 100 kDa and 250 kDa markers.

The formulation can also be assessed for conductance. In some embodiments, acceptable characteristics of the purified mRNA include a conductance of between about 50% and 150% of a reference standard. Accordingly, in some embodiments, the formulation has a conductance of about 50% of a reference standard. In some embodiments, the formulation has a conductance of about 55% of a reference standard. In some embodiments, the formulation has a conductance of about 60% of a reference standard. In some embodiments, the formulation has a conductance of about 65% of a reference standard. In some embodiments, the formulation has a conductance of about 70% of a reference standard. In some embodiments, the formulation has a conductance of about 75% of a reference standard. In some embodiments, the formulation has a conductance of about 80% of a reference standard. In some embodiments, the formulation has a conductance of about 85% of a reference standard. In some embodiments, the formulation has a conductance of about 90% of a reference standard. In some embodiments, the formulation has a conductance of about 95% of a reference standard. In some embodiments, the formulation has a conductance of about 100% of a reference standard. In some embodiments, the formulation has a conductance of about 105% of a reference standard. In some embodiments, the formulation has a conductance of about 110% of a reference standard. In some embodiments, the formulation has a conductance of about 115% of a reference standard. In some embodiments, the formulation has a conductance of about 120% of a reference standard. In some embodiments, the formulation has a conductance of about 125% of a reference standard. In some embodiments, the formulation has a conductance of about 130% of a reference standard. In some embodiments, the formulation has a conductance of about 135% of a reference standard. In some embodiments, the formulation has a conductance of about 140% of a reference standard. In some embodiments, the formulation has a conductance of about 145% of a reference standard. In some embodiments, the formulation has a conductance of about 150% of a reference standard.

The CFTR mRNA in the formulation can also be assessed for Cap percentage. Various methods can be used to assess Cap percentage, for example Ultra Performance Liquid Chromatography ("UPLC"). In some embodiments, an acceptable Cap percentage includes Cap1, % area of not less than about 80%, 85%, 90%, or 95%. Accordingly, in some embodiments, an acceptable Cap percentage includes Cap1, % area of not less than about 80%. In some embodiments, an acceptable Cap percentage includes Cap1, % area of not less than about 85%. In some embodiments, an acceptable Cap percentage includes Cap1, % area of not less than about 90%. In some embodiments, an acceptable Cap percentage includes Cap1, % area of not less than about 95%.

Furthermore, the CFTR mRNA in the formulation can be assessed for PolyA tail length. Various methods can be used to assess PolyA tail length, for example capillary electrophoresis. In some embodiments, an acceptable PolyA tail length is about 100-1500 nucleotides (e.g., 100, 150, 200, 250, 300, 350, 400, 450, 500, 550, 600, 650, 700, 750, 800, 850, 900, 950, and 1000, 1100, 1200, 1300, 1400, or 1500 nucleotides). Accordingly, in some embodiments an acceptable PolyA tail length is about 100 nucleotides. In some embodiments, an acceptable PolyA tail length is about 200 nucleotides. In some embodiments, an acceptable PolyA tail length is about 250 nucleotides. In some embodiments, an acceptable PolyA tail length is about 300 nucleotides. In some embodiments, an acceptable PolyA tail length is about 350 nucleotides. In some embodiments, an acceptable PolyA tail length is about 400 nucleotides. In some embodiments, an acceptable PolyA tail length is about 450 nucleotides. In some embodiments, an acceptable PolyA tail length is about 500 nucleotides. In some embodiments, an acceptable PolyA tail length is about 550 nucleotides. In some embodiments, an acceptable PolyA tail length is about 600 nucleotides. In some embodiments, an acceptable PolyA tail length is about 650 nucleotides. In some embodiments, an acceptable PolyA tail length is about 700 nucleotides. In some embodiments, an acceptable PolyA tail length is about 750 nucleotides. In some embodiments, an acceptable PolyA tail length is about 800 nucleotides. In some embodiments, an acceptable PolyA tail length is about 850 nucleotides. In some embodiments, an acceptable PolyA tail length is about 900 nucleotides. In some embodiments, an acceptable PolyA tail length is about 950 nucleotides. In some embodiments, an acceptable PolyA tail length is about 1000 nucleotides. In some embodiments, an acceptable PolyA tail length is about 1100 nucleotides. In some embodiments, an acceptable PolyA tail length is about 1200 nucleotides. In some embodiments, an acceptable PolyA tail length is about 1300 nucleotides. In some embodiments, an acceptable PolyA tail length is about 1400 nucleotides. In some embodiments, an acceptable PolyA tail length is about 1500 nucleotides. In some embodiments, an acceptable PolyA tail length is between about 200-1000 nt. In some embodiments, an acceptable PolyA tail length is between about 300-900 nt. In some embodiments, an acceptable PolyA tail length is between about 400 and 800 nt.

Pulmonary Delivery

A CFTR mRNA may be formulated for delivery via different administration routes including, but not limited to, oral, rectal, vaginal, transmucosal, or intestinal administration; parenteral delivery, including intradermal, transdermal (topical), intramuscular, subcutaneous, intramedullary injections, as well as intrathecal, direct intraventricular, intravenous, intraperitoneal, and/or intranasal administration.

In some embodiments, a CFTR mRNA is formulated for pulmonary delivery. As used herein, pulmonary delivery refers to delivery to lung via, e.g., nasal cavity, trachea, bronchi, bronchioles, and/or other pulmonary system. In particular embodiments, a CFTR mRNA is formulated for nebulization. In these embodiments, the delivery vehicle may be in an aerosolized composition which can be inhaled. In some embodiments, pulmonary delivery involves inhalation (e.g., for nasal, tracheal, or bronchial delivery). In some embodiments, the CFTR mRNA formulation is nebulized prior to inhalation.

Nebulization

Inhaled aerosol droplets of a particle size of 1-5 μm can penetrate into the narrow branches of the lower airways. Aerosol droplets with a larger diameter are typically absorbed by the epithelia cells lining the oral cavity, and are unlikely to reach the lower airway epithelium and the deep alveolar lung tissue.

Particle size in an aerosol is commonly described in reference to the Mass Median Aerodynamic Diameter (MMAD). MMAD, together with the geometric standard deviation (GSD), describes the particle size distribution of any aerosol statistically, based on the weight and size of the particles. Means of calculating the MMAD of an aerosol are well known in the art.

A specific method of calculating the MMAD using a cascade impactor was first described in 1959 by Mitchell et al. The cascade impactor for measuring particle sizes is constructed of a succession of jets, each followed by an impaction slide, and is based on the principle that particles in a moving air stream impact on a slide placed in their path, if their momentum is sufficient to overcome the drag exerted by the air stream as it moves around the slide. As each jet is smaller than the preceding one, the velocity of the air stream and therefore that of the dispersed particles are increased as the aerosol advances through the impactor. Consequently, smaller particles eventually acquire enough momentum to impact on a slide, and a complete particle size classification of the aerosol is achieved. The improved Next Generation Impactor, used herein to measure the MMAD of the pharmaceutical composition of the invention, was first described by Marple et al. in 2003 and has been widely used in the pharmacopoeia since.

Another parameter to describe particle size in an aerosol is the Volume Median Diameter (VIVID). VIVID also describes the particle size distribution of an aerosol based on the volume of the particles. Means of calculating the VIVID of an aerosol are well known in the art. A specific method used for determining the VIVID is laser diffraction, which is used herein to measure the VIVID of the pharmaceutical composition of the invention (see, e.g., Clark, 1995, Int J Pharm. 115:69-78).

In some embodiments, the mean particle size of the nebulized CFTR mRNA formulation of the invention is between about 4 µm and 6 µm, e.g., about 4 µm, about 4.5 µm, about 5 µm, about 5.5 µm, or about 6 µm.

The Fine Particle Fraction (FPF) is defined as the proportion of particles in an aerosol which have an MMAD or a VIVID smaller than a specified value. In some embodiments, the FPF of the nebulized CFTR mRNA formulation of the invention with a particle size <5 µm is at least about 30%, more typically at least about 40%, e.g., at least about 50%, more typically at least about 60%.

In some embodiments, nebulization is performed in such a manner that the mean respirable emitted dose (i.e., the percentage of FPF with a particle size <5 µm; e.g., as determined by next generation impactor with 15 L/min extraction) is at least about 30% of the emitted dose, e.g., at least about 31%, at least about 32%, at least about 33%, at least about 34%, or at least about 35% the emitted dose. In some embodiments, nebulization is performed in such a manner that the mean respirable delivered dose (i.e., the percentage of FPF with a particle size <5 µm; e.g., as determined by next generation impactor with 15 L/min extraction) is at least about 15% of the emitted dose, e.g., at least 16% or 16.5% of the emitted dose.

Nebulizer

Nebulization can be achieved by any nebulizer known in the art. A nebulizer transforms a liquid to a mist so that it can be inhaled more easily into the lungs. Nebulizers are effective for infants, children and adults. Nebulizers are able to nebulize large doses of inhaled medications. Typically, a nebulizer for use with the invention comprises a mouthpiece that is detachable. This is important because only clean mouthpieces that are RNase free should be used when administering the CFTR mRNA formulation of the invention.

In some embodiments, the reservoir volume of the nebulizer ranges from about 5.0 mL to about 8.0 mL. In some embodiments, the reservoir volume of the nebulizer is about 5.0 mL. In some embodiments, the reservoir volume of the nebulizer is about 6.0 mL. In some embodiments, the reservoir volume of the nebulizer is about 7.0 mL. In some embodiments, the reservoir volume of the nebulizer is about 8.0 mL.

One type of nebulizer is a jet nebulizer, which comprises tubing connected to a compressor, which causes compressed air or oxygen to flow at a high velocity through a liquid medicine to turn it into an aerosol, which is then inhaled by the patient.

Another type of nebulizer is the ultrasonic wave nebulizer, which comprises an electronic oscillator that generates a high frequency ultrasonic wave, which causes the mechanical vibration of a piezoelectric element, which is in contact with a liquid reservoir. The high frequency vibration of the liquid is sufficient to produce a vapor mist. Exemplary ultrasonic wave nebulizers are the Omron NE-U17 and the Beurer Nebulizer IH30.

A third type of nebulizer comprises vibrating mesh technology (VMT). A VMT nebulizer typically comprises a mesh/membrane with 1000-7000 holes that vibrates at the top of a liquid reservoir and thereby pressures out a mist of very fine aerosol droplets through the holes in the mesh/membrane. VMT nebulizers suitable for delivery of the CFTR mRNA formulation include any of the following: eFlow (PARI Medical Ltd.), i-Neb (Respironics Respiratory Drug Delivery Ltd), Nebulizer IH50 (Beurer Ltd.), AeroNeb Go (Aerogen Ltd.), InnoSpire Go (Respironics Respiratory Drug Delivery Ltd), Mesh Nebulizer (Shenzhen Homed Medical Device Co, Ltd.), Portable Nebulizer (Microbase Technology Corporation) and Airworks (Convexity Scientific LLC). In some embodiments, the mesh or membrane of the VMT nebulizer is made to vibrate by a piezoelectric element. In some embodiments, the mesh or membrane of the VMT nebulizer is made to vibrate by ultrasound.

VMT nebulizers have been found to be particularly suitable for practicing the invention because they do not affect the mRNA integrity of the CFTR mRNA formulation of the invention. Typically, at least about 60%, e.g., at least about 65% or at least about 70%, of the mRNA in the CFTR mRNA formulation of the invention maintains its integrity after nebulization.

In some embodiments, nebulization is continuous during inhalation and exhalation. More typically, nebulization is breath-actuated. Suitable nebulizers for use with the invention have nebulization rate of >0.2 mL/min. In some embodiments, the nebulization rate is >0.25 mL/min. In other embodiment, the nebulization rate is >0.3 mL/min. In certain embodiments, the nebulization rate is >0.45 mL/min. In a typical embodiment, the nebulization rate ranges between 0.2 mL/minute and 0.5 mL/minute.

In some embodiments, the nebulization volume is at a volume ranging from 13.0 mL to 42.0 mL, e.g., between 14 mL and 28 mL. In some embodiments, the nebulization volume is at a volume less than or equal to 13.9 mL. In some embodiments, the nebulization volume is at a volume less than or equal to 16.0 mL. In some embodiments, the nebulization volume is at a volume less than or equal to 18.0 mL. In some embodiments, the nebulization volume is at a volume less than or equal to 20.0 mL. In some embodiments, the nebulization volume is at a volume less than or equal to 22.0 mL. In some embodiments, the nebulization volume is at a volume less than or equal to 24.0 mL. In some embodiments, the nebulization volume is at a volume less than or equal to 26.0 mL. In some embodiments, the nebulization volume is at a volume less than or equal to 27.9 mL. In some embodiments, the nebulization volume is at a volume less than or equal to 30.0 mL. In some embodiments, the nebulization volume is at a volume less than or equal to 32.0 mL. In some embodiments, the nebulization volume is at a volume less than or equal to 34.0 mL. In some embodiments, the nebulization volume is at a volume less than or equal to 36.0 mL. In some embodiments, the nebulization volume is at a volume less than or equal to 38.0 mL. In some embodiments, the nebulization volume is at a volume less than or equal to 40.0 mL. In some embodiments, the nebulization volume is at a volume less than or equal to 41.8 mL.

A human subject may display adverse effects during treatment, when the nebulization volume exceeds 10 mL. In particular, such adverse effects may be more common when volumes greater than 20 mL are administered. In some embodiments, the nebulization volume does not exceed 20 mL.

In some embodiments, a single dose of the CO-hCFTR mRNA composition of the invention can be administered with only a one or two refills per nebulization treatment. For example, if the total volume of the CO-hCFTR mRNA composition that is to be administered to the patient is 13 mL, then only a single refill is required to administer the entire volume when using a nebulizer with an 8 mL reservoir, but two refills are required to administer the same volume when using a nebulizer with a 5 mL reservoir. In another embodiment, at least three refills are required per nebulization treatment, e.g., to administer a volume of 26 mL, at least three refills are required when using a nebulizer with an 8 mL reservoir. In yet a further embodiment, at least four refills are required. For example, to deliver 42 mL with a nebulizer having a 5 mL reservoir, at least eight refills are required. Typically, no more than 1-3 refills will be required to administer the CO-hCFTR mRNA composition of the invention.

Typically, the duration of nebulization is between 30 and 300 minutes. An average nebulization session may exceed 30 minutes, e.g., it may last for at least 35 minutes or more, at least 45 minutes or more, or at least 1 hour or more. For example, most patients are treated with a nebulization session that last between about 45 minutes to about 90 minutes, although some patients may require nebulization sessions that may last from about 100 minutes to about 180 minutes. Longer treatment may last for 1 hour, 1.5 hours, or 2 hours. Accordingly, in some embodiments, the nebulization session is about 45 minutes, about 60 minutes, about 75 minutes, about 90 minutes, about 105 minutes, about 120 minutes, about 135 minutes, about 150 minutes, about 165 minutes, or about 180 minutes. In some embodiments, the nebulization session is about 45 minutes. In some embodiments, nebulization is about 2 hours and 25 minutes. In some embodiments, patients may require nebulization sessions that may last from about 150 minutes to about 300 minutes, e.g., between 3 hours and 4.5 hours.

In some embodiments, the number of nebulizers used during a single nebulization session ranges from 2-8. In some embodiments, 1 nebulizer is used during a single nebulization session. In some embodiments, 2 nebulizers are used during a single nebulization session. In some embodiments, 3 nebulizers are used during a single nebulization session. In some embodiments, 4 nebulizers are used during a single nebulization session. In some embodiments, 5 nebulizers are used during a single nebulization session. In some embodiments, 6 nebulizers are used during a single nebulization session. In some embodiments, 7 nebulizers are used during a single nebulization session. In some embodiments, 8 nebulizers are used during a single nebulization session.

Pharmacokinetics and Tissue Distribution

According to the present invention, administration of a formulation comprising a CFTR mRNA results in delivery of the mRNA and encoded CFTR protein in various targets tissues described herein. In particular, administration of a formulation comprising a CFTR mRNA according to the present invention results in a therapeutically or clinically effective level or activity of CFTR in the target tissue. In various embodiments, a target tissue includes lung, pancreas, kidney, liver, spleen, testes/ovaries, salivary glands, sweat glands, heart and brain. In some embodiments, a target tissue is lung. In some embodiments, a target tissue is the upper (i.e., superior) lobe of the right or left lung. In some embodiments, a target tissue is the lower (i.e., inferior) lobe of the right or left lung. In some embodiments, a target tissue is the middle lobe of the right lung.

In some embodiments, a target tissue is the apical segment of the right lung or the apicoposterior segment of the left lung. In some embodiments, a target tissue is the posterior segment of the right lung. In some embodiments, a target tissue is the anterior segment of the right or left lung. In some embodiments, a target tissue is the superior segment of the right or left lung. In some embodiments, a target tissue is the lateral basal segment of the right or left lung. In some embodiments, a target tissue is the anterior basal segment of the right lung. In some embodiments, a target tissue is the anteromedial basal segment of the left lung. In some embodiments, a target tissue is the lateral segment of the right lung. In some embodiments, a target tissue is the medial segment of the right lung. In some embodiments, a target tissue is the superior lingular segment of the left lung. In some embodiments, a target tissue is the inferior lingular segment of the left lung. In some embodiments, a target tissue is the posterior basal segment of the right or left lung. In some embodiments, a target tissue is the medial basal segment of the right lung.

In particular embodiments, a target tissue is epithelial cells in the lung. In some embodiments, a target tissue is smooth muscle cells in the lung. In some embodiment, a target tissue is pancreatic duct epithelial cells. In some embodiment, a target tissue is bile-duct epithelial cells. In some embodiment, a target tissue is epithelial cells of the salivary glands. In some embodiments, a target tissue is renal epithelial cells. In some embodiment, a target tissue is beta-S cells in sweat gland secretory coils of sweat glands. In some embodiment, a target tissue is epithelial cells of the reproductive tract.

In some embodiments, a CFTR mRNA delivered according to the present invention achieves a level of CFTR protein expression or activity that is at least 5%, 10%, 20%, 30%, 40%, 50%, 60%, 70%, 80%, 90%, or 95% of the normal level of CFTR protein expression or activity in a target tissue described herein. In some embodiments, a CFTR mRNA delivered according to the present invention achieves a level of CFTR protein expression or activity that is increased by at least 1-fold, 2-fold, 3-fold, 4-fold, 5-fold, 6-fold, 7-fold, 8-fold, 9-fold or 10-fold as compared to a control (e.g., endogenous level of protein or activity without or before the treatment according to the invention, or a historical reference level) in a target tissue described herein.

In general, a CFTR mRNA delivered according to the present invention have sufficiently long half time in a target tissue described herein. In some embodiments, a CFTR mRNA delivered according to the present invention has a half-life of at least approximately 30 minutes, 45 minutes, 60 minutes, 90 minutes, 2 hours, 3 hours, 4 hours, 5 hours, 6 hours, 7 hours, 8 hours, 9 hours, 10 hours, 12 hours, 16 hours, 18 hours, 20 hours, 25 hours, 30 hours, 35 hours, 40 hours, 3 days, 7 days, 14 days, 21 days, or a month. In some embodiments, a CFTR mRNA delivered according to the present invention results in detectable CFTR protein level or activity in a target tissue (e.g., the lung) or bloodstream after 12 hours, 24 hours, 30 hours, 36 hours, 42 hours, 48 hours, 54 hours, 60 hours, 66 hours, 72 hours, 78 hours, 84 hours, 90 hours, 96 hours, 102 hours, a week, two weeks, three weeks, or a month following administration. Detectable level or activity may be determined using various methods known in the art.

In some embodiments, a CFTR mRNA delivered according to the present invention results in increased CFTR protein level or activity in upper lobe lung tissue by e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the invention, or a historical reference level).

In some embodiments, a CFTR mRNA delivered according to the present invention results in increased CFTR protein level or activity in lower lobe lung tissue by e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the invention, or a historical reference level).

In some embodiments, a CFTR mRNA delivered according to the present invention results in increased CFTR protein level or activity in middle lobe lung tissue by e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the invention, or a historical reference level).

In some embodiments, a CFTR mRNA delivered according to the present invention results in increased CFTR protein level or activity in distal lung tissues by, e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 200-fold, 300-fold, 400-fold, or 500-fold as compared to a control (e.g., endogenous level of protein or activity without or before the treatment according to the invention, or a historical reference level).

In some embodiments, a CFTR mRNA delivered according to the present invention results in increased CFTR protein level or activity in distal peripheral lung tissue by e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 200-fold, or 300-fold as compared to a control (e.g., endogenous level of protein or activity without or before the treatment according to the invention, or a historical reference level).

In some embodiments, a CFTR mRNA delivered according to the present invention results in increased CFTR protein level or activity in lateral peripheral lung tissue by e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the invention, or a historical reference level).

In some embodiments, a CFTR mRNA delivered according to the present invention results in increased CFTR protein level or activity in medial peripheral lung tissue by e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, or 1000-fold as compared to a control (e.g., endogenous level of protein or activity without or before the treatment according to the invention, or a historical reference level).

In some embodiments, a CFTR mRNA delivered according to the present invention results in increased CFTR protein level or activity in middle lung tissue by e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 150-fold, 200-fold, 250-fold, 300-fold, 350-fold, 400-fold, 450-fold, or 500-fold as compared to a control (e.g., endogenous level of protein or activity without or before the treatment according to the invention, or a historical reference level).

In some embodiments, a CFTR mRNA delivered according to the present invention results in increased CFTR protein level or activity in proximal lung tissue by, e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the invention, or a historical reference level).

In some embodiments, a CFTR mRNA delivered according to the present invention results in detectable CFTR protein or activity in the larynx, trachea, nasal turbinate, and/or bronchoalveolar lavage fluid (BALF). In some embodiments, a CFTR mRNA delivered according to the present invention results in detectable CFTR protein or activity in blood. In some embodiments, a CFTR mRNA delivered according to the present invention results in detectable CFTR protein or activity in lung, pancreas, kidney, liver, spleen, testes/ovaries, salivary glands, sweat glands, heart and brain.

In some embodiments, a CFTR mRNA delivered according to the present invention results in increased CFTR protein level or activity in larynx, trachea, tracheobronchial lymph node, and/or blood by, e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the invention, or a historical reference level).

The CFTR mRNA expression may be detected or quantified by qPCR on RNA purified from tissue samples. The CFTR protein expression may be determined by measuring immune responses to CFTR protein. In some embodiments, IgG antibody to CFTR protein is measured by an enzyme-linked immunosorbent assay in collected serum samples. In some embodiments, CFTR-specific T cell responses are assessed using collected peripheral blood mononuclear cells. In some embodiments, T cell responses to CFTR are measured by a human interferon-γ enzyme-linked immunospot assay as described by Calcedo et al. (Calcedo et al., Hum Gene Ther Clin Dev. (2013) 24:108-15). Qualitative assessment of CFTR protein may also be performed by Western blot analysis. The CFTR protein activity may be measured by CFTR chloride channel activity in appropriate tissue cells. A stable potential with the mean value of a 10 second scoring interval after perfusion of solution is recorded. CFTR activity is estimated by the change in potential difference following perfusion with chloride-free isoproterenol. Various other methods are known in the art and may be used to determine the CFTR mRNA and CFTR protein expression or activity.

Therapeutic Efficacy

According to the present invention, a CFTR mRNA is delivered to a CF patient in need of treatment at a therapeutically effective dose and an administration interval for a treatment period sufficient to improve, stabilize or reduce one or more symptoms of cystic fibrosis relative to a control. The terms "treat" or "treatment", as used in the context of cystic fibrosis herein, refers to amelioration of one or more symptoms associated with cystic fibrosis, prevention or delay of the onset of one or more symptoms of cystic fibrosis, and/or lessening of the severity or frequency of one or more symptoms of cystic fibrosis.

In some embodiments, a therapeutically effective dose of a CFTR mRNA is or greater than about 2 mg, 4 mg, 6 mg, 8 mg, 10 mg, 12 mg, 14 mg, 16 mg, 18 mg, 20 mg, 22 mg, 24 mg, 26 mg, 28 mg, 30 mg, 32 mg, 34 mg, 36 mg, 38 mg, or 40 mg per dose or equivalent thereof. In some embodiments, a therapeutically effective dose of a CFTR mRNA is or less than about 50 mg, 48 mg, 46 mg, 44 mg, 42 mg, 40 mg, 38 mg, 36 mg, 34 mg, 32 mg, 30 mg, 28 mg, 26 mg, 24 mg, 22 mg, 20 mg, 18 mg, 16 mg, 14 mg, 12 mg, 10 mg, 8 mg, 6 mg, or 4 mg per dose or equivalent thereof. In some embodiments, a therapeutically effective dose of a CFTR mRNA is about 2-50 mg, 4-45 mg, 4-40 mg, 6-40 mg, 6-38 mg, 6-36 mg, 6-34 mg, 6-32 mg, 6-30 mg, 6-28 mg, 6-26 mg, 6-24 mg, 6-22 mg, 6-20 mg, 6-18 mg, 6-16 mg, 8-50 mg, 8-45 mg, 8-40 mg, 8-38 mg, 8-36 mg, 8-34 mg, 8-32 mg, 8-30 mg, 8-28 mg, 8-26 mg, 8-24 mg, 8-22 mg, 8-20 mg per dose, or the equivalent thereof.

In some embodiments, a therapeutically effective dose of a CFTR mRNA is administered daily, twice a week, weekly, once every two weeks, once every three weeks, once every four weeks, monthly, once every two months, once every three months. Typically, weekly administration of a therapeutically effective dose of a CFTR mRNA in accordance with the invention is sufficient to effectively reduce the severity of one or more symptoms in a cystic fibrosis patient. For example, a nominal dose of 4-40 mg of a CFTR mRNA (e.g., a nominal dose of 6-30 mg, e.g., 8 mg, 16 mg, or 24 mg) administered weekly by nebulization is effective in reducing the severity of one or more symptoms in a cystic fibrosis patient.

In some embodiments, a therapeutically effective dose of a CFTR mRNA is administered for a period of at least two weeks, three weeks, four weeks, a month, two months, three months, four months, five months, six months, seven months, eight months, nine months, ten months, eleven months, twelve months, 1 year, 2 years, 3 years, 4 years, 5 years, or 10 years.

Typically, the therapeutic effect of administration of a CFTR mRNA on a cystic fibrosis patient is measured relative to a control. In some embodiments, a control is the severity of one or more symptoms in the same patient before the treatment. In some embodiments, a control is indicative of a historical reference level of one or more symptoms in CF patients. In some embodiments, a control is indicative of a normal level of ability, physical conditions or biomarker corresponding to the one or more symptoms being measured.

In some embodiments, the therapeutic effect of administration of a CFTR mRNA according to the present invention is measured by a score on a Cystic Fibrosis Questionnaire Revise (CFQ-R) respiratory domain. In some embodiments, the therapeutic effect of administration of a CFTR mRNA according to the present invention is measured by a sweat chloride value. In some embodiments, the therapeutic effect of administration of a CFTR mRNA according to the present invention is measured by a body mass index and/or body weight. In some embodiments, the therapeutic effect of administration of a CFTR mRNA according to the present invention is measured by onset or severity of pulmonary exacerbation.

In some embodiments, the therapeutic effect of administration of a CFTR mRNA according to the present invention is measured by minute volume, respiratory rate, and/or tidal volume. In some embodiments, the therapeutic effect of administration of a CFTR mRNA according to the present invention on the respiratory system is determined by performing spirometry and assessing the following parameters: forced expiratory volume in 1 second ($FEV_1$): absolute volume (L) and percent based on the patient's age, gender, and height, forced vital capacity (FVC): absolute volume (L) and percent based on the patient's age, gender, and height, $FEV_1$/FVC: ratio and percent based on the patient's age, gender, and height, and/or forced expiratory flow over the middle one-half of the FVC ($FEF_{25-75}\%$): absolute volume (L) and percent based on the patient's age, gender, and height. In some embodiments, the parameters can be normalized using the ERS Global Lung Function Initiative (GLI) prediction equations. In some embodiments, the therapeutic effect of administration of a CFTR mRNA according to the present invention on the respiratory system is determined by chest x-ray.

In some embodiments, administration of a CFTR mRNA according to the present invention results in a change in the CFQ-R respiratory domain score by at least 1, at least 2, at least 3, at least 4, at least 5, at least 6, at least 7, at least 8, at least 9, at least 10, at least 11, at least 12, at least 13, at least 14, or at least 15 points relative to a control. In some embodiments, administration of a CFTR mRNA according to the present invention results in a change in the CFQ-R respiratory domain score by at least 1%, 2%, 3%, 4%, 5%, 6%, 7%, 8%, 9%, 10%, 11%, 12%, 13%, 14%, 15%, 16%, 17%, 18%, 19%, or 20% relative to a control.

In some embodiments, administration of a CFTR mRNA according to the present invention results in amelioration, prevention or delay in onset of pulmonary exacerbation. As used herein, pulmonary exacerbation refers to one or more of the following sino-pulmonary signs/symptoms: change in sputum, new or increased hemoptysis, increased cough, increased dyspnea, malaise/fatigue/lethargy, temperature >38° C. (~100.4° F.), anorexia/weight loss, sinus pain/tenderness, change in sinus discharge, change in physical chest exam, decrease in pulmonary function and radiographic indication of pulmonary infection.

In some embodiments, administration of a CFTR mRNA according to the present invention results in prevention or reduced inflammation associated with pulmonary exacerbation. For example, administration of a CFTR mRNA according to the present invention results in reduced expression of markers of inflammation and/or lung damage, including but not limited to, C-reactive protein, white cell counts, interleukin-8, neutrophil elastase alpha 1-antiprotease complexes and matrix metalloproteins, in blood or serum as compared to a control indicative of the corresponding level of relevant markers in a CF patient without treatment. Additionally or alternatively, administration of a CFTR mRNA according to the present invention results in reduced sputum concentrations of bioactive lipid mediators, such as the cysteinyl leukotrienes and prostaglandin-E2, or sputum cell counts as compared to a control indicative of the corresponding level of relevant markers in a CF patient without treatment.

In some embodiments, administration of a CFTR mRNA according to the present invention results in a weight gain of at least 1 pound, at least 2 pounds, at least 3 pounds, at least 4 pounds, at least 5 pounds, at least 6 pounds, at least 7 pounds, at least 8 pounds, at least 9 pounds, at least 10 pounds, at least 11 pounds, at least 12 pounds, at least 13 pounds, at least 14 pounds or at least 15 pounds as compared to pre-treatment body weight.

In some embodiments, a CFTR mRNA is administered in combination with one or more CFTR potentiators and/or correctors. Suitable CFTR potentiators and/or correctors include ivacaftor (trade name Kalydeco®), lumacaftor (trade name Orkambi®) or the combination of ivacaftor and lumacaftor. In some embodiments, a CFTR mRNA is administered in combination with one or more other CF treatment such as hormone replacement therapies, thyroid hormone replacement therapy, non-steroidal inflammatory drugs, and prescription dronabinol (Marinol®) during treatment.

In some embodiments, the CF patient receives a concomitant CFTR modulator therapy. In some embodiments, the concomitant CFTR modulator therapy is given during the CFTR mRNA treatment regimen. In some embodiments, the concomitant CFTR modulator therapy is given before commencing the CFTR mRNA treatment regimen. In some embodiments, the concomitant CFTR modulator therapy is commenced after the CFTR mRNA treatment regimen.

Various CFTR modulator therapies are known in the art. For example, in some embodiments, the CF patient receives a CFTR modulator therapy comprising ivacaftor. In some embodiments, the CF patient receives a CFTR modulator therapy comprising lumacaftor. In some embodiments, the CF patient receives a CFTR modulator therapy comprising tezacaftor. In some embodiments, the CF patient receives a CFTR modulator therapy comprising ivacaftor/lumacaftor. In some embodiments, the CF patient receives a CFTR modulator therapy comprising tezacaftor/lumacaftor.

In some embodiments, CFTR potentiators and/or correctors and/or other cystic fibrosis treatments may be administered prior to, concurrently or subsequent to the administration of a CFTR mRNA according to the present invention. For example, CFTR potentiators and/or correctors and/or other cystic fibrosis treatments may be administered at 1 hour or longer, at 2 hours or longer, at 4 hours or longer, at 6 hours or longer, at 8 hours or longer, at 10 hours or longer, at 12 hours or longer, at 18 hours or longer, at 24 hours or longer, at 36 hours or longer, at 48 hours or longer, at 72 hours or longer, at 1 week or longer, at 2 weeks or longer, at 3 weeks or longer, or at 1 month or longer prior to or following administration of a CFTR mRNA according to the invention.

EXAMPLES

While certain compounds, compositions and methods of the present invention have been described with specificity in accordance with certain embodiments, the following examples serve only to illustrate the compounds of the invention and are not intended to limit the same.

Example 1. Formulation of mRNA/Liposome Composition

Codon-optimized Human Cystic Fibrosis Transmembrane Conductance Regulator (CFTR) messenger RNA comprising the sequence of SEQ ID NO:1 was synthesized by in vitro transcription from a plasmid DNA template encoding the CFTR gene, which was followed by the addition of a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A) tail. The mRNA encoding CFTR protein also comprised 5' and 3' untranslated regions (UTRs). The final mRNA construct had the sequence of SEQ ID NO: 6 with a 3' poly(A) tail of approximately 400 to 700 nucleotides in length, as determined by gel electrophoresis.

Three biodegradable lipid components were combined in solid form and then dissolved together in ethanol to provide an ethanol-based lipid solution. An aqueous-based solution comprising the exemplary mRNA encoding CFTR protein in a citrate buffer was combined with the ethanol-based lipid solution, isolated and dialyzed into the final formulation containing 10% (w/v) trehalose in water for injection, adjusted to an mRNA concentration of 0.6 mg/mL. For administration to human subjects, the final formulation was filled into single-use vials. The nominal fill volume of each vial was 3.2 mL.

The three biodegradable components all contributed to the final drug product characteristics. The first component was the ionizable lipid, imidazole cholesterol ester (ICE). This afforded a positively charged environment at low pH which facilitates efficient encapsulation of the negatively charged mRNA. It may also play a key role in cell surface interaction to allow for cellular uptake. The second component of the LNP was 1,2-dioleoyl-sn-glycero-3-phosphoethanolamine (DOPE). DOPE is a zwitterionic lipid that has been reported to have fusogenic properties to enhance uptake and release of the drug payload. The final component was a PEGylated (i.e., PEG-modified) lipid known as 1,2-dimyristoyl-sn-glycerol, methoxypolyethylene glycol (DMG-PEG-2K). The addition of this PEGylated lipid provided control over particle size and stability of the nanoparticle and may provide enhanced mucopentrating properties for lung uptake. The nominal nitrogen/phosphorus (N/P) charge ratio of the LNP was 4 and the average particle size range for the mRNA encapsulated in the LNP was 40-60 nm.

Example 2. Dosing of CFTR mRNA/Liposome Composition

These studies evaluated a CFTR mRNA/liposome composition in a Sprague-Dawley rat model. No adverse effects on the central nervous system (CNS), cardiovascular (CV) system or respiration were observed.

CNS Evaluations

Neurobehavioral evaluations were performed on 6 males/group prior to dosing and on Day 1 (4 and 24 hours post-dosing). Temperature, humidity, noise level, and illumination of each room were measured and recorded to ensure that variations in environmental conditions were minimal during all evaluations. There were no effects on neurobehavior related to treatment with hCFTR mRNA-loaded ICE-based liposomes or ICE-based liposome vehicle control at inhaled doses up to 6.70 mg/kg hCFTR mRNA-loaded ICE-based liposomes.

Cardiovascular Evaluations

Male Sprague-Dawley rats (n=5/group), which had previously been implanted with telemetry devices, were dosed via nose-only inhalation with hCFTR mRNA-loaded ICE-based liposomes for up to 6 hours at target doses of 0 (0.9% Saline control) or 0.7, 3.75 or 6.4 mg/kg of hCFTR mRNA-loaded ICE-based liposomes or ICE-based liposome vehicle control (non-mRNA containing LNP suspended in a solution containing 10% trehalose) (achieved doses of 0, 0.86, 3.52, 6.02 or 0 mg/kg, respectively). For target doses at 0.7 and 3.75 mg/kg, air was administered following the end of exposure to make the total restrained time equivalent among all doses. Each dose day was followed by a minimum 7-day washout period. All animals were returned to the colony upon completion of all evaluations.

Telemetry parameters included cardiovascular parameters (systolic, diastolic, mean blood pressure, pulse pressure, heart rate and electrocardiographic parameters [PR, QRS, QT, QTc]), activity, and body temperature. Other parameters evaluated during the study were viability, clinical observations and body weight. Mean aerosol concentrations and estimated total delivered doses of hCFTR mRNA-loaded ICE-based liposomes and ICE-based liposome vehicle (total lipid) are summarized in Table 3.

TABLE 3

Mean hCFTR mRNA-Loaded Liposome and Liposome Aerosol Concentrations and Estimated Total Delivered Doses

| | hCFTR mRNA-loaded Liposome Aerosol | hCFTR mRNA-loaded Liposome Delivered Dose (mg/kg) | |
|---|---|---|---|
| Treatment | Concentration (µg/L) Achieved | Exposure Duration (mins) | Mean Achieved[a] |
| Control | 0 | 360 | 0 |
| Vehicle | 0 | 360 | 0 |
| Low | 30.5 | 40 | 0.86 |
| Mid | 23.7 | 210 | 3.52 |
| High | 23.7 | 360 | 6.02 |

[a] Overall mean of each individual animal for each treatment group. This dose reflects the total delivered dose of hCFTR mRNA.

In addition to this study in rats, similar cardiovascular evaluations were also performed as repeat-dose studies in rats and monkeys. In those repeat-dose studies, no test article-related effects were observed on any CV parameters evaluated up to the highest doses evaluated (6.7 mg/kg in rats and 0.691 mg/kg in monkeys).

Respiratory Evaluations

Respiratory effects of hCFTR mRNA-loaded ICE-based liposomes were evaluated as part of the single-dose and repeat-dose studies in rats and monkeys. An increase in minute volume was observed after inhalation administration of hCFTR mRNA-loaded ICE-based liposomes to Sprague Dawley rats, as well as respiratory rate and tidal volume, in all dose groups up to 6.4 mg/kg hCFTR mRNA-loaded ICE-based liposomes, as well as in 10% trehalose controls.

No effects were observed on respiratory parameters, including respiration rate, tidal volume and derived minute volume after inhalation administration of hCFTR mRNA-loaded ICE-based liposomes to Sprague-Dawley rats at repeat doses up to 6.7 mg/kg or cynomolgus monkeys at single or repeat doses up to 0.85 mg/kg or 0.691 mg/kg, respectively.

There is minimal toxicological concern regarding ICE, DOPE, and DMG-PEG 2000 as components of the composition developed for inhalation administration. In an in silico genotoxicity evaluation, ICE is predicted to be negative for bacterial mutagenicity. This is consistent with the negative mutagenicity/genotoxicity data that are available for imidazole and propionic acid, the 2 components of the imidazole-propionic acid moiety of ICE, and for cholesterol. DOPE is a variant of the glycerophospholipid, phosphatidylethanolamine, which is a component of lung surfactant. Degradation of DOPE would be expected to follow a similar path as for other glycerophospholipids, with the ultimate formation of ethanolamine and oleic acid, both of which are present in the circulation of infants and adults. DMG PEG 2000 is anticipated to have low toxicity based on information for the anticipated metabolic breakdown products PEG 2000 and myristic acid. There is minimal concern for local or systemic toxicity based on data from studies with PEGs of various sizes, while myristic acid is a fatty acid that is present in most animal and vegetable fats and is present in the circulation of infants and adults.

Example 3. Pharmacokinetics

In the study in this Example, Sprague-Dawley rats or monkeys were dosed for up to 6 hours (for rats) or for up to 2 hours (for monkeys) via inhalation with hCFTR mRNA-loaded ICE-based liposomes or with the ICE-based liposomes alone, and then sacrificed 24 hours later to measure the levels of hCFTR in various tissues. The target doses for are shown in Tables 4-6. The actual doses measured were 420, 630 and 850 µg/kg for hCFTR mRNA-loaded ICE-based liposomes administered to monkeys (corresponding to the target doses in the header of Table 4); 0.77, 4.05 and 6.70 mg/kg for hCFTR mRNA-loaded ICE-based liposomes administered to rats (corresponding to the target doses in the header of Table 5); and 0.77, 4.05 and 6.70 mg/kg for ICE-based liposomes administered to rats (corresponding to the target doses in the header of Table 6). Detailed tissue distribution results are presented below in Tables 4, 5, and 6.

TABLE 4

Mean Concentrations of hCFTR mRNA in Monkey Tissues and Blood 24 Hours Post-Inhalation of hCFTR mRNA-Loaded Liposomes

| | Males | | | | Females | | | |
|---|---|---|---|---|---|---|---|---|
| | | Target Inhaled Dose | | | | Target Inhaled Dose | | |
| Tissue [a] | Vehicle | 500 µg/kg | 750 µg/kg | 1000 µg/kg | Vehicle | 500 µg/kg | 750 µg/kg | 1000 µg/kg |
| Brain | BQL | 3.91 | 0.0968 | BQL | BQL | 2.05 | 0.110 | 1.18 |
| Heart | BQL | BQL | 0.165 | BQL | BQL | BQL | BQL | 0.537 |
| Kidney | BQL | BQL | BQL | 0.0523 | BQL | BQL | BQL | 0.231 |
| Larynx | 0.166 | BQL | 5.54 | 1.87 | BQL | 5.15 | 3.37 | 2.59 |
| Liver | BQL | BQL | 0.0670 | 1.27 | BQL | 0.917 | 0.147 | 8.48 |
| Lung (Average) | 0.110 | 208 | 67.2 | 82.1 | 0.426 | 819 | 1390 | 1880 |
| Spleen | BQL | 0.420 | BQL | BQL | BQL | BQL | 0.307 | 1.85 |
| Testis | BQL | BQL | BQL | 0.0912 | — | — | — | — |
| Ovary | — | — | — | — | BQL | 0.596 | BQL | 0.976 |

TABLE 4-continued

Mean Concentrations of hCFTR mRNA in Monkey Tissues and Blood 24 Hours Post-Inhalation of hCFTR mRNA-Loaded Liposomes

| | | Males | | | | Females | | |
|---|---|---|---|---|---|---|---|---|
| | | Target Inhaled Dose | | | | Target Inhaled Dose | | |
| Tissue [a] | Vehicle | 500 µg/kg | 750 µg/kg | 1000 µg/kg | Vehicle | 500 µg/kg | 750 µg/kg | 1000 µg/kg |
| Trachea | BQL | 0.176 | 0.993 | 1.65 | 0.0657 | 1.54 | 14.4 | 4.72 |
| Tracheobronchial LN | BQL | 30.9 | 0.284 | 70.3 | BQL | 0.147 | 468 | 5.28 |
| Blood | 0.0501 | BQL | 0.0433 | 0.0120 | 0.0188 | 0.00351 | 0.385 | 0.0121 |

BQL: Below limit of quantification

[a] Levels in tissue expressed as $10^6$ – copies/gm and levels in blood as $10^6$ – copies/mL, to express levels in comparable masses since 1 mL of blood~1 gm.

TABLE 5

Mean hCFTR mRNA Concentrations in Rat Tissues and Blood 24 hours Post hCFTR mRNA-Loaded Liposome Doses of 0.7, 3.75 or 6.4 mg/kg

| | | Males | | | | Females | | |
|---|---|---|---|---|---|---|---|---|
| Tissue | Vehicle | 0.7 mg/kg | 3.75 mg/kg | 6.4 mg/kg | Vehicle | 0.7 mg/kg | 3.75 mg/kg | 6.4 mg/kg |
| Brain | BLQ | BLQ | BLQ | 55.4 | BLQ | BLQ | BLQ | 32.4 |
| Heart | BLQ | BLQ | BLQ | 17.0 | BLQ | BLQ | BLQ | 41.1 |
| Kidney | BLQ | BLQ | BLQ | 0.37 | BLQ | BLQ | BLQ | 0.95 |
| Larynx | 0.20 | BLQ | BLQ | 4178 | BLQ | BLQ | BLQ | 1410 |
| Liver | NC | BLQ | BLQ | 2.3 | BLQ | BLQ | BLQ | 9.75 |
| Lung | .061 | 2057 | 59,094 | 156130 | BLQ | 1,361 | 33,649 | 180,000 |
| Nasal Turbinate | .12 | BLQ | BLQ | 792 | BLQ | BLQ | BLQ | 1450 |
| Spleen | BLQ | BLQ | BLQ | 3.8 | BLQ | BLQ | BLQ | 1.09 |
| Testis | 0.08 | BLQ | BLQ | 9.5 | BLQ | BLQ | BLQ | BLQ |
| Ovary | BLQ | BLQ | BLQ | BLQ | BLQ | BLQ | BLQ | 6.99 |
| Trachea | BLQ | BLQ | BLQ | 2980 | BLQ | BLQ | BLQ | 787 |
| Tracheobronchial LN | BLQ | BLQ | BLQ | 108 | BLQ | BLQ | BLQ | 1.48 |
| Blood | 0.076 | 0.68 | 14.7 | 0.20 | .016 | 0.29 | 133 | 1.48 |

BLQ: below level of quantitation

Concentrations in tissues (copies × 106/g)/concentrations in blood (copies × 106/mL), with the assumption that 1 mL of blood ≈ 1 g.

TABLE 6

Mean ICE Concentrations in Rat Tissues (µg/g) and Blood (µg/mL) 24 hours Post-Inhalation Dosing with hCFTR mRNA-Loaded Liposomes (Doses of 0.7, 3.75 or 6.4 mg/kg)

| | | Males | | | | Females | | |
|---|---|---|---|---|---|---|---|---|
| Tissue | Vehicle | 0.7 mg/kg | 3.75 mg/kg | 6.4 mg/kg | Vehicle | 0.7 mg/kg | 3.75 mg/kg | 6.4 mg/kg |
| Brain | BLQ | BLQ | BLQ | BLQ | BLQ | BLQ | BLQ | BLQ |
| Heart | BLQ | BLQ | BLQ | BLQ | BLQ | BLQ | BLQ | BLQ |
| Kidney | BLQ | BLQ | BLQ | BLQ | BLQ | BLQ | BLQ | BLQ |
| Larynx | 1.57 | 2.61 | BLQ | 1.57 | BLQ | BLQ | BLQ | 1.41 |
| Liver | BLQ | BLQ | BLQ | BLQ | BLQ | BLQ | BLQ | BLQ |
| Lung | 317 | 20.3 | 139 | 245 | 293 | 22.5 | 147 | 317 |
| Nasal Turbinate | 0.290 | BLQ | BLQ | 0.796 | BLQ | BLQ | BLQ | 0.724 |
| Spleen | NA | BLQ | BLQ | BLQ | BLQ | BLQ | BLQ | BLQ |
| Testis | BLQ | BLQ | BLQ | BLQ | BLQ | BLQ | BLQ | BLQ |
| Ovary | BLQ | BLQ | BLQ | BLQ | BLQ | BLQ | BLQ | BLQ |

TABLE 6-continued

Mean ICE Concentrations in Rat Tissues (µg/g) and Blood (µg/mL) 24 hours Post-Inhalation Dosing with hCFTR mRNA-Loaded Liposomes (Doses of 0.7, 3.75 or 6.4 mg/kg)

| | Males | | | | Females | | | |
|---|---|---|---|---|---|---|---|---|
| Tissue | Vehicle | 0.7 mg/kg | 3.75 mg/kg | 6.4 mg/kg | Vehicle | 0.7 mg/kg | 3.75 mg/kg | 6.4 mg/kg |
| Trachea | 6.27 | BLQ | BLQ | 3.65 | BLQ | BLQ | BLQ | 2.40 |
| Tracheobronchial LN | BLQ | BLQ | BLQ | BLQ | BLQ | BLQ | BLQ | BLQ |
| Blood | BLQ | BLQ | BLQ | BLQ | BLQ | BLQ | BLQ | BLQ |

BLQ: below level of quantitation
Concentrations in tissues (copies × 106/g)/concentrations in blood (copies × 106/mL), with the assumption that 1 mL of blood ≈ 1 g.

These data show high levels of mRNA in lung tissue and associated respiratory tract issues such as larynx, trachea, tracheobronchial lymph nodes, and nasal turbinates with lower or background levels in heart, brain, liver, kidney, spleen, testis, and ovary, particularly at lower doses of administration, with the highest dose showing hCFTR mRNA distribution across various tissues. Lung levels were high and dose-responsive in both rats and NHP, with the highest levels seen at 6.4 mg/kg in rats.

Figure 2:
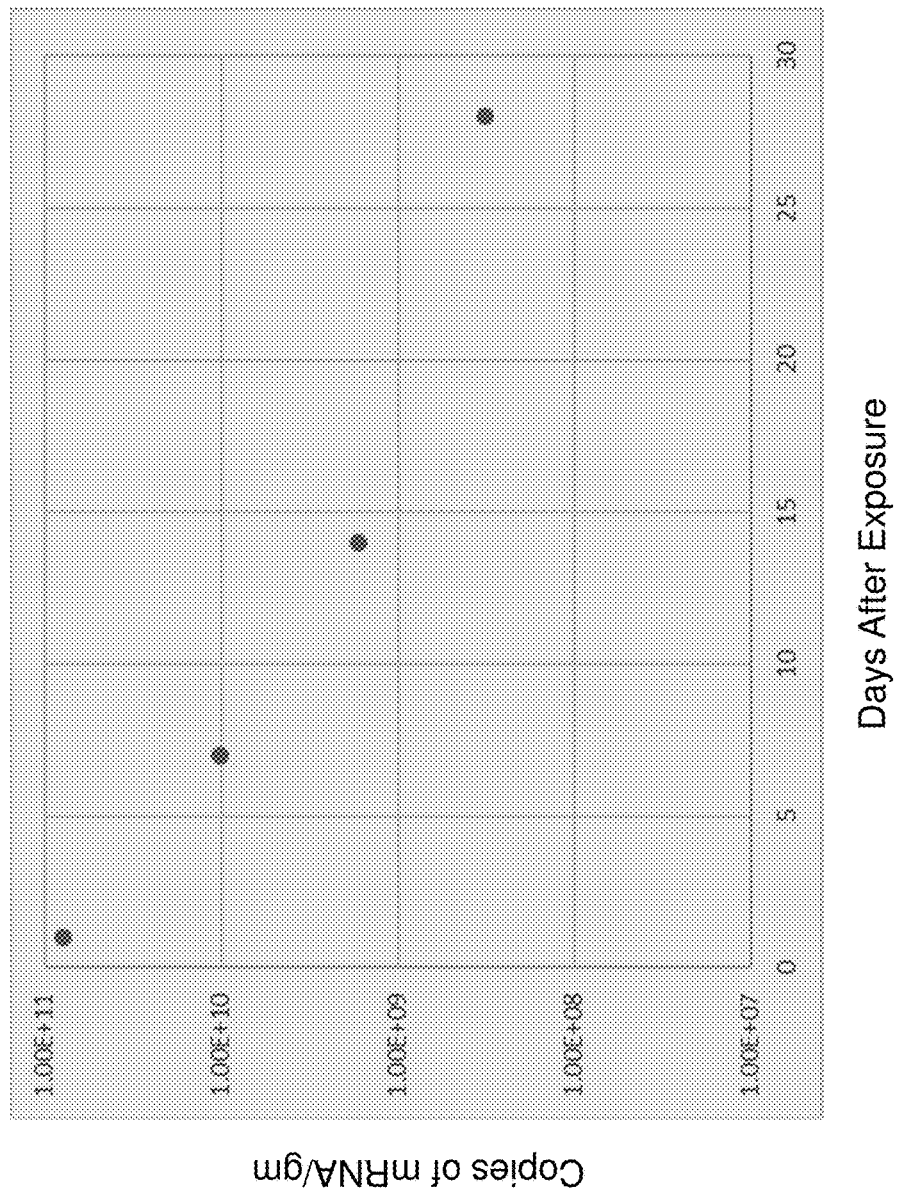
FIG. 2 depicts an exemplary graph of the number of copies of mRNA/gm in rat lung tissue after the rats were treated with hCFTR mRNA-loaded liposomes.
Figure 3:
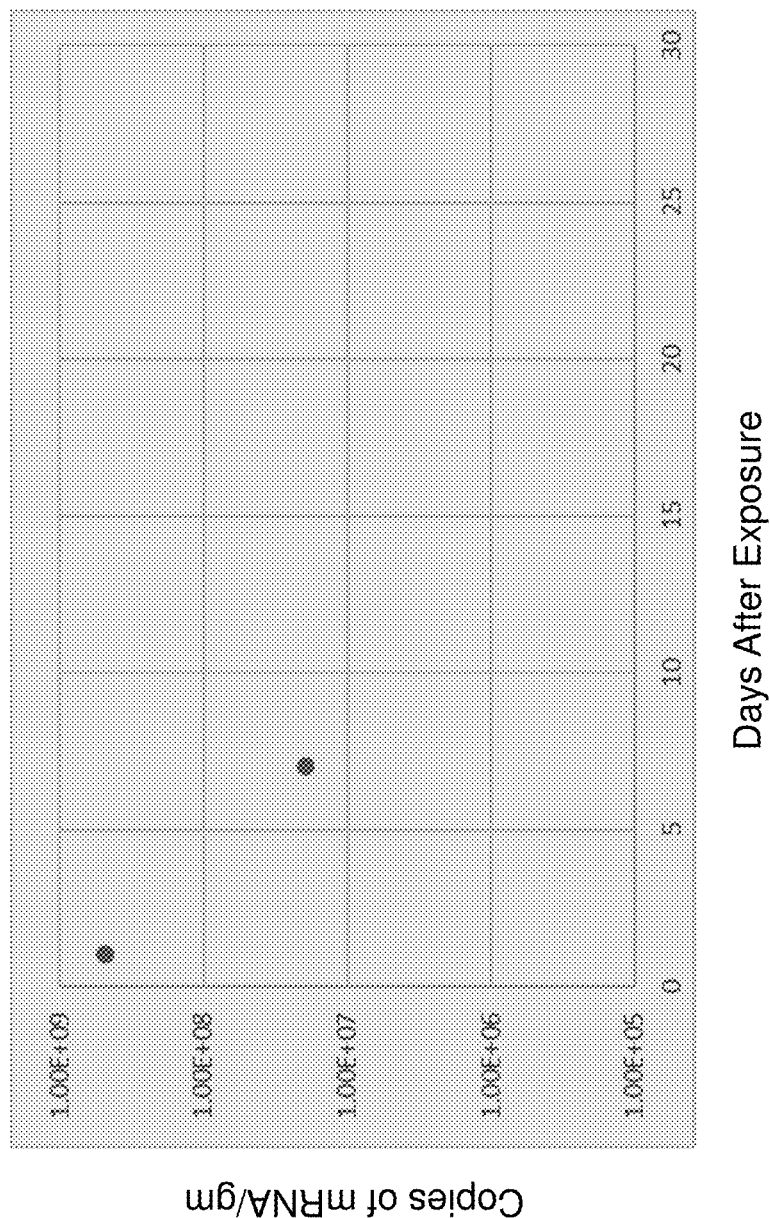
FIG. 3 depicts an exemplary graph of the number of copies of mRNA in non-human primate (NHP) lung tissue after the NHPs were treated with hCFTR mRNA-loaded liposomes.

Kinetics of lung clearance of mRNA was measured reliably in rats since more sacrifice times could be used than for monkeys. FIG. 2 indicates a single component exponential decay with a half-life of approximately 2-3 days. Only two data points were available for NHP (FIG. 3) and these data appear consistent with the rat data in view of differences in dose.

As shown in Table 5, levels of mRNA in the lung were dose-dependent in a relatively linear manner. Lung tissue measurements made after a 28 day recovery period at the end of the 29-day study showed a decline in exposure of approximately 100-fold, similar to that seen 28 days after the single dose study.

The toxicokinetics of ICE liposomes were also examined. There were no measurable levels of ICE liposomes in whole blood. There were, however, measurable and dose-responsive levels of ICE liposomes in the lung tissue in rats (Table 6).

Example 4. In Vitro Activity of hCFTR in Human Bronchial Epithelial Cells

This Example illustrates a study where hCFTR mRNA was transfected into cultured human bronchial epithelial cells, whereupon the protein expressed from transfected hCFTR mRNA provided a significant increase in chloride transport across the bronchial epithelial cell membrane compared to buffer, thereby demonstrating the functional efficacy of the transfected mRNA.

The changes in chloride transport across the bronchial epithelial cell membrane was measured by short circuit current output in a Ussing epithelial voltage clamp apparatus (i.e., a Ussing chamber). Specifically, using an established Ussing Chamber procedure (Charles River Laboratories), hCFTR mRNA encapsulated in a liposome comprising ICE, DOPE, and a PEG-modified lipid was incubated for 2 or 4 hours on the apical (mucosal) or basolateral (serosal) sides, or both sides, of human bronchial epithelial cells. A buffer blank also was included as a control, for example, to assess chloride transport by endogenous CFTR in the cells. Next, Forskolin-induced chloride channel activity was measured using the Ussing chamber assay. Following the measure of the current change as indicative of chloride transport across the bronchial epithelial cell membrane, a CFTR inhibitor was added to the samples to show that current change was due to CFTR activity.

Figure 4:
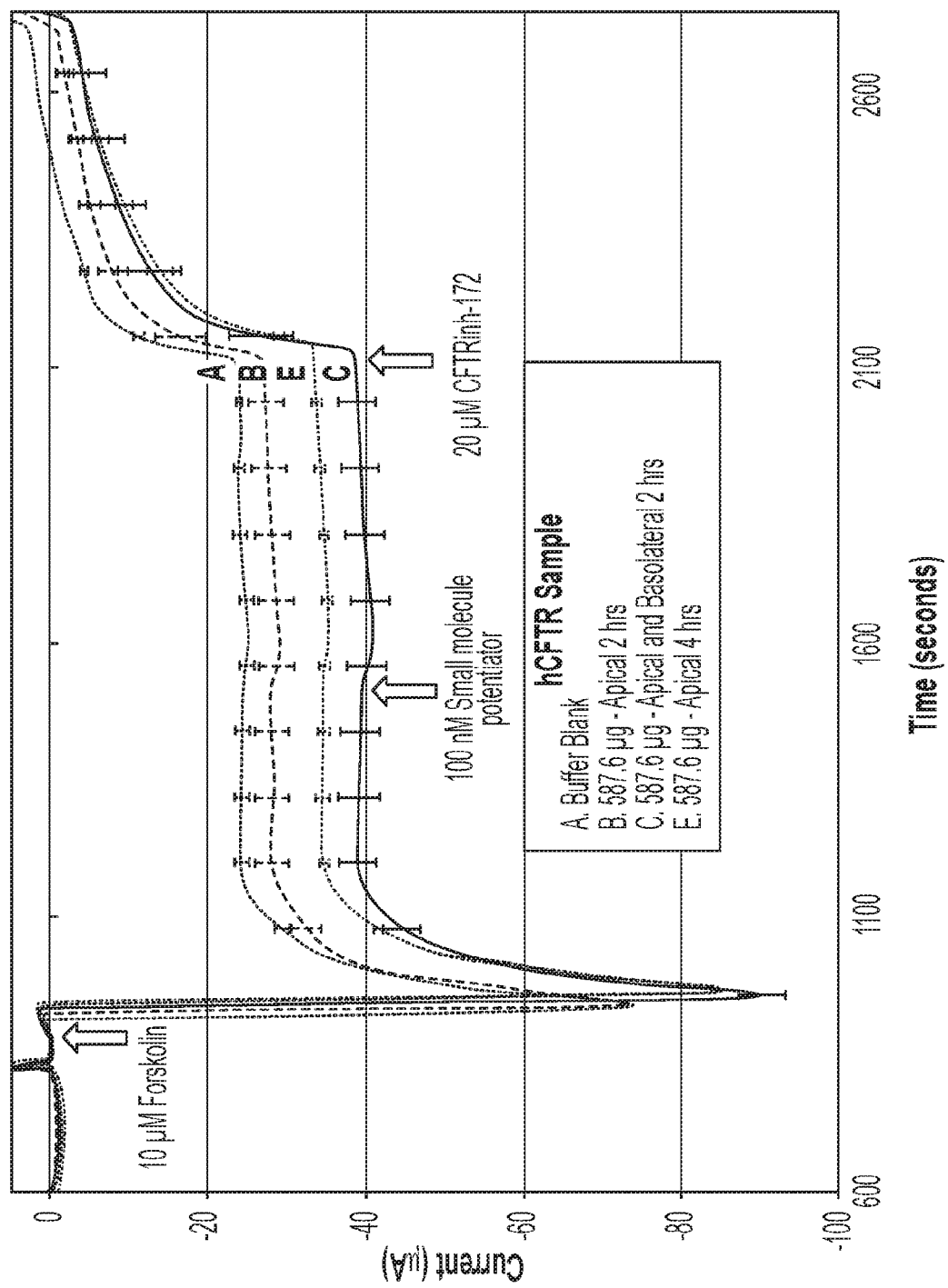
FIG. 4 depicts an exemplary graph showing increased chloride channel activity demonstrated after transfection with hCFTR mRNA-loaded liposomes.

As shown in FIG. 4, compared to the control group (A. Buffer Blank), treatment of the apical (mucosal) epithelial surface for 2 or 4 hours (Samples B and E, respectively) and the apical and basolateral (serosal) epithelial surfaces for 2 hours (Sample C) with hCFTR mRNA provided a significant increase in chloride channel activity. Additionally, the chloride activity in all groups was inhibited by the CFTR inhibitor-172. The results of this study show that the hCFTR mRNA delivered in a liposome to human bronchial epithelial cells produced active CFTR protein in those cells. It also shows that the active CFTR protein produced from the hCFTR mRNA provided significantly increased chloride transport, compared to endogenous CFTR protein, across the cell membranes of the transfected human bronchial epithelial cells.

Example 5. hCFTR Protein Expression in Mice after Single Dose of hCFTR mRNA/Liposome Composition This Example illustrates that CFTR protein deficiency in lung cells of CFTR knockout (KO) mice can be addressed by pulmonary delivery of an hCFTR mRNA/liposome composition.

Delivery of an hCFTR mRNA/liposome composition to the respiratory tract of CFTR KO mice was achieved by nebulization of the composition via a vibrating mesh nebulizer. The dose of the composition delivered was a function of the concentration of the test article, the flow rate of the nebulized material, and the length of the nebulization period. Following dose administration, a human-specific antibody directed to the carboxy terminus of hCFTR was utilized to visualize protein expression and distribution using immunohistochemistry (IHC).

Figure 5:
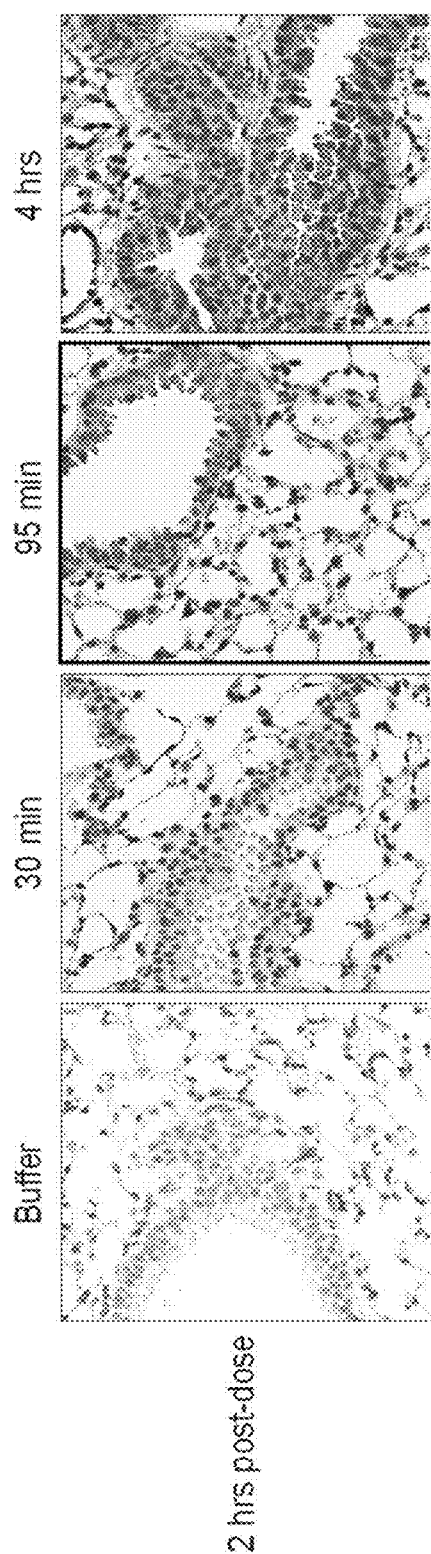
FIG. 5 depicts expression of hCFTR protein in murine airway epithelial cells in lungs of CFTR knock out (KO) mice two hours after administration of hCFTR mRNA-loaded liposomes.
Figure 6:
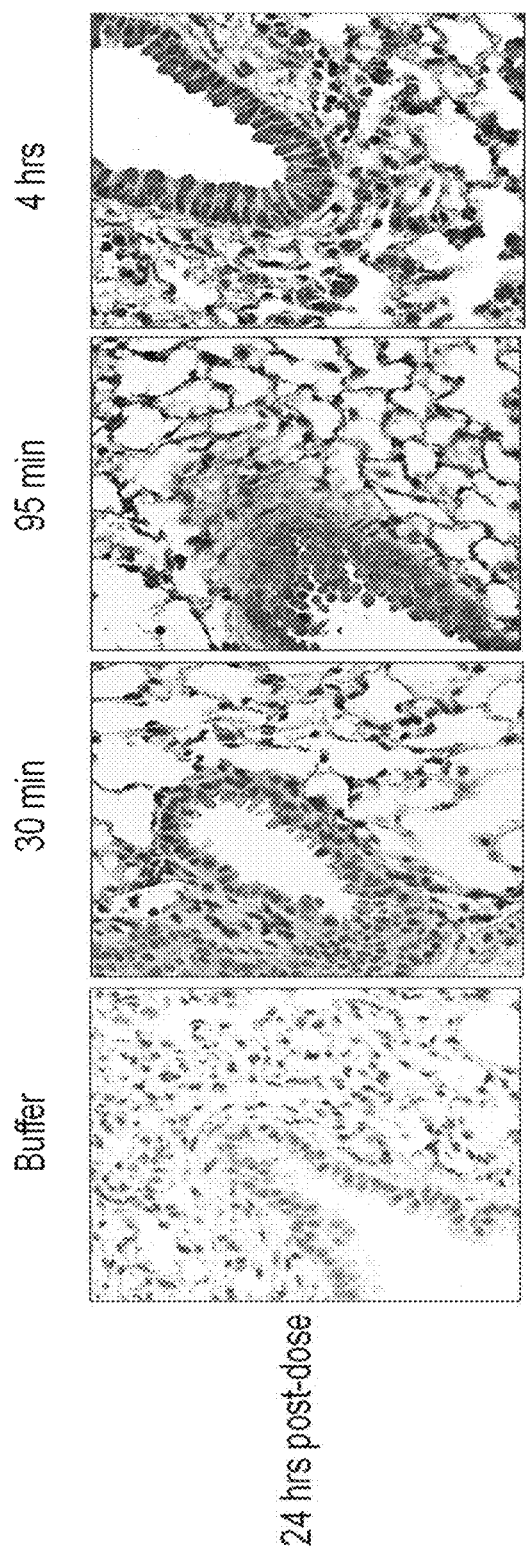
FIG. 6 depicts expression of hCFTR protein in murine airway epithelial cells in lungs of CFTR knock out (KO) mice twenty-four hours after administration of hCFTR mRNA-loaded liposomes.

CFTR KO mice were given a single inhaled administration of the composition for nebulization periods of 30, 95 or 240 minutes. A control group received a 240-minute nebulization with buffer only. At 2 or 24 hours post administration, animals were sacrificed, and lung tissue isolated for IHC (FIGS. 5 and 6). Dose-dependent expression of hCFTR protein was observed, with minimal staining for hCFTR present after a 30-minute nebulization period at both time points. Increased staining was observed in the 90- and 240-minute nebulization periods. Furthermore, an increase in staining was also seen between the 2- and 24-hour time points. Administration of the hCFTR mRNA/liposome composition led to wide distribution of hCFTR protein throughout the lung, including the bronchial epithelium and alveoli of both the upper and lower airways.

Example 6. Distribution of hCFTR after Single Dose of hCFTR mRNA/Liposome Composition in Non-Human Primates This Example illustrates that administration of the hCFTR mRNA/liposome composition to non-human primates (NHPs) by aerosol results in widespread distribution of hCFTR mRNA in the lung and limited delivery thereof to the larynx, trachea and tracheobronchial lymph nodes.

Figure 7:
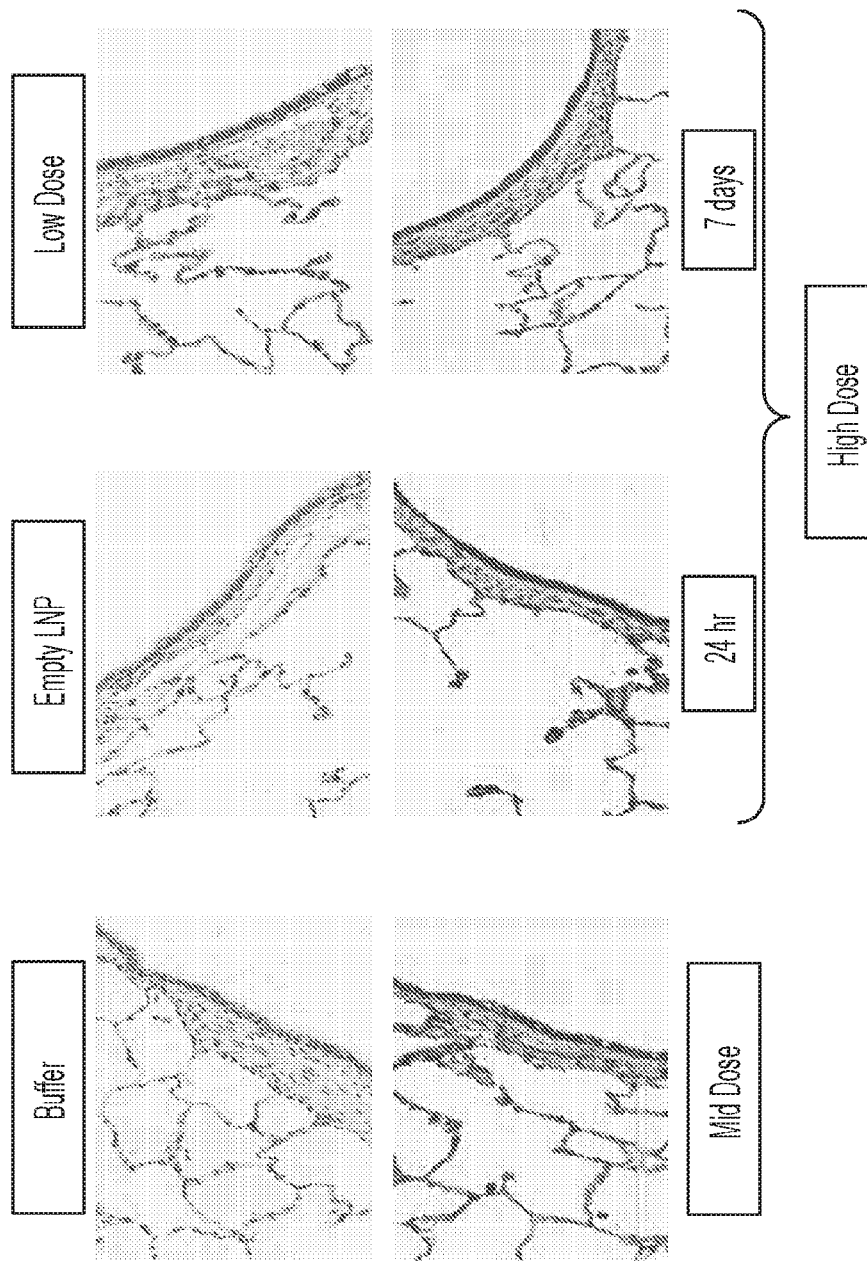
FIG. 7 depicts hCFTR protein expression in lung tissue from a non-human primate (NHP) after a single dose of hCFTR mRNA-loaded liposomes, detected using immunohistochemistry.
Figure 8:
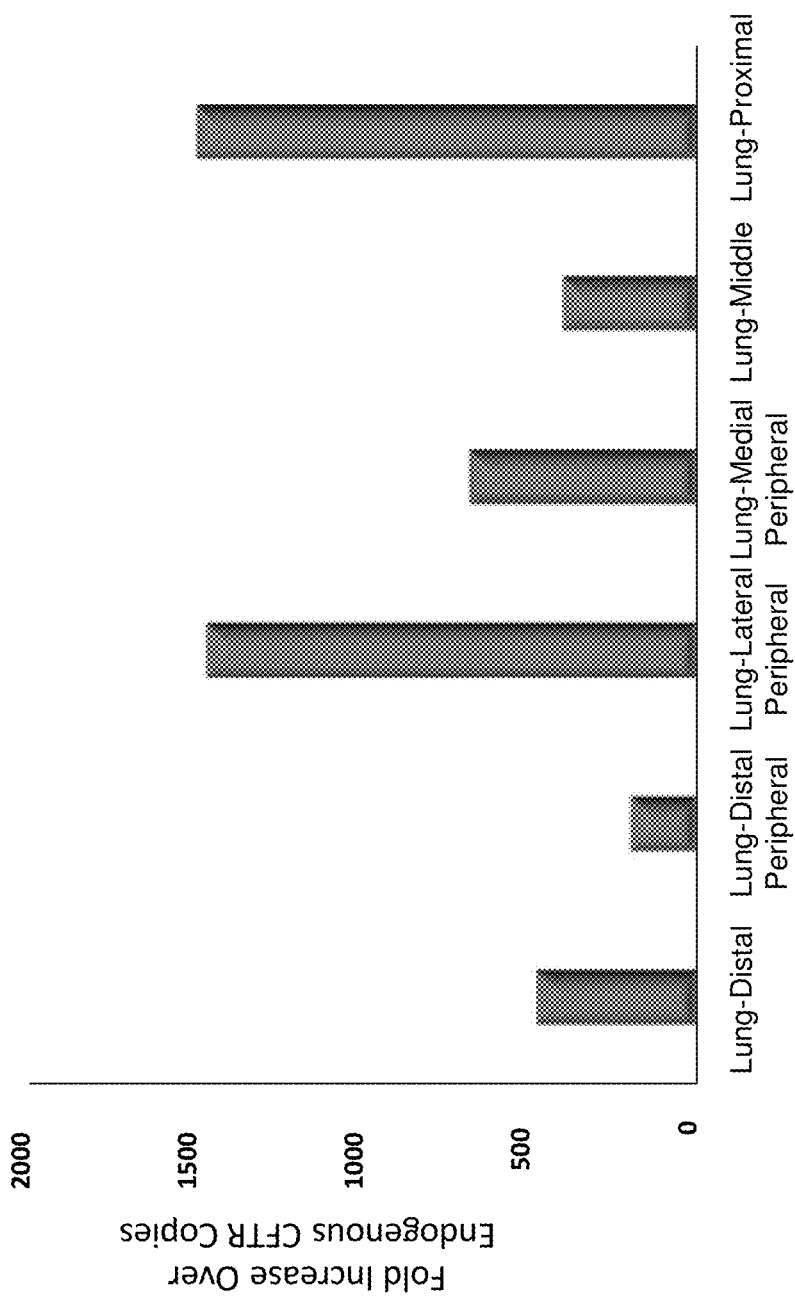
FIG. 8 depicts an exemplary graph of fold-increase of copies of CO-hCFTR mRNA over endogenous levels of CFTR mRNA in non-human primate lung tissue after a single dose of a composition comprising an mRNA encoding a CFTR protein.
Figure 9:
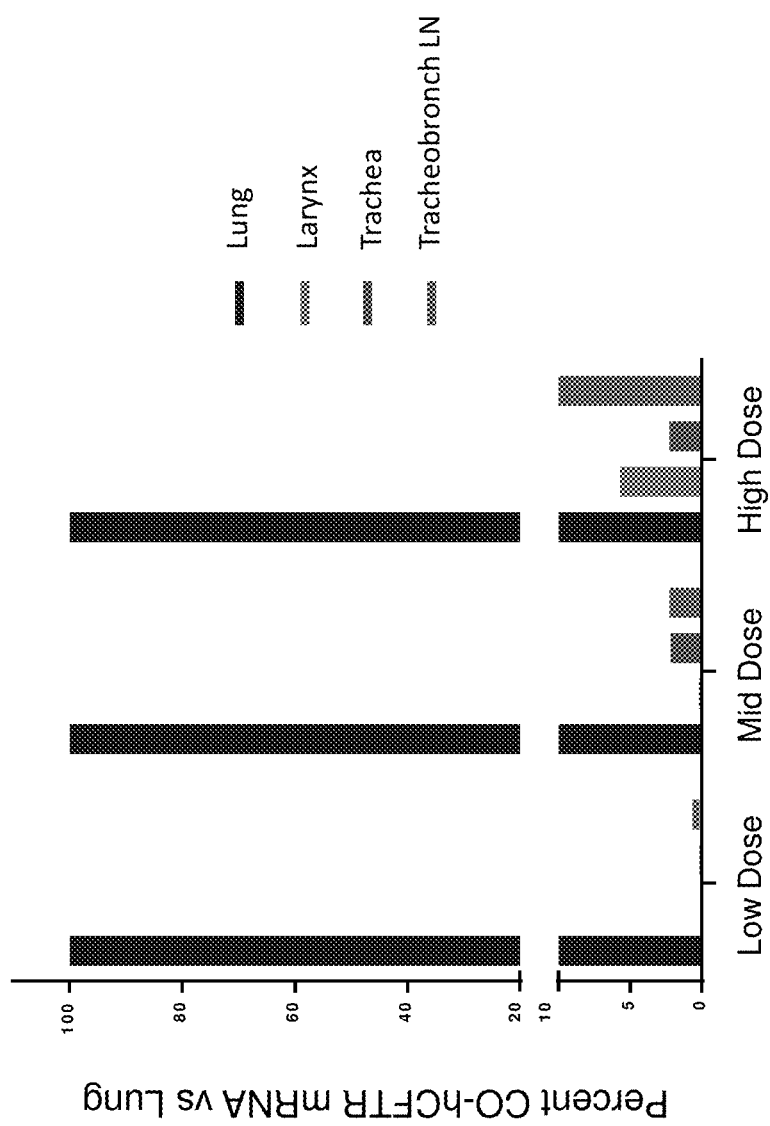
FIG. 9 depicts an exemplary graph of percent of CO-hCFTR mRNA delivered to non-human primate lung tissue as compared to airway tissue after a single dose of a composition comprising an mRNA encoding a CFTR protein.

NHPs were treated with a single aerosol exposure of a CO-hCFTR mRNA/liposome composition. As shown in FIG. 7, immunohistochemistry (IHC) staining of lung cross-sections demonstrate a dose-dependent increase in intensity for positive hCFTR protein detection. Additionally, when hCFTR mRNA was detected and quantified in tissues from the NHPs, widespread distribution was found throughout the lungs of the monkeys, with CO-hCFTR levels orders of magnitude (>200-fold) over endogenous CFTR (FIG. 8). Additionally, the lungs of the monkeys, which were the target organs, received >90% of the CO-CFTR dose that entered the airway, when compared to other respiratory tract tissues that were tested (FIG. 9).

Example 7. Systemic Biodistribution of hCFTR after Single Dose of hCFTR mRNA/Liposome Composition in Non-Human Primates This Example illustrates that administration of the hCFTR mRNA/liposome composition to non-human primates (NHPs) by aerosol results minimal systemic exposure.

NHPs were treated with a single aerosol exposure of a CO-hCFTR mRNA/liposome composition. As shown in Table 7, the biodistribution of hCFTR mRNA in other organs is several orders of magnitude lower than in the lung.

Example 8. Treatment of Cystic Fibrosis Subjects with CO-hCFTR mRNA/Liposome Composition The study in this Example is designed to evaluate a CO-CFTR mRNA liposome composition in patients with cystic fibrosis.

A CO-hCFTR mRNA liposome composition (CO-hCFTR composition) is administered by nebulization to subjects with cystic fibrosis. The concentration of the CO-hCFTR mRNA is 0.6 mg/ml. A nebulizer is used to administer the CO-hCFTR composition by nebulization at a nebulisation rate of approximately 0.3 mL/minute. The CO-hCFTR composition will be administered to subjects at the following 3 dose levels: 8.0, 16.0, or 24.0 mg of CO-hCFTR mRNA (nominal dose levels) either once or once per week for five weeks. Other subjects will be dosed with placebo control.

In order to receive treatment with administration of the CO-hCFTR composition, patients will have a confirmed diagnosis of CF as defined by all of the following: a sweat chloride value of ≥60 mmol/L by quantitative pilocarpine iontophoresis (documented in the subject's medical record), a confirmed disease-causing CFTR mutation (genotype confirmed at the screening visit), and chronic sinopulmonary disease and/or gastrointestinal/nutritional abnormalities consistent with CF disease; clinically stable CF disease, e.g., $FEV_1 \geq 50\%$ and ≤90% of the predicted normal for age, gender, and height at screening, resting oxygen saturation ≥92% on room air (pulse oximetry), and body mass index≥17.5 kg/m' and weight ≥40 kg. Subjects who are receiving lumacaftor/ivacaftor combination drug (ORKAMBI) will remain on it for the duration of the study preferably at a stable dose.

Procedures and tests that will be conducted both for screening subjects and during the study to evaluate the biological activity of the CO-CFTR mRNA liposome composition include: vital signs, pulse oximetry, physical exami-

TABLE 7

Biodistribution of hCFTR mRNA in non-human primates after nebulization of hCFTR mRNA-loaded liposomes.

| Tissue | Males | | | | Females | | | |
|---|---|---|---|---|---|---|---|---|
| | LNP Vehicle | 0.191 mg/kg | 0.329 mg/kg | 0.691 mg/kg | LNP Vehicle | 0.191 mg/kg | 0.329 mg/kg | 0.691 mg/kg |
| Brain | BQL | — | — | 1.75E+06 | BQL | — | — | 6.17E+06 |
| Heart | 1.24E+04 | — | — | 3.02E+05 | 4.67E+05 | — | — | 2.22E+07 |
| Kidney | BQL | — | — | 3.23E+04 | 6.10E+04 | — | — | 1.06E+05 |
| Larynx | 1.26E+04 | — | — | 1.71E+07 | 8.50E+04 | — | — | 1.74E+08 |
| Liver | BQL | — | — | 6.37E+06 | 7.83E+04 | — | — | 4.25E+05 |
| Lung Distal | 4.48E+05 | 5.39E+08 | 1.69E+09 | 8.58E+09 | 1.56E+06 | 9.35E+08 | 3.61E+09 | 9.89E+09 |
| Lung Distal Peripheral | 1.69E+05 | 2.88E+08 | 1.49E+09 | 4.31E+09 | 7.56E+05 | 1.43E+09 | 1.34E+09 | 3.04E+09 |
| Lung Lateral Peripheral | 3.35E+05 | 5.79E+08 | 4.36E+09 | 1.61E+10 | 1.84E+06 | 1.53E+09 | 5.82E+09 | 2.12E+10 |
| Lung Medial Peripheral | 3.89E+05 | 5.97E+08 | 4.91E+09 | 6.28E+09 | 1.86E+06 | 1.88E+09 | 3.17E+09 | 1.21E+10 |
| Lung Middle | 2.01E+05 | 4.88E+08 | 2.59E+09 | 1.49E+10 | 1.40E+06 | 2.12E+09 | 5.34E+09 | 2.45E+10 |
| Lung Proximal | 2.96E+05 | 5.60E+08 | 5.52E+09 | 1.59E+10 | 2.16E+06 | 2.89E+09 | 5.98E+09 | 2.49E+10 |
| Ovary | — | — | — | — | 1.45E+05 | — | — | 5.47E+05 |
| Spleen | 4.43E+04 | — | — | 2.98E+05 | BQL | — | — | 1.85E+07 |
| Testes | BQL | — | — | 1.38E+05 | — | — | — | — |
| Trachea | 2.11E+04 | — | — | 4.92E+06 | 9.34E+05 | — | — | 9.79E+08 |
| Tracheobronchial LN | 1.11E+06 | — | — | 1.95E+09 | 1.39E+05 | — | — | 7.13E+09 |
| Blood (copies/mL) | 6.56E+04 | 5.96E+03 | 3.04E+03 | 9.83E+03 | 6.22E+03 | 8.06E+04 | 5.97E+05 | 1.30E+05 |

—: no sample collected, per study plan;
BQL: below quantifiable level
Lung and blood was collected from all groups, the other tissues were collected only from Groups 2 and 5. LNP vehicle is the 'empty' LNP, without hCFTR mRNA nation, spirometry, clinical laboratory tests (serum chemistry, hematology, coagulation, urinalysis, CRP), ECG, chest x-ray, Cystic Fibrosis Questionnaire-Revised (CFQ-R), serum pregnancy test, AE and concomitant medication reporting, weight measurement, blood sampling for CO-hCFTR mRNA and ICE assays and blood sampling for immune response assays. Subjects who were administered 24.0 mg of CO-hCFTR mRNA once per week for five weeks will additionally undergo bronchoscopy.

Bronchial epithelial cells obtained during bronchoscopies will be prepared for quantification of exogenous CO-hCFTR mRNA and endogenous CFTR mRNA by qPCR, and for a qualitative assessment of CFTR protein by Western blot analysis.

Additionally, during bronchoscopy, lower airway potential difference measurements will be performed to assess CFTR chloride channel activity in the bronchial epithelium. Potential difference measurements will be made at the lingula outlet of the left lung, as described by Dransfield et al. (Dransfield et al., Chest. (2013) 144:498-506). A stable potential with the mean value of a 10 second scoring interval after perfusion of each solution will recorded. CFTR activity will be estimated by the change in potential difference following perfusion with chloride-free isoproterenol.

The Cystic Fibrosis Questionnaire-Revised (CFQ-R; version for adolescents and adults [patients 14 years old and older]) will be completed in order to achieve both a baseline score and scores during the study for comparison. The results of the respiratory domain of the CFQ-R will be of primary interest; the minimal change from baseline representing a clinically important improvement in the respiratory domain was determined to be ≥4 (Quittner et al., Chest. (2009) 135:1610-8).

Example 9. CFTR Colocalization with Membrane Protein in Upper Airway Bronchial Cells This Example demonstrates CFTR protein expression in the lung and colocalization with the membrane tight junctions (ZO-1) after administration of the codon-optimized human CFTR mRNA.

Colocalization study protocol: The immunohistochemistry and colocalization study method described in this paragraph is common for Examples 9, 10, and 11. Lung delivery of the CFTR mRNA in non-human primates was followed by immunohistochemistry to detect the protein expression and membrane colocalization in the upper airway bronchial cells and lower airway epithelial cells and deep alveolar lung. The non-human primates in this study were grouped into five categories and were administered the following: (1) Control, Trehalose 10%; (2) Control, LNP vehicle; (3) CO-hCFTR low dose, 500 µg/kg, (4) CO-hCFTR medium dose, 750 µg/kg, (5) CO-hCFTR high dose, 1000 µg/kg. The mRNA-LNP formulation or controls (without mRNA) were administered daily. Accordingly, the animals were exposed for 60 minutes to the aerosol composition (Group 3, low dose, 500 µg/kg), 90 minutes of aerosol (Group 4, medium dose, 750 µg/kg), or 120 minutes of aerosol (Group 5, high dose) as described in Table 4. At the end of the study the animals were sacrificed and tissues collected for immunohistochemistry to detect the expression and localization of human CFTR protein in the lungs. For immunohistochemical detection of codon-optimized human CFTR protein, lung sections were incubated overnight at 4° C. with a 1:250 dilution of each of mouse monoclonal anti-CFTR antibody (MAB 25031, R & D Systems), and rabbit anti-ZO1 antibody (Ab214228, Abcam); or with anti-CFTR alone; and anti-ZO1 alone. Following overnight incubation, the sections were blocked with first blocking agent containing hydrogen peroxide, incubated with the secondary antibody (anti-mouse DyLight 594 for CFTR antibody, and anti-rabbit DyLight 488 antibody) and followed by second blocking in a solution containing 3% horse serum and 3% BSA and subjected to confocal microscopy for colocalization. DyLight 594 emits red signal, and DyLight 488 emits green, and upon colocalization of the two signals (and therefore the proteins each bind to), the optical merge yields yellow signal.

Figure 10A:
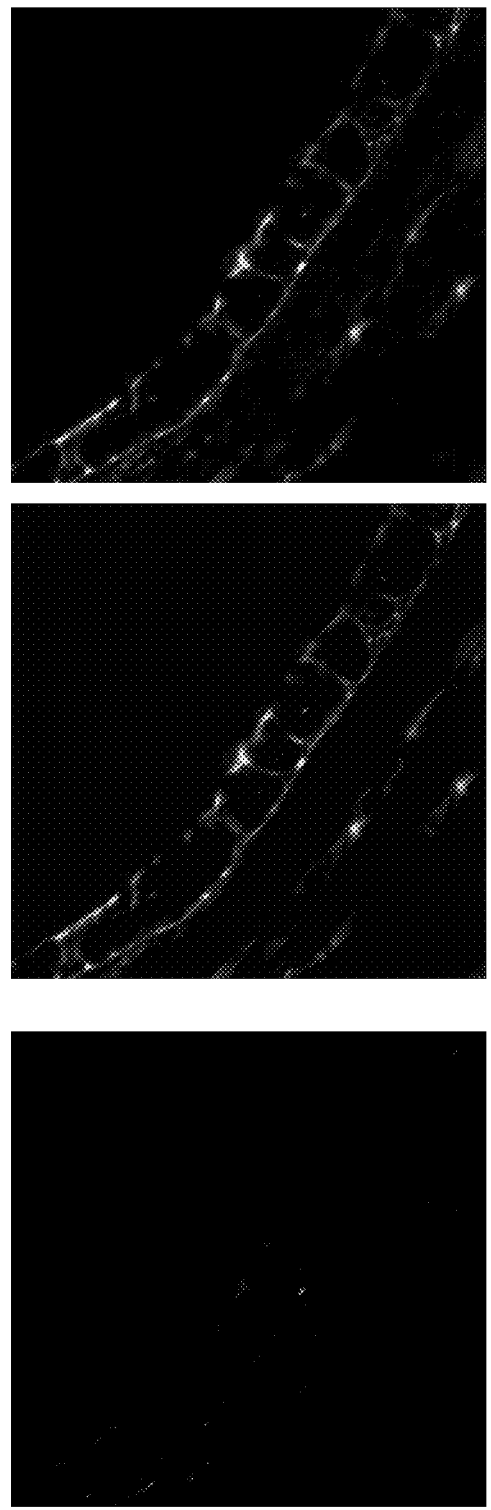
FIGS. 10A-C depicts expression of CFTR mRNA-derived protein in non-human primate upper bronchial epithelial cells and colocalization with endogenous ZO1 protein.
Figure 10B:
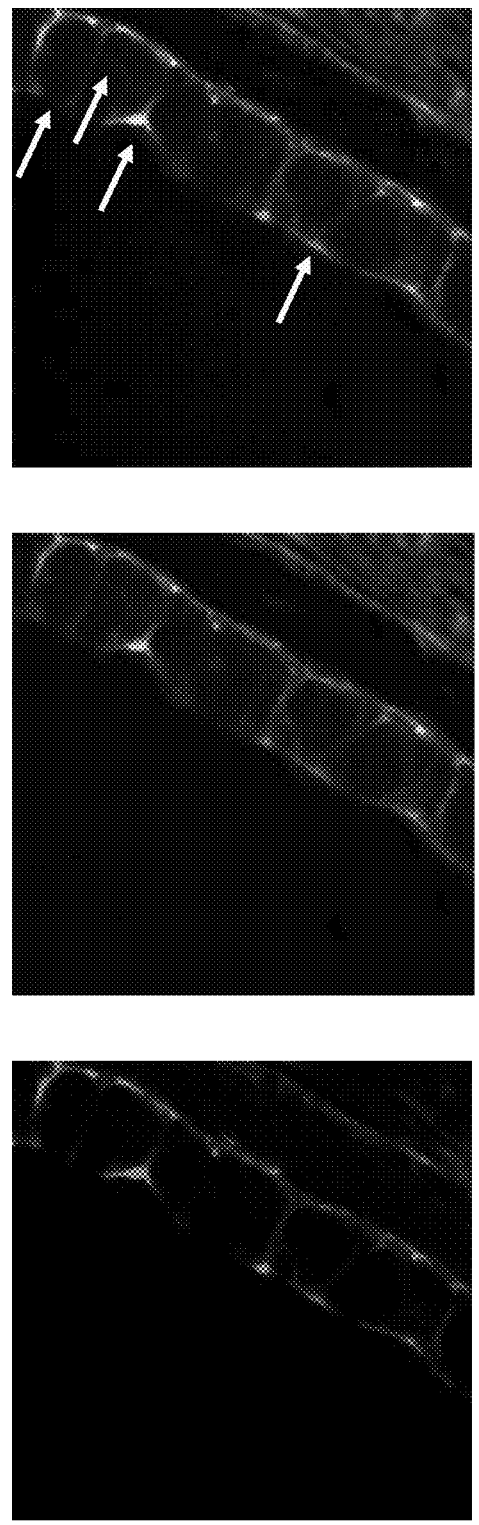
Figure 10C:
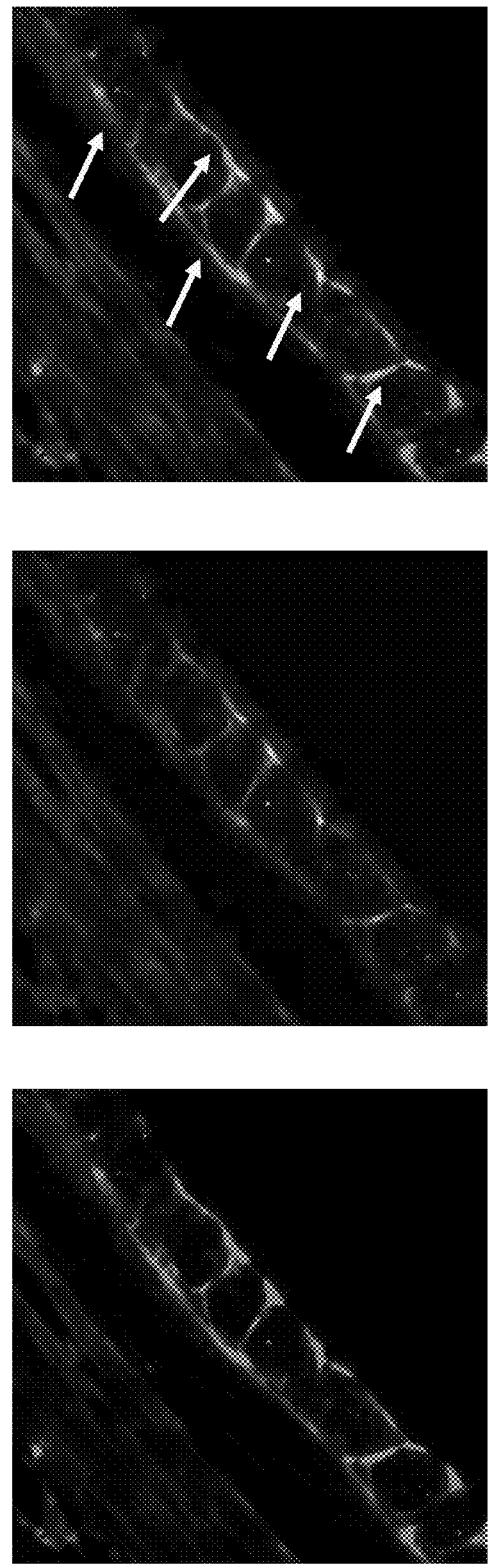

As shown in FIGS. 10A-C, CFTR protein translated from administered CFTR mRNA is expressed in the upper respiratory tract in bronchial epithelial cells. In the exemplary study, CFTR mRNA-derived protein exhibited a dose-dependent expression and colocalized with endogenous membrane tight junction protein ZO1 in upper bronchial epithelial cell membrane. FIG. 10A depicts representative microscopic images of bronchial epithelial cells from a control animal that received 10% treahalose alone, visualized for CFTR staining (left), ZO1staining (middle) and optical merge of CFTR and ZO1 staining (right). FIG. 10B depicts representative microscopic images of bronchial epithelial cells of an animal that received low dose CFTR mRNA (500 µg/kg), visualized for CFTR staining (left), ZO1staining (middle) and optical merge of CFTR and ZO1 staining (right). FIG. 10C depicts representative microscopic images of bronchial epithelial cells of an animal that received high dose CFTR mRNA (1000 µg/kg), visualized for CFTR staining (left), ZO1 staining (middle) and optical merge of CFTR and ZO1 staining (right). As indicated in the figure, the expression of CFTR was dose-dependent, that is, the immunostaining signal was stronger at the higher dose (FIG. 10C left image) than that of the low dose (FIG. 10B, left image). Also, as evident from the positioning of the CFTR and ZO1 signals, CFTR and ZO1 are expressed in the membrane of the epithelial cells. The two proteins colocalized yielding an intensified signal, which was yellow upon visual observation (FIGS. 10B and 10C right image). No red signal corresponding to CFTR was observed in FIG. 10A indicating the specificity of the staining. Also the merged optical signal was not intensified and monochromatic for ZO-1 signal alone.

Figure 11A:
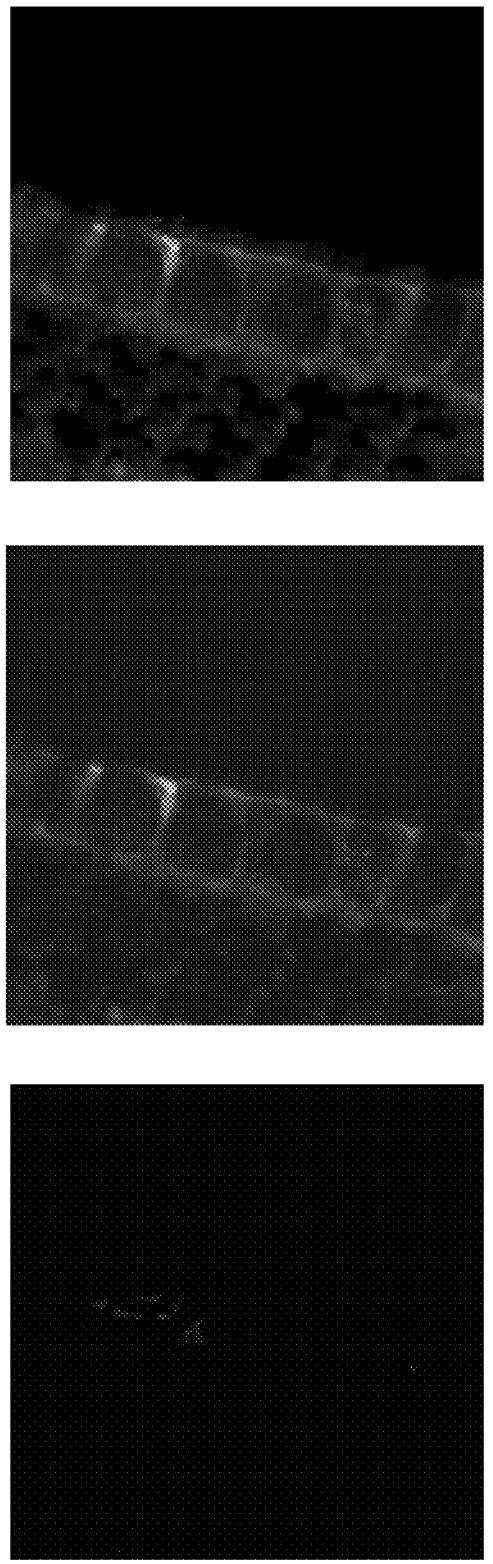
FIGS. 11A-C depicts expression of CFTR mRNA-derived protein in non-human primate lower airway epithelial cells and colocalization with endogenous ZO1 protein.
Figure 11B:
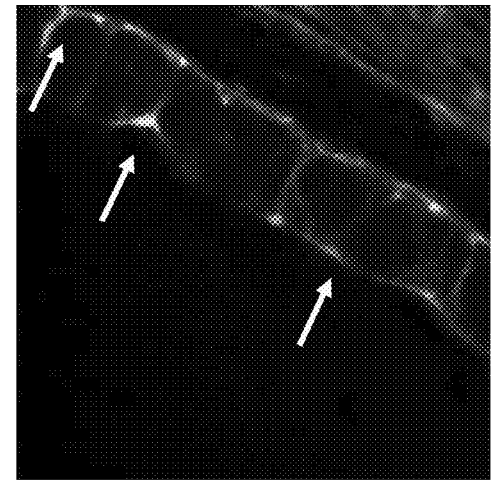
Figure 11B:
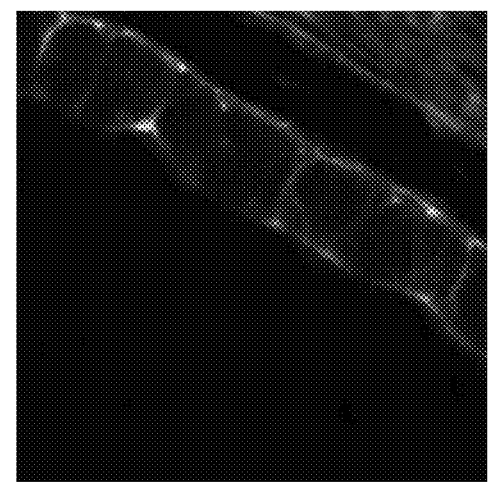
Figure 11B:
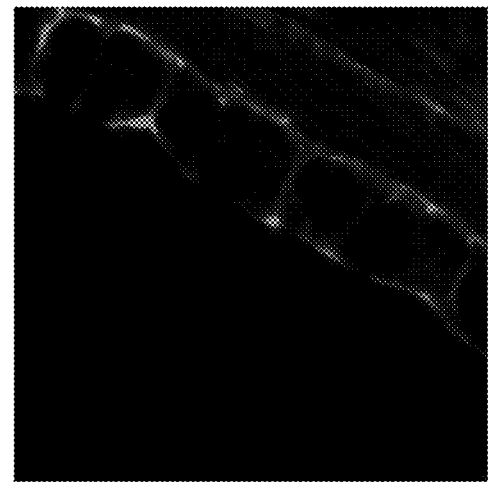
Figure 11C:
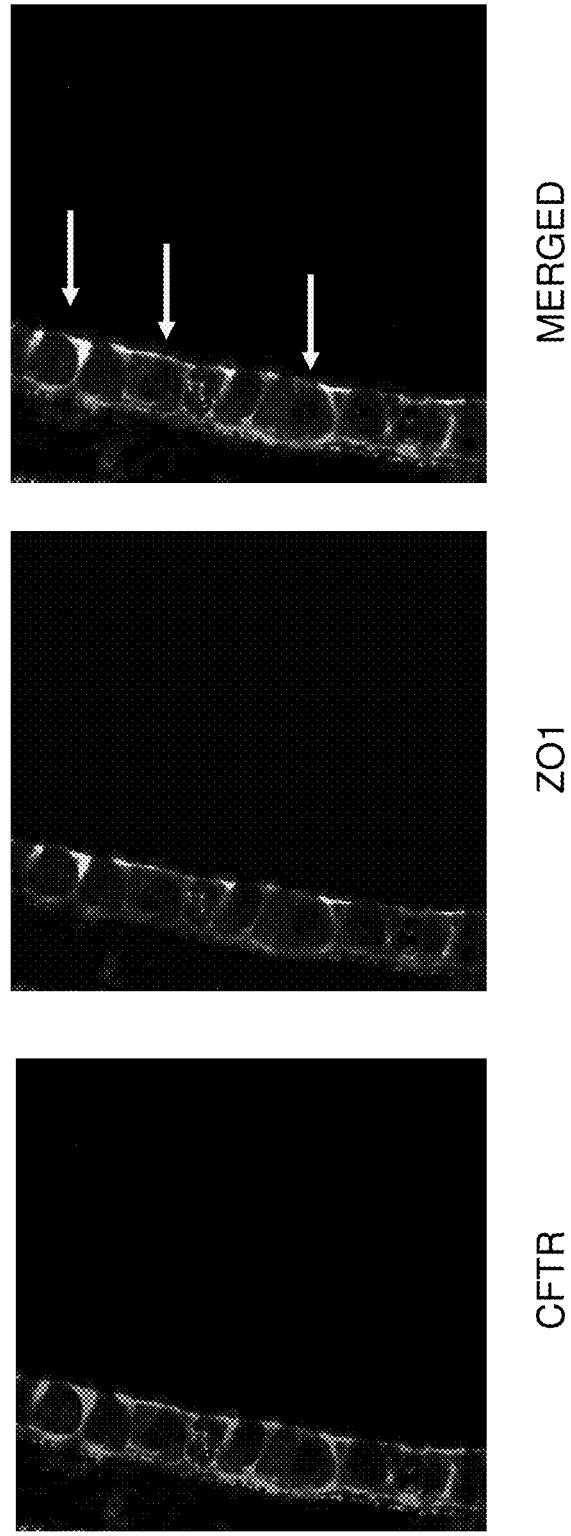

Example 10. CFTR Colocalization with Membrane Protein in Lower Airway Epithelial Cells For successful therapeutic effect, the administered CFTR mRNA has to be delivered to the lower lung. As shown in FIGS. 11A-C, CFTR protein translated from administered CFTR mRNA was expressed in lower respiratory tract epithelial cells. CFTR mRNA-derived protein exhibited a dose-dependent expression and colocalization with endogenous membrane tight junction protein ZO1 protein in lower airway epithelial cell membrane. FIG. 11A shows representative microscopic images of a tissue section from the lower airway epithelial cell membrane from a control animal that received 10% trehalose alone, visualized for CFTR staining (left), ZO1staining (middle) and optical merge of CFTR and ZO1 staining (right). FIG. 11B shows representative microscopic images of a tissue section from the lower airway epithelial cell membrane of an animal that received low dose CFTR mRNA (500 µg/kg), visualized for CFTR staining (left), ZO1staining (middle) and optical merge of CFTR and ZO1 staining (right). FIG. 11C shows representative microscopic images of a tissue section from the lower airway of an animal that received high dose CFTR mRNA (1000

μg/kg), visualized for CFTR staining (left), ZO1 staining (middle) and optical merge of CFTR and ZO1 staining (right). The intensity of the CFTR expression was higher in the high dose (FIG. 11C, left image) compared to low dose (FIG. 11B, left image). The merged image in FIG. 11C was yellow indicating that the proteins colocalized, whereas FIG. 11A had no signal for CFTR (left) as was expected of the control.

Example 11. CFTR mRNA Derived Protein Expression in Alveolar Lung

Figure 12A:
FIGS. 12A-C depicts expression of CFTR mRNA-derived protein in alveolar region of the non-human primate lung, and colocalization with ZO1 in alveolar membrane.
Figure 12A:
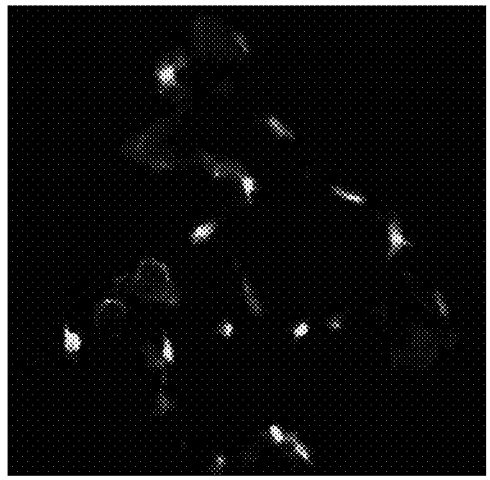
Figure 12A:
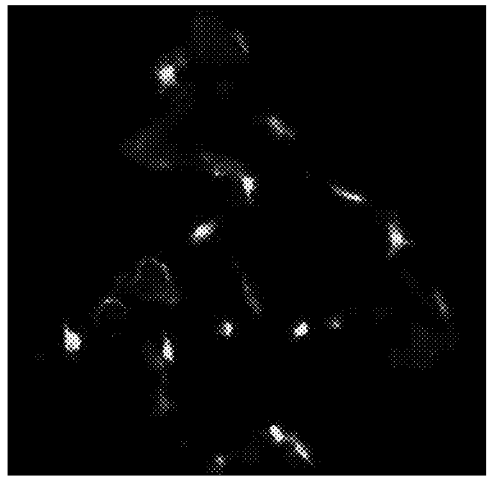
Figure 12B:
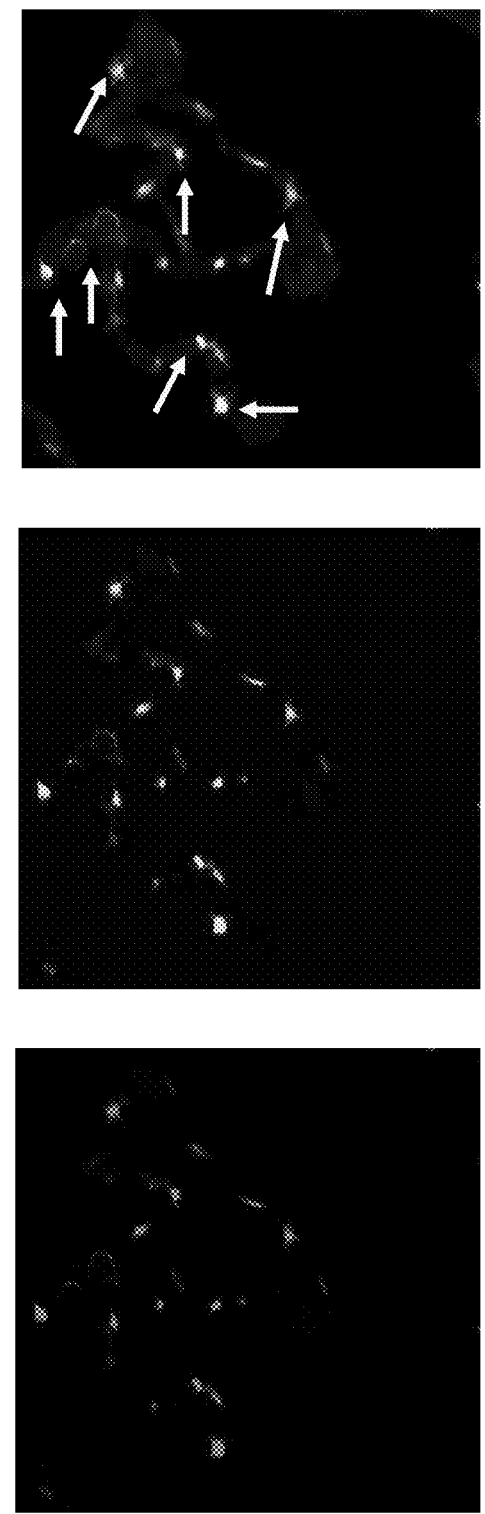
Figure 12C:
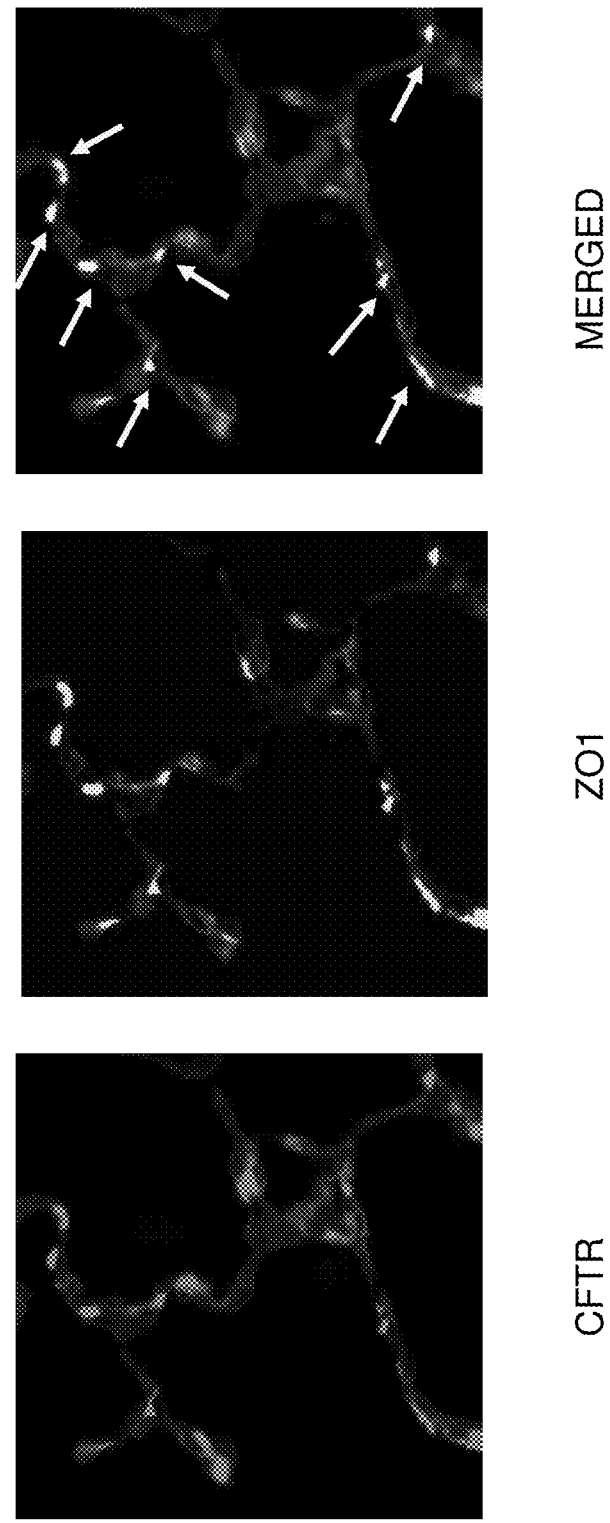

CFTR mRNA was successfully taken up by alveolar cells in the deep lung. As shown in FIGS. 12A-C, CFTR protein translated from administered CFTR mRNA was expressed in alveolar cell membranes and colocalized with endogenous membrane tight junction protein ZO1 protein in the alveolar cell membrane. FIG. 12A shows representative microscopic images of a tissue section from the lower airway epithelial cell membrane from a control animal that received 10% trehalose alone, visualized for CFTR staining (left), ZO1 staining (middle) and optical merge of CFTR and ZO1 staining (right). FIG. 12B shows representative microscopic images of a tissue section from the lower airway epithelial cell membrane of an animal that received low dose CFTR mRNA (500 μg/kg), visualized for CFTR staining (left), ZO1 staining (middle) and optical merge of CFTR and ZO1 staining (right). FIG. 12C shows representative microscopic images of a tissue section from the lower airway of an animal that received high dose CFTR mRNA (1000 μg/kg), visualized for CFTR staining (left), ZO1 staining (middle) and optical merge of CFTR and ZO1 staining (right). The intensity of the CFTR expression was higher in the high dose (FIG. 12C, left image) compared to low dose (FIG. 12B, left image). The merged image in FIG. 12C was yellow indicating that the proteins colocalized, whereas FIG. 12A had no signal for CFTR (left) as was expected for the control.

Example 12. Particle Size Characterization with Simultaneous Emitted Dose and Output Rate Determination Study (VMT Nebulizer 1)

The studies described in Examples 12-15 evaluated nebulized particles of a CFTR mRNA/liposome composition as described in Example 1. The composition was nebulized using three devices of VMT nebulizer 1, a commercially available VMT nebulizer, and the resulting aerosol was examined in triplicate to determine the following parameters:

Volume median diameter (VIVID)
Fine particle fraction (FPF); specifically, the percentage of the aerosol that has a particle size
  <5.0 μm
  <3.3 μm
  <2.0 μm
Span
Simultaneous gravimetric measurements (8 mL fill) were made using continuous 15 L/min extraction. Each nebulizer was run in triplicate to determine:
Delivery efficiency (emitted mass over whole treatment as a percentage of the fill mass [%])
Emitted mass over the first minute of nebulization (gravimetric weight loss [mg/min])
Emitted mass rate over the entire treatment (total output rate [mg dosing solution/min])
Total emitted mass (delivered dose over the entire treatment [mg])
Residual drug solution (mg and μL equivalent of dosing solution)
Treatment time (time to end of aerosol generation [s])

The results demonstrate that the CFTR mRNA/liposome composition described in Example 1 can be delivered from VMT nebulizer 1 with a mean volume median diameter (VIVID) of 4.35 μm (n=9, standard deviation 0.46 μm) and a mean treatment time of 38 minutes 49 seconds (standard deviation 12 minutes 35 seconds) for an 8-mL fill. The specific gravity of the composition was determined to be 1.03 g/mL. A data summary is provided in Table 8.

As the VIVID of the generated particles is <5 μm, the majority of the nebulized composition is capable of penetrating into the lower airways of a patient and therefore reaching a large proportion of the relevant population of epithelial cells. At a CO-hCFTR mRNA concentration of 0.6 mg/mL, a single 8 mL fill can theoretically administer a total dose of 4.2 mg in less than 40 minutes. The treatment time is therefore short enough to be feasibly administered the CO-hCFTR mRNA liposome composition of the invention in an outpatient setting or at home with a commercially available vibrating mesh nebulizer.

TABLE 8

Results Summary of Particle Size Characterization with Simultaneous Emitted Dose and Output Rate Determination (VMT nebulizer 1)

|  |  | Mean | SD | % RSD |
|---|---|---|---|---|
| VMD (um) |  | 4.35 | 0.46 | 10.49 |
| Fine Particle | <5.0 μm | 59.55% | 6.47% | 10.86 |
| Fraction | <3.3 μm | 32.56% | 6.76% | 20.78 |
|  | <2.0 μm | 9.92% | 4.44% | 44.73% |
| Span |  | 1.51 | 0.11 | 7.07 |
| Delivery efficiency |  | 98.3% | 0.31% | 0.32 |
| Emitted mass over first minute of nebulization (mg solution/min) |  | 218.5 | 88.65 | 40.58 |
| Emitted mass rate, entire treatment (mg solution/min) |  | 232.8 | 80.21 | 34.45 |
| Total emitted mass (mg solution) |  | 8165.5 | 28.88 | 0.35 |
| Residual mass (mg solution) |  | 139.2 | 26.04 | 18.71 |
| Residual volume (mL) |  | 135.30 | 25.32 | 18.71 |
| Treatment time (s) |  | 2328.67 | 754.64 | 32.41 |

Abbreviations: mg = milligram(s); μm = micrometer(s); min = minute(s); mL = milliliter(s); s = second(s); RSD = relative standard deviation; SD = standard deviation; VMD = volume median diameter Example 13. Aerodynamic Particle Size Characterization Study by Next Generation Impactor (NGI) at 15 L/Min (VMT Nebulizer 1)

Aerosol from each of three devices of VMT nebulizer 1 as described in Example 12 was examined in triplicate using a Next Generation Impactor (NGI) cooled to 5° C. with 15 L/min extraction to determine the following parameters:

Mass median aerodynamic diameter (MMAD)—the average aerosol particle size
Fine particle fraction (FPF); specifically, the percentage of the aerosol <5.0 μm
Delivered dose to the impactor (quantity of the composition collected in the impactor)

Geometric standard deviation (GSD)—a dimensionless number indicating variability in aerosol particle size Mass balance 1 mL of the composition was nebulized for each analysis. A summary of the results is provided in Table 9.

The average particle size of the nebulized composition ranges from approximately 4.35 μm to approximately 5.58 μm when the VMD and MMAD are measured, respectively. These two methods of measuring the median particle size of the composition are therefore in broad agreement.

TABLE 9

MMAD, GSD, FPF, Mass Balance and Delivered Dose Results (VMT nebulizer 1)

| | Mean | SD | % RSD |
|---|---|---|---|
| MMAD (μm) | 5.58 | 0.36 | 6.52 |
| GSD | 1.72 | 0.05 | 2.90 |
| FPF (% <5.0 μm) | 40.94 | 4.82 | 11.78 |
| Mass Balance (%) | 100.46 | 6.20 | 6.17 |
| Delivered Dose to Impactor (μg)* | 542.72 | 38.38 | 7.07 |

*Total amount of drug delivered to the NGI test apparatus (connector, throat, and NGI cups)
Abbreviations: FPF = fine particle fraction; GSD = geometric standard deviation; μg = microgram(s); μm = micrometer(s); MMAD = mass median aerodynamic diameter; RSD = relative standard deviation; SD = standard deviation

Example 14. Study of Delivered Dose into Adult and Child Breathing Patterns (VMT Nebulizer 1)

To characterize the aerosol output for the CFTR mRNA/liposome composition described in Example 1 during breathing, three devices of VMT nebulizer 1 were each examined in triplicate using two breathing patterns. The breathing patterns utilized were:

Adult 500 mL tidal volume inhalation/exhalation ratio (I/E)=1:1

15 breaths per minute

Child 155 mL tidal volume inhalation/exhalation ratio (I/E)=1:2

25 breaths per minute 1 mL of the composition was nebulized for each analysis. Using the fine particle fraction (FPF, %<5.0 μm) results determined via NGI testing, a number of parameters were calculated. Table 10 summarizes treatment time and nebulizer residual. Table 11 summarizes delivered dose, respirable delivered dose and rates. Table 12 summarizes emitted doses and rates. Table 13 summarizes respirable emitted doses and rates. Table 14 and Table 15 summarize efficiency as a percent of nominal dose.

These studies demonstrate that about 25%-40% of the total nebulized composition (39.6% and 26.3% for adult and child, respectively) will be delivered to the patient upon nebulization. This loss has to be taken into account when dosing patients with the CFTR mRNA/liposome composition.

TABLE 10

Treatment Time and Nebulizer Residual: Nebulization of 1 mL of Composition into Two Breathing Patterns (VMT nebulizer 1)

| | Adult Breathing Pattern | | | Child Breathing Pattern | | |
|---|---|---|---|---|---|---|
| | Mean | SD | % RSD | Mean | SD | % RSD |
| Treatment Time (sec) | 201.1 | 45.8 | 22.8 | 210.6 | 49.9 | 23.7 |
| Nebulizer residual - RiboGreen assay (μg CFTR mRNA) | 124.6 | 23.8 | 19.1 | 187.0 | 44.0 | 23.5 |
| (μL solution equivalent) | 207.6 | 39.6 | 19.1 | 311.6 | 73.3 | 23.5 |
| Nebulizer residual-gravimetric (mg solution) | 146.0 | 31.6 | 21.7 | 162.7 | 35.5 | 21.8 |

Abbreviations:
mg = milligram(s);
μg = microgram(s);
μL = microliter(s);
RSD = relative standard deviation;
SD = standard deviation

TABLE 11

Delivered Dose, Respirable Delivered Dose and Rates: Nebulization of 1 mL of Composition into Two Breathing Patterns (VMT nebulizer 1)

| | | Adult Breathing Pattern | | | Child Breathing Pattern | | |
|---|---|---|---|---|---|---|---|
| | | Mean | SD | % RSD | Mean | SD | % RSD |
| Delivered Dose | (μg CFTR mRNA) | 237.9 | 17.9 | 7.5 | 157.8 | 14.7 | 9.3 |
| | (μL solution equivalent) | 396.6 | 29.8 | 7.5 | 262.9 | 24.5 | 9.3 |
| Delivered Dose Rate | (μg CFTR mRNA/min) | 74.2 | 16.9 | 22.7 | 46.4 | 7.7 | 16.5 |
| | (μL solution equivalent/min) | 123.7 | 28.1 | 22.7 | 77.4 | 12.8 | 16.5 |
| Respirable Delivered Dose (as per FPF (% <5.0 μm) by NGI at 15 L/min) | (μg CFTR mRNA) | 97.2 | 12.3 | 12.6 | 65.0 | 12.2 | 18.8 |
| | (μL solution equivalent) | 162.1 | 20.4 | 12.6 | 108.3 | 20.4 | 18.8 |
| Respirable Delivered Dose Rate (as per FPF (% <5.0 μm) by NGI at 15 L/min) | (μg CFTR mRNA/min) | 29.8 | 4.8 | 16.0 | 18.8 | 2.5 | 13.2 |
| | (μL solution equivalent/min) | 49.7 | 7.9 | 16.0 | 31.3 | 4.1 | 13.2 |

Abbreviations:
FPF = fine particle fraction;
μg = microgram(s);
μL = microliter(s);
μm = micrometer(s);
L = liter(s);
min = minute(s);
NGI = Next Generation Impactor;
RSD = relative standard deviation;
sec = second(s);
SD = standard deviation

TABLE 12

Emitted Doses and Rates: Nebulization of 1 mL of the Composition into Two Breathing Patterns (VMT nebulizer 1)

| | | Adult Breathing Pattern | | | Child Breathing Pattern | | |
|---|---|---|---|---|---|---|---|
| | | Mean | SD | % RSD | Mean | SD | % RSD |
| Emitted Dose - RiboGreen Assay | (µg CFTR mRNA) | 476.3 | 26.2 | 5.5 | 412.1 | 46.5 | 11.3 |
| | (µL solution equivalent) | 793.9 | 43.7 | 5.5 | 686.8 | 77.5 | 11.3 |
| Emitted Dose - gravimetric | (mg solution) | 855.4 | 36.8 | 4.3 | 835.7 | 39.2 | 4.7 |
| Emitted Dose Rate - RiboGreen Assay | (µg CFTR mRNA/min) | 146.8 | 23.8 | 16.2 | 120.7 | 16.7 | 13.9 |
| | (µL solution equivalent | 244.7 | 39.7 | 16.2 | 201.1 | 27.9 | 13.9 |
| Emitted Dose Rate - gravimetric | (mg solution/min) | 264.2 | 44.8 | 17.0 | 248.4 | 51.6 | 20.8 |

Abbreviations:
mg = milligram(s);
µg = microgram(s);
µL = microliter(s);
min = minute(s);
RSD = relative standard deviation;
SD = standarddeviation

TABLE 13

Respirable Emitted Doses and Rates: Nebulization of 1 mL of the Composition into Two Breathing Patterns (VMT nebulizer 1)

| | | Adult Breathing Pattern | | | Child Breathing Pattern | | |
|---|---|---|---|---|---|---|---|
| | | Mean | SD | % RSD | Mean | SD | % RSD |
| Respirable Emitted Dose (as per FPF (% <5.0 µm) by NGI at 15 L/min) - RiboGreen Assay | (µg CFTR mRNA) | 196.0 | 33.8 | 17.2 | 170.5 | 38.6 | 22.6 |
| | (µL solution equivalent) | 326.7 | 56.4 | 17.2 | 284.1 | 64.3 | 22.6 |
| Respirable Emitted Dose - gravimetric | (mg solution) | 351.7 | 56.2 | 16.0 | 342.8 | 49.9 | 14.6 |
| Respirable Emitted Dose Rate (as per FPF by NGI at 15 L/min) - RiboGreen Assay | (µg CFTR mRNA/ min) | 59.3 | 6.4 | 10.7 | 49.1 | 6.4 | 13.1 |
| | (µL solution equivalent/ min) | 98.9 | 10.6 | 10.7 | 81.8 | 10.7 | 13.1 |
| Respirable Emitted Dose Rate - gravimetric | (mg solution/min) | 106.6 | 11.7 | 11.0 | 100.2 | 16.1 | 16.1 |

Abbreviations:
FPF = fine particle fraction;
µg = microgram(s);
µL = microliter(s);
µm = micrometer(s);
L = liter(s);
min = minute(s);
NGI = Next Generation Impactor;
RSD = relative standard deviation;
SD = standard deviation

TABLE 14

Efficiency as a Percentage of Nominal Dose: Nebulization of 1 mL of the Composition into Two Breathing Patterns (VMT nebulizer 1)

| | Adult Breathing Pattern | | | Child Breathing Pattern | | |
|---|---|---|---|---|---|---|
| | Mean | SD | % RSD | Mean | SD | % RSD |
| Emitted Dose (%) | 79.3 | 4.0 | 5.0 | 68.8 | 7.5 | 10.9 |
| Respirable Emitted Dose (as per FPF (% <5.0 µm) by NGI at 15 L/min) (%) | 32.6 | 5.5 | 16.8 | 28.4 | 6.4 | 22.4 |
| Delivered Dose (%) | 39.6 | 3.1 | 7.9 | 26.3 | 2.3 | 8.9 |
| Respirable Delivered Dose (as per FPF (% <5.0 µm) by NGI at 15 L/min) (%) | 16.2 | 2.0 | 12.4 | 10.8 | 2.0 | 18.6 |

Abbreviations:
FPF = fine particle fraction;
µm = micrometer(s);
L = liter(s);
min = minute(s);
NGI = Next Generation Impactor;
RSD = relative standard deviation;
SD = standard deviation

TABLE 15

Efficiency as a Percentage of Nominal Dose (Gravimetric): Nebulization of 1 mL of the Composition into Two Breathing Patterns (VMT nebulizer 1)

| | Adult Breathing Pattern | | | Child Breathing Pattern | | |
|---|---|---|---|---|---|---|
| | Mean | SD | % RSD | Mean | SD | % RSD |
| Emitted Dose (%) | 85.4 | 3.2 | 3.7 | 83.7 | 3.6 | 4.3 |
| Respirable Emitted Dose (as per FPF (% <5.0 µm) by NGI at 15 L/min) (%) | 35.1 | 5.4 | 15.5 | 34.3 | 4.9 | 14.4 |

Abbreviations:
FPF = fine particle fraction;
µm = micrometer(s);
L = liter(s);
min = minute(s);
NGI = Next Generation Impactor;
RSD = relative standard deviation;
SD = standard deviation?

Example 15. Study of Post-Nebulization mRNA Integrity of the Composition (VMT Nebulizer 1)

To determine the mRNA integrity in the nebulized CFTR mRNA/liposome composition produced in during nebulization, three devices of VMT nebulizer 1 were used to each nebulize 8.0 mL of the composition. The composition was nebulized into a cold trap to produce three samples. Three control samples were also generated as follows:

Control 1: the composition as thawed

Control 2: the composition held within the nebulizer drug chamber for the mean duration of time required for nebulization of 8 mL Control 3: the composition held within the cold trap glassware for the mean duration of time required for nebulization of 8 mL 8 mL of the composition was nebulized for each analysis. Samples were stored frozen at not more than −70° C. until mRNA integrity analysis was performed. The composition was deformulated and the resulting CFTR mRNA solutions were analyzed by capillary electrophoresis. The area percent falling within the range of 4,000 to 6,000 nt was quantified to provide an assessment of mRNA integrity. The following observations were made:

For all three aforementioned controls, the mRNA integrity ranged from 53.9% to 71.3%

For all nebulized the composition samples, the mRNA integrity ranged from 61.2% to 70.2%.

These data demonstrate that mRNA integrity of the CFTR mRNBA/liposome composition is not affected by nebulization, thereby supporting the use of a vibrating mesh nebulizer to administer the composition.

Example 16. Particle Size Characterization with Simultaneous Emitted Dose and Output Rate Determination Study (VMT Nebulizer 2)

The studies described in Examples 16-19 evaluated nebulized particles of a CFTR mRNA/liposome composition as described in Example 1. The composition was nebulized using three devices of VMT nebulizer 2, a commercially available VMT nebulizer, and the resulting aerosol was examined in triplicate to determine the following parameters:

Volume median diameter (VIVID)
Fine particle fraction (FPF); specifically, the percentage of the aerosol that has a particle size
<5.0 μm
<3.3 μm
<2.0 μm
Span Simultaneous gravimetric measurements (6 mL fill) were made using continuous 15 L/min extraction. Each nebulizer was run in triplicate to determine:

Delivery efficiency (emitted mass over whole treatment as a percentage of the fill mass [%])
Emitted mass over the first minute of nebulization (gravimetric weight loss [mg/min])
Emitted mass rate over the entire treatment (total output rate [mg dosing solution/min])
Total emitted mass (delivered dose over the entire treatment [mg])
Residual drug solution (mg and μL equivalent of dosing solution)
Treatment time (time to end of aerosol generation [s])

A data summary is provided in Table 16 below.

The results demonstrate that the composition can be delivered from VMT nebulizer 2 with a mean volume median diameter (VIVID) of 4.55 μm (n=9, standard deviation 0.56 μm) and a treatment time of 22 minutes 4 seconds (standard deviation 2 minutes 48 seconds) for a 6-mL fill.

As the VMD of the generated particles is ≤5 μm, the majority of the composition is capable of penetrating into the lower airways of a patient and therefore reaching a large proportion of the relevant population of epithelial cells. At a CO-hCFTR mRNA concentration of 0.6 mg/mL, a single 6 mL fill can theoretically administer a total dose of 3.6 mg in less than 25 minutes. The treatment time is therefore short enough to be feasibly administered the CO-hCFTR mRNA liposome composition of the invention in an outpatient setting or at home with a commercially available vibrating mesh nebulizer.

TABLE 16

Results Summary of Particle Size Characterization with Simultaneous Emitted Dose and Output Rate Determination (VMT nebulizer 2)

| | | Mean | SD | % RSD |
|---|---|---|---|---|
| VMD (μm) | | 4.55 | 0.56 | 12.24 |
| Fine Particle | <5.0 μm | 57.48% | 9.68% | 16.84 |

TABLE 16-continued

Results Summary of Particle Size Characterization with Simultaneous Emitted Dose and Output Rate Determination (VMT nebulizer 2)

| | | Mean | SD | % RSD |
|---|---|---|---|---|
| Fraction | <3.3 μm | 30.61% | 6.68% | 21.81 |
| | <2.0 μm | 8.62% | 1.87% | 21.73% |
| Span | | 1.49 | 0.13 | 8.43 |
| Delivery efficiency | | 96.48% | 0.61% | 0.63 |
| Emitted mass over first minute of nebulization (mg solution/min) | | 271.0 | 42.74 | 15.77 |
| Emitted mass rate, entire treatment (mg solution/min) | | 276.6 | 35.21 | 12.73 |
| Total emitted mass (mg solution) | | 6016.0 | 49.88 | 0.83 |
| Residual mass (mg solution) | | 219.2 | 37.72 | 17.21 |
| Residual volume (mL) | | 213.12 | 36.67 | 17.21 |
| Treatment time (s) | | 1324.11 | 168.18 | 12.70 |

Abbreviations: mg = milligram(s); μm = micrometer(s); min = minute(s); mL = milliliter(s); s = second(s); RSD = relative standard deviation; SD = standard deviation; VMD = volume median diameter

Example 17. Aerodynamic Particle Size Characterization Study by Next Generation Impactor (NGI) at 15 L/min (TMT Nebulizer 2)

Aerosol from each of three devices of VMT nebulizer 2 as described in Example 16 was examined in triplicate using a Next Generation Impactor (NGI) cooled to 5° C. with 15 L/min extraction to determine the following parameters:

Mass median aerodynamic diameter (MMAD)—the average aerosol particle size
Fine particle fraction (FPF); specifically, the percentage of the aerosol ≤5.0 μm
Delivered dose to the impactor (quantity of the composition collected in the impactor)
Geometric standard deviation (GSD)—a dimensionless number indicating variability in aerosol particle size
Mass balance 1 mL of the composition was nebulized for each analysis. A summary of the results is provided in Table 17 below.

TABLE 17

MMAD, GSD, FPF, Mass Balance and Delivered Dose Results (VMT nebulizer 2)

| | Mean | SD | % RSD |
|---|---|---|---|
| MMAD (μm) | 5.76 | 0.24 | 4.18 |
| GSD | 1.86 | 0.06 | 3.02 |
| FPF (% <5.0 μm) | 39.35 | 2.80 | 7.11 |
| Mass Balance (%) | 98.62 | 6.34 | 6.43 |
| Delivered Dose to Impactor (μg)* | 466.86 | 53.50 | 11.46 |

*Total amount of drug delivered to the NGI test apparatus (connector, throat, and NGI cups)
Abbreviations: FPF = fine particle fraction; GSD = geometric standard deviation; μg = microgram(s); μm = micrometer(s); MMAD = mass median aerodynamic diameter; RSD = relative standard deviation; SD = standard deviation

Example 18. Study of Delivered Dose into Adult and Child Breathing Patterns (VMT Nebulizer 2)

To characterize the aerosol output for the CFTR mRNA/liposome composition described in Example 1 during breathing, three devices of VMT nebulizer 2 were each examined in triplicate using two breathing patterns to characterize aerosol output of the composition into the specified breathing patterns. The breathing patterns utilized were:

Adult
  500 mL tidal volume
  inhalation/exhalation ratio (I/E)=1:1
  15 breaths per minute
Child
  155 mL tidal volume
  inhalation/exhalation ratio (I/E)=1:2
  25 breaths per minute 1 mL of the composition was nebulized for each analysis. Using the fine particle fraction (FPF, %≤5.0 μm) results determined via NGI testing, a number of parameters were calculated.

Table 18 summarizes treatment time and nebulizer residual.

Table 19 summarizes delivered dose, respirable delivered dose and rates. Table 20 summarizes emitted doses and rates.

Table 21 summarizes respirable emitted doses and rates.

Table 22 and Table 23 summarize efficiency as a percent of nominal dose.

These studies demonstrate that about 25%-42% of the total nebulized composition will be delivered to the patient upon nebulization (41.5% and 25.0% for adult and child, respectively). This loss has to be taken into account when dosing patients with the CFTR mRNA/liposome composition.

TABLE 18

Treatment Time and Nebulizer Residual: Nebulization of 1 mL of the Composition into Two Breathing Patterns (VMT nebulizer 2)

| | | Adult Breathing Pattern | | | Child Breathing Pattern | | |
|---|---|---|---|---|---|---|---|
| | | Mean | SD | % RSD | Mean | SD | % RSD |
| Treatment Time (sec) | | 241.1 | 30.3 | 12.6 | 256.7 | 62.7 | 24.4 |
| Nebulizer residual - RiboGreen assay | (μg CFTR mRNA) | 91.7 | 45.4 | 49.5 | 94.0 | 36.6 | 38.9 |
| | (μL solution equivalent) | 152.9 | 75.7 | 49.5 | 156.6 | 60.9 | 38.9 |
| Nebulizer residual - gravimetric (mg solution) | | 97.4 | 49.2 | 50.5 | 99.0 | 48.0 | 48.5 |

Abbreviations:
mg = milligram(s);
μg = microgram(s);
μL = microliter(s);
RSD = relative standard deviation;
SD = standard deviation

TABLE 19

Delivered Dose, Respirable Delivered Dose and Rates: Nebulization of 1 mL of the Composition into Two Breathing Patterns (VMT nebulizer 2)

| | | Adult Breathing Pattern | | | Child Breathing Pattern | | |
|---|---|---|---|---|---|---|---|
| | | Mean | SD | % RSD | Mean | SD | % RSD |
| Delivered Dose | (μg CFTR mRNA) | 249.9 | 48.7 | 19.5 | 148.5 | 31.5 | 21.2 |
| | (μL solution equivalent) | 416.4 | 81.2 | 19.5 | 247.6 | 52.5 | 21.2 |
| Delivered Dose Rate | (μg CFTR mRNA/min) | 62.4 | 10.0 | 16.0 | 35.6 | 8.0 | 22.4 |
| | (μL solution equivalent/min) | 103.9 | 16.6 | 16.0 | 59.3 | 13.3 | 22.4 |

TABLE 19-continued

Delivered Dose, Respirable Delivered Dose and Rates: Nebulization of 1 mL of the Composition into Two Breathing Patterns (VMT nebulizer 2)

| | | Adult Breathing Pattern | | | Child Breathing Pattern | | |
|---|---|---|---|---|---|---|---|
| | | Mean | SD | % RSD | Mean | SD | % RSD |
| Respirable Delivered Dose (as per FPF (% <5.0 μm) by NGI at 15 L/min) | (μg CFTR mRNA) | 98.9 | 24.5 | 24.7 | 58.8 | 15.3 | 26.0 |
| | (μL solution equivalent) | 164.9 | 40.8 | 24.7 | 98.0 | 25.5 | 26.0 |
| Respirable Delivered Dose Rate (as per FPF μm) by NGI at 15 L/min) | (μg CFTR mRNA/min) | 24.5 | 4.4 | 17.8 | 13.9 | 2.5 | 18.2 |
| | (μL solution equivalent/min) | 40.9 | 7.3 | 17.8 | 23.1 | 4.2 | 18.2 |

Abbreviations:
FPF = fine particle fraction;
μg = microgram(s);
μL = microliter(s);
μm = micrometer(s);
L = liter(s);
min = minute(s);
NGI = Next Generation Impactor;
RSD = relative standard deviation;
sec = second(s);
SD = standard deviation

TABLE 20

Emitted Doses and Rates: Nebulization of 1 mL of the Composition into Two Breathing Patterns (VMT nebulizer 2)

| | | Adult Breathing Pattern | | | Child Breathing Pattern | | |
|---|---|---|---|---|---|---|---|
| | | Mean | SD | % RSD | Mean | SD | % RSD |
| Emitted Dose - RiboGreen Assay | (μg CFTR mRNA) | 509.6 | 45.7 | 9.0 | 499.8 | 38.4 | 7.7 |
| | (μL solution equivalent) | 849.3 | 76.2 | 9.0 | 833.0 | 63.9 | 7.7 |
| Emitted Dose - gravimetric | (mg solution) | 904.7 | 51.5 | 5.7 | 890.6 | 52.2 | 5.9 |
| Emitted Dose Rate - RiboGreen Assay | (μg CFTR mRNA/min) | 128.1 | 15.5 | 12.1 | 121.7 | 25.1 | 20.6 |
| | (μL solution equivalent) | 213.5 | 25.8 | 12.1 | 202.8 | 41.9 | 20.6 |
| Emitted Dose Rate - gravimetric | (mg solution/min) | 227.5 | 23.7 | 10.4 | 217.2 | 44.6 | 20.6 |

Abbreviations:
mg = milligram(s);
μg = microgram(s);
μL = microliter(s);
min = minute(s);
RSD = relativestandard deviation;
SD = standard deviation

TABLE 21

Respirable Emitted Doses and Rates: Nebulization of 1 mL of the Composition into Two Breathing Patterns (VMT nebulizer 2)

| | | Adult Breathing Pattern | | | Child Breathing Pattern | | |
|---|---|---|---|---|---|---|---|
| | | Mean | SD | % RSD | Mean | SD | % RSD |
| Respirable Emitted Dose (as per FPF (% <5.0 μm) by NGI at 15 L/min) - RiboGreen Assay | (μg CFTR mRNA) | 201.1 | 29.0 | 14.4 | 197.3 | 26.6 | 13.5 |
| | (μL solution equivalent) | 335.2 | 48.3 | 14.4 | 328.8 | 44.4 | 13.5 |
| Respirable Emitted Dose - gravimetric | (mg solution) | 356.7 | 41.3 | 11.6 | 351.2 | 41.1 | 11.7 |
| Respirable Emitted Dose Rate (as per FPF μm) by NGI at 15 L/min) - RiboGreen Assay | (μg CFTR mRNA/min) | 50.3 | 6.0 | 11.9 | 47.4 | 7.7 | 16.2 |
| | (μL solution equivalent/ min) | 83.8 | 10.0 | 11.9 | 79.0 | 12.8 | 16.2 |
| Respirable Emitted Dose Rate - gravimetric | (mg solution/min) | 89.2 | 8.2 | 9.2 | 84.5 | 13.3 | 15.7 |

Abbreviations:
FPF = fine particle fraction;
mg = milligram(s);
μg = microgram(s);
μL = microliter(s);
μm = micrometer(s);
L = liter(s);
min = minute(s);
NGI = Next Generation Impactor;
RSD = relative standard deviation;
SD = standard deviation

TABLE 22

Efficiency as a Percentage of Nominal Dose: Nebulization of 1 mL of the Composition into Two Breathing Patterns (VMT nebulizer 2)

| | Adult Breathing Pattern | | | Child Breathing Pattern | | |
|---|---|---|---|---|---|---|
| | Mean | SD | % RSD | Mean | SD | % RSD |
| Emitted Dose (%) | 84.7 | 7.5 | 8.9 | 84.2 | 6.2 | 7.4 |
| Respirable Emitted Dose (as per (% <5.0 μm) by NGI at 15 L/min) (%) | 33.5 | 4.8 | 14.3 | 33.2 | 4.4 | 13.3 |

TABLE 22-continued

Efficiency as a Percentage of Nominal Dose: Nebulization of 1 mL of the Composition into Two Breathing Patterns (VMT nebulizer 2)

| | Adult Breathing Pattern | | | Child Breathing Pattern | | |
|---|---|---|---|---|---|---|
| | Mean | SD | % RSD | Mean | SD | % RSD |
| Delivered Dose (%) | 41.5 | 7.9 | 19.1 | 25.0 | 5.2 | 20.7 |
| Respirable Delivered Dose (as per FPF (% <5.0 μm) by NGI at 15 L/min) (%) | 16.4 | 4.0 | 24.4 | 9.9 | 2.5 | 25.6 |

Abbreviations:
FPF = fine particle fraction;
μm = micrometer(s);
L = liter(s);
min = minute(s);
NGI = Next Generation Impactor;
RSD = relative standard deviation;
SD = standard deviation

TABLE 23

Efficiency as a Percentage of Nominal Dose (Gravimetric): Nebulization of 1 mL of the Composition into Two Breathing Patterns (VMT nebulizer 2)

| | Adult Breathing Pattern | | | Child Breathing Pattern | | |
|---|---|---|---|---|---|---|
| | Mean | SD | % RSD | Mean | SD | % RSD |
| Emitted Dose (%) | 90.3 | 4.9 | 5.5 | 90.0 | 4.9 | 5.4 |
| Respirable Emitted Dose (as per FPF (% <5.0 μm) by NGI at 15 L/min) (%) | 35.6 | 4.1 | 11.5 | 35.5 | 4.1 | 11.5 |

Abbreviations:
FPF = fine particle fraction;
μm = micrometer(s);
L = liter(s);
min = minute(s);
NGI = Next Generation Impactor;
RSD = relative standard deviation;
SD = standard deviation

Example 19. Study of Post-Nebulization mRNA Integrity of the Composition (TMT Nebulizer 2)

To determine the mRNA integrity in the nebulized CFTR mRNA/liposome composition produced during nebulization, three devices of VMT nebulizer 2 were used to each nebulize 6.0 mL of the composition for post-nebulization mRNA integrity analysis. The composition was nebulized into a cold trap to produce three samples. Three control samples were also generated as follows:

Control 1: the composition as thawed

Control 2: the composition held within the nebulizer drug chamber for the mean duration of time required for nebulization of 6 mL Control 3: the composition held within the cold trap glassware for the mean duration of time required for nebulization of 6 mL 6 mL of the composition was nebulized for each analysis. Samples were stored frozen at NMT −70° C. until mRNA integrity analysis was performed. The composition was deformulated and the resulting CFTR mRNA solutions were analyzed by capillary electrophoresis. The area percent falling within the range of 4,000 to 6,000 nt was quantified to provide an assessment of mRNA integrity. The following observations were made:

For all three aforementioned controls, the mRNA integrity ranged from 49.7% to 72.7%

For all nebulized samples of the composition, the mRNA integrity ranged from 60.8% to 67.3%.

These data demonstrate that mRNA integrity of the CFTR mRNA/liposome composition is not affected by nebulization, thereby supporting the use of a vibrating mesh nebulizer to administer the composition.

The data presented in Examples 16-19 is similar to that presented in Examples 12-15, demonstrating that similar results are achieved when the CFTR mRNA/liposome composition is nebulized using two different commercially available vibrating mesh nebulizers (VMT nebulizer 1 and VMT nebulizer 2).

Example 20. Studies Relating to Diluents in Formulations

In order to study the benefits of different diluents for the LNP formulations described herein, the LNP formulations of Table 24 were prepared.

TABLE 24 mRNA-containing LNPs

| Formulation | LNP | Component lipids | Lipid molar ratio | Cargo | Lyoprotectant |
|---|---|---|---|---|---|
| Ex. 8 | LNP1 | DLinKC2-DMA:DOPE:CHOL:DMG-PEG2000 | 50:25:20:5 | FFL mRNA (mRNA1) | 10% sucrose |
| Ex. 9 | LNP1 | DLinKC2-DMA:DOPE:CHOL:DMG-PEG2000 | 50:25:20:5 | EPO mRNA (mRNA2) | 10% sucrose |
| Ex. 10 | LNP2 | DLinKC2-DMA:DOPE:CHOL:DMG-PEG2000 | 50:25:20:5 | EPO mRNA (mRNA2) | 10% sucrose |
| A | LNP3 | ICE:DOPE:DMG-PEG2000 | 60:35:5 | CFTR mRNA (mRNA3) | 10% sucrose |
| B | LNP3 | ICE:DOPE:DMG-PEG2000 | 60:35:5 | CFTR mRNA (mRNA3) | 10% trehalose |
| C | LNP3 | ICE:DOPE:DMG-PEG2000 | 60:35:5 | CFTR mRNA (mRNA3) + histidine | 10% trehalose |
| D | LNP3 | ICE:DOPE:DMG-PEG2000 | 60:35:5 | CFTR mRNA (mRNA3) | 10% glucose |
| E | LNP4 | ML2:DOPE:CHOL:DMG-PEG2000 | 40:30:20:10 | AS SI mRNA (mRNA4) | 10% glucose |

Formulations Ex. 8, Ex. 9, and Ex. 10 respectively correspond to the formulations of Examples 8-10 in International Publication No. WO/2012/170889, which is hereby incorporated by reference. Formulations A-E were prepared according to the protocol of Table 25.

TABLE 25

Protocol for the preparation of Formulations A-E

| Phase | Type | Setpoint (° C.) | Ramp rate (° C./min) | Time (min) | Time (h) | Total time (h) | Pressure (mTorr) |
|---|---|---|---|---|---|---|---|
| Loading | | 5 | 0 | 0 | 0 | 0 | atm |
| Freeze | Hold | 5 | 0 | 60 | 1 | 1 | atm |
| Freeze | Rate | −5 | 0.3 | 33 | 0.6 | 1.6 | atm |
| Freeze | Hold | −5 | 0 | 30 | 0.5 | 2.1 | atm |
| Freeze | Rate | −25 | 0.3 | 67 | 1.1 | 3.2 | atm |
| Freeze | Hold | −25 | 0 | 30 | 0.5 | 3.7 | atm |
| Freeze | Rate | −50 | 0.3 | 83 | 1.4 | 5.1 | atm |
| Freeze | Hold | −50 | 0 | 180 | 3 | 8.1 | atm |
| Freeze | Rate | −32 | 0.3 | 60 | 1 | 9.1 | atm |
| Freeze | Hold | −32 | 0 | 60 | 1 | 10.1 | atm |
| Primary Drying | Hold | −32 | 0 | 3600 | 60 | 70.1 | 50 |
| Secondary Drying | Rate | 4 | 0.05 | 720 | 12 | 82.1 | 50 |
| Secondary Drying | Hold | 4 | 0 | 360 | 6 | 88.1 | 50 |
| Storage | Hold | 4 | 0 | NA | NA | NA | 1000 |

Physical Properties of the mRNA-LNPs

The physical properties of the fresh (unlyophilized) liposomes and the lyophilized mRNA-LNP formulations were compared in accordance with the methods provided in Example 6 of International Publication No. WO/2012/170889. Stability was assessed by comparing the average size of the particles (Zane), their size homogeneity (indicated by the polydispersity index, PDI) and mRNA encapsulation levels before and after lyophilization. The data from these tests are provided in FIGS. 13-15.

Figure 13:
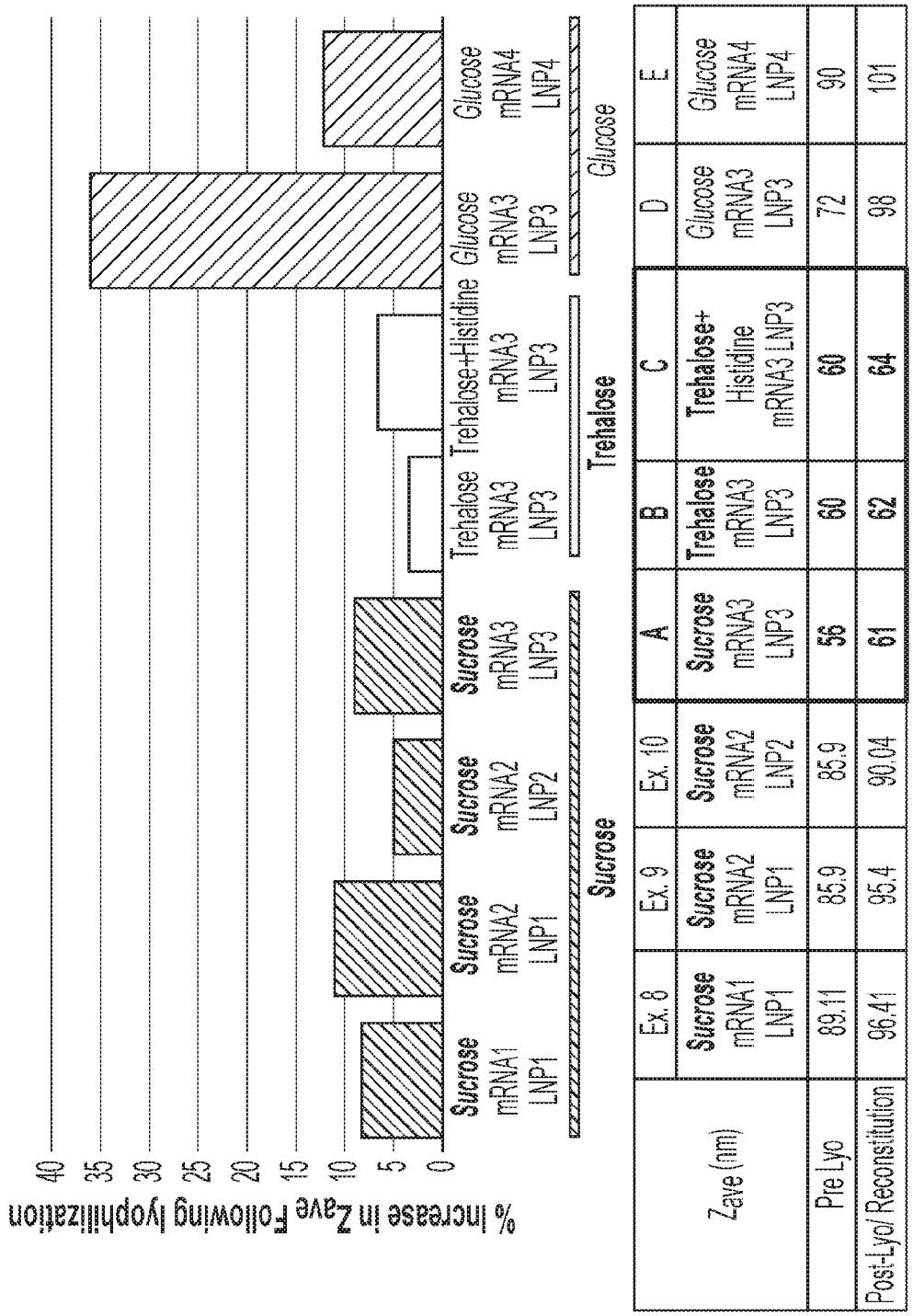
FIG. 13 depicts the percent change in LNP average size (Zave) pre- and post-lyophilization.
Figure 14:
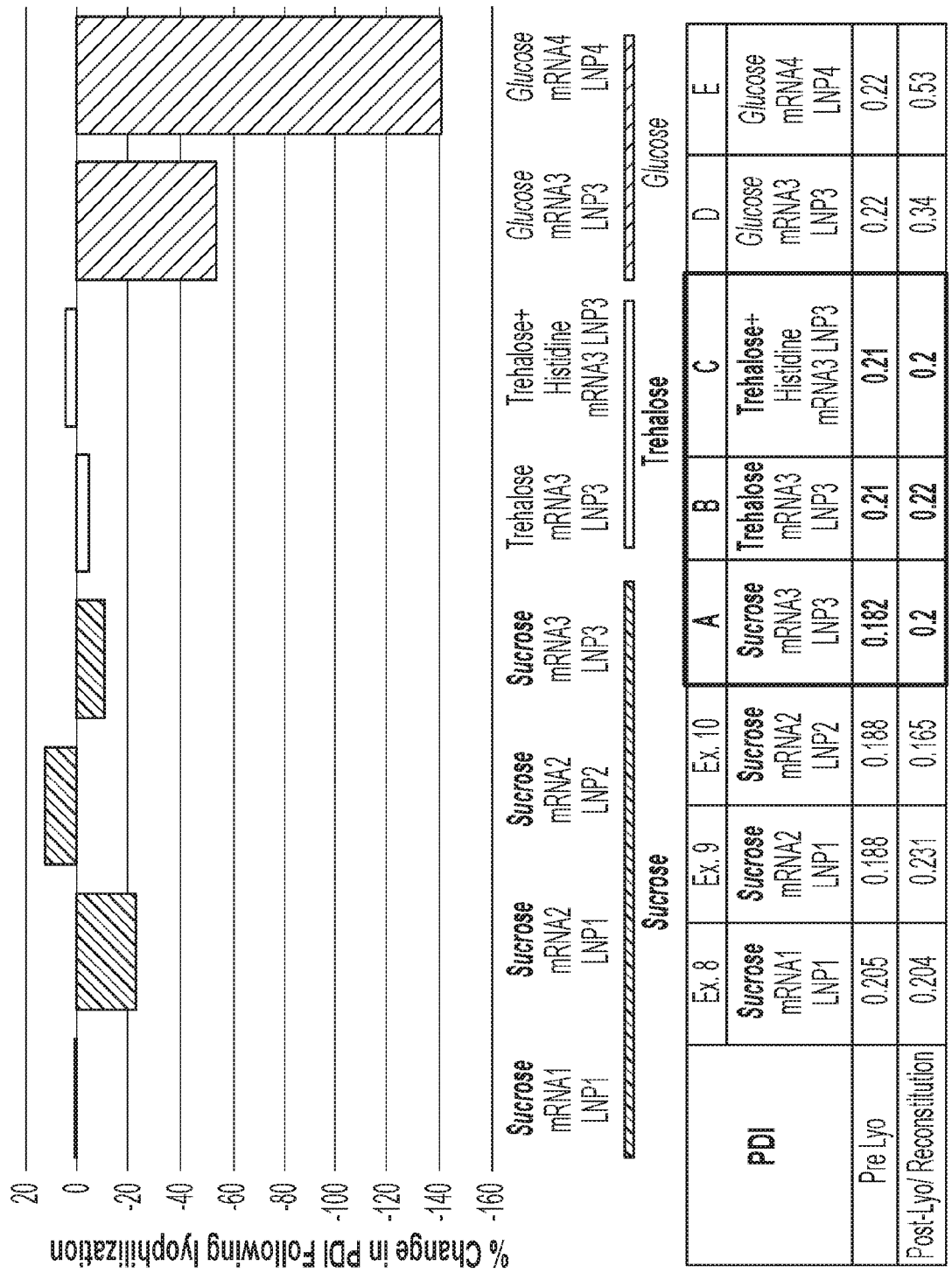
FIG. 14 depicts the percent change in mRNA-LNP size dispersity (PDI) pre- and post-lyophilization.
Figure 15:
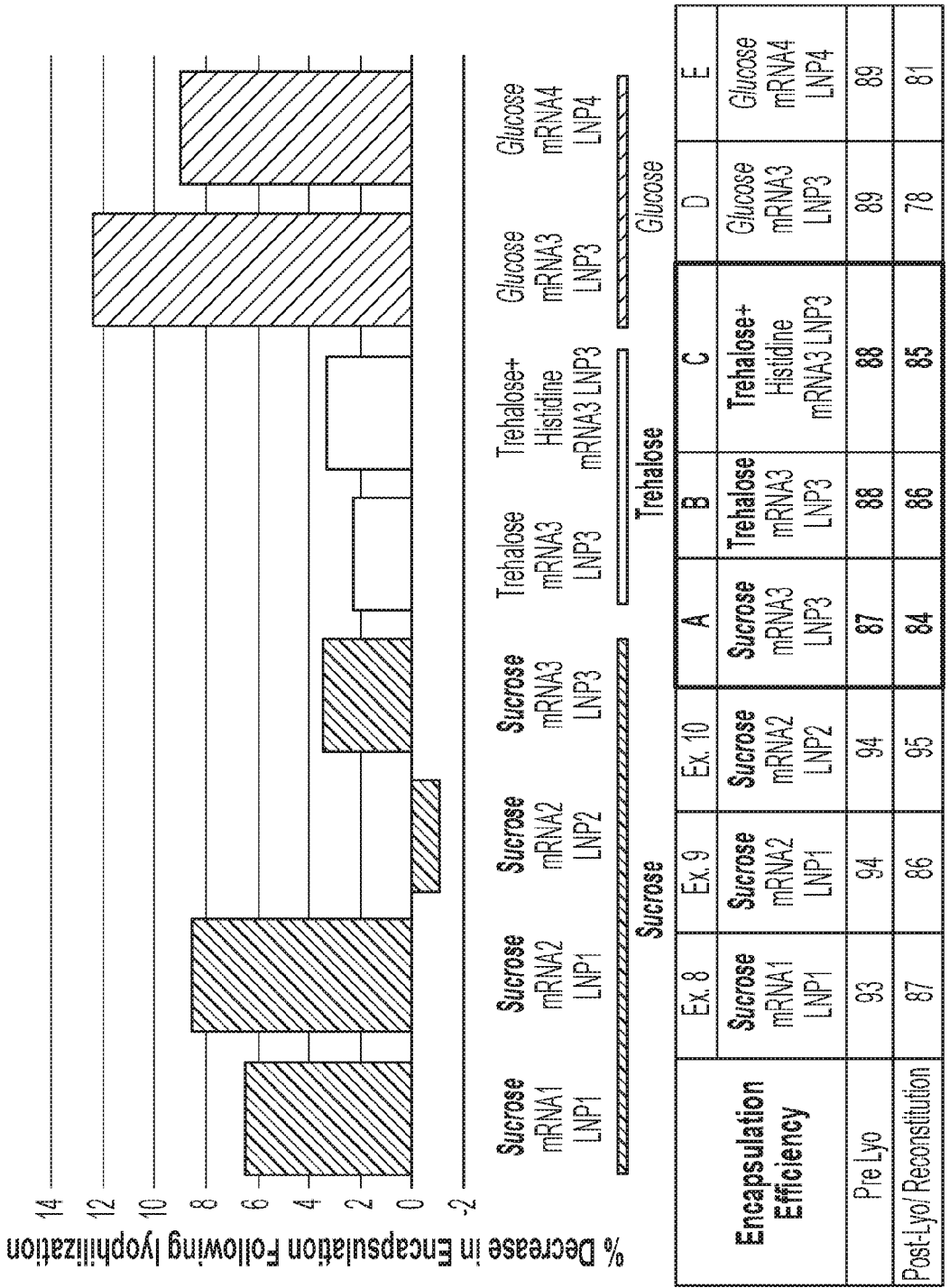
FIG. 15 depicts the percent change in mRNA encapsulation pre- and post-lyophilization.

Each of FIGS. 13-15 show that there were minimal changes in the physical properties of the mRNA-LNPs following their lyophilization and reconstitution when using sucrose or trehalose as a lyoprotectant. For example, the use of sucrose or trehalose as a lyoprotectant for formulations A and B (both of which comprise LNP3 and mRNA 3) resulted in an 8.9% and 3.3% increase in size respectively following lyophilization and reconstitution.

Comparing the data for formulation A (sucrose as a lyoprotectant, lyophilization protocol set out in Table 25 above) with that of Ex. 8, Ex. 9, and Ex. 10 (sucrose as a lyoprotectant, lyophilization protocol set out in Table 3 of International Publication No. WO/2012/170889) shows that similarly stable lyophilized mRNA-LNP compositions can be produced using both lyophilization protocols.

In Vivo and In Vitro Potency of the Lyophilized mRNA-LNPs

Wild type CD-1 mice were used to evaluate in vivo potency of an mRNA-LNP formulation comprising trehalose as a lyoprotectant, both before lyophilization and following lyophilization and reconstitution. The expression of the ASS1 protein from ASS1 mRNA (mRNA 4) in an LNP comprising ML2:DOPE:CHOL:DMG-PEG2000 (LNP4) was measured following a single IV administration of the formulation.

In a second experiment, cells lacking normal CFTR expression in a Ussing chamber assay were used to evaluate the potency of a CFTR-mRNA (mRNA 3) encapsulated in an LNP comprising ICE:DOPE:DMG-PEG2000 (LNP 3) in a formulation comprising trehalose, both before lyophilization and following lyophilization and reconstitution.

Figure 16B:
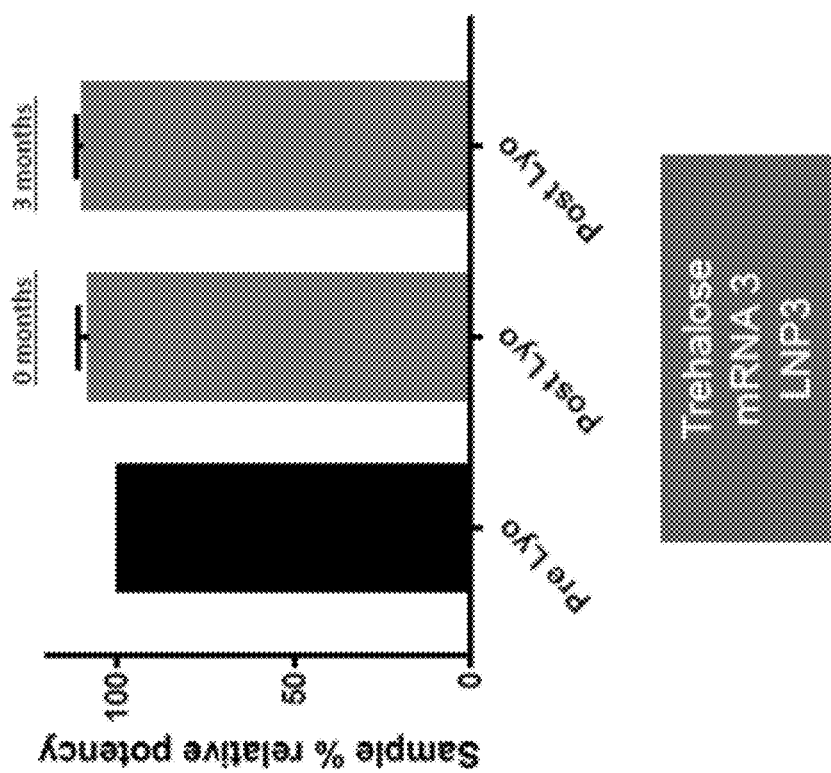
FIG. 16B depicts mRNA activity pre- and post-lyophilization for a LNP formulation comprising mRNA that encodes for CFTR.
Figure 16A:
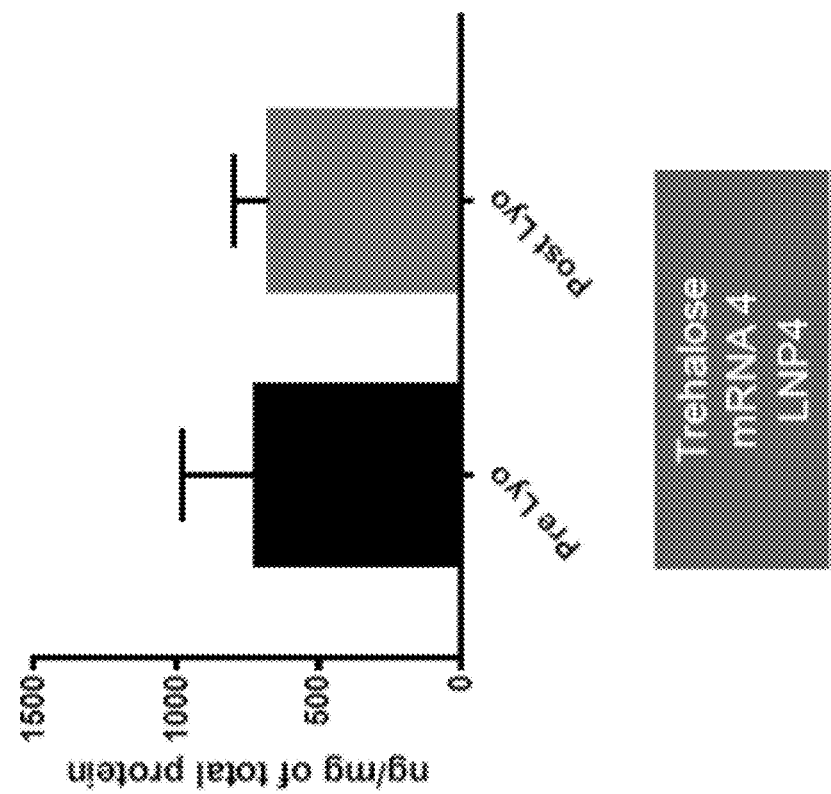
FIG. 16A depicts mRNA activity pre- and post-lyophilization for a LNP formulation comprising mRNA that encodes for ASS1 protein.

FIGS. 16A and 16B, which show the respective results of these two studies, indicate that such mRNA-LNP compositions can be successfully delivered to target cells and expressed following lyophilization and reconstitution. In particular, FIG. 16B shows that the activity of the CFTR mRNA-LNP formulation following lyophilization and reconstitution remained substantially unchanged as compared to pre-lyophilization, even after a storage period of three months at household freezer temperatures (−20° C.). The data therefore show that trehalose can be particularly suitable as a lyoprotectant for maintaining the in vivo potency of mRNA-LNP formulations during storage.

Example 21: Safety and Tolerability of a Single Dose of Inhaled CFTR mRNA Therapeutic in Adult CF Patients Not all people with CF respond to CFTR modulator therapy that is available or in development. A clinical study was conducted in which a biosynthetic mRNA coding for CFTR encapsulated in lipid nanoparticles was delivered by aerosol to adult CF patients. This form of treatment has the potential to be a mutation agnostic therapeutic regimen.

One objective of this study was to evaluate the safety and tolerability of a single dose of inhaled lipid-encapsulated CFTR mRNA or placebo in 12 adult CF patients followed for at least 1 month post-dose. To this end, adult CF patients with class I and/or II mutations and baseline FEV1 values between 50 and 90% predicted were randomized 3:1 to receive a single dose of 8, 16 or 24 mg lipid-encapsulated CFTR mRNA or placebo in a double-blinded study. All doses were administered via a hand-held nebulizer in a clinic setting and patients were followed for at least 1 month after the dose before unblinding and analysis. The concentration of the CO-hCFTR mRNA was 0.6 mg/ml. A nebulizer was used to administer the CO-hCFTR composition by nebulization at a nebulization rate of approximately 0.3 mL/minute.

Analysis of the patients showed that of the 12 enrolled patients, 8 were F508del homozygotes, 3 were F508del heterozygotes and 1 did not have an F508del mutation. Of the 8 F508del homozygotes, 7 were prescribed concomitant CFTR modulator therapy (5 ivacaftor/lumacaftor, 2 tezacaftor/lumacaftor). One subject had a genotype that is not eligible for any of the currently approved modulators or triple combination therapies in development. Mean (SD) baseline FEV1 was 66.3 (14.1) % predicted. Nebulization ranged from approximately 45 minutes to 2 hours and 25 minutes in duration, depending on dose, and was immediately well tolerated. The 8, 16 and 24 mg dose groups have completed dosing. All dose escalations were approved by the Safety Review Committee and implemented as planned. The study assessments included collection of adverse events (AEs), chest radiographs, spirometry and clinical laboratory findings, which will be reported after unblinding.

In summary, twelve subjects have received a single dose of lipid-encapsulated mRNA or placebo in the first-in-human study of nebulized mRNA therapeutic in CF. Detailed, unblinded safety results, as well as FEV1 data, is forthcoming. In parallel, dosing in the multiple dose arm of the study (5 weekly nebulizations) is ongoing.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

We claim:

1. A method of treating cystic fibrosis (CF) in a human subject comprising administering a composition comprising an mRNA encoding a Cystic Fibrosis Transmembrane Conductance Regulator (CFTR) protein at a concentration of 0.6 mg/ml to the human subject, wherein the step of administering comprises the following: (i) the composition is aerosolized using a nebulizer wherein median droplet size in the aerosolized composition is between 4 and 6 μm, and (ii) a nominal dose of the mRNA is administered to the human subject via the nebulizer over a period of time at least 30 minutes at a nebulization rate of 0.2 mL/minute to 0.5 mL/minute, wherein the composition comprises trehalose, and wherein the mRNA encoding the CFTR protein comprises SEQ ID NO: 1.

2. The method of claim 1, wherein at least 25%, at least 35%, or at least 40% of the nominal dose is delivered to the lungs of the human subject.

3. The method of claim 1, wherein at least a portion of the mRNA encoding the CFTR protein is complexed to or encapsulated within nanoparticles.

4. The method of claim 3, wherein the nanoparticles are liposomes and at least 80% of the mRNA encoding the CFTR protein is encapsulated within the liposomes.

5. The method of claim 4, wherein the liposomes have an average size of less than about 100 nm.

6. The method of claim 5, wherein the liposomes have an an average size ranging from 40 nm to 60 nm.

7. The method of claim 4, wherein each of the liposome comprises one or more cationic lipids, one or more non-cationic lipids, and one or more PEG-modified lipids.

8. The method of claim 7, wherein each of the liposomes comprises no more than three distinct lipid components.

9. The method of claim 8, wherein one distinct lipid component is a sterol-based cationic lipid.

10. The method of claim 1, wherein the mRNA has poly-A tail with an average length of at least 100 bases.

11. The method of claim 1, wherein the composition is provided in lyophilized form and reconstituted in an aqueous solution prior to nebulization.

12. The method of claim 1, wherein the human subject is administered the composition at least once per week for a period of at least six months.

13. The method of claim 1, wherein the human subject receives concomitant CFTR modulator therapy.

14. The method of claim 13, wherein the concomitant CFTR modulator therapy is selected from ivacaftor, ivacaftor/lumacaftor, or tezacaftor/lumacaftor.

15. The method of claim 1, wherein the human subject has an F508del mutation.

16. The method of claim 1, wherein the human subject has a forced expiratory volume in one second (FEV1) of between about 50% and 90% of predicted normal.

* * * * *

SEQUENCE LISTING

<160> NUMBER OF SEQ ID NOS: 30

<210> SEQ ID NO 1
<211> LENGTH: 4443
<212> TYPE: RNA
<213> ORGANISM: Artificial Sequence
<220> FEATURE:
<223> OTHER INFORMATION: Synthetic polynucleotide

<400> SEQUENCE: 1

```
augcaacgcu cuccucuuga aaaggccucg guggugucca agcucuucuu cucguggacu      60
agacccaucc ugagaaaggg guacagacag cgcuuggagc uguccgauau cuaucaaauc     120
ccuuccgugg acuccgcgga caaccugucc gagaagcucg agagagaaug ggacagagaa     180
cucgccucaa agaagaaccc gaagcugauu aaugcgcuua ggcggugcuu uuucuggcgg     240
uucauguucu acggcaucuu ccucuaccug ggagagguca ccaaggccgu gcagccccug     300
uugcugggac ggauuauugc cuccuacgac cccgacaaca aggaagaaag aagcaucgcu     360
aucuacuugg gcaucggucu gugccugcuu uucaucgucc ggacccucuu guugcauccu     420
gcuauuuucg gccugcauca cauuggcaug cagaugagaa uugccauguu uucccugauc     480
```

```
uacaagaaaa cucugaagcu cucgagccgc gugcuugaca agauuuccau cggccagcuc    540
gugucccugc ucuccaacaa ucugaacaag uucgacgagg ccucgcccu ggcccacuuc     600 guguggaucg ccccucugca aguggcgcuu cugaugggcc ugaucuggga gcugcugcaa    660
gccucggcau ucugugggcu uggauuccug aucgugcugg cacuguucca ggccggacug    720
gggcggauga ugaugaagua cagggaccag agagccggaa agauuuccga acggcuggug    780
aucacuucgg aaaugaucga aaacauccag ucagugaagg ccuacugcug gaagagggcc    840
auggaaaaga ugauugaaaa ccuccggcaa accgagcuga agcugacccg caaggccgcu    900
uacgugcgcu auuucaacuc guccgcuuuc uucuucccg gguucuucgu ggguguuucuc    960 uccgugcucc ccuacgcccu gauuaaggga aucauccuca ggaagaucuu caccaccauu   1020
uccuucugua ucgugcuccg cauggccgug acccggcagu ucccaugggc cgugcagacu   1080
ugguacgacu cccugggagc cauuaacaag auccaggacu uccuucaaaa gcaggaguac   1140
aagacccucg aguacaaccu gacuacuacc gaggucguga uggaaaacgu caccgccuuu   1200
ugggaggagg gauuuggcga acuguucgag aaggccaagc agaacaacaa caaccgcaag   1260
accucgaacg gugacgacuc ccucuucuuu ucaaacuuca gccugucgg gacgcccgug   1320 cugaaggaca uuaacuucaa gaucgaaaga ggacagcucc uggcgguggc cggaucgacc   1380
ggagccggaa agacuucccu gcugauggug aucaugggag agcuugaacc uagcgaggga   1440
aagaucaagc acuccggccg caucagcuuc guagccagu uuccuggau caugcccgga    1500 accauuaagg aaaacaucau cuuccggcug uccuacgaug aauaccgcua ccgguccgug   1560
aucaaagccu gccagcugga agaggauauu ucaaaguucg cggagaaaga uaacaucgug   1620
cugggcgaag ggguauuac cuugucgggg ggccagcggg cuagaaucuc gcuggccaga   1680
gccguguaua aggacgccga ccuguaucuc cuggacuccc ccuucggaua ccuggacguc   1740
cugaccgaaa aggagaucuu cgaaucugcc gugugcaagc ugauggcuaa caagacgcc   1800 auccucguga ccuccaaaau ggagcaccug aagaaggcag acaagauucu gauucugcau   1860
gagggguccu ccuacuuuua cggcaccuuc ucgagguugc agaacuugca gcccgacuuc   1920
ucaucgaagc ugaugggkuug cgacagcuuc gaccaguucu ccgccgaaag aaggaacucg   1980
auccugacgg aaaccuugca ccgcuucucu uuggaaggcg acgccccugu gucauggacc   2040
gagacuaaga agcagagcuu caagcagacc ggggaauucg cgcgaaagag gaagaacagc   2100
aucuugaacc ccauuaacuc cauccgcaag uucucaaucg ugcaaaagac gccacugcag   2160
augaacggca uugaggagga cuccgacgaa ccccuugaga ggcgccuguc ccuggugccg   2220
gacagcgagc agggagaagc cauccugccu cggauuccg ugaucccac ugguccgacg   2280 cuccaagccc ggcggcggca guccgugcug aaccugauga cccacagcgu gaaccagggc   2340
caaaacauuc accgcaagac uaccgcaucc acccggaaag ugucccuggc accucaagcg   2400
aaucuuaccg agcucgacau cuacucccgg agacugcgc aggaaaccgg gcucgaaauu   2460
uccgaagaaa ucaacgagga ggaucugaaa gagugcuucu cgacgauau ggagucgaua    2520 cccgccguga cgacuuggaa cacuuaucug cggacaucacu ucugugacaa gucauugauc   2580
uucgugcuga uuuggugccu ggaugauuuc cuggccgagg ucgcggccuc acugguggug   2640
cucuggcugu ugggaaacac gccucgcaa gacaagggaa acuccacgca cucgagaaac    2700
aacagcuaug ccgugauuau caucuccacc cccucuuaau acguuucua caucuacguc   2760 ggaguggcgg auacccugcu cgcgaugggu uucuucagag gacugccgcu gguccacacc   2820
```

-continued

| | | | | |
|---|---|---|---|---|
| uugaucaccg | ucagcaagau | ucuucaccac | aagauguugc | auagcgugcu gcaggccccc | 2880 |
| auguccaccc | ucaacacucu | gaaggccgga | ggcauucuga | acagauucuc caaggacauc | 2940 |
| gcuauccugg | acgaucuccu | gccgcuuacc | aucuuugacu | cauccagcu gcugcugauc | 3000 |
| gugauuggag | caaucgcagu | gguggcggug | cugcagccuu | acauuuucgu ggccacugug | 3060 |
| ccggucauug | uggcguucau | caugcugcgg | gccuacuucc | uccaaaccag ccagcagcug | 3120 |
| aagcaacugg | aauccgaggg | acgaucccc | aucuucacuc | accuugugac gucguugaag | 3180 |
| ggacugugga | cccuccgggc | uuucggacgg | cagcccuacu | cgaaacccu cuuccacaag | 3240 |
| gcccugaacc | uccacaccgc | caauugguuc | cuguaccugu | ccacccgcg gugguuccag | 3300 |
| augcgcaucg | agaugauuuu | cgucaucuuc | uucaucgcgg | ucauucau cagcauccug | 3360 |
| acuaccggag | agggagaggg | acgggucgga | auaauccuga | cccucgccau gaacauuaug | 3420 |
| agcacccugc | agugggcagu | gaacagcucg | aucgacgugg | acagccugau gcgaagcguc | 3480 |
| agccgcugu | ucaaguucau | cgacaugccu | acugagggaa | acccacuaa guccacuaag | 3540 |
| cccuacaaaa | auggccagcu | gagcaagguc | augaucaucg | aaaacuccca cgugaagaag | 3600 |
| gacgauauuu | ggcccuccgg | aggucaaaug | accgugaagg | accugaccgc aaaguacacc | 3660 |
| gagggaggaa | acgccauucu | cgaaaacauc | agcuucucca | uuucgccggg acagcgggguc | 3720 |
| ggccuucucg | gcggaccgg | uuccgggaag | ucaacucugc | ugucggcuuu ccuccggcug | 3780 |
| cugaauaccg | aggggaaau | ccaaauugac | ggcgugucuu | gggauccau acucugcag | 3840 |
| caguggcgga | aggccuucgg | cgugauccc | cagaaggugu | ucaucuucuc ggguaccuuc | 3900 |
| cggaagaacc | uggauccuua | cgagcaguggg | agcgaccaag | aaaucuggaa ggucgccgac | 3960 |
| gaggucggcc | ugcgcuccgu | gauugaacaa | uuuccuggaa | agcuggacuu cgugcucguc | 4020 |
| gacggggau | guguccuguc | gcacggacau | aagcagcuca | ugugccucgc acggguccgug | 4080 |
| cucuccaagg | ccaagauucu | gcugcuggac | gaaccuucgg | cccaccugga uccggucacc | 4140 |
| uaccagauca | ucaggaggac | ccugaagcag | gccuuugccg | auugcaccgu gauucucugc | 4200 |
| gagcaccgca | ucgaggccau | gcuggagugc | cagcaguucc | uggucaucga ggagaacaag | 4260 |
| guccgccaau | acgacuccau | ucaaaagcuc | cucaacgagc | ggucgcuguu cagacaagcu | 4320 |
| auuucaccgu | ccgauagagu | gaagcucuuc | ccgcaucgga | acagcucaaa gugcaaaucg | 4380 |
| aagccgcaga | ucgcagccuu | gaaggaagag | acugaggaag | aggugcagga cacccggcuu | 4440 |
| uaa | | | | | 4443 |

<210> SEQ ID NO 2
<211> LENGTH: 1480
<212> TYPE: PRT
<213> ORGANISM: Homo sapiens

<400> SEQUENCE: 2

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
        50                  55                  60

Lys Asn Pro Lys Leu Ile Asn Ala Leu Arg Arg Cys Phe Phe Trp Arg
65                  70                  75                  80

-continued

Phe Met Phe Tyr Gly Ile Phe Leu Tyr Leu Gly Glu Val Thr Lys Ala
                    85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
            210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
            290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
            370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
            435                 440                 445

Glu Arg Gly Gln Leu Leu Ala Val Ala Gly Ser Thr Gly Ala Gly Lys
            450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr

-continued

```
                500                 505                 510
Asp Glu Tyr Arg Tyr Arg Ser Val Ile Lys Ala Cys Gln Leu Glu Glu
            515                 520                 525

Asp Ile Ser Lys Phe Ala Glu Lys Asp Asn Ile Val Leu Gly Glu Gly
            530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
            595                 600                 605

His Leu Lys Lys Ala Asp Lys Ile Leu Ile Leu His Glu Gly Ser Ser
            610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
                660                 665                 670

Gly Asp Ala Pro Val Ser Trp Thr Glu Thr Lys Lys Gln Ser Phe Lys
                675                 680                 685

Gln Thr Gly Glu Phe Gly Glu Lys Arg Lys Asn Ser Ile Leu Asn Pro
            690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
                740                 745                 750

Ser Val Ile Ser Thr Gly Pro Thr Leu Gln Ala Arg Arg Arg Gln Ser
            755                 760                 765

Val Leu Asn Leu Met Thr His Ser Val Asn Gln Gly Gln Asn Ile His
            770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
                820                 825                 830

Phe Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
            850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
            915                 920                 925
```

-continued

```
Met Gly Phe Phe Arg Gly Leu Pro Leu Val His Thr Leu Ile Thr Val
            930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
        995                 1000                1005

Ala Val Leu Gln Pro Tyr Ile Phe Val Ala Thr Val Pro Val Ile
    1010                1015                1020

Val Ala Phe Ile Met Leu Arg Ala Tyr Phe Leu Gln Thr Ser Gln
    1025                1030                1035

Gln Leu Lys Gln Leu Glu Ser Glu Gly Arg Ser Pro Ile Phe Thr
    1040                1045                1050

His Leu Val Thr Ser Leu Lys Gly Leu Trp Thr Leu Arg Ala Phe
    1055                1060                1065

Gly Arg Gln Pro Tyr Phe Glu Thr Leu Phe His Lys Ala Leu Asn
    1070                1075                1080

Leu His Thr Ala Asn Trp Phe Leu Tyr Leu Ser Thr Leu Arg Trp
    1085                1090                1095

Phe Gln Met Arg Ile Glu Met Ile Phe Val Ile Phe Phe Ile Ala
    1100                1105                1110

Val Thr Phe Ile Ser Ile Leu Thr Thr Gly Glu Gly Glu Gly Arg
    1115                1120                1125

Val Gly Ile Ile Leu Thr Leu Ala Met Asn Ile Met Ser Thr Leu
    1130                1135                1140

Gln Trp Ala Val Asn Ser Ser Ile Asp Val Asp Ser Leu Met Arg
    1145                1150                1155

Ser Val Ser Arg Val Phe Lys Phe Ile Asp Met Pro Thr Glu Gly
    1160                1165                1170

Lys Pro Thr Lys Ser Thr Lys Pro Tyr Lys Asn Gly Gln Leu Ser
    1175                1180                1185

Lys Val Met Ile Ile Glu Asn Ser His Val Lys Lys Asp Asp Ile
    1190                1195                1200

Trp Pro Ser Gly Gly Gln Met Thr Val Lys Asp Leu Thr Ala Lys
    1205                1210                1215

Tyr Thr Glu Gly Gly Asn Ala Ile Leu Glu Asn Ile Ser Phe Ser
    1220                1225                1230

Ile Ser Pro Gly Gln Arg Val Gly Leu Leu Gly Arg Thr Gly Ser
    1235                1240                1245

Gly Lys Ser Thr Leu Leu Ser Ala Phe Leu Arg Leu Leu Asn Thr
    1250                1255                1260

Glu Gly Glu Ile Gln Ile Asp Gly Val Ser Trp Asp Ser Ile Thr
    1265                1270                1275

Leu Gln Gln Trp Arg Lys Ala Phe Gly Val Ile Pro Gln Lys Val
    1280                1285                1290

Phe Ile Phe Ser Gly Thr Phe Arg Lys Asn Leu Asp Pro Tyr Glu
    1295                1300                1305

Gln Trp Ser Asp Gln Glu Ile Trp Lys Val Ala Asp Glu Val Gly
    1310                1315                1320
```

| | | | | | | | | | | |
|---|---|---|---|---|---|---|---|---|---|---|
| Leu | Arg | Ser | Val | Ile | Glu | Gln | Phe | Pro | Gly | Lys | Leu | Asp | Phe | Val |
| | 1325 | | | | 1330 | | | | 1335 | | | |

| Leu | Val | Asp | Gly | Gly | Cys | Val | Leu | Ser | His | Gly | His | Lys | Gln | Leu |
| | 1340 | | | | 1345 | | | | 1350 | | | |

| Met | Cys | Leu | Ala | Arg | Ser | Val | Leu | Ser | Lys | Ala | Lys | Ile | Leu | Leu |
| | 1355 | | | | 1360 | | | | 1365 | | | |

| Leu | Asp | Glu | Pro | Ser | Ala | His | Leu | Asp | Pro | Val | Thr | Tyr | Gln | Ile |
| | 1370 | | | | 1375 | | | | 1380 | | | |

| Ile | Arg | Arg | Thr | Leu | Lys | Gln | Ala | Phe | Ala | Asp | Cys | Thr | Val | Ile |
| | 1385 | | | | 1390 | | | | 1395 | | | |

| Leu | Cys | Glu | His | Arg | Ile | Glu | Ala | Met | Leu | Glu | Cys | Gln | Gln | Phe |
| | 1400 | | | | 1405 | | | | 1410 | | | |

| Leu | Val | Ile | Glu | Glu | Asn | Lys | Val | Arg | Gln | Tyr | Asp | Ser | Ile | Gln |
| | 1415 | | | | 1420 | | | | 1425 | | | |

| Lys | Leu | Leu | Asn | Glu | Arg | Ser | Leu | Phe | Arg | Gln | Ala | Ile | Ser | Pro |
| | 1430 | | | | 1435 | | | | 1440 | | | |

| Ser | Asp | Arg | Val | Lys | Leu | Phe | Pro | His | Arg | Asn | Ser | Ser | Lys | Cys |
| | 1445 | | | | 1450 | | | | 1455 | | | |

| Lys | Ser | Lys | Pro | Gln | Ile | Ala | Ala | Leu | Lys | Glu | Glu | Thr | Glu | Glu |
| | 1460 | | | | 1465 | | | | 1470 | | | |

| Glu | Val | Gln | Asp | Thr | Arg | Leu |
| | 1475 | | | | 1480 |

<210> SEQ ID NO 3
<211> LENGTH: 140
<212> TYPE: RNA
<213> ORGANISM: Artificial Sequence
<220> FEATURE:
<223> OTHER INFORMATION: Synthetic polynucleotide

<400> SEQUENCE: 3
ggacagaucg ccuggagacg ccauccacgc uguuugacc uccauagaag acaccgggac    60
cgauccagcc uccgcggccg ggaacggugc auuggaacgc ggauucccg ugccaagagu   120 gacucaccgu ccuugacacg                                              140

<210> SEQ ID NO 4
<211> LENGTH: 105
<212> TYPE: RNA
<213> ORGANISM: Artificial Sequence
<220> FEATURE:
<223> OTHER INFORMATION: Synthetic polynucleotide

<400> SEQUENCE: 4
cggguggcau cccugugacc cucccagu gccucuccug gcccuggaag uugccacucc     60
agugcccacc agccuuguc uaauaaaauu aaguugcauc aagcu                   105

<210> SEQ ID NO 5
<211> LENGTH: 105
<212> TYPE: RNA
<213> ORGANISM: Artificial Sequence
<220> FEATURE:
<223> OTHER INFORMATION: Synthetic polynucleotide

<400> SEQUENCE: 5 gggguggcauc ccugugaccc cucccagug ccucuccugg cccuggaagu ugccacucca    60
gugcccacca gccuuguccu aauaaaauua aguugcauca aagcu                  105

<210> SEQ ID NO 6

<211> LENGTH: 4688
<212> TYPE: RNA
<213> ORGANISM: Artificial Sequence
<220> FEATURE:
<223> OTHER INFORMATION: Synthetic polynucleotide

<400> SEQUENCE: 6

| | | | | | |
|---|---|---|---|---|---|
| ggacagaucg | ccuggagacg | ccauccacgc | uguuugacc | uccauagaag | acaccgggac | 60 |
| cgauccagcc | uccgcggccg | ggaacggugc | auuggaacgc | ggauccccg | ugccaagagu | 120 |
| gacucaccgu | ccuugacacg | augcaacgcu | cuccucuuga | aaaggccucg | gugguguccaga | 180 |
| agcucuucuu | cucgggacu | agacccaucc | ugagaaaggg | guacagacag | cgcuuggagc | 240 |
| uguccgauau | cuaucaaauc | ccuuccgugg | acuccgcgga | caaccugucc | gagaagcucg | 300 |
| agagagaaug | ggacagagaa | cucgccucaa | agaagaaccc | gaagcugauu | aaugcgcuua | 360 |
| ggcggugcuu | uuucuggcgg | uucauguucu | acggcaucuu | ccucuaccug | ggagagguca | 420 |
| ccaaggccgu | gcagccccug | uugcugggac | ggauuauugc | cuccuacgac | cccgacaaca | 480 |
| aggaagaaag | aagcaucgcu | aucuacuugg | gcaucggucu | gugccugcuu | ucaucgucc | 540 |
| ggacccucuu | guugcauccu | gcuauuuucg | gccugcauca | cauuggcaug | cagaugagaa | 600 |
| uugccauguu | ucccugauc | uacaagaaaa | cucgaagcu | cucgagccgc | gugcuugaca | 660 |
| agauuuccau | cggccagcuc | gugucccugc | ucuccaacaa | ucugaacaag | uucgacgagg | 720 |
| gccucgcccu | ggcccacuuc | guguggaucg | ccccucugca | aguggcgcuu | cugaugggcc | 780 |
| ugaucuggga | gcugcugcaa | gccucggcau | cugugggcu | uggauuccug | aucgugcugg | 840 |
| cacuguucca | ggccggacug | gggcggauga | ugaugaagua | cagggaccag | agagccggaa | 900 |
| agauuuccga | acggcuggug | aucacuucgg | aaaugaucga | aaacauccag | ucagugaagg | 960 |
| ccuacugcug | ggaagaggcc | auggaaaaga | ugauugaaaa | ccuccggcaa | accgagcuga | 1020 |
| agcugacccg | caaggccgcu | uacgugcgcu | auuucaacuc | guccgcuuuc | uucuucuccg | 1080 |
| gguucucgu | ggguguuucuc | uccgucuccc | ccuacgcccu | gauuaaggga | aucauccuca | 1140 |
| ggaagaucuu | caccaccauu | uccuucugua | ucgugcuccg | cauggccgug | accggcagu | 1200 |
| ucccaugggc | cgugcagacu | ugguacgacu | cccugggagc | cauuaacaag | auccaggacu | 1260 |
| uccuucaaaa | gcaggaguac | aagacccucg | aguacaaccu | gacuacuacc | gaggucguga | 1320 |
| uggaaaacgu | caccgccuuu | ugggaggagg | gauuuggcga | acuguucgag | aaggccaagc | 1380 |
| agaacaacaa | caaccgcaag | accucgaacg | ugacgacuc | ccucuucuuu | ucaaacuuca | 1440 |
| gccugcucgg | gacgcccgug | cugaaggaca | uuaacuucaa | gaucgaaaga | ggacagcucc | 1500 |
| uggcgguggc | cggaucgacc | ggagccggaa | agacuucccu | gcugauggug | aucaugggag | 1560 |
| agcuugaacc | uagcgaggga | aagaucaagc | acuccggccg | caucagcuuc | uguagccagu | 1620 |
| uuuccuggau | caugcccgga | accauuaagg | aaaacaucau | cuucggcgug | uccuacgaug | 1680 |
| aauaccgcua | ccggucckgug | aucaaagccu | gccagcugga | agaggauauu | caaaguucg | 1740 |
| cggagaaaga | uaacaucgug | cugggcgaag | ggguauuac | cuugucgggg | ggccagcggg | 1800 |
| cuagaaucuc | gcuggccaga | gccguguaua | aggacgccga | ccuguaucuc | cuggacuccc | 1860 |
| ccuucggaua | ccuggacguc | cugaccgaaa | aggagaucuu | cgaaucgugc | gugugcaagc | 1920 |
| ugauggcuaa | caagacucgc | auccucguga | ccuccaaaau | ggagcaccug | aagaaggcag | 1980 |
| acaagauucu | gauucugcau | gaggggugccu | ccuacuuuua | cggccacuuc | ucggaguugc | 2040 |
| agaacuugca | gcccgacuuc | ucaucgaagc | ugaugggguug | cgacagcuuc | gaccaguucu | 2100 |
| ccgccgaaag | aaggaacucg | auccugacgg | aaaccuugca | ccgcuucucu | uuggaaggcg | 2160 |

```
acgccccugu gucauggacc gagacuaaga agcagagcuu caagcagacc ggggaauucg   2220
gcgaaaagag gaagaacagc aucuugaacc ccauuaacuc cauccgcaag uucucaaucg   2280
ugcaaaagac gccacugcag augaacggca uugaggagga cuccgacgaa ccccuugaga   2340
ggcgccuguc ccuggugccg gacagcgagc agggagaagc cauccugccu cggauuccg    2400
ugaucuccac ugguccgacg cuccaagccc ggcggcggca guccgugcug aaccugauga   2460
cccacagcgu gaaccagggc caaaacauuc accgcaagac uaccgcaucc accccggaaag  2520
uguccuggc accucaagcg aaucuuaccg agcucgacau cuacucccgg agacugucgc    2580
aggaaaccgg gcucgaaauu ccgaagaaa ucaacgagga ggaucugaaa gagugcuucu    2640
ucgacgauau ggagucgaua cccgccguga cgacuuggaa cacuuaucug cgguacauca   2700
cugugcacaa gucauugauc uucgugcuga uuuggugccu ggugauuuuc cuggccgagg   2760
ucgcggccuc acugguggug cucuggcugu ugggaaacac gccucugcaa gacaagggaa   2820
acuccacgca cucgagaaac aacagcuaug ccgugauuau cacuuccacc uccucuuauu   2880
acguguucua caucuacguc ggaguggcgg auacccugcu cgcgaugggu ucuucagag    2940
gacugccgcu gguccacacc uugaucaccg ucagcaagau ucuucaccac aagauguugc   3000
auagcgugcu gcaggccccc auguccaccc ucaacacucu gaaggccgga ggcauucuga   3060
acagauucuc caaggacauc gcuauccugg acgaucuccu gccgcuuacc aucuuugacu   3120
ucauccagcu gcugcugauc gugauggag caaucgcagu ggugcggug cugcagccuu     3180
acauuucgu ggccacugug ccggucauug uggcguucau caugcugcgg gccuacuucc    3240
uccaaaccag ccagcagcug aagcaacugg aauccgaggg acgauccccc aucuucacuc   3300
accuugugac gucguugaag ggacugugga cccuccgggc uuucggacgg cagcccuacu   3360
ucgaaacccu cuuccacaag gcccugaacc uccacaccgc caauugguuc cuguaccugu   3420
ccacccugcg gugguuccag augcgcaucg agaugauuuu cgucaucuuc uucaucgcgg   3480
ucacauucau cagcauccug acuaccggag agggagaggg acggucggaa auaauccuga   3540
cccucgccau gaacauuaug agcacccugc aguggcagu gaacagccg aucgacgugg    3600
acagccugau gcgaagcguc agccgcgugu caaguucau cgacaugccu acugagggaa    3660
aacccacuaa guccacuaag cccuacaaaa auggccagcu gagcaagguc augaucaucg   3720
aaaacucca cgugaagaag gacgauauu ggcccuccgg aggucaaaug accgugaagg     3780
accugaccgc aaaguacacc gagggaggaa acgccauucu cgaaaacauc agcuucucca   3840
uuucgccgga acagcgggc ggccuucucg gcggaccgg uucgggaag ucaacucugc      3900
ugucggcuuu ccuccggcug cugaauaccg agggggaaau ccaaauugac ggcgugucuu   3960
gggauuccau uacucugcag cagguggcgga aggccuucgg cgugauccc cagaaggugu   4020
ucaucuucuc ggguaccuuc cggaagaacc ugggauccuua cgagcagugg agcgaccaag   4080
aaaucuggaa ggcgccgac gaggucggcc ugcgcuccgu gauugaacaa uuuccggaa     4140
agcuggacuu cgugcucguc gacggggau gugauccugc gcacggacau aagcagcuca    4200
ugugccucgc acggaccgug cucuccaagg ccaagauucu gcugcuggac gaaccuucgg   4260
cccaccugga uccggucacc uaccagauca ucaggaggac ccugaagcag gccuuugccg   4320
auugcaccgu gauucucugc gagcaccgca ucgaggccau gcuggagugc cagcaguucc   4380
uggcaucga ggagaacaag guccgccaau acgacuccau ucaaaagcuc ucaacgagc     4440
ggucgcuguu cagacaagcu auuucaccgu ccgauagagu gaagcucuuc ccgcaucgga   4500
```

| | |
|---|---|
| acagcucaaa gugcaaaucg aagccgcaga ucgcagccuu gaaggaagag acugaggaag | 4560 |
| aggugcagga cacccggcuu uaacgggugg caucccugug accccucccc agugccucuc | 4620 |
| cuggcccugg aaguugccac uccagugccc accagccuug uccuaauaaa auuaaguugc | 4680 |
| aucaagcu | 4688 |

```
<210> SEQ ID NO 7
<211> LENGTH: 4688
<212> TYPE: RNA
<213> ORGANISM: Artificial Sequence
<220> FEATURE:
<223> OTHER INFORMATION: Synthetic polynucleotide

<400> SEQUENCE: 7
```

| | |
|---|---|
| ggacagaucg ccuggagacg ccauccacgc uguuugacc uccauagaag acaccgggac | 60 |
| cgauccagcc uccgcggccg ggaacggugc auuggaacgc ggauuccccg ugccaagagu | 120 |
| gacucaccgu ccuugacacg augcaacgcu cuccucuuga aaaggccucg gugguguocca | 180 |
| agcucuucuu cucguggacu agaccccaucc ugagaaaggg guacagacag cgcuuggagc | 240 |
| uguccgauau cuaucaaauc ccuuccgugg acuccgcgga caaccugucc gagaagcucg | 300 |
| agagagaaug ggacagagaa cucgccucaa gaagaacccc gaagcugauu aaugcgcuua | 360 |
| ggcggugcuu uuucuggcgg uucauguucu acggcaucuu ccucuaccug ggagaggguca | 420 |
| ccaaggccgu gcagccccug uugcgggac ggauuauugc cuccuacgac cccgacaaca | 480 |
| aggaagaaag aagcaucgcu aucuacuugg gcaucggucu gugccugcuu uucaucgucc | 540 |
| ggacccucuu guugcauccu gcuauuuucg gccugcauca cauuggcaug cagaugagaa | 600 |
| uugccauguu ucccugauc uacaagaaaa cucugaagcu cucgagccgc gugcuugaca | 660 |
| agauuuccau cggccagcuc gugucccugc ucuccaacaa ucugaacaag uucgacgagg | 720 |
| gccucgcccu ggcccacuuc gugguggaucg cccucugca aguggcgcuu cugaugggcc | 780 |
| ugaucuggga gcugcugcaa gcccuggcau ucguggggcu uggauuccug aucgucuggg | 840 |
| cacuguucca ggccggacug gggcggauga ugaugaagua cagggaccag agagccggaa | 900 |
| agauuuccga acggcuggug aucacuuucgg aaaugaucga aaacauccag ucagugaagg | 960 |
| ccuacugcug ggaagaggcc auggaaaaga ugauugaaaa ccuccggcaa accgagcuga | 1020 |
| agcugacccg caaggccgcu uacgugcgcu auuucaacuc guccgcuuuc uucuucuccg | 1080 |
| gguucuucgu ggguguuucuc uccgugcuucc ccuacgcccu gauuaaggga aucauccuca | 1140 |
| ggaagaucuu caccaccauu uccuucugua ucgugcuccg cauggccgug acccggcagu | 1200 |
| ucccaugggc cgugcagacu ugguacgacu cccugggagc cauuaacaag auccaggacu | 1260 |
| uccuucaaaa gcaggaguac aagacccucg uacaaccu gacuacuacc gaggucguga | 1320 |
| uggaaaacgu caccgccuuu ugggaggagg gauuggcga acuguucgag aaggccaagc | 1380 |
| agaacaacaa caaccgcaag accucgaacg ugacgacuc cccucuucuuu ucaaacuuca | 1440 |
| gccugcucgg gacgcccgug cugaaggaca uuaacuucaa gaucgaaaga ggacagcucc | 1500 |
| uggcggugg cggaucgacc ggagccggaa agacuucccu gcugauggug aucaugggag | 1560 |
| agcuugaacc uagcgaggga aagaucaagc acuccggccg caucagcuuc uguagccagu | 1620 |
| uuccuggau caugcccgga accauuaagg aaaacaucau cuucggcgug ccuacgaug | 1680 |
| aauaccgcua ccggucgug aucaaagccu ccagcugga agaggauauu ucaaaguucg | 1740 |
| cggagaaaga uaacaucgug cugggcgaag ggggauauuac cuugucgggg ggccagcggg | 1800 |
| cuagaaucuc gcuggccaga gccguguaua aggacgccga ccuguaucuc cuggacuccc | 1860 |

```
ccuucggaua ccuggacguc cugaccgaaa aggagaucuu cgaaucgugc gugugcaagc      1920
ugauggcuaa caagacucgc auccucguga ccuccaaaau ggagcaccug aagaaggcag      1980
acaagauucu gauucugcau gaggggUccu ccuacuuuua cggcaccuuc ucggaguugc      2040
agaacuugca gcccgacuuc ucaucgaagc ugaugggUug cgacagcuuc gaccaguucu      2100
ccgccgaaag aaggaacucg auccugacgg aaaccuugca ccgcuucucu uuggaaggcg      2160 acgcccugu gucauggacc gagacuaaga agcagagcuu caagcagacc ggggaauucg       2220
gcgaaaagag gaagaacagc aucuugaacc ccauuaacuc cauccgcaag uucucaaucg      2280
ugcaaaagac gccacugcag augaacggca uugaggagga cuccgacgaa cccuugaga       2340 ggcgccuguc ccuggugccg gacagcgagc agggagaagc cauccugccu cggauuuccg      2400
ugaucuccac uggUccgacg cuccaagccc ggcggcggca guccgugcug aaccugauga      2460
cccacagcgu gaaccagggc caaaacauuc accgcaagac uaccgcaucc acccggaaag      2520 uguccuggc accuucaagcg aaucuuaccg agcucgacau cuacucccgg agacugucgc     2580
aggaaaccgg gcucgaaauu uccgaagaaa ucaacgagga ggaucugaaa gagugcuucu      2640
ucgacgauau ggagucgaua cccgccguga cgacuuggaa cacuuaucug cgguacauca     2700
cugugcacaa gucauugauc uucgugcuga uuuggugccu ggugauuuuc cuggccgagg      2760
ucgcggccuc acuggUggUg cucuggcugu ugggaaacac gccucugcaa gacaagggaa     2820
acuccacgca cucgagaaac aacagcuaug ccgugauuau cacuuccacc uccucuuauu      2880
acguguucua caucuacguc ggaguggcgg auacccugcu cgcgaugggu ucuucagag      2940 gacugccgcu ggUccacacc uugaucaccg ucagcaagau ucuucaccac aagauguugc      3000
auagcgugcu gcaggccccc augUccaccc ucaacacucu gaaggccgga ggcauucuga     3060
acagauucuc caaggacauc gcuauccugg acgaucccu gccgcuuacc aucuuugacu       3120
ucauccagcu gcugcugauc gugauuggag caaucgcagu gguggcggug cugcagccuu      3180
acauuuucgu ggccacugUg ccggUcauug uggcguucau caugcugcgg gccuacuucc      3240
uccaaaccag ccagcagcug aagcaacugg aauccgaggg acgauccccc aucuucacuc      3300
accuugugac gucguugaag ggacugugga cccuccgggc uuucgacgg cagcccuacu       3360 ucgaaacccu cuuccacaag gcccugaacc uccacaccgc caauugguuc cuguaccugu      3420
ccacccugcg ugguuccag augcgcaucg agaugauuuu cgucaucuuc uucaucgcgg       3480
ucacauucau cagcauccug acuaccggag agggagaggg acgggucgga auaauccuga     3540
cccucgccau gaacauuaug agcacccgc aguggUcagu gaacagcucg aucgacgugg       3600
acagccugau gcgaagcguc agccgcgugu ucaaguucau cgacaugccu acugagggaa     3660
aacccacuaa guccacuaag cccuacaaaa auggccagcu gagcaagguc augaucaucg      3720
aaaacuccca cgugaagaag gacgauauuu ggcccuccgg aggUcaaaug accgugaagg      3780
accugaccgc aaaguacacc gagggaggaa acgccauucu cgaaaacauc agcuuccuca     3840
uuucgccggg acagcgggUc ggccuucucg ggcggaccgg uuccgggaag ucaacucugc      3900
ugucggcuuu ccuccggcug cugaauaccg aggggaaau ccaaauugac ggcgugcuuu      3960
gggauuccau uacucugcag cagUggcgga aggccucgg cgUauccccc cagaagggUgu     4020 ucaucuucuc ggguaccuuc cggaagaacc uggauccuua cgagcagUgg agcgaccaag     4080
aaaucuggaa ggcgccgac gaggUcgcc ucgcucccgu gauugaacaa uuuccggaa       4140 agcuggacuu cgugcucguc gacgggggau gUgUccuguc gcacgacau aagcagcuca       4200
```

| | |
|---|---|
| ugugccucgc acgguccgug cucuccaagg ccaagauucu gcugcuggac gaaccuucgg | 4260 |
| cccaccugga uccggucacc uaccagauca ucaggaggac ccugaagcag gccuuugccg | 4320 |
| auugcaccgu gauucucugc gagcaccgca ucgaggccau gcuggagugc cagcaguucc | 4380 |
| uggucaucga ggagaacaag guccgccaau acgacuccau ucaaaagcuc cucaacgagc | 4440 |
| ggucgcuguu cagacaagcu auuucaccgu ccgauagagu gaagcucuuc ccgcaucgga | 4500 |
| acagcucaaa gugcaaaucg aagccgcaga ucgcagccuu gaaggaagag acugaggaag | 4560 |
| aggugcagga cacccggcuu uaaggguggc aucccuguga ccccuccca gugccucucc | 4620 |
| uggcccugga aguugccacu ccagugccca ccagccuugu ccuaauaaaa uuaaguugca | 4680 |
| ucaaagcu | 4688 |

<210> SEQ ID NO 8
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 8

| | |
|---|---|
| atgcagagga gcccactgga gaaagcctcc gtggtgagta aactcttttt tagttggacc | 60 |
| agacccatcc tgcgaaaagg atacaggcag cgcctcgagt tgtcagatat ctaccagatt | 120 |
| ccttctgtgg actcagctga caatttgagt gagaagctgg agcggagtg ggatagagag | 180 |
| ctggcgagca aaaaaaaccc caagcttatc aatgctctgc ccgctgctt tttctggagg | 240 |
| ttcatgtttt atgggatctt cctgtacctg ggggaggtca ccaaagctgt tcagccgctc | 300 |
| cttcttggcc gcatcatcgc cagctatgac cctgataata agaagaaag gtctattgct | 360 |
| atttatctgg gaattggcct ctgcttgctc ttcatcgtcc gcacccttct gctgcacc ct | 420 |
| gccattttg gccttcacca atcggcatg caaatgagaa ttgccatgtt ctccctcatt | 480 |
| tacaaaaaga ccctgaaact ttcctcaaga gtgttagata aatatccat ggtcagctg | 540 |
| gtcagcctgc tgtccaacaa tcttaacaaa tttgatgaag gcttggcgct ggcccacttc | 600 |
| gtgtggattg cacctctgca ggtggccctg ttgatgggac ttatatggga gctgcttcaa | 660 |
| gcctctgctt tctgtgggct gggcttttg attgtactgg cacttttca ggctgggctc | 720 |
| ggaagaatga tgatgaaata cagagatcag cgggccggga agatatcaga gcgacttgtg | 780 |
| atcaccagtg aaatgattga aatattcag agcgtgaaag cctactgctg ggaagaagcc | 840 |
| atggagaaga tgattgagaa cctgaggcag acagagctca gctcactcg gaaggctgct | 900 |
| tatgttcgct atttcaacag cagcgccttc ttcttcagtg gcttctttgt tgtcttcctg | 960 |
| tctgttctgc catatgcact gataaaaggc attattttac gaaagatctt caccaccatc | 1020 |
| agttttgca tcgttctcag gatggccgtc acaagacagt tccctgggc tgtgcagacc | 1080 |
| tggtacgatt ccttggggc catcaacaag attcaagatt ccttgcaaaa acaagaatat | 1140 |
| aaaactttag aatacaacct caccaccact gaagtggtca tggaaaatgt gacagccttt | 1200 |
| tgggaggagg ttttggaga attgttcgag aaggcaaagc agaataacaa caacaggaag | 1260 |
| acgagcaatg gggacgactc tctcttcttc agcaactttt cactgctcgg gaccctgtg | 1320 |
| ttgaaagata taaacttcaa gatcgagagg ggccagctct ggctgtggc aggctccact | 1380 |
| ggagctggta aacatctct tctccatggt atcatgggg aactggagcc ttccgaagga | 1440 |
| aaaatcaagc acagtgggag aatctcattc tgcagccagt tttcctggat catgcccggc | 1500 |
| accattaagg aaaacatcat atttggagtg tcctatgatg agtaccgcta ccggtcagtc | 1560 |

```
atcaaagcct gtcagttgga ggaggacatc tccaagtttg cagagaaaga caacattgtg    1620
cttggagagg ggggtatcac tctttctgga ggacaaagag ccaggatctc tttggcccgg    1680
gcagtctaca aggatgcaga cctctacttg ttggacagtc ccttcggcta cctcgacgtg    1740
ctgactgaaa aagaaatttt tgaaagctgt gtgtgcaaac tgatggcaaa caagaccagg    1800
attcttgtca ccagcaagat ggaacatctg aagaaagcgg acaaaattct gattctgcat    1860
gaagggagct cctacttcta tggaacattt agcgagcttc agaacctaca gccagcttc    1920 tcctccaaat taatgggctg tgactccttc gaccagttct ctgcagaaag aagaaactct    1980
atactcacag agaccctcca ccgcttctcc cttgagggag atgccccagt ttcttggaca    2040
gaaaccaaga agcagtcctt taagcagact ggcgagtttg gtgaaaagag gaaaaattca    2100
attctcaatc caattaacag tattcgcaag ttcagcattg tccagaagac acccctccag    2160
atgaatggca tcgaagaaga tagtgacgag ccgctggaga cggctgag tctggtgcca    2220 gattcagaac agggggaggc catcctgccc cggatcagcg tcatttccac aggccccaca    2280
ttacaagcac ggcgccggca gagtgtttta aatctcatga cccattcagt gaaccagggc    2340
caaaatatcc acaggaagac tacagcttct acccggaaag tgtctctggc ccctcaggcc    2400
aatctgaccg agctggacat ctacagcagg aggctctccc aggaaacagg gctggaaata    2460
tctgaagaga ttaatgaaga ggatcttaaa gagtgcttct ttgatgacat ggagagcatc    2520
cccgcggtga ccacatggaa cacctacctt agatatatta ctgtccacaa gagcctcata    2580
tttgtcctca tctggtgcct ggttattttc ctcgctgagg tggcggccag tcttgttgtg    2640
ctctggctgc tgggcaacac tcctctccag gacaagggca atagtactca cagcagaaat    2700
aattcttatg ccgtcatcat tacaagcacc tccagctact acgtgttcta catctatgtg    2760
ggcgtggctg acacctcct ggccatgggt ttcttccggg gcctgccttt ggtgcacacc    2820
ctcatcacag tgtcaaaaat tctgcaccat aaaatgcttc attctgtcct gcaggcaccc    2880
atgagcactt tgaacacatt gaaggctggc ggcatcctca acagattttc taaagatatt    2940
gctatcctgg atgatctcct cccctgaca atctttgact ttatccagct tctgctgatc    3000
gtgattggag ccatagcagt ggttgctgtc ctgcagccct acatttttgt ggccaccgtg    3060
cccgtgattg ttgcctttat tatgctcaga gcttacttcc tgcaaacttc tcaacagctc    3120
aaacagctag aatctgaggg ccggagcccc attttacccc acctggtgac ttccctgaag    3180
ggactgtgga ctctgagagc attcgggcga cagccttact tgagacact gttccacaag    3240 gccctgaact tgcacactgc caactggttt ctttacctga gcacactccg ctggttccag    3300
atgcggatag agatgatctt cgtcatcttt tttatagctg taaccttcat ttctatcctt    3360
acaacaggag aaggagaggg cagggtggga atcatcctca cgctggctat gaacataatg    3420
tccaccttgc agtgggccgt gaattccagt atagatgtgg attctctaat gaggagtgtc    3480
tcccgggtgt ttaaattcat tgatatgcct actgagggga aacccaccaa gtcaacaaaa    3540
ccttataaga atggacagct gagcaaggtg atgataattg agaacagcca cgtgaagaag    3600
gatgacattt ggcccagcgg gggccagatg actgtgaagg acctgacggc caagtacacc    3660
gaaggtggaa atgccatttt ggaaaacatc agcttctcaa tctctcctgg gcagagagtt    3720
ggattgctgg gtcgcacggg cagcggcaaa tcaaccctgc tcagtgcctt ccttcggctc    3780
ctgaatacag aaggcgaaat ccaaattgac ggggtgagct gggacagcat cacccctgcag    3840 cagtggagaa aagcatttgg ggtcattcca cagaaagttt tcatcttctc tggcactttc    3900
```

| | |
|---|---|
| agaaagaacc tggacccta tgagcagtgg agcgaccagg agatctggaa ggttgcagat | 3960 |
| gaagttggcc tgcggagtgt gatagaacaa tttcctggca agctggattt tgtgctggta | 4020 |
| gatggaggct gcgtgctgtc ccacggccac aaacagctga tgtgcctcgc ccgctccgtt | 4080 |
| ctttcaaagg ccaaaatctt gcttttggat gagcccagtg ctcacctcga cccagtgacc | 4140 |
| tatcagataa tccgcaggac cttaaagcaa gcttttgccg actgcaccgt catactgtgt | 4200 |
| gagcaccgga ttgaagcaat gctggaatgc cagcagtttc tggtgatcga ggagaataag | 4260 |
| gtccggcagt acgacagcat ccagaagttg ttgaatgagc gcagccttt ccgccaggcc | 4320 |
| atctccccat ctgacagagt caagctgttt ccacatagga actcctctaa gtgcaagtcc | 4380 |
| aagccccaga tcgctgccct caaggaggaa actgaggaag aggtgcagga tacccgcctg | 4440 |
| tga | 4443 |

<210> SEQ ID NO 9
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 9

| | |
|---|---|
| atgcagagga gcccactgga gaaagcctcc gtggtgagta aactcttttt tagttggacc | 60 |
| agacccatcc tgcgaaaagg atacaggcag cgcctcgagt tgtctgatat ctaccagatt | 120 |
| ccttctgtgg actcagctga caatttgagt gagaagctgg agcgggagtg ggatagagag | 180 |
| ctggcgagca aaaaaaaccc caagcttatc aatgctctgc gccgctgctt tttctggagg | 240 |
| ttcatgtttt atgggatctt cctgtacctg ggggaggtca ccaaagctgt tcagccgctc | 300 |
| cttcttggcc gcatcatcgc cagctatgac cctgataata agaagaaag gtctattgct | 360 |
| attatctgg gaattggcct ctgcttgctc ttcatcgtcc gcacccttct gctgcaccct | 420 |
| gccatttttg gccttcacca catcggcatg caaatgagaa ttgccatgtt ctccctcatt | 480 |
| tacaaaaaga ccctgaaact ttcctcaaga gtgttagata aatatccat tggtcagctg | 540 |
| gtcagcctgc tgtccaacaa tcttaacaaa tttgatgaag gcttggcgct ggcccacttc | 600 |
| gtgtggattg cacctctgca ggtggccctg ttgatgggac ttatatggga gctgcttcaa | 660 |
| gcctctgctt tctgtgggct gggcttttg attgtactgg cactttttca ggctgggctc | 720 |
| ggaagaatga tgatgaaata cagagatcag cgggccggga agatttcaga gcgacttgtg | 780 |
| atcaccagtg aaatgattga aaatattcag agcgtgaaag cctactgctg gaagaagcc | 840 |
| atggagaaga tgattgagaa cctgaggcag acagagctca gctcactcg gaaggctgct | 900 |
| tatgttcgct atttcaacag cagcgccttc ttcttcagtg gcttctttgt tgtcttcctg | 960 |
| tctgttctgc catatgcact gataaaaggc attatttac gaaagatctt caccaccatc | 1020 |
| agtttttgca tcgttctcag gatggccgtc acaagacagt tcccctgggc tgtgcagacc | 1080 |
| tggtacgatt ccttgggggc catcaacaag attcaagatt tcttgcaaaa acaagaatat | 1140 |
| aaaactttag aatacaacct caccaccact gaagtggtca tggaaaatgt gacagccttt | 1200 |
| tgggaggagg ttttggaga attgttcgag aaggcaaagc agaataacaa caacaggaag | 1260 |
| acgagcaatg gggacgactc tctcttcttc agcaacttt cactgctcgg gacccctgtg | 1320 |
| ttgaaagata taaacttcaa gatcgagagg ggccagctct ggctgtggc aggctccact | 1380 |
| ggagctggta aaacatctct tctcatggtg atcatggggg aactggagcc ttccgaagga | 1440 |
| aaaatcaagc acagtgggag aatctcattc tgcagccagt tttcctggat catgcccggc | 1500 |

```
accattaagg aaaacatcat atttggagtg tcctatgatg agtaccgcta ccggtcagtc    1560
atcaaagcct gtcagttgga ggaggacatc tccaagtttg cagagaaaga caacattgtg    1620
cttggagagg ggggtatcac tctttctgga ggacaaagag ccaggatctc tttggcccgg    1680
gcagtctaca aggatgcaga cctctacttg ttggacagtc ccttcggcta cctcgacgtg    1740
ctgactgaaa aagaaatttt tgaaagctgt gtgtgcaaac tgatggcaaa caagaccagg    1800
attcttgtca ccagcaagat ggaacatctg aagaaagcgg acaaaattct gattctgcat    1860
gaagggagct cctacttcta tggaacattt agcgagcttc agaacctaca gccagacttc    1920
tcctccaaat taatgggctg tgactccttc gaccagttct ctgcagaaag aagaaactct    1980
atactcacag agaccctcca ccgcttctcc cttgagggag atgccccagt ttcttggaca    2040
gaaaccaaga agcagtcctt taagcagact ggcgagtttg gtgaaaagag gaaaaattca    2100
attctcaatc caattaacag tattcgcaag ttcagcattg tccagaagac acccctccag    2160
atgaatggca tcgaagaaga tagtgacgag ccgctggaga gacggctgag tctggtgcca    2220
gattcagaac agggggaggc catcctgccc cggatcagcg tcatttccac aggccccaca    2280
ttacaagcac ggcgccggca gagtgtttta aatctcatga cccattcagt gaaccagggc    2340
caaaatatcc acaggaagac tacagcttct acccggaaag tgtctctggc ccctcaggcc    2400
aatctgaccg agctggacat ctacagcagg aggctctccc aggaaacagg gctggaaata    2460
tctgaagaga ttaatgaaga ggatcttaaa gagtgcttct ttgatgacat ggagagcatc    2520
cccgcggtga ccacatggaa cacctacctt agatatatta ctgtccacaa gagcctcata    2580
tttgtcctca tctggtgcct ggttattttc ctcgctgagg tggcggccag tcttgttgtg    2640
ctctggctgc tgggcaacac tcctctccag gacaagggca atagtactca cagcagaaat    2700
aattcttatg ccgtcatcat tacaagcacc tccagctact acgtgttcta catctatgtg    2760
ggcgtggctg acaccctcct ggccatgggt ttcttccggg gcctgccttt ggtgcacacc    2820
ctcatcacag tgtcaaaaat tctgcaccat aaaatgcttc attctgtcct gcaggcaccc    2880
atgagcactt tgaacacatt gaaggctggc ggcatcctca acagatttta taagatatt     2940 gctatcctgg atgatctcct cccctgaca atctttgact ttatccagct tctgctgatc    3000
gtgattggag ccatagcagt ggttgctgtc ctgcagccct acatttttgt ggccaccgtg    3060
cccgtgattg ttgcctttat tatgctcaga gcttacttcc tgcaaacttc tcaacagctc    3120
aaacagctag aatctgaggg ccggagcccc attttacccc acctggtgac ttccctgaag    3180
ggactgtgga ctctgagagc attcgggcga cagccttact tgagacact gttccacaag     3240 gccctgaact tgcacactgc caactggttt ctttacctga gcacactccg ctggttccag    3300
atgcggatag agatgatctt cgtcatcttt tttatagctg taaccttcat ttctatcctt    3360
acaacaggag aaggagaggg cagggtggga atcatcctca cgctggctat gaacataatg    3420
tccaccttgc agtgggccgt gaattccagt atagatgtgg attctctaat gaggagtgtc    3480
tcccgggtgt ttaaattcat tgatatgcct actgagggga aacccaccaa gtcaacaaaa    3540
ccttataaga atggacagct gagcaaggtg atgataattg agaacagcca cgtgaagaag    3600
gatgacattt ggcccagcgg gggccagatg actgtgaagg acctgacggc caagtacacc    3660
gaaggtggaa atgccatttt ggaaaacatc agcttctcaa tctctcctgg gcagagagtt    3720
ggattgctgg gtcgcacggg cagcggcaaa tcaaccctgc tcagtgcctt ccttcggctc    3780
ctgaatacag aaggcgaaat ccaaattgac ggggtgagct gggacagcat caccctgcag    3840
```

| | |
|---|---|
| cagtggagaa aagcatttgg ggtcattcca cagaaagttt tcatcttctc tggcactttc | 3900 |
| agaaagaacc tggaccccta tgagcagtgg agcgaccagg agatctgaa ggttgcagat | 3960 |
| gaagttggcc tgcggagtgt gatagaacaa tttcctggca agctggattt tgtgctggta | 4020 |
| gatgaaggct gcgtgctgtc ccacggccac aaacagctga tgtgcctcgc ccgctccgtt | 4080 |
| ctttcaaagg ccaaaatctt gcttttggat gagcccagtg ctcaccttga cccagtgacc | 4140 |
| tatcagataa tccgcaggac cttaaagcaa gcttttgccg actgcaccgt catactgtgt | 4200 |
| gagcaccgga ttgaagcaat gctggaatgc cagcagtttc tggtgatcga ggagaataag | 4260 |
| gtccggcagt acgacagcat ccagaagttg ttgaatgagc gcagccttt ccgccaggcc | 4320 |
| atctccccat ctgacagagt caagctgttt ccacatagga actcctctaa gtgcaagtcc | 4380 |
| aagccccaga tcgctgccct caaggaggaa actgaggaag aggtgcagga tacccgcctg | 4440 |
| tga | 4443 |

<210> SEQ ID NO 10
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 10

| | |
|---|---|
| atgcagagga gcccactgga gaaagcctcc gtggtgagta aactcttttt tagttggacc | 60 |
| agacccatcc tgcgaaaagg atacaggcag cgcctcgagt tgtcagatat ctaccagatt | 120 |
| ccttctgtgg actcagctga caatttgagt gagaagctgg agcgggagtg ggatagagag | 180 |
| ctggcgagca aaaaaaaccc caagcttatc aatgctctgc gccgctgctt tttctggagg | 240 |
| ttcatgtttt atgggatctt cctgtacctg ggggaggtca ccaaagctgt tcagccgctc | 300 |
| cttcttggcc gcatcatcgc cagctatgac cctgataata agaagaaag gtctattgct | 360 |
| atttatctgg gaattggcct ctgcttgctc ttcatcgtcc gcaccttct gctgcaccct | 420 |
| gccatttttg gccttcacca catcggcatg caaatgagaa ttgccatgtt ctccctcatt | 480 |
| tacaaaaaga ccctgaaact ttcctcaaga gtgttagata aaatatccat tggtcagctg | 540 |
| gtcagcctgc tgtccaacaa tcttaacaaa tttgatgaag cttggcgct ggcccacttc | 600 |
| gtgtggattg cacctctgca ggtggccctg ttgatgggac ttatatggga gctgcttcaa | 660 |
| gcctctgctt tctgtgggct gggcttttg attgtactgg cacttttca ggctgggctc | 720 |
| ggaagaatga tgatgaaata cagagatcag cgggccggga agatatcaga gcgacttgtg | 780 |
| atcaccagtg aaatgattga aatattcag agcgtgaaag cctactgctg gaagaagcc | 840 |
| atggagaaga tgattgagaa cctgaggcag acagagctca gctcactcg gaaggctgct | 900 |
| tatgttcgct atttcaacag cagcgccttc ttcttcagtg gcttctttgt tgtcttcctg | 960 |
| tctgttctgc catatgcact gataaaaggc attattttac gaaagatctt caccaccatc | 1020 |
| agttttttgca tcgttctcag gatggccgtc acaagacagt tccctgggc tgtgcagacc | 1080 |
| tggtacgatt ccttgggggc catcaacaag attcaagatt tcttgcaaaa acaagaatat | 1140 |
| aaaactttag aatacaacct caccaccact gaagtggtca tggaaaatgt gacagccttt | 1200 |
| tgggaggagg ttttggaga attgttcgag aaggcaaagc agaataacaa caacaggaag | 1260 |
| acgagcaatg gggacgactc tctcttcttc agcaactttt cactgctcgg gaccctgtg | 1320 |
| ttgaaagata taaacttcaa gatcgagagg ggccagctct ggctgtggc aggctccact | 1380 |
| ggagctggta aaacatctct tctccatggtg atcatggggg aactggagcc ttccgaagga | 1440 |

```
aaaatcaagc acagtgggag aatctcattc tgcagccagt tttcctggat catgcccggc    1500
accattaagg aaaacatcat atttggagtg tcctatgatg agtaccgcta ccggtcagtc    1560
atcaaagcct gtcagttgga ggaggacatc tccaagtttg cagagaaaga caacattgtg    1620
cttggagagg ggggtatcac tctttctgga ggacaaagag ccaggatctc tttggcccgg    1680
gcagtctaca aggatgcaga cctctacttg ttggacagtc ccttcggcta cctcgacgtg    1740
ctgactgaaa aagaaatttt tgaaagctgt gtgtgcaaac tgatggcaaa caagaccagg    1800
attcttgtca ccagcaagat ggaacatctg aagaaagcgg acaaaattct gattctgcat    1860
gaagggagct cctacttcta tggaacattt agcgagcttc agaacctaca gccagcttc    1920 tcctccaaat taatgggctg tgactccttc gaccagttct ctgcagaaag aagaaactct    1980
atactcacag agaccctcca ccgcttctcc cttgagggag atgccccagt ttcttggaca    2040
gaaaccaaga agcagtcctt taagcagact ggcgagtttg gtgaaaagag gaaaaattca    2100
attctcaatc caattaacag tattcgcaag ttcagcattg tccagaagac acccctccag    2160
atgaatggca tcgaagaaga tagtgacgag ccgctggaga gacggctgag tctggtgcca    2220
gattcagaac aggggaggc catcctgccc cggatcagcg tcatttccac aggccccaca    2280
ttacaagcac ggcgccggca gagtgtttta aatctcatga cccattcagt gaaccagggc    2340
caaaatatcc acaggaagac tacagcttct acccggaaag tgtctctggc ccctcaggcc    2400
aatctgaccg agctggacat ctacagcagg aggctctccc aggaaacagg gcttgaaata    2460
tctgaagaga ttaatgaaga ggatcttaaa gagtgcttct ttgatgacat ggagagcatc    2520
cccgcggtga ccacatggaa cacctacctt agatatatta ctgtccacaa gagcctcata    2580
tttgtcctca tctggtgcct ggttattttc ctcgctgagg tggcggccag tcttgttgtg    2640
ctctggctgc tgggcaacac tccctctccag gacaagggca atagtacaca cagcagaaat    2700
aattcttatg ccgtcatcat tacaagcacc tccagctact acgtgttcta catctatgtg    2760
ggcgtggctg acaccctcct ggccatgggt ttcttccggg gcctgccttt ggtgcacacc    2820
ctcatcacag tgtcaaaaat tctgcaccat aaaatgcttc attctgtcct gcaggcaccc    2880
atgagcactt tgaacacatt gaaggctggc ggcatcctca acagatttc taaagatatt    2940 gctatcctgg atgatctcct ccccctgaca atctttgact ttatccagct tctgctgatc    3000
gtgattggag ccatagcagt ggttgctgtc ctgcagccct acattttttgt ggccaccgtg    3060 cccgtgattg ttgcctttat tatgctcaga gcttacttcc tgcaaacttc tcaacagctc    3120
aaacagctag aatctgaggg ccggagcccc attttacccc acctggtgac ttccctgaag    3180
ggactgtgga ctctgagagc attcgggcga cagccttact tgagacact gttccacaag    3240 gccctgaact tgcacactgc caactggttt ctttacctga gcacactccg ctggttccag    3300
atgcggatag agatgatctt cgtcatcttt tttatagctg taaccttcat ttctatcctt    3360
acaacaggag aaggagaggg cagggtggga atcatcctca cgctggctat gaacataatg    3420
tccaccttgc agtgggccgt gaattccagt atagatgtgg attctctaat gaggagtgtc    3480
tcccgggtgt ttaaattcat tgatatgcct actgagggga acccaccaa gtcaacaaaa    3540 ccttataaga atggacagct gagcaaggtg atgataattg agaacagcca cgtgaagaag    3600
gatgacattt ggcccagcgg gggccagatg actgtgaagg acctgacggc caagtacacc    3660
gaaggtggaa atgccatttt ggaaaacatc agcttctcaa tctctcctgg gcagagagtt    3720
ggattgctgg gtcgcacggg cagcggcaaa tcaaccctgc tcagtgcctt ccttcggctc    3780
```

| | |
|---|---|
| ctgaatacag aaggcgaaat ccaaattgac ggggtgagct gggacagcat caccctgcag | 3840 |
| cagtggagaa aagcatttgg ggtcattcca cagaaagttt tcatcttctc tggcactttc | 3900 |
| agaaagaacc tggaccccta tgagcagtgg agcgaccagg agatctggaa ggttgcagat | 3960 |
| gaagttggcc tgcggagtgt gatagaacaa tttcctggca agctggattt tgtgctggta | 4020 |
| gatggaggct gcgtgctgtc ccacggccac aaacagctga tgtgcctcgc ccgctccgtt | 4080 |
| ctttcaaagg ccaaaatctt gcttttggat gagcccagtg ctcaccttga cccagtgacc | 4140 |
| tatcagataa tccgcaggac cttaaagcaa gcttttgccg actgcaccgt catactgtgt | 4200 |
| gagcaccgga ttgaagcaat gctggaatgc cagcagtttc tggtgatcga ggagaataag | 4260 |
| gtccggcagt acgacagcat ccagaagttg ttgaatgagc gcagccttt ccgccaggcc | 4320 |
| atctccccat ctgacagagt caagctgttt ccacatagga actcctctaa gtgcaagtcc | 4380 |
| aagccccaga tcgctgccct caaggaggaa actgaggaag aggtgcagga tacccgcctg | 4440 |
| tga | 4443 |

<210> SEQ ID NO 11
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 11

| | |
|---|---|
| atgcagagga gcccactgga gaaagcctcc gtggtgagta aactctttt tagttggacc | 60 |
| agacccatcc tgcgaaaagg atacaggcag cgcctcgagt tgtcagatat ctaccagatt | 120 |
| ccttctgtgg actcagctga caatttgagt gagaagctgg agcgggagtg ggatagagag | 180 |
| ctggcgagca aaaaaaaccc caagcttatc aatgctctgc gccgctgctt tttctggagg | 240 |
| ttcatgtttt atgggatctt cctgtacctg ggggaggtca ccaaagctgt tcagccgctc | 300 |
| cttcttggcc gcatcatcgc cagctatgac cctgataata agaagaaag gtctattgct | 360 |
| atttatctgg gaattggcct ctgcttgctc ttcatcgtcc gcaccttct gctgcaccct | 420 |
| gccattttg gccttcacca catcggcatg caaatgagaa ttgccatgtt ctccctcatt | 480 |
| tacaaaaaga ccctgaaact ttcctcaaga gtgttagata aatatccat ggtcagctg | 540 |
| gtcagcctgc tgtccaacaa tcttaacaaa tttgatgaag cttggcgct ggcccacttc | 600 |
| gtgtggattg cacctctgca ggtggccctg ttgatgggac ttatatggga gctgcttcaa | 660 |
| gcctctgctt tctgtgggct gggcttttg attgtactgg cacttttca ggctgggctc | 720 |
| ggaagaatga tgatgaaata cagagatcag cgggccggga agatatcaga gcgacttgtg | 780 |
| atcaccagtg aaatgattga aaatattcag agcgtgaaag cctactgctg gaagaagcc | 840 |
| atggagaaga tgattgagaa cctgaggcag acagagctca agctcactcg gaaggctgct | 900 |
| tatgttcgct atttcaacag cagcgccttc ttcttcagtg gcttctttgt tgtcttcctg | 960 |
| tctgttctgc catatgcact gataaaaggc attatttac gaaagatctt caccaccatc | 1020 |
| agttttgca tcgttctcag gatggccgtc acaagacagt tcccctgggc tgtgcagacc | 1080 |
| tggtacgatt cctgggggc catcaacaag attcaagatt tcttgcaaaa acaagaatat | 1140 |
| aaaactttag aatacaacct caccaccact gaagtggtca tggaaaatgt gacagccttt | 1200 |
| tgggaggagg gttttggaga attgttcgag aaggcaaagc agaataacaa caacaggaag | 1260 |
| acgagcaatg ggacgactc tctcttcttc agcaactttt cactgctcgg gacccctgtg | 1320 |
| ttgaaagata taaacttcaa gatcgagagg ggccagctct ggctgtggc aggctccact | 1380 |

```
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt tcttggaca   2040 gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac aggggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gctgaaata   2460 tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acacctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagatttc taaagatatt   2940 gctatcctgg atgatctcct cccctgaca atctttgact ttatccagct tctgctgatc   3000
gtgattggag ccatagcagt ggttgctgtc ctgcagccct acattttgt ggccaccgtg   3060 cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact tgagacact gttccacaag   3240 gccctgaact tgcacactgc caactggttt ctttacctga gcacactccg ctggttccag   3300
atgcggatag atgatgtctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcca actgagggga aacccaccaa gtcaacaaaa   3540
ccttataaga atggacagct gagcaaggtg atgataattg agaacagcca cgtgaagaag   3600
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
```

```
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
cttccaaagg ccaaaatctt gcttttggat gagcccagtg ctcacctcga cccagtgacc   4140
tatcagataa tccgcaggac cttaaagcaa gcttttgccg actgcaccgt catactgtgt   4200
gagcaccgga ttgaagcaat gctggaatgc agcagtttc tggtgatcga ggagaataag   4260
gtccggcagt acgacagcat ccagaagttg ttgaatgagc gcagccttt ccgccaggcc   4320
atctccccat ctgacagagt caagctgttt ccacatagga actcctctaa gtgcaagtcc   4380
aagccccaga tcgctgccct caaggaggaa actgaggaag aggtgcagga tacccgcctg   4440
tga                                                                  4443

<210> SEQ ID NO 12
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 12
atgcagagga gcccactgga gaaagcctcc gtggtgagta aactctttt tagttggacc     60
agacccatcc tgcgaaaagg atacaggcag cgcctcgagt tgtcagatat ctaccagatt    120
ccttctgtgg actcagctga caatttgagt gagaagctgg agcgggagtg ggatagagag    180
ctggcgagca aaaaaaaccc caagcttatc aatgctctgc gccgctgctt tttctggagg    240
ttcatgtttt atgggatctt cctgtacctg ggggaggtca ccaaagctgt tcagccgctc    300
cttcttggcc gcatcatcgc cagctatgac cctgataata agaagaaag gtctattgct    360
atttatctgg gaattggcct ctgcttgctc ttcatcgtcc gcaccttct gctgcacct    420
gccattttg gccttcacca tcggcatg caaatgagaa ttgccatgtt ctccctcatt    480
tacaaaaaga ccctgaaact ttcctcaaga gtgttagata aatatccat ggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggcttttg attgtactgg cactttttca ggctgggctc    720
ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaggc attatttac gaaagatctt caccaccatc    1020
agttttgca tcgttctcag gatggccgtc acaagacagt tcccctgggc tgtgcagacc    1080
tggtacgatt ccttggggc catcaacaag attcaagatt tcttgcaaaa acaagaatat    1140
aaaactttag aatacaacct caccaccact gaagtggtca tggaaaatgt gacagccttt    1200
tgggaggagg gtttttggaga attgttcgag aaggcaaagc agaataacaa caacaggaag    1260
acgagcaatg gggacgactc tctcttcttc agcaacttt cactgctcgg gacccctgtg    1320
```

```
ttgaaagata taaacttcaa gatcgagagg ggccagctct tggctgtggc aggctccact    1380
ggagctggta aaacatctct tctcatggta atcatggggg aactggagcc ttccgaagga    1440
aaaatcaagc acagtgggag aatctcattc tgcagccagt tttcctggat catgcccggc    1500
accattaagg aaaacatcat atttggagtg tcctatgatg agtaccgcta ccggtcagtc    1560
atcaaagcct gtcagttgga ggaggacatc tccaagtttg cagagaaaga caacattgtg    1620
cttggagagg ggggtatcac tctttctgga ggacaaagag ccaggatctc tttgccccgg    1680
gcagtctaca aggatgcaga cctctacttg ttggacagtc ccttcggcta cctcgacgtg    1740
ctgactgaaa aagaaatttt tgaaagctgt gtgtgcaaac tgatggcaaa caagaccagg    1800
attcttgtca ccagcaagat ggaacatctg aagaaagcgg acaaaattct gattctgcat    1860
gaagggagct cctacttcta tggaacattt agcgagcttc agaacctaca gccagcttc     1920 tcctccaaat taatgggctg tgactccttc gaccagttct ctgcagaaag aagaaactct    1980
atactcacag agaccctcca ccgcttctcc cttgagggag atgccccagt tcttggaca     2040 gaaaccaaga agcagtcctt taagcagact ggcgagtttg gtgaaaagag gaaaaattca    2100
attctcaatc ctattaacag tattcgcaag ttcagcattg tccagaagac ccccctccag    2160
atgaatggca tcgaagaaga tagtgacgag ccgctggaga gacggctgag tctggtgcca    2220
gattcagaac agggggaggc catcctgccc cggatcagcg tcatttccac aggccccaca    2280
ttacaagcac ggcgccggca gagtgtttta aatctcatga cccattcagt gaaccagggc    2340
caaaatatcc acaggaagac tacagcttct acccggaaag tgtctctggc ccctcaggcc    2400
aatctgaccg agctggacat ctacagcagg aggctctccc aggaaacagg gcttgaaata    2460
tctgaagaga ttaatgaaga ggatcttaaa gagtgcttct tgatgacat ggagagcatc     2520 cccgcggtga ccacatggaa cacctacctt agatatatta ctgtccacaa gagcctcata    2580
tttgtcctca tctggtgcct ggttattttc ctcgctgagg tggcggccag tcttgttgtg    2640
ctctggctgc tgggcaacac tcctctccag gacaagggca atagtactca cagcagaaat    2700
aattcttatg ccgtcatcat tacaagcacc tccagctact acgtgttcta catctatgtg    2760
ggcgtggctg acaccctcct ggccatgggt ttcttccggg gcctgcctt ggtgcacacc      2820 ctcatcacag tgtcaaaaat tctgcaccat aaaatgcttc attctgtcct gcaggcaccc    2880
atgagcactt tgaacacatt gaaggctggc ggcatcctca acagatttc taaagatatt     2940 gctatcctgg atgatctcct ccccctgaca atctttgact ttatccagct tctgctgatc    3000
gtgattggag ccatagcagt ggttgctgtc ctgcagccct acattttgt ggccaccgtg     3060 cccgtgattg ttgcctttat tatgctcaga gcttacttcc tgcaaacttc tcaacagctc    3120
aaacagctag aatctgaggg ccggagcccc atttttaccc acctggtgac ttccctgaag    3180
ggactgtgga ctctgagagc attcgggcga cagccttact tgagacact gttccacaag     3240 gccctgaact tgcacactgc caactggttt ctttacctga gcacactccg ctggttccag    3300
atgcggatag agatgatcct cgtcatcttt tttatagctg taaccttcat ttctatcctt    3360
acaacaggag aaggagaggg cagggtggga atcatcctca cgctggctat gaacataatg    3420
tccaccttgc agtgggccgt gaattccagt atagatgtgg attctctaat gagggagtgtc   3480 tcccgggtgt ttaaattcat tgatatgcct actgagggga aacccaccaa gtcaacaaaa    3540
ccttataaga tggacagct  gagcaaggtg atgataattg agaacagcca cgtgaagaag    3600
gatgacattt ggcccagcgg gggccagatg actgtgaagg acctgacggc caagtacacc    3660
```

| | |
|---|---|
| gaaggtggaa atgccatttt ggaaaacatc agcttctcaa tctctcctgg gcagagagtt | 3720 |
| ggattgctgg gtcgcacggg cagcggcaaa tcaaccctgc tcagtgcctt ccttcggctc | 3780 |
| ctgaatacag aaggcgaaat ccaaattgac ggggtgagct gggacagcat caccctgcag | 3840 |
| cagtggagaa aagcatttgg ggtcattcca cagaaagttt tcatcttctc tggcactttc | 3900 |
| agaaagaacc tggacccta tgagcagtgg agcgaccagg agatctggaa ggttgcagat | 3960 |
| gaagttggcc tgcggagtgt gatagaacaa tttcctggca agctggattt tgtgctggta | 4020 |
| gatggaggct gcgtgctgtc ccacggccac aaacagctga tgtgcctcgc ccgctccgtt | 4080 |
| ctttcaaagg ccaaaatctt gcttttggat gagcccagtg ctcacctcga cccagtgacc | 4140 |
| tatcagataa tccgcaggac cttaaagcaa gcttttgccg actgcaccgt catactgtgt | 4200 |
| gagcaccgga ttgaagcaat gctggaatgc cagcagtttc tggtgatcga ggagaataag | 4260 |
| gtccggcagt acgacagcat ccagaagttg ttgaatgagc gcagccttt ccgccaggcc | 4320 |
| atctccccat ctgacagagt caagctgttt ccacatagga actcctctaa gtgcaagtcc | 4380 |
| aagccccaga tcgctgccct caaggaggaa actgaggaag aggtgcagga tacccgcctg | 4440 |
| tga | 4443 |

<210> SEQ ID NO 13
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 13

| | |
|---|---|
| atgcagagga gcccactgga gaaagcctcc gtggtgagta aactctttt tagttggacc | 60 |
| agacccatcc tgcgaaaagg atacaggcag cgcctcgagt tgtcagatat ctaccagatt | 120 |
| ccttctgtgg actcagctga caatttgagt gagaagctgg agcgggagtg ggatagagag | 180 |
| ctggcgagca aaaaaaaccc caagcttatc aatgctctgc gccgctgctt tttctggagg | 240 |
| ttcatgtttt atgggatctt cctgtacctg ggggaggtca ccaaagctgt tcagccgctc | 300 |
| cttcttggcc gcatcatcgc cagctatgac cctgataata agaagaaag gtctattgct | 360 |
| atttatctgg gaattggcct ctgcttgctc ttcatcgtcc gcaccttct gctgcaccct | 420 |
| gccatttttg gccttcacca catcggcatg caaatgagaa ttgccatgtt ctccctcatt | 480 |
| tacaaaaaga ccctgaaact ttcctcaaga gtgttagata aatatccat tggtcagctg | 540 |
| gtcagcctgc tgtccaacaa tcttaacaaa tttgatgaag gcttggcgct ggcccacttc | 600 |
| gtgtggattg cacctctgca ggtggccctg ttgatgggac ttatatggga gctgcttcaa | 660 |
| gcctctgctt tctgtgggct gggcttttg attgtactgg cactttttca ggctgggctc | 720 |
| ggaagaatga tgatgaaata cagagatcag cgggccggga agatttcaga gcgacttgtg | 780 |
| atcaccagtg aaatgattga aaatattcag agcgtgaaag cctactgctg ggaagaagcc | 840 |
| atggagaaga tgattgagaa cctgaggcag acagagctca agctcactcg gaaggctgct | 900 |
| tatgttcgct atttcaacag cagcgccttc ttcttcagtg gcttctttgt tgtcttcctg | 960 |
| tctgttctgc catatgcact gataaaaggc attattttac gaaagatctt caccaccatc | 1020 |
| agttttgca tcgttctcag gatggccgtc acaagacagt tccctgggc tgtgcagacc | 1080 |
| tggtacgatt ccttggggc catcaacaag attcagatt tcttgcaaaa acaagaatat | 1140 |
| aaaactttag aatacaacct caccaccact gaagtggtca tggaaatgt gacagccttt | 1200 |
| tgggaggagg gttttggaga attgttcgag aaggcaaagc agaataacaa caacaggaag | 1260 |

```
acgagcaatg gggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa agaaattttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga cacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct ccccctgaca atctttgact ttatccagct tctgctgatc   3000
gtgattggag ccatagcagt ggttgctgtc ctgcagccct acattttgt ggccaccgtg   3060 cccgtgattg ttgcctttat tatgctcaga gcttacttcc tgcaaacttc tcaacagctc   3120
aaacagctag aatctgaggg ccggagcccc attttaccc acctggtgac ttccctgaag   3180
ggactgtgga ctctgagagc attcgggcga cagccttact tgagacact gttccacaag   3240 gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggcta tgaacataatg   3420 tccaccttgc agtgggccgt gaattccagt atagatgtgg attctctaat gaggagtgtc   3480
tcccgggtgt ttaaattcat tgatatgcca actgagggga aacccaccaa gtcaacaaaa   3540
ccttataaga atggacagct gagcaaggtg atgataattg agaacagcca cgtgaagaag   3600
```

```
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggatt tgtgctggta    4020 gatggaggct gcgtgctgtc ccacggccac aaacagctga tgtgcctcgc ccgctccgtt   4080 cttctcaaagg ccaaaatctt gcttttggat gagcccagtg ctcacctcga cccagtgacc  4140
tatcagataa tccgcaggac cttaaagcaa gcttttgccg actgcaccgt catactgtgt   4200
gagcaccgga ttgaagcaat gctggaatgc cagcagtttc tggtgatcga ggagaataag   4260
gtccggcagt acgacagcat ccagaagttg ttgaatgagc gcagccttt ccgccaggcc    4320 atctccccat ctgacagagt caagctgttt ccacatagga actcctctaa gtgcaagtcc   4380
aagccccaga tcgctgccct caaggaggaa actgaggaag aggtgcagga tacccgcctg   4440
tga                                                                4443

<210> SEQ ID NO 14
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 14
atgcagagga gcccactgga gaaagcctcc gtggtgagta aactcttttt tagttggacc     60
agacccatcc tgcgaaaagg atacaggcag cgcctcgagt tgtctgatat ctaccagatt    120
ccttctgtgg actcagctga caatttgagt gagaagctgg agcgggagtg ggatagagag    180
ctggcgagca aaaaaaaccc caagcttatc aatgctctgc gccgctgctt tttctggagg    240
ttcatgtttt atgggatctt cctgtacctg ggggaggtca ccaaagctgt tcagccgctc    300
cttcttggcc gcatcatcgc cagctatgac cctgataata agaagaaag gtctattgct    360 atttatctgg gaattggcct ctgcttgctc ttcatcgtcc gcacccttct gctgcacccct  420 gccattttg gccttcacca catcggcatg caaatgagaa ttgccatgtt ctccctcatt     480
tacaaaaaga ccctgaaact ttcctcaaga gtgttagata aatatccat ggtcagctg    540 gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggcttttttg attgtactgg cacttttttca ggctgggctc    720 ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca gctcactcg gaaggctgct     900 tatgttcgct atttcaacag cagcgccttc ttcttcagtg gcttctttgt tgtcttcctg    960
tctgttctgc catatgcact gataaaaggc attatttac gaaagatctt caccaccatc    1020 agttttttgca tcgttctcag gatggccgtc acaagacagt tccctgggc tgtgcagacc   1080 tggtacgatt ccttggggc catcaacaag attcaagatt tcttgcaaaa acaagaatat    1140
aaaactttag aatacaacct caccaccact gaagtggtca tggaaaatgt gacagccttt    1200
```

```
tgggaggagg gttttggaga attgttcgag aaggcaaagc agaataacaa caacaggaag   1260
acgagcaatg gggacgactc tctcttcttc agcaacttt  cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtccgtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac aggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gcttgaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gctgcccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagatttc taaagatatt   2940 gctatcctgg atgatctcct ccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc attttaccc  acctggtgac ttccctgaag   3180
ggactgtgga ctctgagagc attcgggcga cagccttact tgagacact  gttccacaag   3240 gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcct actgagggga aacccaccaa gtcaacaaag   3540
```

```
ccttataaga atggacagct gagcaaggtg atgataattg agaacagcca cgtgaagaag    3600
gatgacattt ggcccagcgg gggccagatg actgtgaagg acctgacggc caagtacacc    3660
gaaggtggaa atgccatttt ggaaaacatc agcttctcaa tctctcctgg cagagagtt    3720
ggattgctgg gtcgcacggg cagcggcaaa tcaaccctgc tcagtgcctt ccttcggctc    3780
ctgaatacag aaggcgaaat ccaaattgac ggggtgagct gggacagcat caccctgcag    3840
cagtggagaa aagcatttgg ggtcattcca cagaaagttt tcatcttctc tggcactttc    3900
agaaagaacc tggacccta tgagcagtgg agcgaccagg agatctggaa ggttgcagat    3960
gaagttggcc tgcggagtgt gatagaacaa tttcctggca agctggattt tgtgctggta    4020
gatggaggct gcgtgctgtc ccacggccac aaacagctga tgtgcctcgc ccgctccgtt    4080
ctttcaaagg ccaaaatctt gcttttggat gagcccagtg ctcacctcga cccagtgacc    4140
tatcagataa tccgcaggac cttaaagcaa gcttttgccg actgcaccgt catactgtgt    4200
gagcaccgga ttgaagcaat gctggaatgc cagcagtttc tggtgatcga ggagaataag    4260
gtccggcagt acgacagcat ccagaagttg ttgaatgagc gcagccttttt ccgccaggcc    4320
atctccccat ctgacagagt caagctgttt ccacatagga actcctctaa gtgcaagtcc    4380
aagccccaga tcgctgccct caaggaggaa actgaggaag aggtgcagga tacccgcctg    4440
tga                                                                4443

<210> SEQ ID NO 15
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 15
atgcagagga gcccactgga gaaagcctcc gtggtgagta aactcttttt tagttggacc      60
agacccatcc tgcgaaaagg atacaggcag cgcctcgagt tgtcagatat ctaccagatt     120
ccttctgtgg actcagctga caatttgagt gagaagctgg agcgggagtg ggatagagag     180
ctggcgagca aaaaaaaccc caagcttatc aatgctctgc gccgctgctt tttctggagg     240
ttcatgtttt atgggatctt cctgtacctg ggggaggtca ccaaagctgt tcagccgctc     300
cttcttggcc gcatcatcgc cagctatgac cctgataata agaagaaag gtctattgct     360
atttatctgg gaattggcct ctgcttgctc ttcatcgtcc gcaccttct gctgcaccct     420
gccatttttg gccttcacca catcggcatg caaatgagaa ttgccatgtt ctcccctcatt    480
tacaaaaaga ccctgaaact ttcctcaaga gtgttagata aatatccat tggtcagctg     540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggcttttttg attgtactgg cacttttca ggctgggctc    720
ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttcttttgt tgtcttcctg    960
tctgttctgc catatgcact gataaaaggc attattttac gaaagatctt caccaccatc   1020
agttttttgca tcgttctcag gatggccgtc acaagacagt tccctgggc tgtgcagacc   1080
tggtacgatt ccttgggggc catcaacaag attcaagatt tcttgcaaaa acaagaatat   1140
```

```
aaaactttag aatacaacct caccaccact gaagtggtca tggaaaatgt gacagccttt    1200 tggggaggagg gttttggaga attgttcgag aaggcaaagc agaataacaa caacaggaag    1260
acgagcaatg gggacgactc tctcttcttc agcaactttt cactgctcgg gaccCctgtg    1320
ttgaaagata taaacttcaa gatcgagagg ggccagctct tggctgtggc aggctccact    1380
ggagctggta aaacatctct tctcatggtg atcatggggg aactggagcc ttccgaagga    1440
aaaatcaagc acagtgggag aatctcattc tgcagccagt tttcctggat catgcccggc    1500
accattaagg aaaacatcat atttggagtg tcctatgatg agtaccgcta ccggtcagtc    1560
atcaaagcct gtcagttgga ggaggacatc tccaagtttg cagagaaaga caacattgtg    1620
cttggagagg ggggtatcac tctttctgga ggacaaagag ccaggatctc tttggcccgg    1680
gcagtctaca aggatgcaga cctctacttg ttggacagtc ccttcggcta cctcgacgtg    1740
ctgactgaaa agaaattttt tgaaagctgt gtgtgcaaac tgatggcaaa caagaccagg    1800
attcttgtca ccagcaagat ggaacatctg aagaaagcgg acaaaattct gattctgcat    1860
gaagggagct cctacttcta tggaacattt agcgagcttc agaacctaca gccagacttc    1920
tcctccaaat taatgggctg tgactccttc gaccagttct ctgcagaaag aagaaactct    1980
atactcacag agaccctcca ccgcttctcc cttgagggag atgccccagt tcttggaca    2040 gaaaccaaga agcagtcctt taagcagact ggcgagtttg gtgaaaagag gaaaaattca    2100
attctcaatc ctattaacag tattcgcaag ttcagcattg tccagaagac acccctccag    2160
atgaatggca tcgaagaaga tagtgacgag ccgctggaga gacggctgag tctggtgcca    2220
gattcagaac aggggggaggc catcctgccc cggatcagcg tcatttccac aggccccaca    2280
ttacaagcac ggcgccggca gagtgtttta aatctcatga cccattcagt gaaccagggc    2340
caaaatatcc acaggaagac tacagcttct acccggaaag tgtctctggc ccctcaggcc    2400
aatctgaccg agctggacat ctacagcagg aggctctccc aggaaacagg gcttgaaata    2460
tctgaagaga ttaatgaaga ggatcttaaa gagtgcttct ttgatgacat ggagagcatc    2520
cccgcggtga ccacatggaa caccctacctt agatatatta ctgtccacaa gagcctcata    2580
tttgtcctca tctggtgcct ggttattttc ctcgctgagg tggcggccag tcttgttgtg    2640
ctctggctgc tgggcaacac tcctctccag gacaagggca atagtacaca cagcagaaat    2700
aattcttatg ccgtcatcat tacaagcacc tccagctact acgtgttcta catctatgtg    2760
ggcgtggctg acaccctcct ggccatgggt ttcttccggg gcctgccttt ggtgcacacc    2820
ctcatcacag tgtcaaaaat tctgcaccat aaaatgcttc attctgtcct gcaggcaccc    2880
atgagcactt tgaacacatt gaaggctggc ggcatcctca acagattttc taaagatatt    2940
gctatcctgg atgatctcct ccccctgaca atctttgact ttatccagct tctgctgatc    3000
gtgattggag ccatagcagt ggttgctgtc ctgcagccct acatttttgt ggccaccgtg    3060
cccgtgattg ttgcctttat tatgctcaga gcttacttcc tgcaaacttc tcaacagctc    3120
aaacagctag aatctgaggg ccggagcccc attttaccc acctggtgac ttccctgaag    3180
ggactgtgga ctctgagagc attcgggcga cagccttact tgagacact gttccacaag    3240 gccctgaact tgcacactgc caactggttt ctttacctga gcacactccg ctggttccag    3300
atgcggatag agatgatctt cgtcatcttt tttatagctg taaccttcat ttctatcctt    3360
acaacaggag aaggagaggg cagggtggga atcatcctca cgctggctat gaacataatg    3420
tccacccttg cagtgggccg tgaattccagt atagatgtgg attctctaat gaggagtgtc    3480
```

```
tcccgggtgt ttaaattcat tgatatgcct actgagggga aacccaccaa gtcaacaaaa    3540
ccttataaga atggacagct gagcaaggtg atgataattg agaacagcca cgtgaagaag    3600
gatgacattt ggcccagcgg gggccagatg actgtgaagg acctgacggc caagtacacc    3660
gaaggtggaa atgccatttt ggaaaacatc agcttctcaa tctctcctgg gcagagagtt    3720
ggattgctgg gtcgcacggg cagcggcaaa tcaaccctgc tcagtgcctt ccttcggctc    3780
ctgaatacag aaggcgaaat ccaaattgac ggggtgagct gggacagcat caccctgcag    3840
cagtggagaa aagcatttgg ggtcattcca cagaaagttt tcatcttctc tggcactttc    3900
agaaagaacc tggaccccta tgagcagtgg agcgaccagg agatctggaa ggttgcagat    3960
gaagttggcc tgcggagtgt gatagaacaa tttcctggca agctggattt tgtgctggta    4020
gatgaaggct gcgtgctgtc ccacggccac aaacagctga tgtgcctcgc ccgctccgtt    4080 cttttcaaagg ccaaaatctt gcttttggat gagcccagtg ctcacctcga cccagtgacc    4140
tatcagataa tccgcaggac cttaaagcaa gcttttgccg actgcaccgt catactgtgt    4200
gagcaccgga ttgaagcaat gctggaatgc cagcagtttc tggtgatcga ggagaataag    4260
gtccggcagt acgacagcat ccagaagttg ttgaatgagc gcagccttt ccgccaggcc    4320 atctccccat ctgacagagt caagctgttt ccacatagga actcctctaa gtgcaagtcc    4380
aagccccaga tcgctgccct caaggaggaa actgaggaag aggtgcagga tacccgcctg    4440
tga                                                                 4443

<210> SEQ ID NO 16
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 16
atgcagagga gcccactgga gaaagcctcc gtggtgagta aactctttt tagttggacc      60 agacccatcc tgcgaaaagg atacaggcag cgcctcgagt tgtcagatat ctaccagatt     120
ccttctgtgg actcagctga caatttgagt gagaagctgg agcgggagtg ggatagagag     180
ctggcgagca aaaaaaaccc caagcttatc aatgctctgc gccgctgctt tttctggagg     240
ttcatgtttt atgggatctt cctgtacctg ggggaggtca ccaaagctgt tcagccgctc     300
cttcttggcc gcatcatcgc cagctatgac cctgataata agaagaaag gtctattgct     360 atttatctgg gaattggcct ctgcttgctc ttcatcgtcc gcaccttct gctgcaccct     420 gccatttttg gccttcacca catcggcatg caaatgagaa ttgccatgtt ctccctcatt     480
tacaaaaaga ccctgaaact ttcctcaaga gtgttagata aatatccat ggtcagctg      540 gtcagcctgc tgtccaacaa tcttaacaaa tttgatgaag gcttggcgct ggcccacttc     600
gtgtggattg cacctctgca ggtggccctg ttgatgggac ttatatggga gctgcttcaa     660
gcctctgctt tctgtgggct gggctttttg attgtactgg cactttttca ggctgggctc     720
ggaagaatga tgatgaaata cagagatcag cgggccggga gatatcaga gcgacttgtg     780 atcaccagtg aaatgattga aaatattcag agcgtgaaag cctactgctg ggaagaagcc     840
atggagaaga tgattgagaa cctgaggcag acagagctca agctcactcg gaaggctgct     900
tatgttcgct atttcaacag cagcgccttc ttcttcagtg gcttctttgt tgtcttcctg     960
tctgttctgc catatgcact gataaaaggc attattttac gaaagatctt caccaccatc    1020 agttttgca tcgttctcag gatggccgtc acaagacagt tcccctgggc tgtgcagacc    1080
```

```
tggtacgatt ccttgggggc catcaacaag attcaagatt tcttgcaaaa acaagaatat    1140
aaaactttag aatacaacct caccaccact gaagtggtca tggaaaatgt gacagccttt    1200
tgggaggagg gttttggaga attgttcgag aaggcaaagc agaataacaa caacaggaag    1260
acgagcaatg gggacgactc tctcttcttc agcaacttttt cactgctcgg gaccccctgtg   1320 ttgaaagata taaacttcaa gatcgagagg ggccagctct ggctgtggc aggctccact     1380 ggagctggta aacatctct tctcatggtg atcatggggg aactggagcc ttccgaagga    1440
aaaatcaagc acagtgggag aatctcattc tgcagccagt tttcctggat catgcccggc    1500
accattaagg aaaacatcat atttggagtg tcctatgatg agtaccgcta ccggtccgtc    1560
atcaaagcct gtcagttgga ggaggacatc tccaagtttg cagagaaaga caacattgtg    1620
cttggagagg ggggtatcac tctttctgga ggacaaagag ccaggatctc tttggcccgg    1680
gcagtctaca aggatgcaga cctctacttg ttggacagtc ccttcggcta cctcgacgtg    1740
ctgactgaaa aagaaattttt tgaaagctgt gtgtgcaaac tgatggcaaa caagaccagg    1800
attcttgtca ccagcaagat ggaacatctg aagaaagcgg acaaaattct gattctgcat    1860
gaagggagct cctacttcta tggaacattt agcgagcttc agaacctaca gccagcttc     1920 tcctccaaat taatgggctg tgactccttc gaccagttct ctgcagaaag aagaaactct    1980
atactcacag agaccctcca ccgcttctcc cttgagggag atgccccagt ttcttggaca    2040
gaaaccaaga agcagtcctt taagcagact ggcgagtttg gtgaaaagag gaaaaattca    2100
attctcaatc caattaacag tattcgcaag ttcagcattg tccagaagac accccctccag   2160 atgaatggca tcgaagaaga tagtgacgag ccgctggaga gacggctgag tctggtgcca    2220
gattcagaac aggggaggc catcctgccc cggatcagcg tcatttccac aggcccaca     2280 ttacaagcac ggcgccggca gagtgtttta aatctcatga cccattcagt gaaccagggc    2340
caaaatatcc acaggaagac tacagcttct acccggaaag tgtctctggc ccctcaggcc    2400
aatctgaccg agctggacat ctacagcagg aggctctccc aggaaacagg gctggaaata    2460
tctgaagaga ttaatgaaga ggatcttaaa gagtgcttct ttgatgacat ggagagcatc    2520
cccgcggtga ccacatggaa cacctacctt agatatatta ctgtccacaa gagcctcata    2580
tttgtcctca tctggtgcct ggttattttc ctcgctgagg tggcggccag tcttgttgtg    2640
ctctggctgc tgggcaacac tcctctccag gacaagggca atagtactca cagcagaaat    2700
aattcttatg ccgtcatcat tacaagcacc tccagctact acgtgttcta catctatgtg    2760
ggcgtggctg acaccctcct ggccatgggt ttcttccggg gcctgccttt ggtgcacacc    2820
ctcatcacag tgtcaaaaat tctgcaccat aaaatgcttc attctgtcct gcaggcaccc    2880
atgagcactt tgaacacatt gaaggctggc ggcatcctca acagattttc taaagatatt    2940
gctatcctgg atgatctcct ccccctgaca atctttgact ttatccagct tctgctgatc    3000
gtgattggag ccatagcagt ggttgctgtc ctgcagccct acattttgt ggccaccgtg     3060 cccgtgattg ttgcctttat tatgctcaga gcttacttcc tgcaaacttc tcaacagctc    3120
aaacagctag agtctgaggg ccggagcccc atttttaccc acctggtgac ttccctgaag    3180
ggactgtgga ctctgagagc attcgggcga cagccttact tgagacact gttccacaag    3240 gccctgaact tgcacactgc caactggttt ctttacctga gcacactccg ctggttccag    3300
atgcggatag agatgatctt cgtcatcttt tttatagctg taaccttcat ttctatcctt    3360
acaacaggag aaggagaggg cagggtggga atcatcctca cgctggctat gaacataatg    3420
```

| | |
|---|---|
| tccaccttgc agtgggccgt gaattccagt atagatgtgg attctctaat gaggagtgtc | 3480 |
| tcccgggtgt ttaaattcat tgatatgcct actgagggga aacccaccaa gtcaacaaaa | 3540 |
| ccttataaga atggacagct gagcaaggtg atgataattg agaacagcca cgtgaagaag | 3600 |
| gatgacattt ggcccagcgg gggccagatg actgtgaagg acctgacggc caagtacacc | 3660 |
| gaaggtggaa atgccatttt ggaaaacatc agcttctcaa tctctcctgg cagagagtt | 3720 |
| ggattgctgg gtcgcacggg cagcggcaaa tcaaccctgc tcagtgcctt ccttcggctc | 3780 |
| ctgaatacag aaggcgaaat ccaaattgac ggggtgagct gggacagcat caccctgcag | 3840 |
| cagtggagaa aagcatttgg ggtcattcca cagaaagttt tcatcttctc tggcactttc | 3900 |
| agaaagaacc tggacccta tgagcagtgg agcgaccagg agatctggaa ggttgcagat | 3960 |
| gaagttggcc tgcggagtgt gatagaacaa tttcctggca agctggattt tgtgctggta | 4020 |
| gatggaggct gcgtgctgtc ccacggccac aaacagctga tgtgcctcgc ccgctccgtt | 4080 |
| ctttcaaagg ccaaaatctt gcttttggat gagcccagtg ctcacctcga cccagtgacc | 4140 |
| tatcagataa tccgcaggac cttaaagcaa gcttttgccg actgcaccgt catactgtgt | 4200 |
| gagcaccgga ttgaagcaat gctggaatgc cagcagtttc tggtgatcga ggagaataag | 4260 |
| gtccggcagt acgacagcat ccagaagttg ttgaatgagc gcagccttt ccgccaggcc | 4320 |
| atctccccat ctgacagagt caagctgttt ccacatagga actcctctaa gtgcaagtcc | 4380 |
| aagcccagga tcgctgccct caaggaggaa actgaggaag aggtgcagga tacccgcctg | 4440 |
| tga | 4443 |

<210> SEQ ID NO 17
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 17

| | |
|---|---|
| atgcagagga gcccactgga gaaagcctcc gtggtgagta aactctttt tagttggacc | 60 |
| agacccatcc tgcgaaaagg atacaggcag cgcctcgagt tgtctgatat ctaccagatt | 120 |
| ccttctgtgg actcagctga caatttgagt gagaagctgg agcgggagtg ggatagagag | 180 |
| ctggcgagca aaaaaaaccc caagcttatc aatgctctgc gccgctgctt tttctggagg | 240 |
| ttcatgtttt atgggatctt cctgtacctg ggggaggtca ccaaagctgt tcagccgctc | 300 |
| cttcttggcc gcatcatcgc cagctatgac cctgataata agaagaaag gtctattgct | 360 |
| atttatctgg gaattggcct ctgcttgctc ttcatcgtcc gcaccttct gctgcaccct | 420 |
| gccattttg gccttcacca catcggcatg caaatgagaa ttgccatgtt ctccctcatt | 480 |
| tacaaaaga ccctgaaact ttcctcaaga gtgttagata aatatccat ggtcagctg | 540 |
| gtcagcctgc tgtccaacaa tcttaacaaa tttgatgaag gcttggcgct ggcccacttc | 600 |
| gtgtggattg cacctctgca ggtggccctg ttgatggac ttatatggga gctgcttcaa | 660 |
| gcctctgctt tctgtgggct gggcttttg attgtactgg cactttttca ggctgggctc | 720 |
| ggaagaatga tgatgaaata cagagatcag cgggccggga agatttcaga gcgacttgtg | 780 |
| atcaccagtg aaatgattga aaatattcag agcgtgaaag cctactgctg ggaagaagcc | 840 |
| atggagaaga tgattgagaa cctgaggcag acagagctca agctcactcg gaaggctgct | 900 |
| tatgttcgct atttcaacag cagcgccttc ttcttcagtg gcttctttgt tgtcttcctg | 960 |
| tctgttctgc catatgcact gataaaaggc attatttac gaaagatctt caccaccatc | 1020 |

```
agtttttgca tcgttctcag gatggccgtc acaagacagt tcccctgggc tgtgcagacc    1080
tggtacgatt ccttgggggc catcaacaag attcaagatt tcttgcaaaa acaagaatat    1140
aaaactttag aatacaacct caccaccact gaagtggtca tggaaaatgt gacagccttt    1200
tgggaggagg gttttggaga attgttcgag aaggcaaagc agaataacaa caacaggaag    1260
acgagcaatg gggacgactc tctcttcttc agcaactttt cactgctcgg gacccctgtg    1320
ttgaaagata taaacttcaa gatcgagagg gccagctct tggctgtggc aggtccact     1380 ggagctggta aaacatctct tctcatggtg atcatggggg aactggagcc ttccgaagga    1440
aaaatcaagc acagtgggag aatctcattc tgcagccagt tttcctggat catgcccggc    1500
accattaagg aaaacatcat atttggagtg tcctatgatg agtaccgcta ccggtcagtc    1560
atcaaagcct gtcagttgga ggaggacatc tccaagtttg cagagaaaga caacattgtg    1620
cttggagagg ggggtatcac tctttctgga ggacaaagag ccaggatctc tttggcccgg    1680
gcagtctaca aggatgcaga cctctacttg ttggacagtc ccttcggcta cctcgacgtg    1740
ctgactgaaa aagaaatttt tgaaagctgt gtgtgcaaac tgatggcaaa caagaccagg    1800
attcttgtca ccagcaagat ggaacatctg aagaaagcgg acaaaattct gattctgcat    1860
gaagggagct cctacttcta tggaacattt agcgagcttc agaacctaca gccagacttc    1920
tcctccaaat taatgggctg tgactccttc gaccagttct ctgcagaaag aagaaactct    1980
atactcacag agaccctcca ccgcttctcc cttgagggag atgccccagt tcttggaca     2040 gaaaccaaga agcagtcctt taagcagact ggcgagtttg gtgaaaagag gaaaaattca    2100
attctcaatc ctattaacag tattcgcaag ttcagcattg tccagaagac acccctccag    2160
atgaatggca tcgaagaaga tagtgacgag ccgctggaga gacggctgag tctggtgcca    2220
gattcagaac agggggaggc catcctgccc cggatcagcg tcatttccac aggccccaca    2280
ttacaagcac ggcgccggca gagtgtttta aatctcatga cccattcagt gaaccagggc    2340
caaaatatcc acaggaagac tacagcttct acccggaaag tgtctctggc ccctcaggcc    2400
aatctgaccg agctggacat ctacagcagg aggctctccc aggaaacagg gctggaaata    2460
tctgaagaga ttaatgaaga ggatcttaaa gagtgcttct ttgatgacat ggagagcatc    2520
cccgcggtga ccacatggaa cacctacctt agatatatta ctgtccacaa gagcctcata    2580
tttgtcctca tctggtgcct ggttattttc ctcgctgagg tggcggccag tcttgttgtg    2640
ctctggctgc tgggcaacac tcctctccag gacaagggca atagtacaca cagcagaaat    2700
aattcttatg ccgtcatcat tacaagcacc tccagctact acgtgttcta catctatgtg    2760
ggcgtggctg acaccctcct ggccatgggt ttcttccggg gcctgccttt ggtgcacacc    2820
ctcatcacag tgtcaaaaat tctgcaccat aaaatgcttc attctgtcct gcaggcaccc    2880
atgagcactt tgaacacatt gaaggctggc ggcatcctca acagatttc taaagatatt    2940 gctatcctgg atgatctcct ccccctgaca atctttgact ttatccagct tctgctgatc    3000
gtgattggag ccatagcagt ggttgctgtc ctgcagccct acatttttgt ggccaccgtg    3060
cccgtgattg ttgcctttat tatgctcaga gcttacttcc tgcaaacttc tcaacagctc    3120
aaacagctag aatctgaggg ccggagcccc attttaccc acctggtgac ttccctgaag    3180
ggactgtgga ctctgagagc attcgggcga cagccttact tgagacact gttccacaag    3240 gccctgaact tgcacactgc caactggttt ctttacctga gcacactccg ctggttccag    3300
atgcggatag agatgatctt cgtcatcttt tttatagctg taaccttcat ttctatcctt    3360
```

```
acaacaggag aaggagaggg cagggtggga atcatcctca cgctggctat gaacataatg    3420
tccaccttgc agtgggccgt gaattccagt atagatgtgg attctctaat gaggagtgtc    3480
tcccgggtgt ttaaattcat tgatatgcct actgagggga aacccaccaa gtcaacaaaa    3540
ccttataaga atggacagct gagcaaggtg atgataattg agaacagcca cgtgaagaag    3600
gatgacattt ggcccagcgg gggccagatg actgtgaagg acctgacggc caagtacacc    3660
gaaggtggaa atgccatttt ggaaaacatc agcttctcaa tctctcctgg gcagagagtt    3720
ggattgctgg gtcgcacggg cagcggcaaa tcaaccctgc tcagtgcctt ccttcggctc    3780
ctgaatacag aaggcgaaat ccaaattgac ggggtgagct gggacagcat caccctgcag    3840
cagtggagaa aagcatttgg ggtcattcca cagaaagttt tcatcttctc tggcactttc    3900
agaaagaacc tggaccccta tgagcagtgg agcgaccagg agatctggaa ggttgcagat    3960
gaagttggcc tgcggagtgt gatagaacaa tttcctggca agctggattt tgtgctggta    4020
gatggaggct gcgtgctgtc ccacggccac aaacagctga tgtgcctcgc ccgctccgtt    4080 cttttcaaagg ccaaaatctt gcttttggat gagcccagtg ctcacctcga cccagtgacc    4140
tatcagataa tccgcaggac cttaaagcaa gcttttgccg actgcaccgt catactgtgt    4200
gagcaccgga ttgaagcaat gctggaatgc cagcagtttc tggtgatcga ggagaataag    4260
gtccggcagt acgacagcat ccagaagttg ttgaatgagc gcagccttttt ccgccaggcc    4320 atctccccat ctgacagagt caagctgttt ccacatagga actcctctaa gtgcaagtcc    4380
aagccccaga tcgctgccct caaggaggaa actgaggaag aggtgcagga tacccgcctg    4440
tga                                                                  4443
```

<210> SEQ ID NO 18
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 18

```
atgcagagaa gccccctgga gaaggcctct gtggtgagca agctgttctt cagctggacc      60
agacccatcc tgagaaaggg ctacagacag agactggagc tgtctgacat ctaccagatc     120
ccctctgtgg actctgccga caacctgtct gagaagctgg agagagagtg ggacagagag     180
ctggccagca agaagaaccc caagctgatc aatgccctga agatgcttt cttctggaga     240 ttcatgttct atggcatctt cctgtacctg ggagaggtga ccaaggccgt gcagcccctg     300
ctgctgggca ggatcattgc cagctatgac cctgacaaca aggaggagag aagcattgcc     360
atctacctgg gcattggcct gtgcctgctg ttcattgtga aaccctgct gctgcaccct     420 gccatctttg gcctgcacca cattggcatg cagatgagaa ttgccatgtt cagcctgatc     480
tacaagaaga ccctgaagct gagcagcaga gtgctggaca agatcagcat tggccagctg     540
gtgagcctgc tgagcaacaa cctgaacaag tttgatgagg gcctggccct ggcccacttt     600
gtgtggattg ccccccctgca ggtggccctg ctgatgggcc tgatctggga gctgctgcag     660
gcctctgcct tctgtggcct gggcttcctg attgtgctgg ccctgttcca ggccggcctg     720
ggcagaatga tgatgaagta cagagaccag agagccggca gatctctga gagactggtg     780 atcacctctg agatgattga gaacatccag tctgtgaagg cctactgctg ggaggaggcc     840
atggagaaga tgattgagaa cctgagacag acagagctga agctgaccag gaaggccgcc     900
tatgtgagat acttcaacag ctctgccttc ttcttctctg gcttctttgt ggtgttcctg     960
```

```
tctgtgctgc cctatgccct gatcaagggc atcatcctga ggaagatctt caccaccatc    1020
agcttctgca ttgtgctgag gatggccgtg accaggcagt tcccctgggc cgtgcagacc    1080
tggtatgaca gcctgggggc catcaacaag atccaggact tcctgcagaa gcaggagtac    1140
aagaccctgg agtacaacct gaccaccaca gaggtggtga tggagaatgt gacagccttc    1200
tgggaggagg gctttggaga gctgtttgag aaggccaagc agaacaacaa caacagaaag    1260
accagcaatg gagatgacag cctgttcttc agcaacttca gcctgctggg caccctgtg    1320 ctgaaggaca tcaacttcaa gattgagagg ggccagctgc tggccgtggc cggcagcaca    1380
ggagccggca agaccagcct gctgatggtg atcatgggag agctggagcc ctctgagggc    1440
aagatcaagc actctggcag aatcagcttc tgcagccagt tcagctggat catgcctggc    1500
accatcaagg agaacatcat ctttggggtg agctatgatg agtacaggta cagatctgtg    1560
atcaaggcct gccagctgga ggaggacatc tccaagtttg ccgagaagga caacattgtg    1620
ctgggggagg gaggcatcac cctgtctggg gccagagag ccagaatcag cctggccaga    1680
gccgtgtaca aggatgccga cctgtacctg ctggacagcc cctttggcta cctggatgtg    1740
ctgacagaga aggagatctt tgagagctgt gtgtgcaagc tgatggccaa caagaccagg    1800
atcctggtga ccagcaagat ggagcacctg aagaaggccg acaagatcct gatcctgcat    1860
gagggcagca gctacttcta tggcaccttc tctgagctgc agaacctgca gcctgacttc    1920
agcagcaagc tgatgggctg tgacagcttt gaccagttct ctgctgagag aagaaacagc    1980
atcctgacag agaccctgca caggttcagc ctggaggggg atgcccctgt gagctggaca    2040
gagaccaaga agcagagctt caagcagaca ggagagtttg gggagaagag gaagaacagc    2100
atcctgaacc ccatcaacag catcaggaag ttcagcattg tgcagaagac ccccctgcag    2160
atgaatggca ttgaggagga ctctgatgag cccctggaga aagactgag cctggtgcca    2220 gactctgagc agggagaggc catcctgccc aggatctctg tgatcagcac aggccccacc    2280
ctgcaggcca aagaagaca gtctgtgctg aacctgatga cccactctgt gaaccagggc    2340
cagaatatcc acagaaagac cacagccagc accagaaagg tgagcctggc ccccaggcc    2400 aacctgacag agctggacat ctacagcaga aggctgagcc aggagacagg cctggagatc    2460
tctgaggaga tcaatgagga ggacctgaag gagtgcttct ttgatgacat ggagagcatc    2520
cctgccgtga ccacctggaa caccctacctg agatacatca cagtgcacaa gagcctgatc    2580
tttgtgctga tctggtgcct ggtgatcttc ctggccgagg tggccgccag cctggtggtg    2640
ctgtggctgc tgggcaacac ccccctgcag gacaagggca acagcaccca cagcagaaac    2700
aacagctatg ctgtgatcat caccagcacc agcagctact atgtgttcta catctatgtg    2760
ggagtggctg acaccctgct ggccatgggc ttcttcagag cctgcccct ggtgcacacc    2820 ctgatcacag tgagcaagat cctgcaccac aagatgctgc actctgtgct gcaggcccccc    2880 atgagcaccc tgaacaccct gaaggctgga ggcatcctga acagattcag caaggacatt    2940
gccatcctgg atgacctgct gccctgacc atctttgact tcatccagct gctgctgatt    3000
gtgattggag ccattgccgt ggtggccgtg ctgcagccct acatctttgt ggccacagtg    3060
cctgtgattg tggccttcat catgctgagg gcctacttcc tgcagaccag ccagcagctg    3120
aagcagctgg agtctgaggg cagaagcccc atcttcaccc acctggtgac cagcctgaag    3180
ggcctgtgga ccctgagggc cttggcaga cagcccctact ttgagaccct gttccacaag    3240
gccctgaacc tgcacacagc caactggttc ctgtacctga gcaccctgag atggttccag    3300
```

| | |
|---|---|
| atgaggattg agatgatctt tgtgatcttc ttcattgccg tgaccttcat cagcatcctg | 3360 |
| accacagggg agggcgaggg cagagtgggc atcatcctga ccctggccat gaacatcatg | 3420 |
| agcaccctgc agtgggccgt gaacagcagc attgatgtgg acagcctgat gagatctgtg | 3480 |
| agcagagtgt tcaagttcat tgacatgccc acagagggca agcccaccaa gagcaccaag | 3540 |
| ccctacaaga tggccagct gagcaaggtg atgatcattg agaacagcca tgtgaagaag | 3600 |
| gatgacatct ggccctctgg aggccagatg acagtgaagg acctgacagc caagtacaca | 3660 |
| gagggggca atgccatcct ggagaacatc agcttcagca tcagccctgg ccagagggtg | 3720 |
| ggcctgctgg gcagaacagg ctctggcaag agcaccctgc tgtctgcctt cctgaggctg | 3780 |
| ctgaacacag agggagagat ccagattgat ggggtgagct gggacagcat caccctgcag | 3840 |
| cagtggagga aggcctttgg ggtgatcccc cagaaggtgt tcatcttctc tggcaccttc | 3900 |
| aggaagaacc tggaccccta tgagcagtgg tctgaccagg agatctggaa ggtggccgat | 3960 |
| gaggtgggcc tgagatctgt gattgagcag ttccctggca agctggactt tgtgctggtg | 4020 |
| gatggaggct gtgtgctgag ccatggccac aagcagctga tgtgcctggc cagatctgtg | 4080 |
| ctgagcaagg ccaagatcct gctgctggat gagccctctg cccacctgga ccctgtgacc | 4140 |
| taccagatca tcagaagaac cctgaagcag gcctttgccg actgcacagt gatcctgtgt | 4200 |
| gagcacagaa ttgaggccat gctggagtgc cagcagttcc tggtgattga ggagaacaag | 4260 |
| gtgaggcagt atgacagcat ccagaagctg ctgaatgaga gaagcctgtt cagacaggcc | 4320 |
| atcagcccct ctgacagagt gaagctgttc ccccacagga acagcagcaa gtgcaagagc | 4380 |
| aagccccaga ttgccgcccct gaaggaggag acagaggagg aggtgcagga caccagactg | 4440 |
| tga | 4443 |

<210> SEQ ID NO 19
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 19

| | |
|---|---|
| atgcagagga gccccctgga gaaggccagc gtggtgagca agctgttctt cagctggacc | 60 |
| aggcccatcc tgaggaaggg ctacaggcag aggctggagc tgagcgacat ctaccagatc | 120 |
| cccagcgtgg acagcgccga caacctgagc gagaagctgg agagggagtg ggacagggag | 180 |
| ctggccagca gaagaaccc caagctgatc aacgccctga ggaggtgctt cttctggagg | 240 |
| ttcatgttct acggcatctt cctgtacctg ggcgaggtga ccaaggccgt gcagcccctg | 300 |
| ctgctgggca ggatcatcgc cagctacgac cccgacaaca aggaggagag gagcatcgcc | 360 |
| atctacctgg gcatcggcct gtgcctgctg ttcatcgtga ggaccctgct gctgcacccc | 420 |
| gccatcttcg gcctgcacca catcggcatg cagatgagga tcgccatgtt cagcctgatc | 480 |
| tacaagaaga ccctgaagct gagcagcagg gtgctggaca gatcagcat cggccagctg | 540 |
| gtgagcctgc tgagcaacaa cctgaacaag ttcgacgagg cctggcccct ggcccacttc | 600 |
| gtgtggatcg cccccctgca ggtggccctg ctgatgggcc tgatctggga gctgctgcag | 660 |
| gccagcgcct tctgcggcct gggcttcctg atcgtgctgg ccctgttcca ggccggcctg | 720 |
| ggcaggatga tgatgaagta cagggaccag agggccggca agatcagcga gaggctggtg | 780 |
| atcaccagcg agatgatcga gaacatccag agcgtgaagg cctactgctg ggaggaggcc | 840 |
| atggagaaga tgatcgagaa cctgaggcag accgagctga agctgaccag gaaggccgcc | 900 |

```
tacgtgaggt acttcaacag cagcgccttc ttcttcagcg gcttcttcgt ggtgttcctg    960
agcgtgctgc cctacgccct gatcaagggc atcatcctga ggaagatctt caccaccatc   1020
agcttctgca tcgtgctgag gatggccgtg accaggcagt tccctgggc cgtgcagacc    1080
tggtacgaca gcctgggcgc catcaacaag atccaggact tcctgcagaa gcaggagtac   1140
aagaccctgg agtacaacct gaccaccacc gaggtggtga tggagaacgt gaccgccttc   1200
tgggaggagg gcttcggcga gctgttcgag aaggccaagc agaacaacaa caacaggaag   1260
accagcaacg gcgacgacag cctgttcttc agcaacttca gcctgctggg cacccccgtg   1320
ctgaaggaca tcaacttcaa gatcgagagg ggccagctgc tggccgtggc cggcagcacc   1380
ggcgccggca agaccagcct gctgatggtg atcatgggcg agctggagcc cagcgagggc   1440
aagatcaagc acagcggcag gatcagcttc tgcagccagt tcagctggat catgcccggc   1500
accatcaagg agaacatcat cttcggcgtg agctacgacg agtacaggta caggagcgtg   1560
atcaaggcct gccagctgga ggaggacatc agcaagttcg ccgagaagga caacatcgtg   1620
ctgggcgagg gcggcatcac cctgagcggc ggccagaggg ccaggatcag cctggccagg   1680
gccgtgtaca aggacgccga cctgtacctg ctggacagcc ccttcggcta cctggacgtg   1740
ctgaccgaga aggagatctt cgagagctgc gtgtgcaagc tgatggccaa caagaccagg   1800
atcctggtga ccagcaagat ggagcacctg aagaaggccg acaagatcct gatcctgcac   1860
gagggcagca gctacttcta cggcaccttc agcgagctgc agaacctgca gcccgacttc   1920
agcagcaagc tgatgggctg cgacagcttc gaccagttca gcgccgagag gaggaacagc   1980
atcctgaccg agaccctgca caggttcagc ctggagggcg acgccccgt gagctggacc   2040
gagaccaaga agcagagctt caagcagacc ggcgagttcg gcgagaagag gaagaacagc   2100
atcctgaacc ccatcaacag catcaggaag ttcagcatcg tgcagaagac ccccctgcag   2160
atgaacggca tcgaggagga cagcgacgag cccctggaga ggaggctgag cctggtgccc   2220
gacagcgagc agggcgaggc catcctgccc aggatcagcg tgatcagcac cggccccacc   2280
ctgcaggcca ggaggaggca gagcgtgctg aacctgatga cccacagcgt gaaccagggc   2340
cagaacatcc acaggaagac caccgccagc accaggaagg tgagcctggc cccccaggcc   2400
aacctgaccg agctggacat ctacagcagg aggctgagcc aggagaccgg cctggagatc   2460
agcgaggaga tcaacgagga ggacctgaag gagtgcttct tcgacgacat ggagagcatc   2520
cccgccgtga ccacctggaa cacctacctg aggtacatca ccgtgcacaa gagcctgatc   2580
ttcgtgctga tctggtgcct ggtgatcttc ctggccgagg tggccgccag cctggtggtg   2640
ctgtggctgc tgggcaacac ccccctgcag gacaagggca acagcaccca gcaggaac    2700
aacagctacg ccgtgatcat caccagcacc agcagctact acgtgttcta catctacgtg   2760
ggcgtggccg acaccctgct ggccatgggc ttcttcaggg gcctgcccct ggtgcacacc   2820
ctgatcaccg tgagcaagat cctgcaccac aagatgctgc acagcgtgct gcaggccccc   2880
atgagcaccc tgaacaccct gaaggccggc ggcatcctga acaggttcag caaggacatc   2940
gccatcctgg acgacctgct gcccctgacc atcttcgact tcatccagct gctgctgatc   3000
gtgatcggcg ccatcgccgt ggtggccgtg ctgcagccct acatcttcgt ggccaccgtg   3060
cccgtgatcg tggccttcat catgctgagg gcctacttcc tgcagaccag ccagcagctg   3120
aagcagctgg agagcgaggg caggagcccc atcttcaccc acctggtgac cagcctgaag   3180
ggcctgtgga ccctgagggc cttcggcagg cagccctact cgagaccct gttccacaag   3240
```

```
gccctgaacc tgcacaccgc caactggttc ctgtacctga gcaccctgag gtggttccag    3300
atgaggatcg agatgatctt cgtgatcttc ttcatcgccg tgaccttcat cagcatcctg    3360
accaccggcg agggcgaggg cagggtgggc atcatcctga ccctggccat gaacatcatg    3420
agcaccctgc agtgggccgt gaacagcagc atcgacgtgg acagcctgat gaggagcgtg    3480
agcagggtgt tcaagttcat cgacatgccc accgagggca gcccaccaa gagcaccaag     3540 ccctacaaga cggccagct gagcaaggtg atgatcatcg agaacagcca cgtgaagaag      3600
gacgacatct ggcccagcgg cggccagatg accgtgaagg acctgaccgc caagtacacc    3660
gagggcggca cgccatcct ggagaacatc agcttcagca tcagccccgg ccagagggtg     3720
ggcctgctgg gcaggaccgg cagcggcaag agcaccctgc tgagcgcctt cctgaggctg    3780
ctgaacaccg agggcgagat ccagatcgac ggcgtgagct gggacagcat caccctgcag    3840
cagtggagga aggccttcgg cgtgatcccc cagaaggtgt tcatcttcag cggcaccttc    3900
aggaagaacc tggaccccta cgagcagtgg agcgaccagg agatctggaa ggtggccgac    3960
gaggtgggcc tgaggagcgt gatcgagcag ttccccggca agctggactt cgtgctggtg    4020
gacggcggct gcgtgctgag ccacggccac aagcagctga tgtgcctggc caggagcgtg    4080
ctgagcaagg ccaagatcct gctgctggac gagcccagcg cccacctgga ccccgtgacc    4140
taccagatca tcaggaggac cctgaagcag gccttcgccg actgcaccgt gatcctgtgc    4200
gagcacagga tcgaggccat gctggagtgc agcagttcc tggtgatcga ggagaacaag     4260
gtgaggcagt acgacagcat ccagaagctg ctgaacgaga ggagcctgtt caggcaggcc    4320
atcagcccca cgacagggt gaagctgttc ccccacagga acagcagcaa gtgcaagagc     4380
aagccccaga tcgccgccct gaaggaggag accgaggagg aggtgcagga caccaggctg    4440
tga                                                                  4443
```

<210> SEQ ID NO 20
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 20

```
atgcagagat cccctctgga gaaggcctca gtggtgtcca gcttttctt ctcctggacc       60 aggcccattt taagaaaggg ctacaggcag agacttgagc tgtctgacat ctatcagatc    120
ccttctgtgg attctgctga caatcttagt gaaaaattgg aaagggagtg ggacagagag    180
ctggcaagta aaagaaccc caagctgatt aatgccctga ggcgctgctt tttttggaga     240
ttcatgttct atggcatatt cctctacctt ggagaagtaa ccaaagctgt acagcctctc    300
ctccttggca gaatcattgc ctcctatgat cctgataaca aggaggagag aagcatagcc    360
atctacctgg gcattgggct gtgcctcttg tttattgtga ggacccttct cttgcaccct    420
gccatctttg gccttcatca cattggcatg caaatgagaa tagcaatgtt tagtcttatt    480
tacaaaaaaa cattaaaact ctcttccagg gtgttggaca agatcagtat ggacaactg      540 gtcagcctgc tgagcaacaa cctgaacaag tttgatgaag actggccct ggcccacttt     600 gtctggattg cccccttca ggtggctctt ttgatgggcc tgatctggga actcctgcag     660
gcctctgcct tctgtgggtt aggcttcctg atagtgctag ctctcttca ggcagggttg    720 ggtagaatga tgatgaagta cagagaccag agggctggga agatatctga aggctggtc   780 attacttctg aaatgataga aacatccag tctgttaaag cttactgctg ggaggaggct   840
```

```
atggaaaaga tgattgagaa cttgaggcaa acagagctca agctgactag gaaggcagcc    900
tatgtcaggt atttcaacag cagtgctttc ttcttctcag gcttttcgt ggtcttcttg     960 agtgttctgc cctatgccct catcaagggg ataattttga gaaagatttt caccactatt   1020
tccttttgca ttgtcctgag gatggctgtc accaggcaat tcccctgggc tgtgcagaca   1080
tggtatgact ctctggggc catcaacaaa atccaagatt tcctgcagaa gcaggagtac    1140
aagaccctgg aatacaacct caccaccaca gaagttgtga tggagaatgt gactgcattc   1200
tgggaggaag gatttgggga gctgtttgag aaagcaaaac aaaacaataa taacaggaaa   1260
accagcaatg gagatgactc cctgttcttt tccaacttct ctttgttggg cacccctgtc   1320
ctgaaagata taaactttaa aattgaaaga gggcagctgt ggcagttgc tggctccaca    1380 ggagctggaa aaacttcact actgatggtg atcatggggg agttagaacc ctctgaaggg   1440
aaaataaaac attctgggag gattagtttc tgcagccagt tcagctggat catgcctggg   1500
accattaaag aaaatattat atttggagtg agctatgatg aatatagata taggagtgtc   1560
atcaaagcct gtcagttgga ggaagacatc agcaaatttg cagagaaaga caacattgtt   1620
ctgggtgaag gtggcatcac cctgtcagga gggcaagggc caggatcag cttggccaga   1680 gcagtctata aagatgctga tctgtacctc ctggatagcc cttttggcta tctggatgtt   1740
ttgacagaga aggaaatttt tgagtcctgt gtctgcaagt taatggcaaa taaaacaagg   1800
atacttgtga cctcaaaaat ggaacacctg aagaaggctg acaaaattct gatcctgcat   1860
gagggcagca gctactttta tggaacattt tctgaactgc agaatttgca accagacttt   1920
tcatcaaagc tcatgggatg tgacagtttt gatcagtttt ctgcagaaag gagaaactcc   1980
attttgactg agaccctgca caggttcagt ctggagggg atgccccagt gagttggact   2040
gagacaaaga aacagagctt caagcagact ggagagtttg gagaaaagag gaaaaactca   2100
attctcaatc ccatcaatag catcaggaag ttcagcatag ttcagaagac tccttttgcag  2160 atgaatggga ttgaagagga ctcagatgag cccctggaaa ggagactctc cttggtgcca   2220
gattcagagc aggggaagc catactgcca aggatctctg tgatttctac agggcccacc    2280
ctccaagcaa gaaggagaca gtcagtttta aacctgatga cccactctgt caaccaggga   2340
cagaacattc atagaaagac aacagcatct acaagaaaag tttcactggc ccctcaagcc   2400
aatttaactg aactagatat ctacagcagg aggctcagcc aagaaacagg cctggagatc   2460
tcagaagaaa taaatgagga ggatttgaag gaatgcttct ttgatgatat ggagagcatc   2520
ccagctgtca caacctggaa cacctacctg agatacatca cagtgcacaa atccctcatc   2580
tttgtactta tatggtgcct tgtcatcttc ttagctgagg tggctgcttc cctggtggtg   2640
ctgtggctgc tgggaaacac acccctccag gataaaggga actctactca cagcaggaac   2700
aacagttatg ctgtgatcat caccagtacc tcctcctact atgtgttcta catttatgtt   2760
ggagttgcag acacattgct tgccatgggt ttttttagag gactccccct ggtgcatact   2820
ctcatcactg tttccaaaat ccttcaccac aagatgctgc acagtgtact acaggctccc   2880
atgagcaccc tcaacactct taaagcagga ggaatcttga acagatttag caaggacatt   2940
gcaattcttg atgacctgct tccactgacc atctttgact tcatccagct tctgctcatt   3000
gtaattggtg ccattgctgt ggtagcagtg ctccagccat atatttttgt ggccactgtg   3060
cctgttattg tggccttcat tatgttgaga gcctacttcc tgcagacctc tcagcagctc   3120
aagcaacttg aaagtgaggg caggagcccc atatttacac acttggtcac ttccctcaaa   3180
```

```
ggcctctgga cactcagagc tttttggaaga caaccttatt ttgaaactct cttccacaag   3240
gctctgaatc tccacacagc caactggttt ctgtatcttt caacactgcg ctggttccag   3300
atgaggattg agatgatctt tgttatcttc ttcatagctg ttaccttcat ctctattctg   3360
acaactggtg aggggggaagg gagagtaggc atcatcctca cactagccat gaacataatg   3420
tctaccttac aatgggccgt gaacagctcc atagatgtgg acagcctcat gagaagtgtg   3480
tcaagagttt tcaaattcat tgacatgccc acagaaggca aaccaaccaa gagcacaaaa   3540
ccctacaaga atggccagct gagtaaggtc atgatcattg aaaattctca tgtgaagaag   3600
gatgatattt ggcccagtgg gggccagatg acagtcaagg acctcactgc caaatacaca   3660
gagggtggaa atgctatcct agagaacatc tccttctcca tctccccagg ccaaagagtt   3720
ggcttgctgg gcaggactgg cagtggcaag tccaccttgc tctcagcatt tctcaggctt   3780
ttaaatacag agggagagat tcaaattgat ggggtgtctt gggatagtat aacacttcaa   3840
cagtggagga aagcctttgg tgtgattcct cagaaagtgt ttatcttctc tggcacttc   3900 agaaaaaatc tggaccccta tgaacagtgg agtgaccagg aaatctggaa ggtggcagat   3960
gaagtgggcc taagatcagt catagagcag tttcctggaa agttggattt tgtgcttgta   4020
gatggaggct gtgtgctgtc ccatggccat aaacagctaa tgtgcctggc taggtcagtg   4080
ctgagcaagg ccaagatcct gctgttagat gagccttcag cccatctgga ccctgtgaca   4140
taccagatta tcagaagaac tctgaagcag gcctttgctg actgcactgt catcctgtgt   4200
gagcacagaa ttgaggccat gctggagtgc cagcagttcc ttgttataga agagaataag   4260
gttaggcagt atgacagcat tcagaaactg ctaaatgaaa gatctctctt caggcaagct   4320 atttccaccat ctgatagagt gaaacttttt ccccacagaa attcctctaa atgtaaatct   4380
aagccccaga tagctgcctt gaaagaggag actgaagaag aagtccagga caccagactg   4440
tga                                                                4443
```

<210> SEQ ID NO 21
<211> LENGTH: 4443
<212> TYPE: DNA
<213> ORGANISM: Artificial Sequence
<220> FEATURE:
<223> OTHER INFORMATION: Synthetic polynucleotide
<400> SEQUENCE: 21

```
atgcagagat ccccgctgga gaaggcatct gtggtgtcaa aactgttctt tagctggaca     60
aggcccatcc ttaggaaagg gtacagacag aggttggagc tgtcagacat atatcagatc    120
ccttcagtgg actctgcaga caacctctct gaaaagctgg agagggaatg ggacagggaa    180
ctggccagca aaaaaaaccc taaactgatt aatgccctga ggaggtgctt cttttggaga    240
ttcatgttct atgggatctt cctttacctg ggggaggtga ctaaagctgt tcagcctctt    300
cttctgggga ggattattgc ctcctatgac ccagacaaca agaagaaag aagcatagcc    360 atttacttag gcataggcct ctgcttgctc ttcatagtta gaaccctcct actccaccca    420
gccatctttg gtctccacca cataggtatg cagatgagaa tagcaatgtt ctccttgatc    480
tacaagaaga ccctcaagct gtccagcagg gtgctggaca gatctccat aggccagtta    540 gtcagtctac tgtccaataa cttaaataag tttgatgagg gactggcact ggcacatttt    600
gtgtggattg ccccccctcca agtggcccctt cttatggccc ttatctggga gctgttgcag    660
gcctctgctt tctgtggcct gggttttcctc atagtcctag ccttattcca ggctggactg    720
ggcagaatga tgatgaagta tagggaccaa agagcaggga gatttctga aaggctggtt    780
```

```
ataacttctg agatgattga gaacattcag tcagtgaaag cttactgctg ggaagaagct      840
atggaaaaaa tgattgaaaa tctcagacag actgaattaa agttgaccag gaaagctgct      900
tatgtcagat acttcaactc ctcagccttc tttttttctg gcttctttgt tgtattcctt      960
tcagtcctcc cctatgccct gattaagggc attatcttga ggaaaatttt cacaaccatc     1020
tccttttgta ttgtcctcag gatggctgtt acaaggcaat ttccttgggc tgtgcaaact     1080
tggtatgata gccttggagc aatcaacaag atccaggatt cctgcaaaa gcaggagtac      1140 aagacattgg aatacaacct taccaccact gaggtggtga tggaaaatgt gactgccttc     1200
tgggaggagg ggtttggaga gctgtttgag aaagccaaac agaacaacaa caatagaaag     1260
acctctaatg gtgatgattc cctgttcttt tctaacttta gtcttctggg acccccagtt     1320
ctgaaagata ttaactttaa aattgaaagg ggacagttgc tggctgtggc tgggtccact     1380
ggggctggga agacaagcct gctcatggtg atcatgggag agctggaacc cagtgaagga     1440
aagatcaaac actcaggcag gatctccttc tgcagccagt tctcatggat tatgccaggc     1500
actattaaag aaaatatcat ctttggtgta agctatgatg agtacaggta tagatctgta     1560
attaaagcct gccagctgga ggaagacatc tctaagtttg ctgagaagga taacattgtg     1620 ttggggaag ggggcatcac cctttctggt gggcagaggg ctaggatctc ccttgctagg      1680
gcagtataca aggatgctga cttgtacctc ttggatagtc cttttggcta cctagatgtg     1740
ctgacagaga aagaaatatt tgaaagctgt gtgtgtaagc tcatggctaa caagaccagg     1800
atcctggtca ccagtaaaat ggaacacctc aaaaaagcag acaagatcct tattctccat     1860
gagggctcct cctacttcta tgggaccttc agtgagctgc agaatctgca gccagacttc     1920
tcctcaaaac ttatgggctg tgactccttt gaccaattct ctgcagaaag aaggaatagc     1980
atactgacag aaacactgca tagattctcc ctggaaggag atgccccagt gagttggaca     2040
gaaaccaaaa agcagagctt caagcagact ggtgagtttg gtgaaaagag aagaattct      2100 atcctgaacc ccatcaatag catcaggaaa tttagcatag tccaaaagac cccctccag      2160 atgaatggaa tagaggagga tagtgatgag cctcttgaga aaggctgtc cctggttcca      2220 gacagtgaac agggtgaagc cattcttccg aggatcagtg tcatctccac tgggcccaca     2280
ttgcaggcca aagaagaca gtctgttctg aatttgatga cacattctgt gaatcaaggc      2340
cagaatatcc atagaaaaac cactgccagc accagaaaag tttctctagc cccccaggct     2400
aacctgactg agttagacat ctacagcaga aggctgagcc aagagactgg cttggaaata     2460
tctgaggaga tcaatgagga ggacctcaag gagtgcttct ttgatgacat ggagtcaatc     2520
cctgcagtca ctacatggaa cacttaccta aggtacatca cagttcataa gagcctcatc     2580
tttgtcctca tatggtgtct ggtcatcttt ttagcagaag tggctgccag cctagttgtg     2640
ctgtggttac tgggcaatac acctcttcag gacaaaggca atagcacaca cagcagaaac     2700
aactcctatg cagtgatcat cacctctaca agctcttact atgtattcta tatatatgtg     2760
ggagtggcag atactctcct ggccatggga ttcttcaggg gattacctct agttcacaca     2820
ttgatcacag tgtcaaaaat tctccaccac aagatgttac acagtgtcct gcaagcccca     2880
atgtctactc tgaacacact taaggcaggt ggaattttga ataggtttag caaggacata     2940
gctatcctgg atgatctcct ccctctgacc atctttgact tcatccagtt actgctcatt     3000
gtaattggag ccattgcagt ggtagcagtc ctacagcctt acattttgt ggctactgtt      3060 cctgttattg tggccttcat tatgctaaga gcttacttcc tgcaaacaag ccaacagttg     3120
```

```
aaacagctag aaagtgaggg aaggtccccc atcttcaccc acctggtgac atcactcaag    3180
gggctatgga ctcttagggc ttttgggaga cagccgtact ttgagacctt attccataag    3240
gcccttaacc tccatacagc aaactggttc ttatacctga gtactctgag gtggtttcaa    3300
atgaggattg aaatgatttt tgtgatcttc ttcattgctg tgaccttcat ctcaatcttg    3360
accacaggag aggggaggg cagggtgggc atcatactga ccttggccat gaacattatg    3420
tcaaccctgc agtgggctgt caatagctcc attgatgtgg acagtctgat gaggagtgtc    3480
tccagggtct tcaagtttat tgacatgcca actgagggca aacccaccaa aagcactaag    3540
ccatataaaa atggccaact gtccaaagtg atgatcattg aaaattcaca tgtaaagaag    3600
gatgatatct ggccctctgg aggacagatg acagtgaaag acctgactgc caagtacaca    3660
gagggtggta atgccattct tgagaacatt agtttcagta tttccccggg gcaaagggtg    3720
ggcctccttg gcagaacagg ctctggcaag agtaccctgc tgtcagcctt tttaagactg    3780
ttgaacactg agggagaaat tcagattgat ggtgtctcct gggatagcat caccctccag    3840
cagtggagaa aagcttttgg agtgatcccg caaaaggttt tcatcttttc aggcaccttc    3900
cggaagaacc tggaccccta tgagcagtgg tctgaccagg aaatatggaa ggtagctgat    3960
gaagttgggc ttaggtcagt catagagcag ttcccaggca aactggactt tgtcctggtg    4020
gatggtggat gtgtactgag tcatgggcac aaacagctga tgtgcctagc caggtctgtg    4080
ctcagcaagg caaagatatt gctgcttgat gaacccagtg cccatctgga cccagtcaca    4140
tatcagatca tcagaagaac attgaagcag gcctttgctg attgcacagt tatcctctgt    4200
gagcacagga ttgaggccat gctggagtgc cagcagtttc tggtgattga ggagaataaa    4260
gtaaggcagt atgactccat ccagaagctg ctcaatgaaa aagcctctct tagacaagct    4320
atctccccct cagacagggt caaattgttc cctcacagaa acagcagcaa gtgcaagagc    4380
aagccccaaa ttgcagcctt gaaagaggag acagaggaag aggtgcagga caccagactc    4440
tga                                                                 4443

<210> SEQ ID NO 22
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 22
atgcagagaa gccccctgga aaggccagc gtggtgagca agctgttctt cagctggacc      60
agacccatcc tgagaaaggg ctacagacag agactggagc tgagcgacat ctaccagatc     120
cccagcgtgg acagcgccga caacctgagc gagaagctgg agagagtg ggacagagag      180
ctggccagca agaagaaccc caagctgatc aacgccctga agatgctt cttctggaga      240
ttcatgttct acggcatctt cctgtacctg ggcgaggtga ccaaggccgt gcagcccctg     300
ctgctgggca gaatcatcgc cagctacgac cccgacaaca aggaggagag aagcatcgcc     360
atctacctgg gcatcggcct gtgcctgctg ttcatcgtga aaccctgct gctgcacccc     420
gccatcttcg gcctgcacca catcggcatg cagatgagaa tcgccatgtt cagcctgatc     480
tacaagaaga ccctgaagct gagcagcaga gtgctggaca agatcagcat cggccagctg     540
gtgagcctgc tgagcaacaa cctgaacaag ttcgacgagg gcctggccct ggcccacttc     600
gtgtggatcg ccccccctgca gtggccctg ctgatgggcc tgatctggga gctgctgcag     660
gccagcgcct tctgcggcct gggcttcctg atcgtgctgg ccctgttcca ggccggcctg     720
```

```
ggcagaatga tgatgaagta cagagaccag agagccggca agatcagcga gagactggtg    780
atcaccagcg agatgatcga gaacatccag agcgtgaagg cctactgctg ggaggaggcc    840
atggagaaga tgatcgagaa cctgagacag accgagctga agctgaccag aaaggccgcc    900
tacgtgagat acttcaacag cagcgccttc ttcttcagcg gcttcttcgt ggtgttcctg    960
agcgtgctgc cctacgccct gatcaagggc atcatcctga aaagatcttc caccaccatc    1020
agcttctgca tcgtgctgag aatggccgtg accagacagt tccctgggc cgtgcagacc    1080
tggtacgaca gcctgggcgc catcaacaag atccaggact tcctgcagaa gcaggagtac    1140
aagaccctgg agtacaacct gaccaccacc gaggtggtga tggagaacgt gaccgccttc    1200
tgggaggagg gcttcggcga gctgttcgag aaggccaagc agaacaacaa caacagaaag    1260
accagcaacg cgacgacag cctgttcttc agcaacttca gcctgctggg cacccccgtg    1320
ctgaaggaca tcaacttcaa gatcgagaga ggccagctgc tggccgtggc cggcagcacc    1380
ggcgccggca agaccagcct gctgatggtg atcatgggcg agctggagcc cagcgagggc    1440
aagatcaagc acagcggcag aatcagcttc tgcagccagt tcagctggat catgcccggc    1500
accatcaagg agaacatcat cttcggcgtg agctacgacg agtacagata cagaagcgtg    1560
atcaaggcct gccagctgga ggaggacatc agcaagttcg ccgagaagga caacatcgtg    1620
ctgggcgagg gcggcatcac cctgagcggc ggccagagag ccagaatcag cctggccaga    1680
gccgtgtaca aggacgccga cctgtacctg ctggacagcc ccttcggcta cctggacgtg    1740
ctgaccgaga aggagatctt cgagagctgc gtgtgcaagc tgatggccaa caagaccaga    1800
atcctggtga ccagcaagat ggagcacctg aagaaggccg acaagatcct gatcctgcac    1860
gagggcagca gctacttcta cggcaccttc agcgagctgc agaacctgca gcccgacttc    1920
agcagcaagc tgatgggctg cgacagcttc gaccagttca gcgccgagag aagaaacagc    1980
atcctgaccg agaccctgca cagattcagc ctggagggcg acgcccccgt gagctggacc    2040
gagaccaaga agcagagctt caagcagacc ggcgagttcg gcgagaagag aaagaacagc    2100
atcctgaacc ccatcaacag catcagaaag ttcagcatcg tgcagaagac ccccctgcag    2160
atgaacggca tcgaggagga cagcgacgag ccctggaga aagactgag cctggtgccc    2220
gacagcgagc agggcgaggc catcctgccc agaatcagcg tgatcagcac cggcccacc    2280
ctgcaggcca gaagaagaca gagcgtgctg aacctgatga cccacagcgt gaaccagggc    2340
cagaacatcc acagaaagac caccgccagc accagaaagg tgagcctggc ccccaggcc    2400
aacctgaccg agctggacat ctacagcaga agactgagcc aggagaccgg cctggagatc    2460
agcgaggaga tcaacgagga ggacctgaag gagtgcttct tcgacgacat ggagagcatc    2520
cccgccgtga ccacctggaa cacctacctg agatacatca ccgtgcacaa gagcctgatc    2580
ttcgtgctga tctggtgcct ggtgatcttc ctggccgagg tggccgccag cctggtggtg    2640
ctgtggctgc tgggcaacac cccctgcag gacaagggca acagcaccca gcagaaac    2700
aacagctacg ccgtgatcat caccagcacc agcagctact acgtgttcta catctacgtg    2760
ggcgtggccg acaccctgct ggccatgggc ttcttcagag gcctgccct ggtgcacacc    2820
ctgatcaccg tgagcaagat cctgcaccac aagatgctgc acagcgtgct gcaggcccc    2880
atgagcaccc tgaacaccct gaaggccggc ggcatcctga acagattcag caaggacatc    2940
gccatcctgg acgacctgct gcccctgacc atcttcgact tcatccagct gctgctgatc    3000
gtgatcggcg ccatcgccgt ggtggccgtg ctgcagcccct acatcttcgt ggccaccgtg    3060
```

```
cccgtgatcg tggccttcat catgctgaga gcctacttcc tgcagaccag ccagcagctg    3120
aagcagctgg agagcgaggg cagaagcccc atcttcaccc acctggtgac cagcctgaag    3180
ggcctgtgga ccctgagagc cttcggcaga cagccctact tcgagaccct gttccacaag    3240
gccctgaacc tgcacaccgc caactggttc ctgtacctga gcaccctgag atggttccag    3300
atgagaatcg agatgatctt cgtgatcttc ttcatcgccg tgaccttcat cagcatcctg    3360
accaccggcg agggcgaggg cagagtgggc atcatcctga ccctggccat gaacatcatg    3420
agcaccctgc agtgggccgt gaacagcagc atcgacgtgg acagcctgat gagaagcgtg    3480
agcagagtgt tcaagttcat cgacatgccc accgagggca agcccaccaa gagcaccaag    3540
ccctacaaga acggccagct gagcaaggtg atgatcatcg agaacagcca cgtgaagaag    3600
gacgacatct ggcccagcgg cggccagatg accgtgaagg acctgaccgc caagtacacc    3660
gagggcggca acgccatcct ggagaacatc agcttcagca tcagccccgg ccagagagtg    3720
ggcctgctgg gcagaaccgg cagcggcaag agcaccctgc tgagcgcctt cctgagactg    3780
ctgaacaccg agggcgagat ccagatcgac ggcgtgagct gggacagcat caccctgcag    3840
cagtggagaa aggccttcgg cgtgatcccc cagaaggtgt tcatcttcag cggcaccttc    3900
agaaagaacc tggaccccta cgagcagtgg agcgaccagg agatctggaa ggtggccgac    3960
gaggtgggcc tgagaagcgt gatcgagcag ttccccggca agctggactt cgtgctggtg    4020
gacggcggct gcgtgctgag ccacggccac aagcagctga tgtgcctggc cagaagcgtg    4080
ctgagcaagg ccaagatcct gctgctggac gagcccagcg cccacctgga ccccgtgacc    4140
taccagatca tcagaagaac cctgaagcag gccttcgccg actgcaccgt gatcctgtgc    4200
gagcacagaa tcgaggccat gctggagtgc cagcagttcc tggtgatcga ggagaacaag    4260
gtgagacagt acgacagcat ccagaagctg ctgaacgaga aagcctgtt cagacaggcc    4320
atcagcccca gcgacagagt gaagctgttc ccccacagaa acagcagcaa gtgcaagagc    4380
aagccccaga tcgccgccct gaaggaggag accgaggagg aggtgcagga caccagactg    4440
tga                                                                    4443

<210> SEQ ID NO 23
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 23
atgcagcgca gcccctggga aaggccagc gtggtgagca agctgttctt cagctggacc      60
cgccccatcc tgcgcaaggg ctaccgccag cgcctggagc tgagcgacat ctaccagatc    120
cccagcgtgg acagcgccga caacctgagc gagaagctgg agcgcgagtg ggaccgcgag    180
ctggccagca gaagaacccc aagctgatc aacgccctgc cgctgcttct tctgctgcgc    240
ttcatgttct acggcatctt cctgtacctg ggcgaggtga ccaaggccgt gcagcccctg    300
ctgctgggcc gcatcatcgc cagctacgac cccgacaaca aggaggagcg cagcatcgcc    360
atctacctgg catcggcct gtgcctgctg ttcatcgtgc gcaccctgct gctgcacccc    420
gccatcttcg gcctgcacca catcggcatg cagatgcgca tcgccatgtt cagcctgatc    480
tacaagaaga ccctgaagct gagcagccgc gtgctggaca gatcagcat cggccagctg    540
gtgagcctgc tgagcaacaa cctgaacaag ttcgacgagg gcctggccct ggcccacttc    600
gtgtggatcg ccccctgca ggtggccctg ctgatgggcc tgatctggga gctgctgcag    660
```

-continued

```
gccagcgcct tctgcggcct gggcttcctg atcgtgctgg ccctgttcca ggccggcctg      720
ggccgcatga tgatgaagta ccgcgaccag cgcgccggca agatcagcga gcgcctggtg      780
atcaccagcg agatgatcga gaacatccag agcgtgaagg cctactgctg ggaggaggcc      840
atggagaaga tgatcgagaa cctgcgccag accgagctga agctgacccg caaggccgcc      900
tacgtgcgct acttcaacag cagcgccttc ttcttcagcg gcttcttcgt ggtgttcctg      960
agcgtgctgc cctacgccct gatcaagggc atcatcctgc gcaagatctt caccaccatc     1020
agcttctgca tcgtgctgcg catggccgtg acccgccagt tcccctgggc cgtgcagacc     1080
tggtacgaca gcctgggcgc catcaacaag atccaggact tcctgcagaa gcaggagtac     1140
aagaccctgg agtacaacct gaccaccacc gaggtggtga tggagaacgt gaccgccttc     1200
tgggaggagg gcttcggcga gctgttcgag aaggccaagc agaacaacaa caaccgcaag     1260
accagcaacg gcgacgacag cctgttcttc agcaacttca gcctgctggg caccccgtg     1320 ctgaaggaca tcaacttcaa gatcgagcgc ggccagctgc tggccgtggc cggcagcacc     1380
ggcgccggca agaccagcct gctgatggtg atcatgggcg agctggagcc cagcgagggc     1440
aagatcaagc acagcggccg catcagcttc tgcagccagt tcagctggat catgcccggc     1500
accatcaagg agaacatcat cttcggcgtg agctacgacg agtaccgcta ccgcagcgtg     1560
atcaaggcct gccagctgga ggaggacatc agcaagttcg ccgagaagga caacatcgtg     1620
ctgggcgagg gcggcatcac cctgagcggc ggccagcgcg cccgcatcag cctggcccgc     1680
gccgtgtaca aggacgccga cctgtacctg ctggacagcc ccttcggcta cctggacgtg     1740
ctgaccgaga aggagatctt cgagagctgc gtgtgcaagc tgatggccaa caagacccgc     1800
atcctggtga ccagcaagat ggagcacctg aagaaggccg acaagatcct gatcctgcac     1860
gagggcagca gctacttcta cggcaccttc agcgagctgc agaacctgca gcccgacttc     1920
agcagcaagc tgatgggctg cgacagcttc gaccagttca cgccgagcg ccgcaacagc     1980 atcctgaccg agaccctgca ccgcttcagc ctggagggcg acgccccgt gagctggacc     2040 gagaccaaga gcagagctt caagcagacc ggcgagttcg gcgagaagcg caagaacagc     2100
atcctgaacc ccatcaacag catccgcaag ttcagcatcg tgcagaagac cccctgcag     2160 atgaacggca tcgaggagga cagcgacgag cccctggagc gccgcctgag cctggtgccc     2220
gacagcgagc agggcgaggc catcctgccc cgcatcagct gatcagcac cggccccacc     2280 ctgcaggccc gccgccgcca gagcgtgctg aacctgatga cccacagcgt gaaccagggc     2340
cagaacatcc accgcaagac caccgccagc acccgcaagg tgagcctggc cccccaggcc     2400
aacctgaccg agctggacat ctacagccgc cgcctgagcc aggagaccgg cctggagatc     2460
agcgaggaga tcaacgagga ggacctgaag gagtgcttct tcgacgacat ggagagcatc     2520
cccgccgtga ccacctggaa cacctacctg cgctacatca ccgtgcacaa gagcctgatc     2580
ttcgtgctga tctggtgcct ggtgatcttc tggccgagg tggccgccag cctggtggtg     2640
ctgtggctgc tgggcaacac ccccctgcag gacaagggca cagcaccca cagccgcaac     2700 aacagctacg ccgtgatcat caccagcacc agcagctact acgtgttcta catctacgtg     2760 ggcgtggcc acaccctgct ggccatgggc ttcttccgcg cctgccct ggtgcacacc     2820 ctgatcaccg tgagcaagat cctgcaccac aagatgctgc acagcgtgct gcaggccccc     2880
atgagcaccc tgaacaccct gaaggccggc ggcatcctga accgcttcag caaggacatc     2940
gccatcctgg acgacctgct gccctgacc atcttcgact tcatccagct gctgctgatc     3000
```

```
gtgatcggcg ccatcgccgt ggtggccgtg ctgcagccct acatcttcgt ggccaccgtg    3060
cccgtgatcg tggccttcat catgctgcgc gcctacttcc tgcagaccag ccagcagctg    3120
aagcagctgg agagcgaggg ccgcagcccc atcttcaccc acctggtgac cagcctgaag    3180
ggcctgtgga ccctgcgcgc cttcggccgc cagccctact cgagaccct gttccacaag    3240 gccctgaacc tgcacaccgc caactggttc ctgtacctga gcaccctgcg ctggttccag    3300
atgcgcatcg agatgatctt cgtgatcttc ttcatcgccg tgaccttcat cagcatcctg    3360
accaccggcg agggcgaggg ccgcgtgggc atcatcctga ccctggccat gaacatcatg    3420
agcaccctgc agtgggccgt gaacagcagc atcgacgtgg acagcctgat gcgcagcgtg    3480
agccgcgtgt tcaagttcat cgacatgccc accgagggca agcccaccaa gagcaccaag    3540
ccctacaaga acggccagct gagcaaggtg atgatcatcg agaacagcca cgtgaagaag    3600
gacgacatct ggcccagcgg cggccagatg accgtgaagg acctgaccgc caagtacacc    3660
gagggcggca cgccatcct ggagaacatc agcttcagca tcagccccgg ccagcgcgtg    3720
ggcctgctgg gccgcaccgg cagcggcaag agcaccctgc tgagcgcctt cctgcgcctg    3780
ctgaacaccg agggcgagat ccagatcgac ggcgtgagct gggacagcat caccctgcag    3840
cagtggcgca aggccttcgg cgtgatcccc cagaaggtgt tcatcttcag cggcaccttc    3900
cgcaagaacc tggaccccta cgagcagtgg agcgaccagg agatctggaa ggtggccgac    3960
gaggtgggcc tgcgcagcgt gatcgagcag ttccccggca gctggacttc cgtgctggtg    4020
gacggcggct gcgtgctgag ccacggccac aagcagctga tgtgcctggc ccgcagcgtg    4080
ctgagcaagg ccaagatcct gctgctggac gagcccagcg cccacctgga ccccgtgacc    4140
taccagatca tccgccgcac cctgaagcag gccttcgccg actgcaccgt gatcctgtgc    4200
gagcaccgca tcgaggccat gctggagtgc agcagttcc tggtgatcga ggagaacaag    4260
gtgcgccagt acgacagcat ccagaagctg ctgaacgagc gcagcctgtt ccgccaggcc    4320
atcagcccca gcgaccgcgt gaagctgttc ccccaccgca acagcagcaa gtgcaagagc    4380
aagccccaga tcgccgccct gaaggaggag accgaggagg aggtgcagga cacccgcctg    4440
taa                                                                   4443

<210> SEQ ID NO 24
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 24
atgcagagaa gccccctgga gaaggccagc gtggtgagca agctgttctt cagctggacc      60
agacccatcc tgagaaaggg ctacagacag agactggagc tgagcgacat ctaccagatc     120
cccagcgtgg acagcgccga caacctgagc gagaagctgg agagagagtg ggacagagag     180
ctggccagca gaagaaaccc caagctgatc aacgccctga agatgcttt cttctggaga     240 ttcatgttct acggcatctt cctgtacctg ggcgaggtga ccaaggccgt gcagcccctg     300
ctgctgggca gaatcatcgc cagctacgac cccgacaaca ggaggagag aagcatcgcc     360 atctacctgg gcatcggcct gtgcctgctg ttcatcgtga acccctgct gctgcacccc     420 gccatcttcg gcctgcacca catcggcatg cagatgagaa tcgccatgtt cagcctgatc     480
tacaagaaga ccctgaagct gagcagcaga gtgctggaca agatcagcat cggccagctg     540
gtgagcctgc tgagcaacaa cctgaacaag ttcgacgagg gcctggccct ggcccacttc     600
```

```
gtgtggatcg ccccctgca ggtggccctg ctgatgggcc tgatctggga gctgctgcag    660
gccagcgcct tctgcggcct gggcttcctg atcgtgctgg ccctgttcca ggccggcctg    720
ggcagaatga tgatgaagta cagggaccag agagccggca agatcagcga gagactggtg    780
atcaccagcg agatgatcga gaacatccag agcgtgaagg cctactgctg ggaggaggcc    840
atggagaaga tgatcgagaa cctgagacag accgagctga agctgaccag aaaggccgcc    900
tacgtgagat acttcaacag cagcgccttc ttcttcagcg gcttcttcgt ggtgttcctg    960
agcgtgctgc cctacgccct gatcaagggc atcatcctga aaagatcttc accaccatc    1020 agcttctgca tcgtgctgag aatggccgtg accagacagt tcccctgggc cgtgcagacc   1080
tggtacgaca gcctgggcgc catcaacaag atccaggact tcctgcagaa gcaggagtac   1140
aagaccctgg agtacaacct gaccaccacc gaggtggtga tggagaacgt gaccgccttc   1200
tgggaggagg gcttcggcga gctgttcgag aaggccaagc agaacaacaa caacagaaag   1260
accagcaacg cgacgacag cctgttcttc agcaacttca gcctgctggg cacccccgtg    1320
ctgaaggaca tcaacttcaa gatcgagaga ggccagctgc tggccgtggc cggcagcacc   1380
ggcgccggca agaccagcct gctgatggtg atcatgggcg agctggagcc cagcgagggc   1440
aagatcaagc acagcggcag aatcagcttc tgcagccagt tcagctggat catgcccggc   1500
accatcaagg agaacatcat cttcggcgtg agctacgacg agtacagata cagaagcgtg   1560
atcaaggcct gccagctgga ggaggacatc agcaagttcg ccgagaagga caacatcgtg   1620
ctgggcgagg gcggcatcac cctgagcggc ggccagagag ccagaatcag cctggccaga   1680
gccgtgtaca aggacgccga cctgtacctg ctggacagcc ccttcggcta cctggacgtg   1740
ctgaccgaga aggagatctt cgagagctgc gtgtgcaagc tgatggccaa caagaccaga   1800
atcctggtga ccagcaagat ggagcacctg aagaaggccg acaagatcct gatcctgcac   1860
gagggcagca gctacttcta cggcaccttc agcgagctgc agaacctgca gcccgacttc   1920
agcagcaagc tgatgggctg cgacagcttc gaccagttca gcgccgagag aagaaacagc   1980
atcctgaccg agaccctgca cagattcagc ctggagggcg acgcccccgt gagctggacc   2040
gagaccaaga agcagagctt caagcagacc ggcgagttcg gcgagaagag aaagaacagc   2100
atcctgaacc ccatcaacag catcagaaag ttcagcatcg tgcagaagac ccccctgcag   2160
atgaacggca tcgaggagga cagcgacgag ccctggaga aagactgag cctggtgccc    2220 gacagcgagc agggcgaggc catcctgccc agaatcagcg tgatcagcac cggccccacc   2280
ctgcaggcca agaagagaca gagcgtgctg aacctgatga cccacagcgt gaaccagggc   2340
cagaacatcc acagaaagac caccgccagc accagaaagg tgagcctggc cccccaggcc   2400
aacctgaccg agctggacat ctacagcaga agactgagcc aggagaccgg cctggagatc   2460
agcgaggaga tcaacgagga ggacctgaag gagtgcttct tcgacgacat ggagagcatc   2520
cccgccgtga ccacctggaa cacctacctg agatacatca ccgtgcacaa gagcctgatc   2580
ttcgtgctga tctggtgcct ggtgatcttc ctggccgagg tggccgccag cctggtggtg   2640
ctgtggctgc tgggcaacac ccccctgcag gacaagggca acagcaccca gcagaaac    2700 aacagctacg ccgtgatcat caccagcacc agcagctact acgtgttcta catctacgtg   2760
ggcgtggccg acaccctgct ggccatgggc ttcttcagag gcctgccct ggtgcacacc    2820 ctgatcaccg tgagcaagat cctgcaccac aagatgctgc acagcgtgct gcaggccccc   2880
atgagcaccc tgaacaccct gaaggccggc ggcatcctga acagattcag caaggacatc   2940
```

```
gccatcctgg acgacctgct gccctgacc atcttcgact tcatccagct gctgctgatc    3000
gtgatcggcg ccatcgccgt ggtggccgtg ctgcagccct acatcttcgt ggccaccgtg    3060
cccgtgatcg tggccttcat catgctgaga gcctacttcc tgcagaccag ccagcagctg    3120
aagcagctgg agagcgaggg caggagcccc atcttcaccc acctggtgac cagcctgaag    3180
ggcctgtgga ccctgagagc cttcggcaga cagccctact tcgagaccct gttccacaag    3240
gccctgaacc tgcacaccgc caactggttc ctgtacctga gcaccctgag atggttccag    3300
atgagaatcg agatgatctt cgtgatcttc ttcatcgccg tgaccttcat cagcatcctg    3360
accaccggcg agggcgaggg cagagtgggc atcatcctga ccctggccat gaacatcatg    3420
agcaccctgc agtgggccgt gaacagcagc atcgacgtgg acagcctgat gagaagcgtg    3480
agcagagtgt tcaagttcat cgacatgccc accgagggca agcccaccaa gagcaccaag    3540
ccctacaaga acggccagct gagcaaggtg atgatcatcg agaacagcca cgtgaagaag    3600
gacgacatct ggcccagcgg cggccagatg accgtgaagg acctgaccgc caagtacacc    3660
gagggcggca acgccatcct ggagaacatc agcttcagca tcagccccgg ccagagagtg    3720
ggcctgctgg gcagaaccgg cagcggcaag agcaccctgc tgagcgcctt cctgagactg    3780
ctgaacaccg agggcgagat ccagatcgac ggcgtgagct gggacagcat caccctgcag    3840
cagtggagaa aggccttcgg cgtgatcccc agaaggtgt tcatcttcag cggcaccttc    3900
agaaagaacc tggaccccta cgagcagtgg agcgaccagg agatctggaa ggtggccgac    3960
gaggtgggcc tgagaagcgt gatcgagcag ttccccggca agctggactt cgtgctggtg    4020
gacggcggct gcgtgctgag ccacggccac aagcagctga tgtgcctggc cagaagcgtg    4080
ctgagcaagg ccaagatcct gctgctggac gagcccagcg cccacctgga ccccgtgacc    4140
taccagatca tcagaagaac cctgaagcag gccttcgccg actgcaccgt gatcctgtgc    4200
gagcacagaa tcgaggccat gctggagtgc cagcagttcc tggtgatcga ggagaacaag    4260
gtgagacagt acgacagcat ccagaagctg ctgaacgaga aagcctgtt cagacaggcc    4320
atcagcccca gcgacagagt gaagctgttc ccccacagaa acagcagcaa gtgcaagagc    4380
aagccccaga tcgccgccct gaaggaggag accgaggagg aggtgcagga caccagactg    4440
tga                                                                  4443

<210> SEQ ID NO 25
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 25
atgcagaggt cacctctgga aaaggctagc gtggtcagca agctatttt ttcctggacc     60
cgcccgatac tcaggaaggg ctaccgacag cggctggagc tgagtgacat ttatcagatt    120
ccctccgtcg attccgctga caacctgtct gagaaactgg agcgggaatg ggatagggaa    180
ctggcgtcca aaaaaaaccc caaactcatc aatgcactcc gcagatgctt cttctggcgg    240
tttatgtttt atggcatatt cctgtatctg gggaggtga cgaaagccgt gcagccgctg    300
ctgcttggtc gcattatcgc gtcatacgat ccagataaca aggaggaaag aagtatcgct    360
atctatctcg ggataggct gtgcctgctc ttcattgtgc ggactcttct cttgcacccc    420
gccatttcg tctgcatca tataggtatg cagatgagaa ttgcgatgtt ctcattgatt    480
tacaaaaaaa cgcttaagct aagttcaagg gtgctagata agatatcgat cggccagctg    540
```

```
gtgtctctgc ttagcaacaa cctcaataaa ttcgacgaag gccttgcact ggcccacttc    600
gtgtggatcg cccctctgca ggtggctctg ctgatggggt taatatggga gctgttgcag    660
gcctccgctt tttgtggcct ggggtttctc atcgtgttgg ccttgtttca ggcagggctg    720
ggacgtatga tgatgaaata tagggatcag agggctggca aaatctctga gcgcctggtt    780
attacgagtg aaatgattga gaacatccag tcagtgaagg cctattgctg ggaggaggcc    840
atggaaaaaa tgattgagaa cctacgccag actgagctga agttaaccag aaaagccgcc    900
tatgtgcgct actttaacag tagcgcattt ttcttctccg ttttttcgt ggtgtttctt     960 agtgtgttgc cgtatgcctt aatcaaggga ataatactcc ggaagatttt cactaccatc    1020
agcttctgta tcgtgttgcg gatggccgtc acccggcagt ttccctgggc agtacagact    1080
tggtacgatt ctctcggagc aattaacaaa atccaagact ttctacaaaa gcaggagtac    1140
aagaccctgg agtacaatct gaccaccaca gaagtcgtaa tggagaatgt aactgccttc    1200
tgggaagagg gctttggcga actctttgaa aaggccaagc agaacaataa caaccggaag    1260
acctccaacg gggacgacag cttatttttc agcaattttt ctttgctcgg gacccctgta    1320
ctgaaagata ttaactttaa gatcgagcgc ggacaactcc tggctgtcgc cggcagcact    1380
ggagctggaa aaacatcact gcttatggtg ataatgggag aactcgaacc aagcgaggga    1440
aaaataaagc actctggacg gattagtttt tgctcccagt tctcgtggat aatgcctggc    1500
accattaagg agaatatcat cttttggagtg agttacgacg aataccggta ccggtccgtt    1560
atcaaggctt gtcaactcga ggaggacatt tctaaattcg ccgaaaaaga taatatagtg    1620
ctgggcgaag gaggcattac actgagcggg ggtcagagag ctcgaattag cctcgcccga    1680
gcagtctata aagacgccga tctttacctg ctggattccc cttttgggta tttggatgtt    1740
ctgacagaga aggaaatctt tgaatcatgt gtctgtaaac tgatggccaa taagactagg    1800
attctagtga cttcgaaaat ggagcacctg aaaaaagcgg acaaaattct gatactccat    1860
gaagggtctt cctacttcta cggcaccttc tcagagttgc agaacttaca acctgatttt    1920
tcatctaagc ttatgggggtg cgactcgttt gaccagttct ccgctgaaag acgaaacagc    1980
atcttaacgg aaactcttca caggttctca ttagagggag atgcgccggt gtcctggaca    2040
gagacaaaaa aacagtcttt caaacagaca ggagagtttg gcgagaagag aaaaaactca    2100
atcctcaatc ccatcaattc tattagaaag tttagcatcg tccaaaaaac accattgcag    2160
atgaatggga ttgaggagga cagtgatgag cctttggaac aagactgtc cctggtaccc    2220 gatagcgaac agggtgaggc catccttcct aggatctcgg tcataagtac agggcccaca    2280
ctgcaggcca ggcgacgtca aagtgtcctc aatcttatga cgcacagtgt gaatcagggg    2340
cagaacatcc atcgtaagac gacagcttca actcgaaagg tcagtctagc tccacaagcc    2400
aatcttacag agctggacat ttattcccgc cgcctcagtc aggagaccgg attggaaata    2460
tcagaggaaa ttaatgaaga ggatctgaag gaatgcttct tgatgacat ggaatcgatc     2520 cccgctgtta ctacctggaa cacatatctg agatatatta ccgtccataa gagcttaatc    2580
tttgtactga tatggtgctt ggtgattttc ctggcagagg ttgcggcgag tttggtcgtg    2640
ctatggctcc ttggaaacac tcccctgcag gataagggga actccactca tagcaggaat    2700
aacagctatg ccgtgatcat cacctctacc tcctcttatt acgtgtttta catatacgtc    2760
ggtgttgcgg ataccctgtt ggcaatgggg ttctttagag gactacccct agttcacacc    2820
ctgatcaccg tttcgaagat cttgcaccac aagatgcttc atagcgttct ccaagctcct    2880
```

-continued

| | |
|---|---|
| atgagcaccc ttaatacact gaaagcagga ggtatcctta accgcttttc caaagacatc | 2940 |
| gctatactcg acgatttgct cccattgacc atcttcgact tcattcagct gctcctcatt | 3000 |
| gtgatcggcg ccattgccgt ggtcgcagtg ttacagccat atattttcgt agccaccgtg | 3060 |
| cccgtcatcg tggcatttat catgctgcgc gcatatttct tacagacatc tcagcaactg | 3120 |
| aagcagctgg aatctgaggg cagatctcct attttacac acctggttac cagcctgaag | 3180 |
| ggcctgtgga ccctgcgtgc tttcggtcgc caaccctact ttgagactct cttccataag | 3240 |
| gctctgaatt tacatactgc caattggttc ctataccta gtaccctcg gtggttccag | 3300 |
| atgcggatag aaatgatctt cgtgattttc ttcatcgcag tcactttcat ctctattttg | 3360 |
| acgaccggtg agggcgaggg cagggtgggc atcattctga ctttggccat gaacattatg | 3420 |
| tcaacactcc agtgggccgt taattcaagc attgatgtgg attccttgat gcgttccgtc | 3480 |
| agcagggtat ttaaattcat agacatgccc accgagggca agccaacaaa atctaccaag | 3540 |
| ccatacaaaa atggccaact aagcaaggtc atgattatcg agaattctca tgtgaaaaag | 3600 |
| gacgacattt ggccttccgg gggtcaaatg actgtaaagg acctgacggc taaatacact | 3660 |
| gagggcggta atgctatctt ggagaacatc tctttcagca tctcccctgg ccagagagtg | 3720 |
| ggactgctcg ggcggacagg ctccggaaag tctacgctcc tttcagcatt ccttagactt | 3780 |
| ctgaacaccg aaggtgagat tcagattgac ggggtctctt gggactccat cacacttcag | 3840 |
| caatggagga aggcattcgg tgtaatcccc caaaaggttt ttatcttctc cggaacattt | 3900 |
| cgtaagaatc tggacccgta cgagcagtgg tcagatcagg agatctggaa agtagcagac | 3960 |
| gaggtcgggc tacggagcgt tattgaacag tttcctggca aactggactt cgttttggtg | 4020 |
| gacggaggct gtgtgctgag tcacggccat aaacaactga tgtgcttagc taggtctgtt | 4080 |
| ctcagcaagg caaagatttt actgctggat gaaccaagcg cccaccttga tccagtgaca | 4140 |
| tatcaaatca tcagaagaac tcttaaacag gcgttcgccg actgcacagt gatcctgtgt | 4200 |
| gagcacagaa tagaagccat gctggaatgt caacagtttc tcgtgattga ggagaacaag | 4260 |
| gtgcgccagt acgatagcat ccagaagtta ctcaatgaaa ggtcactctt caggcaggcc | 4320 |
| atctcaccca cgaccgcgt taagctgttt ccacaccgaa acagttccaa gtgcaaaagt | 4380 |
| aagccacaga ttgctgcact gaaggaagag acagaagaag aagttcagga cactcggctc | 4440 |
| tga | 4443 |

<210> SEQ ID NO 26
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 26

| | |
|---|---|
| atgcagagga gcccactgga gaaagcctcc gtggtgagta aactctttt tagttggacc | 60 |
| agacccatcc tgcgaaaagg atacaggcag cgcctcgagt tgtcagatat ctaccagatt | 120 |
| ccttctgtgg actcagctga caatttgagt gagaagctgg agcgggagtg ggatagagag | 180 |
| ctggcgagca aaaaaaaccc caagcttatc aatgctctgc gccgctgctt tttctggagg | 240 |
| ttcatgtttt atgggatctt cctgtacctg ggggaggtca ccaaagctgt tcagccgctc | 300 |
| cttcttggcc gcatcatcgc cagctatgac cctgataata agaagaaag gtctattgct | 360 |
| atttatctgg gaattggcct ctgcttgctc ttcatcgtcc gcaccttct gctgcaccct | 420 |
| gccattttg gccttcacca catcggcatg caaatgagaa ttgccatgtt ctcccctcatt | 480 |

-continued

```
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggcttttg attgtactgg cacttttca ggctgggctc     720 ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020 agttttgca tcgttctcag gatggccgtc acaagacagt tcccctgggc tgtgcagacc    1080
tggtacgatt ccttggggc catcaacaag attcaagatt tcttgcaaaa acaagaatat    1140
aaaactttag aatacaacct caccaccact gaagtggtca tggaaaatgt gacagccttt   1200
tgggaggagg gttttggaga attgttcgag aaggcaaagc agaataacaa caacaggaag    1260
acgagcaatg gggacgactc tctcttcttc agcaacttt cactgctcgg gaccccgtgt    1320
ttgaaagata taaacttcaa gatcgagagg ggccagctct ggctgtggc aggctccact    1380 ggagctggta aacatctct tctcatggtg atcatggggg aactggagcc ttccgaagga    1440
aaaatcaagc acagtgggag aatctcattc tgcagccagt tttcctggat catgcccggc    1500
accattaagg aaaacatcat atttggagtg tcctatgatg agtaccgcta ccggtcagtc    1560
atcaaagcct gtcagttgga ggaggacatc tccaagtttg cagagaaaga caacattgtg    1620
cttggagagg ggggtatcac tctttctgga ggacaaagag ccaggatctc tttggcccgg    1680
gcagtctaca aggatgcaga cctctacttg ttggacagtc ccttcggcta cctcgacgtg    1740
ctgactgaaa aagaaatttt tgaaagctgt gtgtgcaaac tgatggcaaa caagaccagg    1800
attcttgtca ccagcaagat ggaacatctg aagaaagcgg acaaaattct gattctgcat    1860
gaagggagct cctacttcta tggaacattt agcgagcttc agaacctaca gccagcttc    1920 tcctccaaat taatgggctg tgactccttc gaccagttct ctgcagaaag aagaaactct    1980
atactcacag agaccctcca ccgcttctcc cttgagggag atgccccagt ttcttggaca    2040
gaaaccaaga agcagtcctt taagcagact ggcgagtttg gtgaaaagag gaaaaattca    2100
attctcaatc caattaacag tattcgcaag ttcagcattg tccagaagac acccctccag    2160
atgaatggca tcgaagaaga tagtgacgag ccgctggaga gacggctgag tctggtgcca    2220
gattcagaac aggggaggc catcctgccc cggatcagcg tcatttccac aggccccaca    2280
ttacaagcac ggcgccggca gagtgtttta aatctcatga cccattcagt gaaccagggc    2340
caaaatatcc acaggaagac tacagcttct acccggaaag tgtctctggc ccctcaggcc    2400
aatctgaccg agctggacat ctacagcagg aggctctccc aggaaacagg ctgaaaata    2460 tctgaagaga ttaatgaaga ggatcttaaa gagtgcttct ttgatgacat ggagagcatc    2520
cccgcggtga ccacatggaa cacctacctt agatatatta ctgtccacaa gagcctcata    2580
tttgtcctca tctggtgcct ggttattttc ctcgctgagg tggcggccag tcttgttgtg    2640
ctctggctgc tgggcaacac tcctctccag gacaagggca atagtactca cagcagaaat    2700
aattcttatg ccgtcatcat tacaagcacc tccagctact acgtgttcta catctatgtg    2760
ggcgtggctg acaccctcct ggccatgggt ttcttccggg gcctgccttt ggtgcacacc    2820
```

```
ctcatcacag tgtcaaaaat tctgcaccat aaaatgcttc attctgtcct gcaggcaccc    2880
atgagcactt tgaacacatt gaaggctggc ggcatcctca acagatttc taaagatatt    2940 gctatcctgg atgatctcct cccctgaca atctttgact ttatccagct tctgctgatc    3000
gtgattggag ccatagcagt ggttgctgtc ctgcagccct acattttgt ggccaccgtg    3060 cccgtgattg ttgcctttat tatgctcaga gcttacttcc tgcaaacttc tcaacagctc    3120
aaacagctag aatctgaggg ccggagcccc attttacc acctggtgac ttccctgaag    3180
ggactgtgga ctctgagagc attcgggcga cagccttact ttgagacact gttccacaag    3240
gccctgaact tgcacactgc caactggttt ctttacctga gcacactccg ctggttccag    3300
atgcggatag agatgatctt cgtcatcttt tttatagctg taaccttcat ttctatcctt    3360
acaacaggag aaggagaggg cagggtggga atcatcctca cgctggctat gaacataatg    3420
tccaccttgc agtgggccgt gaattccagt atagatgtgg attctctaat gaggagtgtc    3480
tcccgggtgt ttaaattcat tgatatgcct actgagggga acccaccaa gtcaacaaaa    3540 ccttataaga atggacagct gagcaaggtg atgataattg agaacagcca cgtgaagaag    3600
gatgacattt ggcccagcgg gggccagatg actgtgaagg acctgacggc caagtacacc    3660
gaaggtggaa atgccatttt ggaaaacatc agcttctcaa tctctcctgg gcagagagtt    3720
ggattgctgg gtcgcacggg cagcggcaaa tcaaccctgc tcagtgcctt ccttcggctc    3780
ctgaatacag aaggcgaaat ccaaattgac ggggtgagct gggacagcat caccctgcag    3840
cagtggagaa aagcatttgg ggtcattcca cagaaagttt tcatcttctc tggcacttt    3900 agaaagaacc tggacccta tgagcagtgg agcgaccagg atctggaa ggttgcagat    3960 gaagttggcc tgcggagtgt gatagaacaa tttcctggca agctggattt tgtgctggta    4020
gatgagggct gcgtgctgtc ccacggccac aaacagctga tgtgcctcgc ccgctccgtt    4080 cttcaaagg ccaaatctt gcttttggat gagcccagtg ctcacctcga cccagtgacc    4140
tatcagataa tccgcaggac cttaaagcaa gttttgccg actgcaccgt catactgtgt    4200
gagcaccgga ttgaagcaat gctggaatgc cagcagttc tggtgatcga ggagaataag    4260
gtccggcagt acgacagcat ccagaagttg ttgaatgagc gcagccttt ccgccaggcc    4320 atctccccat ctgacagagt caagctgttt ccacatagga actcctctaa gtgcaagtcc    4380 aagcccaga tcgctgccct caaggaggaa actgaggaag aggtgcagga tacccgcctg    4440
tga                                                                4443

<210> SEQ ID NO 27
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 27
atgcaacgga gtcctctgga aaaagcctct gtcgtatcta agcttttctt cagttggaca     60
cgcccgattt tgagaaaggg ttatcggcaa cgcttggaac ttagtgacat ctaccaaatt    120
ccaagtgtag actcagccga taacttgagc gaaaagctcg aacgagagtg ggatcgagaa    180
ctggctagca aaaaaaatcc caaactcata aatgccctgc gacgctgttt cttttggcga    240
tttatgtttt acggtatttt cctttatttg ggtgaggtca cgaaggctgt acagccactg    300
ctgctgggtc gcatcattgc ctcttacgac cctgacaaca agaggagcg gtcaatagct    360 atctaccttg gtataggact ttgcttgctc ttcatagtcc gcacgttgct tctccaccct    420
```

```
gctatatttg gtctccatca cattgggatg caaatgcgga tcgcgatgtt cagtcttata      480 tataaaaga ctcttaaact ttccagccgg gttctggata agatctctat tggtcaactg       540
gtatctcttt tgtctaacaa cctgaataag ttcgacgagg gccttgcatt ggcccatttt      600
gtatggattg cccctttgca agtcgccctc ctgatgggat tgatctggga actcctgcaa      660
gctagtgctt tttgcggatt gggattcctc atagtccttg cgctctttca ggcgggactt      720
ggacgcatga tgatgaagta tcgcgaccaa cgagctggca agatcagtga acggcttgta      780
ataaccagtg aaatgataga gaacatccag agcgtaaaag cttactgttg ggaagaagcg      840
atggaaaaga tgattgagaa ccttcgccag acagaactta aacttacacg aaaggccgct      900
tatgtccggt acttcaactc ttcagcattt tttttagtg gcttctttgt agtgttcctg        960
tccgtccttc cgtatgcact tatcaagggt ataatactta ggaaaatctt cacaacaatc     1020 agttttttgca tagtccttcg catggcagta actcgccaat ttccctgggc agttcagacg    1080
tggtacgact cacttggcgc aattaacaaa attcaagatt tcctccaaaa gcaagagtat     1140
aaaaccttgg aatacaacct taccaccaca gaagttgtaa tggaaaatgt cacagccttc     1200
tgggaggaag gttcggcga acttttttgag aaggcgaagc aaaataacaa taatcggaaa     1260
acatcaaacg gtgacgattc actgttcttt tctaacttta gccttcttgg gacgcccgtc     1320
ctgaaggaca taaactttaa gattgaacgg ggtcaacttc tcgcggtcgc agggagtact     1380
ggagcgggga aaacgagcct gctgatggtg ataatggggg agttggagcc ctcagaaggc    1440
aagatcaagc atagtggtag aattagcttc tgcagtcaat ttagttggat tatgccgggc    1500
acgatcaaag aaaatataat ctttggggta tcctacgatg aatacaggta ccgatcagtg    1560
ataaaagcgt gccagcttga agaagacatt tcaaagtttg ctgagaagga taatatcgta    1620
cttggagaag gaggtatcac cctgtctggg ggtcaacgag cgaggatctc cctggcacgc    1680
gccgtctaca aggacgcgga cctctatctg ttggattcac cgttcggata tttggacgtg    1740
cttacggaga aagaaatatt tgagagctgt gttttgcaagc tcatggcaaa taaaaccaga    1800
atattggtta caagcaagat ggagcatctt aagaaagcag ataaaatcct gatattgcac    1860
gagggctctt catacttcta cgggacgttt tctgagttgc agaacctcca gccggatttc    1920
agctctaagc tgatgggctg tgattccttt gatcagttta gtgcggaaag acgaaacagt    1980
atactcaccg aaacactgca caggttctct ctggagggcg acgccccggt ttcctggaca    2040
gagacgaaga agcagtcctt caaacagaca ggcgagtttg gggagaaaag gaaaaatagc    2100
atactcaacc cgattaacag cattcgcaag ttcagtatag tacaaaagac cccgttgcag    2160
atgaacggta tagaggaaga ttctgatgag ccactggaaa gacggctttc tctcgttccg    2220
gacagtgaac agggagaggc aatactgcct cggatcagcg ttatctctac aggacctact    2280
ttgcaagctc ggcgccgaca gtcagtcttg aatcttatga ctcatagtgt taatcaaggc    2340
cagaatatcc atcgcaagac caccgcaagt acaaggaaag tgagcttggc acctcaagca    2400
aaccttactg aacttgatat ctactcacgg cgactttcac aggagaccgg acttgaaatt    2460
agtgaagaaa ttaacgagga ggaccctcaag gagtgcttct tcgatgacat ggaatcaatc    2520
cccgcagtca caacctggaa cacttatctg aggtatataa cagttcacaa gagcctcatt    2580
tttgtactta tttggtgttt ggtaatttttc ctggcggagg ttgctgcttc tttggtcgtc    2640
ctttggctcc tcgggaatac accgctccaa gacaaaggca actctaccca tagtaggaac   2700
aattcatatg cagtgattat aaccagtaca tcatcttatt acgttttcta tatttatgtc    2760
```

| | |
|---|---:|
| ggggtagctg acacgctgtt ggcgatgggc ttctttaggg gcctcccctt ggtacacacc | 2820 |
| cttatcacgg tgagtaaaat cctgcatcac aaaatgcttc attctgtact ccaagcgccg | 2880 |
| atgagtacgc ttaatacgct gaaagcagga gggatactga atcggttcag caaggacatc | 2940 |
| gccattctgg atgacctgct tccattgaca atatttgatt tcattcagct ccttctcata | 3000 |
| gttattggag ccatagcggt ggtggctgtg cttcagcctt atatattcgt tgccacagtt | 3060 |
| cccgttatag tggcatttat aatgctcagg gcctactttc tccagacttc ccagcagttg | 3120 |
| aagcaactcg aatcagaagg aaggtcacct attttcacac atcttgtgac ttccttgaag | 3180 |
| ggcttgtgga cgctgcgggc cttcggaaga caaccatatt tgaaactct cttccacaaa | 3240 |
| gctttgaatc ttcatactgc gaactggttc ctgtatttga gtactttgcg ctggttccag | 3300 |
| atgaggatag aaatgatatt cgttatcttc tttatcgcgg ttacgttcat aagtatcctc | 3360 |
| actacggggg agggtgaggg tagagtgggc ataatactga ccctcgccat gaacattatg | 3420 |
| tccaccctgc agtgggcggt aaacagcagc atagatgtgg attctttgat gcgcagtgtg | 3480 |
| agcagggttt ttaagtttat cgatatgccg acggaaggaa agcccactaa agcacgaaa | 3540 |
| ccctataaaa atggacagct tagcaaagta atgataatcg agaatagcca tgtgaaaaag | 3600 |
| gatgacatat ggccttccgg aggccaaatg actgttaaag atctgaccgc taaatatacc | 3660 |
| gagggcggca acgcaatact cgaaaacata agcttttcca taagccccgg ccaacgcgtg | 3720 |
| ggtcttctgg ggaggactgg ctccggaaaa tcaacgttgc ttagcgcgtt tttgcggctc | 3780 |
| cttaacactg aaggtgagat ccaaatagat ggcgttagtt gggactctat aacactgcaa | 3840 |
| caatggcgga aagctttcgg cgtcatacct cagaaggtgt tcatctttag cggaacgttc | 3900 |
| aggaagaact tggatcccta cgaacaatgg agtgatcaag aaatatggaa agtggcagat | 3960 |
| gaggtaggct tgcgcagtgt cattgaacaa ttcccaggga aactcgactt tgtactggtg | 4020 |
| gacggcggtt gcgtcttgtc acacgggcac aaacagttga tgtgtttggc ccgcagtgtt | 4080 |
| ttgtctaagg cgaagattct gttgctcgac gaaccgagtg ctcatcttga tcccgtcacc | 4140 |
| taccaaatca tcagaaggac gttgaagcaa gctttcgccg actgcactgt aatcctttgt | 4200 |
| gagcatagga tcgaagcaat gctcgagtgc aacagttct tggttataga ggagaataag | 4260 |
| gttcggcaat acgactcaat acagaaactg cttaatgagc ggtcactctt tcgacaagct | 4320 |
| atctctccta gtgacagggt aaagcttttt cctcatcgga attccagcaa gtgtaagagt | 4380 |
| aaaccacaga tcgccgccct taaagaggag accgaagaag aggtgcagga tacgagactt | 4440 |
| tag | 4443 |

<210> SEQ ID NO 28
<211> LENGTH: 4688
<212> TYPE: RNA
<213> ORGANISM: Artificial Sequence
<220> FEATURE:
<223> OTHER INFORMATION: Synthetic polynucleotide

<400> SEQUENCE: 28

| | |
|---|---:|
| ggacagaucg ccuggagacg ccauccacgc uguuugacc uccauagaag acaccgggac | 60 |
| cgauccagcc uccgcggccg ggaacggugc auuggaacgc ggauuccccg ugccaagagu | 120 |
| gacucaccgu ccuugacacg augcaacgcu cuccucuuga aaaggccucg guggugucca | 180 |
| agcucuucuu cucguggacu agacccaucc ugagaaaggg guacagacag cgcuuggagc | 240 |
| uguccgauau cuaucaaauc ccuuccgugg acuccgcgga caaccugucc gagaagcucg | 300 |
| agagagaaug ggacagagaa cucgcccucaa agaagaaccc gaagcugauu aaugcgcuua | 360 |

```
ggcggugcuu uuucuggcgg uucauguucu acggcaucuu ccucuaccug ggagagguca      420
ccaaggccgu gcagccccug uugcugggac ggauuauugc cuccuacgac cccgacaaca      480
aggaagaaag aagcaucgcu aucuacuugg gcaucggucu gugccugcuu ucaucgucc       540 ggacccucuu guugcauccu gcuauuuucg gccugcauca cauuggcaug cagaugagaa      600
uugccauguu ucccugauc uacaagaaaa cucugaagcu cucgagccgc gugcuugaca       660
agauuuccau cggccagcuc ugucccugc ucuccaacaa ucugaacaag uucgacgagg       720
gccucgcccu ggcccacuuc gugggaucg ccccucugca aguggcgcuu cugaugggcc       780
ugaucuggga gcugcugcaa gccucggcau ucgugggcu uggauccug aucgugcugg        840 cacuguucca ggccggacug gggcggauga ugaugaagua cagggaccag agagccggaa      900
agauuuccga acggcuggug aucacuucgg aaaugaucaa aaacauccag ucagugaagg      960
ccuacugcug ggaagaggcc auggaaaaga ugauugaaaa ccuccggcaa accgagcuga     1020
agcugacccg caaggccgcu acgugcgcu auuucaacuc guccgcuuuc uucuucccg       1080 gguucuucgu ggguguucuc uccgugcucc ccuacgcccu gauuaaggga aucauccuca     1140
ggaagaucuu caccaccauu uccuucugua ucgugucccg cauggccgug acccggcagu     1200
ucccaugggc cgugcagacu gguacgacu cccugggagc cauuaacaag uccaggacu       1260 uccuucaaaa gcaggaguac aagacccucg aguacaaccu gacuacuacc gaggucguga     1320
uggaaaacgu caccgccuuu ugggaggagg gauuggcga acguucgag aaggccaagc       1380 agaacaacaa caaccgcaag accucgaacg gugacgacuc ccucuucuuu ucaaacuuca     1440
gccugcucgg gacgcccgug cugaaggaca uuaacuucaa gaucgaaaga ggacagcucc    1500
uggcgguggc cggaucgacc ggagccgaa agacuucccu gcugauggug ucaugggag      1560 agcuugaacc uagcgaggga aagaucaagc acuccggccg caucagcuuc uguagccagu    1620
uuuccuggau caugcccgga accauuaagg aaaacaucau cuucggcgug uccuacgaug    1680
aauaccgcua ccggucgug aucaaagccu gccagcugga agaggauauu caaaguucg      1740 cggagaaaga uaacaucgug cugggcgaag ggguauuac cuugucgggg ggccagcggg     1800
cuagaaucuc gcuggccaga gccguguaua aggacgccga ccuguaucuc cuggacuccc    1860
ccuucggaua ccuggacguc cugaccgaaa aggagaucuu cgaaucgugc gugugcaagc    1920
ugauggcuaa caagacucgc auccucguga ccuccaaaau ggagcaccug aagaaggcag    1980
acaagauucu gauucugcau gaggggaccu ccuacuuuua cggcaccuuc ucggagcugc    2040
agaacuugca gcccgacuuc ucaucgaagc ugaugggug cgacagcuuc gaccaguucu    2100
ccgccgaaag aaggaacucg auccugacgg aaaccuugca ccgcuucucu uggaaggcg    2160 acgcccugu gucauggacc gagacuaaga agcagcuu caagcagacc ggggaauucg     2220
gcgaaaagag gaaaacagc aucuugaacc ccauuaacuc caucgcaag uucucaaucg     2280 ugcaaaagac gccacugcag augaacggca uugaggagga cucgacgaa ccccuugaga    2340 ggcgccuguc ccuggugccg acagcgagc agggagaagc cauccugccu cggauuuccg    2400
ugaucuccac uggguccgacg cuccaagccc ggcggcggca guccgugcug aaccugauga    2460
cccacagcgu gaaccagggc caaaacauuc accgcaagac uaccgcaucc acccggaaag    2520 uguccccuggc accucaagcg aaucuuaccg agcucgacau cuaccccggg agacugucgc    2580
aggaaaccgg gcucgaaauu uccgaagaaa ucaacgagga ggaucugaaa gagugcuucu    2640
ucgacgauau ggagucgaua cccgccguga cgacuuggaa cacuuaucug cgguacauca    2700
```

| | |
|---|---|
| cugugcacaa gucauugauc uucgugcuga uuuggugccu ggugauuuuc cuggccgagg | 2760 |
| ucgcggccuc acugguggug cucuggcugu ugggaaacac gccucugcaa gacaagggaa | 2820 |
| acuccacgca cucgagaaac aacagcuaug ccguugauuau cacuuccacc uccucuuauu | 2880 |
| acguuucua caucuacguc ggaguggcgg auaccugcu cgcgaugggu uucuucagag | 2940 |
| gacugccgcu gguccacacc uugaucaccg ucagcaagau cuucaccac aagauguugc | 3000 |
| auagcgugcu gcaggccccc augccaccc ucaacacucu gaaggccgga ggcauucuga | 3060 |
| acagauucuc caaggacauc gcuauccugg acgaucuccu gccgcuuacc aucuuugacu | 3120 |
| ucauccagcu gcugcugauc gugauuggag caaucgcagu ggguggcggug cugcagccuu | 3180 |
| acauuuucgu ggccacugug ccggucauug uggcguucau caugcugcgg gccuacuucc | 3240 |
| uccaaaccag ccagcagcug aagcaacugg aauccgaggg acgaucccc aucuucacuc | 3300 |
| accuugugac gucguugaag ggacuggga ccuccgggc uuucggacgg cagcccuacu | 3360 |
| ucgaaacccu cuuccacaag gcccugaacc uccacaccgc caauugguuc cuguaccugu | 3420 |
| ccacccugcg gugguuccag augcgcaucg agaugauuuu cgucaucuuc uucaucgcgg | 3480 |
| ucacauucau cagcauccug acuaccggag agggagaggg acgggucgga auaauccuga | 3540 |
| cccucgccau gaacauuaug agcacccgc aguggcagu gaacagccg aucgacgugg | 3600 |
| acagccugau gcgaagcguc agccgcgugu caaguucau cgacaugccu acugagggaa | 3660 |
| aacccacuaa guccacuaag cccuacaaaa uggccagcu gagcaagguc augaucaucg | 3720 |
| aaaacuccca cgugaagaag gacgauauuu ggcccuccgg aggucaaaug accgugaagg | 3780 |
| accugaccgc aaaguacacc gagggaggaa acgccauucu cgaaaacauc agcuucucca | 3840 |
| uuucgccggg acagcggguc ggccuucucg ggcggaccgg uuccgggaag ucaacucugc | 3900 |
| ugucggcuuu ccuccggcug cugaauaccg aggggaaau ccaaauugac ggcgugucuu | 3960 |
| gggauuccau uacucugcag caguggcgga aggccuucgg cgugauccc cagaagggugu | 4020 |
| ucaucuucuc ggguaccuuc cggaagaacc uggauccuua cgagcaguge agcgaccaag | 4080 |
| aaaucuggaa ggucgccgac gaggucggcc ugcgcuccgu gauugaacaa uuccuggaa | 4140 |
| agcuggacuu cgucgucguc gacggggggau guguccuguc gcacggacau aagcagcuca | 4200 |
| ugugccucgc acguccgug cucuccaagg ccaagauucu gcugcuggac gaaccuucgg | 4260 |
| cccaccugga uccggucacc uaccagauca ucaggaggac ccugaagcag gccuuugccg | 4320 |
| auugcaccgu gauucucugc gagcaccgca ucgaggccau gcuggagugc cagcaguucc | 4380 |
| uggcaucga ggagaacaag guccgccaau acgacuccau ucaaaagcuc ucaacgagc | 4440 |
| ggucgcuguu cagacaagcu auuucaccgu ccgauagagu gaagcucuuc ccgcaucgga | 4500 |
| acagcucaaa gugcaaaucg aagccgcaga ucgcagccuu gaaggaagag acugaggaag | 4560 |
| aggugcagga caccggcuu uaacggguggg cauccougug acccucccc agugccucuc | 4620 |
| cuggcccugg aaguugccac uccagugccc accagccuug uccuaauaaa auuaaguugc | 4680 |
| aucaagcu | 4688 |

<210> SEQ ID NO 29
<211> LENGTH: 4688
<212> TYPE: RNA
<213> ORGANISM: Artificial Sequence
<220> FEATURE:
<223> OTHER INFORMATION: Synthetic polynucleotide

<400> SEQUENCE: 29

| | |
|---|---|
| ggacagaucg ccuggagacg ccauccacgc uguuuugacc uccauagaag acaccgggac | 60 |

```
cgauccagcc uccgcggccg ggaacggugc auuggaacgc ggauucccg ugccaagagu      120
gacucaccgu ccuugacacg augcagcggu ccccgcucga aaaggccagu gucgugucca      180
aacucuucuu cucauggacu cggccuaucc uuagaaaggg guaucggcag aggcuugagu      240
ugucugacau cuaccagauc cccucgguag auucggcgga uaaccucucg gagaagcucg      300
aacgggaaug ggaccgcgaa cucgcgucua agaaaaaccc gaagcucauc aacgcacuga      360
gaaggugcuu cuucuggcgg uucauguucu acgguaucuu cuuguaucuc ggggagguca      420
caaaagcagu ccaacccug uguuggguc gcauuaucgc cucguacgac cccgauaaca       480
aagaagaacg gagcaucgcg aucuaccucg ggaucgacu uguuugcuu ucaucguca        540
gaacacuuuu guugcaucca gcaaucuucg gccuccauca caucgguaug cagaugcgaa      600
ucgcuauguu uagcuugauc uacaaaaaga cacugaaacu cucgucgcgg uguuggaua      660
agauuuccau cggucaguug guguccugc uuaguaauaa cccaacaaa uucgaugagg       720
gacuggcgcu ggcacauuuc guguggauu ccccguugca agucgcccuu ugaugggcc       780
uuauugggga gcuguugcag gcaucugccu uuguggccu gggauuucug auuguguugg      840
cauuguuuca ggcugggcuu gggcggauga ugaug -continued

| | |
|---|---|
| ugauuucaac cggaccuaca cuucaggcga ggcgaaggca auccgugcuc aaccucauga | 2460 |
| cgcauucggu aaaccagggg caaaacauuc accgcaaaac gacggccuca acgagaaaag | 2520 |
| ugucacuugc accccaggcg aauuugacug aacucgacau cuacagccgu aggcuuucgc | 2580 |
| aagaaaccgg acuugagauc agcgaagaaa ucaaugaaga agauuugaaa gaguguuucu | 2640 |
| uugaugacau ggaaucaauc ccagcgguga caacguggaa cacauacuug cguuacauca | 2700 |
| cggugcacaa guccuugauu uucguccuca ucuggugucu cgugaucuuu ucgcugagg | 2760 |
| ucgcagcguc acugugguc cucuggcugc uuggu aauac gcccuugcaa gacaaaggca | 2820 |
| auucuacaca cucaagaaac aauuccuaug ccgugauuau cacuucuaca agcucguauu | 2880 |
| acguguuuua caucuacgua ggaguggccg acacucugcu cgcgaugggu uucuuccgag | 2940 |
| gacucccacu cguucacacg cuuaucacug ucuccaagau ucuccaccau aagaugcuuc | 3000 |
| auagcguacu gcaggcuccc auguccaccu ugaauacgcu caaggcggga gguauuuuga | 3060 |
| aucgcuucuc aaaagauauu gcaauuuugg augaccuucu gccccugacg aucuucgacu | 3120 |
| ucauccaguu guugcugauc gugauggggg cuauugcagu agcgcuguc cuccagccuu | 3180 |
| acauuuugu cgcgaccguu ccggugaucu uggcguuuau caugcugcgg gccuauuucu | 3240 |
| ugcagacguc acagcagcuu aagcaacugg agucugaagg gaggucgccu aucuuuacgc | 3300 |
| aucuugugac caguuugaag ggauugugga cguugcgcgc cuuuggcagg cagcccuacu | 3360 |
| uugaaacacu guuccacaaa gcgcugaauc uccauacggc aaauuggu uuguauuuga | 3420 |
| guacccuccg augguuucag augcgcauug agaugauuuu ugugaucuuc uuuaucgcgg | 3480 |
| ugacuuuuau cuccaucuug accacgggag agggcgaggg acgggucggu auuauccuga | 3540 |
| cacucgccau gaacauuaug agcacuuugc agugggcagu gaacagcucg auugaugugg | 3600 |
| auagccugau gaggucccguu ucgagggucu uuaaguucau cgacaugccg acggagggaa | 3660 |
| agcccacaaa aaguacgaaa cccuauaaga augggcaauu gaguaaggua augaucaucg | 3720 |
| agaacaguca cgugaagaag gaugacaucu ggccuagcgg gggucagaug accgugaagg | 3780 |
| accugacggc aaaauacacc gagggaggga acgcaauccu ugaaaacauc ucguucagca | 3840 |
| uuagccccgg ucagcgugug ggguugcucg ggaggaccgg gucaggaaaa ucgacguugc | 3900 |
| ugucggccuu cuugagacuu cugaauacag agggugagau ccagaucgac ggcguuucgu | 3960 |
| gggauagcau caccuugcag cagugcggaa aagcguuugg aguaauccc caaaaggucu | 4020 |
| uuaucuuuag cggaaccuuc cgaaagaauc ucgauccuua ugaacagugg ucagaucaag | 4080 |
| agauuuggaa agcgcggac gagguuggcc uucggagugu aaucgagcag uuucgggaa | 4140 |
| aacucgacuu uguccuugua gaugggggau gcguccuguc gcaugggcac aagcagcuca | 4200 |
| ugugccuggc gcgauccguc cucucuaaag cgaaaauucu ucucuuggau gaaccuucgg | 4260 |
| cccaucugga cccgguaacg uaucagauca ucagaaggac acuuaagcag gcguuugccg | 4320 |
| acugcacggu gauucucugu gagcaucgua ucgaggccau gcgaaugc cagcaauuuc | 4380 |
| uugucaucga agagaauaag guccgccagu acgacuccau ccagaagcug cuuaaugaga | 4440 |
| gaucauuguu ccggcaggcg auuucaccau ccgauagggu gaaacuuuuu ccacacagaa | 4500 |
| auucgucgaa gugcaagucc aaaccgcaga ucgggccuu gaagaagag acugaagaag | 4560 |
| aaguucaaga cacgcgucuu uaacggguggg caucccugug accccucccc agugccucuc | 4620 |
| cuggcccugg aaguugccac uccagugccc accagccuug uccuaauaaa auuaaguugc | 4680 |
| aucaagcu | 4688 |

<210> SEQ ID NO 30
<211> LENGTH: 4688
<212> TYPE: RNA
<213> ORGANISM: Artificial Sequence
<220> FEATURE:
<223> OTHER INFORMATION: Synthetic polynucleotide

<400> SEQUENCE: 30

| | | | | | |
|---|---|---|---|---|---|
| ggacagaucg | ccuggagacg | ccauccacgc | uguuuugacc | uccauagaag | acaccgggac | 60 |
| cgauccagcc | uccgcggccg | ggaacggugc | auuggaacgc | ggauucccccg | ugccaagagu | 120 |
| gacucaccgu | ccuugacacg | augcagagga | gcccacugga | gaaagccucc | gugguagagua | 180 |
| aacucuuuuu | uaguuggacc | agacccaucc | ugcgaaaagg | auacaggcag | cgccucgagu | 240 |
| ugucugauau | cuaccagauu | ccuucugugg | acucagcuga | caauuugagu | gagaagcugg | 300 |
| agcgggagug | ggauagagag | cuggcgagca | aaaaaaaccc | caagcuuauc | aaugcucugc | 360 |
| gccgcugcuu | uuucuggagg | uucauguuuu | augggaucuu | ccuguaccug | ggggaggauca | 420 |
| ccaaagcugu | cagccgcuc | cuucuuggcc | gcaucaucgc | cagcuaugac | ccugauaaua | 480 |
| aagaagaaag | gucuauugcu | auuuaucugg | gaauuggccu | cugcuugcuc | uucaucgucc | 540 |
| gcacccuucu | gcugcacccu | gccauuuuug | gccuucacca | caucggcaug | caaaugagaa | 600 |
| uugccauguu | cucccucauu | uacaaaaaga | cccugaaacu | uccucaaga | guguuagaua | 660 |
| aaauauccau | uggucagcug | gucagccugc | ugccaacaa | ucuuaacaaa | uuugaugaag | 720 |
| gcuuggcgcu | ggcccacuuc | guguggauug | caccucugca | ggugcccug | uugaugggac | 780 |
| uuauauggga | gcugcuucaa | gcccucugcu | ucuguggcu | gggcuuuuug | auuguacugg | 840 |
| cacuuuuuca | ggcugggcuc | ggaagaauga | ugaugaaaua | cagagaucag | cgggccggga | 900 |
| agauuucaga | gcgacuugug | auccaccagug | aaaugauuga | aaauauucag | agcgugaaag | 960 |
| ccuacugcug | ggaagaagcc | auggagaaga | ugauugaaa | ccgaggcag | acagagcuca | 1020 |
| agcucacgcg | gaaggcugcu | uauguucgcu | auuucaacag | cagcgccuuc | uucuucagug | 1080 |
| gcuucuuugu | ugucuuccug | ucuguucgc | cauaugcacu | gauaaaaggc | auuauuuuac | 1140 |
| gaaagaucuu | caccaccauc | aguuuugca | ucguucucag | gauggccguc | acaagacagu | 1200 |
| uccccugggc | ugugcagacc | ugguacgauu | ccuuggggc | caucaacaag | auucaagauu | 1260 |
| ucuugcaaaa | acaagaauau | aaaacuuuag | aauacaaccu | caccaccacu | gaaguggca | 1320 |
| uggaaaaugu | gacagccuuu | ugggaggagg | guuuggaga | auuguucgag | aaggcaaagc | 1380 |
| agaauaacaa | caacaggaag | acgagcaaug | gggacgacuc | ucuucuucuu | agcaacuuuu | 1440 |
| cacugcucgg | gaccccugug | uugaaagaua | uaaacuucaa | gaucgagagg | ggccagcucu | 1500 |
| uggcugugggc | aggcuccacu | ggagcuggua | aacaucucu | ucucaugguc | aucaugggg | 1560 |
| aacuggagcu | uucgaagga | aaaaucaagc | acagugggag | aaucucauuc | ugcagccagu | 1620 |
| uuuccuggau | caugccccggc | accauuaagg | aaaacaucau | auuggagug | uccaugaug | 1680 |
| aguaccgcua | ccggucaguc | aucaaagccu | gucaggugga | ggacaucauc | uccaaguuu | 1740 |
| cagagaaaga | caacauugug | cuggagaggg | gggguaucac | ucuuucugga | ggacaaagag | 1800 |
| ccaggaucuc | uuuggcccgg | gcagucuaca | aggaugcaga | ccucuacuug | uuggacaguc | 1860 |
| ccuucggcua | cccucgacgug | cugacugaaa | aagaaauuuu | ugaaagcugu | gugugcaaac | 1920 |
| ugauggcaaa | caagaccagg | auucuuguca | ccagcaagau | ggaacaucug | aagaaagcgg | 1980 |
| acaaaauucu | gauucugcau | gaagggagcu | ccuacuucua | uggaacauuu | agcgagcuuc | 2040 |
| agaaccuaca | gccagacuuc | uccuccaaau | uaaugggcug | ugacuccuuc | gaccaguucu | 2100 |

```
cugcagaaag aagaaacucu auacucacag agacccucca ccgcuucucc cuugagggag    2160
augccccagu uucuuggaca gaaaccaaga agcagccuu uaagcagacu ggcgaguuug     2220
gugaaaagag gaaaaauuca auucucaauc caauuaacag uauucgcaag uucagcauug    2280
uccagaagac accccuccag augaauggca ucgaagaaga uagugacgag ccgcuggaga    2340
gacggcugag ucggugcca gauucagaac aggggggaggc cauccugccc cggaucagcg   2400
ucauuuccac aggccccaca uuacaagcac ggcgccggca gaguguuuua aaucucauga   2460
cccauucagu gaaccagggc caaaauaucc acaggaagac uacagcuucu acccggaaag   2520
ugucucuggc cccucaggcc aaucugaccg cuggacau cuacagcagg aggcucuccc    2580
aggaaacagg gcuggaaaua ucugaagaga uuaaugaaga ggaucuuaaa gagugcuucu   2640
uugaugacau ggagagcauc cccgcgguga ccacauggaa caccuaccuu agauauauua   2700
cuguccacaa gagccucaua uuuguccuca ucuggugccu gguuauuuuc cucgcugagg   2760
uggcggccag ucuuguugug cucuggcugc ugggcaacac uccuccag gacaagggca    2820 auaguacuca cagcagaaau aauucuuaug ccgucaucau uacaagcacc uccagcuacu   2880
acguguucua caucuaugug ggcguggcug acacccuccu ggccaugggu uucuuccggg   2940
gccugccuuu ggugcacacc cucaucacag ugucaaaaau ucugcaccau aaaaugcuuc   3000 auucugccu gcaggcaccc augagcacuu ugaacacauu gaaggcuggc ggcauccuca   3060
acagauuuuc uaaagauauu gcuauccugg augaucccu cccccugaca aucuuugacu    3120 uuaccagcu ucugcugauc gugauggag ccauagcagu gguugcuguc cugcagcccu    3180 acauuuugu ggccaccgug cccgugauug uugccuuuau uaugcucaga gcuuacuucc    3240
ugcaaacuuc ucaacagcuc aaacagcuag aaucugaggg ccggagcccc auuuuuaccc   3300
accuggugac uucccugaag ggacuggga cucgagagc auucgggcga cagccuuacu    3360
uugagacacu guuccacaag gcccugaacu ugcacacugc caacugguuu cuuuaccuga   3420 gcacacccg cugguccag augcggauag agaugaucuu cgucaucuuu uuuauagcug   3480
uaaccuucau uucuauccuu acaacaggag aaggagaggg caggguggga aucauccuca   3540
cgcuggcuau gaacauaaug uccaccuugc agugggccgu gaauuccagu auagaugugg   3600
auucucuaau gaggagugug ucccggugu uuaaauucau ugauaugccu acugagggga   3660
aacccaccaa gucaacaaaa ccuuauaaga auggacagcu gagcaaggug augauaauug   3720
agaacagcca cgugaagaag gaugacauuu ggcccagcgg gggccagaug acugugaagg   3780
accugacggc caaguacacc gaaggugaa augccauuuu ggaaaacauc agcuucucaa    3840
ucucuccugg gcagagaguu ggauugcugg gucgcacggg cagcggcaaa ucaacccugc   3900
ucagugccuu ccuucggcuc cugaauacag aaggcgaaau ccaaauugac ggggugagcu   3960
gggacagcau cacccugcag caguggagaa aagcauuugg ggucauucca cagaaaguuu   4020
ucaucuucuc uggcacuuuc agaaagaacc uggaccccua ugagcagugg agcgaccagg   4080
agaucuggaa gguugcagau gaaguuggcc ugcggagugu gauagaacaa uuuccuggca   4140
agcuggauuu ugcugguga gauggaggcu gcgugcuguc ccacggccac aaacagcuga   4200
ugugccucgc ccgcuccguu cuuucaaagg ccaaaaucuu gcuuuggau gagcccagug    4260 cucaccuuga cccagugacc uaucagauaa uccgcaggac cuuaaagcaa gcuuuugccg   4320
acugcaccgu cauacugugu gagcaccgga uugaagcaau gcuggaaugc cagcaguuuc   4380 ugguugaucga ggagaauaag guccggcagu acgacgcau ccagaaguug uugaaugagc   4440
gcagccuuuu ccgccaggcc aucucccat cugacagagu caagcuguuu ccacauagga   4500
```

```
acuccucuaa gugcaagucc aagccccaga ucgcugcccu caaggaggaa acugaggaag    4560
aggugcagga uacccgccug ugacgggugg caucccugug accccucccc agugccucuc    4620
cuggcccugg aaguugccac uccagugccc accagccuug uccuaauaaa auuaaguugc    4680
aucaagcu                                                             4688
```